(12) United States Patent
Beusker et al.

(10) Patent No.: US 11,052,155 B2
(45) Date of Patent: Jul. 6, 2021

(54) CONJUGATES OF CC-1065 ANALOGS AND BIFUNCTIONAL LINKERS

(71) Applicant: SYNTARGA BV, Nijmegen (NL)

(72) Inventors: Patrick Henry Beusker, Nijmegen (NL); Rudy Gerardus Elisabeth Coumans, Nijmegen (NL); Ronald Christiaan Elgersma, Nijmegen (NL); Wiro Michael Petrus Bernardus Menge, Nijmegen (NL); Johannes Albertus Frederikus Joosten, Nijmegen (NL); Henri Johannes Spijker, Nijmegen (NL); Franciscus Marinus Hendrikus De Groot, Nijmegen (NL)

(73) Assignee: SYNTARGA BV, Nijmegen (NL)

( * ) Notice: Subject to any disclaimer, the term of this patent is extended or adjusted under 35 U.S.C. 154(b) by 368 days.

(21) Appl. No.: 15/461,560

(22) Filed: Mar. 17, 2017

(65) Prior Publication Data

US 2017/0274090 A1   Sep. 28, 2017
US 2018/0133316 A9   May 17, 2018

Related U.S. Application Data

(62) Division of application No. 13/642,847, filed as application No. PCT/NL2011/050278 on Apr. 21, 2011, now Pat. No. 96,299,240.

(Continued)

(51) Int. Cl.
*A61K 39/44*     (2006.01)
*A61K 47/64*     (2017.01)
(Continued)

(52) U.S. Cl.
CPC ............ *A61K 47/64* (2017.08); *A61K 31/437* (2013.01); *A61K 38/385* (2013.01); *A61K 39/44* (2013.01);
(Continued)

(58) Field of Classification Search
None
See application file for complete search history.

(56) References Cited

U.S. PATENT DOCUMENTS 5,475,092 A    12/1995  Chari
5,502,068 A     3/1996  Lown
(Continued)

FOREIGN PATENT DOCUMENTS

EP    0 154 445 A1    9/1985
EP    0 263 526 A1    4/1988
(Continued)

OTHER PUBLICATIONS

Bagshawe, K.D., et al., "A Cytotoxic Agent Can be Generated Selectively at Cancer Sites," *British Journal of Cancer* 58:700-703, The Macmillan Press Ltd., England (1988).

(Continued)

*Primary Examiner* — Karl J Puttlitz
(74) *Attorney, Agent, or Firm* — Sterne, Kessler, Goldstein & Fox P.L.L.C.

(57) ABSTRACT

This invention relates to novel analogs of the DNA-alkylating agent CC-1065 and to their conjugates. Furthermore this invention concerns intermediates for the preparation of said agents and conjugates. The conjugates are designed to release their (multiple) payload after one or more activation steps and/or at a rate and time span controlled by the conjugate in order to selectively deliver and/or controllably release one or more of said DNA alkylating agents. The agents, conjugates, and intermediates can be used to treat an (Continued)

illness that is characterized by undesired (cell) proliferation. As an example, the agents and the conjugates of this invention may be used to treat a tumor.

8 Claims, 4 Drawing Sheets

Related U.S. Application Data

(60) Provisional application No. 61/421,824, filed on Dec. 10, 2010, provisional application No. 61/326,437, filed on Apr. 21, 2010.

(51) Int. Cl.
*A61K 31/437* (2006.01)
*C07D 471/04* (2006.01)
*A61K 47/65* (2017.01)
*A61K 47/60* (2017.01)
*A61K 47/54* (2017.01)
*A61K 38/38* (2006.01)
*A61K 47/68* (2017.01)

(52) U.S. Cl.
CPC ............ *A61K 47/545* (2017.08); *A61K 47/60* (2017.08); *A61K 47/643* (2017.08); *A61K 47/646* (2017.08); *A61K 47/65* (2017.08); *A61K 47/6803* (2017.08); *A61K 47/6851* (2017.08); *C07D 471/04* (2013.01)

(56) References Cited

U.S. PATENT DOCUMENTS

| | | | |
|---|---|---|---|
| 5,585,499 | A | 12/1996 | Chari |
| 5,629,430 | A | 5/1997 | Terashima |
| 5,646,298 | A | 7/1997 | Powell |
| 5,662,911 | A | 9/1997 | Huber et al. |
| 5,670,492 | A | 9/1997 | Amishiro |
| 5,739,350 | A | 4/1998 | Kelly |
| 5,843,937 | A | 12/1998 | Wang |
| 5,846,545 | A | 12/1998 | Chari |
| 7,223,837 | B2 | 5/2007 | De Groot |
| 7,705,045 | B2 | 4/2010 | De Groot |
| 8,012,978 | B2 | 9/2011 | Zhao et al. |
| 8,680,293 | B2 | 3/2014 | Beusker et al. |
| 8,889,868 | B2 | 11/2014 | Beusker et al. |
| 9,421,278 | B2 | 8/2016 | Dokter et al. |
| 9,427,480 | B2 | 8/2016 | Santin et al. |
| 9,629,924 | B2 | 4/2017 | Beusker et al. |
| 9,815,784 | B2 | 11/2017 | Beusker et al. |
| 9,890,159 | B2 | 2/2018 | Huijbregts et al. |
| 9,901,567 | B2 | 2/2018 | Beusker et al. |
| 10,092,659 | B2 | 10/2018 | Santin et al. |
| 2003/0050331 | A1 | 3/2003 | Ng |
| 2004/0033962 | A1 | 2/2004 | Tietze et al. |
| 2004/0120958 | A1 | 6/2004 | Bander et al. |
| 2005/0026987 | A1 | 2/2005 | Boger |
| 2005/0148651 | A1 | 7/2005 | Denny |
| 2006/0233794 | A1 | 10/2006 | Law et al. |
| 2007/0037739 | A1 | 2/2007 | Wang |
| 2008/0279868 | A1 | 11/2008 | Boyd |
| 2008/0311136 | A1 | 12/2008 | Beusker |
| 2009/0010945 | A1 | 1/2009 | Alley et al. |
| 2009/0111805 | A1 | 4/2009 | Morris et al. |
| 2009/0162372 | A1 | 6/2009 | King |
| 2009/0318668 | A1 | 12/2009 | Beusker |
| 2010/0113476 | A1 | 5/2010 | Chen |
| 2011/0065767 | A1 | 3/2011 | Beusker |
| 2011/0207767 | A1 | 8/2011 | Beusker |
| 2012/0214864 | A1 | 8/2012 | Richer et al. |
| 2013/0095172 | A1 | 4/2013 | Alavattam et al. |
| 2015/0216844 | A1 | 8/2015 | Beusker et al. |
| 2016/0008486 | A1 | 1/2016 | Dokter et al. |
| 2016/0008487 | A1 | 1/2016 | Santin et al. |
| 2016/0052880 | A1 | 2/2016 | Beusker et al. |
| 2016/0324979 | A1 | 11/2016 | De Roo et al. |
| 2017/0007717 | A1 | 1/2017 | Santin et al. |
| 2017/0014525 | A1 | 1/2017 | Dokter et al. |
| 2017/0080103 | A1 | 3/2017 | Ariaans et al. |
| 2017/0145006 | A1 | 5/2017 | Huijbregts et al. |
| 2017/0333567 | A1 | 11/2017 | Beusker et al. |
| 2018/0140711 | A1 | 5/2018 | Dokter et al. |

FOREIGN PATENT DOCUMENTS

| | | |
|---|---|---|
| EP | 0154 445 B1 | 5/1989 |
| EP | 0 65 360 A1 | 6/1995 |
| EP | 0 656 360 A1 | 6/1995 |
| EP | 0 702 014 A1 | 3/1996 |
| JP | 2008-531542 A | 8/2008 |
| JP | 2009-529030 A | 8/2009 |
| WO | WO 88/04659 | 6/1988 |
| WO | WO 90/02746 | 3/1990 |
| WO | WO 91/16324 | 10/1991 |
| WO | WO 94/24304 A1 | 10/1994 |
| WO | WO 95/31971 | 11/1995 |
| WO | WO 97/07097 | 2/1997 |
| WO | WO 97/12862 | 4/1997 |
| WO | WO 97/32850 | 9/1997 |
| WO | WO 97/44000 | 11/1997 |
| WO | WO 97/44000 A2 | 11/1997 |
| WO | WO 97/45411 | 12/1997 |
| WO | WO 98/11101 A2 | 3/1998 |
| WO | WO 98/25898 | 6/1998 |
| WO | WO 98/25900 A1 | 6/1998 |
| WO | WO 98/52925 | 11/1998 |
| WO | WO 99/19298 | 4/1999 |
| WO | WO 99/31120 A1 | 6/1999 |
| WO | WO 01/83448 A2 | 11/2001 |
| WO | WO 01/83482 | 11/2001 |
| WO | WO 02/30894 | 4/2002 |
| WO | WO 02/059122 | 8/2002 |
| WO | WO 02/067930 | 9/2002 |
| WO | WO 02/067937 | 9/2002 |
| WO | WO 02/068412 | 9/2002 |
| WO | WO 02/096910 A1 | 12/2002 |
| WO | WO 03/022806 | 3/2003 |
| WO | WO 03/086318 | 10/2003 |
| WO | WO 03/097635 A1 | 11/2003 |
| WO | WO 2004/069159 A2 | 8/2004 |
| WO | WO 2004/069201 A2 | 8/2004 |
| WO | WO 2004/101767 A2 | 11/2004 |
| WO | WO 2005/032594 A2 | 4/2005 |
| WO | WO 2005/079398 A2 | 9/2005 |
| WO | WO 2005/103040 | 11/2005 |
| WO | WO 2005/105154 A1 | 11/2005 |
| WO | WO 2005/112919 A2 | 12/2005 |
| WO | WO 2006/002895 | 1/2006 |
| WO | WO 2006/012527 A1 | 2/2006 |
| WO | WO 2006/034488 A2 | 3/2006 |
| WO | WO 2006/037052 A2 | 4/2006 |
| WO | WO 2006/043839 | 4/2006 |
| WO | WO 2006/110476 | 10/2006 |
| WO | WO 2007/038658 A2 | 4/2007 |
| WO | WO 2007/051081 | 5/2007 |
| WO | WO 2007/059404 | 5/2007 |
| WO | WO 2007/089149 | 8/2007 |
| WO | WO 2008/063378 A2 | 5/2008 |
| WO | WO 2008/074004 A2 | 6/2008 |
| WO | WO 2008/083312 | 7/2008 |
| WO | WO 2008/103693 A2 | 8/2008 |
| WO | WO 2009/017394 A1 | 2/2009 |
| WO | WO 2009/026274 | 2/2009 |
| WO | WO 2009/064908 | 5/2009 |
| WO | WO 2009/073524 | 6/2009 |
| WO | WO 2009/073533 | 6/2009 |
| WO | WO 2009/073546 | 6/2009 |
| WO | WO 2009/134977 | 11/2009 |
| WO | WO 2010/027280 A1 | 3/2010 |
| WO | WO 2010/033733 A1 | 3/2010 |
| WO | WO 2010/062171 A2 | 6/2010 |
| WO | WO 2011/133039 A2 | 10/2011 |

(56) References Cited

FOREIGN PATENT DOCUMENTS

| | | |
|---|---|---|
| WO | WO 2013/049410 A1 | 4/2013 |
| WO | WO 2013/093809 A1 | 6/2013 |
| WO | WO 2015/104359 A2 | 7/2015 |
| WO | WO 2015/104373 A2 | 7/2015 |
| WO | WO 2015/104385 A2 | 7/2015 |
| WO | WO 2015/185142 A1 | 12/2015 |
| WO | WO 2016/046173 A1 | 3/2016 |

OTHER PUBLICATIONS

Bagshawe, K.D., "Antibody-Directed Enzyme Prodrug Therapy: A Review," *Drug Development Research* 34:220-230, Wiley-Liss, Inc., United States (1995).

Boger, D.L. and Johnson, D.S., "CC-1065 and the Duocarmycins: Unraveling the Keys to a New Class of Naturally Derived DNA Alkylating Agents," *Proceedings of the National Academy of Sciences, USA* 92:3642-3649, National Academy of Sciences, United States (1995).

Boger, D.L., et al., "Synthesis and Properties of Substituted CBI Analogs of CC-1065 and the Duocarmycins Incorporating the 7-Methoxy-1,2,9,9a-tetrahydrocyclopropa[c]benz[e]indol-4-one (MCBI) Alkylation Subunit: Magnitude of Electronic Effects on the Functional Reactivity," *Journal of Organic Chemistry* 61:1710-1729, American Chemical Society, United States (1996).

Carter, P., et al., "Identification and Validation of Cell Surface Antigens for Antibody Targeting in Oncology," *Endocrine-Related Cancer* 11:659-687, Society for Endocrinology, England (2004).

Duncan, R., "The Dawning Era of Polymer Therapeutics," *Nature Reviews Drug Discovery* 2:347-360, Nature Publisher Group, England (2003).

Elvira, C., et al., "Covalent Polymer-Drug Conjugates," *Molecules* 10:114-125, MDPI AG, Switzerland (2005).

Frankel, A.E., et al., "Cell Surface Receptor-Targeted Therapy of Acute Myeloid Leukemia: A Review," *Cancer Biotherapy & Radiopharmaceuticals* 15(5):459-476, Mary Ann Liebert, Inc., United States (2000).

Greenwald, R.B., et al., "Effective Drug Delivery by PEGylated Drug Conjugates," *Advanced Drug Delivery Reviews* 55:217-250, Elsevier Science Publishers, B.V., Netherlands (2003).

Greenwald, R.B., et al., "A New Aliphatic Amino Prodrug System for the Delivery of Small Molecules and Proteins Utilizing Novel PEG Derivatives," *Journal of Medicinal Chemistry* 47:726-734, American Chemical Society, United States (2004).

Huber, B.E., et al., "Retroviral-Mediated Gene Therapy for the Treatment of Hepatocellular Carcinoma: An Innovative Approach for Cancer Therapy," *Proceedings of the National Academy of Sciences, USA* 88:8039-8043, National Academy of Sciences, United States (1991).

Kingsbury, W.D., et al., "A Novel Peptide Delivery System Involving Peptidase Activated Prodrugs as Antimicrobial Agents. Synthesis and Biological Activity of Peptidyl Derivatives of 5-Fluorouracil," *Journal of Medicinal Chemistry* 27:1447-1451, American Chemical Society, United States (1984).

McGovren, J.P., et al., "Preliminary Toxicity Studies with the DNA-Binding Antibiotic, CC-1065," *The Journal of Antibiotics* 37(1):63-70, Antibiotics Research Association, Japan (1984).

Melton, R., et al., "The Use of Prodrugs in Targeted Anticancer Therapies," *S.T.P. Pharma Sciences* 9(1): 13-33, Éditions de Santé, France (1999).

Murray, J.L., "Monoclonal Antibody Treatment of Solid Tumors: A Coming of Age," *Seminars in Oncology* 27(6 Suppl 11):64-70, W.B. Saunders Company, United States (2000).

Pettit, G.R., et al., "The Dolastatins; 18: Stereospecific Synthesis of Dolaproine," *Synthesis* 1996(6):719-725, Thieme Medical Publishers, Inc., United States (1996).

Ringsdorf, H., "Structure and Properties of Pharmacologically Active Polymers," *Journal of Polymer Science: Polymer Symposia* 51:135-153, John Wiley & Sons, United States (1975).

Tietze, L.F., et al., "A Strategy for Tumor-Selective Chemotherapy by Enzymatic Liberation of seco-duocarmycin SA-Derivatives from Nontoxic Prodrugs," *Bioorganic & Medicinal Chemistry* 9:1929-1939, Elsevier Science Ltd., England (2001).

Tietze, L.F., et al., "Highly Selective Glycosylated Prodrugs of Cytostatic CC-1065 Analogues for Antibody-Directed Enzyme Tumor Therapy," *ChemBioChem* 2(10):758-765, Wiley-VCH-Verlag GmbH, Germany (2001).

Tietze, L.F., et al., "Synthesis and Biological Evaluation of Novel Analogues and Prodrugs of the Cytotoxic Antibiotic CC-1065 for Selective Cancer Therapy," *European Journal of Organic Chemistry* 10:1634-1645, Wiley-VCH Verlag GmbH, Germany (2002).

Tietze, L.F., et al., "Antitumor Agents: Development of Highly Potent Glycosidic Duocarmycin Analogues for Selective Cancer Therapy," *Angewandte Chemie International Edition* 45:6574-6577, Wiley-VCH Verlag GmbH & Co. KGaA, Germany (2006).

Tietze, L.F., et al., "Determination of the Biological Activity and Structure Activity Relationships of Drugs Based on the Highly Cytotoxic Duocarmycins and CC-1065," *Toxins* 1:134-150, MDPI AG, Switzerland (Dec. 2009).

Toki, B.E., et al., "Protease-Mediated Fragmentation of p-Amidobenzyl Ethers: A New Strategy for the Activation of Anticancer Prodrugs," *Journal of Organic Chemistry* 67:1866-1872, American Chemical Society, United States (2002).

Vippagunta, S.R., et al., "Crystalline Solids," *Advanced Drug Delivery Reviews* 48:3-26, Elsevier Science B.V., Netherlands (2001).

Wrasidlo, W., et al., "Induction of Endonucleolytic DNA Fragmentation and Apoptosis by the Duocarmycins," *Bioorganic & Medicinal Chemistry Letters* 4(4):631-636, Elsevier Science Ltd., England (1994).

English language translation of WO 98/25900 (cited as document FP4 on accompanying form PTO/SB/08a), Google translate, Apr. 30, 2013, 40 pages.

International Search Report for International Application No. PCT/NL2011/50278, European Patent Office, Rijswijk, Netherlands, dated Feb. 24, 2012, 11 pages.

International Preliminary Report on Patentability and Written Opinion for International Application No. PCT/NL2011/50278, The International Bureau of WIPO, Geneva, Switzerland, dated Oct. 23, 2012, 14 pages.

Non-Final Office Action in U.S. Appl. No. 12/671,609, inventors Beusker, P. et al., filed Oct. 26, 2010, 13 pages, U.S. Patent Office, United States, dated Oct. 24, 2012.

Final Office Action in U.S. Appl. No. 12/671,609, inventors Beusker, P. et al., filed Oct. 26, 2010, 13 pages, U.S. Patent Office, United States, dated May 8, 2013.

Notice of Allowance in U.S. Appl. No. 12/671,609, inventors Beusker, P. et al., filed Oct. 26, 2010, 15 pages, U.S. Patent Office, United States, dated Nov. 6, 2013.

Non-Final Office Action in U.S. Appl. No. 13/126,920, inventors Beusker, P. et al., filed Apr. 29, 2011, 20 pages, U.S. Patent Office, United States, dated Apr. 22, 2013.

Final Office Action in U.S. Appl. No. 13/126,920, inventors Beusker, P. et al., filed Apr. 29, 2011, 22 pages, U.S. Patent Office, United States, dated Jan. 7, 2014.

Notice of Allowance in U.S. Appl. No. 13/126,920, inventors Beusker, P. et al., filed Apr. 29, 2011, 5 pages, U.S. Patent Office, United States, dated Jul. 7, 2014.

Non-Final Office Action in U.S. Appl. No. 14/174,794, inventors Beusker, P. et al., filed Feb. 6, 2014, 21 pages, U.S. Patent Office, United States, dated Dec. 18, 2015.

Parrish, J.P. et al., "Establishment of Substituent Effects in the DNA Binding Subunit of CBI Analogues of the Duocarmycins and CC-1065," *Bioorganic & Medicinal Chemistry Letters* 11(17):3815-3838, Elsevier Ltd., England (2003).

Atwell, G.J. et al., "5-Amino-1-(chloromethyl)-1,2-dihydro-3H-benz[e]indoles: Relationships between Structure and Cytotoxicity for Analogues Bearing Different DNA Minor Groove Binding Subunits," *Journal of Medicinal Chemistry* 42(17):3400-3411, American Chemical Society, United States (1999).

Wang, Y. et al., "CC-1065 Analogues Bearing Different DNA-Binding Subunits: Synthesis, Antitumor Activity, and Preliminary

(56) References Cited

OTHER PUBLICATIONS

Toxicity Study," *Journal of Medicinal Chemistry* 46(4):634-637, American Chemical Society, United States (2003).
Parrish, J.P. et al., "Synthesis and Evaluation of N-aryl and N-alkenyl CBI Derivatives," *Bioorganic & Medicinal Chemistry* 12(22):5845-5856, Elsevier Ltd., England (2004).
Boger, D.L. et al., "Synthesis and Evaluation of a Series of C3-Substituted CBI Analogues of CC-1065 and the Duocarmycins," *The Journal of Organic Chemistry* 66(15):5163-5173, American Chemical Society, United States (2001).
Tietze, L.F. et al., "Selective Treatment of Cancer: Synthesis, Biological Evaluation and Structural Elucidation of Novel Analogues of the Antibiotic CC-1065 and the Duocarmycins," *Chemistry—A European Journal* 13(16):4396-4409, Wiley-VCH, Germany (2007).
Wang, Y, et al., "Design, Synthesis, Cytotoxic Properties and Preliminary DNA Sequencing Evaluation of CPI—N-methylpyrrole Hybrids. Enhancing Effect of a Trans Double Bond Linker and Role of the Terminal Amide Functionality on Cytotoxic Potency," *Anti-Cancer Drug Design* 11(1):15-34, Oxford University Press, United States (1996).
Amishiro, N. et al., "New Water-Soluble Duocarmycin Derivatives: Synthesis and Antitumor Activity of A-Ring Pyrrole Compounds Bearing β-heteroarylacryloyl Groups," *Journal of Medicinal Chemistry* 42(4):669-676, American Chemical Society, United States (1999).
Schuster, H.J. et al., "Synthesis of the First Spacer Containing Prodrug of a Duocarmycin Analogue and Determination of Its Biological Activity," *Organic & Biomolecular Chemistry* 8(8):1833-1842, Royal Society of Chemistry, England (Apr. 21, 2010).
Aristoff, P.A. & Johnson, P.D., "Synthesis of CBI-PDE-I-Dimer, the Benzannelated Analog of CC-1065," *The Journal of Organic Chemistry* 57(23):6234-6239, American Chemical Society, United States (1992).
Bando, T. and Sugiyama, H., "Synthesis and Biological Properties of Sequence-Specific DNA-Alkylating Pyrrole-imidazole Polyamides," *Accounts of Chemical Research* 39(12):935-944, American Chemical Society, United States (2006).
Boger, D.L. et al., "Examination of the Role of the Duocarmycin SA Methoxy Substituents: Identification of the Minimum, Fully Potent DNA Binding Subunit," *Bioorganic and Medicinal Chemistry Letters* 6(18):2207-2210, Elsevier Science, England (1996).
Boger, D.L. et al., "Substituent Effects within the DNA Binding Subunit of CBI Analogues of the Duocarmycins and CC-1065," *Bioorganic & Medicinal Chemistry Letters* 11(15):2021-2024, Elsevier Ltd., England (2001).
Boger, D.L. et al., "CC-1065 and the Duocarmycins: Synthetic Studies," *Chemical Reviews* 97(3):787-828, American Chemical Society, United States (1997).
Boyle, K.E. et al., "Synthesis and Evaluation of Duocarmycin SA Analogs Incorporating the Methyl 1,2,8,8a-tetrahydrocyclopropa[c]oxazolo[2,3-e]indol-4-one-6-carboxylate (COI) Alkylation Subunit," *Bioorganic & Medicinal Chemistry Letters* 20(6):1854-1857, Elsevier Ltd., England (Mar. 2010).
Chavda, S. et al., "A Novel Achiral Seco-cyclopropylpyrido[e]indolone (CPyI) Analog of CC-1065 and the Duocarmycins: Synthesis, DNA Interactions, in Vivo Anticancer and Anti-parasitic Evaluation," *Bioorganic & Medicinal Chemistry* 18(14):5016-5024, Elsevier Science Ltd., England (Jul. 2010).
Daniell, K. et al., "Design, Synthesis, and Biological Evaluation of Achiral Analogs of Duocarmycin SA," *Bioorganic & Medicinal Chemistry Letters* 15(1):177-180, Elsevier Ltd., England (2005).
Gauss, C.M. et al., "Synthesis and Preliminary Evaluation of Duocarmycin Analogues Incorporating the 1,2,11,11a-Tetrahydrocyclopropa[c]naphtho[2,3-e]indol-4-one (CNI) and 1,2,11,11a-Tetrahydrocyclopropa[c]naphtho[1,2-e]indol-4-one (iso-CNI) Alkylation Subunits," *Tetrahedron* 65(33):6591-6599, Pergamon Press, England (2009).

Jeffrey, S.C. et al., "Design, Synthesis, and in Vitro Evaluation of Dipeptide-Based Antibody Minor Groove Binder Conjugates," *Journal of Medicinal Chemistry* 48(5):1344-1358, American Chemical Society, United States (2005).
Li, L.S. and Sinha, S.C., "Studies Toward the Duocarmycin Prodrugs for the Antibody Prodrug Therapy Approach," *Tetrahedron Letters* 50(24):2933-2935, Elsevier Ltd., England (2009).
MacMillan, K.S. et al., "Total Synthesis and Evaluation of iso-Duocarmycin SA and iso-Yatakemycin," *Journal of the American Chemical Society* 131(3):1187-1194, American Chemical Society, United States (2009).
Milbank, J.B. et al., "Synthesis of 1-Substituted 3-(Chloromethyl)-6-aminoindoline (6-Amino-seco-CI) DNA Minor Groove Alkylating Agents and Structure-Activity Relationships for Their Cytotoxicity," *Journal of Medicinal Chemistry* 42(4):649-658, American Chemical Society, United States (1999).
Purnell, B. et al., "DNA Interstrand Crosslinking Agents: Synthesis, DNA Interactions, and Cytotoxicity of Dimeric Achiral Seco-Amino-CBI and Conjugates of Achiral Seco-Amino-CBI with Pyrrolobenzodiazepine (PBD)," *Bioorganic & Medicinal Chemistry Letters* 16(21):5677-5681, Elsevier Science Ltd., England (2006).
Robertson, W.M. et al., "Synthesis and Evaluation of a Series of C5'-Substituted Duocarmycin SA Analogs," *Bioorganic & Medicinal Chemistry Letters* 20(9):2722-2725, Elsevier Science Ltd., England (May 2010).
Suzawa, T. et al., "Synthesis of a Novel Duocarmycin Derivative DU-257 and its Application to Immunoconjugate Using Poly(ethylene glycol)-dipeptidyl Linker Capable of Tumor Specific Activation," *Bioorganic & Medicinal Chemistry* 8(8):2175-2184, Elsevier Science., England (2000).
Tichenor, M.S. et al., "Asymmetric Total Synthesis of (+)- and ent-(−)-Yatakemycin and Duocarmycin SA: Evaluation of Yatakemycin Key Partial Structures and its Unnatural Enantiomer," *Journal of the American Chemical Society* 128(49):15683-15696, American Chemical Society, United States (2006).
Tichenor, M.S. & Boger, D.L., "Yatakemycin: Total Synthesis, DNA Alkylation, and Biological Properties," *Natural Product Reports* 25(2):220-226, Royal Society of Chemistry, England (2008).
Tietze, L.F. et al., "Glycosidic Prodrugs of Highly Potent Bifunctional Duocarmycin Derivatives for Selective Treatment of Cancer," *Angewandte Chemie (International Edition in English)* 49(40):7336-7339, Wiley-VCH, Germany (Sep. 2010).
Tietze, L.F. & Krewer, B., "Novel Analogues of CC-1065 and the Duocarmycins for the Use in Targeted Tumour Therapies," *Anticancer Agents in Medicinal Chemistry* 9(3):304-325, Bentham Science Publishers, Netherlands (2009).
Tietze, L.F. et al., "Synthesis of a Novel Pentagastrin-Drug Conjugate for a Targeted Tumor Therapy," *Chemistry—A European Journal* 14(9):2811-2818, Wiley-VCH, Germany (2008).
Tietze, L.F. et al., "Asymmetric Synthesis and Biological Evaluation of Glycosidic Prodrugs for a Selective Cancer Therapy," *ChemMedChem* 3(12):1946-1955, Wiley-VCH, Germany (2008).
Wang, Y. et al., "Synthesis and Antitumor Activity of CBI-bearing Ester and Carbamate Prodrugs of CC-1065 Analogue," *Bioorganic and Medicinal Chemistry* 14(23):7854-7861, Elsevier Ltd., England (2006).
Wang, Y. et al., "Synthesis and Preliminary Biological Evaluations of CC-1065 Analogues: Effects of Different Linkers and Terminal Amides on Biological Activity," *Journal of Medicinal Chemistry* 43(8):1541-1549, American Chemical Society, United States (2000).
Amishiro, N. et al., "Synthesis and Antitumor Activity of Duocarmycin Derivatives: A-Ring Pyrrole Compounds Bearing β-(5',6',7'-trimethoxy-2'-indolyl)acryloyl Group," *Bioorganic and Medicinal Chemistry* 8(7):1637-1643, Elsevier Science Ltd., England (2000).
Attard, G., et al., "A phase Ib study of pertuzumab, a recombinant humanised antibody to HER2, and docetaxel in patients with advanced solid tumours," *British Journal of Cancer* 97(10):1338-1343, Cancer Research UK, England (Nov. 2007).
Haymarket Media, Inc., "Endometrial Carcinoma Chemotherapy and Other Treatment Regimens," 1 page (Mar. 2012).
Mellstedt, H., "Clinical considerations for biosimilar antibodies," *EJC Supplements* 11(3):1-11, Elsevier Ltd., England (2013).

(56) References Cited

OTHER PUBLICATIONS

Roitt, I.M., "Antigens," in *Immunology*, 3rd Edition, Roitt, I.M., et al., eds., p. 1.7, Mosby—Year Book Europe Limited, England (1993).
Non-Final Office Action dated Oct. 21, 2016 in U.S. Appl. No. 15/216,407, inventors Dokter, W. et al., filed Jul. 21, 2016.
Non-Final Office Action dated Nov. 22, 2016 in U.S. Appl. No. 15/216,366, inventors Santin, A.D. et al., filed Jul. 21, 2016.
Final Office Action dated Aug. 22, 2017 in U.S. Appl. No. 15/216,407, inventors Dokter, W. et al., filed Jul. 21, 2016.
Final Office Action dated Sep. 20, 2017 in U.S. Appl. No. 15/216,366, inventors Santin, A.D. et al., filed Jul. 21, 2016.
Notice of Allowance dated Oct. 3, 2017 in U.S. Appl. No. 14/174,794, inventors Beusker, P.H. et al., filed Feb. 6, 2014.
Amishiro, N., et al., "New Water-Soluble Duocarmycin Derivatives: Synthesis and Antitumor Activity of A-ring Pyrrole Compounds Bearing [beta]-Heteroarylacrylol Groups," J. Med. Chem 42:669-676, (Feb. 1999).
Atwell, et al., "5-Amino-1-(chloromethyl)-1,2-dihydro-3H-benz[eindoles," J. Med Chem. 42:3400-3411, (Aug. 1999).
Boger, D., et al., "Synthesis and Evaluation of a Series of C3-Substitued CBI Analogues of CC-1065 and the Duocarmycins," J. Org. Chem. 66:5163-5173, (Jun. 2001).
Parrish, J., et al., "Establishment of Substituent Effects in the DNA Binding subunit of CBI Analogues of the Duocarmycins and CC-1065," Bioorg Med. Chem 11:3815-3838, (Aug. 2003).
Parrish, J., et al., "Synthesis and evaluation of N-aryl and N-alkenyl CBI derivatives," Bioorg Med. Chem 12:5845-5856, (Nov. 2004).
Tietze, L., et al., "Selective Treatment of Cancer: Synthesis, Biological Evaluation and Structural Elucidation of Novel Analogues of the Antibiotic CC-1065 and the Duocarmycins," Chemistry 13:4396-4409, (2007).
Yuqiang Wang, et al., "CC-1065 Analogues Bearing Different DNA-Binding Subunits: Synthesis, Antitumor Activity, and Preliminary Toxicity Study," J. Med. Chem. 46:634-637, (2003).
Notice of allowance dated May 18, 2018 in U.S. Appl. No. 15/216,366, inventors Santin, A.D. et al., filed Jul. 21, 2016.
Final Office Action dated Aug. 2, 2017 in U.S. Appl. No. 15/316,444, inventors Huijbregts, et al., filed Dec. 5, 2016.
Notice of allowance dated Oct. 11, 2017 in U.S. Appl. No. 15/316,444, inventors Huijbregts. et al., filed Dec. 5, 2016.
Non-Final Office Action dated Apr. 11, 2018 in U.S. Appl. No. 15/798,695, inventors Dokter. et al., filed Oct. 31, 2017.
Cumnock, K., et al., "Trisulfide Modification Impacts the Reduction Step in Antibody-Drug Conjugation Process," *Bioconjugate Chemistry* 24(7):1154-1160, American Chemical Society, United States (2013).
Dokter, W.H.A., et al., "Abstract 2652: In vitro and in vivo antitumor activity of SYD985, a novel HER2-targeting ADC: a comparison with T-DM1," *Cancer Research* 74(Suppl 19):Abstract 2652, Proceedings of the 105th Annual Meeting of the American Association for Cancer Research, Apr. 5-9, 2014, San Diego, CA (Oct. 1, 2014).
Foulkes, W.D., et al., "Triple-Negative Breast Cancer," *The New England Journal of Medicine* 363:1938-1948, Massachusetts Medical Society, United States (Nov. 2010).
Hamblett, K.J., et al., "Effects of Drug Loading on the Antitumor Activity of a Monoclonal Antibody Drug Conjugate," *Clinical Cancer Research* 10(20):7063-7070, American Association for Cancer, United States (2004).
Dokter, W., et al., "Preclinical Profile of the HER2-Targeting ADC SYD983/SYD985: Introduction of a New Duocarmycin-Based Linker-Drug Platform"(Supplemental Data Included) *Molecular Cancer Therapeutics* 13(11):2618-2629, American Association of Cancer Research, United States (Sep. 2014).
McDonagh, C.F., et al., "Engineered antibody-drug conjugates with defined sites and stoichiometries of drug attachment," *Protein Engineering, Design & Selection* 19(7):299-307, Oxford University Press, England (2006).
Shen, B-Q., et al., "Conjugation site modulates the in vivo stability and therapeutic activity of antibody-drug conjugates," *Nature Biotechnology* 30(2):184-189, Nature Publishing Group, United States (2012).
Ouyang, J., "Drug-to-antibody ratio (DAR) and drug load distribution by hydrophobic interaction chromatography and reversed phase high-performance liquid chromatography," *Methods in Molecular Biology* 1045:275-283, Springer Science+Business Media, LLC, England (2013).
Sun, M.M.C., et al., "Reduction-Alkylation Strategies for the Modification of Specific Monoclonal Antibody Disulfides," *Bioconjugate Chem.* 16(5):1282-1290, American Chemical Society, United States (2005).
Van Der Lee, M., et al., "Poster 2652:The HER2-targeting ADC SYD985 shows superior antitumor activity compared to T-DM1 in preclinical studies with an activity profile that includes low-HER2 expressing breast cancers," AACR Annual Meeting 2014, Apr. 5-9, 2014, San Diego, CA.
Van Der Lee, M.M., et al., "The Preclinical Profile of the Duocarmycin-Based HER2-Targeting ADC SYD985 Predicts for Clinical Benefit in Low HER2-Expressing Breast Cancers," *Mol Cancer Ther.* 14(3):692-703, American Association for Cancer Research, United States (published online Jan. 14, 2015).
Verheijden, G., et al., "Poster 850294: Preclinical Data of SYD985 Support the Clinical Investigation of This Novel Anti-HER2 Antibody-Drug Conjugate in Breast Cancer Patients with Low Levels of HER2 Expression," 2014 San Antonio Breast Cancer Symposium, (Dec. 2014).
Braga, D., et al., "Crystal Polymorphism and Multiple Crystal Forms" *Struct. Bond.* 132:25-50, Springer-Verlag, Germany (2009).
Popowycz, F. et al., "Synthesis and reactivity of 4-, 5- and 6-azaindoles," *Tetrahedron* 63(36): 8689-8707, Elsevier Ltd., The Netherlands (2007).
Notice of Allowance dated Jan. 11, 2017 in U.S. Appl. No. 13/642,847, inventors Beusker, P.H. et al., § 371(c) date Nov. 27, 2012.
Final Office Action dated Jan. 13, 2017 in U.S. Appl. No. 14/526,462, inventors Beusker, P.H. et al., filed Oct. 28, 2014.
Non-Final Office Action dated Mar. 9, 2017 in U.S. Appl. No. 15/316,444, inventors Huibregts, T. et al., § 371(c) date Dec. 5, 2016.
Junutula, J.R., et al., "Site-specific conjugation of a cytotoxic drug to an antibody improves the therapeutic index," *Nature Biotechnology* 26(8):925-932, Nature Publishing Group, England (2008).
Tietze, L.F., et al., "Synthesis of Fluorescence-Labelled Glycosidic Prodrugs Based on the Cytotoxic Antibiotic Duocarmycin," *Eur. J. Org. Chem.* 2010(36):6909-6921, Wiley-VCH Verlag GmbH & Co., Germany (Dec. 2010).
Tietze, L.F., et al., "Enantio- and Diastereoselective Synthesis of Duocarmycine-Based Prodrugs for a Selective Treatment of Cancer by Epoxide Opening," *Chemistry—A European Journal* 14(3):895-901, Wiley-VCH Verlag GmbH & Co., Germany (2008).
Tietze, L.F., et al., "Atropisomerism of Aromatic Carbamates," *Chemistry—A European Journal* 16(42):12678-12682, Wiley-VCH Verlag GmbH & Co., Germany (Nov. 2010).
Sigma-Aldrich Co. LLC, "Product Information," Catalog No. B3773, sigma-aldrich.com, accessed at http://www.sigmaaldrich.com/content/dam/sigma-aldrich/docs/Sigma/Datasheet/b3773dat.pdf, accessed on Apr. 20, 2017, 1 page.
Non-Final Office Action dated May 4, 2017 in U.S. Appl. No. 14/174,794, inventors Beusker, P.H. et al., filed Feb. 6, 2014.
Advisory Action dated May 15, 2017 in U.S. Appl. No. 14/526,462, inventors Beusker, P.H. et al., filed Oct. 28, 2014.
Notice of Allowance dated Jun. 29, 2017 in U.S. Appl. No. 14/526,462, inventors Beusker, P.H. et al., filed Oct. 28, 2014.
Non-Final Office Action dated Mar. 20, 2015 in U.S. Appl. No. 13/642,847, inventors Beusker, P.H. et al., § 371(c) date Nov. 27, 2012.
Final Office Action dated Dec. 2, 2015 in U.S. Appl. No. 13/642,847, inventors Beusker, P.H. et al., § 371(c) date Nov. 27, 2012.
Non-Final Office Action dated Jun. 2, 2016 in U.S. Appl. No. 13/642,847, inventors Beusker, P.H. et al., § 371(c) date Nov. 27, 2012.

(56) References Cited

OTHER PUBLICATIONS

El-Sahwi, K.S., et al., "Development of targeted therapy in uterine serous carcinoma, a biologically aggressive variant of endometrial cancer," *Expert Review of Anticancer Therapy* 12(1):41-49, Expert Reviews Ltd., England (2012).
Kovtun, Y.V. and Goldmacher, V.S., "Cell killing by antibody-drug conjugates," *Cancer Letters* 255(2):232-240, Elsevier Ireland Ltd., Ireland (2007).
Müller, U., "Polymorphism," in *Inorganic Structural Chemistry*, pp. 14-15, John Wiley & Sons Ltd, England (1993).
Non-Final Office Action dated Mar. 16, 2016 in U.S. Appl. No. 14/859,201, inventors Dokter, W. et al., filed Sep. 18, 2015.
Notice of Allowance dated Jun. 30, 2016 in U.S. Appl. No. 14/859,201, inventors Dokter, W. et al., filed Sep. 18, 2015.
Final Office Action dated Jul. 27, 2016 in U.S. Appl. No. 14/174,794, inventors Beusker, P.H. et al., filed Feb. 6, 2014.
Non-Final Office Action dated Mar. 9, 2016 in U.S. Appl. No. 14/859,221, inventors Santin, A.D. et al., filed Sep. 18, 2015.
Notice of Allowance dated Jun. 29, 2016 in U.S. Appl. No. 14/859,221, inventors Santin, A.D. et al., filed Sep. 18, 2015.
Non-Final Office Action dated Jun. 2, 2016 in U.S. Appl. No. 14/526,462, inventors Beusker, P.H. et al., filed Oct. 28, 2014.

CONJUGATES OF CC-1065 ANALOGS AND BIFUNCTIONAL LINKERS

FIELD OF THE INVENTION

This invention relates to novel analogs of the DNA-alkylating agent CC-1065 and to their conjugates. Furthermore this invention concerns intermediates for the preparation of said agents and conjugates. The conjugates are designed to release their (multiple) payload after one or more activation steps and/or at a rate and time span controlled by the conjugate in order to selectively deliver and/or controllably release one or more of said DNA-alkylating agents. The agents, conjugates, and intermediates can be used to treat an illness that is characterized by undesired (cell) proliferation. As an example, the agents and the conjugates of this invention may be used to treat a tumor.

BACKGROUND OF THE INVENTION

The duocarmycins, first isolated from a culture broth of *Streptomyces* species, are members of a family of antitumor antibiotics that also includes CC-1065. These extremely potent agents allegedly derive their biological activity from an ability to sequence-selectively alkylate DNA at the N3 of adenine in the minor groove, which initiates a cascade of events that terminates in an apoptotic cell death mechanism.[1]

Although CC-1065 has shown very potent cytotoxicity, it could not be used in the clinic because of serious delayed hepatotoxicity.[2] This observation led to the development of synthetic analogs of CC-1065 (see for CC-1065 derivatives for example Aristoff et al., *J. Org. Chem.* 1992, 57, 6234; Boger et al., *Bioorg. Med. Chem. Lett.* 1996, 6, 2207; Boger et al., *Chem. Rev.* 1997, 97, 787; Milbank et al., *J. Med. Chem.* 1999, 42, 649; Atwell et al., *J. Med. Chem.* 1999, 42, 3400; Wang et al., *J. Med. Chem.* 2000, 43, 1541; Boger et al., *Bioorg. Med. Chem. Lett.* 2001, 11, 2021; Parrish et al., *Bioorg. Med. Chem.* 2003, 11, 3815; Daniell et al., *Bioorg. Med. Chem. Lett.* 2005, 15, 177; Tichenor et al., *J. Am. Chem. Soc.* 2006, 128, 15683; Purnell et al., *Bioorg. Med. Chem.* 2006, 16, 5677; Bando and Sugiyama, *Acc. Chem. Res.* 2006, 39, 935; Tichenor et al., *Nat. Prod. Rep.* 2008, 25, 220; MacMillan et al., *J. Am. Chem. Soc.* 2009, 131, 1187; Tietze et al., *Anti-Cancer Agents Med. Chem.* 2009, 9, 304; Gauss et al., *Tetrahedron* 2009, 65, 6591; Robertson et al., *Bioorg. Med. Chem. Lett.* 2010, 20, 2722; Boyle et al., *Bioorg. Med. Chem. Lett.* 2010, 20, 1854; Chavda et al., *Bioorg. Med. Chem.* 2010, 18, 5016; EP 0154445; WO 88/04659; WO 90/02746; WO 97/12862; WO 97/32850; WO 97/45411; WO 98/52925; WO 99/19298; WO 01/83482; WO 02/067937; WO 02/067930; WO 02/068412; WO 03/022806; WO 2004/101767; WO 2006/043839; and WO 2007/051081), which generally showed to have similar cytotoxicity, but reduced hepatotoxicity. Still, however, these derivatives lack sufficient selectivity for tumor cells, as the selectivity of these agents—and cytotoxic agents in general—is for a certain part based on the difference in the rate of proliferation of tumor cells and normal cells, and therefore they also affect healthy cells that show a relatively high proliferation rate. This typically leads to severe side effects. Drug concentrations that would completely eradicate the tumor cannot be reached because of dose-limiting side effects such as gastrointestinal tract and bone marrow toxicity. In addition, tumors can develop resistance against anticancer agents after prolonged treatment. In modern drug development, targeting of cytotoxic drugs to the tumor site can therefore be considered one of the primary goals.

One promising approach to obtain increased selectivity for tumor cells or tumor tissue is to exploit the existence of tumor-associated antigens, receptors, and other receptive moieties, which can serve as a target. Such a target may be upregulated or to some degree be specifically present in tumor tissue or in closely associated tissue, such as neovascular tissue, with respect to other tissues in order to achieve efficient targeting. Many targets have been identified and validated and several methods to identify and validate targets have been developed.[3] By coupling a ligand, e.g. an antibody or antibody fragment, for such a tumor-associated antigen, receptor, or other receptive moiety to a therapeutic agent, this agent can be selectively targeted to tumor tissue.

Another promising approach to obtain selectivity for tumor cells or tumor tissue is to exploit the existence of tumor-associated enzymes. An enzyme that is mainly localized at the tumor site can convert a pharmacologically inactive prodrug, which consists of an enzyme substrate directly or indirectly linked to the toxic drug, to the corresponding drug in the vicinity of or inside the tumor. Via this concept a high concentration of toxic anticancer agent can be selectively generated at the tumor site. All tumor cells may be killed if the dose is sufficiently high, which may decrease development of drug-resistant tumor cells.

Enzymes can also be transported to the vicinity of or inside target cells or target tissue via for example antibody-directed enzyme prodrug therapy (ADEPT)[4], polymer-directed enzyme prodrug therapy (PDEPT) or macromolecular-directed enzyme prodrug therapy (MDEPT)[5], virus-directed enzyme prodrug therapy (VDEPT)[6], or gene-directed enzyme prodrug therapy (GDEPT)[7]. With ADEPT, for example, a non-toxic prodrug is selectively converted into a cytotoxic compound at the surface of target cells by an antibody-enzyme conjugate that has been pretargeted to the surface of those cells.

Yet another promising approach to obtain selectivity for tumor cells or tumor tissue is to exploit the enhanced permeability and retention (EPR) effect. Through this EPR effect, macromolecules passively accumulate in solid tumors as a consequence of the disorganized pathology of angiogenic tumor vasculature with its discontinuous endothelium, leading to hyperpermeability to large macromolecules, and the lack of effective tumor lymphatic drainage.[8] By coupling a therapeutic agent directly or indirectly to a macromolecule, said agent can be selectively targeted to tumor tissue.

Besides efficient targeting, other important criteria for the successful application of targeted conjugates of cytotoxic agents in tumor therapy are that the one or more agents are released efficiently from the conjugate at the tumor site and that the conjugate is non-cytotoxic or only very weakly cytotoxic, whereas the cytotoxic agent itself exhibits highly potent cytotoxicity. Ideally, this leads to the generation of cytotoxic molecules only at the tumor site, which results in a greatly increased therapeutic index with respect to the untargeted cytotoxic agent. Another important criterion for a successful targeted conjugate is that the conjugate must have suitable pharmacological properties, such as sufficient stability in the circulation, low aggregation tendency, and good water solubility. Appropriate water-solubility and hydrophilicity of the drug and/or the linker may contribute to improved pharmacological properties.

Several conjugates of CC-1065 and derivatives have been described (see for conjugates of CC-1065 derivatives for example Suzawa et al., *Bioorg. Med. Chem.* 2000, 8, 2175; Jeffrey et al., *J. Med. Chem.* 2005, 48, 1344; Wang et al., Bioorg. Med. Chem. 2006, 14, 7854; Tietze et al., *Chem. Eur. J.* 2007, 13, 4396; Tietze et al., *Chem. Eur. J.* 2008, 14, 2811; Tietze et al., *Chem Med Chem* 2008, 3, 1946; Li et al., *Tetrahedron Lett.* 2009, 50, 2932; Tietze et al., *Angew. Chem. Int. Ed.* 2010, 49, 7336; WO 91/16324; WO 94/04535; WO 95/31971; U.S. Pat. Nos. 5,475,092; 5,585,499; 5,646,298; WO 97/07097; WO 97/44000; U.S. Pat. No. 5,739,350; WO 98/11101; WO 98/25898; U.S. Pat. Nos. 5,843,937; 5,846,545; WO 02/059122; WO 02/30894; WO 03/086318; WO 2005/103040; WO 2005/112919; WO 2006/002895; WO 2006/110476; WO 2007/038658; WO 2007/059404; WO 2008/083312; WO 2008/103693; WO 2009/026274; WO 2009/064908; WO 2009/073533; WO 2009/073524; WO 2009/073546; WO 2009/134977; and US 2009/0162372). In these conjugates, one or more of the favorable properties discussed above may be non-optimal.

Accordingly, there is still a clear need for conjugates of CC-1065 derivatives that show a high therapeutic window, contain CC-1065 derivatives that have potent cytotoxicity and favorable pharmacological properties, and release the CC-1065 derivatives efficiently.

SUMMARY OF THE INVENTION

The present invention fulfils the above-mentioned need with a compound of formula (I) or (II):

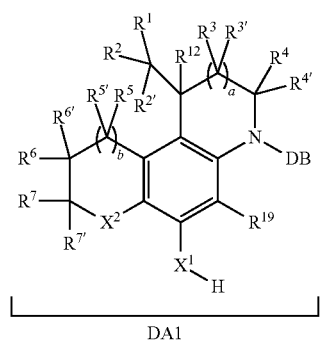

(I)

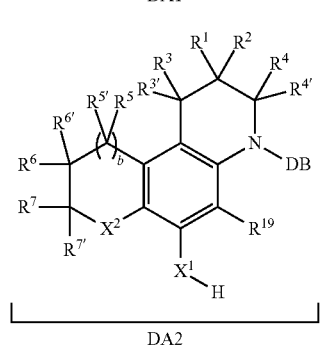

(II)

or a pharmaceutically acceptable salt, hydrate, or solvate thereof, wherein
DB is a DNA-binding moiety and is selected from the group consisting of

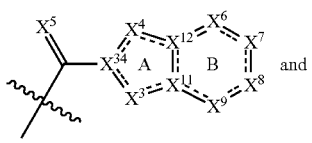

DB1

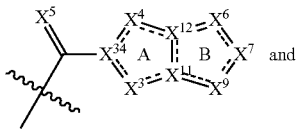

DB2

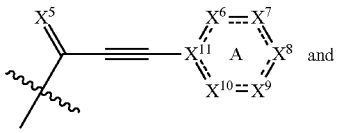

DB3

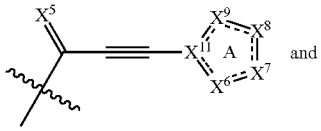

DB4

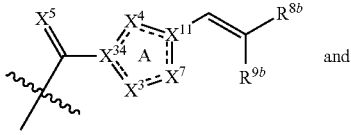

DB5

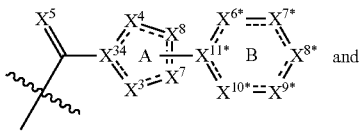

DB6

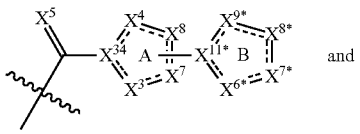

DB7

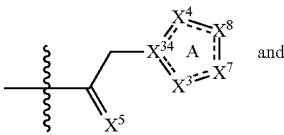

DB8

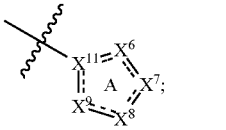

DB9

$R^1$ is a leaving group;
$R^2$, $R^{2'}$, $R^3$, $R^{3'}$, $R^4$, $R^{4'}$, $R^{12}$, and $R^{19}$ are independently selected from H, OH, SH, $NH_2$, $N_3$, $NO_2$, NO, $CF_3$, CN, $C(O)NH_2$, $C(O)H$, $C(O)OH$, halogen, $R^a$, $SR^a$, $S(O)R^a$, $S(O)_2R^a$, $S(O)OR^a$, $S(O)_2OR^a$, $OS(O)R^a$, $OS(O)_2R^a$, $OS(O)OR^a$, $OS(O)_2OR^a$, $OR^a$, $NHR^a$, $N(R^a)R^b$, $^+N(R^a)(R^b)R^c$, $P(O)(OR^a)(OR^b)$, $OP(O)(OR^a)(OR^b)$, $SiR^aR^bR^c$, $C(O)R^a$, $C(O)OR^a$, $C(O)N(R^a)R^b$, $OC(O)R^a$, $OC(O)OR^a$, $OC(O)N(R^a)R^b$, $N(R^a)C(O)R^b$, $N(R^a)C(O)OR^b$, and $N(R^a)C(O)N(R^b)R^c$, wherein
  $R^a$, $R^b$, and $R^c$ are independently selected from H and optionally substituted $C_{1-3}$ alkyl or $C_{1-3}$ heteroalkyl,
or $R^3+R^{3'}$ and/or $R^4+R^{4'}$ are independently selected from =O, =S, $=NOR^{18}$, $=C(R^{18})R^{18'}$, and $=NR^{18}$, $R^{18}$ and $R^{18'}$ being independently selected from H and optionally substituted $C_{1-3}$ alkyl, two or more of $R^2$, $R^{2'}$, $R^3$, $R^{3'}$, $R^4$, $R^{4'}$, and $R^{12}$ optionally being joined by one or more bonds to form one or more optionally substituted carbocycles and/or heterocycles;

$X^2$ is selected from O, $C(R^{14})(R^{14'})$, and $NR^{14}$, wherein $R^{14}$ and $R^{14'}$ have the same meaning as defined for $R^7$ and are independently selected, or $R^{14'}$ and $R^{7'}$ are absent resulting in a double bond between the atoms designated to bear $R^{7'}$ and $R^{14}$;

$R^5$, $R^{5'}$, $R^6$, $R^{6'}$, $R^7$, and $R^{7'}$ are independently selected from H, OH, SH, $NH_2$, $N_3$, $NO_2$, NO, $CF_3$, CN, $C(O)NH_2$, C(O)H, C(O)OH, halogen, $R^e$, $SR^e$, $S(O)R^e$, $S(O)_2R^e$, $S(O)OR^e$, $S(O)_2OR^e$, $OS(O)R^e$, $OS(O)_2R^e$, $OS(O)OR^e$, $OS(O)_2OR^e$, $OR^e$, $NHR^e$, $N(R^e)R^f$, $^+N(R^e)(R^f)R^g$, $P(O)(OR^e)(OR^f)$, $OP(O)(OR^e)(OR^f)$, $SiR^eR^fR^g$, $C(O)R^e$, $C(O)OR^e$, $C(O)N(R^e)R^f$, $OC(O)R^e$, $OC(O)OR^e$, $OC(O)N(R^e)R^f$, $N(R^e)C(O)R^f$, $N(R^e)C(O)OR^f$, $N(R^e)C(O)N(R^f)R^g$, and a water-soluble group, wherein

- $R^e$, $R^f$, and $R^g$ are independently selected from H and optionally substituted $(CH_2CH_2O)_{ee}CH_2CH_2X^{13}R^{e1}$, $C_{1-15}$ alkyl, $C_{1-15}$ heteroalkyl, $C_{3-15}$ cycloalkyl, $C_{1-15}$ heterocycloalkyl, $C_{5-15}$ aryl, or $C_{1-15}$ heteroaryl, wherein ee is selected from 1 to 1000, $X^{13}$ is selected from O, S, and $NR^{f1}$, and $R^{f1}$ and $R^{e1}$ are independently selected from H and $C_{1-3}$ alkyl, one or more of the optional substituents in $R^e$, $R^f$, and/or $R^g$ optionally being a water-soluble group, two or more of $R^e$, $R^f$, and $R^g$ optionally being joined by one or more bonds to form one or more optionally substituted carbocycles and/or heterocycles, or $R^5+R^{5'}$ and/or $R^6+R^{6'}$ and/or $R^7+R^{7'}$ are independently selected from =O, =S, $=NOR^{e3}$, $=C(R^{e3})R^{e4}$, and $=NR^{e3}$, $R^{e3}$ and $R^{e4}$ being independently selected from H and optionally substituted $C_{1-3}$ alkyl, or $R^5+R^6$ and/or $R^{6'}+R^{7'}$ and/or $R^{7'}+R^{14'}$ are absent, resulting in a double bond between the atoms designated to bear $R^{5'}$ and $R^6$, and/or $R^{6'}$ and $R^7$, and/or $R^{7'}$ and $R^{14'}$, respectively, two or more of $R^5$, $R^{5'}$, $R^6$, $R^{6'}$, $R^7$, $R^{7'}$, $R^{14}$, and $R^{14'}$ optionally being joined by one or more bonds to form one or more optionally substituted carbocycles and/or heterocycles;

$X^1$ is selected from O, S, and $NR^{13}$, wherein $R^{13}$ is selected from H and optionally substituted $C_{1-8}$ alkyl or $C_{1-8}$ heteroalkyl and not joined with any other substituent;

$X^3$ is selected from O, S, $C(R^{15})R^{15'}$, $-C(R^{15})(R^{15'})-C(R^{15})(R^{15'})-$, $-N(R^{15})-N(R^{15'})-$, $-C(R^{15})(R^{15'})-N(R^{15''})-$, $-N(R^{15''})-C(R^{15})(R^{15'})-$, $-C(R^{15})(R^{15'})-O-$, $-O-C(R^{15})(R^{15'})-$, $-C(R^{15})(R^{15'})-S-$, $-S-C(R^{15})(R^{15'})-$, $-C(R^{15})=C(R^{15'})-$, $=C(R^{15})-C(R^{15'})=$, $-N=C(R^{15})-$, $=N-C(R^{15})=$, $-C(R^{15})=N-$, $=C(R^{15})-N=$, $-N=N-$, $=N-N=$, $CR^{15}$, N, and $NR^{15}$, or in DB1 and DB2 $-X^3-$ represents $-X^{3a}$ and $X^{3b}-$, wherein $X^{3a}$ is connected to $X^{34}$, a double bond is present between $X^{34}$ and $X^4$, and $X^{3b}$ is connected to $X^{11}$, wherein $X^{3a}$ is independently selected from H and optionally substituted $(CH_2CH_2O)_{ee}CH_2CH_2X^{13}R^{e1}$, $C_{1-8}$ alkyl, or $C_{1-8}$ heteroalkyl and not joined with any other substituent;

$X^4$ is selected from O, S, $C(R^{16})R^{16'}$, $NR^{16}$, N, and $CR^{16}$;

$X^5$ is selected from O, S, $C(R^{17})R^{17'}$, $NOR^{17}$, and $NR^{17}$, wherein $R^{17}$ and $R^{17'}$ are independently selected from H and optionally substituted $C_{1-8}$ alkyl or $C_{1-8}$ heteroalkyl and not joined with any other substituent;

$X^6$ is selected from $CR^{11}$, $CR^{11}(R^{11'})$, N, $NR^{11}$, O, and S;

$X^7$ is selected from $CR^8$, $CR^8(R^{8'})$, N, $NR^8$, O, and S;

$X^8$ is selected from $CR^9$, $CR^9(R^{9'})$, N, $NR^9$, O, and S;

$X^9$ is selected from $CR^{10}$, $CR^{10}(R^{10'})$, N, $NR^{10}$, O, and S;

$X^{10}$ is selected from $CR^{20}$, $CR^{20}(R^{20'})$, N, $NR^{20}$, O, and S;

$X^{11}$ is selected from C, $CR^{21}$, and N, or $X^{11}-X^{3b}$ is selected from $CR^{21}$, $CR^{21}(R^{21'})$, N, $NR^{21}$, O, and S;

$X^{12}$ is selected from C, $CR^{22}$, and N;

$X^6$, $X^7$, $X^8$, $X^9$, $X^{10}$, and $X^{11*}$ have the same meaning as defined for $X^6$, $X^7$, $X^8$, $X^9$, $X^{10}$, and $X^{11}$, respectively, and are independently selected;

$X^{34}$ is selected from C, $CR^{23}$, and N;

the ring B atom of $X^{11*}$ in DB6 and DB7 is connected to a ring atom of ring A such that ring A and ring B in DB6 and DB7 are directly connected via a single bond;

=== means that the indicated bond may be a single bond or a non-cumulated, optionally delocalized, double bond;

$R^8$, $R^{8'}$, $R^9$, $R^{9'}$, $R^{10}$, $R^{10'}$, $R^{11}$, $R^{11'}$, $R^{15}$, $R^{15'}$, $R^{15''}$, $R^{15'''}$, $R^{16}$, $R^{16'}$, $R^{20}$, $R^{20'}$, $R^{21}$, $R^{21'}$, $R^{22}$, and $R^{23}$ each independently selected from H, OH, SH, $NH_2$, $N_3$, $NO_2$, NO, $CF_3$, CN, $C(O)NH_2$, C(O)H, C(O)OH, halogen, $R^h$, $SR^h$, $S(O)R^h$, $S(O)_2R^h$, $S(O)OR^h$, $S(O)_2OR^h$, $OS(O)R^h$, $OS(O)_2R^h$, $OS(O)OR^h$, $OS(O)_2OR^h$, $OR^h$, $NHR^h$, $N(R^h)R^i$, $^+N(R^h)(R^i)R^j$, $P(O)(OR^h)(OR^i)$, $OP(O)(OR^h)(OR^i)$, $SiR^hR^iR^j$, $C(O)R^h$, $C(O)OR^h$, $C(O)N(R^h)R^i$, $OC(O)R^h$, $OC(O)OR^h$, $OC(O)N(R^h)R^i$, $N(R^h)C(O)R^i$, $N(R^h)C(O)OR^i$, $N(R^h)C(O)N(R^i)R^j$, and a water-soluble group, wherein

- $R^h$, $R^i$, and $R^j$ are independently selected from H and optionally substituted $(CH_2CH_2O)_{ee}CH_2CH_2X^{13}R^{e1}$, $C_{1-15}$ alkyl, $C_{1-15}$ heteroalkyl, $C_{3-15}$ cycloalkyl, $C_{1-15}$ heterocycloalkyl, $C_{5-15}$ aryl, or $C_{1-15}$ heteroaryl, one or more of the optional substituents in $R^h$, $R^i$, and/or $R^j$ optionally being a water-soluble group, two or more of $R^h$, $R^i$, and $R^j$ optionally being joined by one or more bonds to form one or more optionally substituted carbocycles and/or heterocycles, or $R^8+R^{8'}$ and/or $R^9+R^{9'}$ and/or $R^{10}+R^{10'}$ and/or $R^{11}+R^{11'}$ and/or $R^{15}+R^{15'}$ and/or $R^{15''}+R^{15'''}$ and/or $R^{16}+R^{16'}$ and/or $R^{20}+R^{20'}$ and/or $R^{21}+R^{21'}$ are independently selected from =O, =S, $=NOR^{h1}$, $=C(R^{h1})R^{h2}$, and $=NR^{h1}$, $R^{h1}$ and $R^{h2}$ being independently selected from H and optionally substituted $C_{1-3}$ alkyl, two or more of $R^8$, $R^{8'}$, $R^9$, $R^{9'}$, $R^{10}$, $R^{10'}$, $R^{11}$, $R^{11'}$, $R^{15}$, $R^{15'}$, $R^{15''}$, $R^{15'''}$, $R^{16}$, $R^{16'}$, $R^{20}$, $R^{20'}$, $R^{21}$, $R^{21'}$, $R^{22}$, and $R^{23}$ optionally being joined by one or more bonds to form one or more optionally substituted carbocycles and/or heterocycles;

$R^{8b}$ and $R^{9b}$ are independently selected and have the same meaning as $R^8$, except that they may not be joined with any other substituent;

one of $R^4$ and $R^{4'}$ and one of $R^{16}$ and $R^{16'}$ may optionally be joined by one or more bonds to form one or more optionally substituted carbocycles and/or heterocycles;

one of $R^2$, $R^{2'}$, $R^3$, and $R^{3'}$ and one of $R^5$ and $R^{5'}$ may optionally be joined by one or more bonds to form one or more optionally substituted carbocycles and/or heterocycles; and a and b are independently selected from 0 and 1.

In a further aspect this invention relates to a compound of formula (I') or (II'):

(I')

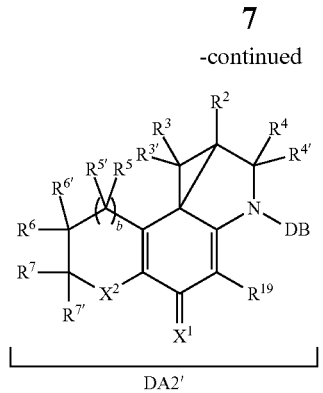

(II'')

DA2' which is formed through rearrangement of and concomitant elimination of H—$R^1$ from the corresponding compounds of formulae (I) and (II), which are seco compounds (see FIG. 1). Said cyclopropyl ring-containing analogs are believed to be active species, allegedly being formed from compounds of formulae (I) and (II) in vivo via said rearrangement.

In a more specific embodiment, this invention relates to a compound of formula (I) or (II) as described hereinabove, wherein
  a) the DB moiety does not comprise a DA1, DA2, DA1', or DA2' moiety; and
  b) ring B in DB1 is a heterocycle; and
  c) if $X^3$ in DB1 represents —$X^{3a}$ and $X^{3b}$— and ring B is aromatic, then two vicinal substituents on said ring B are joined to form an optionally substituted carbocycle or heterocycle fused to said ring B; and
  d) if $X^3$ in DB2 represents —$X^{3a}$ and $X^{3b}$— and ring B is aromatic, then two vicinal substituents on said ring B are joined to form an optionally substituted heterocycle fused to said ring B, an optionally substituted non-aromatic carbocycle fused to said ring B, or a substituted aromatic carbocycle which is fused to said ring B and to which at least one substituent is attached that contains a hydroxy group, a primary amino group, or a secondary amino group, the primary or secondary amine not being a ring atom in an aromatic ring system nor being part of an amide; and
  e) if ring A in DB2 is a 6-membered aromatic ring, then substituents on ring B are not joined to form a ring fused to ring B; and
  f) two vicinal substituents on ring A in DB8 are joined to form an optionally substituted carbocycle or heterocycle fused to said ring A to form a bicyclic moiety to which no further rings are fused; and
  g) ring A in DB9 together with any rings fused to said ring A contains at least two ring heteroatoms.

In a further embodiment, this invention relates to a compound of formula (I) or (II) as described hereinabove, wherein at least one of the substituents $R^1$, $R^5$, $R^{5'}$, $R^6$, $R^{6'}$, $R^7$, $R^{7'}$, $R^{14}$, $R^{14'}$, $R^8$, $R^{8'}$, $R^9$, $R^{9'}$, $R^{10}$, $R^{10'}$, $R^{11}$, $R^{11'}$, $R^{15}$, $R^{15'}$, $R^{15''}$, $R^{15'''}$, $R^{16}$, $R^{16'}$, $R^{20}$, $R^{20'}$, $R^{21}$, $R^{21'}$, $R^{22}$, and $R^{23}$ contains a $X^{14}(CH_2CH_2O)_{ff}CH_2CH_2X^{14}$ moiety, wherein ff is selected from 1 to 1000 and each $X^{14}$ is independently selected from

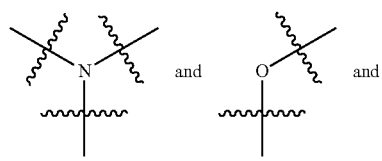

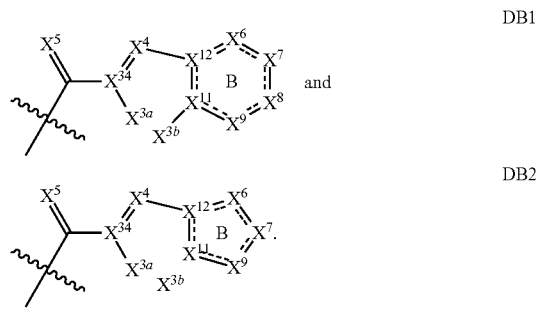

that is connected to the attachment site of said substituent either via a direct bond or via a moiety, being part of said same substituent, that does not comprise a disulfide, a hydrazone, a hydrazide, an ester, a natural amino acid, or a peptide containing at least one natural amino acid, and wherein if ring B in DB1 is an all-carbon ring, $X^3$ is O or $NR^{15}$, $X^4$ is CH, $X^{34}$ is C, there is only one $X^{14}(CH_2CH_2O)_{ff}CH_2CH_2X^{14}$ moiety present in said compound of formula (I) or (II) and said moiety is part of $R^6$, $R^7$, $R^8$, $R^{10}$, or $R^{15}$, then b=1 and ff is ≥5.

A compound of formula (I) or (II) or a conjugate thereof in which ff is larger than 1000 is encompassed by this invention.

In a further embodiment, this invention relates to a compound of formula (I) or (II) as described hereinabove, wherein at least one of the substituents $R^1$, $R^5$, $R^{5'}$, $R^6$, $R^{6'}$, $R^7$, $R^{7'}$, $R^{14}$, $R^{14'}$, $R^8$, $R^{8'}$, $R^9$, $R^{9'}$, $R^{10}$, $R^{10'}$, $R^{11}$, $R^{11'}$, $R^{15}$, $R^{15'}$, $R^{15''}$, $R^{15'''}$, $R^{16}$, $R^{16'}$, $R^{20}$, $R^{20'}$, $R^{21}$, $R^{21'}$ $R^{22}$ and $R^{23}$ contains a triazole moiety.

It is to be understood that if —$X^3$— represents —$X^{3a}$ and $X^{3b}$— in moieties DB1 and DB2 these moieties are actually represented by the following structures:

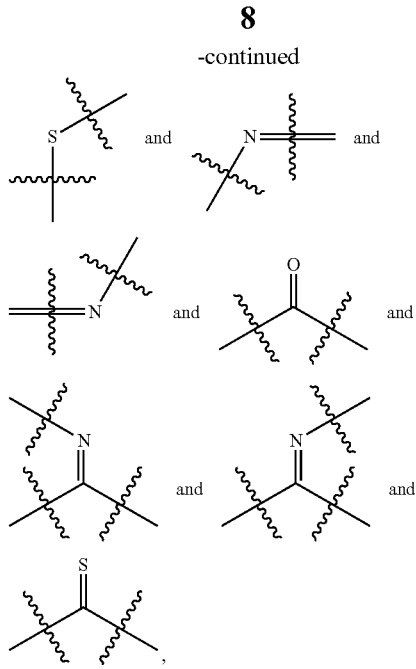

In another aspect, the present invention relates to a conjugate of a compound of formula (I), (II), (I'), or (II').

In yet another aspect, this invention relates to a compound of formula (III):

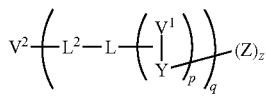
(III)

or a pharmaceutically acceptable salt, hydrate, or solvate thereof, wherein
$V^2$ is either absent or a functional moiety;
each $L^2$ is independently absent or a linking group linking $V^2$ to L;
each L is independently absent or a linking group linking $L^2$ to one or more $V^1$ and/or Y;
each $V^1$ is independently absent or a conditionally-cleavable or conditionally-transformable moiety, which can be cleaved or transformed by a chemical, photochemical, physical, biological, or enzymatic process;
each Y is independently absent or a self-eliminating spacer system which is comprised of 1 or more self-elimination spacers and is linked to $V^1$, optionally L, and one or more Z;
each p and q are numbers representing a degree of branching and are each independently a positive integer;
z is a positive integer equal to or smaller than the total number of attachment sites for Z;
each Z is independently a compound of formula (I), (II), (I'), or (II') as defined hereinabove wherein one or more of $X^1$, $R^5$, $R^{5'}$, $R^6$, $R^{6'}$, $R^7$, $R^{7'}$, $R^{14}$, $R^{14'}$, $R^8$, $R^{8'}$, $R^9$, $R^{9'}$, $R^{10}$, $R^{10'}$, $R^{11}$, $R^{11'}$, $R^{15}$, $R^{15'}$, $R^{15''}$, $R^{15'''}$, $R^{16}$, $R^{16'}$, $R^{20}$, $R^{20'}$, $R^{21}$, $R^{21'}$, $R^{22}$, and $R^{23}$ may optionally in addition be substituted by or be a substituent of formula (V):

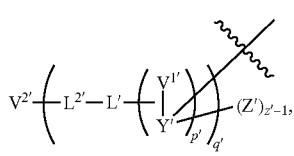
(V)

wherein each $V^{2'}$, $L^{2'}$, $L'$, $V^{1'}$, $Y'$, $Z'$, $p'$, $q'$, and $z'$ has the same meaning as defined for $V^2$, $L^2$, L, $V^1$, Y, Z, p, q, and z, respectively, and is independently selected, the one or more substituents of formula (V) being independently connected via $Y'$ to one or more of $X^1$, $R^5$, $R^{5'}$, $R^6$, $R^{6'}$, $R^7$, $R^{7'}$, $R^{14}$, $R^{14'}$, $R^8$, $R^{8'}$, $R^9$, $R^{9'}$, $R^{10}$, $R^{10'}$, $R^{11}$, $R^{11'}$, $R^{15}$, $R^{15'}$, $R^{15''}$, $R^{15'''}$, $R^{16}$, $R^{16'}$, $R^{20}$, $R^{20'}$, $R^{21}$, $R^{21'}$, $R^{22}$, $R^{23}$ and/or to one or more atoms bearing these R substituents;
each Z is independently connected to Y through either $X^1$, an atom in $R^5$, $R^{5'}$, $R^6$, $R^{6'}$, $R^7$, $R^{7'}$, $R^{14}$, $R^{14'}$, $R^8$, $R^{8'}$, $R^9$, $R^{9'}$, $R^{10}$, $R^{10'}$, $R^{11}$, $R^{11'}$, $R^{15}$, $R^{15'}$, $R^{15''}$, $R^{15'''}$, $R^{16}$, $R^{16'}$, $R^{20}$, $R^{20'}$, $R^{21}$, $R^{21'}$, $R^{22}$, $R^{23}$, or an atom bearing any of these R substituents; and
at least $V^2$ or a $V^1$ is present.

It is noted that in a compound of formula (III), $V^2$ or a $V^1$ needs to be present. However, in the one or more moieties of formula (V) that are optionally present in Z, each $V^{2'}$ and $V^{1'}$ may be independently selected to be absent or present.

In a further aspect, this invention relates to a compound of formula (III), wherein
$V^2$ is present and selected to be a targeting moiety and there is at least one group of formula (V) that contains a $V^{1'}$ moiety and either comprises a $V^{2'}$, $L^{2'}$, or $L'$ moiety that contains a $X^{14}(CH_2CH_2O)_{gg}CH_2CH_2X^{14}$ moiety, wherein gg is selected from 3 to 1000 and each $X^{14}$ is independently selected from

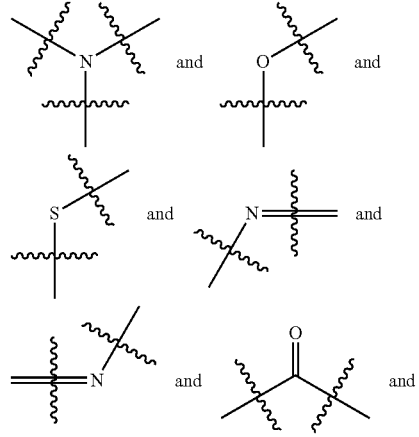

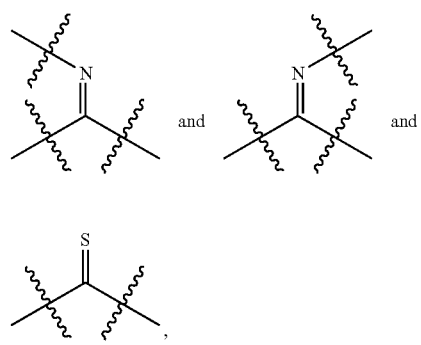

or said same group of formula (V) comprises at least 2 $X^{14}CH_2CH_2OCH_2CH_2X^{14}$ moieties, in which each $X^{14}$ is independently selected.

It is noted that the separate $X^{14}$ moieties in the $-CH_2CH_2X^{14}$ moieties that may be present in a compound of formula (III) are independently selected.

It is further noted that z does not represent a degree of polymerization; hence z does not indicate that a number of moieties Z or RM2 are connected to one another.

It is further noted that if Y or Y' is connected to an atom of Z or RM2 bearing a specific R substituent instead of to this R substituent itself, this in fact means that this R substituent is absent if this is necessary to meet valency rules.

It is further noted that if $X^{14}$ in for example $-CH_2CH_2X^{14}$ represents

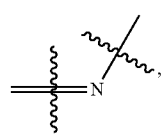 [SMILES: *N=*]

then $-CH_2CH_2X^4$ should be read as $-CH_2CHX^{14}$.

The present invention also relates to a compound of formula (IV):

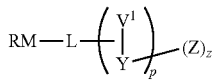

(IV)

or a pharmaceutically acceptable salt, hydrate, or solvate thereof, wherein
RM is a reactive moiety and L, $V^1$, Y, Z, p, and z are as defined hereinabove, except that L is now linking RM to one or more $V^1$ and/or Y, and $V^1$, Y, and Z may contain protecting groups, and the one or more $V^{2'}$-$L^{2'}$ moieties optionally present in Z as defined hereinabove may optionally and independently be RM' instead, which is a reactive moiety, and wherein, if there is more than 1 reactive moiety in (IV), some or all reactive moieties are the same or different. These linker-agent conjugates of formula (IV) may or may not be considered intermediates for compounds of formula (III).

In a further aspect, the present invention relates to a compound of formula (IV), wherein RM is a reactive moiety selected from carbamoyl halide, acyl halide, active ester, anhydride, α-haloacetyl, α-haloacetamide, maleimide, isocyanate, isothiocyanate, disulfide, thiol, hydrazine, hydrazide, sulfonyl chloride, aldehyde, methyl ketone, vinyl sulfone, halomethyl, and methyl sulfonate, and wherein at least one group of formula (V), being part of Z, contains a $V^{1'}$ moiety and either comprises a $V^{2'}$, $L^{2'}$, or L' moiety that contains a $X^{14}(CH_2CH_2O)_{gg}CH_2CH_2X^{14}$ moiety, wherein gg is selected from 3 to 1000 and each $X^{14}$ is independently selected from

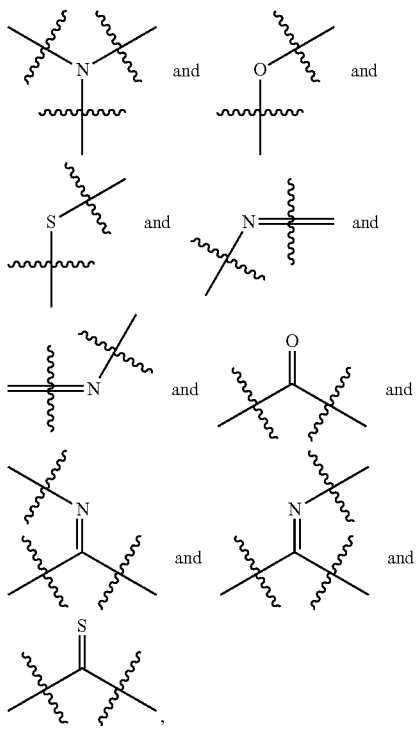

or said same group of formula (V) comprises at least 2 $X^{14}CH_2CH_2OCH_2CH_2X^{14}$ moieties, in which each $X^{14}$ is independently selected. These linker-agent conjugates of formula (IV) may or may not be considered intermediates for compounds of formula (III).

In yet a further aspect, this invention relates to novel bifunctional linkers that contain a cleavage site, a self-elimination spacer system and two reactive moieties, one of which can be reacted with a therapeutic or diagnostic moiety, e.g. a compound of formula (II or (II), and the other of which can be reacted with a functional moiety, such as a targeting moiety. These bifunctional linkers can be used to prepare conjugates of formulae (III) and (IV) of this invention or similar compounds with different therapeutic or diagnostic moieties.

More specifically, this invention relates to a compound of formula (VIII):

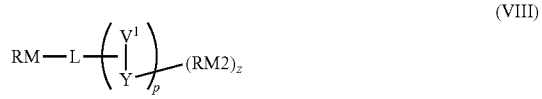

(VIII)

or a pharmaceutically acceptable salt, hydrate, or solvate thereof, wherein
L, $V^1$, Y, RM, p, and z are as defined for a compound of formula (IV), and RM2 is a reactive moiety or a leaving group. RM and each RM2 are independently selected. These bifunctional linkers of formula (VIII) may or may not be considered intermediates for compounds of formula (III) and (IV).

This invention relates to enantiomerically pure and/or diastereomerically pure compounds of formulae (I), (II), (III), (IV), and (VIII) as well as to enantiomeric and/or diastereomeric mixtures of compounds of formulae (I), (II), (III), (IV), and (VIII). This invention relates to pure compounds of formulae (I), (II), (III), (IV), and (VIII) as well as to mixtures of isomers of compounds of formulae (I), (II), (III), (IV), and (VIII).

Compounds of formulae (I) and (II) represent duocarmycin derivatives that preferably have heteroatoms or polar groups at selected positions in the DNA-binding moiety or in substituents on the DNA-binding or DNA-alkylating moiety. Compounds of formula (III), which are conjugates of compounds of formulae (I) and (II), were unexpectedly found to be more efficacious in vivo and to have improved properties, such as increased polarity and optimized drug release, compared to similar compounds from the prior art.

In one embodiment, the current invention relates to a conjugate of a compound of formula (I) or (II) according to one of the above embodiments and to derivatives thereof. Such a conjugate contains one or more promoieties. Advantageously, such a conjugate has a sufficient stability in the circulation, but is efficiently and selectively activated to release the compound of formula (I) or (II) at the target site, leading to a suitable therapeutic window. The length and nature of the linker between functional moiety and the compound of formula (I) or (II) proved to be an important contributor. In one aspect of this invention, the linker has a reduced linker length with respect to linker lengths in similar conjugates from the prior art, which leads to improved efficacy. In another aspect, the linker contains a self-elimination spacer system with improved properties, which leads for example to an optimized self-elimination rate, optimized drug release and/or increased polarity. In yet another aspect, the linker between functional moiety and the compound of formula (I) or (II) contains one or more groups designed to improve the pharmacokinetic properties of the conjugate. These groups may be present in L and/or Y and/or in any of the other moieties making up a compound of formula (III).

Premature release of the parent agent, i.e., the compound of formula (I) or (II), in the circulation may not be desirable, but a relatively fast deactivation of the released compound might reduce toxic side effects in this case. Deactivation may be tuned by choosing the appropriate DNA-alkylating and DNA-binding moiety. Deactivation may occur by several mechanisms, including enzymatic or hydrolytic cleavage of the DNA-alkylating unit from the DNA-binding unit.

Compounds of formulae (I) and (II) are suited for application in drug delivery purposes, including drug targeting and controlled release applications, using compounds of formulae (III) and (IV).

BRIEF DESCRIPTION OF DRAWINGS

FIG. 4A shows the average tumor burden for each group, FIG. 4B shows the average body weight change for each group, and FIG. 4C shows the survival percentage in each group.

DESCRIPTION OF THE INVENTION

Figure 1:
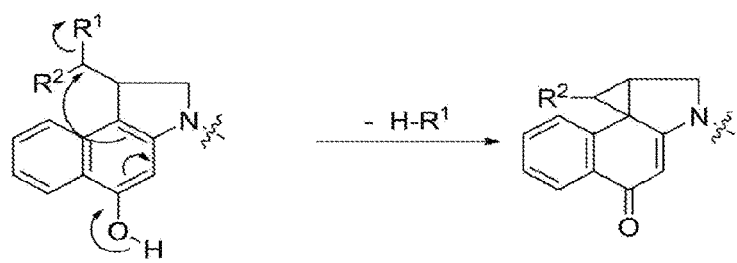
FIG. 1. Rearrangement of a seco compound to a cyclopropyl-containing compound.

The following detailed description is provided so that the invention may be more fully understood.

Definitions

Unless defined otherwise, all technical and scientific terms used herein have the same meaning as commonly understood by one of ordinary skill in the art.

The term "antibody", as used herein, refers to a full-length immunoglobulin molecule, an immunologically active portion of a full-length immunoglobulin molecule, or a derivative of a full-length immunoglobulin molecule or an active portion thereof, i.e., a molecule that contains an antigen-binding site that immunospecifically binds an antigen of a target of interest or part thereof, such targets including, but not limited to, tumor cells. A fragment or derivative of a full-length immunoglobulin molecule therefore immunospecifically binds the same antigen as said full-length immunoglobulin molecule. The immunoglobulin can be of any type (e.g., IgG, IgE, IgM, IgD, IgA, or IgY), class (e.g., IgG1, IgG2, IgG3, IgG4, IgA1, or IgA2), or subclass. The immunoglobulin, or a derivative or active portion thereof, can be derived from any species, e.g., human, rodent (e.g., mouse, rat, or hamster), donkey, sheep, rabbit, goat, guinea pig, camelid, horse, cow, or chicken, but preferably, it is of human, murine, or rabbit origin, or it is derived from more than one species. Antibodies useful in the invention include, but are not limited to, monoclonal, polyclonal, bispecific, multispecific, human, humanized, chimeric, and engineered antibodies, single chain antibodies, Fv fragments, Fd fragments, Fab fragments, F(ab') fragments, F(ab')$_2$ fragments, dAb fragments, fragments produced by a Fab expression library, anti-idiotypic antibodies, isolated CDRs, and epitope-binding fragments of any of the above that immunospecifically bind to an antigen-of-interest.

The term "leaving group" refers to a group that can be substituted by another group in a substitution reaction. Such leaving groups are well-known in the art, and examples include, but are not limited to, a halide (fluoride, chloride, bromide, and iodide), azide, a sulfonate (e.g., an optionally substituted $C_{1-6}$ alkanesulfonate, such as methanesulfonate, trifluoromethanesulfonate, and trifluoroethanesulfonate, or an optionally substituted benzenesulfonate, such as p-toluenesulfonate and nosylate), imidazole, a cyclic imide thione, succinimide-N-oxide, phtalimide-N-oxide, p-nitrophenoxide, o-nitrophenoxide, pentafluorophenoxide, tetrafluorophenoxide, 1,3,5-trichlorophenoxide, 1,3,5-trifluorophenoxide, a carboxylate, an aminocarboxylate (carbamate), and an alkoxycarboxylate (carbonate). For substitutions at saturated carbon, halides and sulfonates are preferred leaving groups. For substitutions at a carbonyl carbon a halide, succinimide-N-oxide, p-nitrophenoxide, pentafluorophenoxide, tetrafluorophenoxide, a carboxylate, or an alkoxycarboxylate (carbonate) may for example be used as a leaving group. The term "leaving group" also refers to a group that is eliminated as a consequence of an elimination reaction, e.g., an electronic cascade reaction or a spirocyclization reaction. In this instance, a halide, a sulfonate, azide, an aminocarboxylate (carbamate) or an alkoxycarboxylate (carbonate) may for example be used as a leaving group. Therefore, an agent or a derivative thereof released from a conjugate through a (multiple) self-elimination is defined as a leaving group according to this definition.

The term "active ester" refers to a functional group in which the alkoxy group of the ester moiety is a good leaving group. Examples of such alkoxy groups include, but are not limited to, succinimide-N-oxide, p-nitrophenoxide, pentafluorophenoxide, tetrafluorophenoxide, 1-hydroxybenzotriazole, and 1-hydroxy-7-azabenzotriazole, and groups with comparable leaving capability. Unsubstituted alkyl-based alkoxy groups such as methoxy, ethoxy, isopropoxy, and t-butoxy do not qualify as good leaving groups and methyl, ethyl, isopropyl, and t-butyl esters are therefore not considered to be active esters.

The term "reactive moiety" herein refers to a functional group that can react with a second functional group under relatively mild conditions and without the need of prior functionalization of the reactive moiety. The reaction between the reactive moiety and said second functional group will only require the application of some heat, pressure, a catalyst, acid, and/or base. Examples of reactive moieties include, but are not limited to, carbamoyl halide, acyl halide, active ester, anhydride, α-haloacetyl, α-haloacetamide, maleimide, isocyanate, isothiocyanate, disulfide, thiol, hydrazine, hydrazide, sulfonyl chloride, aldehyde, methyl ketone, vinyl sulfone, halomethyl, and methyl sulfonate.

The term "promoiety" refers to a moiety that is coupled to a compound of formula (I) or (II) to modify its properties and that is to be (partly) removed in vivo from said compound of formula (I) or (II).

The term "water-soluble group" refers to a functional group that is well solvated in aqueous environments and that imparts improved water solubility to the compound to which it is attached. Examples of water-soluble groups include, but are not limited to, polyalcohols, straight chain or cyclic saccharides, primary, secondary, tertiary, or quaternary amines and polyamines, sulfate groups, sulfonate groups, sulfinate groups, carboxylate groups, phosphate groups, phosphonate groups, phosphinate groups, ascorbate groups, glycols, including polyethylene glycols, and polyethers. Preferred water-soluble groups are primary, secondary, tertiary, and quaternary amines, carboxylates, phosphonates, phosphates, sulfonates, sulfates, —$(CH_2CH_2O)_{yy}$ $CH_2CH_2X^{17}R^{yy}$, —$(CH_2CH_2O)_{yy}CH_2CH_2X^{17}$—, —$X^{17}$ $(CH_2CH_2O)_{yy}CH_2CH_2$—, glycol, oligoethylene glycol, and polyethylene glycol, wherein yy is selected from 1 to 1000, $X^{17}$ is selected from O, S, and $NR^{zz}$, and $R^{zz}$ and $R^{yy}$ are independently selected from H and $C_{1-3}$ alkyl.

The term "substituted", when used as an adjective to "alkyl", "heteroalkyl", "cycloalkyl", "heterocycloalkyl", "aryl", "heteroaryl", or the like, indicates that said "alkyl", "heteroalkyl", "cycloalkyl", "heterocycloalkyl", "aryl", "heteroaryl", or similar group contains one or more substituents (introduced by substitution for hydrogen). Exemplary substituents include, but are not limited to, OH, =O, =S, =$NR^k$, =N—$OR^k$, SH, $NH_2$, $NO_2$, NO, $N_3$, $CF_3$, CN, OCN, SCN, NCO, NCS, $C(O)NH_2$, $C(O)H$, $C(O)OH$, halogen, $R^k$, $SR^k$, $S(O)R^k$, $S(O)OR^k$, $S(O)_2R^k$, $S(O)_2OR^k$, $OS(O)$ $R^k$, $OS(O)OR^k$, $OS(O)_2R^k$, $OS(O)_2OR^k$, $S(O)N(R^k)R^l$, $OS(O)N(R^k)R^l$, $S(O)_2N(R^k)R^l$, $OS(O)_2N(R^k)R^l$, $OP(O)$ $(OR^k)(OR^l)$, $P(O)(OR^k)(OR^l)$, $OR^k$, $NHR^k$, $N(R^k)R^l$, $^+N(R^k)$ $(R^l)R^m$, $Si(R^k)(R^l)(R^m)$, $C(O)R^k$, $C(O)OR^k$, $C(O)N(R^k)R^l$, $OC(O)R^k$, $OC(O)OR^k$, $OC(O)N(R^k)R^l$, $N(R^k)C(O)R^l$, $N(R^k)$ $C(O)OR^l$, $N(R^k)C(O)N(R^l)R^m$, a water-soluble group, and the thio derivatives of these substituents, and protonated, charged, and deprotonated forms of any of these substituents, wherein $R^k$, $R^l$, and $R^m$ are independently selected from H and optionally substituted —$(CH_2CH_2O)_{yy}$ $CH_2CH_2X^7R^{yy}$, $C_{1-15}$ alkyl, $C_{1-15}$ heteroalkyl, $C_{3-15}$ cycloalkyl, $C_{1-15}$ heterocycloalkyl, $C_{5-15}$ aryl, or $C_{1-15}$ heteroaryl, or a combination thereof, wherein yy is selected from 1 to 1000, $X^{17}$ is independently selected from O, S, and $NR^{zz}$, and $R^{zz}$ and $R^{yy}$ are independently selected from H and $C_{1-3}$ alkyl, two or more of $R^k$, $R^l$, and $R^m$ optionally being joined by one or more bonds to form one or more optionally substituted carbocycles and/or heterocycles. When there is more than one substituent, each substituent is independently selected. Two or more substituents may be connected to each other by replacement of one or more hydrogen atoms on each of the substituents by one or more connecting bonds, which may be single, double, or triple bonds, or, if resonance structures are possible, the bond order of said bonds may be different in two or more of these resonance structures. Two substituents may thus be joined under formation of one or more rings.

When substituents may be "joined by one or more bonds to form one or more optionally substituted carbocycles and/or heterocycles", this means that the substituents may be connected to each other through replacement of one or more hydrogen atoms on each of the substituents by one or more connecting bonds.

The term "aryl" as used herein refers to a carbocyclic aromatic substituent comprising 5 to 24 ring carbon atoms, which may be charged or uncharged and which may consist of one ring or two or more rings fused together. Examples of aryl groups include, but are not limited to, phenyl, naphthyl, and anthracenyl.

The term "heteroaryl" as used herein refers to a heterocyclic aromatic substituent comprising 1 to 24 ring carbon atoms and at least one ring heteroatom, e.g., oxygen, nitrogen, sulfur, silicon, or phosphorus, wherein nitrogen and sulfur may optionally be oxidized and nitrogen may optionally be quaternized, which may consist of one ring or two or more rings fused together. Heteroatoms may be directly connected to each other. Examples of heteroaryl groups include, but are not limited to, pyridinyl, pyrimidyl, furanyl, pyrrolyl, triazolyl, pyrazolyl, pyrazinyl, oxazolyl, isoxazolyl, thiazolyl, imidazolyl, thienyl, indolyl, benzofuranyl, benzimidazolyl, benzothiazolyl, purinyl, indazolyl, benzotriazolyl, benzisoxazolyl, quinoxalinyl, isoquinolyl, and quinolyl. In one embodiment, a heteroaryl group comprises 1 to 4 heteroatoms. It should be noted that "$C_1$ heteroaryl group" denotes that there is only one carbon present in the ring system of the heteroaromatic group (carbon atoms in optional substituents are thus not counted). An example of such a heteroaromatic group is a tetrazolyl group.

"Aryl" and "heteroaryl" groups also encompass ring systems in which one or more non-aromatic rings are fused to an aryl or heteroaryl ring or ring system.

The term "alkyl" as used herein refers to a straight chain or branched, saturated or unsaturated hydrocarbyl substituent. Examples of alkyl groups include, but are not limited to, methyl, ethyl, propyl, butyl, pentyl, hexyl, octyl, decyl, isopropyl, sec-butyl, isobutyl, tert-butyl, isopentyl, 2-methylbutyl, vinyl, allyl, 1-butenyl, 2-butenyl, isobutylenyl, 1-pentenyl, 2-pentenyl, and 1-butynyl.

The term "heteroalkyl" as used herein refers to a straight chain or branched, saturated or unsaturated hydrocarbyl substituent in which at least one carbon atom is replaced by a heteroatom, e.g., by oxygen, nitrogen, sulfur, silicon, or phosphorus, wherein nitrogen and sulfur may optionally be oxidized and nitrogen may optionally be quaternized. Heteroatoms may be directly connected to each other. Examples include, but are not limited to, methoxy, ethoxy, propoxy, isopropoxy, n-butyloxy, tert-butyloxy, methyloxymethyl, ethyloxymethyl, methyloxyethyl, ethyloxyethyl, methylaminomethyl, dimethylaminomethyl, methylaminoethyl, dimethylaminoethyl, methylthiomethyl, ethylthiomethyl, ethylthioethyl, and methylthioethyl.

The term "cycloalkyl" as used herein refers to a saturated or unsaturated non-aromatic cyclic hydrocarbyl substituent, which may consist of one ring or two or more rings fused together. Examples include, but are not limited to, cyclopropyl, cyclobutyl, cyclopentyl, cyclopentenyl, cyclopentadienyl, cyclohexyl, cyclohexenyl, 1,3-cyclohexadienyl, decalinyl, and 1,4-cyclohexadienyl.

The term "heterocycloalkyl" as used herein refers to a saturated or unsaturated non-aromatic cyclic hydrocarbyl substituent, which may consist of one ring or two or more rings fused together, wherein at least one carbon in one of the rings is replaced by a heteroatom, e.g., by oxygen, nitrogen, sulfur, silicon, or phosphorus, wherein nitrogen and sulfur may optionally be oxidized and nitrogen may optionally be quaternized. Heteroatoms may be directly connected to each other. Examples include, but are not limited to, tetrahydrofuranyl, pyrrolidinyl, piperidinyl, 1,4-dioxanyl, decahydroquinolinyl, piperazinyl, oxazolidinyl, and morpholinyl. It should be noted that "$C_1$ heterocycloalkyl group" denotes that there is only one carbon present in the ring system of the heterocycloalkane (carbon atoms in optional substituents are thus not counted). An example of such a group is a dioxiranyl group.

The number of carbon atoms that an "alkyl", "heteroalkyl", "cycloalkyl", "heterocycloalkyl", "aryl", "heteroaryl", and the like, may contain is indicated by a designation preceding said terms, i.e., $C_{1-10}$ alkyl means that said alkyl may contain from one to ten carbons (carbon atoms in optional substituents attached to this alkyl are not counted).

The term "carbocycle" herein refers to a saturated or unsaturated cycloalkane or arene moiety, wherein the terms "cycloalkane" and "arene" are defined as parent moieties of the "cycloalkyl" and "aryl" substituents, respectively, as defined hereinabove.

The term "heterocycle" herein refers to a saturated or unsaturated heterocycloalkane or heteroarene moiety, wherein the terms "heterocycloalkane" and "heteroarene" are defined as parent moieties of the "heterocycloalkyl" and "heteroaryl" substituents, respectively, as defined hereinabove.

The extension "-ylene" as opposed to "-yl" in for example "alkylene" as opposed to "alkyl" indicates that said for example "alkylene" is a divalent (or multivalent) moiety connected to one or more other moieties via at least one or more double bonds or two or more single bonds, as opposed to being a monovalent group connected to one moiety via one single bond in said for example "alkyl". The term "alkylene" therefore refers to a straight chain or branched, saturated or unsaturated hydrocarbylene moiety; the term "heteroalkylene" as used herein refers to a straight chain or branched, saturated or unsaturated hydrocarbylene moiety in which at least one carbon is replaced by a heteroatom; the term "arylene" as used herein refers to a carbocyclic aromatic moiety, which may consist of one ring or two or more rings fused together; the term "heteroarylene" as used herein refers to a carbocyclic aromatic moiety, which may consist of one ring or two or more rings fused together, wherein at least one carbon in one of the rings is replaced by a heteroatom; the term "cycloalkylene" as used herein refers to a saturated or unsaturated non-aromatic cyclic hydrocarbylene moiety, which may consist of one ring or two or more rings fused together; the term "heterocycloalkylene" as used herein refers to a saturated or unsaturated non-aromatic cyclic hydrocarbylene moiety, which may consist of one ring or two or more rings fused together, wherein at least one carbon in one of the rings is replaced by a heteroatom. Exemplary divalent moieties include those examples given for the monovalent groups hereinabove in which one hydrogen atom is removed.

The prefix "poly" in "polyalkylene", "polyheteroalkylene", "polyarylene", "polyheteroarylene", polycycloalkylene", "polyheterocycloalkylene", and the like, indicates that two or more of such "-ylene" moieties, e.g., alkylene moieties, are joined together to form a branched or unbranched multivalent moiety containing two or more attachment sites for adjacent moieties. Similarly, the prefix "oligo" in for example oligoethylene glycol indicates that two or more ethylene glycol moieties are joined together to form a branched or unbranched multivalent moiety. The difference between the prefixes "oligo" and "poly" is that the prefix "oligo" is most frequently used to denote a relatively small number of repeating units, while the prefix "poly" usually refers to a relatively large number of repeating units.

Certain compounds of the invention possess chiral centers and/or double bonds, and/or may have tautomers or atropisomers; the tautomeric, enantiomeric, diastereomeric, atropisomeric, and geometric mixtures of two or more isomers, in any composition, as well as the individual isomers (including tautomers and atropisomers) are encompassed within the scope of the present invention. Whenever the term "isomer" is used, it refers to an atropisomeric, tautomeric, enantiomeric, diastereomeric, and/or geometric isomer or to a mixture of two or more of these isomers, unless the context dictates otherwise.

The term "peptidomimetic" refers to a group or moiety that has a structure that is different from the general chemical structure of an amino acid or peptide, but functions in a manner similar to a naturally occurring amino acid or peptide. Therefore, a peptidomimetic is an amino acid mimic or peptide mimic.

The term "unnatural amino acid" is intended to represent the D stereoisomer of a naturally occurring amino acid.

The term "bond" herein refers to a covalent connection between two atoms and may refer to a single bond, a double bond, or a triple bond, or, if resonance structures are possible, the bond order of said bond may be different in two or more of these resonance structures. For example, if the bond is part of an aromatic ring, the bond may be a single bond in one resonance structure and a double bond in another resonance structure. If it is stated that a "double bond" or "triple bond" is present between two atoms, this double, or triple bond may be localized, but it may also be that this double or triple bond is delocalized, which means that only in one or some resonance structures a double or triple bond is indeed present between the two atoms, whereas the bond order may be different in one or more other resonance structures. At the same time, bonds marked as single bond in one resonance structure, may be double bonds in another resonance structure.

Compounds of the invention may also contain unnatural proportions of atomic isotopes at one or more atoms that constitute such compounds. All isotopic variations of compounds of this invention, whether radioactive or not, are intended to be encompassed within the scope of this invention.

The phrase "pharmaceutically active salt" as used herein refers to a pharmaceutically acceptable organic or inorganic salt of a compound of the invention. For compounds containing one or more basic groups, e.g., an amine group, acid addition salts can be formed. For compounds containing one or more acidic groups, e.g., a carboxylic acid group, base addition salts can be formed. For compounds containing both acidic and basic groups, zwitterions may in addition be obtained as salts. When the compound of the invention comprises more than one charged atom or group, there may be multiple (distinct) counterions.

The phrase "pharmaceutically acceptable solvate" refers to an association of one or more solvent molecules with a compound of the invention. Examples of solvents that form pharmaceutically acceptable solvates include, but are not limited to, water, isopropyl alcohol, ethanol, methanol, DMSO, ethyl acetate, and acetic acid. When referring to water as a solvate, the term "hydrate" can be used.

The term "conjugate" hereinbelow refers to a compound of formula (III) or to a conjugate of a compound of formula (I) or (II) or a derivative thereof, unless the context dictates otherwise. The term "linker-agent conjugate" hereinbelow refers to a compound of formula (IV), unless the context dictates otherwise. The term "agent" hereinbelow refers to a compound of formula (I), (II), (I'), or (II'), unless the context dictates otherwise.

The term "bifunctional linker" hereinbelow refers to a compound of formula (VIII), unless the context dictates otherwise. The term "linker" generally refers to the moiety linking $V^2$ to Z in a compound of formula (III) or the promoiety connected to Z in a compound of formula (IV).

The term "core" or "core structure" of a moiety, for example the DNA-binding or DNA-alkylating moiety, refers to the structure that remains when all R substituents are removed from the formula representing said moiety.

The term "targeting moiety" refers to any moiety that specifically binds or reactively associates or complexes with a moiety specifically or in relative excess present at or near the target site, on, in, or near the target cell, or in (the proximity of) the target tissue or organ, e.g., a receptor, a receptor complex, substrate, antigenic determinant, or other receptive moiety, or that can target the conjugate to the target site via other mechanisms by virtue of its nature, e.g., through the EPR effect. Examples of a targeting moiety include, but are not limited to, an aptamer, an antibody or antibody fragment or derivative, a polymer, a dendrimer, a lectin, a biologic response modifier, an enzyme, a vitamin, a growth factor, a steroid, a sugar residue, an oligosaccharide residue, a carrier protein, and a hormone, or any combination thereof.

The phrase "moiety that improves the pharmacological properties of the compound" refers to a moiety that changes the pharmacological properties (e.g., pharmacodynamic, pharmacokinetic, physicochemical, and biopharmaceutic properties) of a compound of this invention in such a way that a better therapeutic effect can be obtained. The moiety can for example increase the water solubility, increase the circulation time, increase the therapeutic index, or reduce immunogenicity.

The term "linking group" refers to a structural element of a compound that links one structural element of said compound to one or more other structural elements of said same compound. The phrase "a number representing degree of branching" is used to denote that the subscript number next to a closing bracket represents how many units of the moiety within the brackets are each directly attached to the moiety immediately to the left of the corresponding opening bracket. For example, A-(B)$_b$ with b being a number representing a degree of branching means that b units B are all directly attached to A. This means that when b is 2, the formula reduces to B-A-B.

The phrase "a number representing degree of polymerization" is used to denote that the subscript number next to a closing bracket represents how many units of the moiety within the brackets are connected to each other. For example, A-(B)$_b$ with b being a number representing a degree of polymerization means that when b is 2, the formula reduces to A-B-B.

The term "single-release spacer" refers to a self-elimination spacer that can release one moiety upon self-immolation.

The term "multiple-release spacer" refers to a self-elimination spacer that can release two or more moieties upon (repetitive) self-immolation.

The term "electronic cascade spacer" refers to a self-elimination spacer, either branched or unbranched, which may self-eliminate through one or more 1,2+2n electronic cascade eliminations (n≥1).

The term "ω-amino aminocarbonyl cyclization spacer" refers to a self-elimination spacer that may eliminate through a cyclization process under formation of a cyclic ureum derivative.

The term "spacer system" refers to a single self-eliminating spacer moiety or to two or more of the same or different self-eliminating spacer moieties coupled together. A spacer system may be branched or unbranched and contain one or more attachment sites for Z as well as V$^1$ and optionally L.

In this document and in its claims, the verbs "to comprise", "to have", "to contain" and their conjugations are used in their non-limiting sense to mean that items that are "comprised", "had", or "contained" are included, but items non-specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one".

This specification includes many embodiments. It is noted that embodiments that are not specifically mentioned and that result from combination of two or more of said mentioned embodiments are also encompassed by this invention.

In the generic structures throughout this description and in the claims letters are used to define structural elements. Some of these letters can be mistaken to represent an atom, such as C, N, O, P, K, B, F, S, U, V, W, I, and Y. To avoid confusion whenever these letters do not represent an atom they are given in bold typeface.

When there are one or more adjectives and/or adjective phrases to a noun that is a) the first in a list of nouns or b) anywhere in the middle of a list of nouns and said noun and adjectives together are preceded by the word "and" or "or", the adjectives do not only bear on said noun, but on all following nouns separately, unless the context dictates otherwise. This for example means that the phrase "optionally substituted $C_{1-4}$ alkyl, $C_{1-4}$ heteroalkyl, $C_{3-7}$ cycloalkyl, or $C_{1-7}$ heterocycloalkyl" should be read as "optionally substituted $C_{1-4}$ alkyl, optionally substituted $C_{1-4}$ heteroalkyl, optionally substituted $C_{3-7}$ cycloalkyl, or optionally substituted $C_{1-7}$ heterocycloalkyl" and that the phrase "$C_{1-4}$ alkyl, $C_{1-4}$ heteroalkyl, and optionally substituted $C_{3-7}$ cycloalkyl, $C_{5-8}$ aryl, or $C_{1-7}$ heterocycloalkyl" should be read as "$C_{1-4}$ alkyl, $C_{1-4}$ heteroalkyl, and optionally substituted $C_{3-7}$ cycloalkyl, optionally substituted $C_{5-8}$ aryl, or optionally substituted $C_{1-7}$ heterocycloalkyl".

Throughout this description and in the claims molecular structures or parts thereof are drawn. As usual in such drawings bonds between atoms are represented by lines, in some cases, to indicate stereochemistry, by wavy, bold, or broken or wedged lines. A bond represented by a wavy line indicates unspecified stereochemistry at the chiral center to which it is connected; a structure or substructure with one or more of such wavy bonds in fact represents a set of (sub) structures in which each chiral center can either have the R or S configuration. Usually a line ending in space (a "loose" end), i.e., at one end not having another line or specific atom connected to it, represents a CH$_3$ group. This is correct for the drawings representing the compounds of this invention. For those structures representing a structural element of the compounds of this invention a line ending in space may indicate the position of attachment of another structural element of the compound. This has been indicated with a wavy line perpendicular to and crossing the "loose" line.

Furthermore, the structures or parts thereof have been drawn, under the assumption that the structures are read from left to right, meaning that for example in the drawings of compounds of formula (III) V$^2$ (if present) is located on the left side and Z is located on the right side of such structures or parts thereof, unless the context implies otherwise.

The following abbreviations are used herein and have the indicated definitions: Ac: acetyl; Bn: benzyl; Boc: tert-butyloxycarbonyl; CBI: 1,2,9,9α-tetrahydrocyclopropa[c]benz[e]indol-4-one; Cbz: carbobenzyloxy; Cit: citrulline; DCC: N,N'-dicyclohexylcarbodiimide; DCE: 1,2-dichloroethane; DCM: dichloromethane; DMAP: 4-dimethylaminopyridine; DMF: N,N-dimethylformamide; DMSO: dimethylsulfoxide; DiPEA: N,N-diisopropylethylamine; EEDQ: 2-ethoxy-1-ethoxycarbonyl-1,2-dihydroquinoline; ESI: electrospray ionization; Fmoc: fluorenylmethyloxycarbonyl; HOBt: 1-hydroxybenzotriazole; HOSu: hydroxysuccinimide; HSA: human serum albumin; LC/MS: liquid chromatography-mass spectrometry; MOMCl: methyl chloromethyl ether; PABA: p-aminobenzyl alcohol; PNPCl: p-nitrophenyl chloroformate; RT: room temperature; SEC: size-exclusion chromatography; TCEP: tris(2-carboxyethyl) phosphine; TFA: trifluoroacetic acid; THF: tetrahydrofuran; Val: valine.

Agents, Linker-Agent Conjugates, Conjugates, and Bifunctional Linkers

This invention relates to novel analogs of the DNA-alkylating agent CC-1065. The agents of the present invention are deemed to be used to treat an illness that is characterized by undesired (cell) proliferation. For example, an agent of this invention can be used to treat a tumor, cancer, an autoimmune disease, or an infectious disease.

The conjugates of the present invention are in one aspect deemed to be applicable to target agents of formulae (I) and (II) to a specific target site where the conjugate can be converted into one or more agents or be induced to be converted into one or more of said agents. This invention can furthermore find application in (non-specific) controlled release of one or more of said agents from a conjugate, with the aim of for example enhancing physicochemical, biopharmaceutic, pharmacodynamic, and/or pharmacokinetic properties.

Compounds of formulae (I) and (II) represent duocarmycin derivatives that preferably have heteroatoms or polar groups at selected positions in the DNA-binding moiety or in substituents on the DNA-binding or DNA-alkylating moiety. Compounds of formula (III), which are conjugates of compounds of formulae (I) and (II), were unexpectedly found to be more efficacious in vivo and to have improved properties, such as increased polarity and optimized drug release, compared to similar compounds from the prior art.

In one embodiment, the current invention relates to a conjugate of a compound of formula (I) or (II) according to one of the above embodiments and to derivatives thereof. Such a conjugate contains one or more promoieties. In a more specific embodiment, such a conjugate has a sufficient stability in the circulation, but is efficiently and selectively activated to release the compound of formula (I) or (II) at the target site, leading to a suitable therapeutic window. The length and nature of the linker between functional moiety and the compound of formula (I) or (II) proved to be an important contributor. In one aspect of this invention, the linker has a reduced linker length with respect to linker lengths in similar conjugates from the prior art, which leads to improved efficacy. In another aspect, the linker contains a self-elimination spacer system with improved properties, which leads for example to an optimized self-elimination rate, optimized drug release and/or increased polarity. In yet another aspect, the linker between functional moiety and the compound of formula (I) or (II) contains one or more groups designed to improve the pharmacokinetic properties of the conjugate. These groups may be present in L and/or Y and/or in any of the other moieties making up a compound of formula (III). Pharmacokinetic properties affected may for example include water solubility, multi-drug resistance, plasma stability, proteolytic lability, absorption, distribution, metabolism, excretion, and internalization. Some of these properties may not only affect in vivo behavior, but also in vitro behavior and behavior during the preparation of a compound of formula (III). For example, increased water solubility of a compound of formula (IV) may favorably affect conjugation of such a compound to a functional moiety in aqueous medium.

Premature release of the parent agent, i.e., the compound of formula (I) or (II), in the circulation may not be desirable, but a relatively fast deactivation of the released compound might reduce toxic side effects in this case. Deactivation may be tuned by choosing the appropriate DNA-alkylating and DNA-binding moiety. Deactivation may occur by several mechanisms, including enzymatic or hydrolytic cleavage of the DNA-alkylating unit from the DNA-binding unit.

Compounds of formulae (I) and (II) are suited for application in drug delivery purposes, including drug targeting and controlled release applications, using compounds of formulae (III) and (IV).

In a further aspect, this invention relates to novel bifunctional linkers that contain a cleavage site, a self-elimination spacer system and two reactive moieties, one of which can be reacted with a therapeutic or diagnostic moiety and the other of which can be reacted with a functional moiety, such as a targeting moiety. These bifunctional linkers contain the novel linker elements of this invention and can be used to prepare conjugates of formulae (III) and (IV) of this invention or similar compounds with different therapeutic or diagnostic moieties.

Agents

In one aspect, the present invention provides a compound of formula (I) or (II):

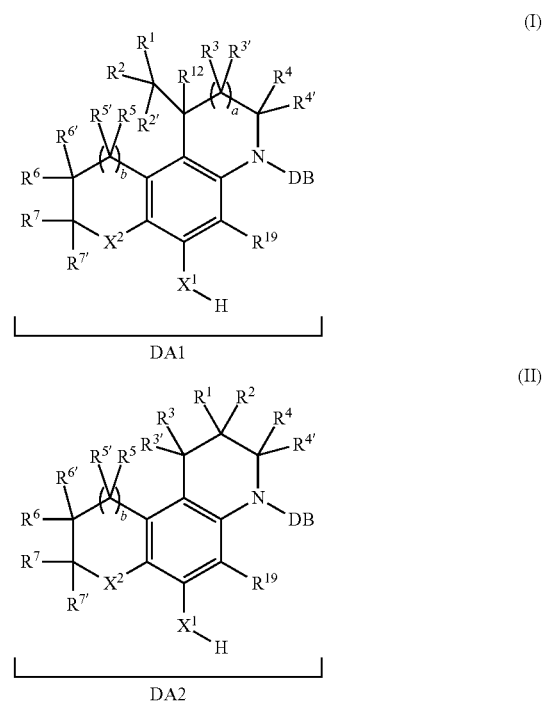

or a pharmaceutically acceptable salt, hydrate, or solvate thereof, wherein

DB is a DNA-binding moiety and is selected from the group consisting of

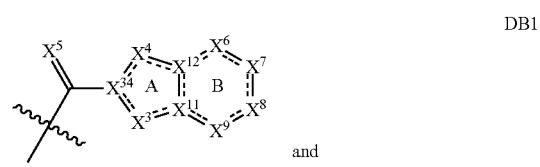

and

-continued

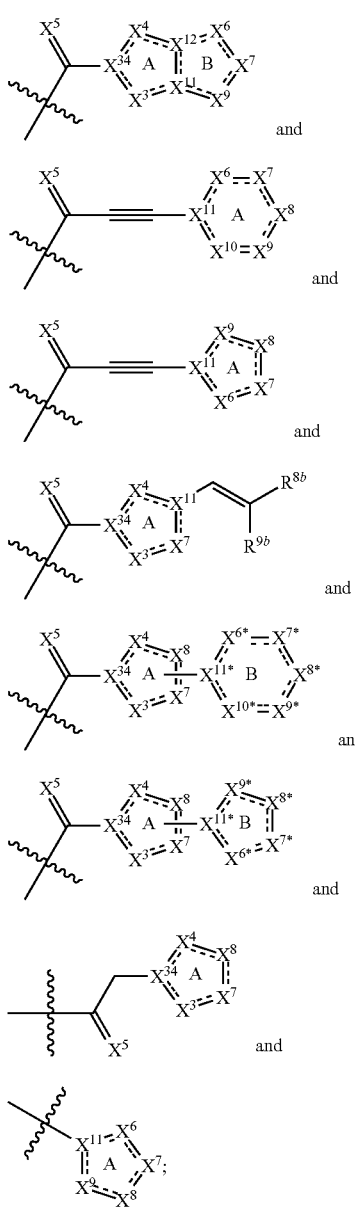

$R^1$ is a leaving group;
$R^2$, $R^{2'}$, $R^3$, $R^{3'}$, $R^4$, $R^{4'}$, $R^{12}$, and $R^{19}$ are independently selected from H, OH, SH, $NH_2$, $N_3$, $NO_2$, NO, $CF_3$, CN, $C(O)NH_2$, C(O)H, C(O)OH, halogen, $R^a$, $SR^a$, $S(O)R^a$, $S(O)_2R^a$, $S(O)OR^a$, $S(O)_2OR^a$, $OS(O)R^a$, $OS(O)_2R^a$, $OS(O)OR^a$, $OS(O)_2OR^a$, $OR^a$, $NHR^a$, $N(R^a)R^b$, $^+N(R^a)(R^b)R^c$, $P(O)(OR^a)(OR^b)$, $OP(O)(OR^a)(OR^b)$, $SiR^aR^bR^c$, $C(O)R^a$, $C(O)OR^a$, $C(O)N(R^a)R^b$, $OC(O)R^a$, $OC(O)OR^a$, $OC(O)N(R^a)R^b$, $N(R^a)C(O)R^b$, $N(R^a)C(O)OR^b$, and $N(R^a)C(O)N(R^b)R^c$, wherein
 $R^a$, $R^b$, and $R^c$ are independently selected from H and optionally substituted $C_{1-3}$ alkyl or $C_{1-3}$ heteroalkyl, or $R^3+R^{3'}$ and/or $R^4+R^{4'}$ are independently selected from =O, =S, =$NOR^{18}$, =$C(R^{18})R^{18'}$, and =$NR^{18}$, $R^{18}$ and $R^{18'}$ being independently selected from H and optionally substituted $C_{1-3}$ alkyl, two or more of $R^2$, $R^{2'}$, $R^3$, $R^{3'}$, $R^4$, $R^{4'}$, and $R^{12}$ optionally being joined by one or more bonds to form one or more optionally substituted carbocycles and/or heterocycles;

$X^2$ is selected from O, $C(R^{14})(R^{14'})$, and $NR^{14'}$, wherein $R^{14}$ and $R^{14'}$ have the same meaning as defined for $R^7$ and are independently selected, or $R^{14'}$ and $R^{7'}$ are absent resulting in a double bond between the atoms designated to bear $R^{7'}$ and $R^{14'}$;
$R^5$, $R^{5'}$, $R^6$, $R^{6'}$, $R^7$, and $R^{7'}$ are independently selected from H, OH, SH, $NH_2$, $N_3$, $NO_2$, NO, $CF_3$, CN, $C(O)NH_2$, C(O)H, C(O)OH, halogen, $R^e$, $SR^e$, $S(O)R^e$, $S(O)_2R^e$, $S(O)OR^e$, $S(O)_2OR^e$, $OS(O)R^e$, $OS(O)_2R^e$, $OS(O)OR^e$, $OS(O)_2OR^e$, $OR^e$, $NHR^e$, $N(R^e)R^f$, $^+N(R^e)(R^f)R^g$, $P(O)(OR^e)(OR^f)$, $OP(O)(OR^e)(OR^f)$, $SiR^eR^fR^g$, $C(O)R^e$, $C(O)OR^e$, $C(O)N(R^e)R^f$, $OC(O)R^e$, $OC(O)OR^e$, $OC(O)N(R^e)R^f$, $N(R^e)C(O)R^f$, $N(R^e)C(O)OR^f$, $N(R^e)C(O)N(R^f)R^g$, and a water-soluble group, wherein
 $R^e$, $R^f$, and $R^g$ are independently selected from H and optionally substituted $(CH_2CH_2O)_{ee}CH_2CH_2X^{13}R^{e1}$, $C_{1-15}$ alkyl, $C_{1-15}$ heteroalkyl, $C_{3-15}$ cycloalkyl, $C_{1-15}$ heterocycloalkyl, $C_{5-15}$ aryl, or $C_{1-15}$ heteroaryl, wherein ee is selected from 1 to 1000, $X^{13}$ is selected from O, S, and $NR^{f1}$, and $R^{f1}$ and $R^{e1}$ are independently selected from H and $C_{1-3}$ alkyl, one or more of the optional substituents in $R^e$, $R^f$, and/or $R^g$ optionally being a water-soluble group, two or more of $R^e$, $R^f$, and $R^g$ optionally being joined by one or more bonds to form one or more optionally substituted carbocycles and/or heterocycles,
or $R^5+R^{5'}$ and/or $R^6+R^{6'}$ and/or $R^7+R^{7'}$ are independently selected from =O, =S, =$NOR^{e3}$, =$C(R^{e3})R^{e4}$, and =$NR^{e3}$, $R^{e3}$ and $R^{e4}$ being independently selected from H and optionally substituted $C_{1-3}$ alkyl, or $R^{5'}+R^{6'}$ and/or $R^{6'}+R^{7'}$ and/or $R^{7'}+R^{14'}$ are absent, resulting in a double bond between the atoms designated to bear $R^{5'}$ and $R^{6'}$, and/or $R^{6'}$ and $R^{7'}$, and/or $R^{7'}$ and $R^{14'}$, respectively, two or more of $R^5$, $R^{5'}$, $R^6$, $R^{6'}$, $R^7$, $R^{7'}$, $R^{14}$, and $R^{14'}$ optionally being joined by one or more bonds to form one or more optionally substituted carbocycles and/or heterocycles;
$X^1$ is selected from O, S, and $NR^{13}$, wherein $R^{13}$ is selected from H and optionally substituted $C_{1-8}$ alkyl or $C_{1-8}$ heteroalkyl and not joined with any other substituent;
$X^3$ is selected from O, S, $C(R^{15})R^{15'}$, —$C(R^{15})(R^{15'})$—$C(R^{15})(R^{15'})$—, —$N(R^{15})$—$N(R^{15'})$—, —$C(R^{15})(R^{15'})$—$N(R^{15''})$—, —$N(R^{15''})$—$C(R^{15})(R^{15'})$—$C(R^{15})(R^{15'})$—O—, —O—$C(R^{15})(R^{15'})$—, —$C(R^{15})(R^{15'})$—S—, —S—$C(R^{15})(R^{15'})$—, —$C(R^{15})$=$C(R^{15'})$—, =$C(R^{15})$—$C(R^{15'})$=, —N=$C(R^{15'})$—, =N—$C(R^{15})$=, —$C(R^{15})$=N—, =$C(R^{15})$—N=, —N=N—, =N—N=, $CR^{15}$, N, and $NR^{15}$, or in DB1 and DB2 —$X^3$— represents —$X^{3a}$ and $X^{3b}$—, wherein $X^{3a}$ is connected to $X^{34}$, a double bond is present between $X^{34}$ and $X^4$, and $X^{3b}$ is connected to $X^{11}$, wherein $X^{3a}$ is independently selected from H and optionally substituted $(CH_2CH_2O)_{ee}CH_2CH_2X^{13}R^{e1}$, $C_{1-8}$ alkyl, or $C_{1-8}$ heteroalkyl and not joined with any other substituent;
$X^4$ is selected from O, S, $C(R^{16})R^{16'}$, $NR^{16}$, N, and $CR^{16}$;
$X^5$ is selected from O, S, $C(R^{17})R^{17'}$, $NOR^{17}$, and $NR^{17}$, wherein $R^{17}$ and $R^{17'}$ are independently selected from H and optionally substituted $C_{1-8}$ alkyl or $C_{1-8}$ heteroalkyl and not joined with any other substituent;
$X^6$ is selected from $CR^{11}$, $CR^{11}(R^{11'})$, N, $NR^{11}$, O, and S;
$X^7$ is selected from $CR^8$, $CR^8(R^{8'})$, N, $NR^8$, O, and S;
$X^8$ is selected from $CR^9$, $CR^9(R^{9'})$, N, $NR^9$, O, and S;
$X^9$ is selected from $CR^{10}$, $CR^{10}(R^{10'})$, N, $NR^{10}$, O, and S;
$X^{10}$ is selected from $CR^{20}$, $CR^{20}(R^{20'})$, N, $NR^{20}$, O, and S;
$X^{11}$ is selected from C, $CR^{21}$, and N, or $X^{11}$—$X^{3b}$ is selected from $CR^{21}$, $CR^{21}(R^{21'})$, N, $NR^{21}$, O, and S;
$X^{12}$ is selected from C, $CR^{22}$, and N;

$X^{6*}$, $X^{7*}$, $X^{8*}$, $X^{9*}$, $X^{10*}$, and $X^{11*}$ have the same meaning as defined for $X^6$, $X^7$, $X^8$, $X^9$, $X^{10}$, and $X^{11}$, respectively, and are independently selected;

$X^{34}$ is selected from C, $CR^{23}$, and N;

the ring B atom of $X^{11*}$ in DB6 and DB7 is connected to a ring atom of ring A such that ring A and ring B in DB6 and DB7 are directly connected via a single bond;

⸺ means that the indicated bond may be a single bond or a non-cumulated, optionally delocalized, double bond;

$R^8$, $R^{8'}$, $R^9$, $R^{9'}$, $R^{10}$, $R^{10'}$, $R^{11}$, $R^{11'}$, $R^{15}$, $R^{15'}$, $R^{15''}$, $R^{15'''}$, $R^{16}$, $R^{16'}$, $R^{20}$, $R^{20'}$, $R^{21}$, $R^{21'}$, $R^{22}$, and $R^{23}$ each independently selected from H, OH, SH, $NH_2$, $N_3$, $NO_2$, NO, $CF_3$, CN, $C(O)NH_2$, C(O)H, C(O)OH, halogen, $R^h$, $SR^h$, $S(O)R^h$, $S(O)_2R^h$, $S(O)OR^h$, $S(O)_2OR^h$, $OS(O)R^h$, $OS(O)_2R^h$, $OS(O)OR^h$, $OS(O)_2OR^h$, $OR^h$, $NHR^h$, $N(R^h)R^i$, $^+N(R^h)(R^i)R^j$, $P(O)(OR^h)(OR^i)$, $OP(O)(OR^h)(OR^i)$, $SiR^hR^iR^j$, $C(O)R^h$, $C(O)OR^h$, $C(O)N(R^h)R^i$, $OC(O)R^h$, $OC(O)OR^h$, $OC(O)N(R^h)R^i$, $N(R^h)C(O)R^i$, $N(R^h)C(O)OR^i$, $N(R^h)C(O)N(R^i)R^j$, and a water-soluble group, wherein $R^h$, $R^i$, and $R^j$ are independently selected from H and optionally substituted $(CH_2CH_2O)_{ee}CH_2CH_2X^{13}R^{e1}$, $C_{1-15}$ alkyl, $C_{1-15}$ heteroalkyl, $C_{3-15}$ cycloalkyl, $C_{1-15}$ heterocycloalkyl, $C_{5-15}$ aryl, or $C_{1-15}$ heteroaryl, one or more of the optional substituents in $R^h$, $R^i$, and/or $R^j$ optionally being a water-soluble group, two or more of $R^h$, $R^i$, and $R^j$ optionally being joined by one or more bonds to form one or more optionally substituted carbocycles and/or heterocycles, or $R^8+R^{8'}$ and/or $R^9+R^{9'}$ and/or $R^{10}+R^{10'}$ and/or $R^{11}+R^{11'}$ and/or $R^{15}+R^{15'}$ and/or $R^{15''}+R^{15'''}$ and/or $R^{16}+R^{16'}$ and/or $R^{20}+R^{20'}$ and/or $R^{21}+R^{21'}$ are independently selected from =O, =S, $=NOR^{h1}$, $=C(R^{h1})R^{h2}$, and $=NR^{h1}$, $R^{h1}$ and $R^{h2}$ being independently selected from H and optionally substituted $C_{1-3}$ alkyl, two or more of $R^8$, $R^{8'}$, $R^9$, $R^{9'}$, $R^{10}$, $R^{10'}$, $R^{11}$, $R^{11'}$, $R^{15}$, $R^{15'}$, $R^{16}$, $R^{16'}$, $R^{20}$, $R^{20'}$, $R^{21}$, $R^{21'}$, $R^{22}$, and $R^{23}$ optionally being joined by one or more bonds to form one or more optionally substituted carbocycles and/or heterocycles;

$R^{8b}$ and $R^{9b}$ are independently selected and have the same meaning as $R^8$, except that they may not be joined with any other substituent;

one of $R^4$ and $R^{4'}$ and one of $R^{16}$ and $R^{16'}$ may optionally be joined by one or more bonds to form one or more optionally substituted carbocycles and/or heterocycles;

one of $R^2$, $R^{2'}$, $R^3$, and $R^{3'}$ and one of $R^5$ and $R^{5'}$ may optionally be joined by one or more bonds to form one or more optionally substituted carbocycles and/or heterocycles; and a and b are independently selected from 0 and 1.

In a further aspect, this invention relates to a compound of formula (I') or (II'):

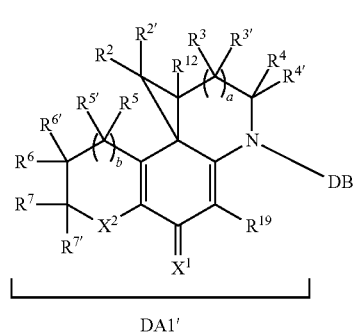

DA1'

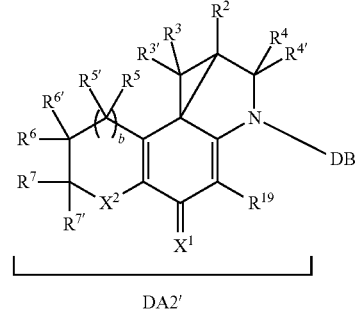

DA2' or a pharmaceutically acceptable salt, hydrate, or solvate thereof, wherein all substituents have the same meaning as described for compounds of formulae (I) and (II). Compounds of formulae (I) and (II) are alleged to be converted to (I') and (II'), respectively, in vivo with concomitant elimination of H—$R^1$.

Therefore, this invention relates to a compound of formula (I') or (II'), said compound comprising a cyclopropyl group, which can be formed through rearrangement of and concomitant elimination of H—$R^1$ from a compound of formula (I) or (II). All embodiments for a compound of formula (I) or (II) or a moiety thereof also hold for a compound of formula (I') or (II') or a moiety thereof, unless the context dictates otherwise.

In a more specific embodiment, this invention relates to a compound of formula (I) or (II) as described hereinabove, wherein a) the DB moiety does not comprise a DA1, DA2, DA1', or DA2' moiety; and
b) ring B in DB1 is a heterocycle; and
c) if $X^3$ in DB1 represents —$X^{3a}$ and $X^{3b}$— and ring B is aromatic, then two vicinal substituents on said ring B are joined to form an optionally substituted carbocycle or heterocycle fused to said ring B; and
d) if $X^3$ in DB2 represents —$X^{3a}$ and $X^{3b}$— and ring B is aromatic, then two vicinal substituents on said ring B are joined to form an optionally substituted heterocycle fused to said ring B, an optionally substituted non-aromatic carbocycle fused to said ring B, or a substituted aromatic carbocycle which is fused to said ring B and to which at least one substituent is attached that contains a hydroxy group, a primary amino group, or a secondary amino group, the primary or secondary amine not being a ring atom in an aromatic ring system nor being part of an amide; and
e) if ring A in DB2 is a 6-membered aromatic ring, then substituents on ring B are not joined to form a ring fused to ring B; and
f) two vicinal substituents on ring A in DB8 are joined to form an optionally substituted carbocycle or heterocycle fused to said ring A to form a bicyclic moiety to which no further rings are fused; and
g) ring A in DB9 together with any rings fused to said ring A contains at least two ring heteroatoms.

In a further more specific embodiment, this invention relates to a compound of formula (I) or (II) as described hereinabove, wherein at least one of the substituents $R^1$, $R^5$, $R^{5'}$, $R^6$, $R^{6'}$, $R^7$, $R^{7'}$, $R^{14}$, $R^{14'}$, $R^8$, $R^{8'}$, $R^9$, $R^{9'}$, $R^{10}$, $R^{10'}$, $R^{11}$, $R^{11'}$, $R^{15}$, $R^{15'}$, $R^{15''}$, $R^{15'''}$, $R^{16}$, $R^{16'}$, $R^{20}$, $R^{20'}$, $R^{21}$, $R^{21'}$, $R^{22}$ and $R^{23}$ contains a $X^{14}(CH_2CH_2O)_{ff}CH_2CH_2X^{14}$ moiety, wherein ff is selected from 1 to 1000 and each $X^{14}$ is independently selected from

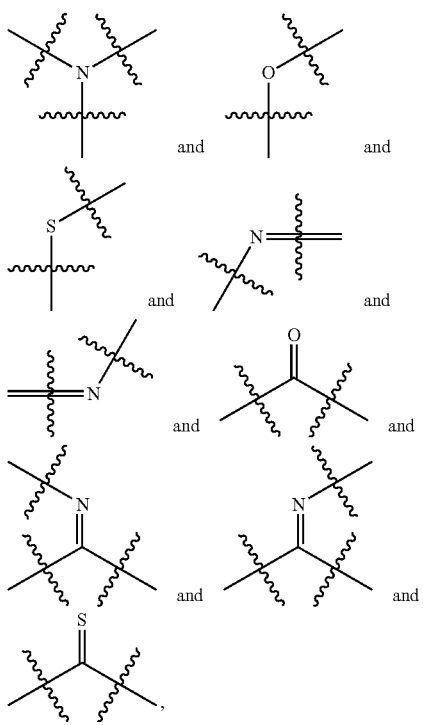

that is connected to the attachment site of said substituent either via a direct bond or via a moiety, being part of said same substituent, that does not comprise a disulfide, a hydrazone, a hydrazide, an ester, a natural amino acid, or a peptide containing at least one natural amino acid, and wherein if ring B in DB1 is an all-carbon ring, $X^3$ is O or $NR^{15}$, $X^4$ is CH, $X^{34}$ is C, there is only one $X^{14}(CH_2CH_2O)_{ff}CH_2CH_2X^{14}$ moiety present in said compound of formula (I) or (II) and said moiety is part of $R^6$, $R^7$, $R^8$, $R^{10}$, or $R^{15}$, then b=1 and ff is ≥5.

A compound of formula (I) or (II) or a conjugate thereof in which ff is larger than 1000 is encompassed by this invention.

In a further more specific embodiment, this invention relates to a compound of formula (I) or (II) as described hereinabove, wherein at least one of the substituents $R^1$, $R^5$, $R^{5'}$, $R^6$, $R^{6'}$, $R^7$, $R^{7'}$, $R^{14}$, $R^{14'}$, $R^8$, $R^{8'}$, $R^9$, $R^{9'}$, $R^{10}$, $R^{10'}$, $R^{11}$, $R^{11'}$, $R^{15}$, $R^{15'}$, $R^{15''}$, $R^{15'''}$, $R^{16}$, $R^{16'}$, $R^{20}$, $R^{2'}$, $R^{21}$, $R^{21'}$, $R^{22}$ and $R^{23}$ contains a triazole moiety.

It should be understood that in this entire document, when referring to a compound of formula (I) or (II), this includes reference to a compound of formula (I') or (II'), respectively, unless structural parts of (I) and (II) not present in (I') and (II') are concerned or the context dictates otherwise. Similarly, when referring to a structural part (fragment), linker-agent conjugate, or conjugate derived from a compound of formula (I) or (II), this includes reference to a similar structural part (fragment), linker-agent conjugate, or conjugate derived from a compound of formula (I') or (II'), respectively, unless structural parts of (I) and (II) not present in (I') and (II') are concerned or the context dictates otherwise.

It should also be understood that when reference is made to a compound of formula (I) or (II) or a fragment, derivative, or conjugate thereof and the scope of $R^{2'}$ or $R^{12}$ is specified, this specification only affects a compound of formula (I) as $R^{2'}$ and $R^{12}$ are absent in a compound of formula (II). Therefore, wherever it reads "$R^{2'}$" or "$R^{12}$" in this document, one could read "$R^{2'}$ (if present)" or "$R^{12}$ (if present)", respectively. This holds as well for (other) substituents that may be present or absent in compounds of formulae (I) and (II) and their fragments, linker-agent conjugates, and conjugates.

It should further be understood that this invention relates to enantiomerically pure and/or diastereomerically pure compounds of formulae (I) and (II) as well as to enantiomeric and/or diastereomic mixtures of compounds of formulae (I) and (II).

Considerations about substituent effects and the effects of linkers, DNA-alkylating units and DNA-binding units in compounds of formulae (I) and (II), their cyclopropyl-containing analogs, and their conjugates and linker-agent conjugates given in this document are presented without consenting to a specific mechanism of action for compounds of formulae (I) and (II), their cyclopropyl-containing analogs, and their linker-agent conjugates and conjugates.

Compounds of formula (I) and (II) can be considered to be built up of a DNA-binding unit (DB1-DB9) and a DNA-alkylating unit (DA1, DA2, DA1', or DA2'), as indicated in the figures hereinabove.

The DNA-alkylating unit of compounds of formulae (I) and (II) is considered to contain the site of alkylation. Alkylation of DNA may occur through attack of DNA on the carbon bearing $R^1$ in a compound of formula (I) or (II) or on that same carbon in the cyclopropyl-containing analog of said compound.

The DNA-binding unit of compounds of formulae (I) and (II) is considered to assist in efficient binding of these compounds to DNA. It may be coupled to the DNA-alkylating moiety via, for instance, an amide bond. Therefore in one embodiment, $X^5$ is O.

In one embodiment, this invention relates to a compound of formula (I). In another embodiment, this invention relates to a compound of formula (II).

$R^1$ in a compound of formula (I) or (II) is a leaving group. In one embodiment, the leaving group $R^1$ is selected from halogen, azide ($N_3$), carboxylate [OC(O)R''], carbonate [OC(O)OR''], carbamate [OC(O)N(R'')R''^1], $^+N(R'')(R''^1)R''^2$, $S(O)_2R°$, and $OS(O)_2R°$, wherein R'', R''^1, R''^2, and R° are independently selected from H and optionally substituted $C_{1-10}$ alkyl, $C_{1-10}$ heteroalkyl, $C_{5-10}$ aryl, or $C_{1-10}$ heteroaryl. An optional substituent may be an oligoethylene glycol or a polyethylene glycol moiety. When the $R^1$ group comprises an oligoethylene glycol or polyethylene glycol moiety, i.e., a $X^{14}(CH_2CH_2O)_{ff}CH_2CH_2X^{14}$ moiety, a compound of formula (I) or (II) or its conjugate may show improved physicochemical, biopharmaceutical, pharmacodynamic, and/or pharmacokinetic properties, which, as indicated hereinabove, may also be valid for the presence of oligoethylene glycol or polyethylene glycol moieties at other positions in a compound of formula (I) or (II). In addition, however, the relatively large size of the $R^1$ substituent may reduce non-specific alkylation of a compound of formula (I) or (II) or its conjugate. Furthermore, the $R^1$ group will be eliminated when the compound of formula (I) or (II) rearranges to a compound of formula (I') or (II'). This means that the oligoethylene glycol or polyethylene glycol moiety may not have a negative effect on the cytotoxic potential of the compound of formula (I) or (II).

In one embodiment, $R^1$ is selected from halogen and $OS(O)_2R$. In another embodiment, the leaving group $R^1$ in a compound of formula (I) or (II) is a halogen. In another embodiment, $R^1$ is selected from chloro (Cl), bromo (Br), and iodo (I). In yet another embodiment, $R^1$ is chloro (Cl).

In yet another embodiment, $R^1$ is bromo (Br). In yet another embodiment, $R^1$ is $OS(O)_2R$. In yet another embodiment, $R^1$ is $OS(O)_2R^o$ and $R^o$ contains a $X^{14}(CH_2CH_2O)_{\!f\!f}CH_2CH_2X^{14}$ moiety. In yet another embodiment, $R^1$ is selected from $OS(O)_2CF_3$, $OS(O)_2C_6H_4CH_3$, and $OS(O)_2CH_3$.

By varying the leaving group $R^1$, one may tune the alkylating activity of the seco agents and affect the transformation rate of a seco agent to a cyclopropyl-containing agent of formula (I') or (II'). If the leaving capability of $R^1$ is too good, this may cause the seco agent to become an aspecific alkylating agent, which may decrease the cytotoxicity quotient and therapeutic index of conjugates of compounds of formulae (I) and (II) as the agent may for example be able to alkylate while still being bound in the conjugate. On the other hand, if $R^1$ is too bad a leaving group, the seco agent may not close to form a cyclopropyl-containing agent, believed to be the active species, which may reduce its cytotoxicity and the cytotoxicity quotient. Therefore, in one embodiment, the Swain-Scott parameter s of the alkylating site is larger than 0.3. In other embodiments, the Swain-Scott parameter s is larger than 0.5 or 0.7 or 1.0.

The size of $R^1$ may affect the non-DNA alkylation rate of a compound of formula (I) or (II) or a conjugate thereof. If $R^1$ is a relatively bulky group, aspecific alkylation may be reduced as the carbon bearing $R^1$ is somewhat shielded.

Another means to tune the alkylating activity of the seco agents and their cyclopropyl-containing derivatives may be to somewhat shield the carbon to which the leaving group $R^1$ is attached or on which nucleophilic attack can occur by choosing at least one of $R^2$, $R^{2'}$, $R^3$, $R^{3'}$, $R^4$, $R^{4'}$, $R^5$, $R^{5'}$, $R^6$, $R^{6'}$, $R^{12}$, $R^{16}$, and $R^{16'}$ present to be other than hydrogen. Shielding of said carbon may reduce aspecific alkylation by compounds of formulae (I) and (II), their cyclopropyl-containing analogs, and their conjugates. Although introduction of steric hindrance may also affect the DNA alkylation rate, it may be reasonable to assume that aspecific alkylation may be affected relatively more than DNA alkylation as the latter occurs presumably after the agent is ideally positioned for nucleophilic attack being bound to the DNA minor groove. The carbon bearing $R^1$ in a compound of formula (II), being a secondary carbon atom (when $R^2$ is H), is already somewhat shielded in comparison to the carbon bearing $R^1$ in a compound of formula (I) when $R^2$ and $R^{2'}$ are both H. In this respect, a compound of formula (II) may be compared to a compound of formula (I) in which $R^{2'}$ is other than hydrogen. Further shielding may however be accomplished by choosing one or more of $R^2$, $R^3$, $R^{3'}$, $R^4$, $R^{4'}$, $R^5$, $R^{5'}$, $R^6$, $R^{6'}$, $R^{16}$, and $R^{16'}$ present to be other than hydrogen.

In one embodiment, $R^2$ and $R^{2'}$ are both hydrogen. In another embodiment, $R^{2'}$ is hydrogen and $R^2$ is not hydrogen. In another embodiment, $R^2$ is selected from $N_3$, $NO_2$, NO, $CF_3$, CN, $C(O)NH_2$, $C(O)H$, $C(O)OH$, halogen, $R^a$, $SR^a$, $S(O)R^a$, $S(O)_2R^a$, $S(O)OR^a$, $S(O)_2OR^a$, $OS(O)R^a$, $OS(O)_2R^a$, $OS(O)OR^a$, $OS(O)_2OR^a$, $OR^a$, $N(R^a)R^b$, $^+N(R^a)(R^b)R^c$, $P(O)(OR^a)(OR^b)$, $OP(O)(OR^a)(OR^b)$, $SiR^aR^bR^c$, $C(O)R^a$, $C(O)OR^a$, $C(O)N(R^a)R^b$, $OC(O)R^a$, $OC(O)OR^a$, $OC(O)N(R^a)R^b$, $N(R^a)C(O)R^b$, $N(R^a)C(O)OR^b$, and $N(R^a)C(O)N(R^b)R^c$, wherein $R^a$, $R^b$, and $R^c$ are independently selected from H and optionally substituted $C_{1-3}$ alkyl or $C_{1-3}$ heteroalkyl.

In one embodiment, $R^2$ is selected from optionally substituted $C_{1-3}$ alkyl and $C_{1-3}$ heteroalkyl. In another embodiment, $R^2$ is optionally substituted $C_{1-3}$ alkyl. In another embodiment, $R^2$ is selected from methyl, ethyl, propyl, and isopropyl. In another embodiment, $R^2$ is methyl.

In yet another embodiment, $R^2$ and $R^{2'}$ are both other than hydrogen. In one embodiment, both $R^2$ and $R^{2'}$ are methyl.

Alternatively, or simultaneously, steric shielding of the carbon bearing $R^1$ may be introduced by choosing one or more of $R^3$, $R^{3'}$, $R^4$, $R^{4'}$, $R^{12}$, $R^{16}$, and $R^{16'}$ present to be other than hydrogen. In one embodiment, $R^3$, $R^{3'}$, $R^4$, and $R^{4'}$ are each H. In another embodiment, $R^3$ and $R^{3'}$ are both H. In another embodiment, $R^4$ and $R^{4'}$ are both H. In another embodiment, one of $R^3$ and $R^{3'}$ is $C_{1-3}$ alkyl while the other is H. In another embodiment, one of $R^4$ and $R^{4'}$ is $C_{1-3}$ alkyl while the other is H. In another embodiment, one of $R^3$ and $R^{3'}$ is $C_{1-3}$ alkyl and one of $R^4$ and $R^{4'}$ is $C_{1-3}$ alkyl while the others are H. In another embodiment, both $R^3$ and $R^{3'}$ are independently $C_{1-3}$ alkyl. In another embodiment, both $R^4$ and $R^{4'}$ are independently $C_{1-3}$ alkyl. In another embodiment, one of $R^3$, $R^{3'}$ $R^4$, and $R^{4'}$ is methyl. In another embodiment, one of $R^4$ and $R^{4'}$ is methyl. In yet another embodiment, both $R^4$ and $R^{4'}$ are methyl. In yet other embodiments, one or both of $R^4$ and $R^{4'}$ are fluoro.

In one embodiment, $R^{12}$ is H. In another embodiment, $R^{12}$ is $C_{1-3}$ alkyl. In yet other embodiments, $R^{12}$ is methyl or ethyl. In yet another embodiment, $R^{12}$ equals $C(R^{2'})(R^2)R^1$, which means that the carbon bearing $R^{12}$ bears two identical groups.

In another embodiment, $R^{16}$ and $R^{16'}$ are both H. In another embodiment, $R^{16}$ is H. In other embodiments, $R^{16}$ is fluoro (F) or methyl or ethyl.

The alkylating activity of a compound of formula (I) or (II) or its cyclopropyl-containing analog may also be affected by the nature of $X^1$. The nature of $X^1$ may affect the rate at which and the conditions under which the seco agents ring close to the cyclopropyl analogs and/or the rate at which the cyclopropyl ring is opened by nucleophilic attack (by DNA), and thus affect the alkylation behavior. In one embodiment, $X^1$ is O. In another embodiment, $X^1$ is $NR^{13}$.

The substituents $R^5$, $R^{5'}$, $R^6$, $R^{6'}$, $R^7$, $R^{7'}$, and $X^2$ as well as the size of the ring connected to the left-hand side of the ring bearing $X^1$ may for example, each independently or two or more taken together, affect the pharmacological properties of the agent, e.g., affect the water solubility, affect the aggregation behavior, affect the DNA alkylation process, and/or affect the DNA binding strength. Furthermore, especially $R^5$ and $R^{5'}$, and to some degree $R^6$ and $R^{6'}$ as well, may also affect the degree of shielding of the carbon on which nucleophilic attack should occur.

$R^5$ and $R^{5'}$ may both be H, or $R^5$ may be H while $R^{5'}$ is absent. In another embodiment, at least one of $R^5$ and $R^{5'}$ is not hydrogen nor absent. In another embodiment, $R^5$ is not hydrogen.

In one embodiment, $R^5$ is selected from OH, SH, $NH_2$, $N_3$, $NO_2$, NO, $CF_3$, CN, $C(O)NH_2$, $C(O)H$, $C(O)OH$, halogen, $R^{e2}$, $SR^{e2}$, $S(O)R^{e2}$, $S(O)_2R^{e2}$, $S(O)OR^{e2}$, $S(O)_2OR^{e2}$, $OS(O)R^{e2}$, $OS(O)_2R^{e2}$, $OS(O)OR^{e2}$, $OS(O)_2OR^{e2}$, $OR^{e2}$, $NHR^{e2}$, $N(R^{e2})R^{f2}$, $^+N(R^{e2})(R^{f2})R^{g2}$, $P(O)(OR^{e2})(OR^{f2})$, $OP(O)(OR^{e2})(OR^{f2})$, $SiR^{e2}R^{f2}R^{g2}$, $C(O)R^{e2}$, $C(O)OR^{e2}$, $C(O)N(R^{e2})R^{f2}$, $OC(O)R^{e2}$, $OC(O)OR^{e2}OC(O)N(R^{e2})R^{f2}$, $N(R^{e2})C(O)R^{f2}$, $N(R^{e2})C(O)OR^2$, and $N(R^{e2})C(O)N(R^{f2})R^{g2}$, wherein $R^{e2}$, $R^{f2}$, and $R^{g2}$ are independently selected from H and optionally substituted $C_{1-3}$ alkyl, $C_{1-3}$ heteroalkyl, $C_3$ cycloalkyl, or $C_{1-3}$ heterocycloalkyl, two or more of $R^{e2}$, $R^{f2}$, and $R^{g2}$ optionally being joined by one or more bonds to form one or more optionally substituted carbocycles and/or heterocycles.

In another embodiment, $R^5$ is selected from OH, SH, $NH_2$, $N_3$, $NO_2$, NO, $CF_3$, CN, $C(O)NH_2$, $C(O)H$, $C(O)OH$, halogen, $R^{e2}$, $SR^{e2}$, $S(O)R^{e2}$, $S(O)_2R^{e2}$, $S(O)OR^{e2}$, $S(O)_2OR^{e2}$, $OS(O)R^{e2}$, $OS(O)_2R^{e2}$, $OS(O)OR^{e2}$, $OS(O)_2OR^{e2}$, OR$^{e2}$, NHR$^{e2}$, N(R$^{e2}$)R$^{f2}$, $^+$N(R$^{e2}$)(R$^{f2}$)R$^{g2}$, P(O)(OR$^{e2}$)(OR$^{f2}$), OP(O)(OR$^{e2}$)(OR$^{f2}$), SiR$^{e2}$R$^{f2}$R$^{g2}$, C(O)R$^{e2}$, C(O)OR$^{e2}$, C(O)N(R$^{e2}$)R$^{f2}$, OC(O)R$^{e2}$, OC(O)OR$^{e2}$, OC(O)N(R$^{e2}$)R$^{f2}$, N(R$^{e2}$)C(O)R$^{f2}$, N(R$^{e2}$)C(O)OR$^{f2}$, and N(R$^{e2}$)C(O)N(R$^{f2}$)R$^{g2}$, wherein R$^{e2}$, R$^{f2}$, and R$^{g2}$ are independently selected from H and optionally substituted $C_{1-3}$ alkyl, $C_{1-3}$ heteroalkyl, $C_3$ cycloalkyl, or $C_{1-3}$ heterocycloalkyl, two or more of R$^{e2}$, R$^{f2}$, and R$^{g2}$ optionally being joined by one or more bonds to form one or more optionally substituted carbocycles and/or heterocycles, provided that R$^{e2}$ is not H when R$^5$ is R$^{e2}$.

In another embodiment, R$^5$ is selected from nitro, halogen, amino, cyano, hydroxy, and optionally substituted $C_{1-3}$ alkylamino, di($C_{1-3}$ alkyl)amino, $C_{1-3}$ alkylcarbonylamino, $C_{1-3}$ alkoxycarbonylamino, $C_{1-3}$ alkylaminocarbonylamino, $C_{1-3}$ alkyloxy, $C_{1-3}$ alkylcarbonyloxy, $C_{1-3}$ alkoxycarbonyloxy, $C_{1-3}$ alkylaminocarbonyloxy, or $C_{1-3}$ alkyl. In yet another embodiment, R$^5$ is optionally substituted linear $C_{1-3}$ alkyl. In another embodiment, R$^5$ is unsubstituted linear $C_{1-3}$ alkyl. In another embodiment, R$^5$ is selected from methyl, ethyl, propyl, isopropyl, nitro, $CF_3$, F, Cl, Br, cyano, methoxy, ethoxy, propoxy, isopropoxy, amino ($NH_2$), methylamino, formyl, hydroxymethyl, and dimethylamino. In another embodiment, R$^5$ is methyl, ethyl, methoxy, or ethoxy. In another embodiment, R$^5$ is methyl. In other embodiments, R$^5$ is ethyl or methoxy or ethoxy.

R$^6$ and R$^{6'}$ may both be hydrogen, or R$^6$ may be hydrogen while R$^{6'}$ is absent. In another embodiment, at least one of R$^6$ and R$^{6'}$ is not hydrogen nor absent. In another embodiment, R$^6$ is not hydrogen.

R$^5$ and R$^6$ may be joined to form, together with the two carbon atoms to which they are attached, an optionally substituted 5- or 6-membered ring. This ring may for example be a dihydropyrrole, dihydrofuran, cyclopentene, 1,3-dioxolene, pyrrolidine, tetrahydrofuran, cyclopentane, or 1,3-dioxolane moiety.

The substituents R$^{16}$ and R$^{16'}$ may affect the degree of shielding of the carbon on which nucleophilic attack can occur as well. In one embodiment X$^4$ is CR$^{16}$. In a further embodiment, R$^{16}$ is hydrogen. In yet another embodiment, R$^{16}$ is $C_{1-3}$ alkyl or $C_{1-3}$ heteroalkyl. In another embodiment, R$^{16}$ is methyl or ethyl. In yet another embodiment, R$^{16}$ is methyl. In yet another embodiment, R$^{16}$ is fluoro.

R$^{14}$ and R$^{14'}$ may affect the degree of shielding of X$^1$, or when a compound of formula (I) or (II) is part of a conjugate or linker-agent conjugate in which the compound of formula (I) or (II) is connected via X$^1$, they may affect the degree of shielding of the linkage between the compound of formula (I) or (II) and the promoiety. To increase the stability of this linkage, R$^{14}$ may be selected to be other than hydrogen. In one embodiment, R$^{14}$ is hydrogen. In another embodiment, R$^{14}$ is methyl. In yet other embodiments, R$^{14}$ is chloro or ethyl or isopropyl. In yet another embodiment, R$^5$ and R$^{14}$ are the same and not hydrogen. For example, both R$^5$ and R$^{14}$ may be methyl.

In one embodiment, R$^2$, R$^{2'}$, R$^3$, R$^{3'}$, R$^4$, R$^{4'}$, R$^5$, R$^{5'}$, R$^6$, R$^{6'}$, R$^{12}$, R$^{16}$, and R$^{16'}$ present are each hydrogen. In another embodiment R$^2$, R$^{2'}$, R$^3$, R$^{3'}$, R$^4$, R$^{4'}$, R$^{5'}$, R$^6$, R$^{6'}$, R$^{12}$, R$^{16}$, and R$^{16'}$ present are each hydrogen. In yet another embodiment, R$^2$, R$^{2'}$, R$^3$, R$^{3'}$, R$^4$, R$^{4'}$, R$^5$, R$^{5'}$, R$^6$, R$^{6'}$, R$^7$, R$^{7'}$, R$^{12}$, R$^{14}$, R$^{14'}$, R$^{16}$, R$^{16'}$, and R$^{19}$ present are each hydrogen. In yet another embodiment, R$^2$, R$^{2'}$, R$^3$, R$^{3'}$, R$^4$, R$^{4'}$, R$^5$, R$^{5'}$, R$^6$, R$^{6'}$, R$^7$, R$^{7'}$, R$^{12}$, R$^{14}$, R$^{14'}$, R$^6$, R$^{16'}$, and R$^{19}$ present are each hydrogen.

Although the alkylation rate and efficiency of compounds of formulae (I) and (II) may optionally be tuned in several ways, in one aspect of this invention, this may be achieved by introducing steric shielding choosing for a compound of formula (I) one or more of R$^2$, R$^{2'}$, R$^3$, R$^{3'}$, R$^4$, R$^{4'}$, R$^5$, R$^{5'}$, R$^6$, R$^{6'}$, R$^{12}$, R$^{16}$, and R$^{16'}$ present to be other than hydrogen and for a compound of formula (II) one or more of R$^2$, R$^3$, R$^{3'}$, R$^4$, R$^{4'}$, R$^5$, R$^{5'}$, R$^6$, R$^{6'}$, R$^{16}$, and R$^{16'}$ present to be other than hydrogen. Substituents should not cause too much steric hindrance, however, especially when more than one of these substituents is other than hydrogen, as this might adversely affect DNA alkylation. Furthermore, it may provide for less efficient binding in the DNA minor groove and may pose synthetic difficulties.

In one embodiment, at least one of R$^1$, R$^5$, R$^{5'}$, R$^6$, R$^{6'}$, R$^7$, R$^{7'}$, R$^{14}$, R$^{14'}$, R$^8$, R$^{8'}$, R$^9$, R$^{9'}$, R$^{10}$, R$^{10'}$, R$^{11}$, R$^{11'}$, R$^{15}$, R$^{15'}$, R$^{15''}$, R$^{15'''}$, R$^{16}$, R$^{16'}$, R$^{20}$, R$^{2'}$, R$^{21}$, R$^{21'}$, R$^{22}$ and R$^{23}$ contains a X$^{14}$(CH$_2$CH$_2$O)$_{ff}$CH$_2$CH$_2$X$^{14}$ moiety, wherein ff is selected from 1 to 1000 and each X$^{14}$ is independently selected from

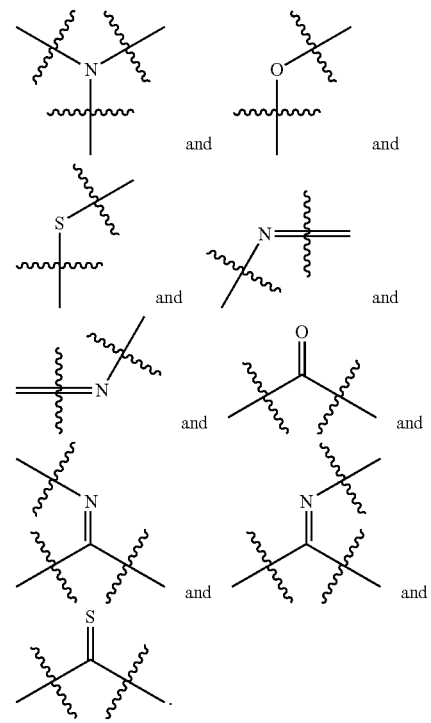

This moiety must be connected to the core of the DNA-alkylating moiety or DNA-binding moiety via a direct bond or via a linking unit that is part of said same R group and that does not comprise a disulfide, a hydrazone, a hydrazide, an ester, a natural amino acid, or a peptide containing at least one natural amino acid. Said linking unit should preferably be cleaved less than 20%, more preferably less than 10%, and most preferably less than 5% in 24 hours upon administration of a compound of formula (I) or (II) in vivo.

The X$^{14}$(CH$_2$CH$_2$O)$_{ff}$CH$_2$CH$_2$X$^{14}$ moiety may for example be selected to be

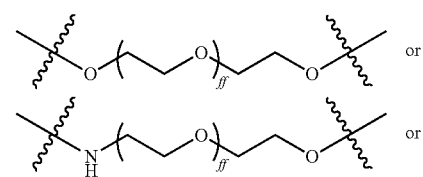

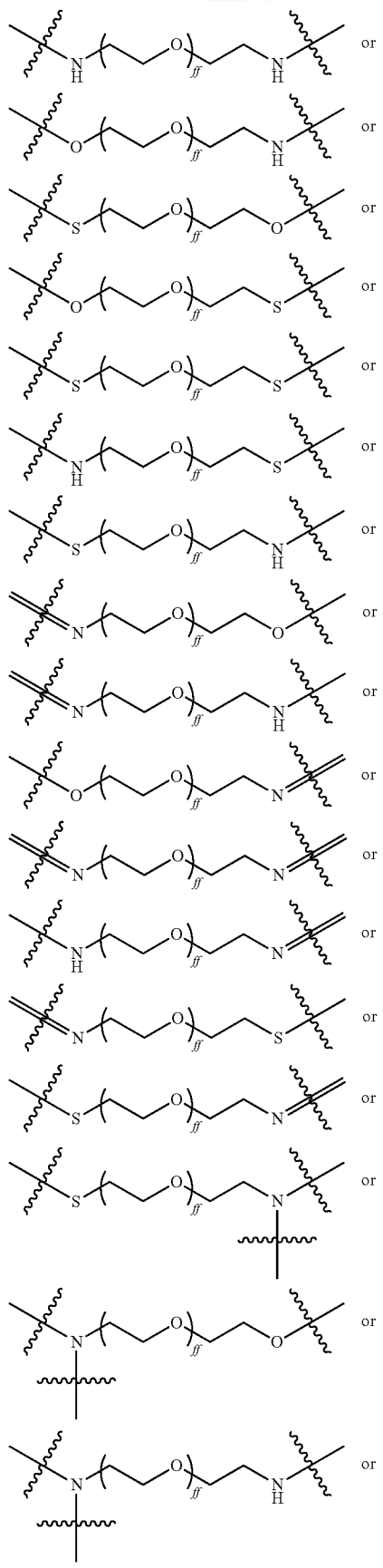
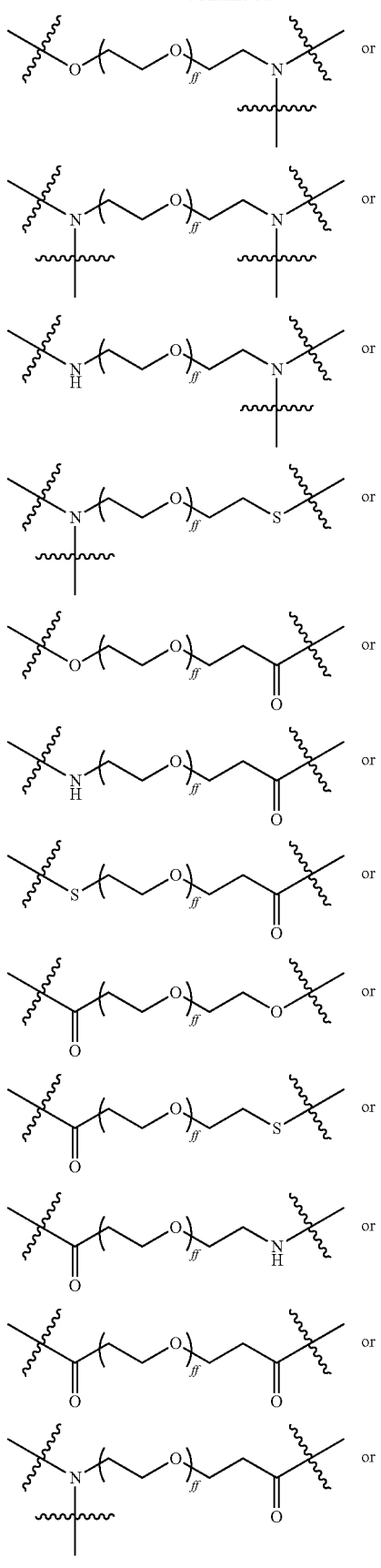

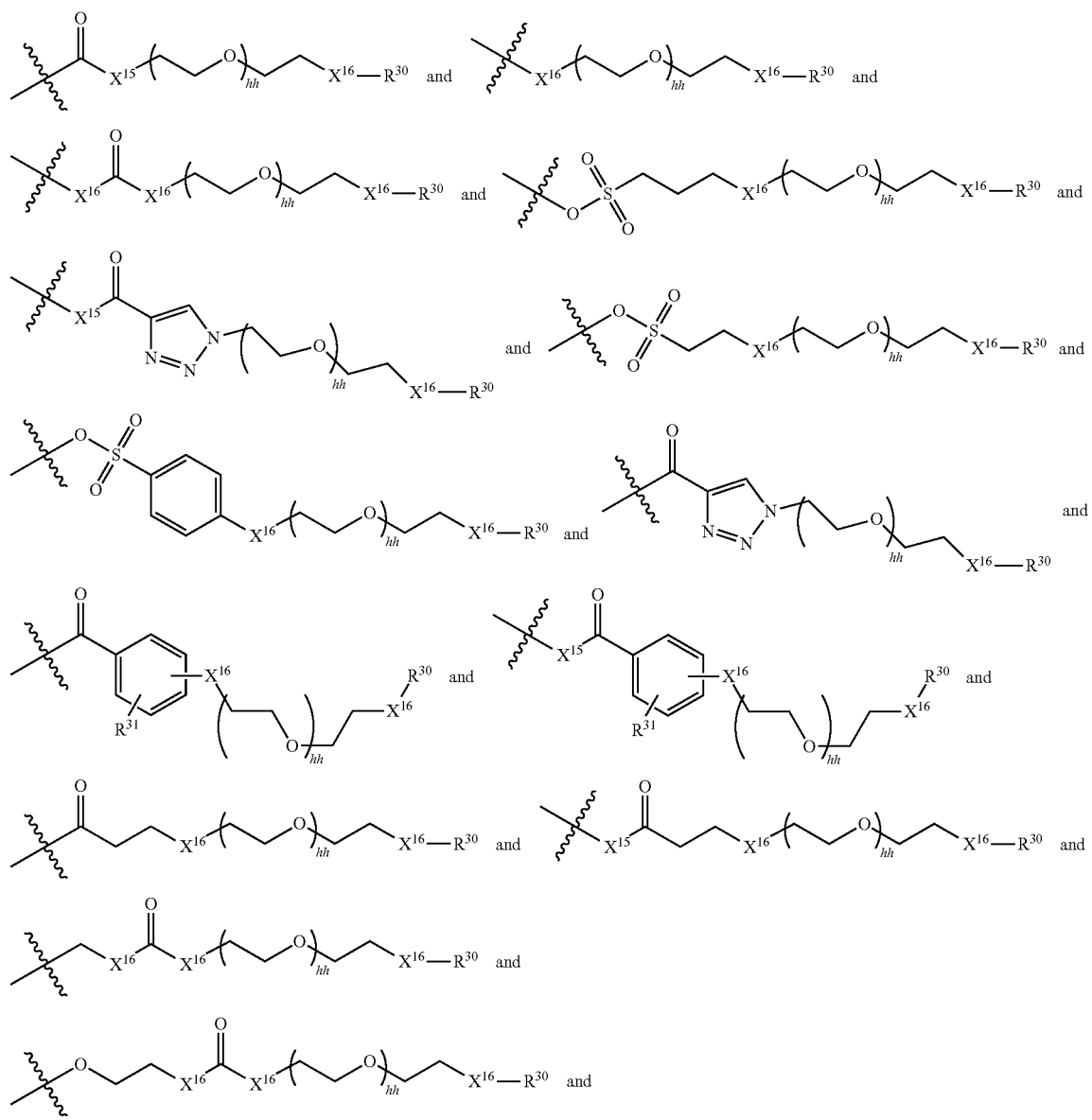

wherein ff is selected from 1 to 1000. In more specific embodiments, ff is selected from 1 to 100 or from 1 to 10. In other embodiments, ff is selected to be 1 or 2 or 3 or 4. In another embodiment, ff is 3 or 4.

The oligoethylene glycol or polyethylene glycol moiety or derivative thereof is connected via a linking unit to the core structure of a compound of formula (I) or (II). Such a linking unit may be a single bond, in which case the oligoethylene glycol or polyethylene glycol or derivative thereof is connected to the core structure via for example an amine, ether, or sulfide bond. Alternatively, the oligoethylene glycol or polyethylene glycol moiety or derivative thereof may be connected to the core structure via for example a carbamate, a carbonate, an amide, an alkyl, a heteroalkyl, an aryl, or a heteroaryl moiety, or a combination of any of these. In one embodiment, at least one of $R^1$, $R^5$, $R^{5'}$, $R^6$, $R^{6'}$, $R^7$, $R^{7'}$, $R^{14}$, $R^{14'}$, $R^8$, $R^{8'}$, $R^9$, $R^{9'}$, $R^{10}$, $R^{10'}$, $R^{11}$, $R^{11'}$, $R^{15}$, $R^{15'}$, $R^{15''}$, $R^{15'''}$, $R^{16}$, $R^{16'}$, $R^{20}$, $R^{20'}$, $R^{21}$, $R^{21'}$, $R^{22}$, and $R^{23}$ is selected from -continued

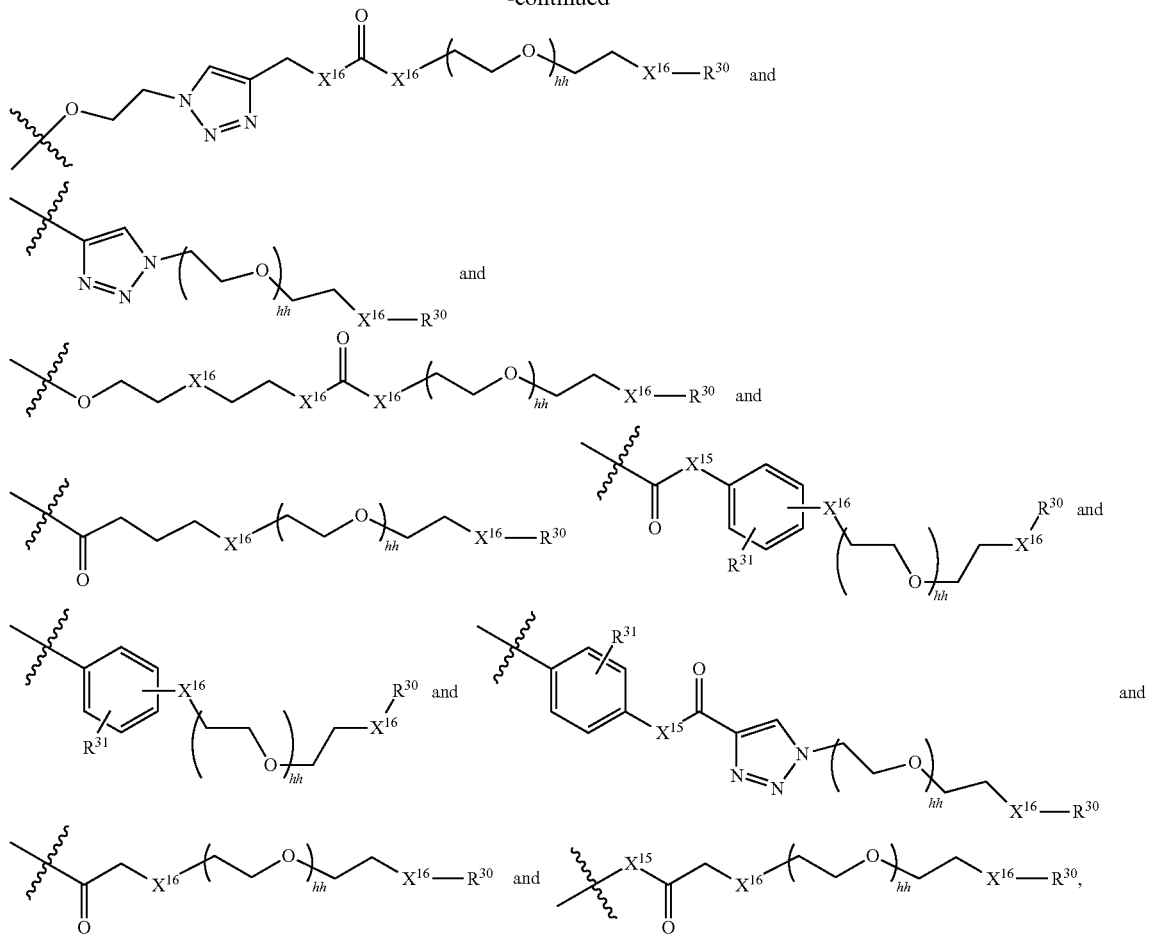

wherein hh is selected from 1 to 1000, $X^{15}$ is selected from S and $NR^{32}$, each $X^{16}$ is independently selected from O, S, and $NR^{34}$, $R^{30}$ is independently selected from H and optionally substituted $C_{1-10}$ alkyl, $C_{1-10}$ heteroalkyl, $C_{3-10}$ cycloalkyl, $C_{1-10}$ heterocycloalkyl, $C_{5-10}$ aryl, or $C_{1-10}$ heteroaryl, $R^{32}$, $R^{33}$, and $R^{34}$ are independently selected from H and $C_{1-3}$ alkyl, and $R^{31}$ has the same meaning as defined for $R^7$.

$R^{30}$ may for example be selected from H, methyl, ethyl, methoxymethyl, p-aminobenzoyl, and p-aminoanilinocarbonyl.

In a further embodiment, at least one of $R^1$, $R^5$, $R^{5'}$, $R^6$, $R^{6'}$, $R^7$, $R^{7'}$, $R^{14}$, $R^{14'}$, $R^8$, $R^{8'}$, $R^9$, $R^{9'}$, $R^{10}$, $R^{10'}$, $R^{11}$, $R^{11'}$, $R^{15}$, $R^{15'}$, $R^{15''}$, $R^{15'''}$, $R^{16}$, $R^{16'}$, $R^{20}$, $R^{20'}$, $R^{21}$, $R^{21'}$, $R^{22}$, and $R^{23}$ is selected from

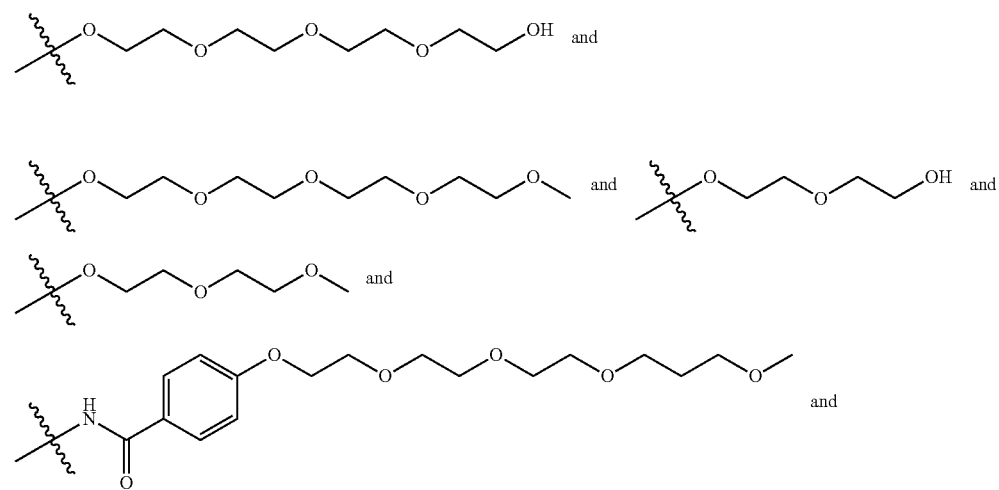

-continued

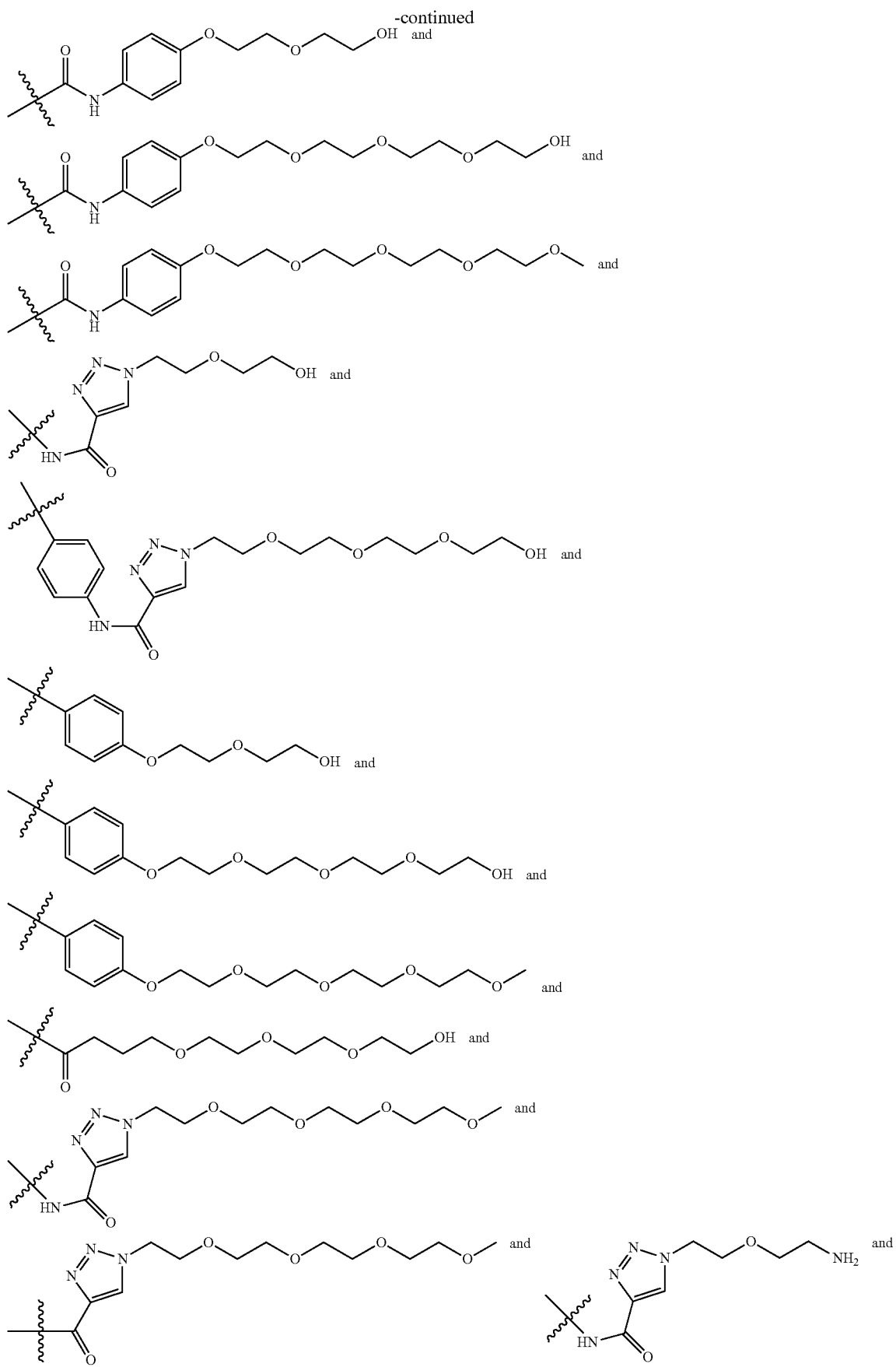

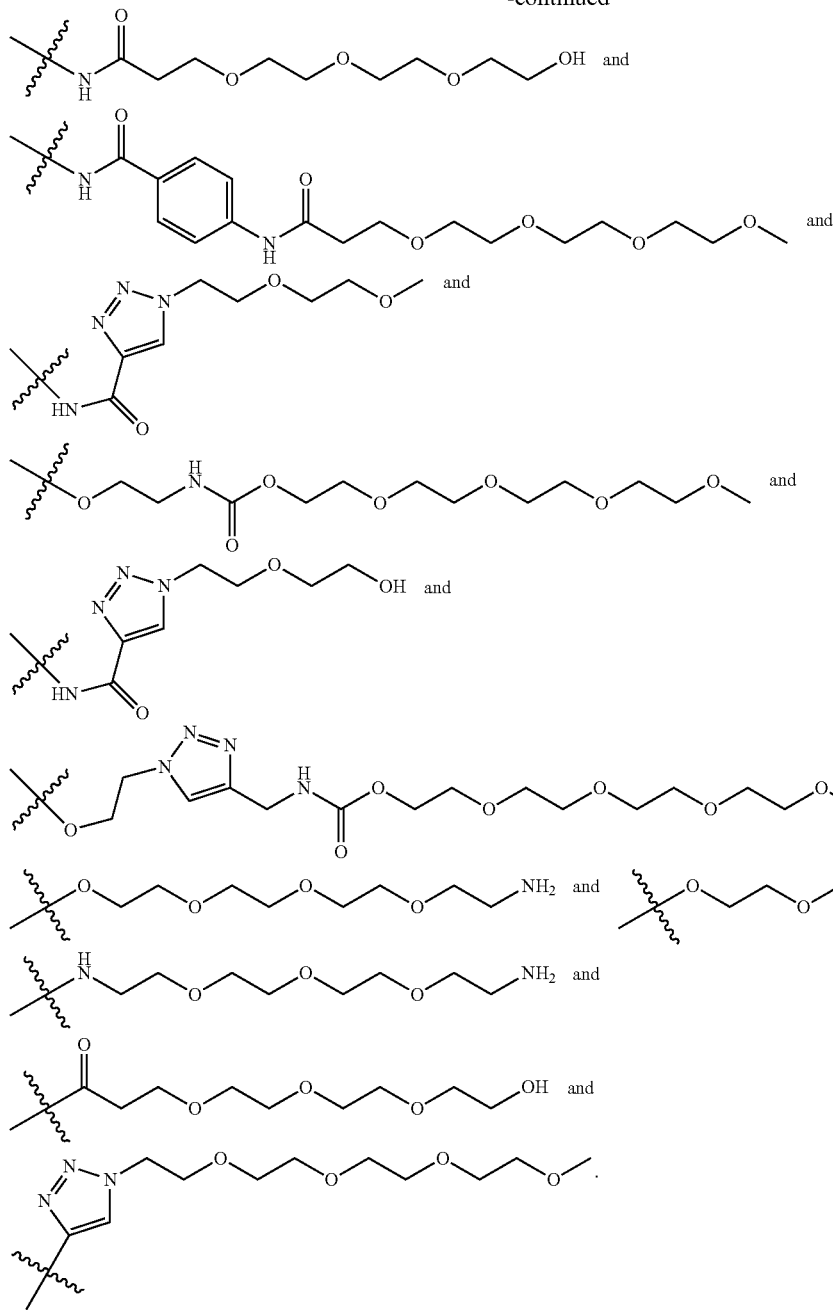
In another embodiment, $R^1$ is selected from
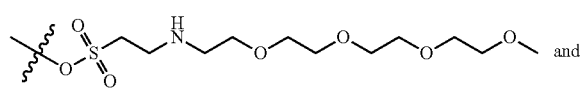
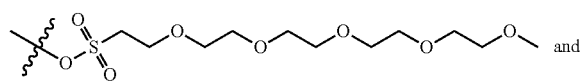
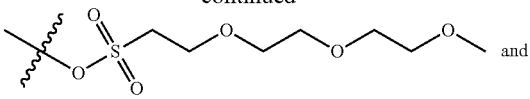
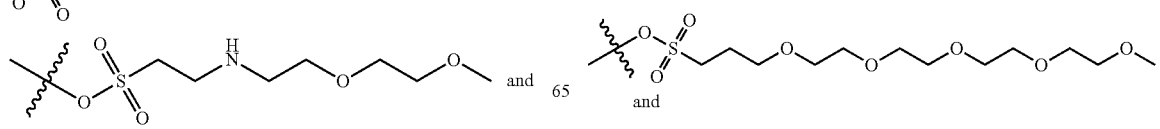

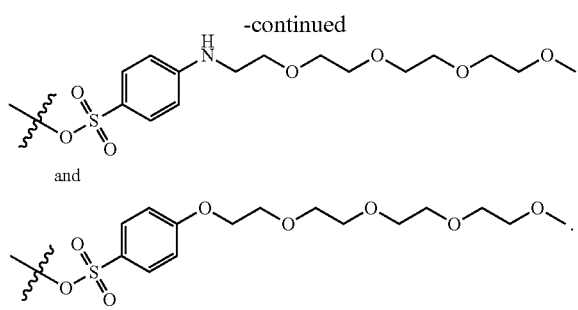

and

In one embodiment, at least one of $R^1$, $R^5$, $R^{5'}$, $R^6$, $R^{6'}$, $R^7$, $R^{7'}$, $R^{14}$, $R^{14'}$, $R^8$, $R^{8'}$, $R^9$, $R^{9'}$, $R^{10}$, $R^{10'}$, $R^{11}$, $R^{11'}$, $R^{15}$, $R^{15'}$, $R^{15''}$, $R^{15'''}$, $R^{16}$, $R^{16'}$, $R^{20}$, $R^{20'}$, $R^{21}$, $R^{21'}$, $R^{22}$, and $R^{23}$ contains a $X^{14}(CH_2CH_2O)_{ff}CH_2CH_2X^{14}$ moiety. In another embodiment, at least one of $R^5$, $R^6$, $R^7$, and $R^{14}$ contains a $X^{14}(CH_2CH_2O)_{ff}CH_2CH_2X^{14}$ moiety. In yet another embodiment, at least one of $R^6$ and $R^7$ contains a $X^{14}(CH_2CH_2O)_{ff}CH_2CH_2X^{14}$ moiety. In yet another embodiment, at least one of $R^8$, $R^{8'}$, $R^9$, $R^{9'}$, $R^{10}$, $R^{10'}$, $R^{11}$, $R^{11'}$, $R^{15}$, $R^{15'}$, $R^{15''}$, $R^{15'''}$, $R^{16}$, $R^{16'}$, $R^{20}$, $R^{20'}$, $R^{21}$, $R^{21'}$, $R^{22}$ and $R^{23}$ contains a $X^{14}(CH_2CH_2O)_{ff}CH_2CH_2X^{14}$ moiety. In yet another embodiment, at least one of $R^8$, $R^9$, $R^{10}$, $R^{11}$, $R^{20}$, $R^{21}$, and $R^{22}$ contains a $X^{14}(CH_2CH_2O)_{ff}CH_2CH_2X^{14}$ moiety. In yet another embodiment, at least one of $R^8$ and $R^9$ contains a $X^{14}(CH_2CH_2O)_{ff}CH_2CH_2X^{14}$ moiety. In yet another embodiment, at least $R^1$ contains a $X^{14}(CH_2CH_2O)_{ff}CH_2CH_2X^{14}$ moiety.

A compound of formula (I) or (II) may also contain 2 or more $X^{14}(CH_2CH_2O)_{ff}CH_2CH_2X^{14}$ moieties. In one embodiment, a compound of formula (I) or (II) contains 2 $X^{14}(CH_2CH_2O)_{ff}CH_2CH_2X^{14}$ moieties. In another embodiment, a compound of formula (I) or (II) contains 2 $X^{14}(CH_2CH_2O)_{ff}CH_2CH_2X^{14}$ moieties that are part of 2 separate R groups. It may be beneficial to put the two or more $X^{14}(CH_2CH_2O)_{ff}CH_2CH_2X^{14}$ moieties at distant positions in the compound of formula (I) or (II) as this may shield the relatively hydrophobic core more efficiently.

Compounds of formulae (I) and (II) may contain one or more oligoethylene glycol or polyethylene glycol moieties or derivatives thereof. Such a moiety may improve the water solubility and aggregation behavior of a compound of formula (I) or (II) and may cause increased activity against multidrug-resistant targets due to increased polarity. If a compound of formula (I) or (II) with such a moiety is incorporated in a conjugate, it may be that the oligoethylene glycol or polyethylene glycol moiety is located in between the promoiety and the remainder of the compound of formula (I) or (II) or that it is located at a position somewhat opposite to the attachment site of the promoiety, thus placing the remainder of the compound of formula (I) or (II) in between the promoiety and the oligoethylene glycol or polyethylene glycol moiety. The latter may be more beneficial for the water solubility of the conjugates. Improved water solubility of compounds of formulae (I) and (II) and their conjugates may lead to improved yields and purity of the conjugates during synthesis, for example due to reduced aggregate formation. Furthermore, a reduced tendency for aggregation and a higher purity of the conjugate may for example lead to fewer side effects after administration of the conjugate. In addition, the presence of one or more oligoethylene glycol and/or polyethylene glycol moieties in a conjugate may reduce excretion of the conjugate via the kidneys or liver, which increases the circulation time in the body.

In another aspect of this invention, compounds of formula (I) and (II) may contain one or more triazole rings. Incorporation of a 1,2,3-triazole ring may provide for a synthetic advantage as the two moieties that eventually may become attached to the 1,2,3-triazole ring may be attached to each other via said triazole ring using a mild and efficient cycloaddition reaction between an alkyne and azide moiety. Because the conditions for this cycloaddition reaction are very mild and are compatible with almost all functional groups, the reaction can be performed in one of the last steps of the synthetic route towards a compound of formula (I) or (II), its linker-agent conjugate, or conjugate, thus allowing for easy generation of series of compounds of formula (I) and (II) and their conjugates for SAR (structure-activity relationship) studies.

Preferably, the triazole moiety is located in such a way within the DNA-alkylating unit or DNA-binding unit that it can contribute to the binding of the compound to DNA. Additional DNA-binding moieties, such as indole or benzofuran moieties, that are connected to the DNA-binding or DNA-alkylating unit may increase the potency of the compound, allegedly through enhanced DNA binding. These additional aromatic moieties may however have a detrimental effect on pharmacological properties, such as water solubility. A triazole, being an aromatic group, may also enhance binding to DNA and thus increase cytotoxic potency of the compound, but as it is more polar than other aromatic moieties such as a phenyl ring, negative effects on pharmacological properties may be less pronounced.

In one embodiment, this invention relates to a compound of formula (I) or (II) wherein at least one of $R^1$, $R^5$, $R^{5'}$, $R^6$, $R^{6'}$, $R^7$, $R^{7'}$, $R^{14}$, $R^{14'}$, $R^8$, $R^{8'}$, $R^9$, $R^{9'}$, $R^{10}$, $R^{10'}$, $R^{11}$, $R^{11'}$, $R^{15}$, $R^{15'}$, $R^{15''}$, $R^{15'''}$, $R^{16}$, $R^{16'}$, $R^{20}$, $R^{20'}$, $R^{21}$, $R^{21'}$, $R^{22}$, and $R^{23}$ contains a triazole moiety.

In another embodiment, at least one of $R^8$, $R^{8'}$, $R^9$, $R^{9'}$, $R^{10}$, $R^{10'}$, $R^{11}$, $R^{11'}$, $R^{15}$, $R^{1'}$, $R^{15''}$, $R^{15'''}$, $R^{16}$, $R^{16'}$, $R^{20}$, $R^{20'}$, $R^{21}$, $R^{21'}$, $R^{22}$, and $R^{23}$ contains a triazole moiety. In another embodiment, at least one of $R^8$, $R^9$, and $R^{10}$ contains a triazole moiety. In another embodiment, at least one of $R^8$ and $R^9$ contains a triazole moiety. In yet another embodiment, at least $R^8$ contains a triazole moiety.

In another embodiment, at least one of $R^5$, $R^{5'}$, $R^6$, $R^{6'}$, $R^7$, $R^{7'}$, $R^{14}$, and $R^{14'}$ contains a triazole moiety. In another embodiment, at least one of $R^6$, $R^{6'}$, $R^7$, and $R^{7'}$ contains a triazole moiety. In yet another embodiment, $R^1$ contains a triazole moiety.

For an optimum DNA-binding effect, the triazole moiety may be connected via a linker that keeps the triazole moiety in conjugation with or in close proximity to the core of the DNA-binding or DNA-alkylating unit. The linker may for example be a single bond, $-N(R^{35})C(O)-$, $-C(O)N(R^{35})-$, $-C(O)-$, $-C(R^{35})(R^{36})-$, $-C(R^{35})=C(R^{36})-$, $-O-$, $-S-$, or $-N(R^{35})-$, wherein $R^{35}$ and $R^{36}$ are selected from H and optionally substituted $C_{1-4}$ alkyl or $C_{1-4}$ heteroalkyl, or be any other optionally substituted small linker that does not have more than 4 connecting atoms (e.g., the $-N(R^{20})C(O)-$ moiety has two connecting atoms: N and C) in between the core of the DNA-binding unit or DNA-alkylating unit and the triazole ring.

The triazole ring may be a 1,2,3-triazole or a 1,2,4-triazole. In one embodiment, the triazole ring is a 1,2,3-triazole. In another embodiment, the triazole is a 1,2,4-triazole. A 1,2,3-triazole ring may be 4,5-, 1,5-, or 1,4-disubstituted. If the 1,2,3-triazole ring is 1,4-substituted, this means that the substituent that contains the 1,2,3-triazole ring has an extended form. If the 1,2,3-triazole ring is 4,5- or 1,5-substituted, the 1,2,3-triazole ring in fact forms a kind of turn and puts the two substituents on the triazole in close proximity to each other. The triazole ring may also be located at the end of the substituent, in which case the triazole ring is only monosubstituted. Substitution may in this case occur at N-1 or C-4. A 1,2,4-triazole may be 1,3-, 1,5-, or 3,5-disubstituted. A substituent that contains a 1,3- or 3,5-disubstituted 1,2,4-triazole has an extended form, whereas in a 1,5-disubstituted 1,2,4-triazole both substituents on the triazole are in close proximity to each other. The triazole ring may also be trisubstituted.

In one aspect, at least one of $R^1$, $R^5$, $R^{5'}$, $R^6$, $R^{6'}$, $R^7$, $R^{7'}$, $R^{14}$, $R^{14'}$, $R^8$, $R^{8'}$, $R^9$, $R^{9'}$, $R^{10}$, $R^{10'}$, $R^{11}$, $R^{11'}$, $R^{15}$, $R^{15'}$, $R^{15''}$, $R^{15'''}$, $R^{16}$, $R^{16'}$, $R^{20}$, $R^{20'}$, $R^{21}$, $R^{21'}$, $R^{22}$ and $R^{23}$ in a compound of formula (I) or (II) is

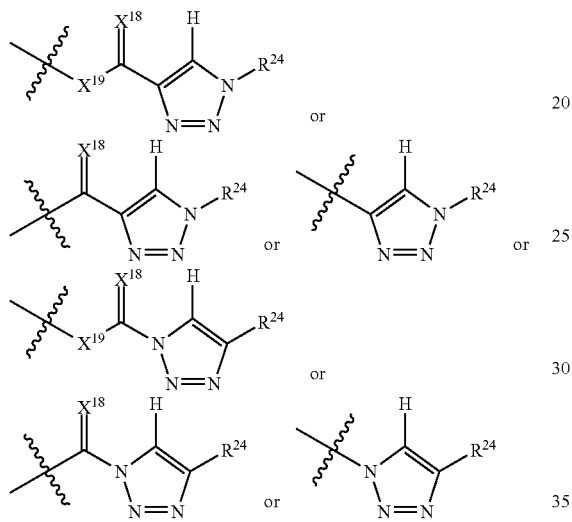

wherein $X^{18}$ and $X^{19}$ are selected from O, S, $NR^{25}$, $H_2$, and $C(R^{25})R^{26}$, wherein $R^{25}$ and $R^{26}$ are selected from H and optionally substituted $C_{1-3}$ alkyl or $C_{1-3}$ heteroalkyl, and $R^{24}$ has the same meaning as $R^8$ and is independently selected.

$R^{24}$ may for example be selected from H and wherein jj, jj', jj", and jj''' are independently selected from 0 to 8, $X^{74}$ is selected from

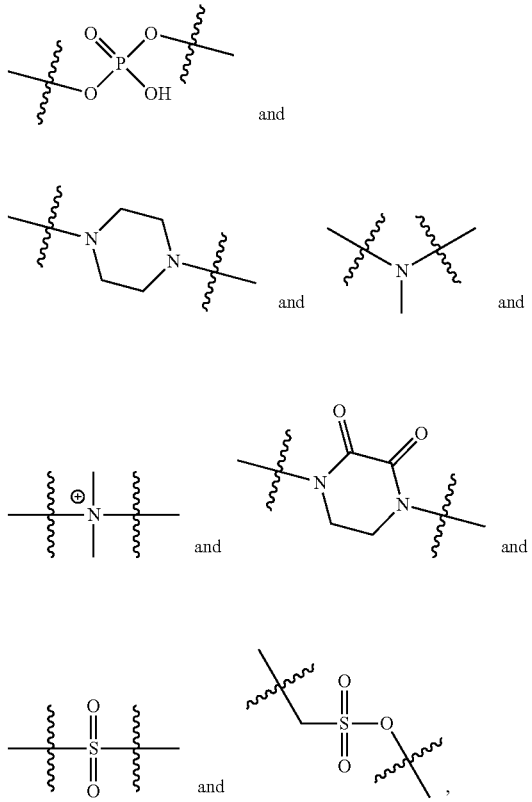

each tt, tt', and tt" is independently selected from 0 and 1, each $X^{21}$ and $X^{22}$ is independently selected from O, S, $NR^{67}$, $H_2$, and $C(R^{67})R^{68}$, wherein $R^{67}$ and $R^{68}$ are independently selected from H and optionally substituted $C_{1-3}$ alkyl or $C_{1-3}$ heteroalkyl, and $R^{66}$ is selected from H, COOH, $CO_2Me$, OH, OMe, $NR^{69}R^{70}$, $NR^{69}C(O)CH_3$, SH, SMe,

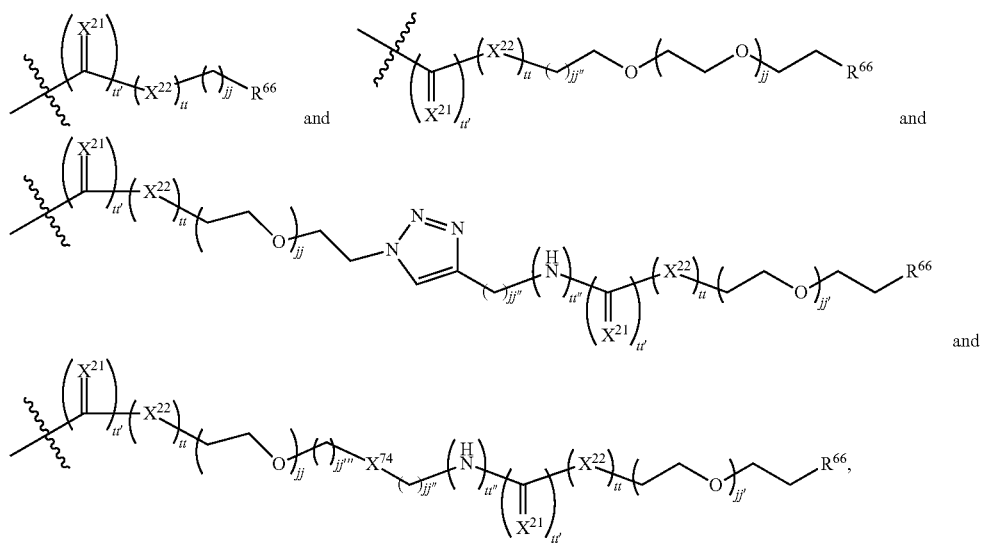

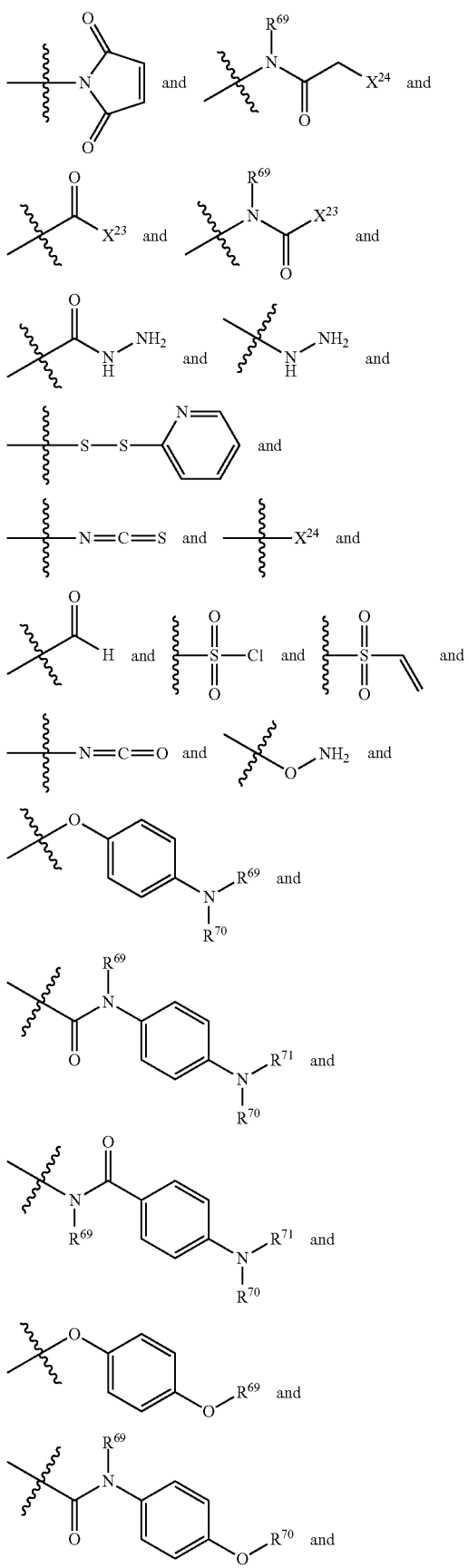
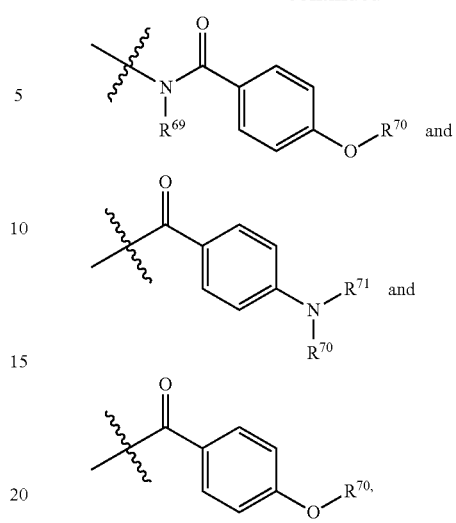
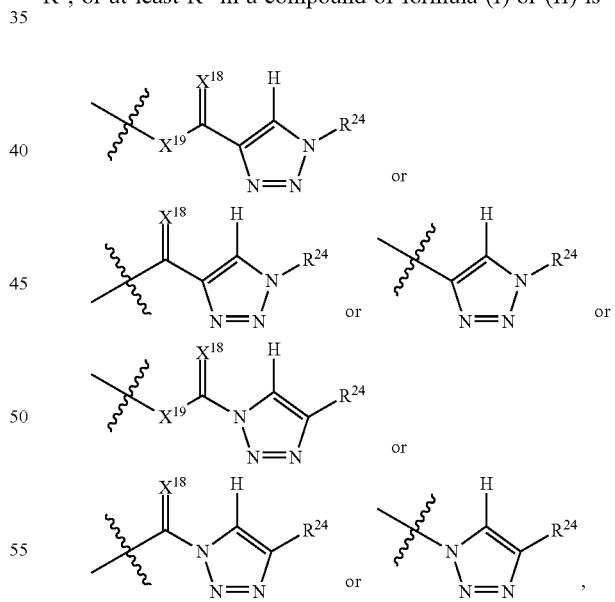

wherein $X^{23}$ is selected from halide, hydroxy, $OC(O)R^{bb}$, and $OC(O)OR^{bb}$, or $C(O)$—$X^{23}$ is an active ester, $X^{24}$ is selected from halide, mesyloxy, triflyloxy, and tosyloxy, $R^{bb}$ is selected from optionally substituted $C_{1-10}$ alkyl, $C_{1-10}$ heteroalkyl, $C_{3-10}$ cycloalkyl, $C_{1-10}$ heterocycloalkyl, $C_{5-10}$ aryl, and $C_{1-10}$ heteroaryl, and $R^{69}$, $R^{70}$, and $R^{71}$ are independently selected from methyl and H.

In other embodiments, at least one of $R^5$, $R^6$, $R^7$, and $R^{14}$, Or at least one of $R^8$, $R^9$, $R^{10}$ and $R^{11}$, or at least one of $R^6$ and $R^7$, or at least one of $R^8$ and $R^9$, or at least $R^8$, or at least $R^6$, or at least $R^7$ in a compound of formula (I) or (II) is wherein $R^{24}$, $X^{18}$, and $X^{19}$ are as defined hereinabove.

In some embodiments, at least one of $R^1$, $R^5$, $R^{5'}$, $R^6$, $R^{6'}$, $R^7$, $R^{7'}$, $R^{14}$, $R^{14'}$, $R^8$, $R^{8'}$, $R^9$, $R^{9'}$, $R^{10}$, $R^{10'}$, $R^{11}$, $R^{11'}$, $R^{15}$, $R^{15'}$, $R^{15''}$, $R^{15'''}$, $R^{16}$, $R^{16'}$, $R^{20}$, $R^{20'}$, $R^{21}$, $R^{21'}$, $R^{22}$, and $R^{23}$, r at least one of $R^8$, $R^9$, $R^{10}$ and $R^{11}$, or at least one of $R^8$ and $R^9$, or at least $R^8$, or at least one of $R^5$, $R^6$, $R^7$, and $R^{14}$, or at least one of $R^6$ and $R^7$ in a compound of formula (I) or (II) is selected from

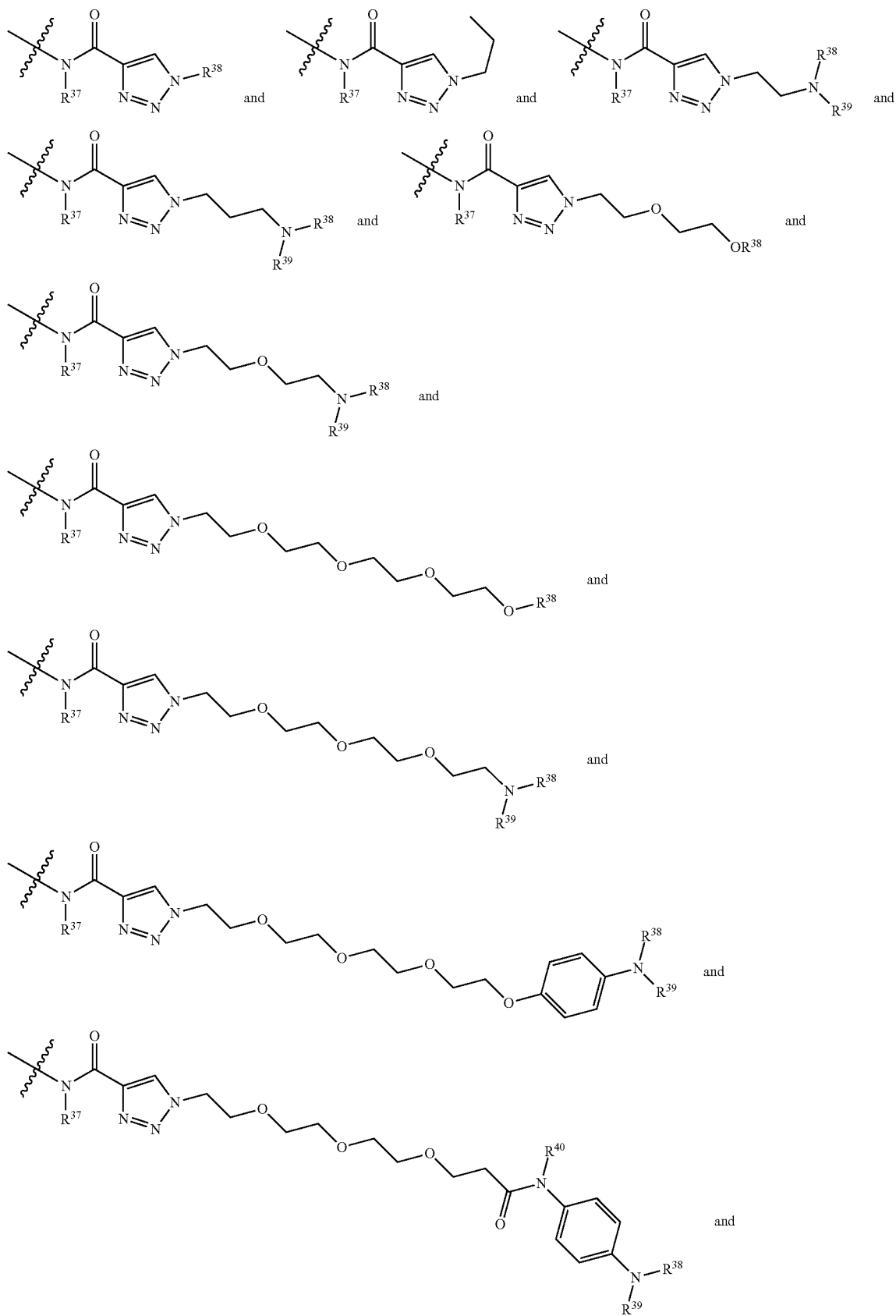

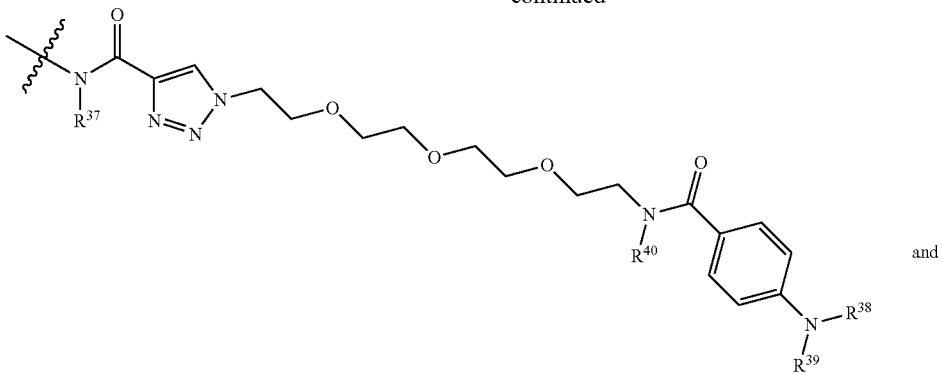

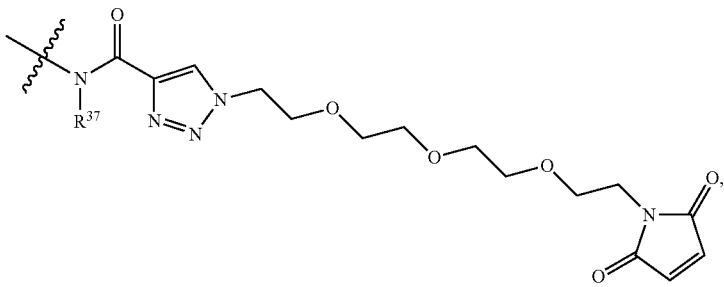

wherein $R^{37}$, $R^{38}$, $R^{39}$, and $R^{40}$ are independently selected from H and methyl.

In other embodiments, at least one of $R^1$, $R^5$, $R^{5'}$, $R^6$, $R^{6'}$, $R^7$, $R^{7'}$, $R^{14}$, $R^{14'}$, $R^8$, $R^{8'}$, $R^9$, $R^{9'}$, $R^{10}$, $R^{10'}$, $R^{11}$, $R^{11'}$, $R^{15}$, $R^{15'}$, $R^{15''}$, $R^{15'''}$, $R^{16}$, $R^{16'}$, $R^{20}$, $R^{20'}$, $R^{21}$, $R^{21'}$, $R^{22}$, and $R^{23}$, r at least one of $R^8$, $R^9$, $R^{10}$ and $R^{11}$, or at least one of $R^8$ and $R^9$, or at least $R^8$, or at least one of $R^5$, $R^6$, $R^7$, and $R^{14}$, or at least one of $R^6$ and $R^7$ in a compound of formula (I) or (II) is selected from

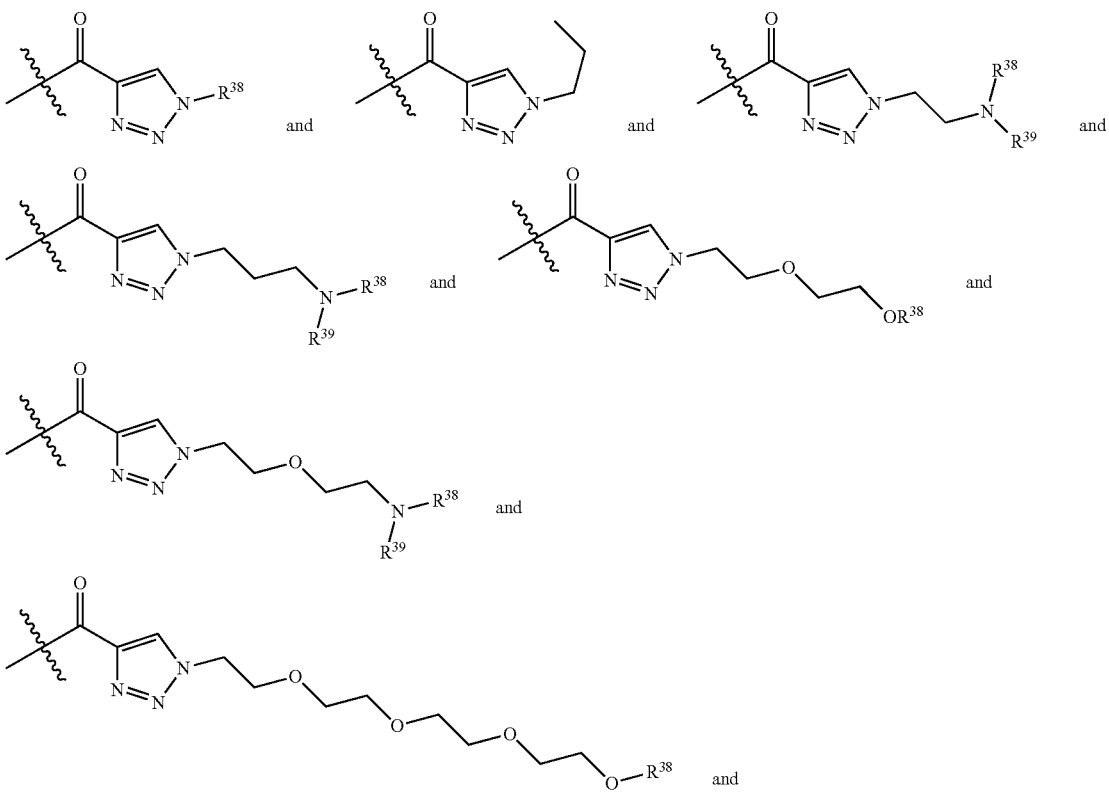

-continued

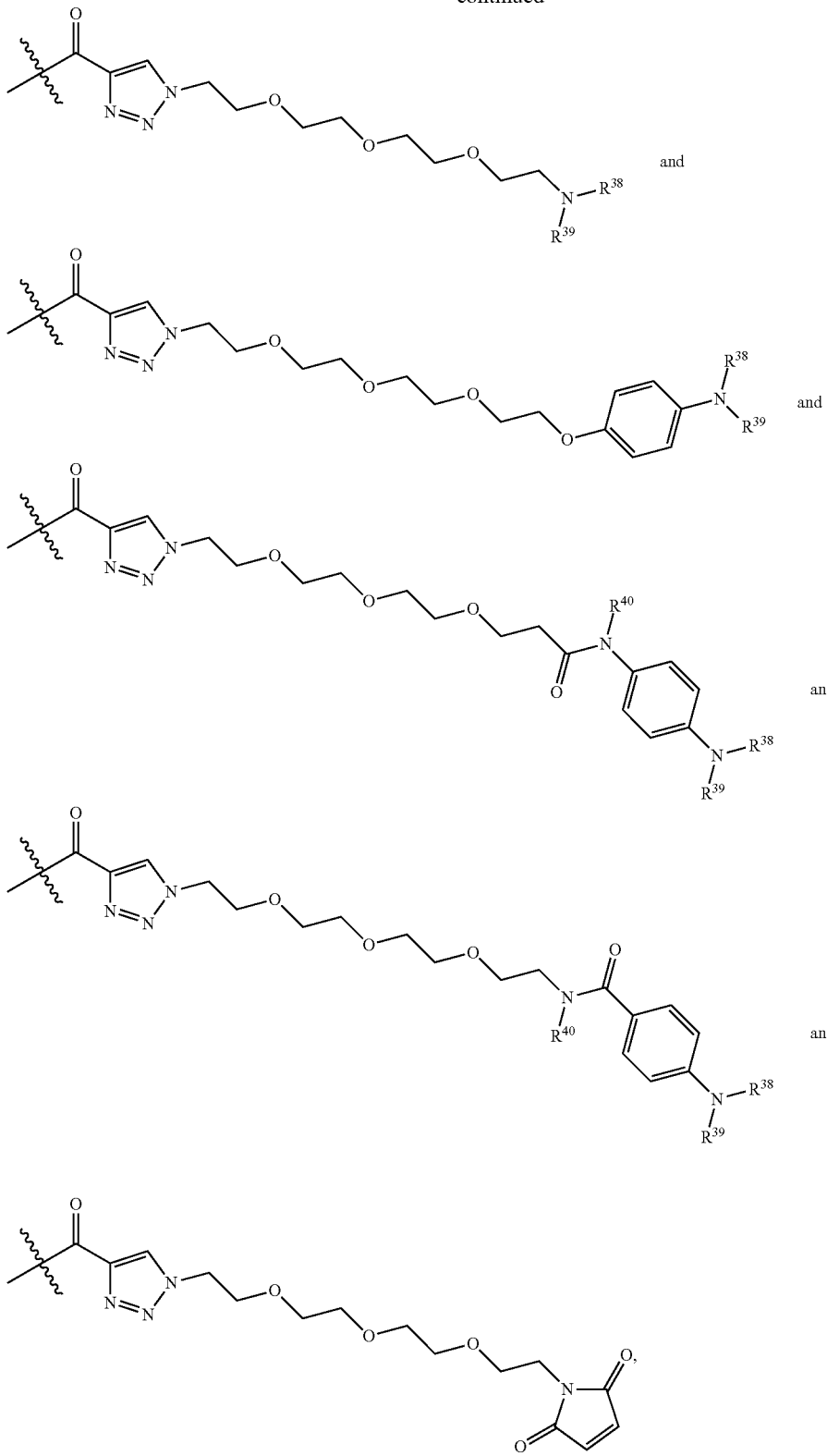

wherein $R^{38}$, $R^{39}$, and $R^{40}$ are independently selected from H and methyl.

In other embodiments, at least one of $R^1$, $R^5$, $R^{5'}$, $R^6$, $R^{6'}$, $R^7$, $R^{7'}$, $R^{14}$, $R^{14'}$, $R^8$, $R^{8'}$, $R^9$, $R^{9'}$, $R^{10}$, $R^{10'}$, $R^{11}$, $R^{11'}$, $R^{15}$, $R^{15'}$, $R^{15''}$, $R^{15'''}$, $R^{16}$, $R^{16'}$, $R^{20}$, $R^{20'}$, $R^{21}$, $R^{22}$, and $R^{23}$, or at least one of $R^8$, $R^9$, $R^{10}$ and $R^{11}$, or at least one of $R^8$ and $R^9$, or at least $R^8$, or at least one of $R^5$, $R^6$, $R^7$, and $R^{14}$, or at least one of $R^6$ and $R^7$ in a compound of formula (I) or (II) is selected from

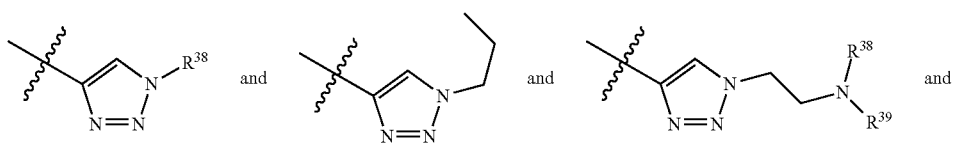
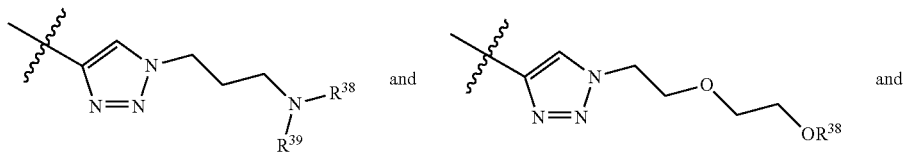
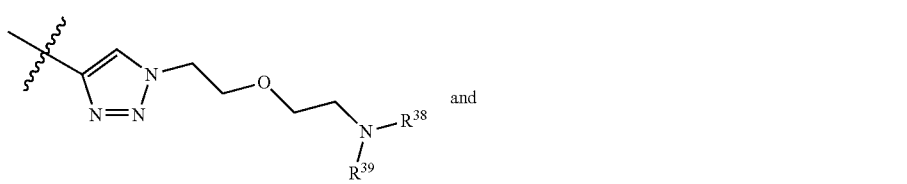
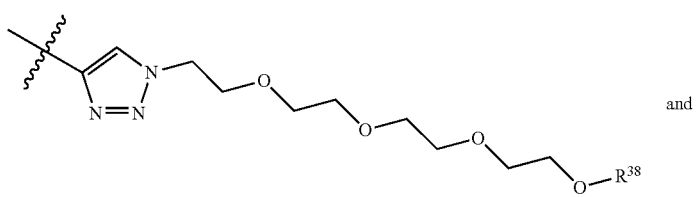
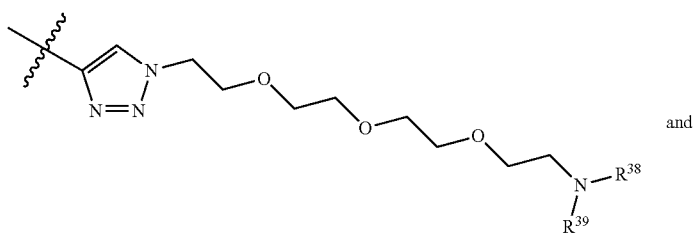
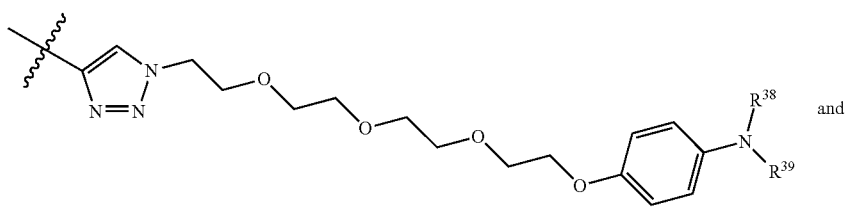
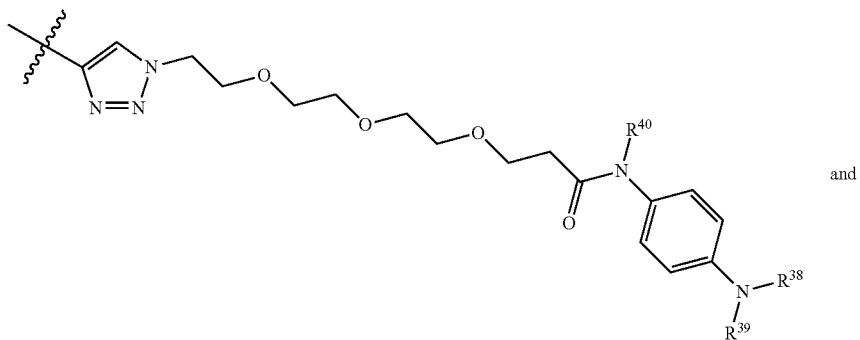

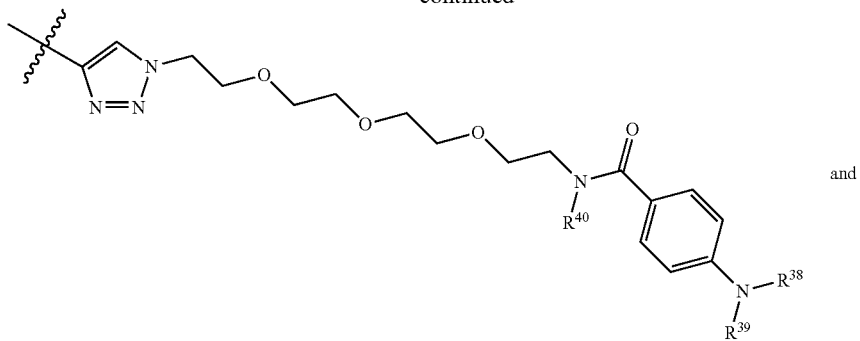

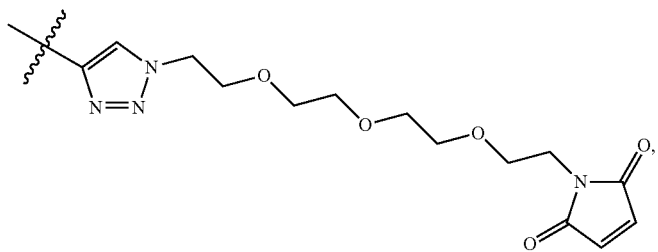

wherein $R^{38}$, $R^{39}$, and $R^{40}$ are independently selected from H and methyl.

In other embodiments, at least one of $R^1$, $R^5$, $R^{5'}$, $R^6$, $R^{6'}$, $R^7$, $R^{7'}$, $R^{14}$, $R^{14'}$, $R^8$, $R^{8'}$, $R^9$, $R^{9'}$, $R^{10}$, $R^{10'}$, $R^{11}$, $R^{11'}$, $R^{15}$, $R^{15'}$, $R^{15''}$, $R^{15'''}$, $R^{16}$, $R^{16'}$, $R^{20}$, $R^{20'}$, $R^{21}$, $R^{21'}$, $R^{22}$, and $R^{23}$, or at least one of $R^8$, $R^9$, $R^{10}$ and $R^{11}$, or at least one of $R^8$ and $R^9$, or at least $R^8$, or at least one of $R^5$, $R^6$, $R^7$, and $R^{14}$, or at least one of $R^6$ and $R^7$ in a compound of formula (I) or (II) is selected from

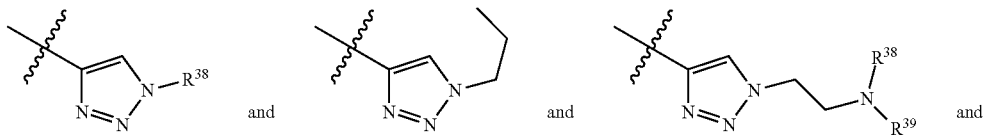

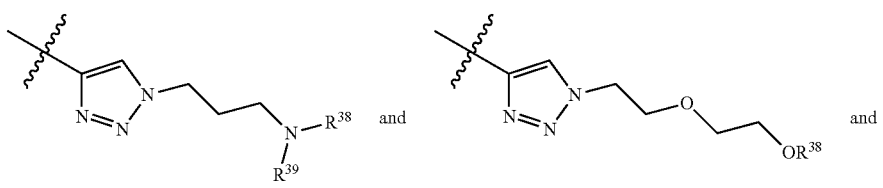

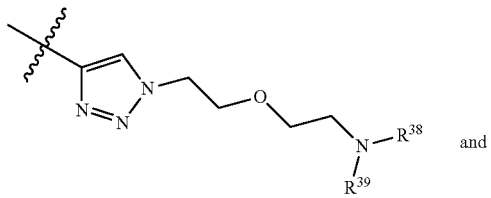

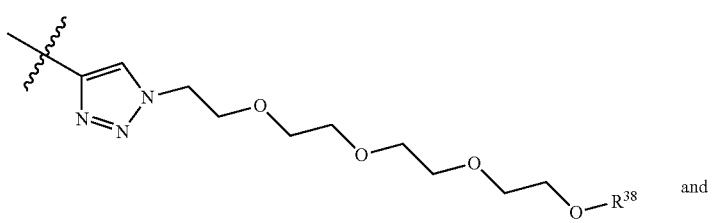

-continued
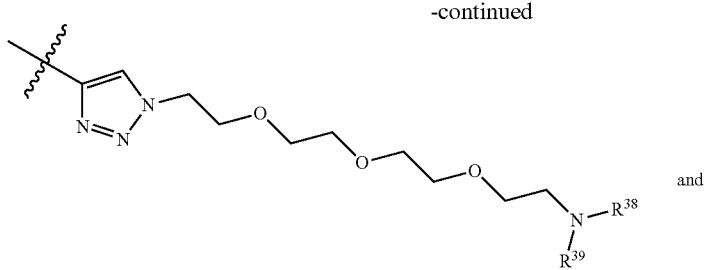
and
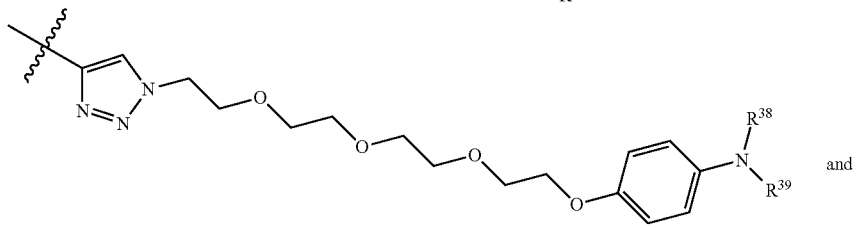
and
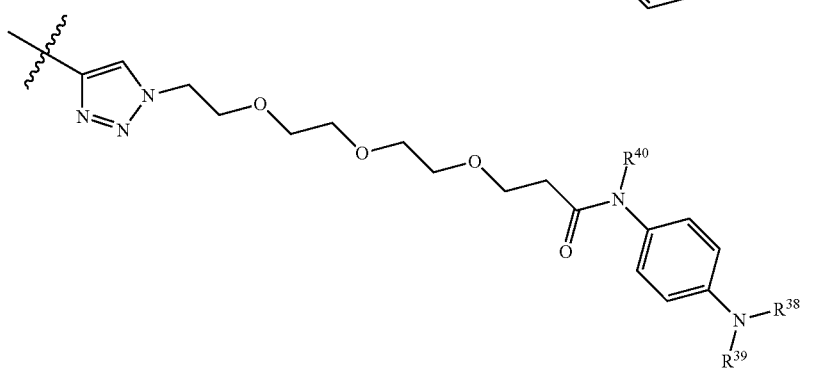
and
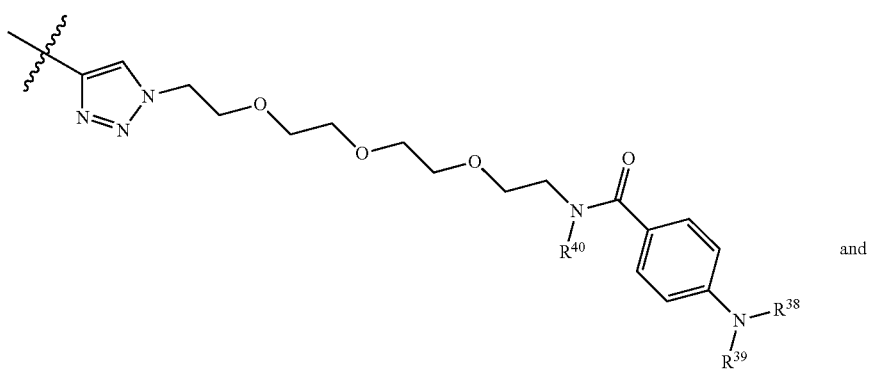
and
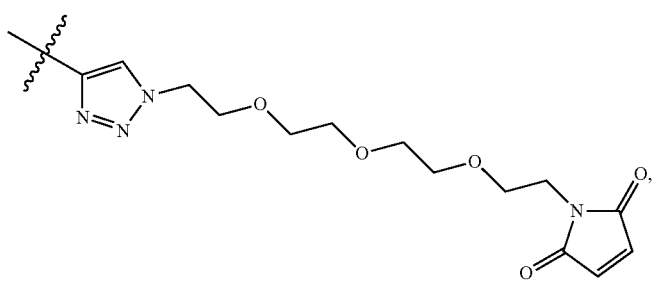
wherein $R^{38}$, $R^{39}$, and $R^{40}$ are independently selected from H and methyl.

In one aspect, compounds of formulae (I) and (II) are represented by compounds of formulae (Ib) and (IIb), respectively:

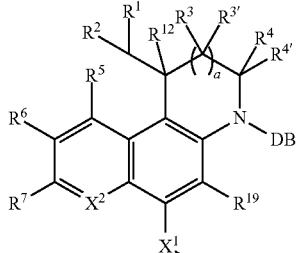
(Ib)

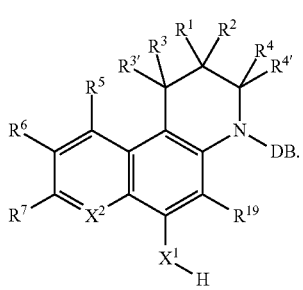
(IIb)

In one embodiment, $X^2$ in (Ib) or (IIb) is N.

In another embodiment, $X^2$ in (Ib) or (IIb) is $CR^{14}$.

In a further embodiment, $X^2$ in (Ib) is $CR^{14}$ and a is 0.

In another embodiment, $X^2$ in (Ib) or (IIb) is CH.

In yet another embodiment, $R^5$ in (Ib) or (IIb) is selected from nitro, halogen, amino, cyano, hydroxy, and optionally substituted $C_{1-3}$ alkylamino, di($C_{1-3}$ alkyl)amino, $C_{1-3}$ alkylcarbonylamino, $C_{1-3}$ alkoxycarbonylamino, $C_{1-3}$ alkylaminocarbonylamino, $C_{1-3}$ alkyloxy, $C_{1-3}$ alkylcarbonyloxy, $C_{1-3}$ alkylaminocarbonyloxy, or $C_{1-3}$ alkyl. In yet another embodiment, $R^5$ in (Ib) or (IIb) is optionally substituted linear $C_{1-3}$ alkyl. In another embodiment, $R^5$ in (Ib) or (IIb) is unsubstituted linear $C_{1-3}$ alkyl. In another embodiment, $R^5$ in (Ib) or (IIb) is methyl. In other embodiments, $R^5$ in (Ib) or (IIb) is ethyl or methoxy or ethoxy.

In yet another aspect, compounds of formulae (I) and (II) are represented by compounds of formulae (Ic) and (IIc), respectively:

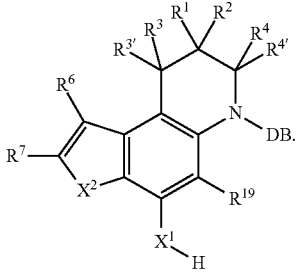
(Ic)

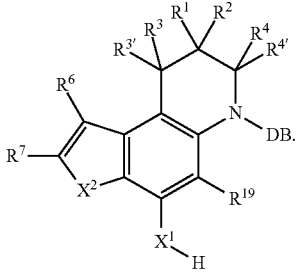
(IIc)

In one embodiment, $X^2$ in (Ic) or (IIc) is NH.

In yet another aspect, compounds of formulae (I) and (II) are represented by compounds of formulae (Id) and (IId), respectively:

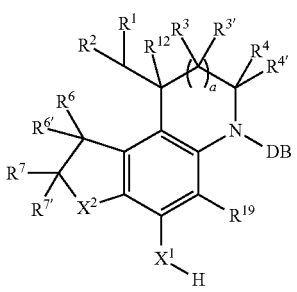
(Id)

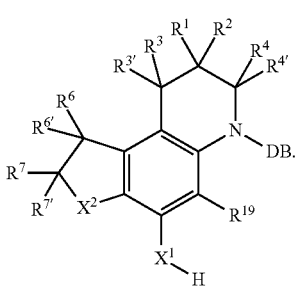
(IId)

In one embodiment, $X^2$ in (Id) or (IId) is NH.

In another embodiment, compounds of formulae (I) and (II) are represented by (Ia) and (IIa), respectively:

DA1-DB (Ia)

DA2-DB (IIa)

wherein DA1 is

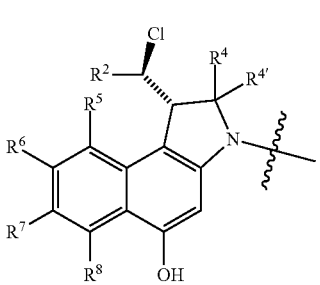

or an isomer or a mixture of isomers thereof.

In other embodiments, compounds of formulae (I) and (II) are represented by (Ia) and (IIa), respectively:
DA1-DB (Ia)
DA2-DB (IIa)
wherein DA1 is
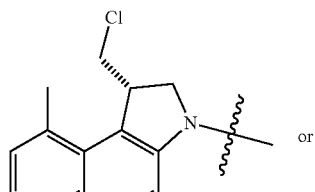 or
 or
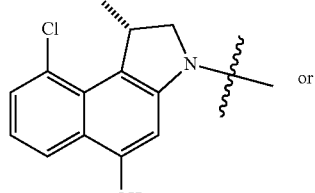 or
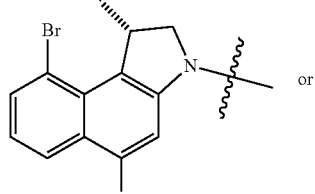 or
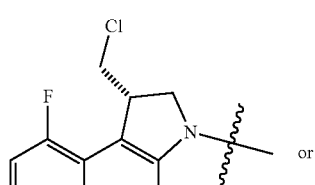 or
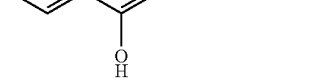
-continued
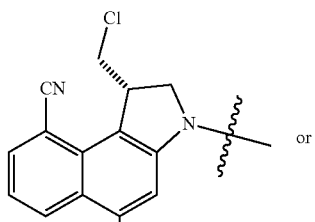 or
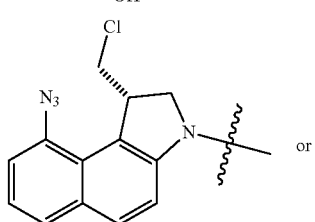 or
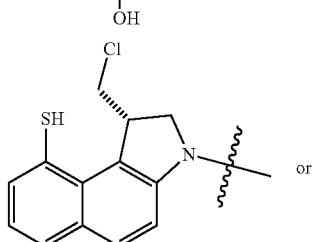 or
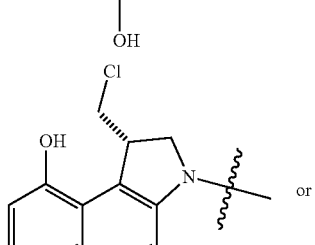 or
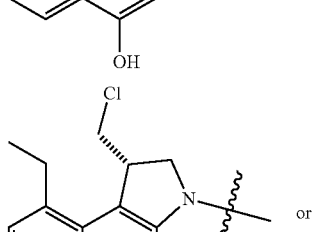 or
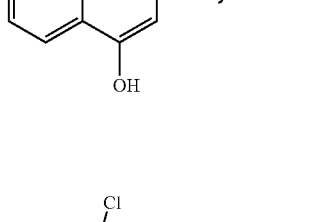 or
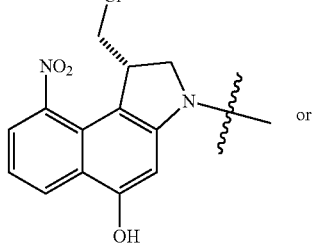 or

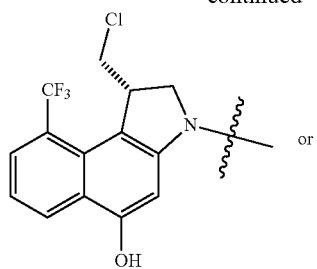
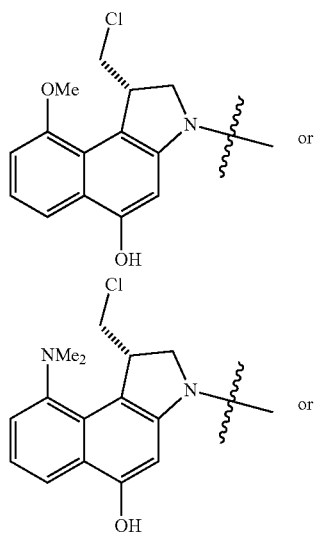
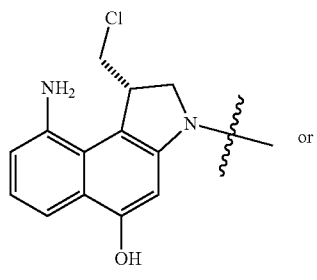
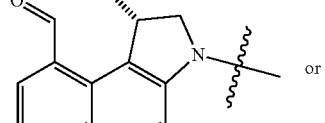
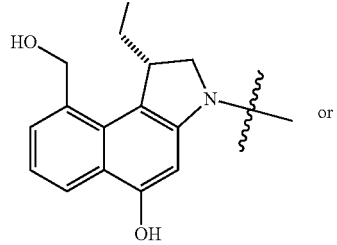
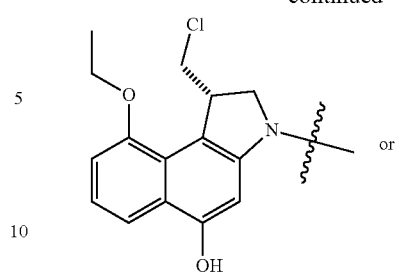
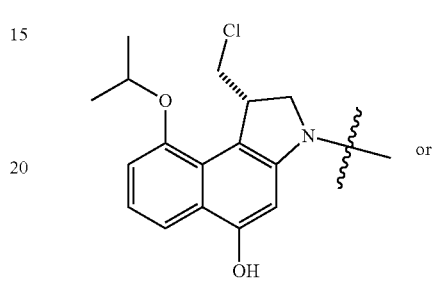

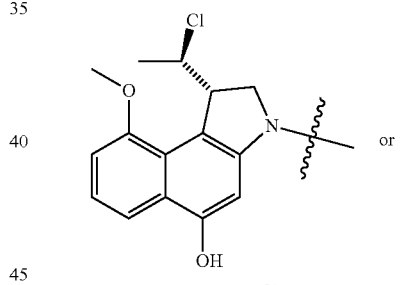
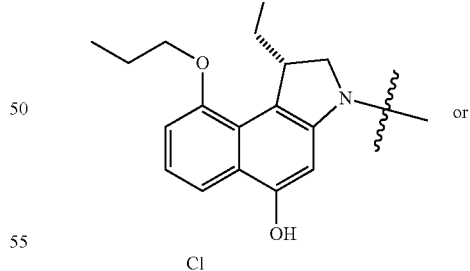
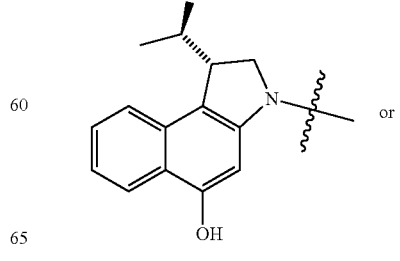

69
-continued
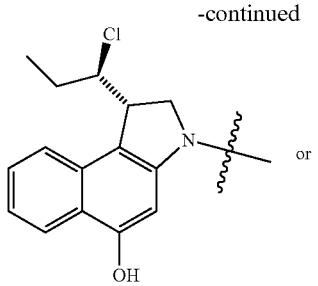
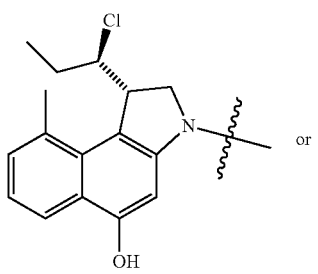
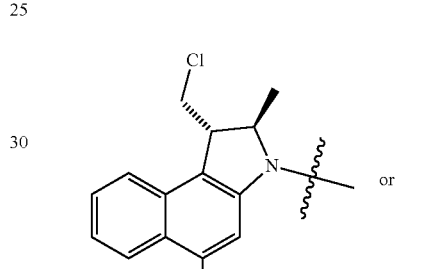
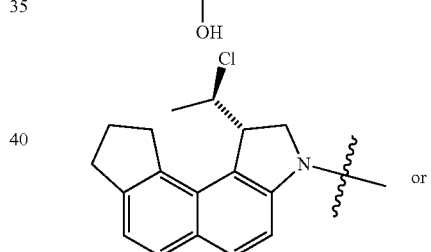
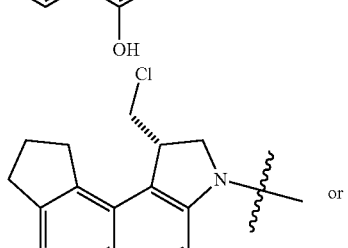
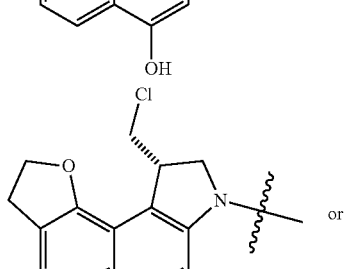
70
-continued
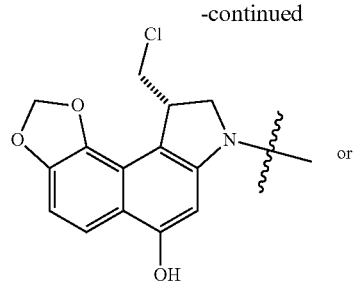
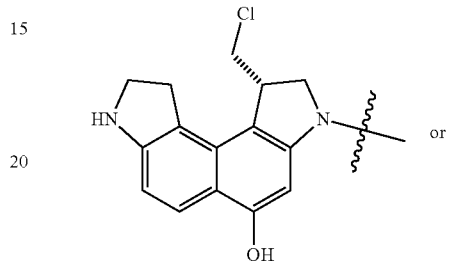
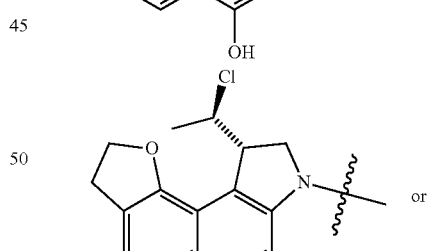
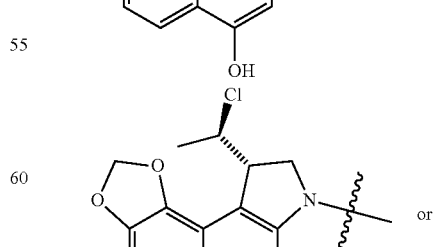
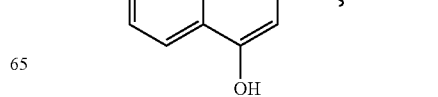

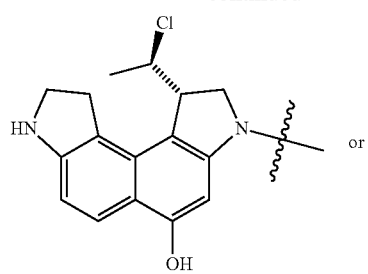
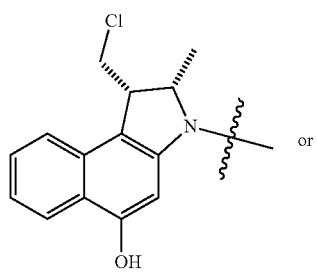
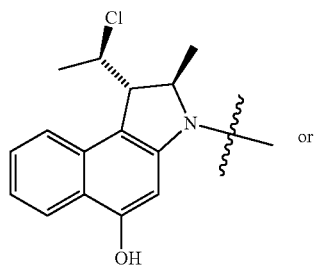
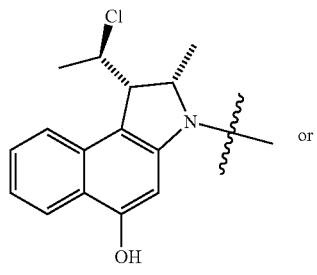
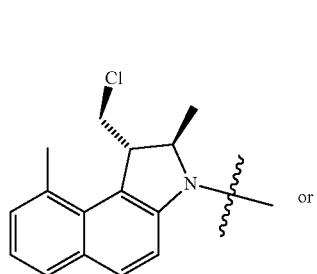
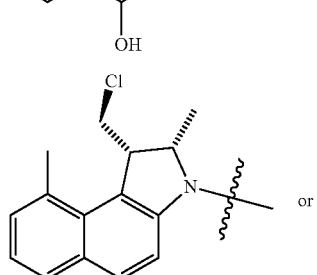
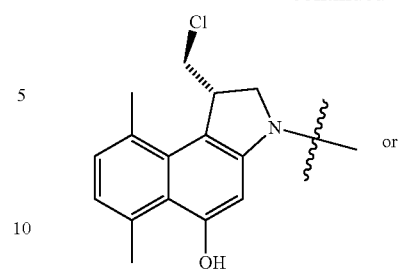
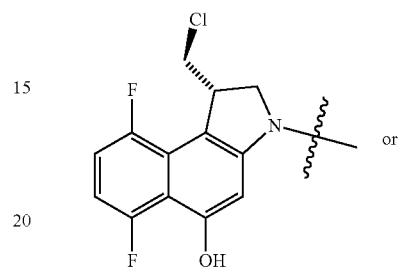
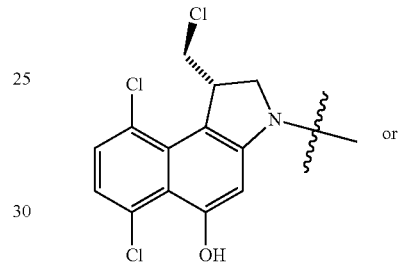
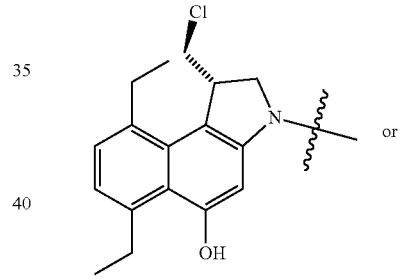
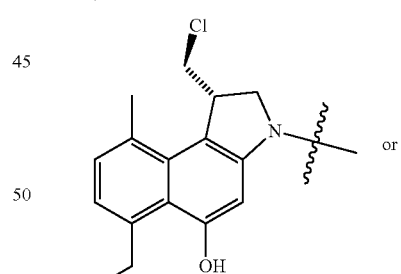
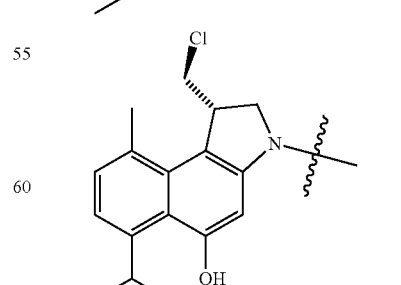
or an isomer of one of these, or a mixture of isomers.

In other embodiments, compounds of formulae (I) and (II) are represented by (Ia) and (IIa), respectively:

DA1-DB (Ia)

DA2-DB (IIa)

wherein DA1 is

[structure] or

[structure] or

[structure] or

[structure] or

[structure] or

-continued

[structure] or

[structure] or

[structure] or

[structure]

or an isomer of one of these, or a mixture of isomers.

In yet other embodiments, compounds of formulae (I) and (II) are represented by (Ia) and (IIa), respectively:

DA1-DB (Ia)

DA2-DB (IIa)

wherein DA1 is

[structure with $R^{51}$, $R^{52}$, $R^{54}$, $R^{55}$] or

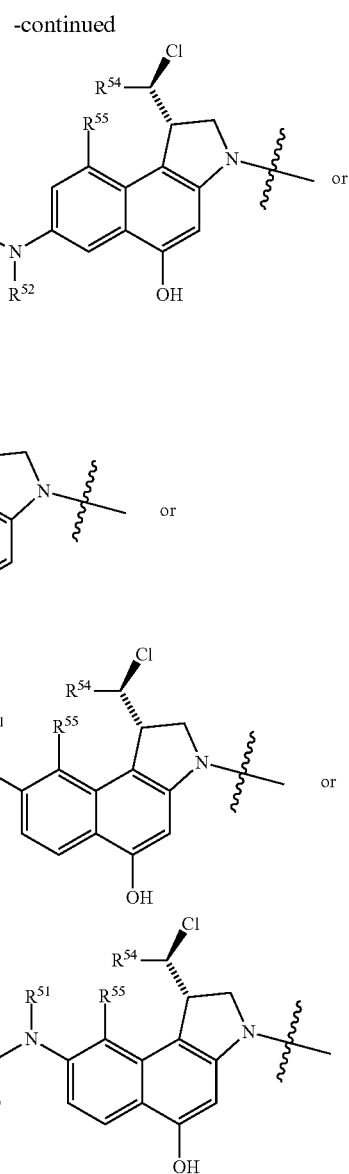
wherein $R^{54}$ is selected from H and optionally substituted $C_{1-3}$ alkyl (e.g., methyl or trifluoromethyl), $R^{55}$ is selected from H, methyl, ethyl, and methoxy, $X^{25}$ and $X^{26}$ are independently selected from O, S, $CH_2$, and $NR^{51}$, and $R^{51}$, $R^{52}$, and $R^{53}$ are independently selected from H, $C_{1-3}$ alkyl and
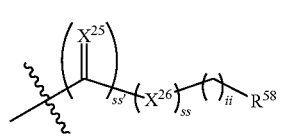 and 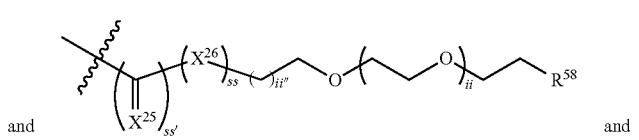 and

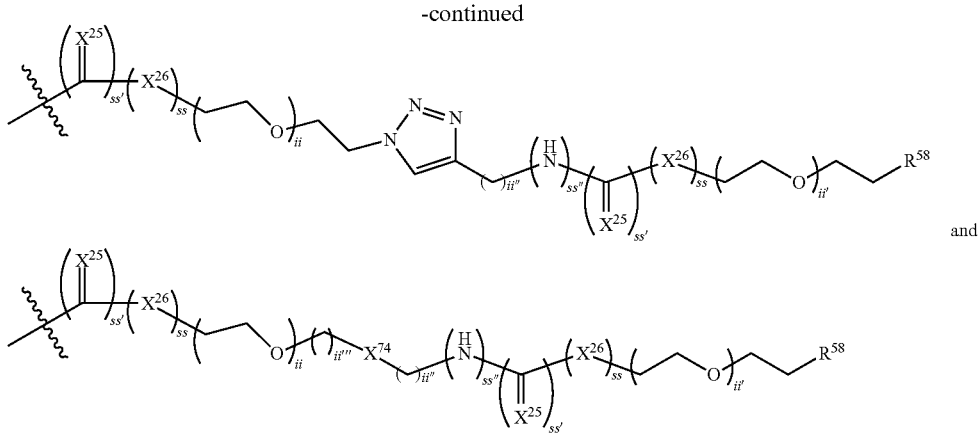

and wherein ii, ii', ii", and ii'" are independently selected from 0 to 8, $X^{74}$ is selected from

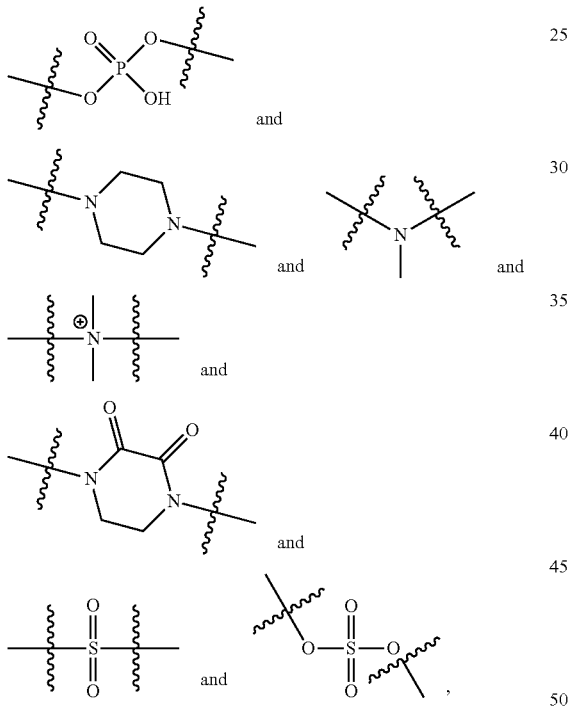

, each ss, ss', and ss" is independently selected from 0 and 1, each $X^{25}$ and $X^{26}$ is independently selected from O, S, $NR^{56}$, $H_2$, and $C(R^{56})R^{57}$, wherein $R^{56}$ and $R^{57}$ are independently selected from H and optionally substituted $C_{1-3}$ alkyl or $C_{1-3}$ heteroalkyl, and $R^{58}$ is selected from H, COOH, $CO_2Me$, OH, OMe, $NR^{59}R^{60}$, $NR^{59}C(O)CH_3$, SH, SMe,

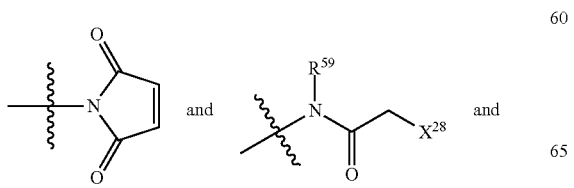

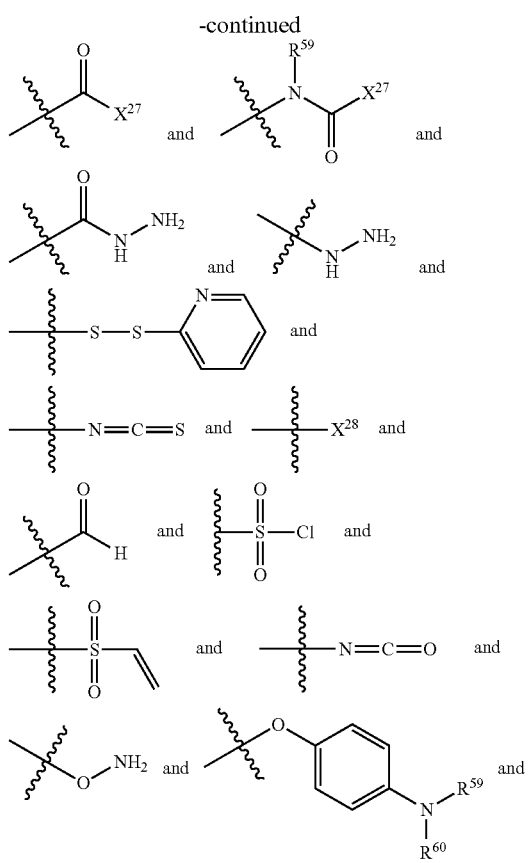

-continued

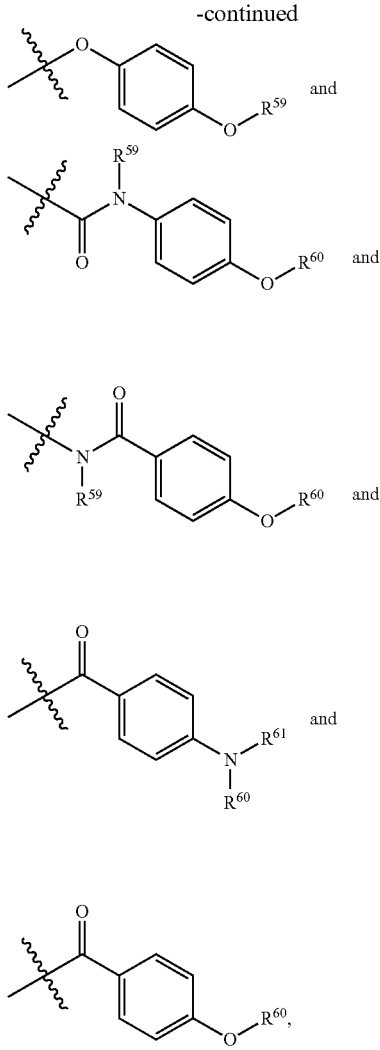

wherein $X^{27}$ is selected from halide, hydroxy, $OC(O)R^{aa}$, and $OC(O)OR^{aa}$, or $C(O)-X^{23}$ is an active ester, $X^{24}$ is selected from halide, mesyloxy, triflyloxy, and tosyloxy, $R^{aa}$ is selected from optionally substituted $C_{1-10}$ alkyl, $C_{1-10}$ heteroalkyl, $C_{3-10}$ cycloalkyl, $C_{1-10}$ heterocycloalkyl, $C_{5-10}$ aryl, and $C_{1-10}$ heteroaryl, and $R^{59}$, $R^{60}$, and $R^{61}$ are independently selected from methyl and H, or an isomer of one of these, or a mixture of isomers.

In another embodiment, a compound of formula (I) or (II) is

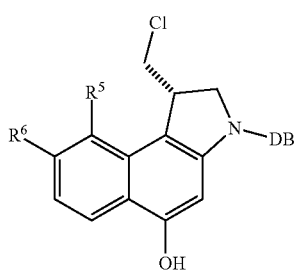

or an isomer thereof, or a mixture of isomers.

In another embodiment, a compound of formula (I) or (II) is

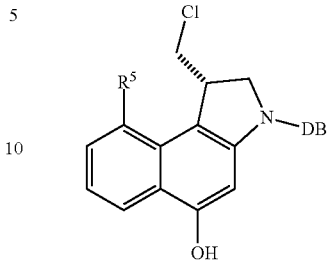

or an isomer thereof, or a mixture of isomers.

In other embodiments, a compound of formula (I) or (II) is

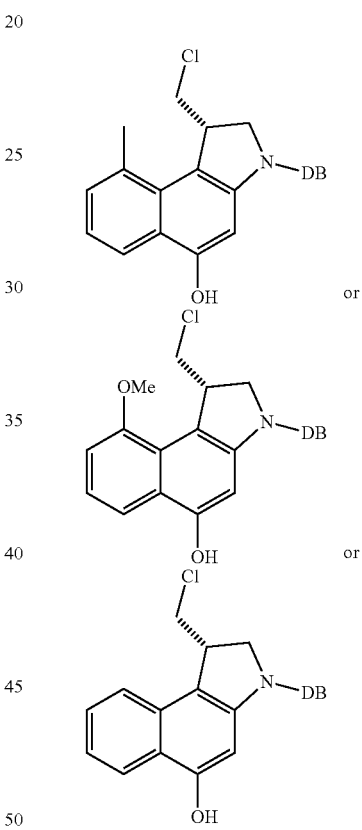

or an isomer of one of these, or a mixture of isomers.

In one embodiment, in a compound of formula (I) or (II), b=1. In another embodiment, b=0. In another embodiment, a=0. In yet another embodiment, a=1. In yet another embodiment, a=0 and b=1.

Increased water solubility of a compound of formula (I) or (II) may not only be achieved through the introduction of water-soluble or polar groups, such as a triazole group or an oligoethylene glycol or polyethylene glycol moiety or a combination thereof, but may also be achieved through substitution of carbon ring atoms by heteroatoms, for example in the DNA-binding unit. Improved water solubility of compounds of formulae (I) and (II) and their conjugates may lead to improved yields and purity of the conjugates during synthesis, for example due to reduced aggregate formation. Furthermore, a reduced tendency for aggregation and a higher purity of the conjugate may for example lead to fewer side effects after administration of the conjugate.

Increased metabolic degradation, e.g., in the liver, may for example be achieved through the introduction of groups in the DNA-binding units that can be oxidized with relative ease, for example acetylene and alkene moieties. Oxidation of toxic compounds is one of the mechanisms by which a mammal may detoxify such compounds. If compounds of this invention are taken up in the liver, efficient detoxification may for example circumvent liver toxicity as a side effect.

The stability of the linkage between the DNA-binding unit and DNA-alkylating unit, for example in the circulation, may be tuned by modifications in the DNA-binding unit. It may be favorable to have the DNA-alkylating unit and DNA-binding unit linked via an essentially non-cleavable bond. Especially when the compound of formula (I) or (II) is administered as the active ingredient, stability in the circulation may be desired. However, when a compound of formula (I) or (II) is administered as a part of a conjugate, it may be favorable to have a bond between the DNA-alkylating unit and the DNA-binding unit that becomes less stable in the circulation as soon as the compound of formula (I) or (II) is prematurely released from the conjugate. This may reduce toxic side effects as a consequence of premature release of the agent. The DNA-binding units of this invention may cause a compound of formula (I) or (II) or its conjugate or linker-agent conjugate to have a more stable linkage between DNA-binding and DNA-alkylating unit in the circulation than a compound of formula (I') or (II'), which may be formed from a compound of formula (I) or (II) as soon as $X^1$ is unprotected.

Extension of the π-conjugated system in the DNA-binding moiety may increase the binding affinity of the DNA binder for DNA. The π system may be extended by the introduction of additional aromatic rings and/or conjugated double and/or triple bonds.

Promoieties may be connected to the DNA-binding units if a suitable functional group is present. This may for example be a hydroxyl group or a primary or secondary amino group. Coupling of a promoiety to the DNA-binding unit in addition to or instead of to the alkylating unit, e.g., to $X^1$, may provide advantages. For example, the presence of two promoieties may increase target-selective delivery and/or activation and/or reduce the amount of free agent in non-targeted areas, thereby reducing side effects and increasing the therapeutic index.

The DNA-binding unit DB in a compound of formula (I) or (II) is selected from structures DB1-DB9:

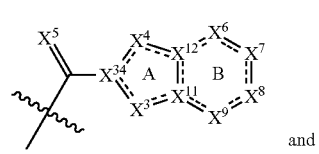

and

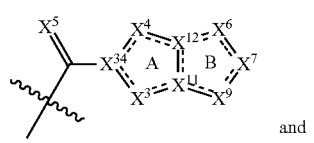

and

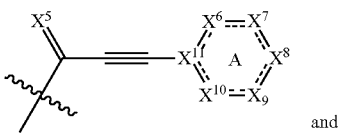

and

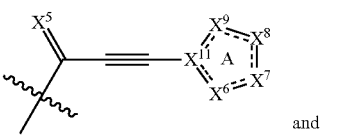

and

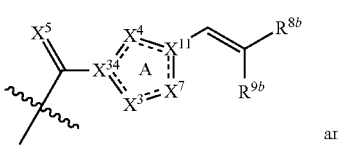

and

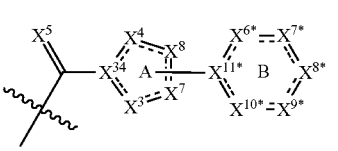

and

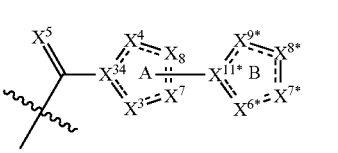

and

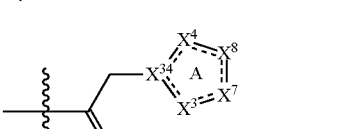

and

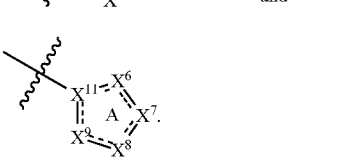

In one embodiment, the DNA-binding unit comprises at least two aromatic rings of which at least one contains at least one ring atom that is a heteroatom or the DNA-binding unit comprises at least a bicyclic aromatic system in which at least one ring atom is a heteroatom. In another embodiment, the DNA-binding unit comprises at least two aromatic rings and both contain at least one ring atom that is a heteroatom or the DNA-binding unit comprises at least a bicyclic aromatic system in which at least two ring atoms are a heteroatom.

In one aspect of this invention, a compound of formula (I) or (II) has a DNA-binding unit of formula DB1. This moiety comprises structures that at least contain a 6-membered ring B that is connected to the DNA-alkylating unit via a fused 5- or 6-membered ring A or vinyl group. The optional heteroatom in said ring B may provide for improved water solubility with respect to DNA binder analogs having an all-carbon ring. In one embodiment, ring B in unit DB1 contains a heteroatom.

Preferably, ring B is aromatic. It may for example be a phenyl, pyridine, pyrimidine, pyridazine, pyrazine, 1,3,5-triazine, 1,2,3,5-tetrazine, 1,2,3,4-tetrazine, pentazine, phosphinine, 1,3-diphosphinine, or 1,3-azaphosphinine moiety. Alternatively, this ring may be non-aromatic and either be unsaturated or completely saturated.

A compound of formula (I) or (II) wherein ring B is connected to the DNA-alkylating unit via a vinyl group may contain a handle that allows for detoxification by means of for example oxidation or hydration of the double bond.
The moiety DB1 may for example be
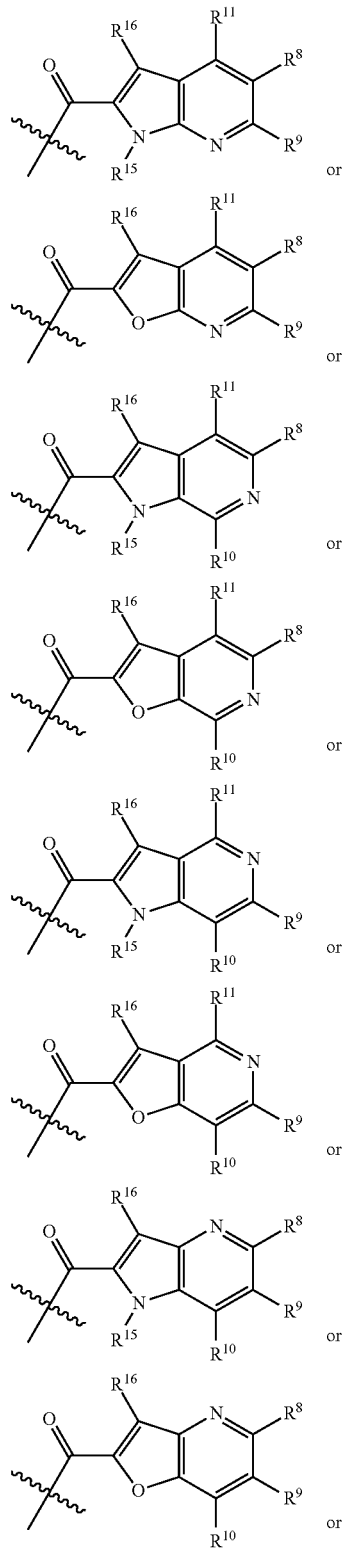
or
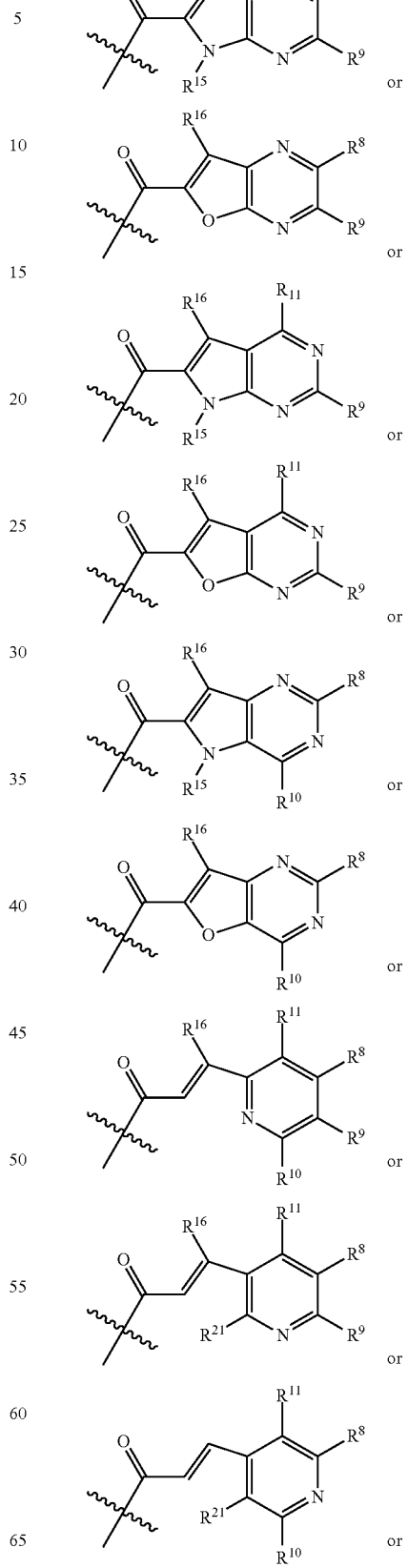
or

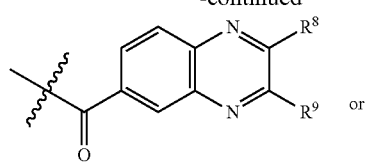 or
 or
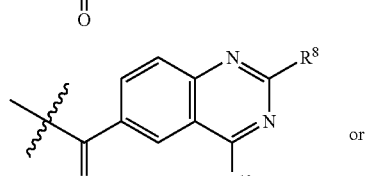 or
 or
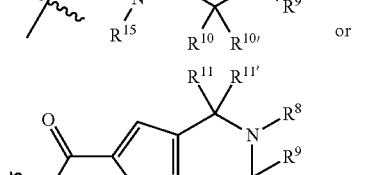 or
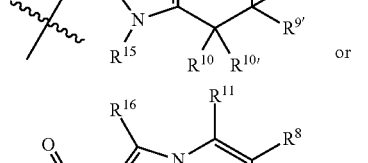 or
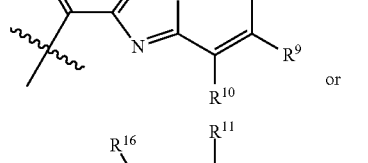 or
 or
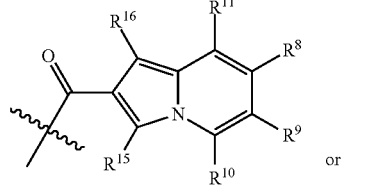 or
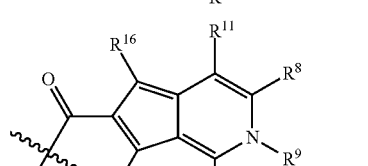 or
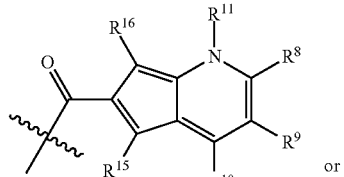 or
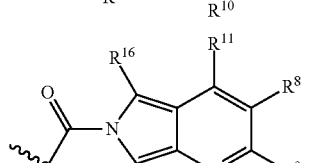 or
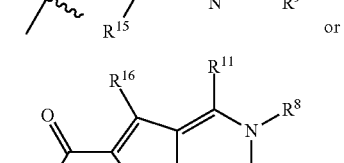 or
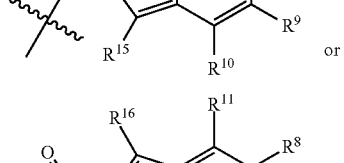 or
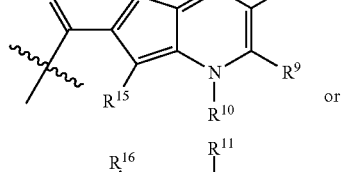 or
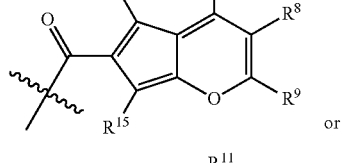 or
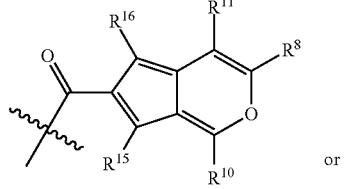 or
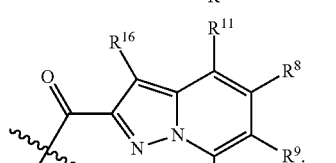 or
Moiety DB1 may for example also be
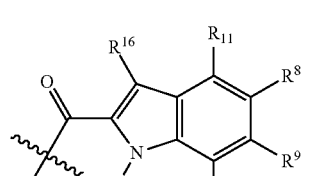 or

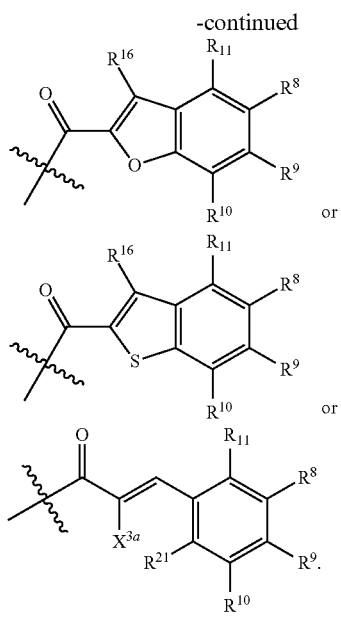
In another embodiment, the moiety DB1 may be
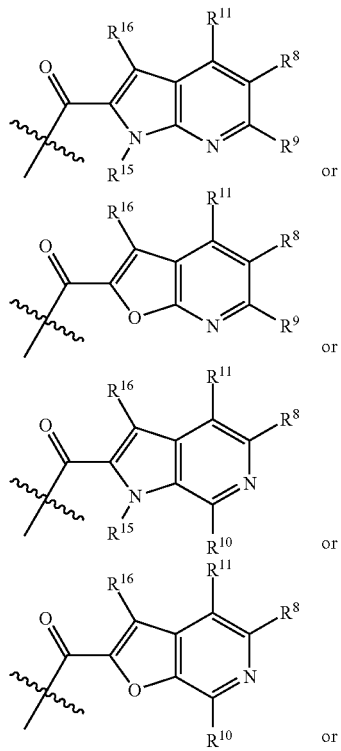
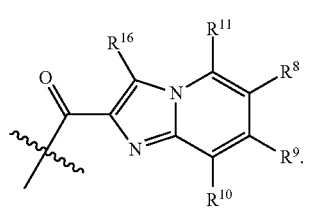
In another embodiment, the moiety DB1 may be
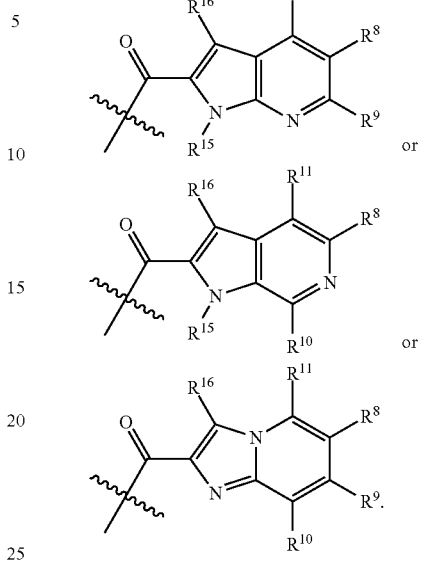
In another embodiment, the moiety DB1 may for example be
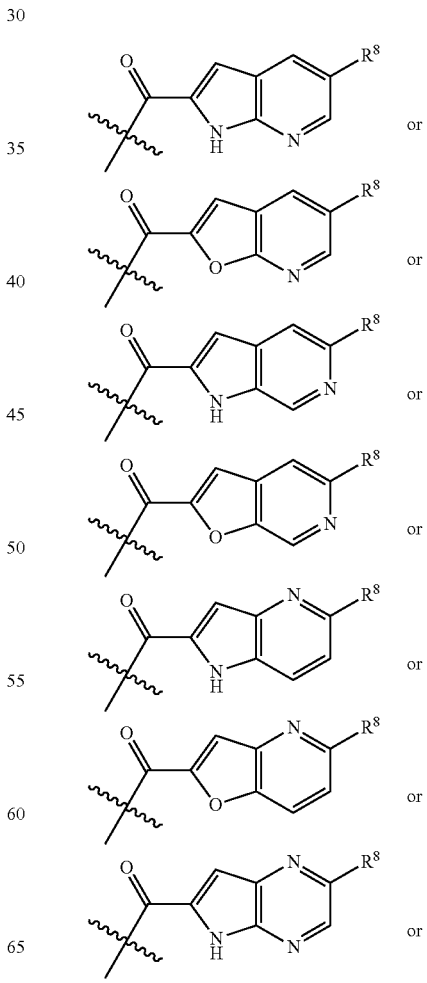

-continued
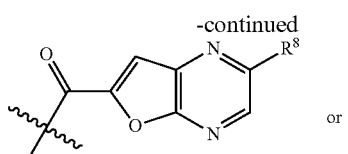
or
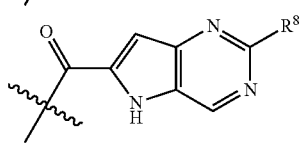
or
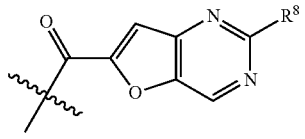
or
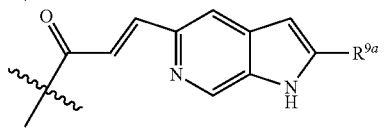
or
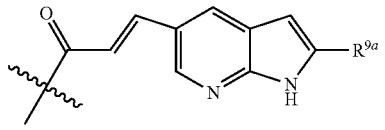
or
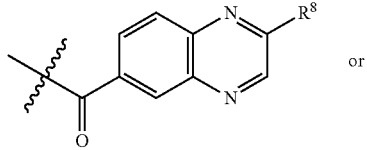
or
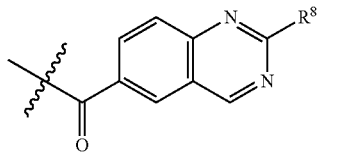
or
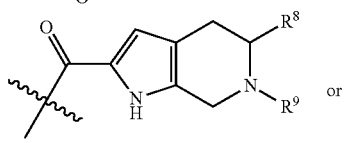
or

or
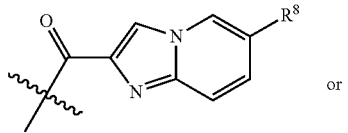
or
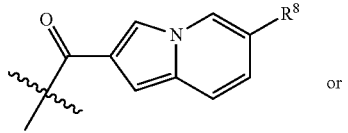
or
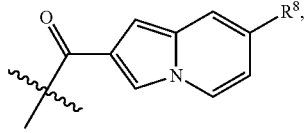
,
wherein $R^{9a}$ has the same meaning as defined for $R^9$ and is independently selected.
In a further embodiment, the moiety DB1 may be selected from
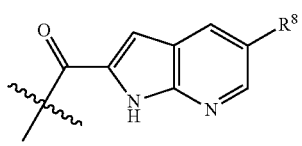
and
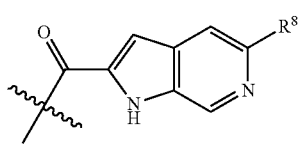
and
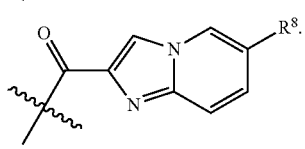
.
In one embodiment, the moiety DB1 is
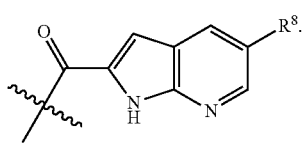
.
In another embodiment, the moiety DB1 is
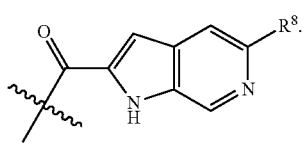
.
In yet another embodiment; the moiety DB1 is
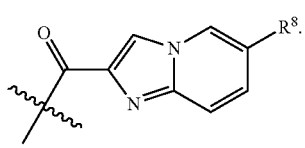
.
The moiety DB1 may for example also be
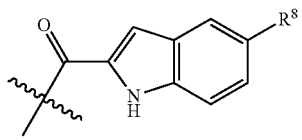
or
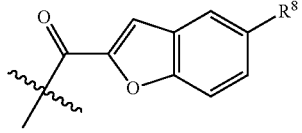
or

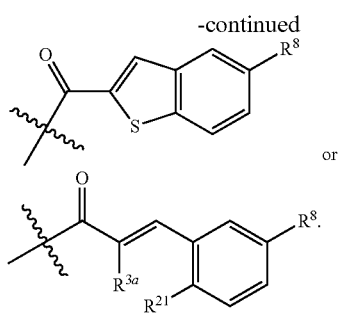
or
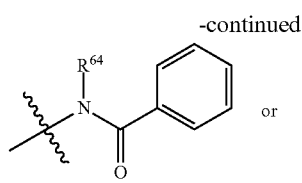
or
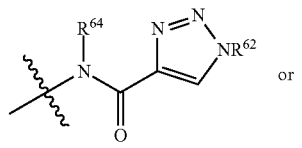
or
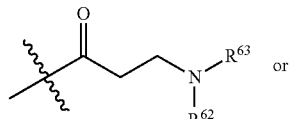
or
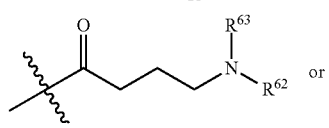
or
In the exemplary structures of DB1, $R^8$, $R^{8'}$, $R^9$, $R^{9'}$, $R^{9a}$, $R^{10}$, $R^{10'}$, $R^{11}$, $R^{11'}$, $R^{15}$, $R^{16}$, and $R^{21}$ may for example each independently be selected to be H, be or contain another moiety selected from structures DB1-DB9 or a derivative thereof, or be
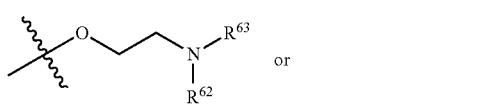
or
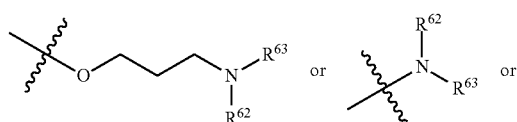
or
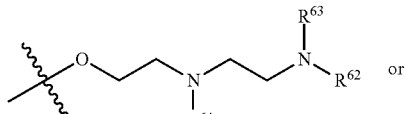
or
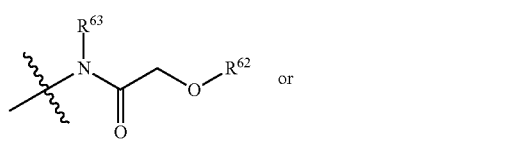
or

or
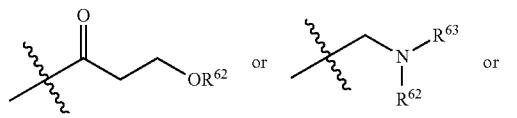
or
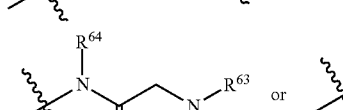
or
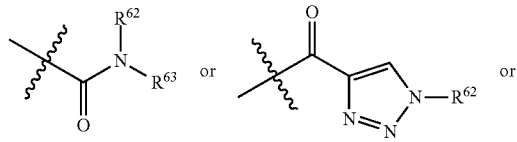
or
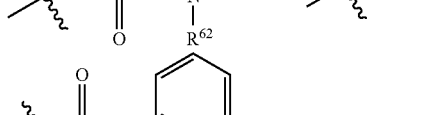
or
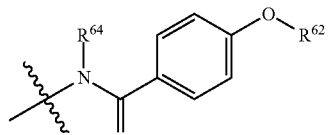
or
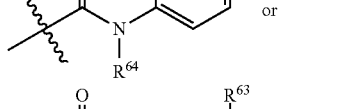
or

or

or
or
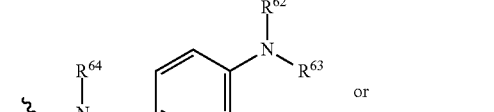
or
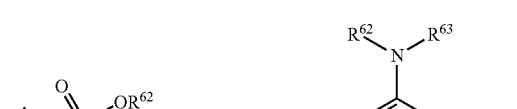
or

or
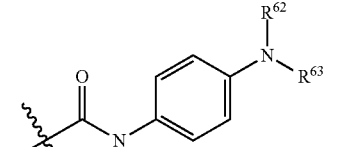
or
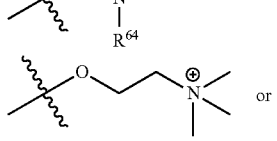
or -continued
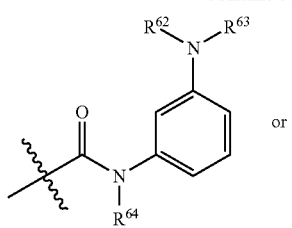 or
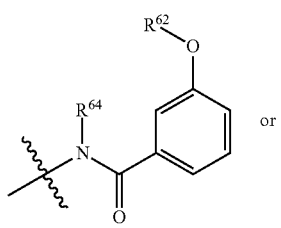 or
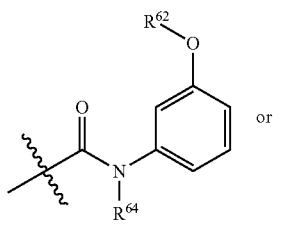 or
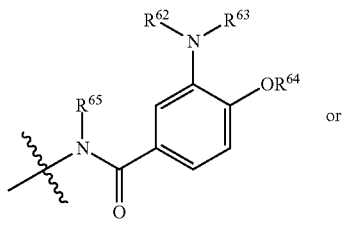 or
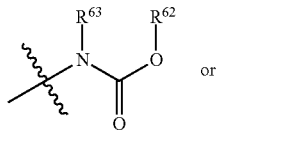 or
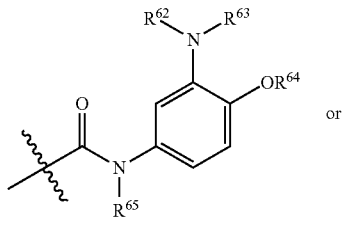 or
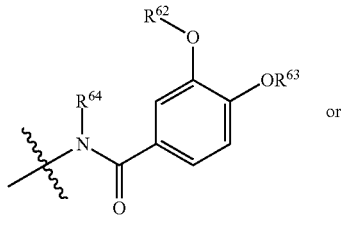 or
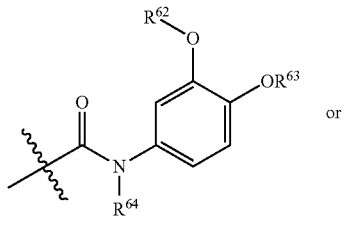 or
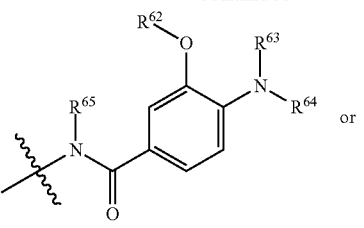 or
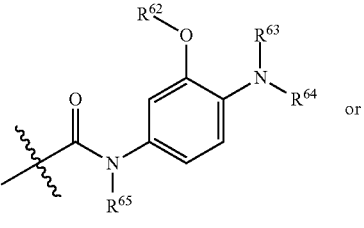 or
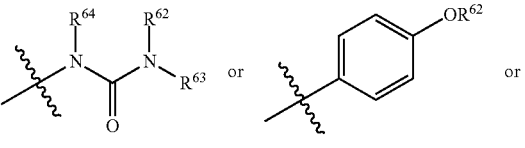 or
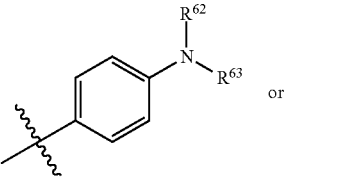 or
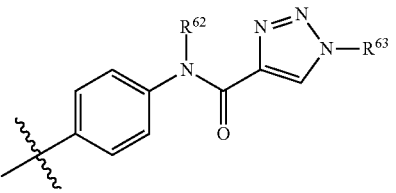 or
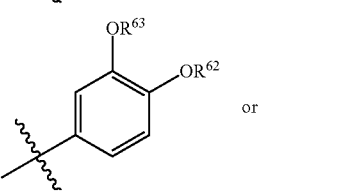 or
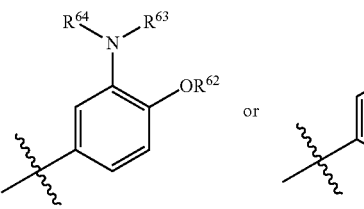 or
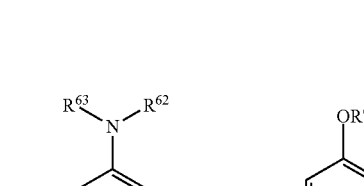 or
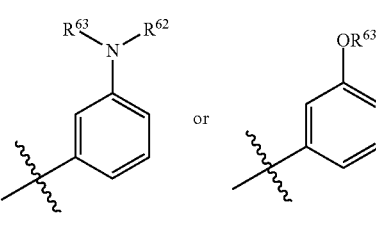 or -continued
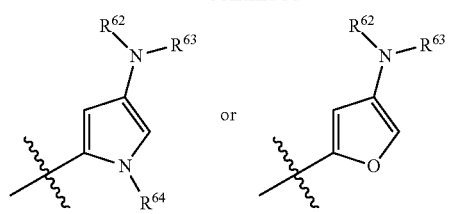 or
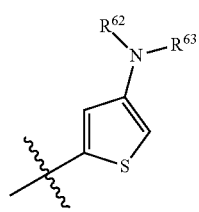 or
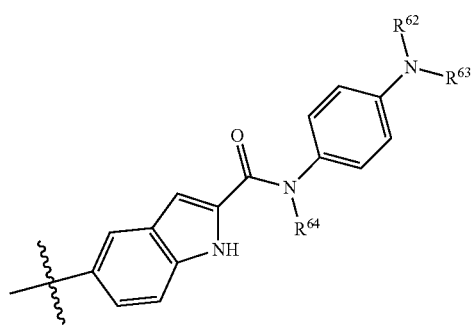 or
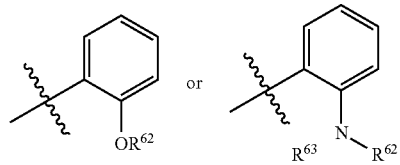 or
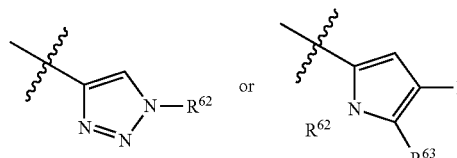 or
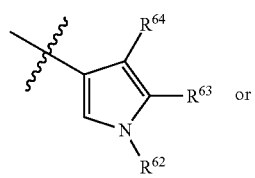 or
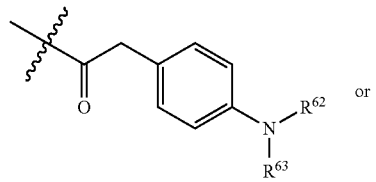 or
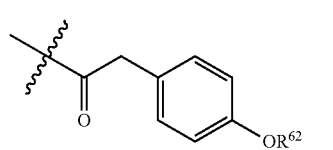 or
-continued
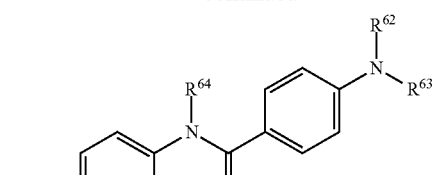 or
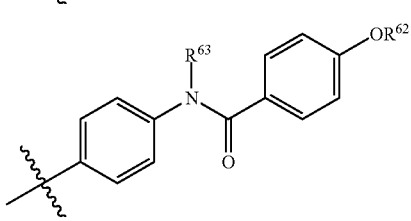 or
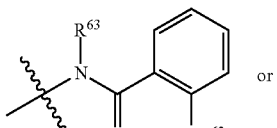 or
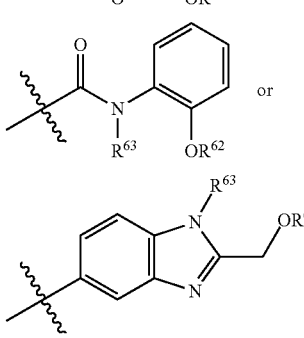 or
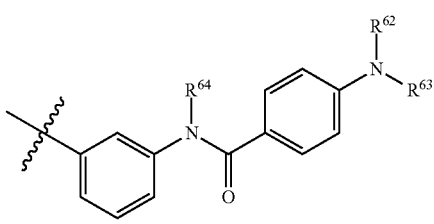 or
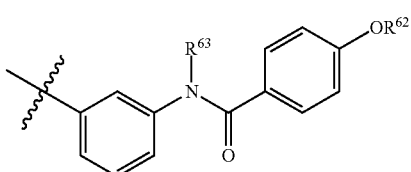 or
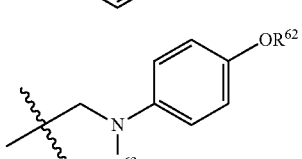 or
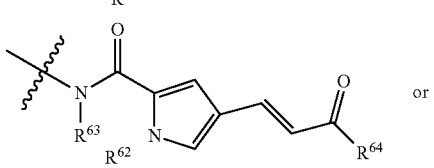 or -continued

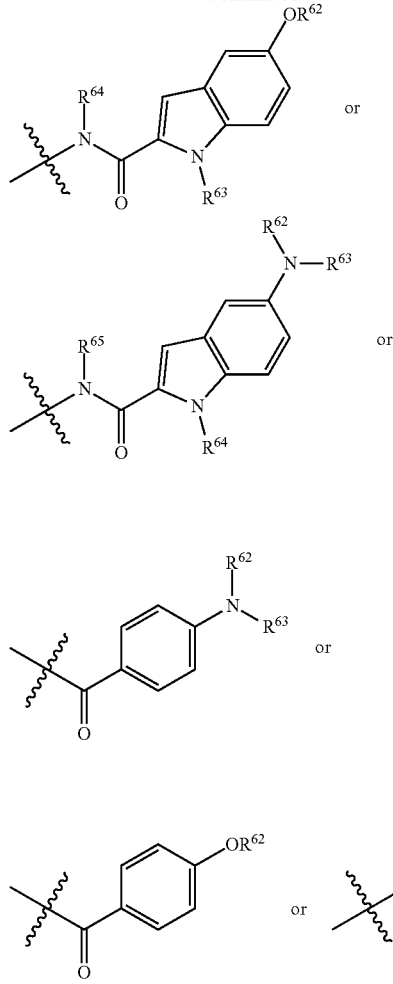

wherein $R^{62}$, $R^{63}$, $R^{64}$ and $R^{65}$ are independently selected from H, $C_{1-3}$ alkyl, and wherein jj, jj', jj", and jj'" are independently selected from 0 to 8, $X^{74}$ is selected from

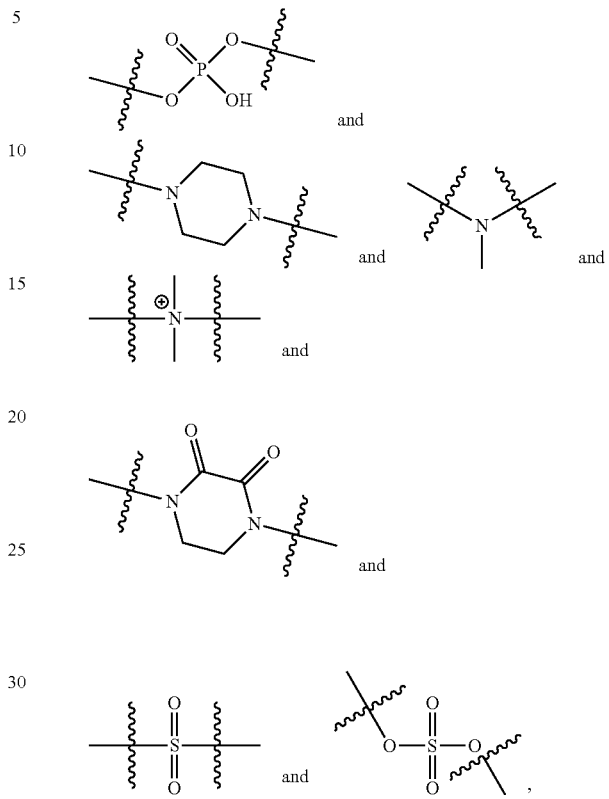

each tt, tt', and tt" is independently selected from 0 and 1, each $X^{21}$ and $X^{22}$ is independently selected from O, S, $NR^{67}$, $H_2$, and $C(R^{67})R^{68}$, wherein $R^{67}$ and $R^{68}$ are independently selected from H and optionally substituted $C_{1-3}$ alkyl or $C_{1-3}$ heteroalkyl, and $R^{66}$ is selected from H, COOH, $CO_2Me$, OH, OMe, $NR^{69}R^{70}$, $NR^{69}C(O)CH_3$, SH, SMe,

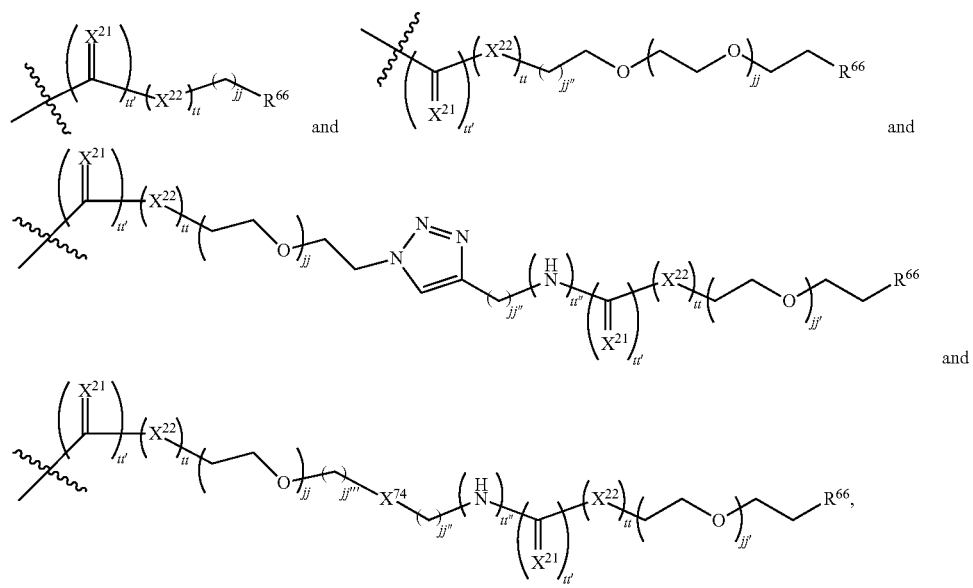

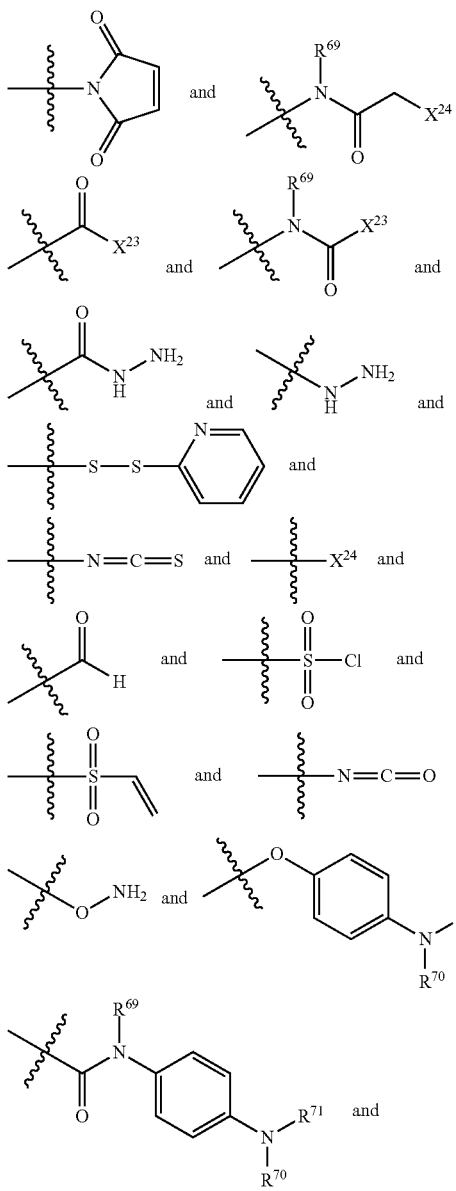

-continued

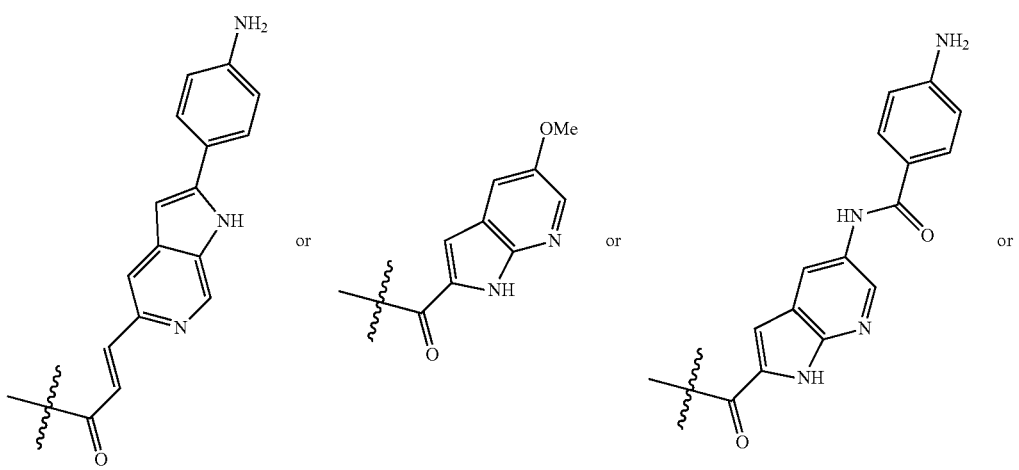

wherein $X^{23}$ is selected from halide, hydroxy, $OC(O)R^{bb}$, and $OC(O)OR^{bb}$, or $C(O)-X^{23}$ is an active ester, $X^{24}$ is selected from halide, mesyloxy, triflyloxy, and tosyloxy, $R^{bb}$ is selected from optionally substituted $C_{1-10}$ alkyl, $C_{1-10}$ heteroalkyl, $C_{3-10}$ cycloalkyl, $C_{1-10}$ heterocycloalkyl, $C_{5-10}$ aryl, and $C_{1-10}$ heteroaryl, and $R^{69}$, $R^{70}$, and $R^{71}$ are independently selected from methyl and H.

In a further embodiment, the moiety DB1 may for example be

-continued
101                                    102
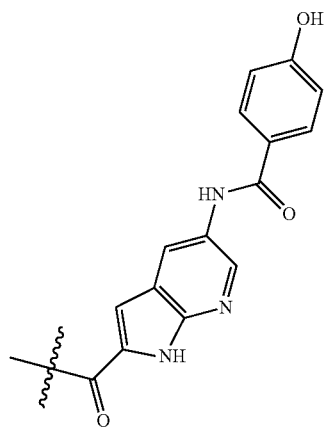 or 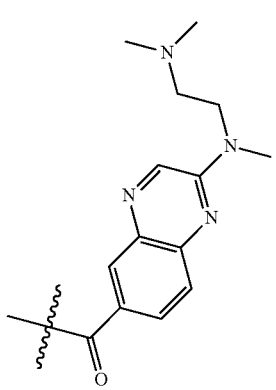 or
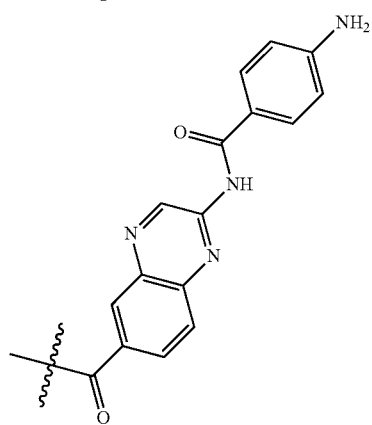 or 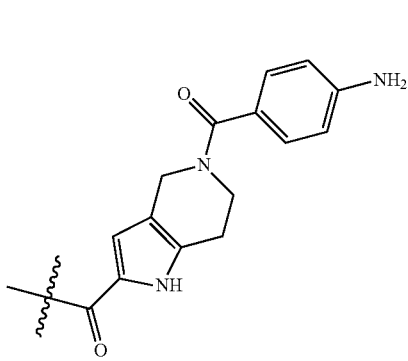 or
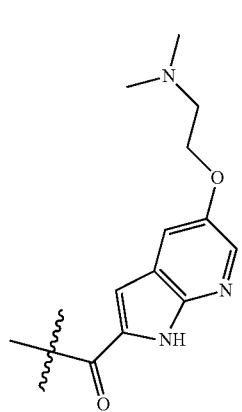 or 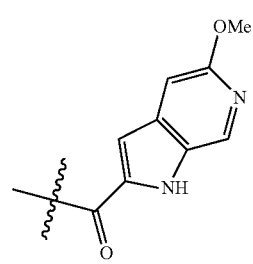 or 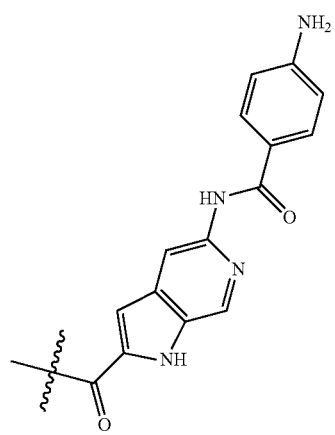 or
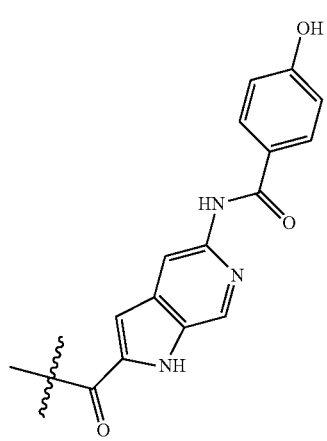 or  or 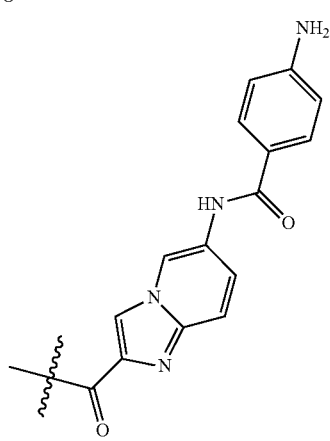 or 103
-continued
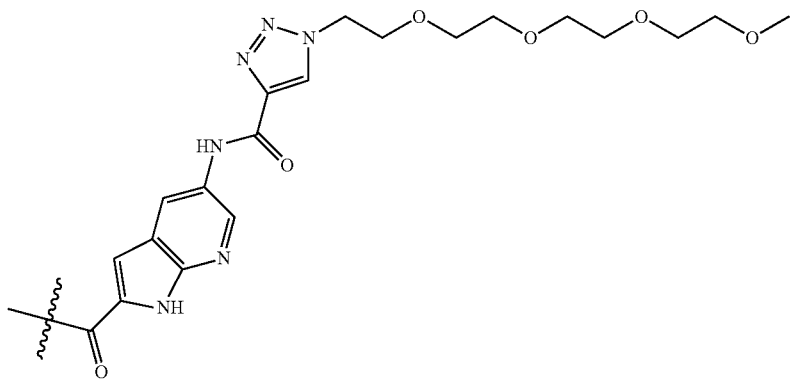
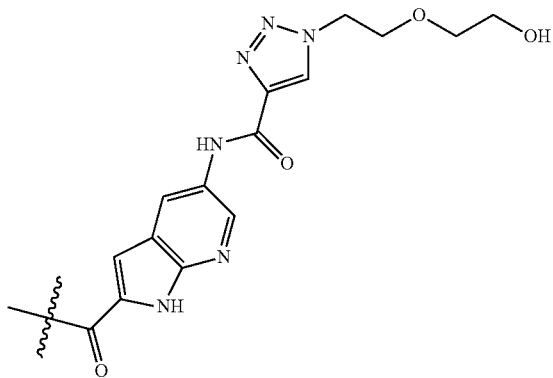
or
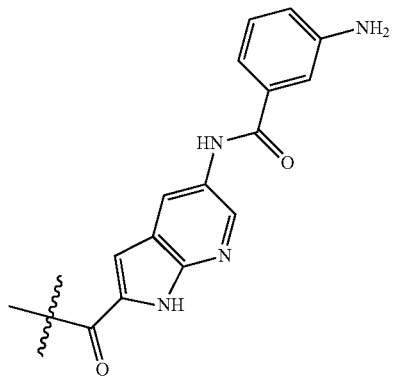
or
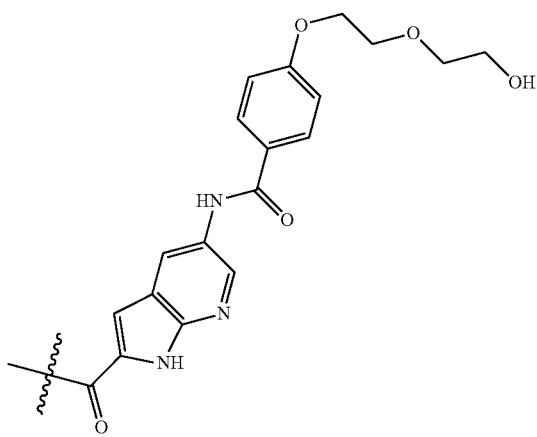
or
104
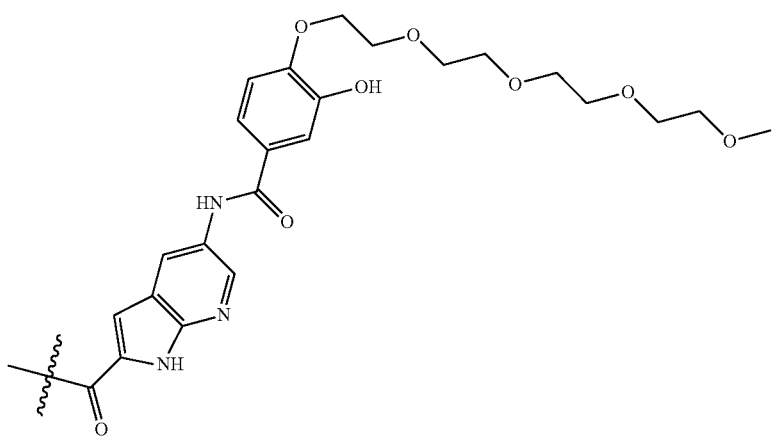
or

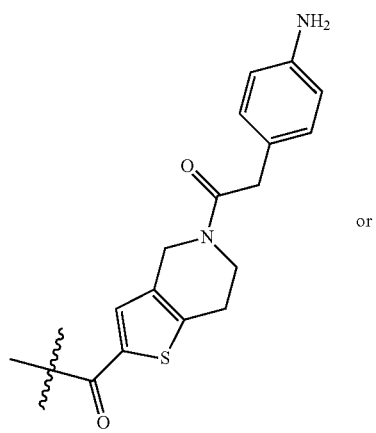
or
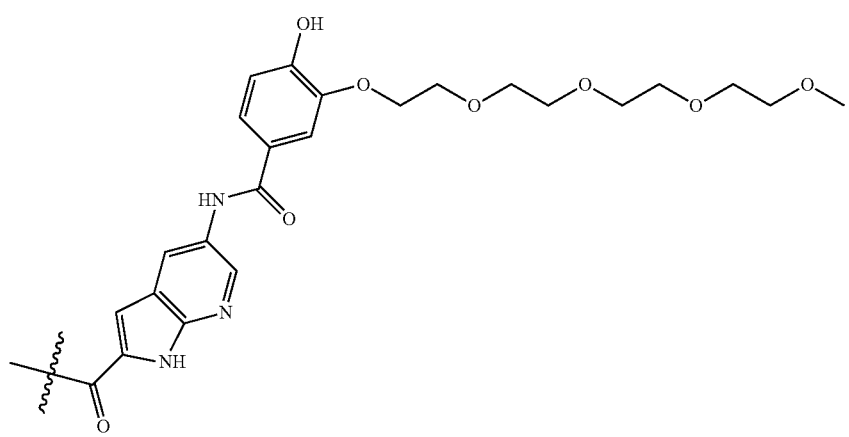
or
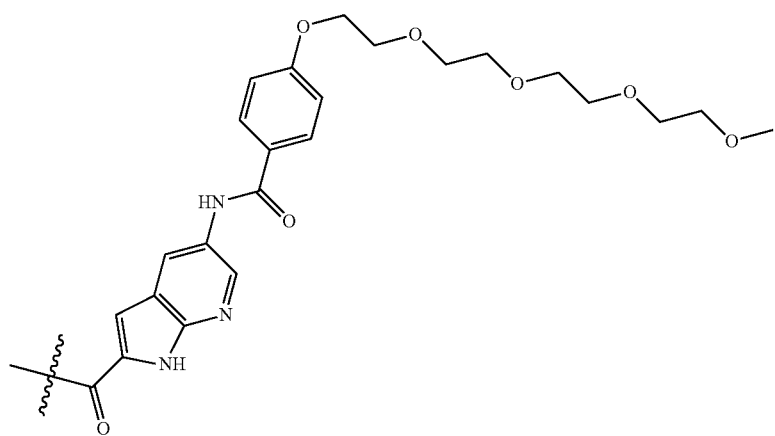
or

-continued
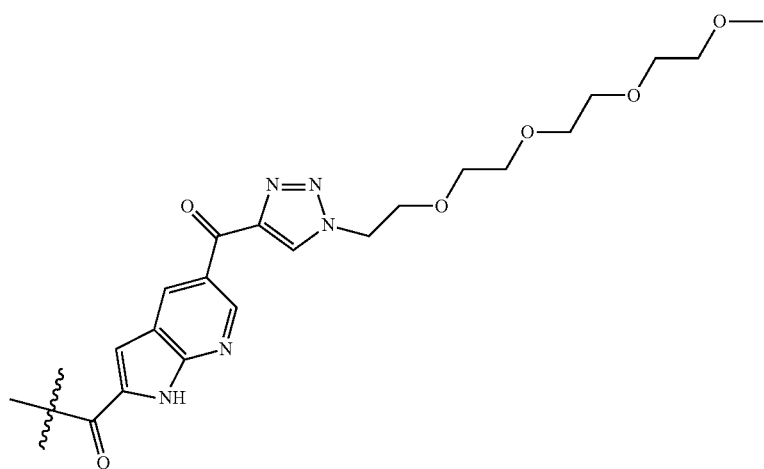
or
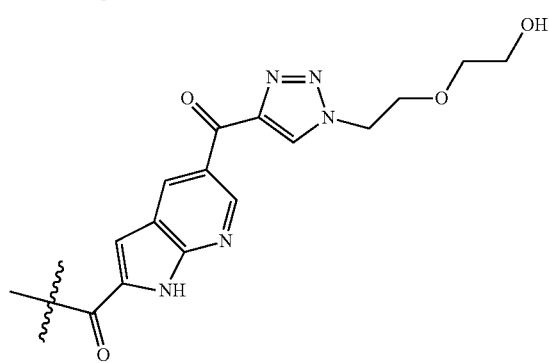
or
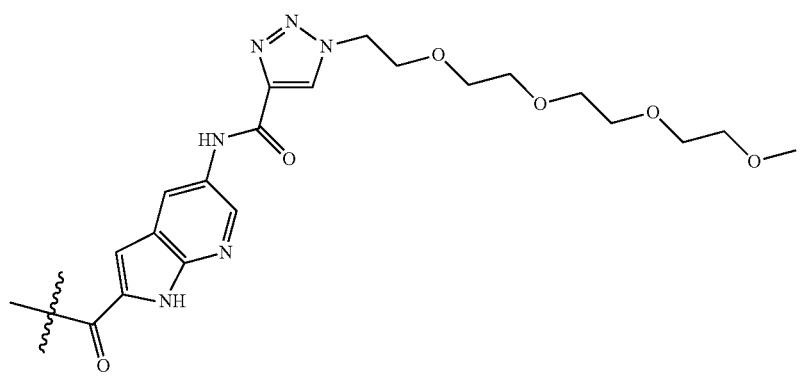
or
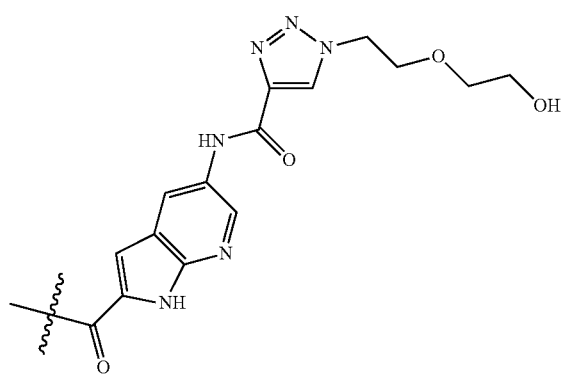
or

-continued
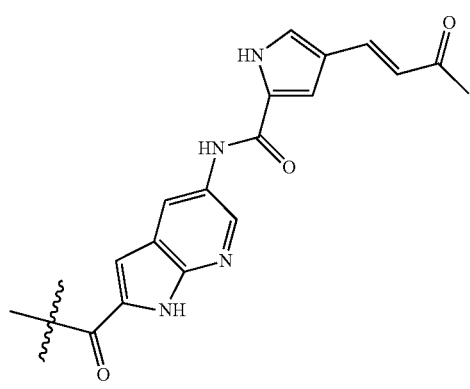 or 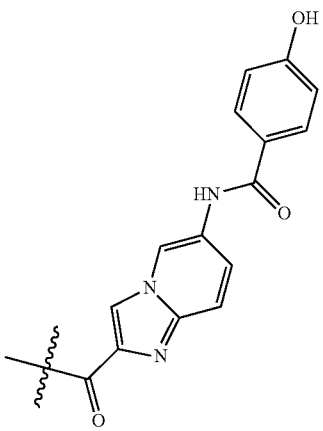 or
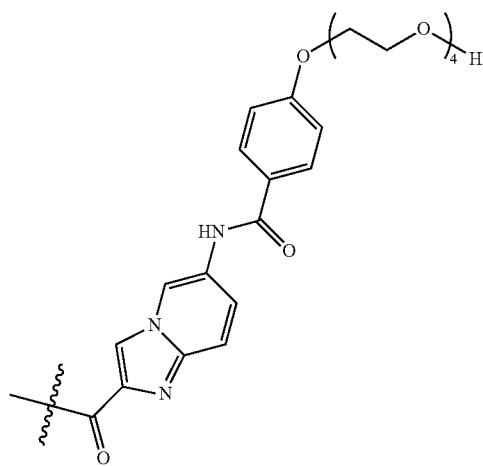 or 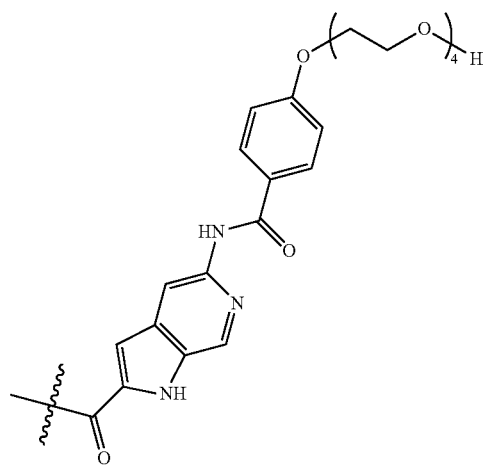 or
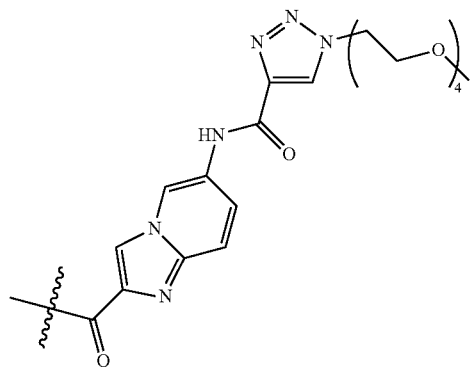 or 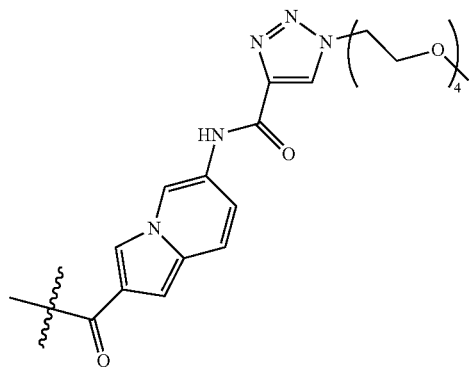 or
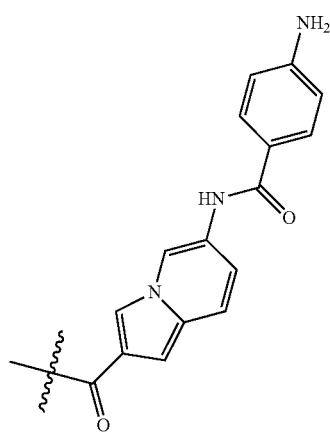 or 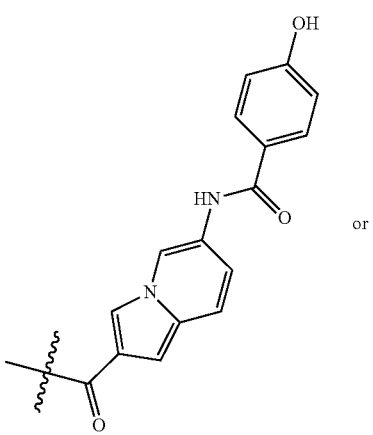 or -continued
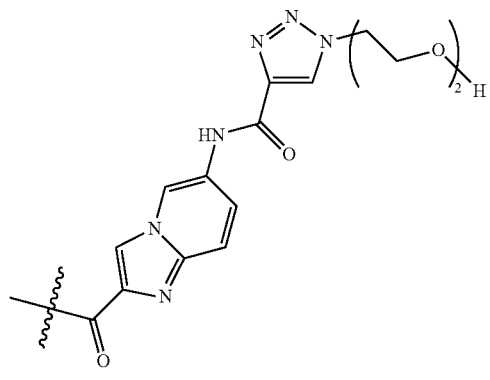 or 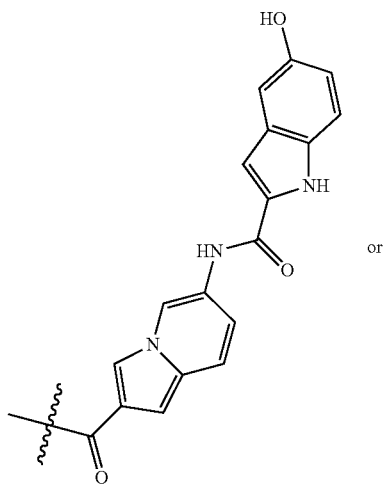 or
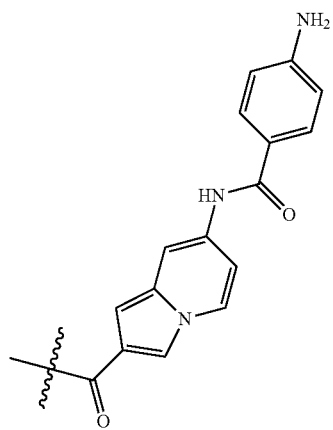 or 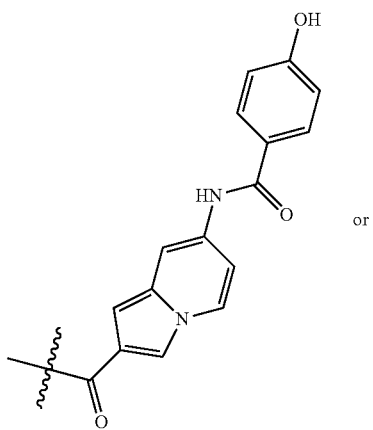 or
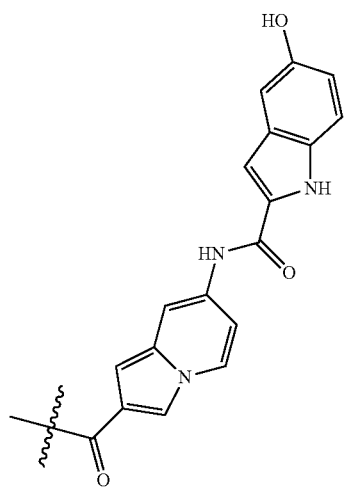 or 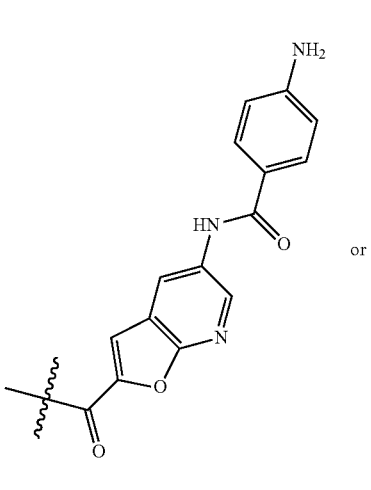 or -continued
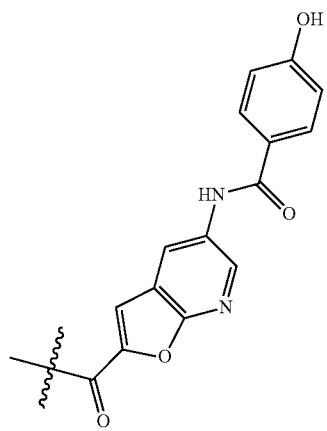 or 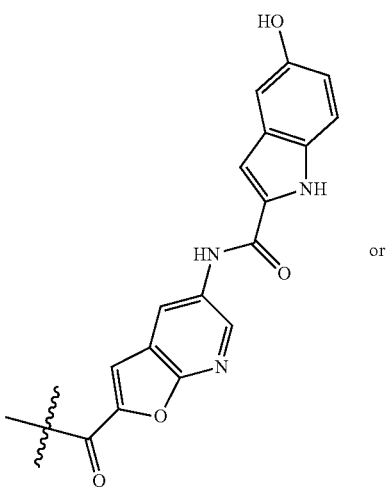 or
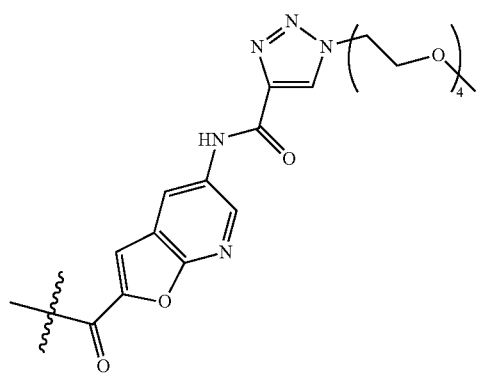 or 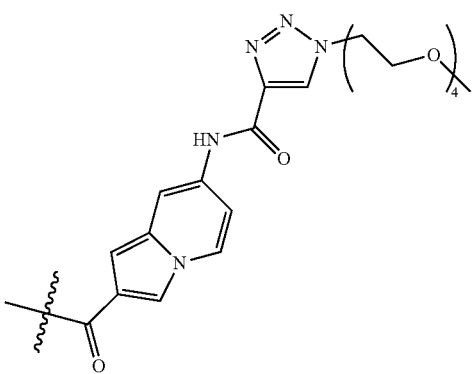 or
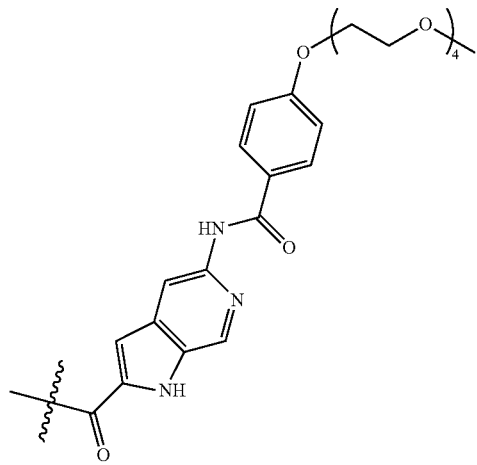 or 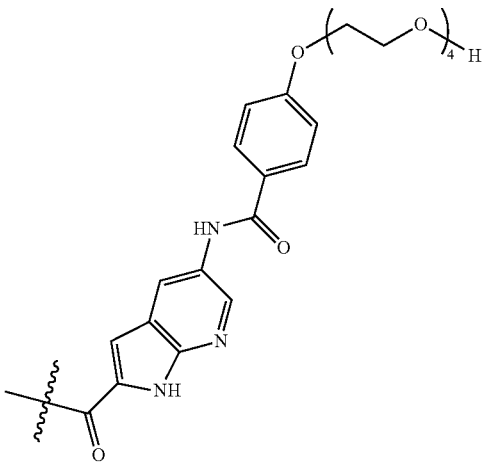 or -continued
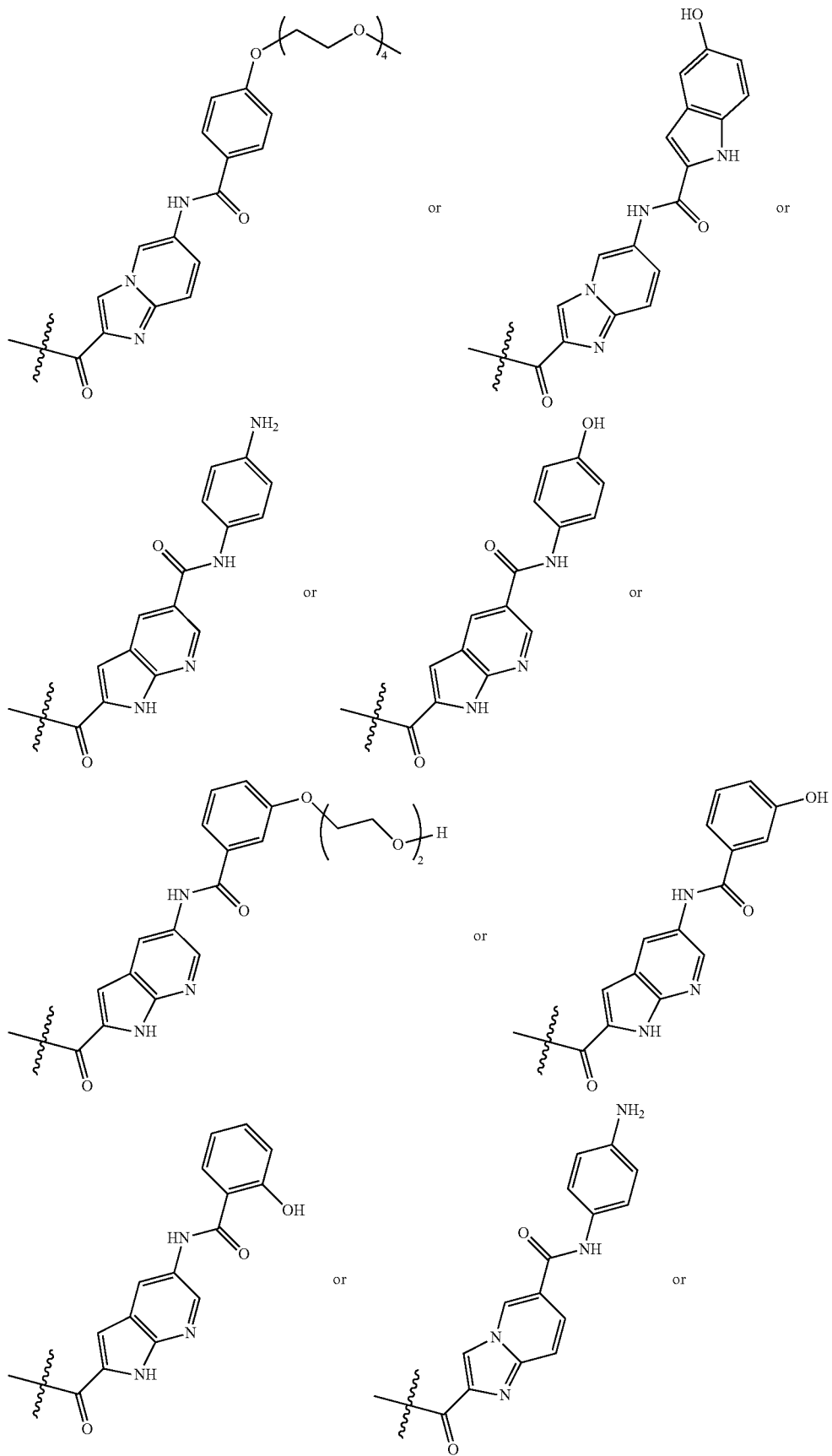

-continued
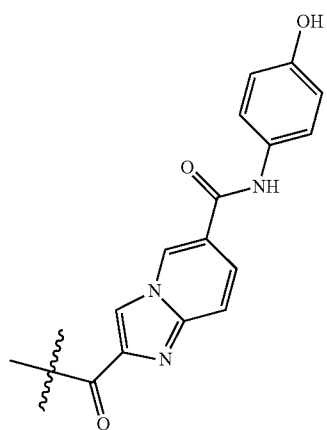 or 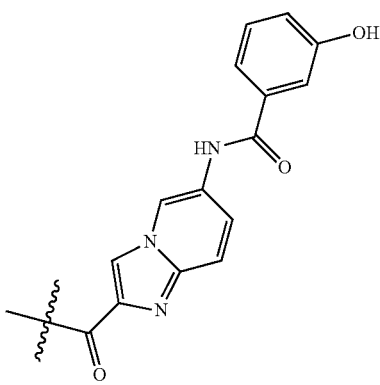 or
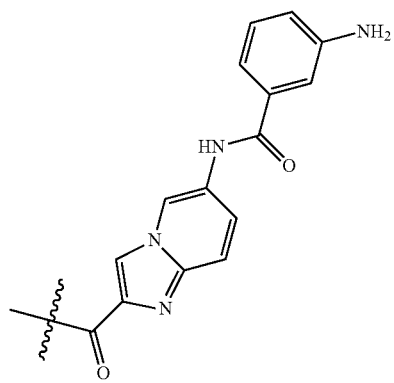 or 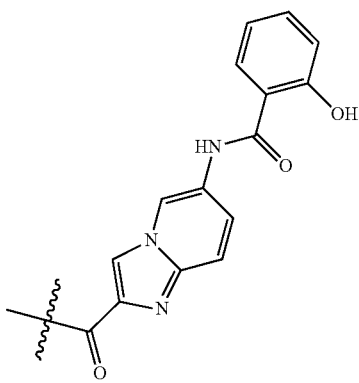 or
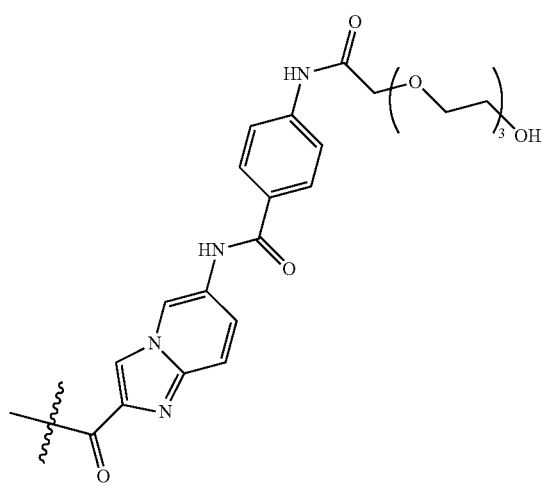 or 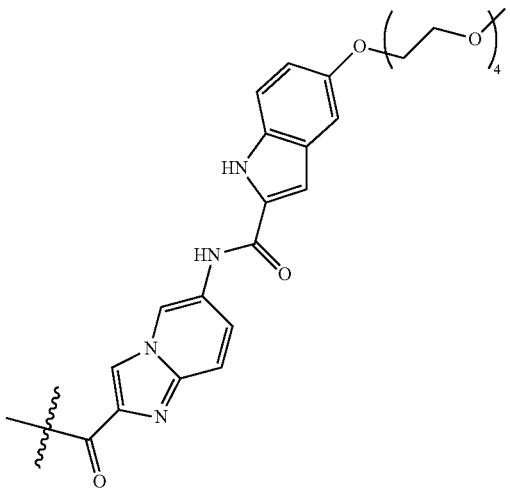 or -continued
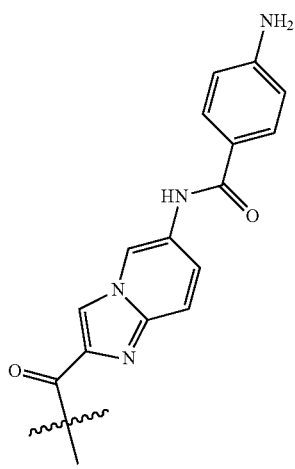 or 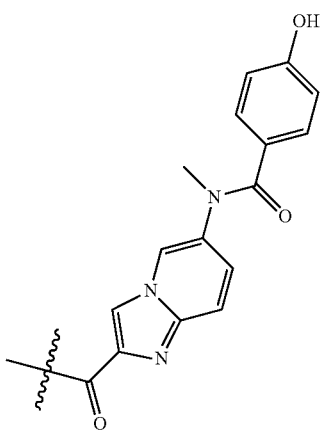 or 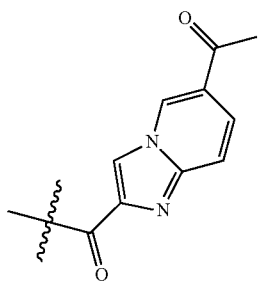 or
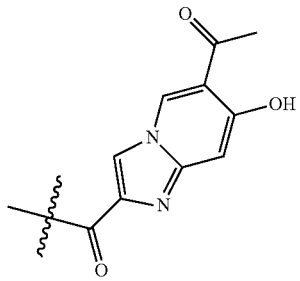 or 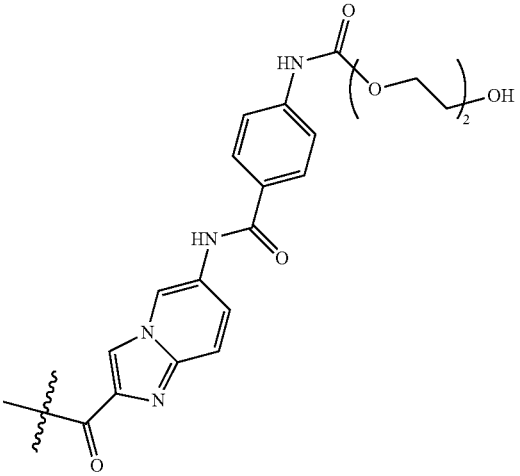 or
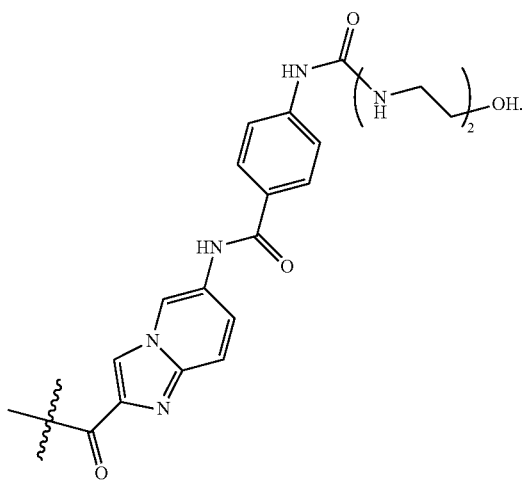

In a further embodiment, the moiety DB1 may be selected from
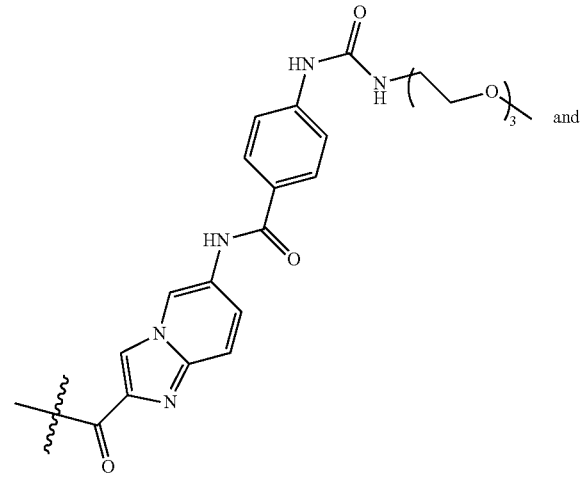
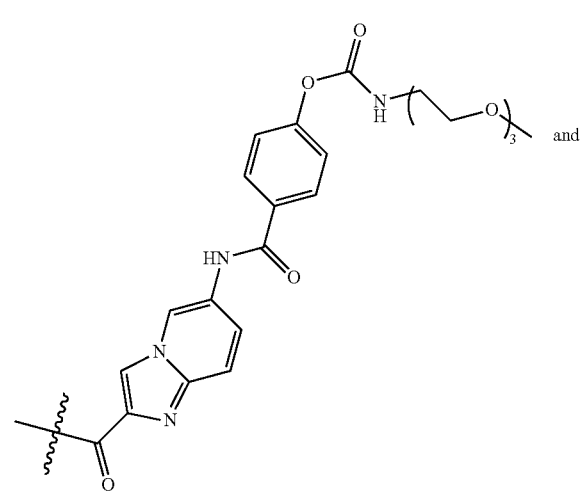
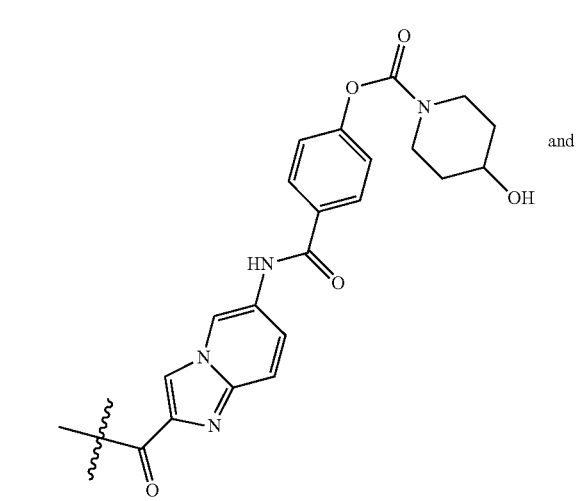
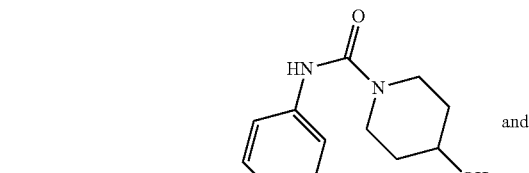
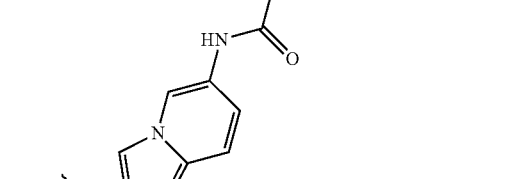
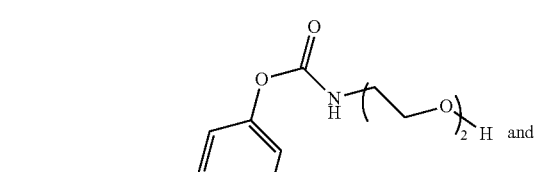
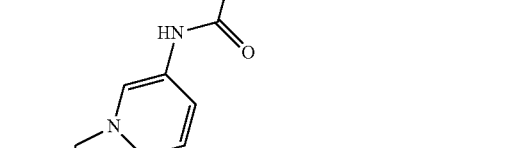
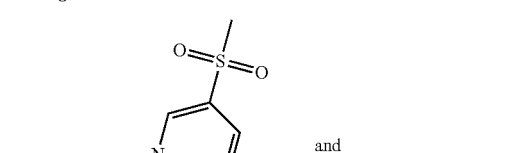

123
-continued
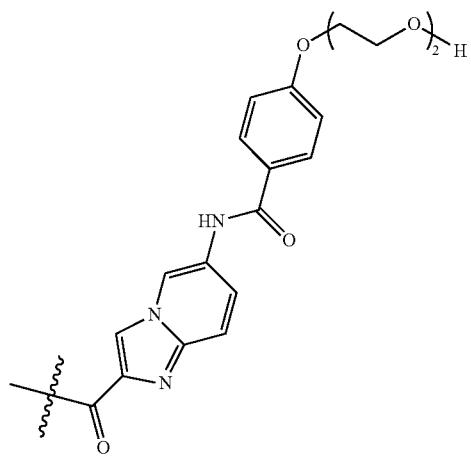
and
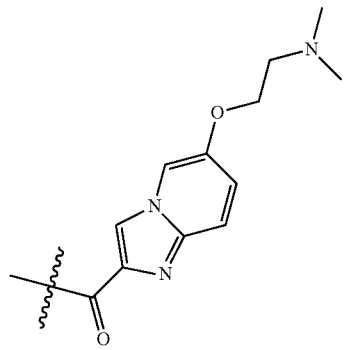
and
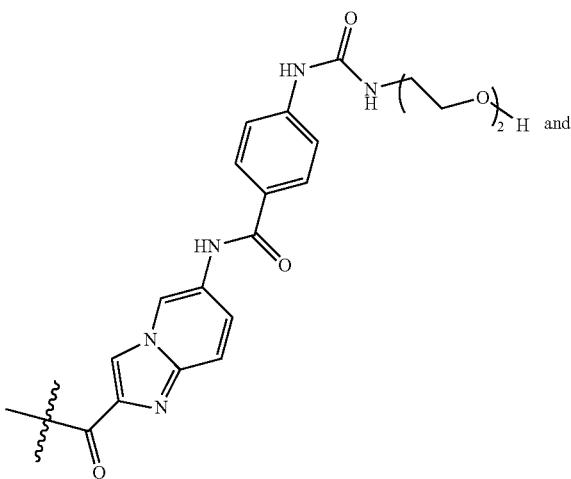
124
-continued
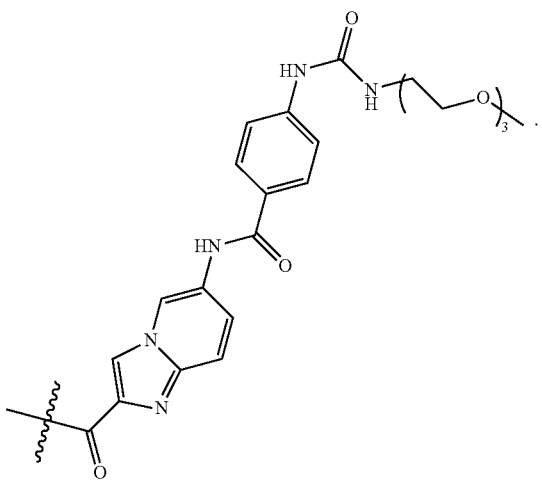
In a further embodiment, the moiety DB1 may be selected from
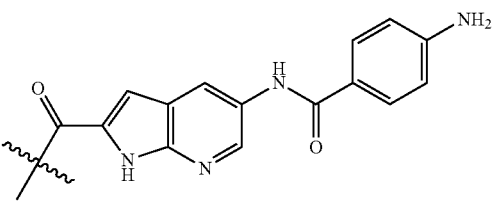
and
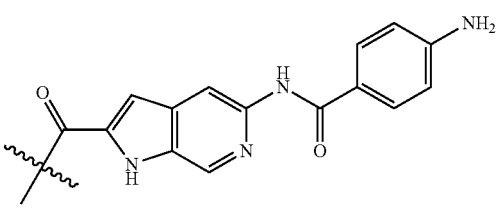
and
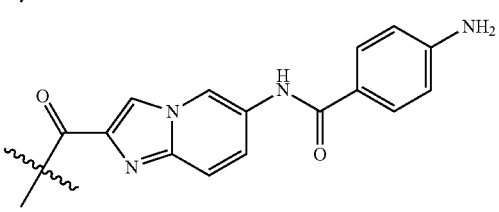
and
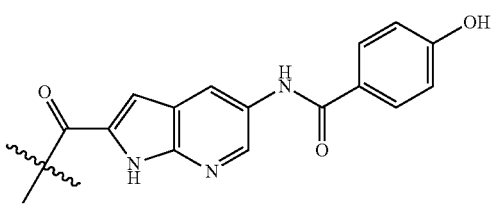
and
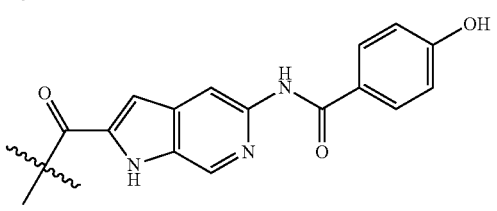
and

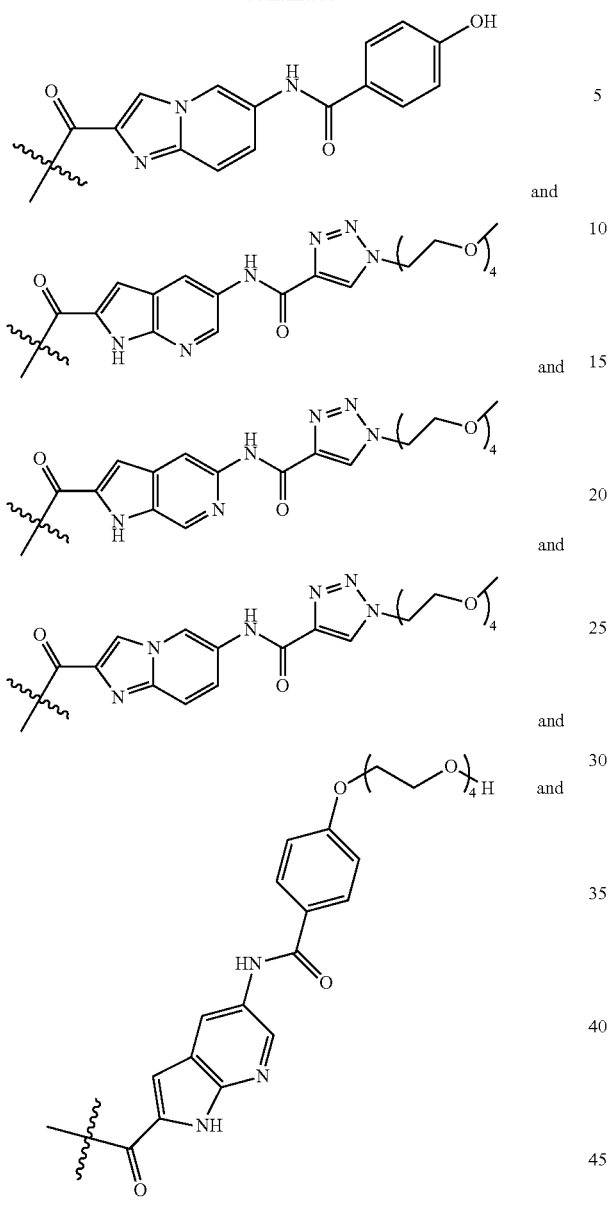
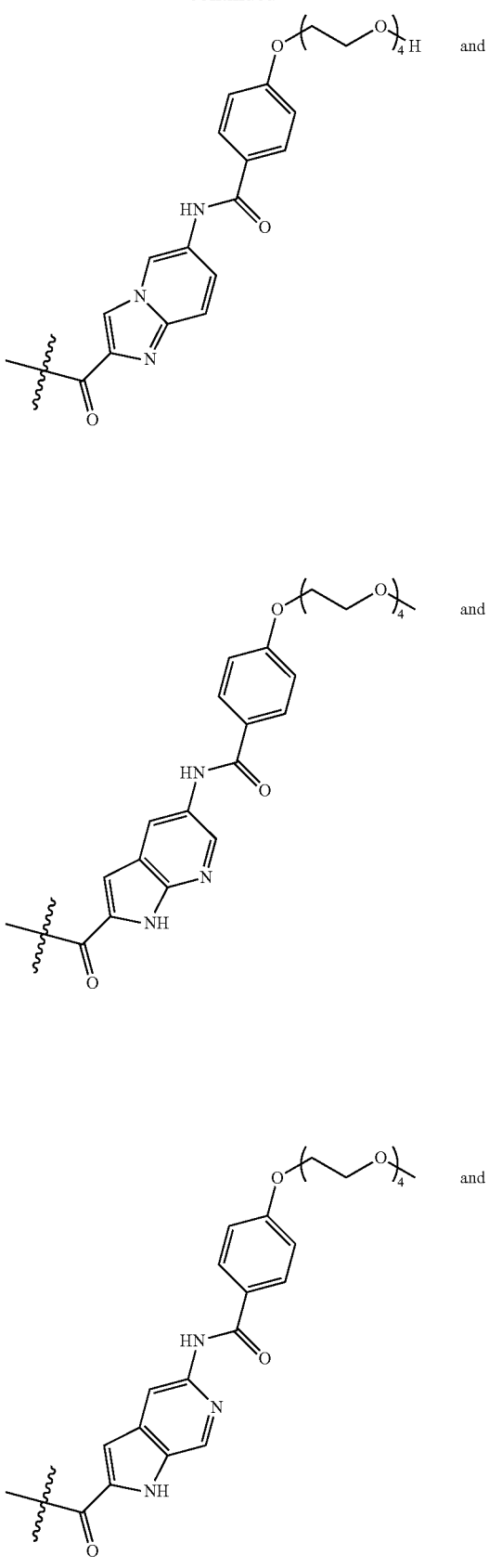

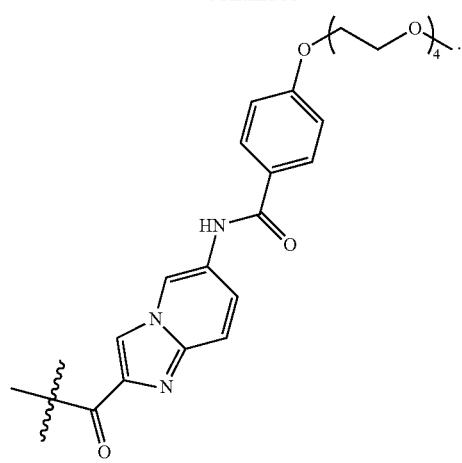
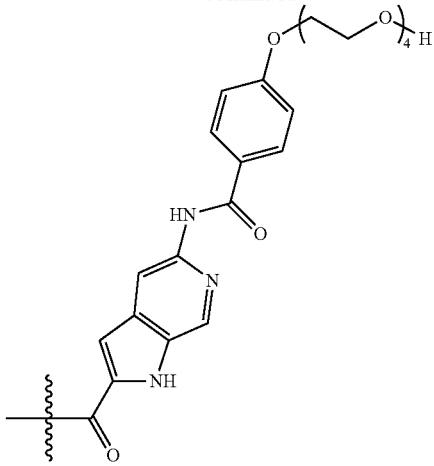
In a further embodiment, the moiety DB1 may be selected from
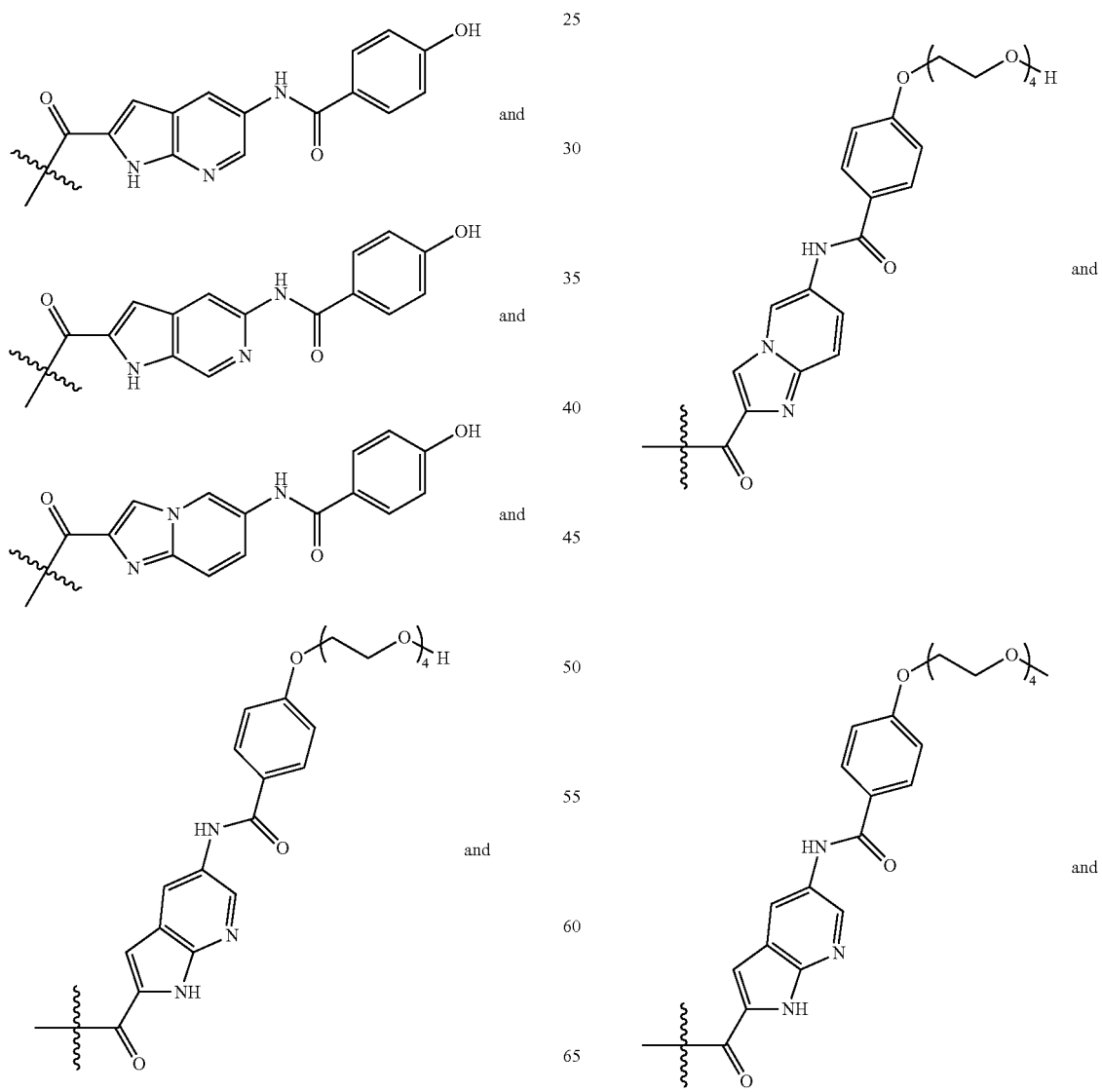

129
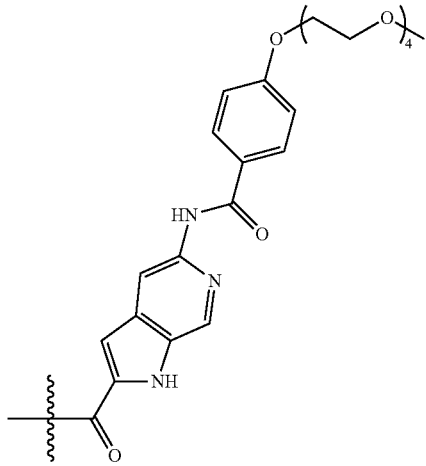
and
130
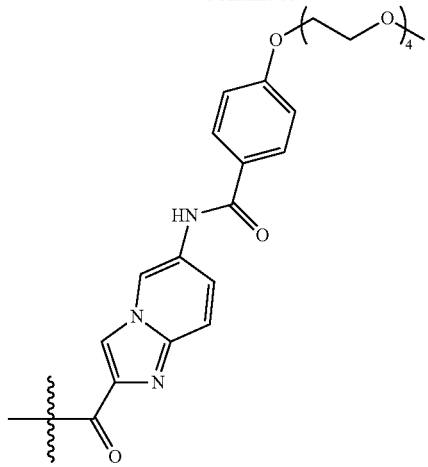
In another embodiment, the moiety DB1 may for example be
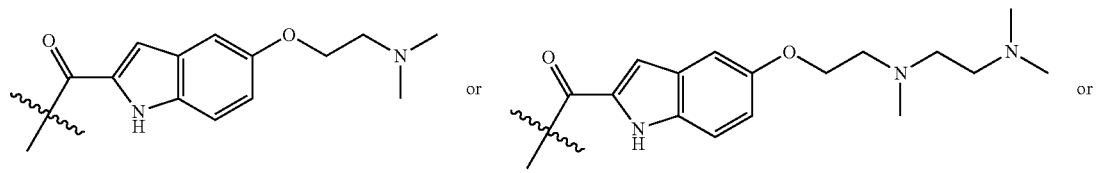
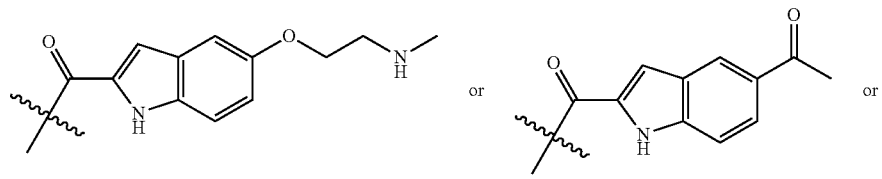
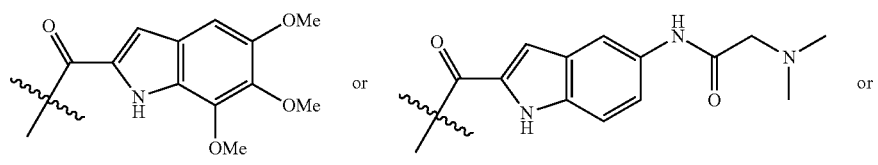
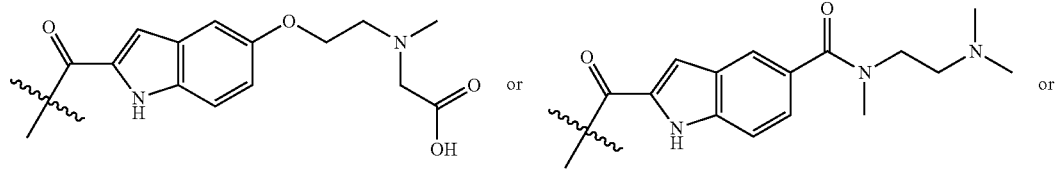
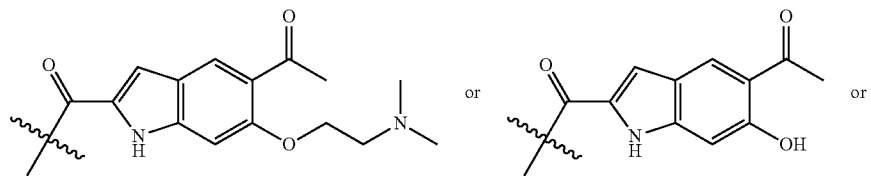
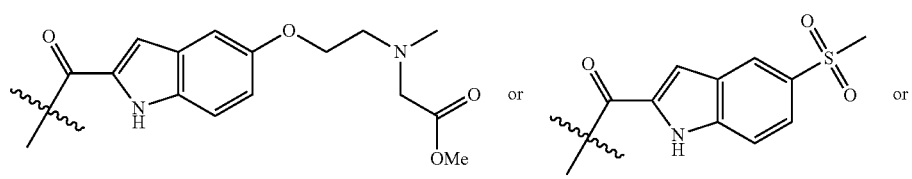

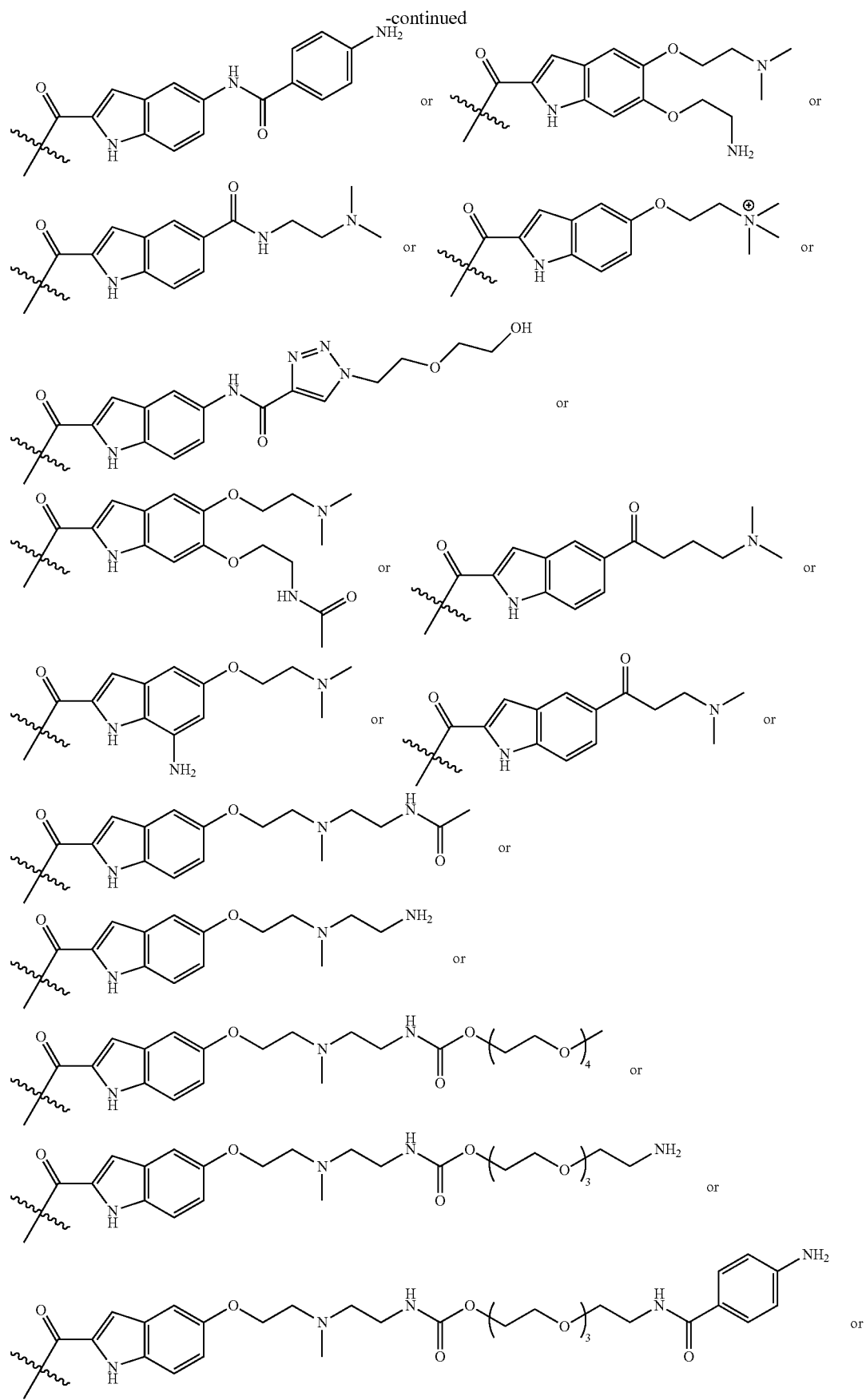

-continued
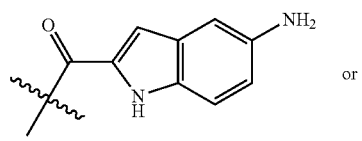 or
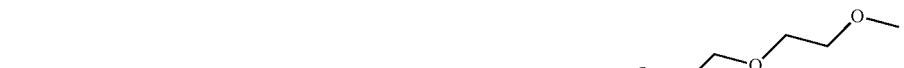 or
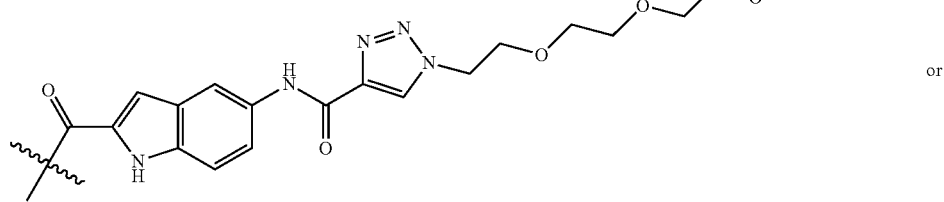 or
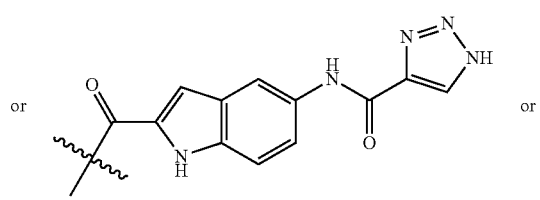 or
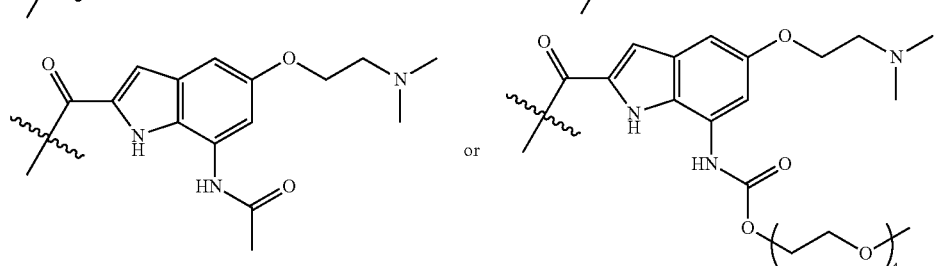 or
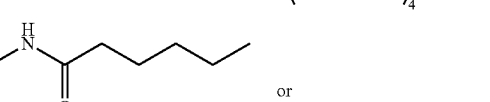 or
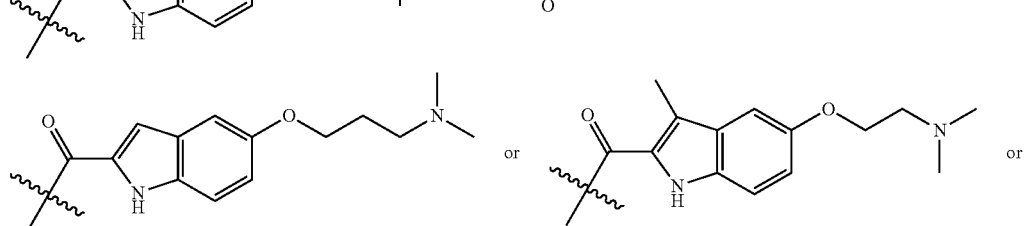 or
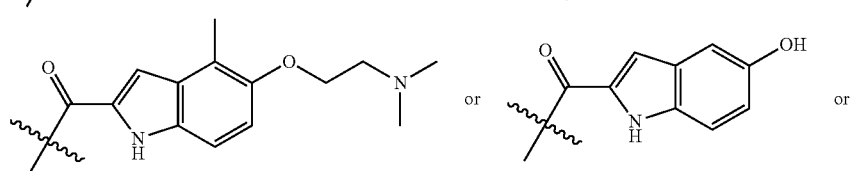 or
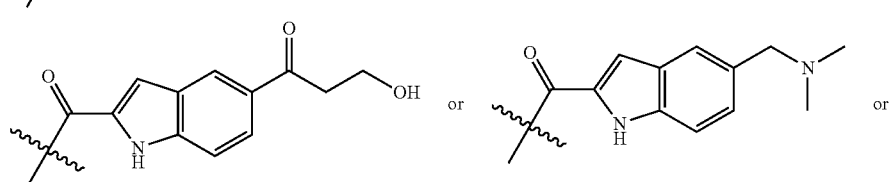 or
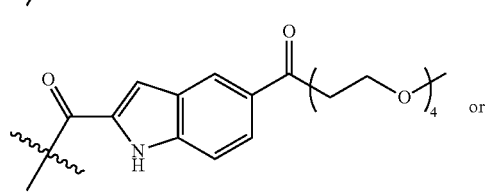 or

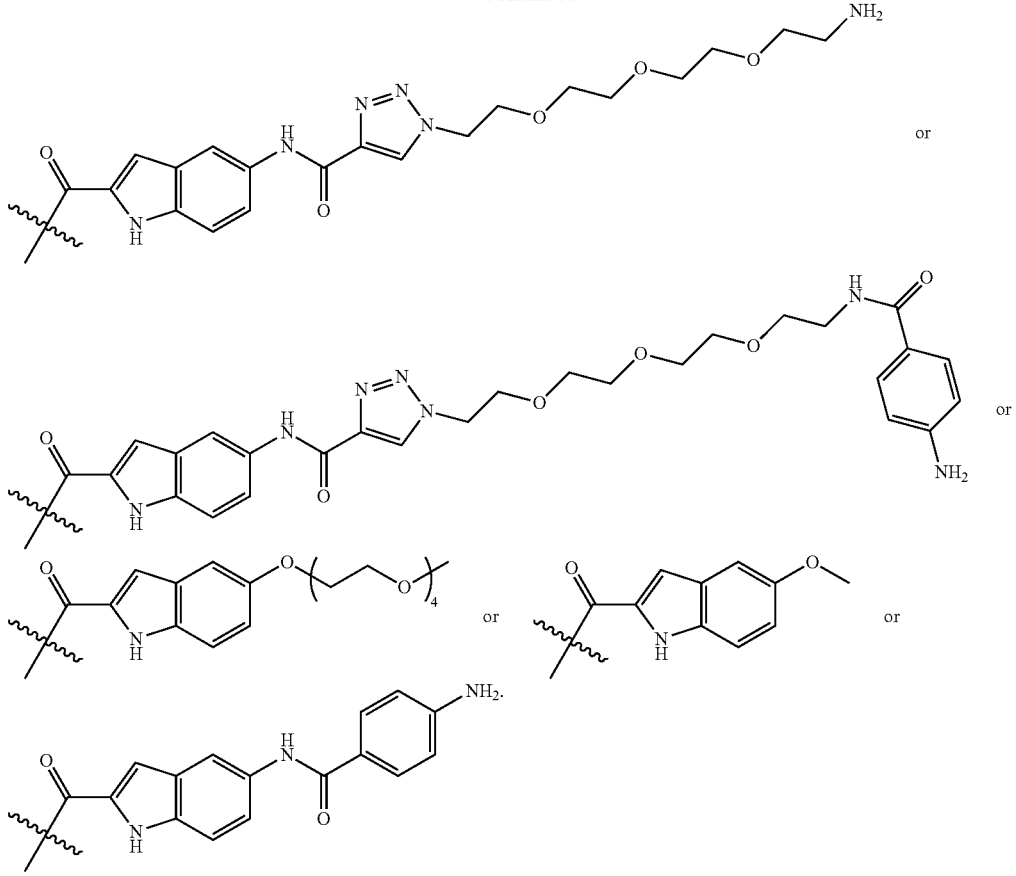

In another aspect of this invention, a compound of formula (I) or (II) has a DNA-binding unit of formula DB2. This moiety comprises structures that at least contain a 5-membered ring B that is connected to the DNA-alkylating unit via a fused 5- or 6-membered ring A or a vinyl group. Especially in the latter case, ring B may be fused to another heterocyclic or carbocyclic aromatic or non-aromatic ring in order to have an improved DNA-binding affinity. For reasons of increased water solubility, the fused ring may be a heterocycle, or a carbocycle substituted with relatively polar groups that at the same time may provide handles for coupling to promoieties. A DNA binder in which three or more rings are fused together to form an aromatic multicyclic system may be less favorable as this may increase the hydrophobicity and/or the aggregation tendency of the DNA-binder and therefore increase the hydrophobicity and/or the aggregation tendency of a compound of formula (I) or (II) and its conjugates. This may be especially true for multicyclic aromatic systems in which none or only one of the ring atoms is a heteroatom.

DNA binder DB2 may comprise an aromatic core structure. Alternatively, one or more rings may be non-aromatic and be either unsaturated or completely saturated.

A compound of formula (I) or (II) wherein ring B is connected to the DNA-alkylating unit via a vinyl group may contain a handle that allows for detoxification by means of for example oxidation or hydration of the double bond.

The moiety DB2 may for example be

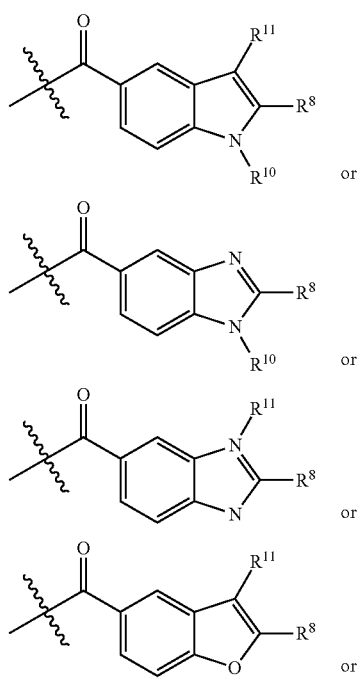

-continued

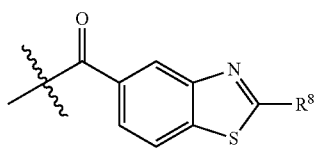
or
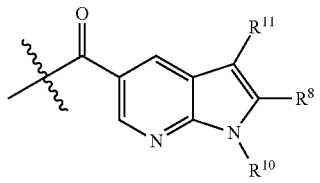
or
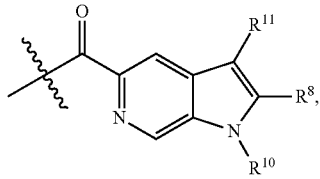
wherein $R^{8a}$, $R^{9a}$, $R^{10a}$, and $R^{11a}$ have the same meaning as defined for $R^8$, $R^9$, $R^{10}$, and $R^{11}$, respectively, and are independently selected.
In a more specific embodiment, the moiety DB2 may for example be
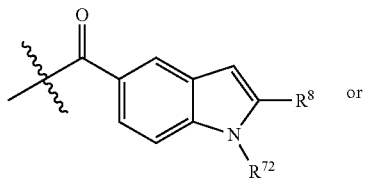
or
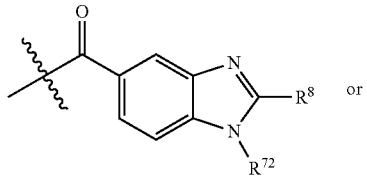
or
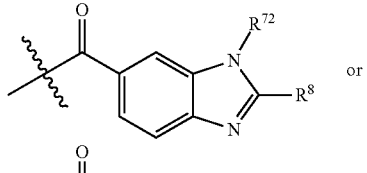
or
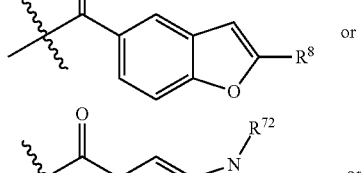
or
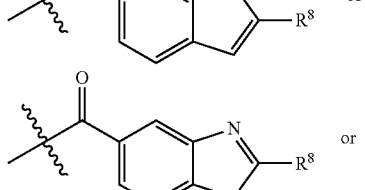
or
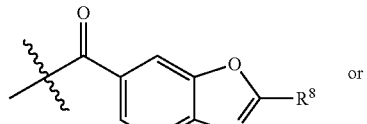
or
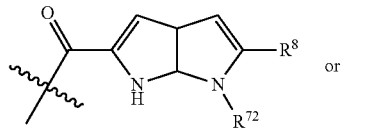
or
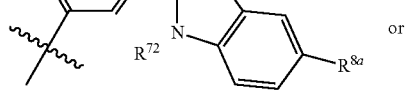
or
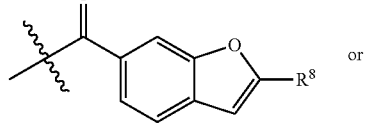
or
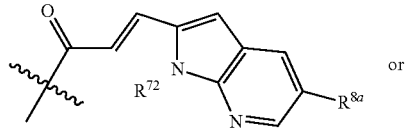
or
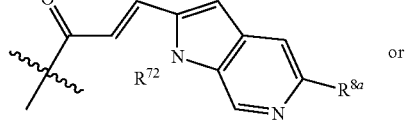
or
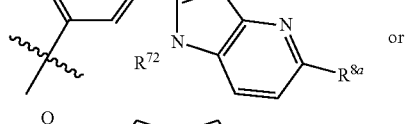
or
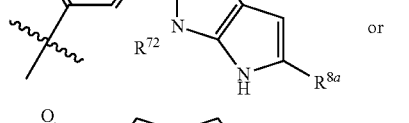
or
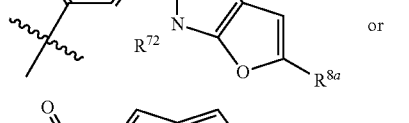
or
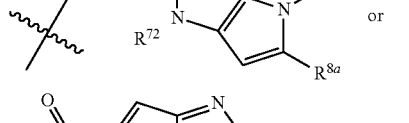
or
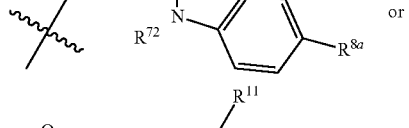
or

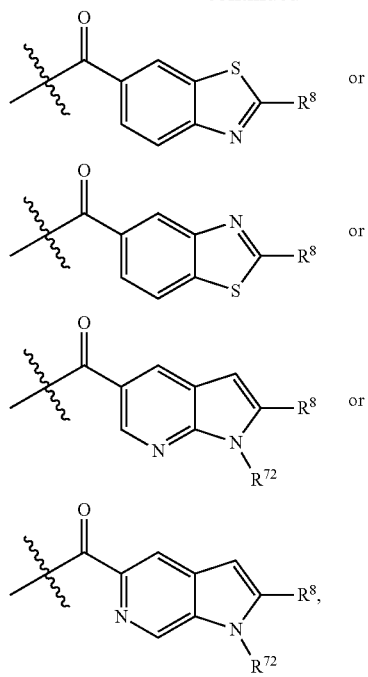
wherein $R^{72}$ and $R^{73}$ are independently selected from H and methyl.
In the exemplary structures of DB2, $R^8$, $R^{8a}$, $R^{9a}$, $R^{10}$, $R^{10a}$, $R^{11}$, $R^{11a}$, $R^{15}$, $R^{16}$, and $R^{21}$ may for example each independently be selected to be H, be or contain another moiety selected from structures DB1-DB9 or a derivative thereof, or be
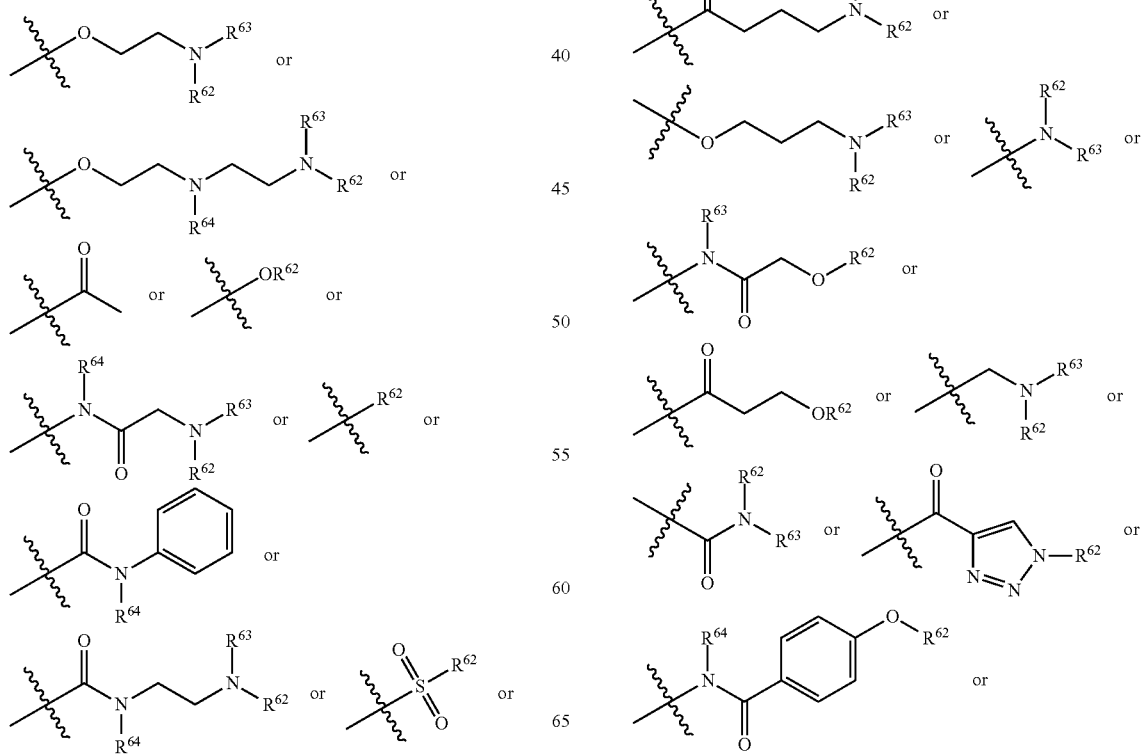

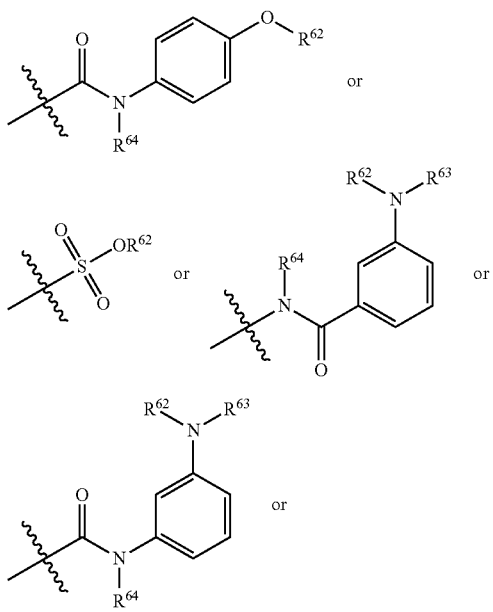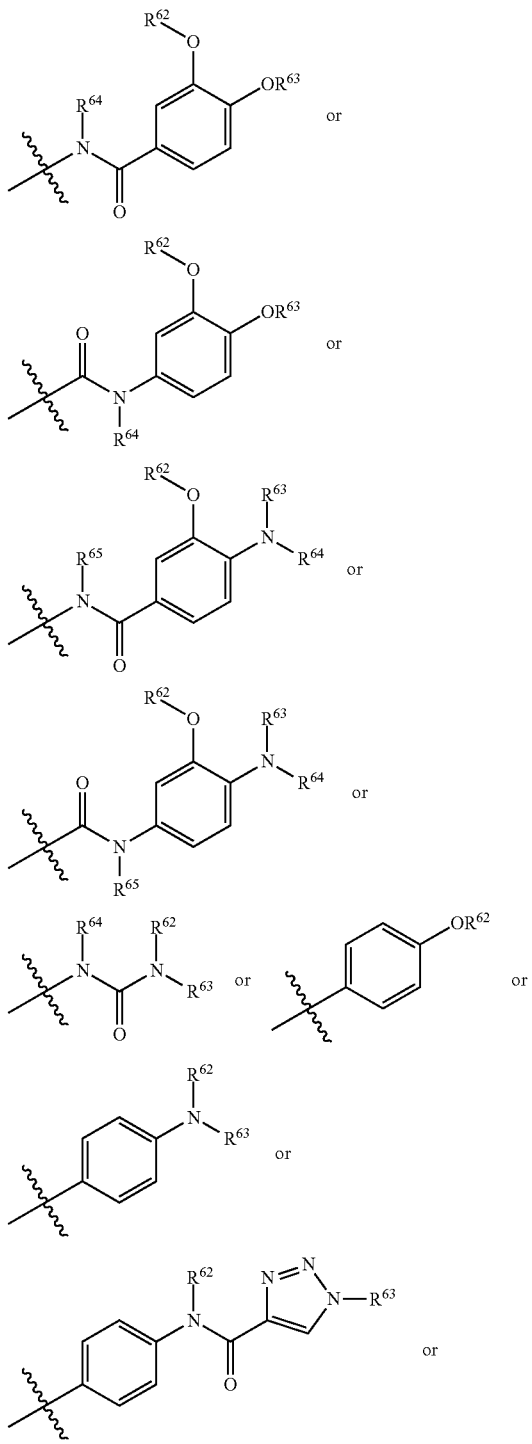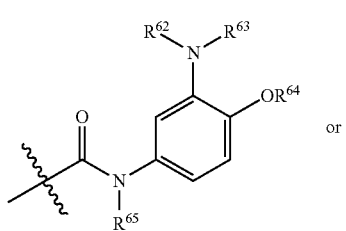

-continued

-continued
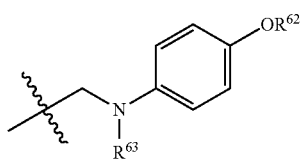
or
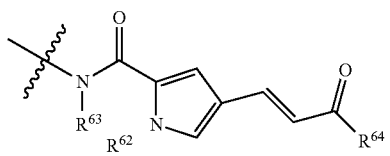
or
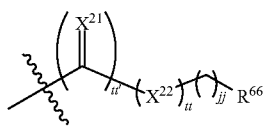
-continued
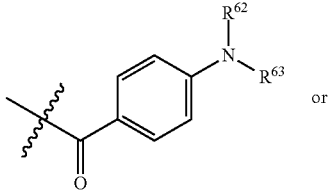
or
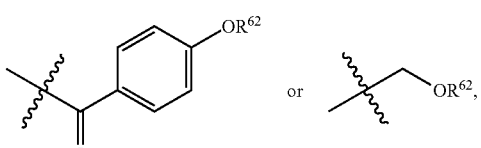 or 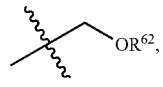,
wherein $R^{62}$, $R^{63}$, $R^{64}$, and $R^{65}$ are independently selected from H, $C_{1-3}$ alkyl, and
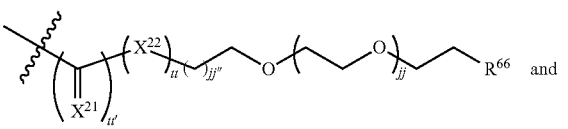 and
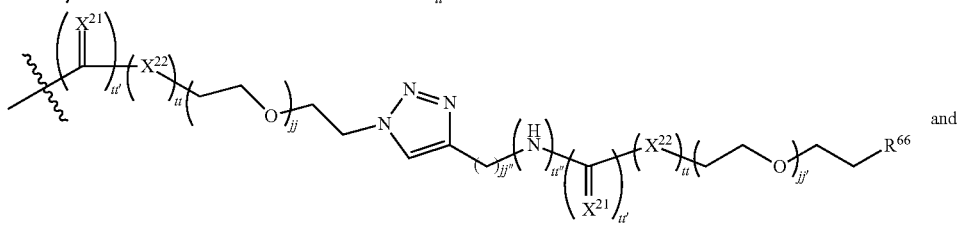 and
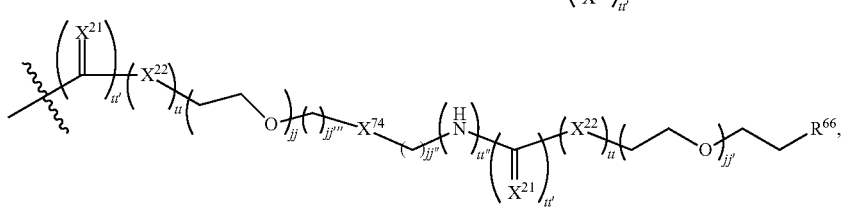,
wherein jj, jj', jj", and jj'" are independently selected from 0 to 8, $X^{74}$ is selected from
 and
 and  and
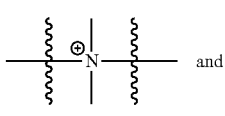 and

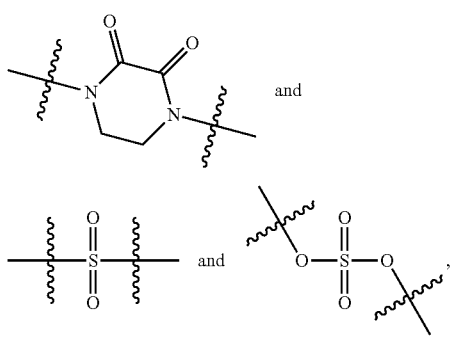

each tt, tt', and tt" is independently selected from 0 and 1, each $X^{21}$ and $X^{22}$ is independently selected from O, S, $NR^{67}$, $H_2$, and $C(R^{67})R^{68}$, wherein $R^{67}$ and $R^{68}$ are independently selected from H and optionally substituted $C_{1-3}$ alkyl or $C_{1-3}$ heteroalkyl, and $R^{66}$ is selected from H, COOH, $CO_2Me$, OH, OMe, $NR^{69}R^{70}$, $NR^{69}C(O)CH_3$, SH, SMe,

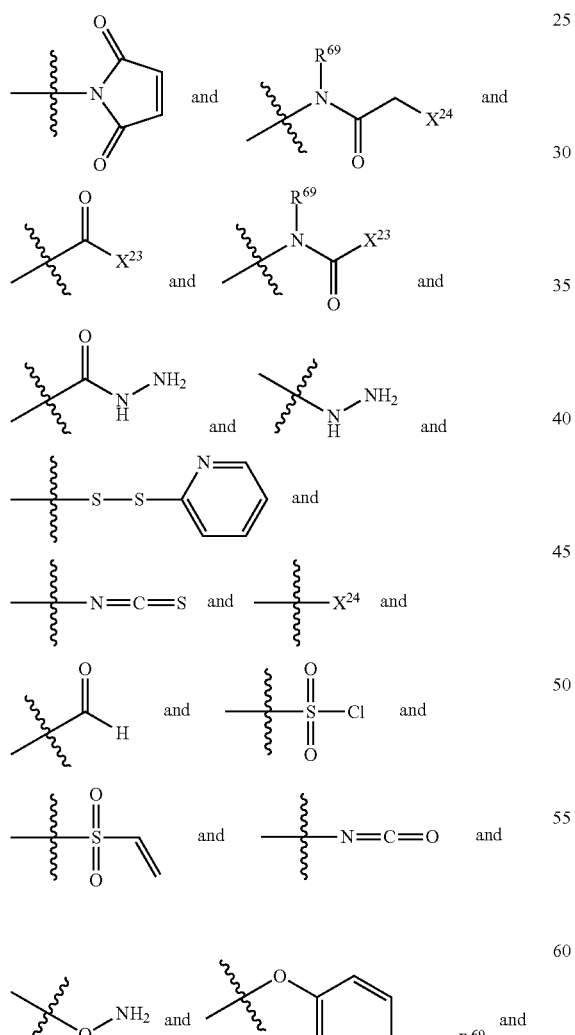

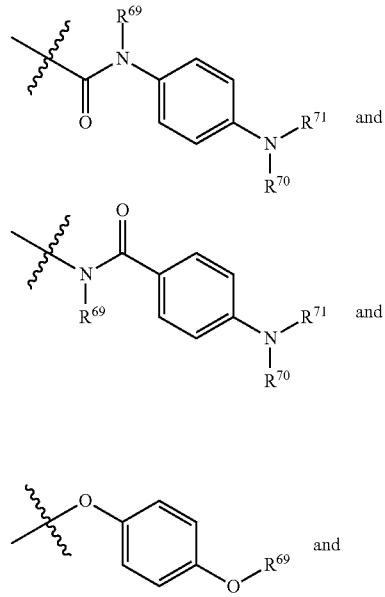

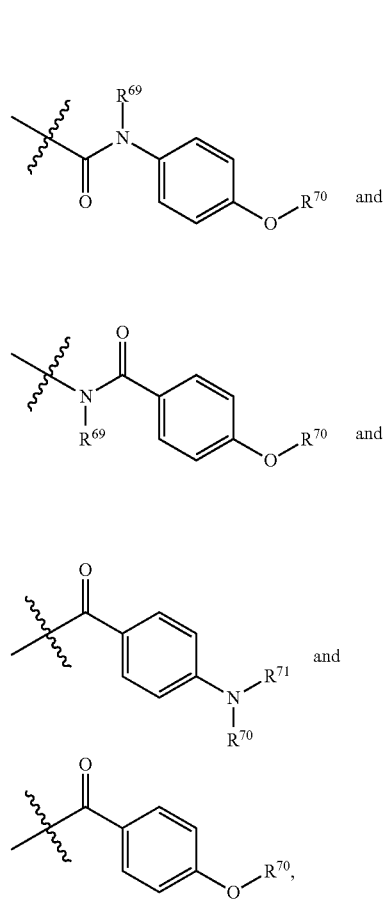

wherein $X^{23}$ is selected from halide, hydroxy, $OC(O)R^{bb}$, and $OC(O)OR^{bb}$, or $C(O)$—$X^{23}$ is an active ester, $X^{24}$ is selected from halide, mesyloxy, triflyloxy, and tosyloxy, $R^{bb}$ is selected from optionally substituted $C_{1-10}$ alkyl, $C_{1-10}$ heteroalkyl, $C_{3-10}$ cycloalkyl, $C_{1-10}$ heterocycloalkyl, $C_{5-10}$ aryl, and $C_{1-10}$ heteroaryl, and $R^{69}$, $R^{70}$, and $R^{71}$ are independently selected from methyl and H.

In a further embodiment, the moiety DB2 may for example be
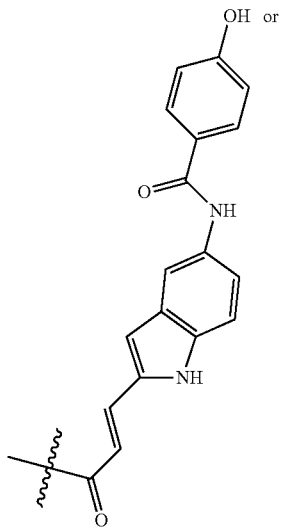
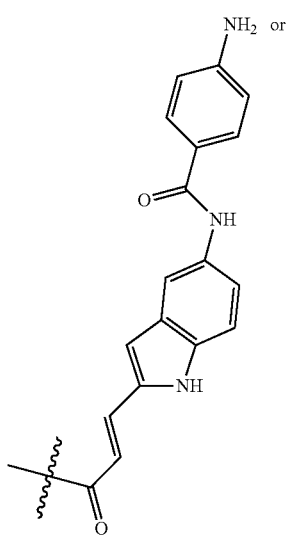
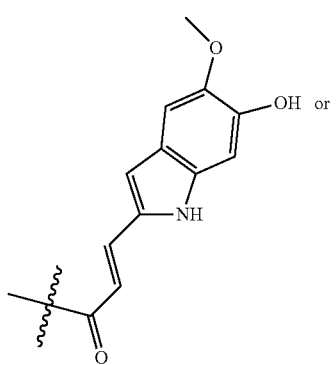
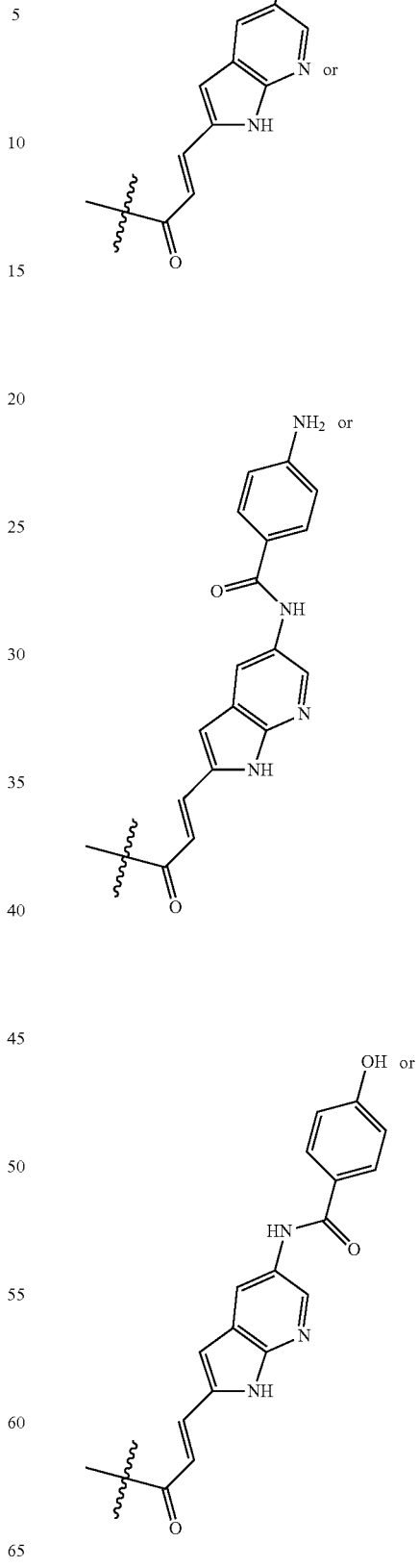

153
-continued
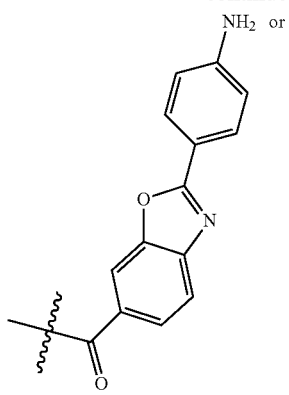
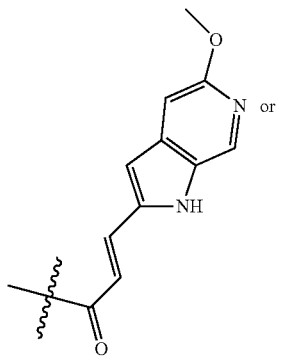
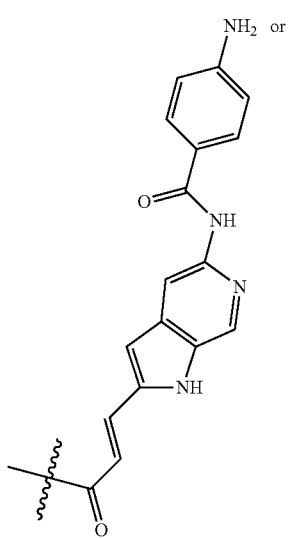
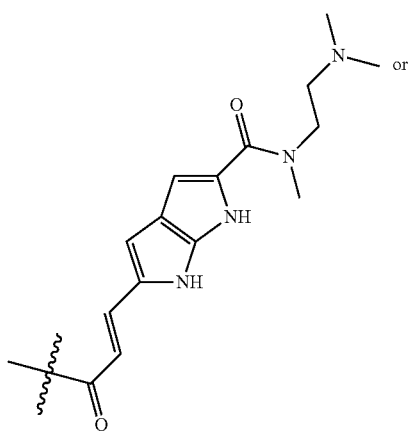
154
-continued
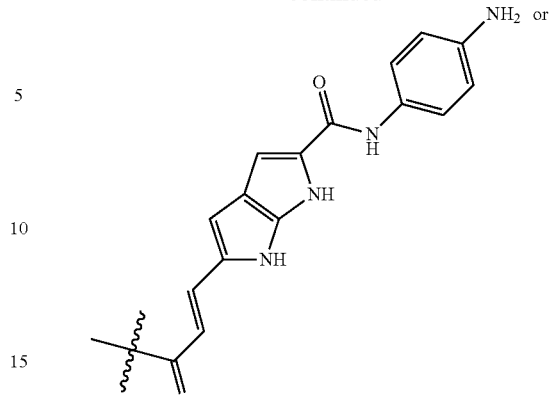
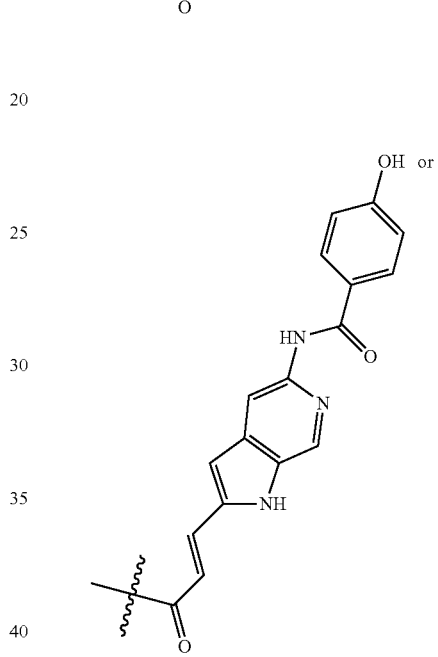
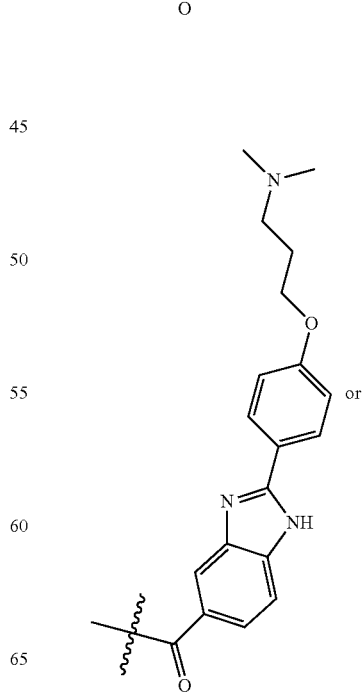

155
-continued
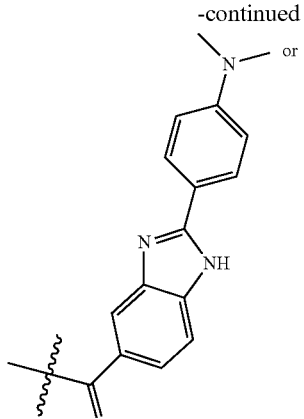
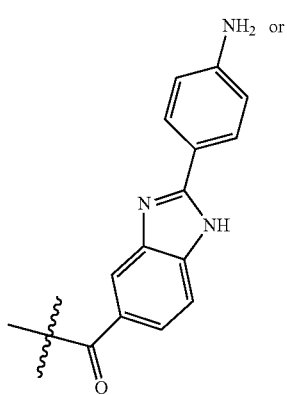
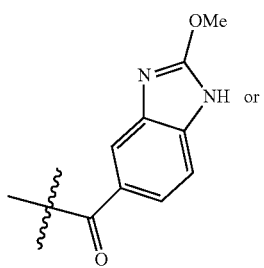
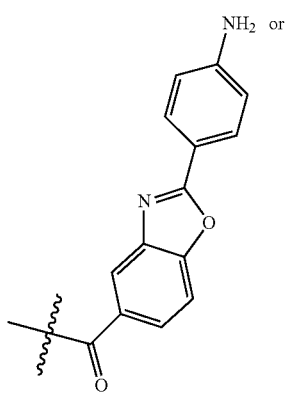
156
-continued
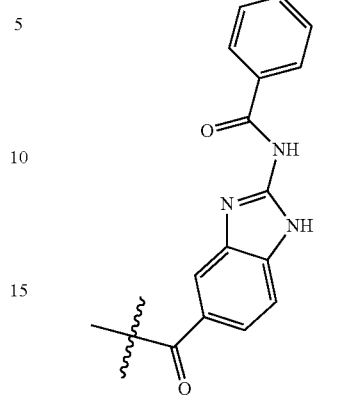
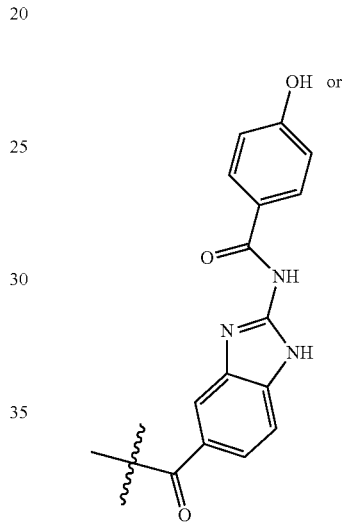
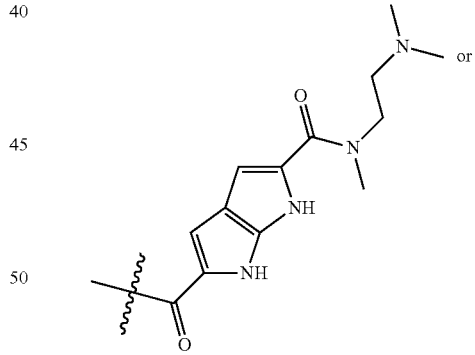
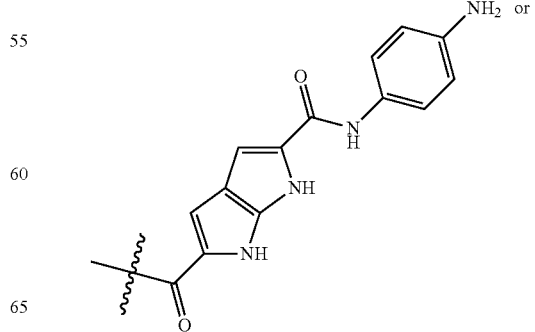

157
-continued
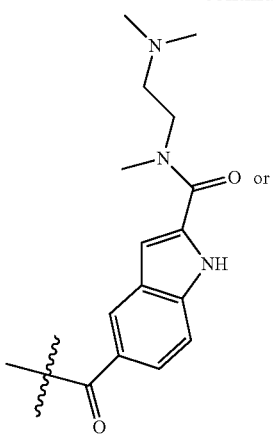
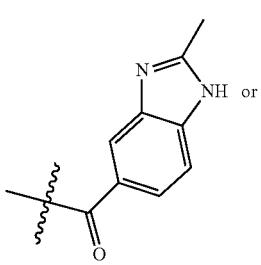
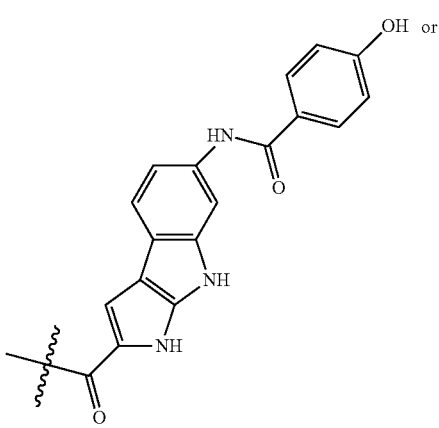
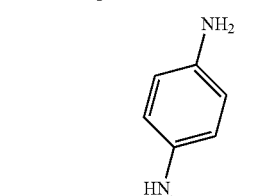
158
-continued
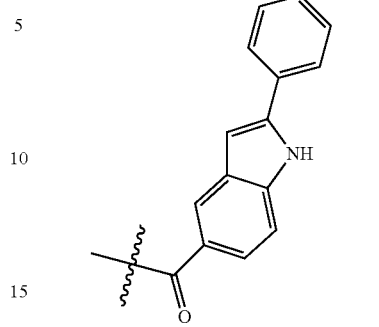
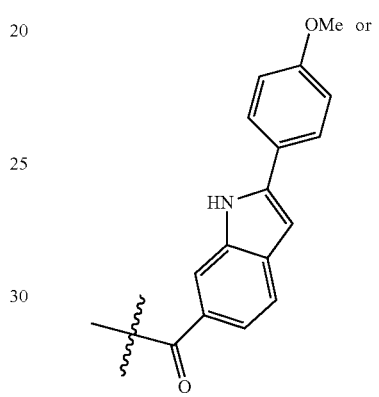
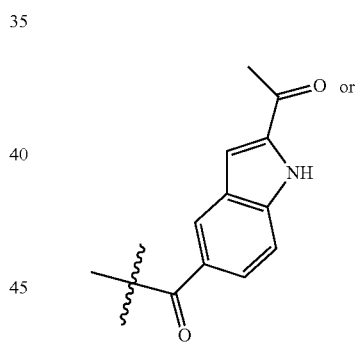
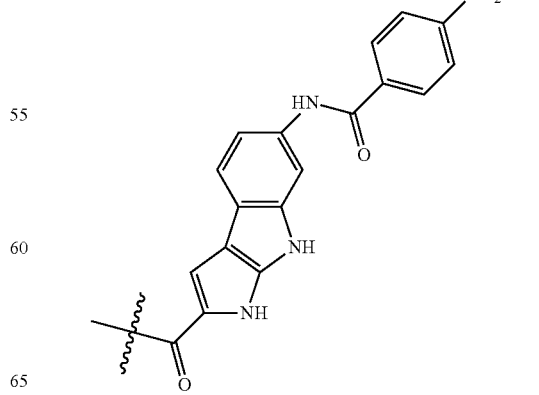

-continued
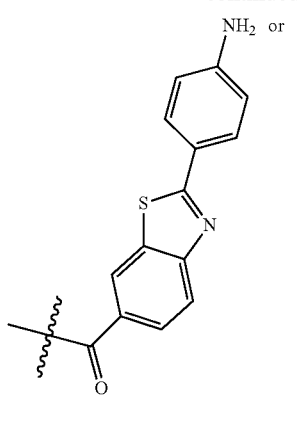
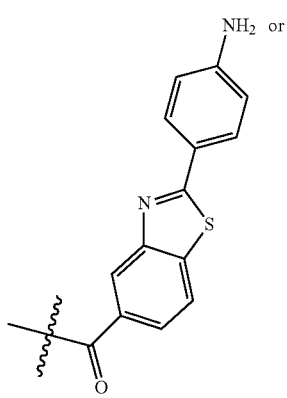

-continued
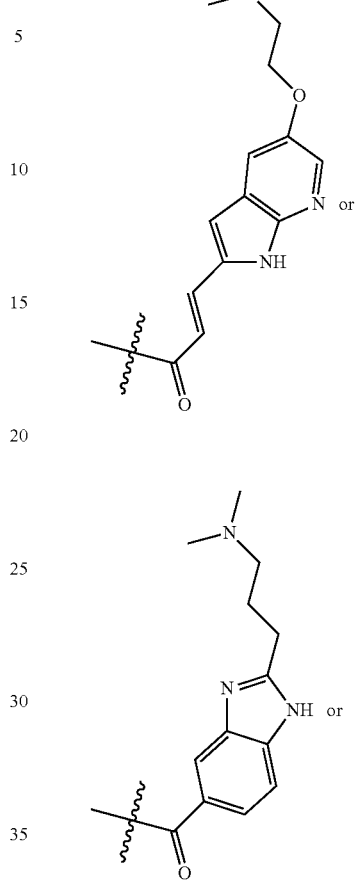
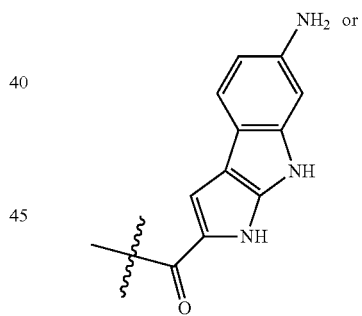
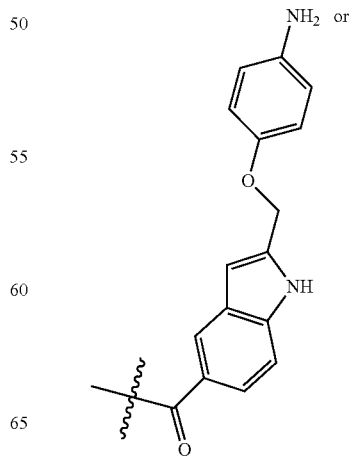

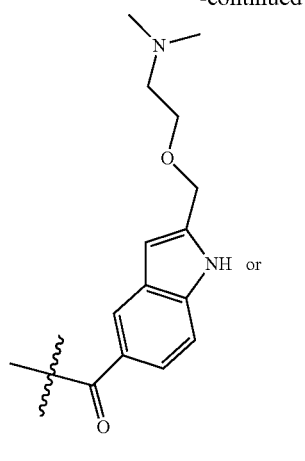
or
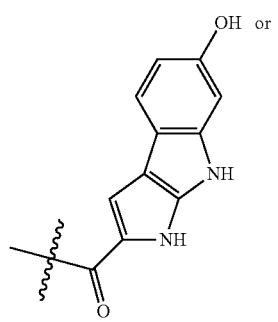
or
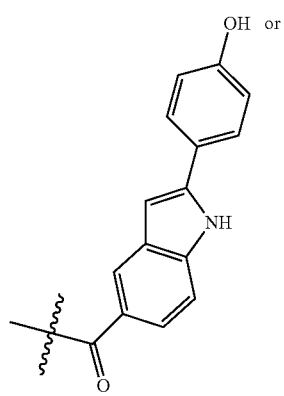
or

or
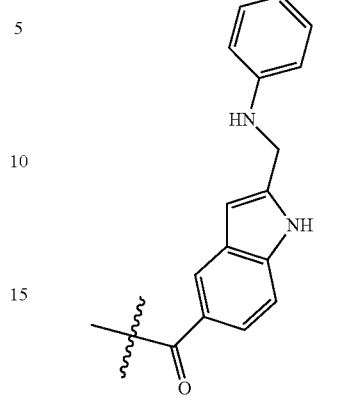
or
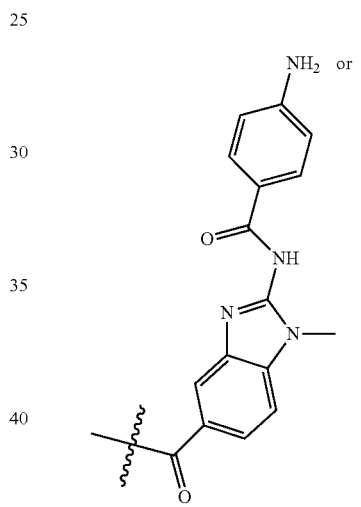
or
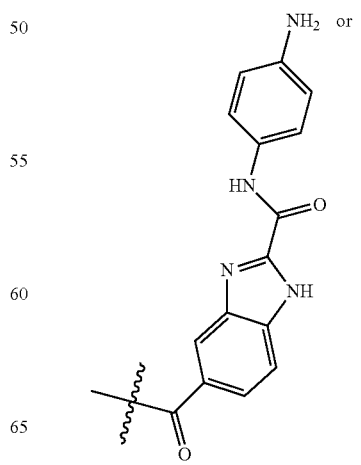
or 163
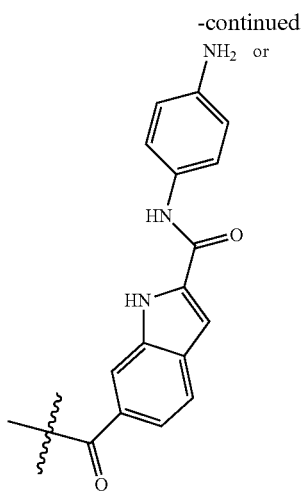
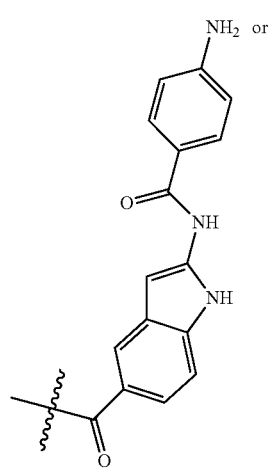
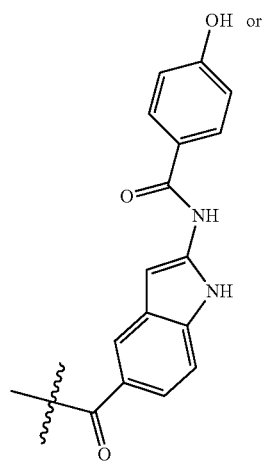
164
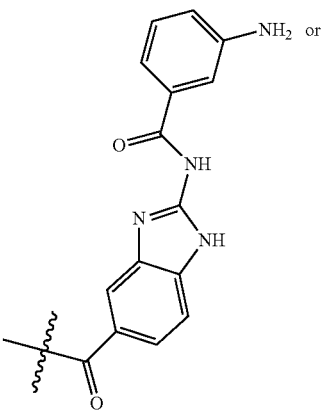
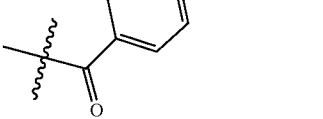
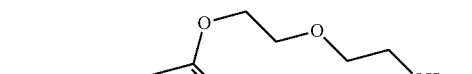
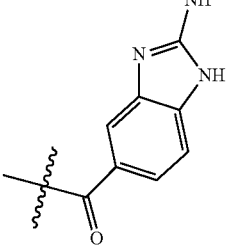
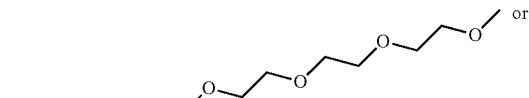
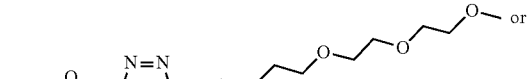

165
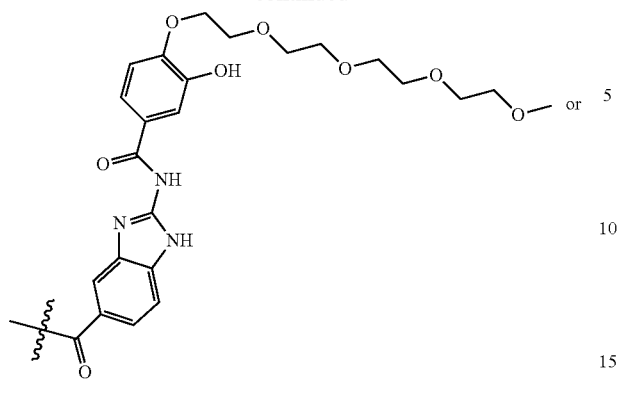
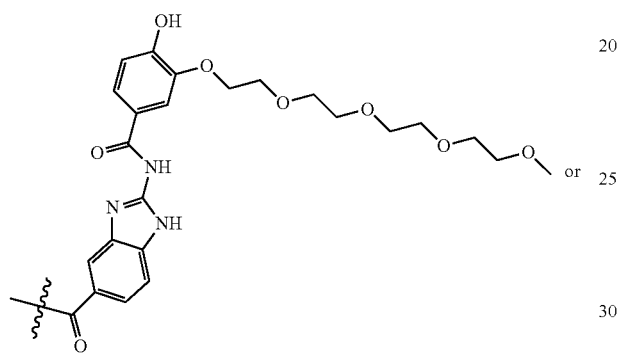
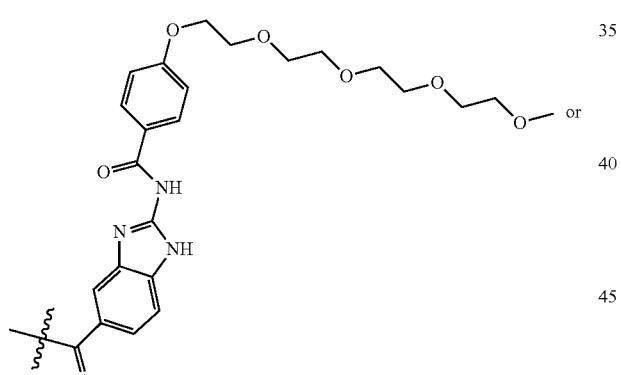
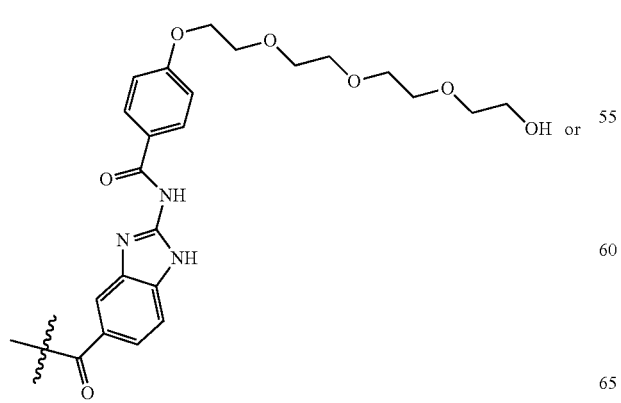
166
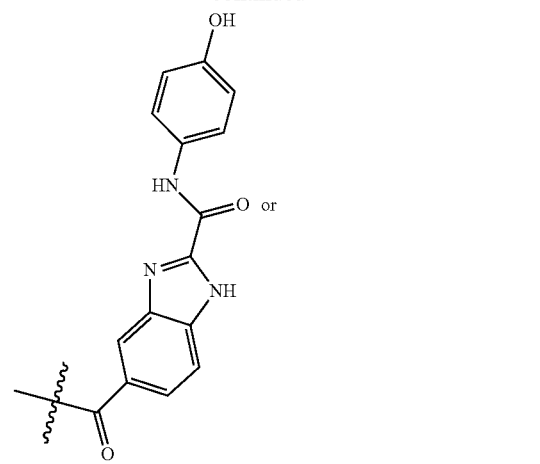
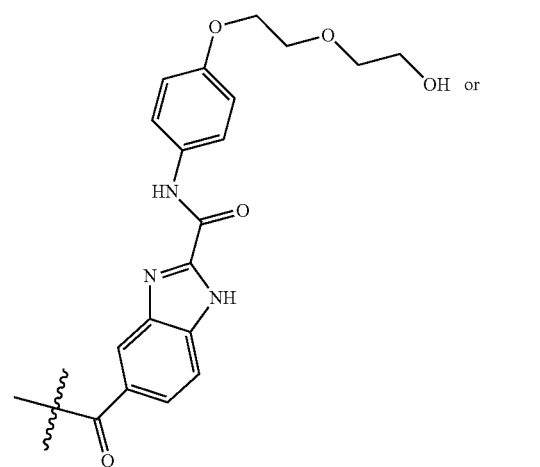
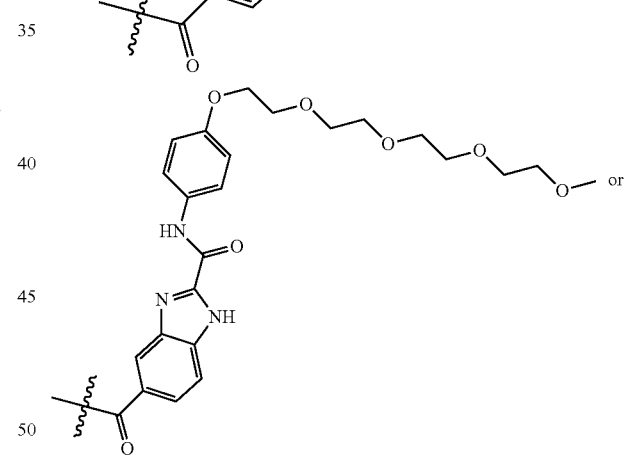
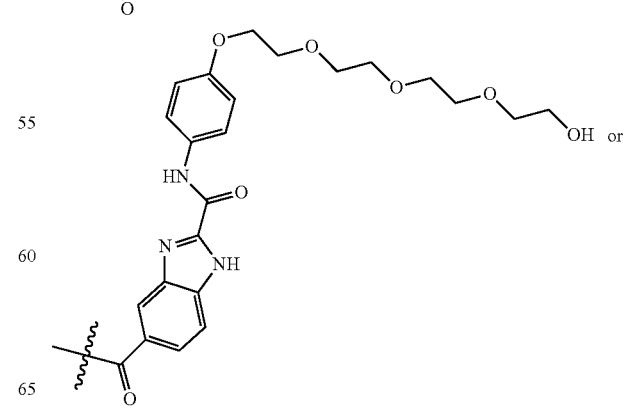

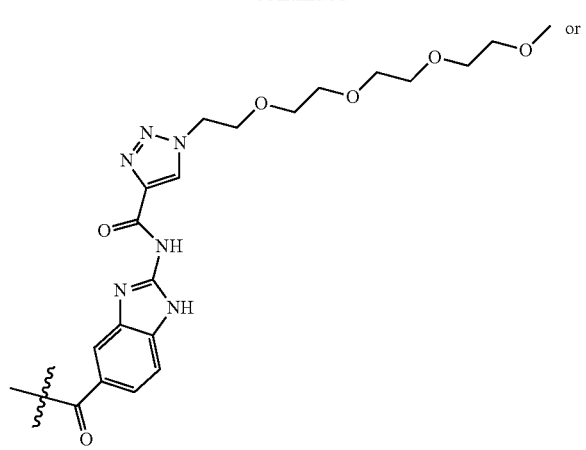
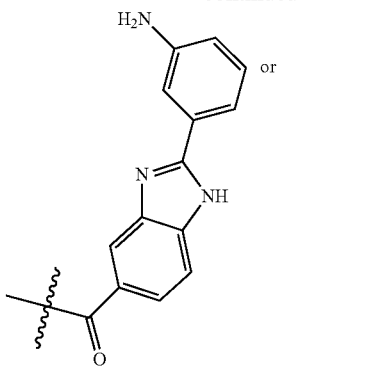
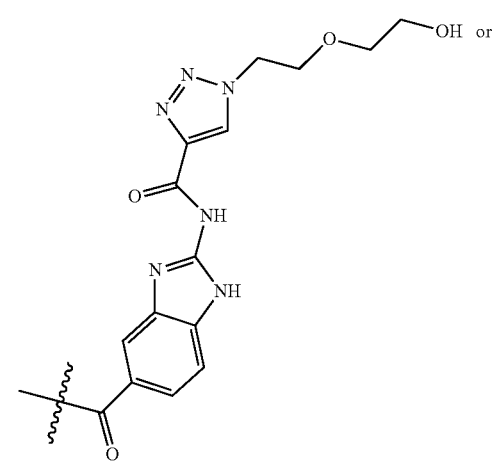
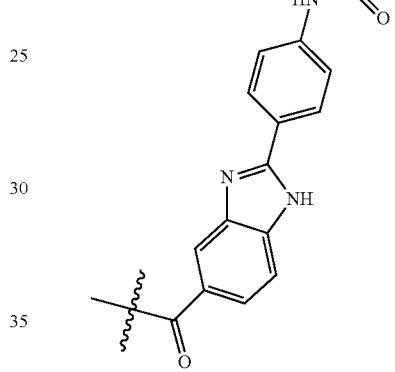
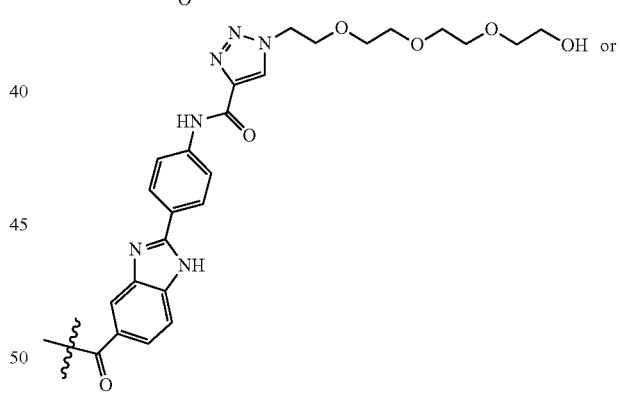
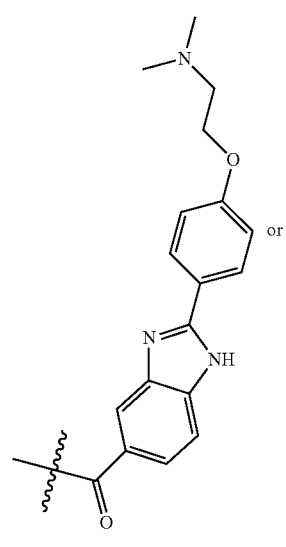
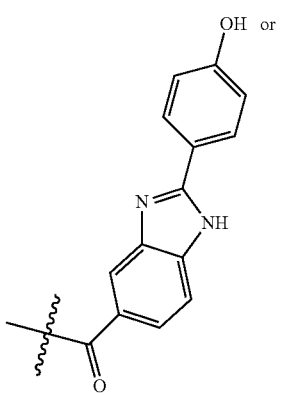

169
-continued
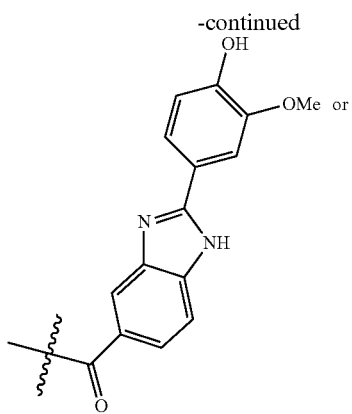
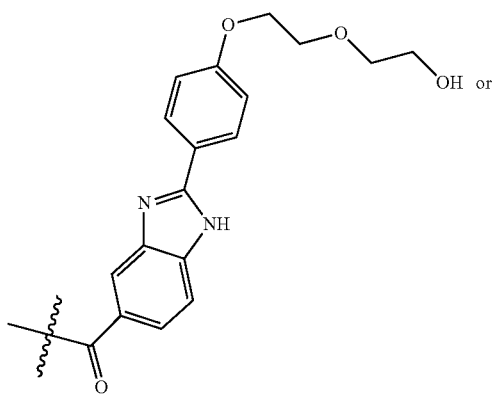
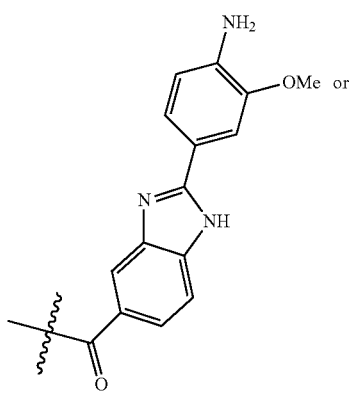
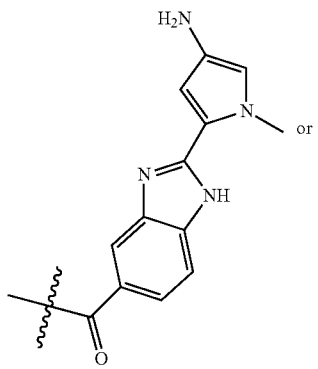
170
-continued
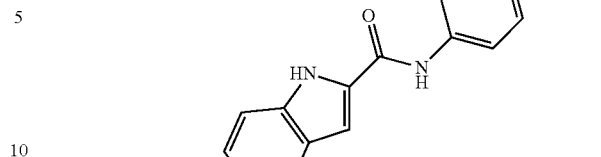
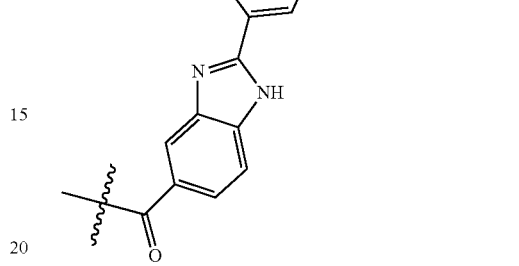
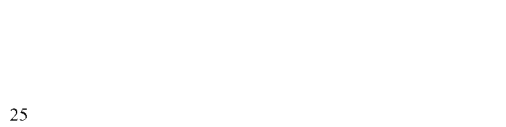
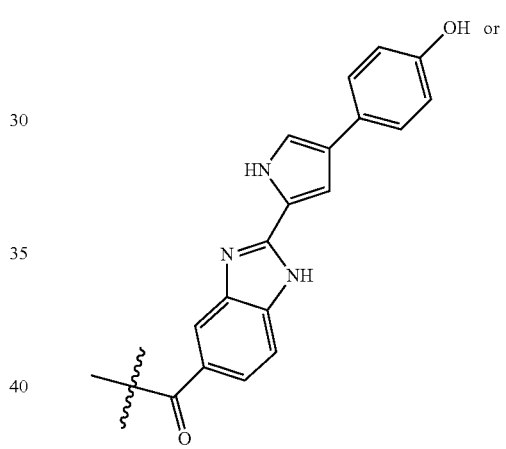
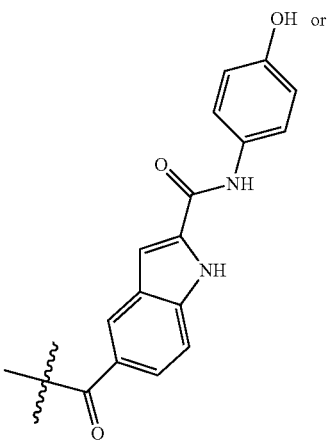

171
-continued
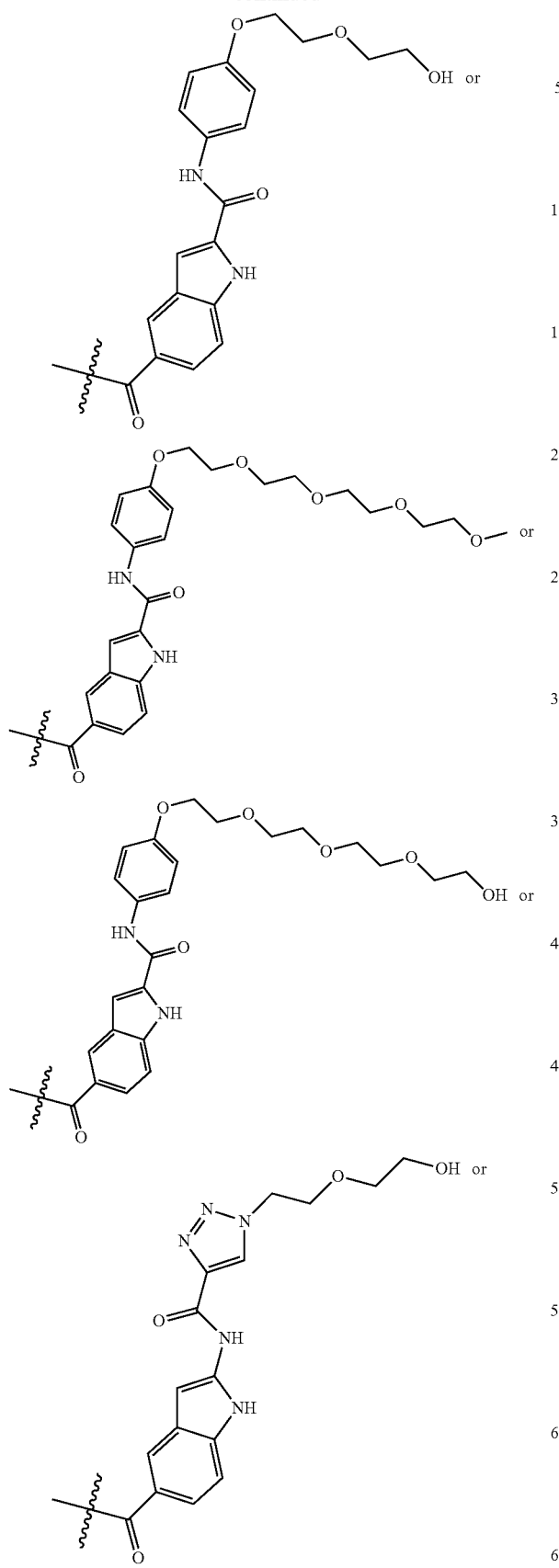
172
-continued
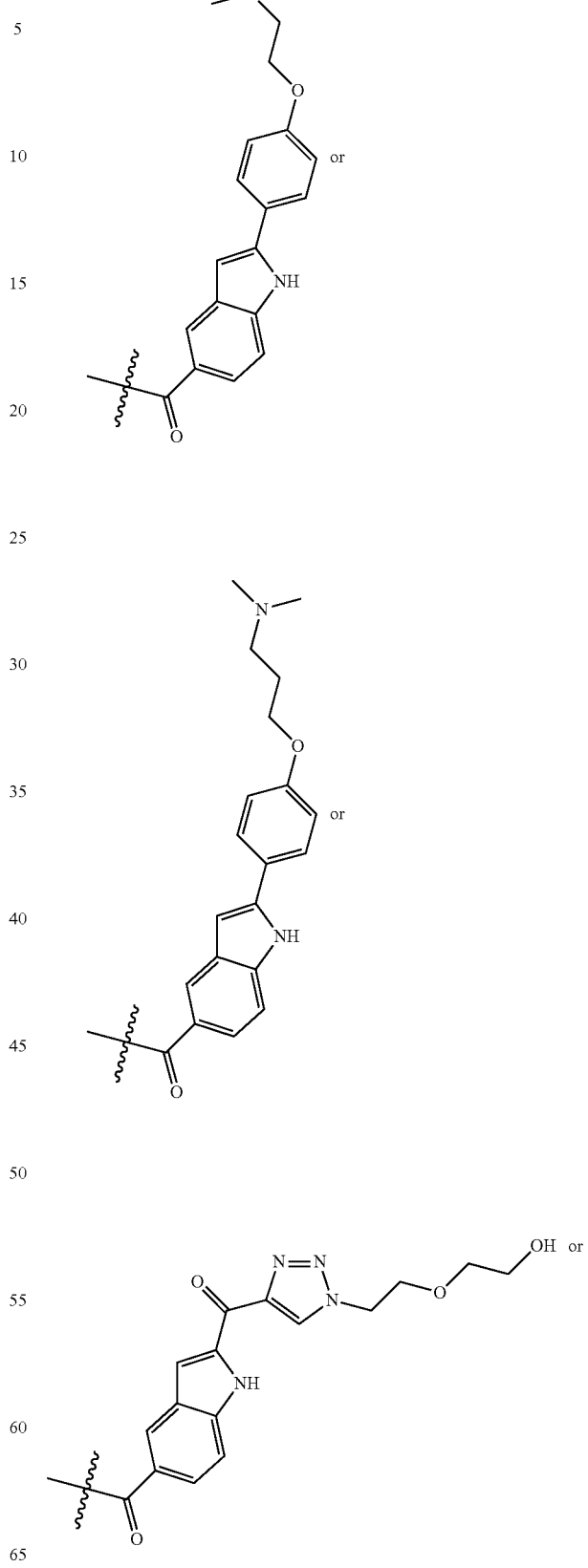

173
-continued
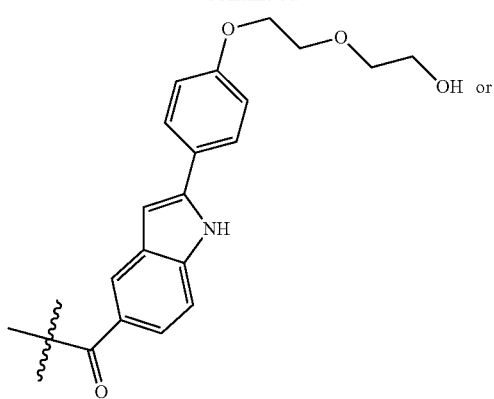
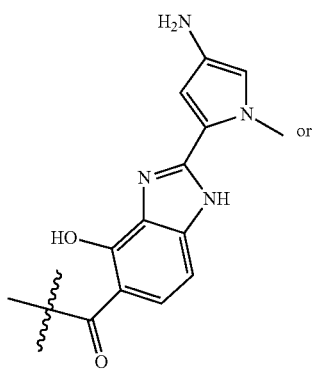
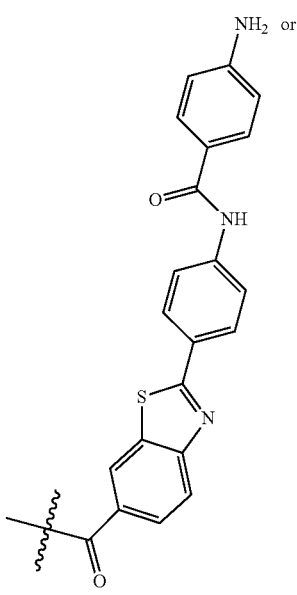
174
-continued
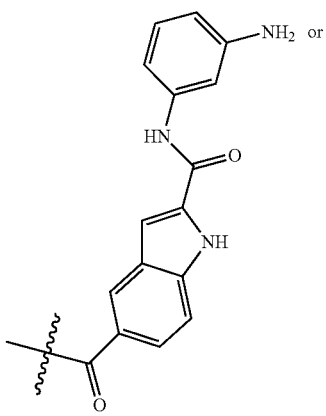
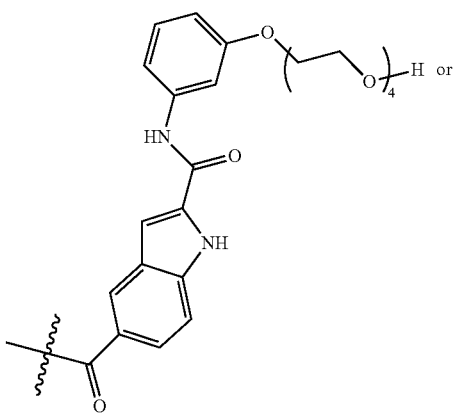
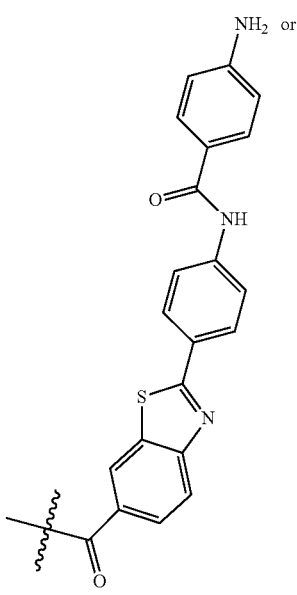

175
-continued
176
-continued
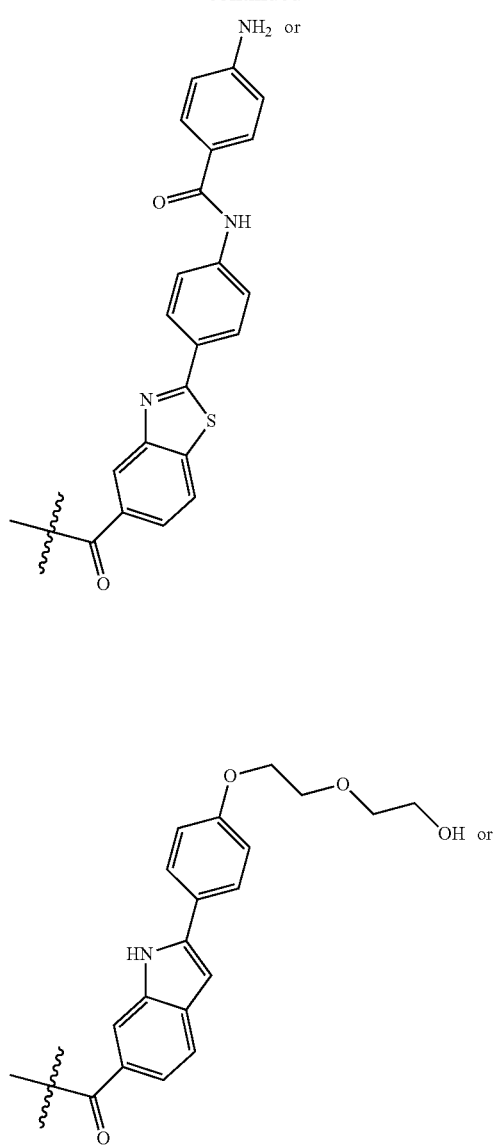
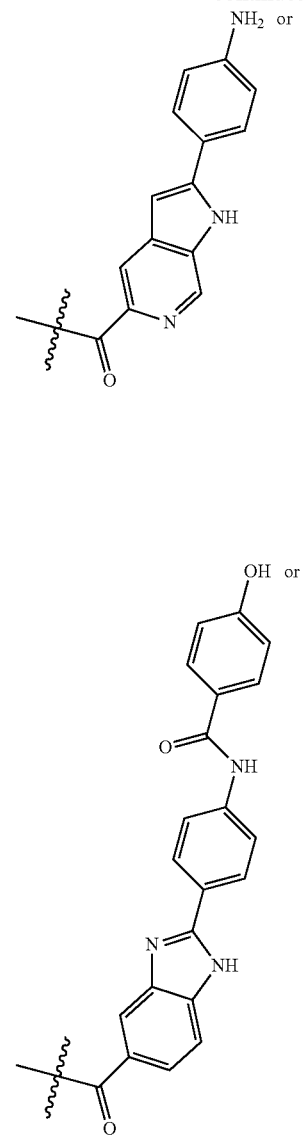
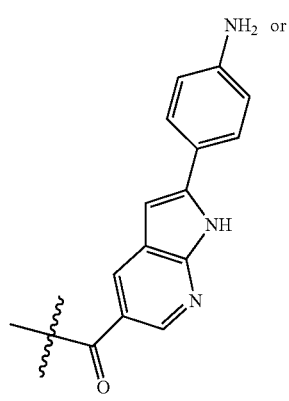
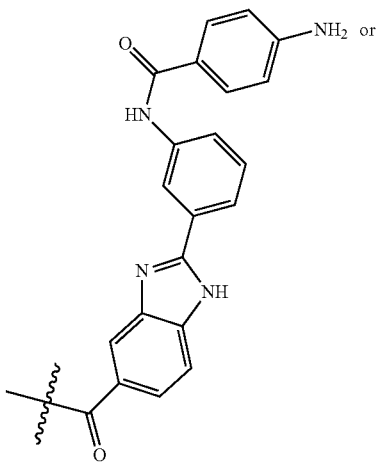

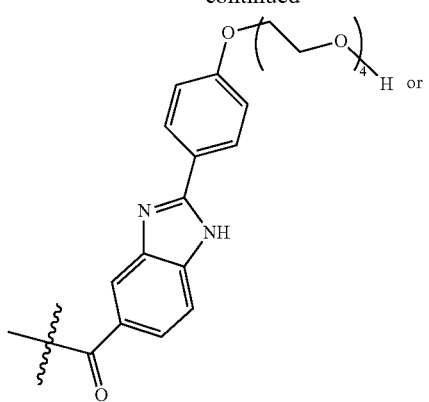
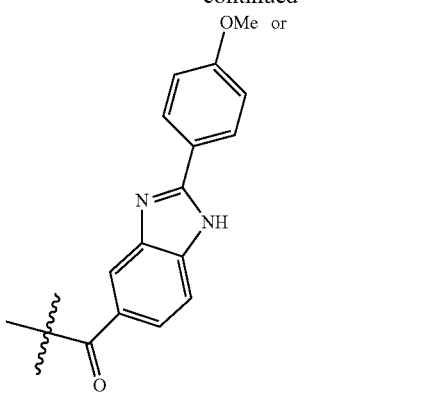

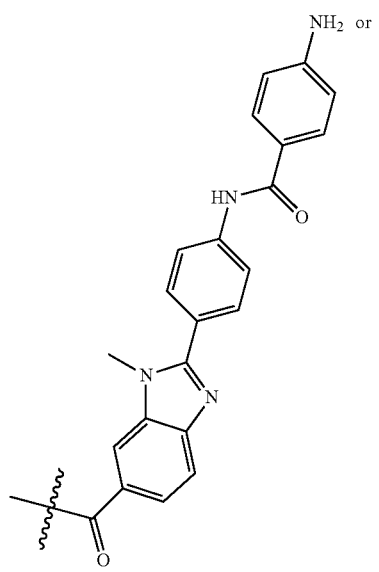
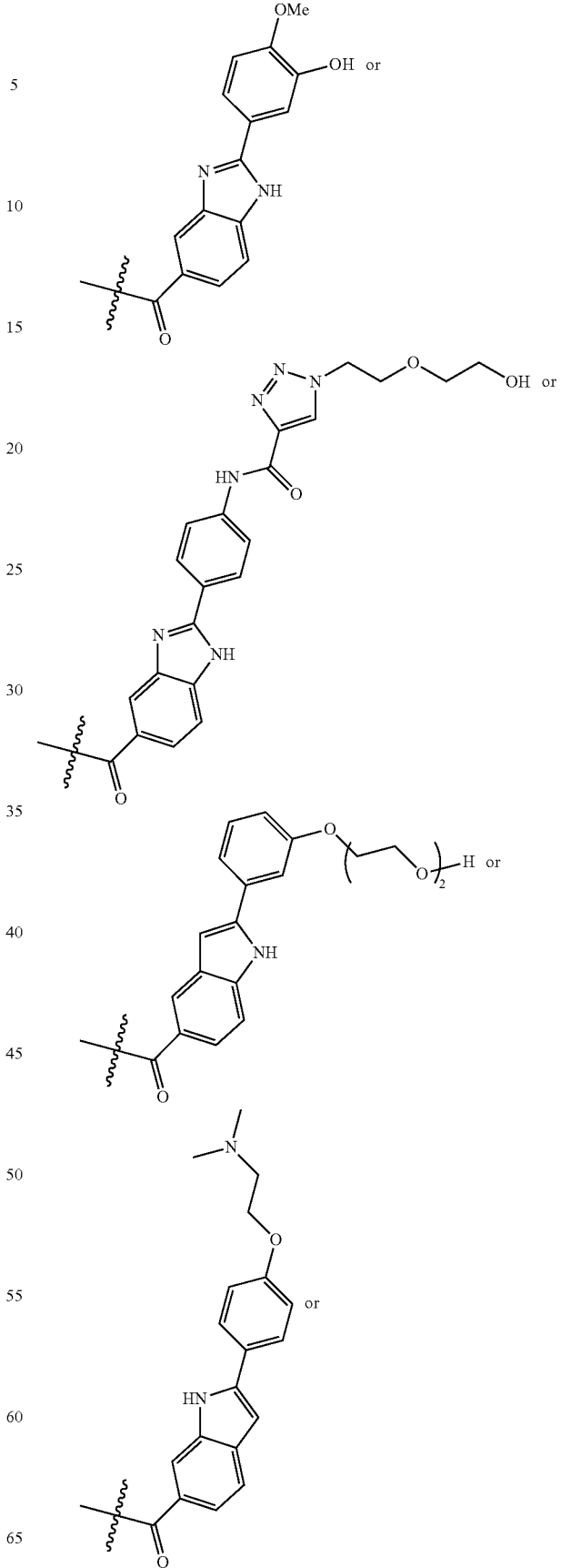

-continued

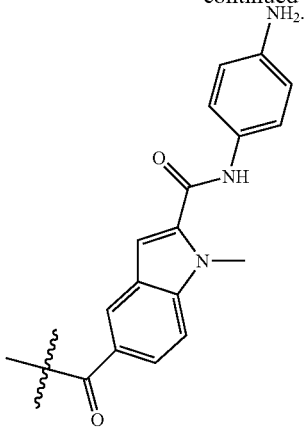

In another aspect of this invention, a compound of formula (I) or (II) has a DNA-binding unit of formula DB3 or DB4. These two moieties comprises structures that are built up of an acetylene moiety coupled to a 5- or 6-membered ring. This ring may be aromatic or non-aromatic. In the latter case, it may be either unsaturated or completely saturated. Furthermore, the 5- or 6-membered ring may be fused to one or more other rings to form an aromatic or non-aromatic ring system. Such a ring system is preferably flat as this may increase the DNA binding affinity. Either polar substituents or heteroatoms in the ring may provide for increased water solubility and may favorably affect the pharmacological properties of a compound of formula (I) or (II). The presence of an acetylene moiety in DNA-binding units DB3 and DB4 may provide for a handle that allows detoxification by means of for example oxidation or hydration.

The moiety DB3 may for example be

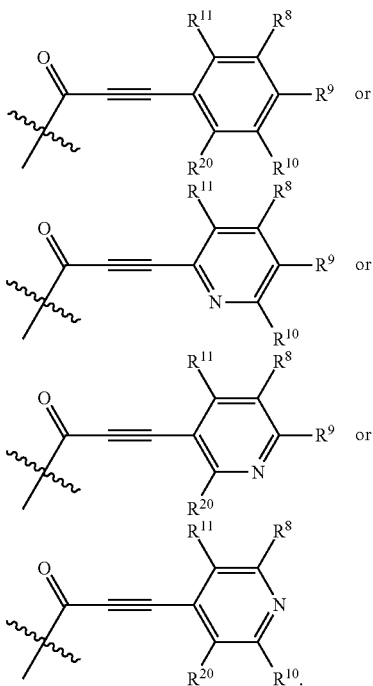

The moiety DB4 may for example be

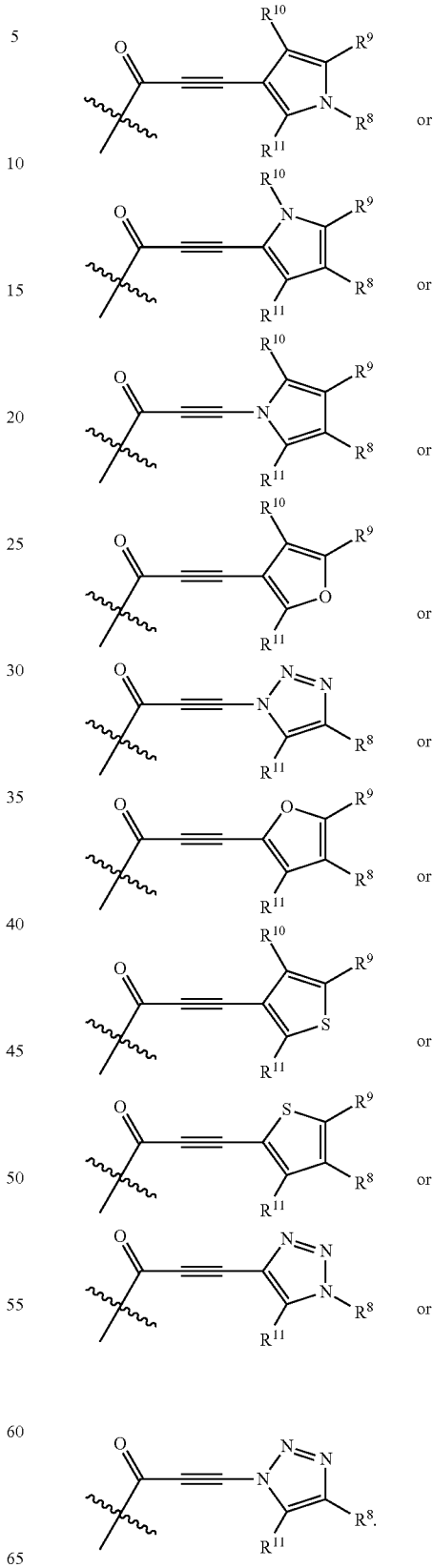

In a more specific embodiment, the moiety DB3 may for example be

 or

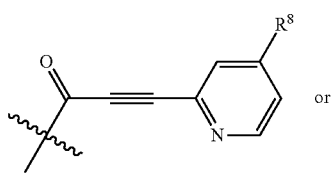 or

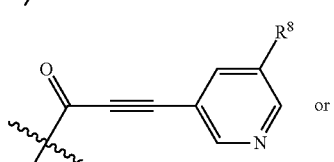 or

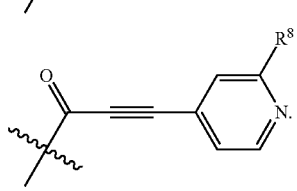

In another more specific embodiment, the moiety DB4 may for example be

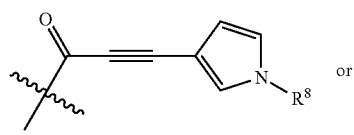 or

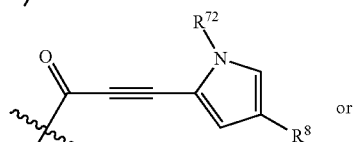 or

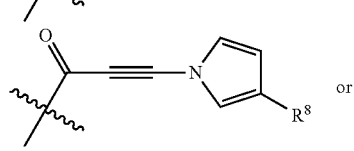 or

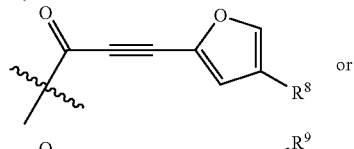 or

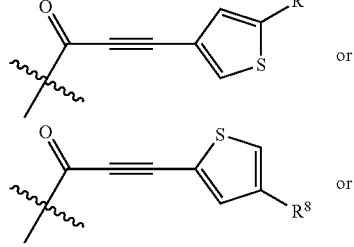 or

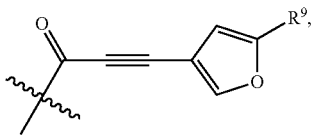

wherein $R^{72}$ is selected from H and methyl.

In the exemplary structures of DB3 and DB4, $R^8$, $R^9$, $R^{10}$, $R^{11}$, and $R^{20}$ may for example each independently be selected to be H, be or contain another moiety selected from structures DB1-DB9 or a derivative thereof, or be

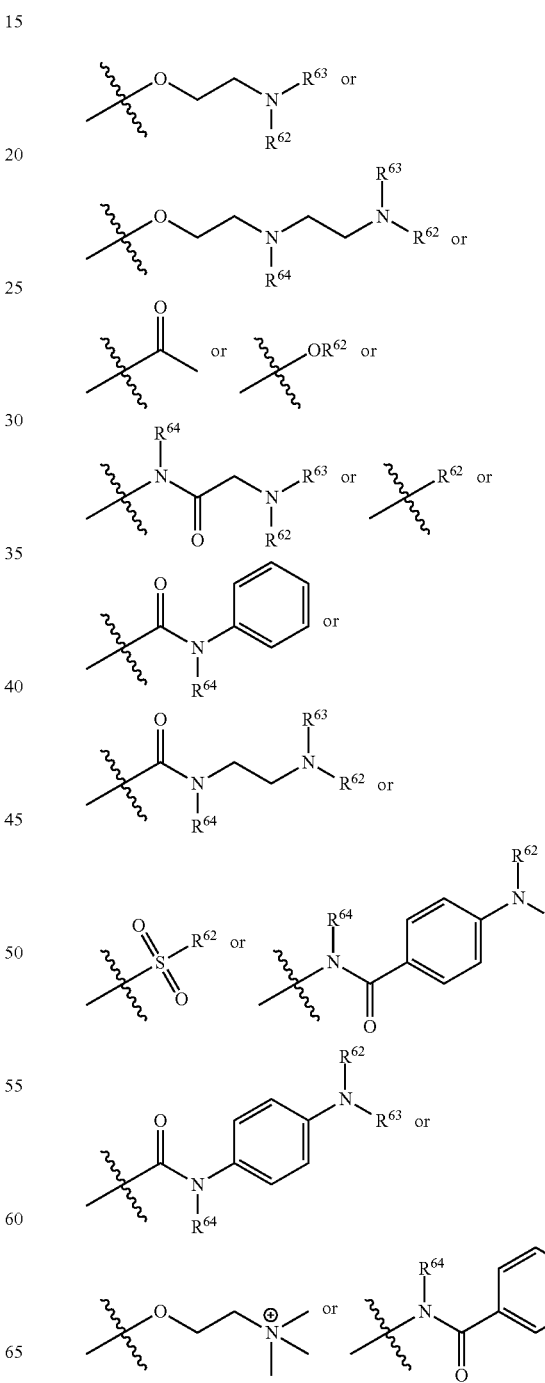

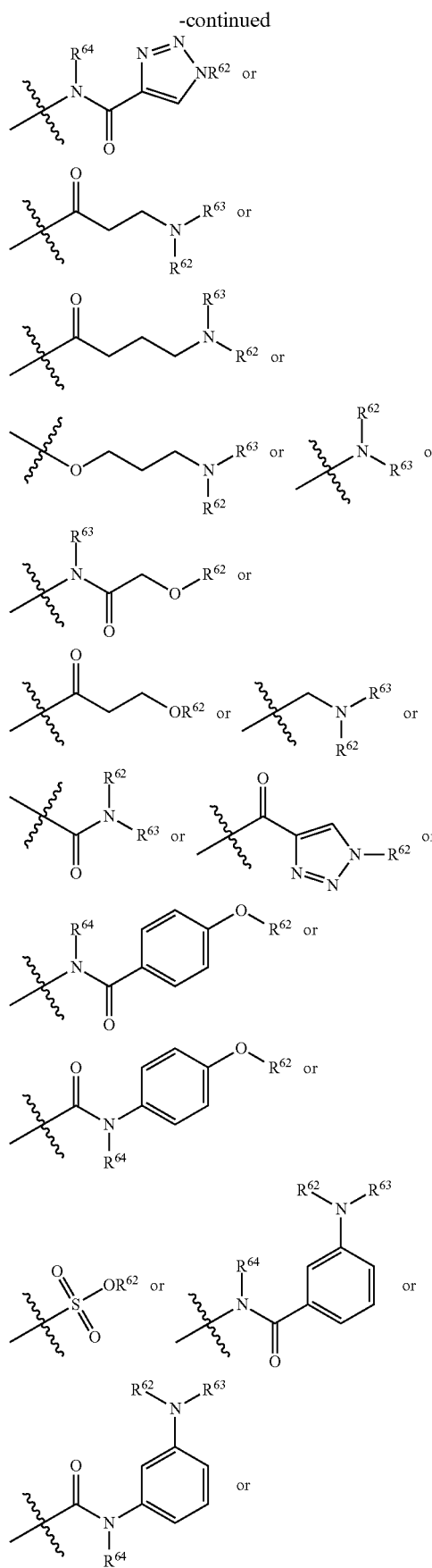
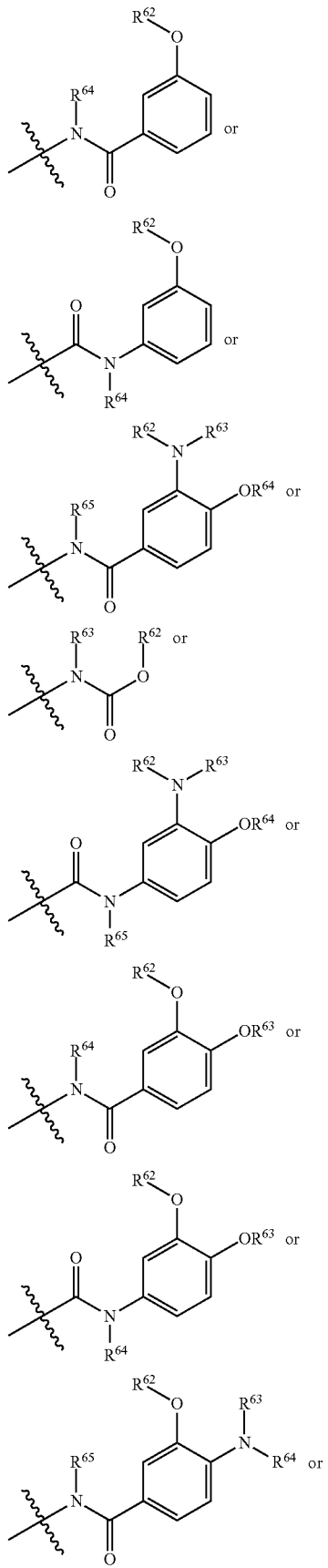

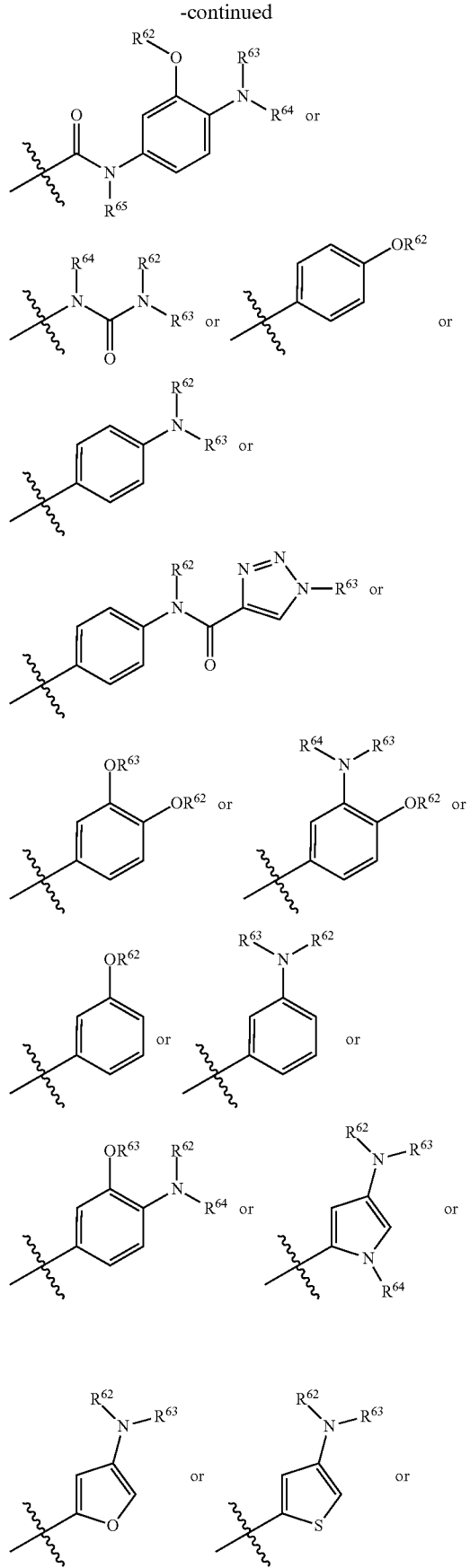
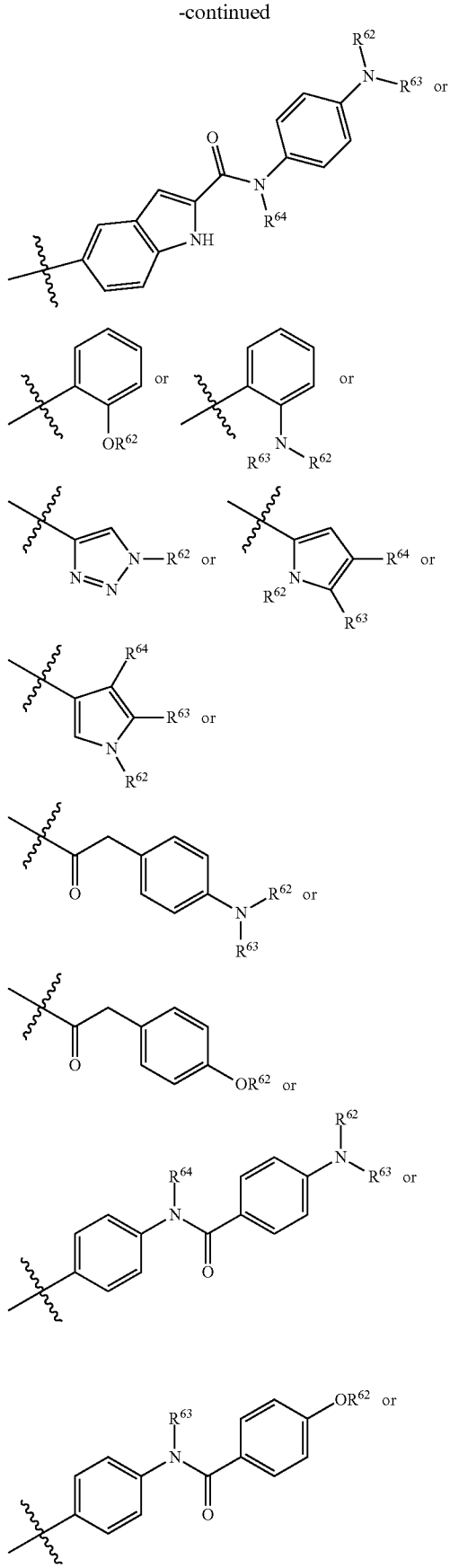

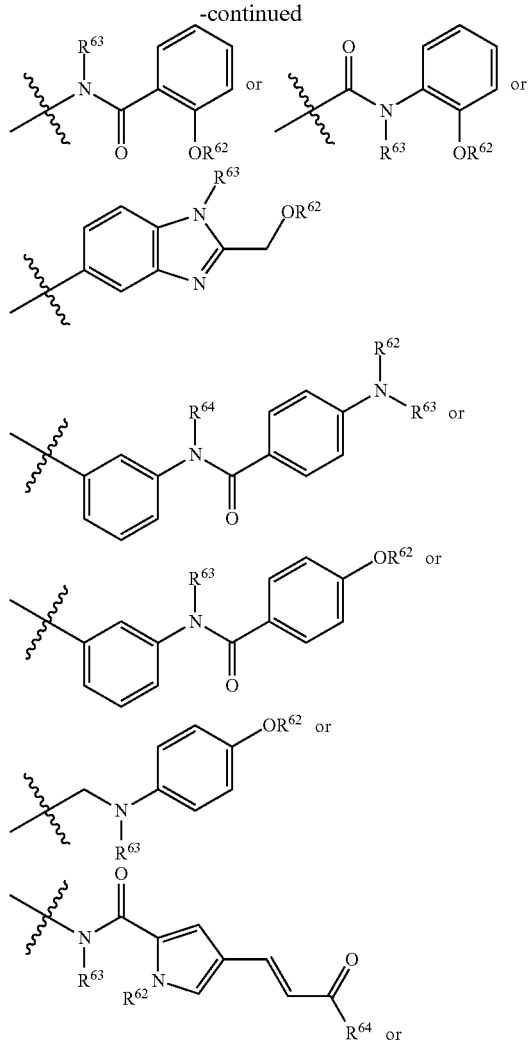
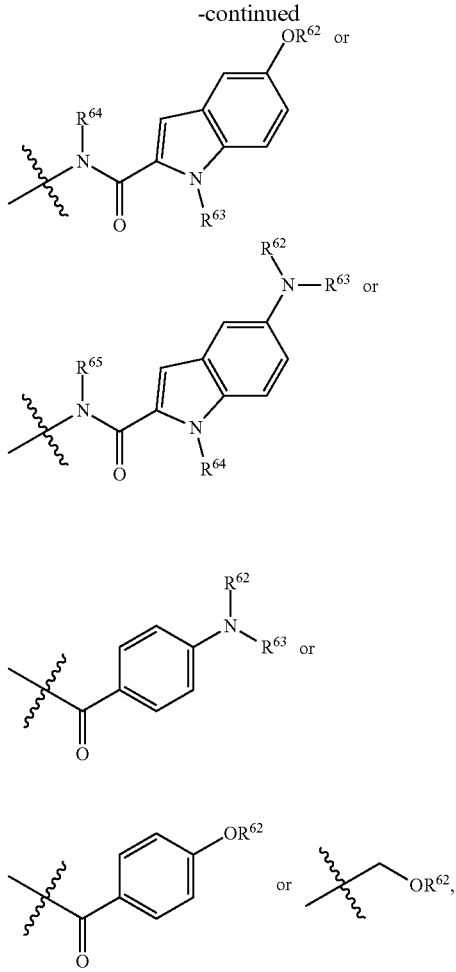
wherein $R^{62}$, $R^{63}$, $R^{64}$, and $R^{65}$ are independently selected from H, $C_{1-3}$ alkyl, and
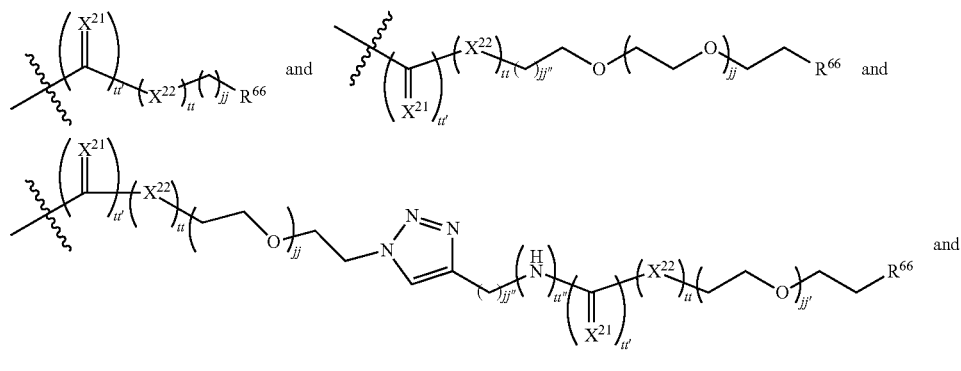
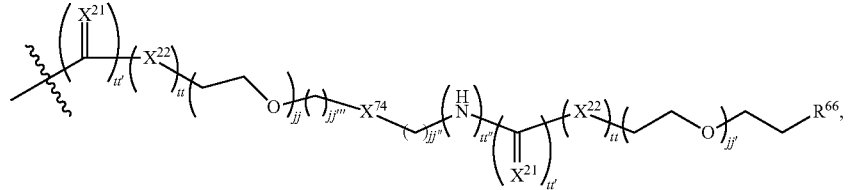

wherein jj, jj', jj", and jj''' are independently selected from 0 to 8, $X^{74}$ is selected from

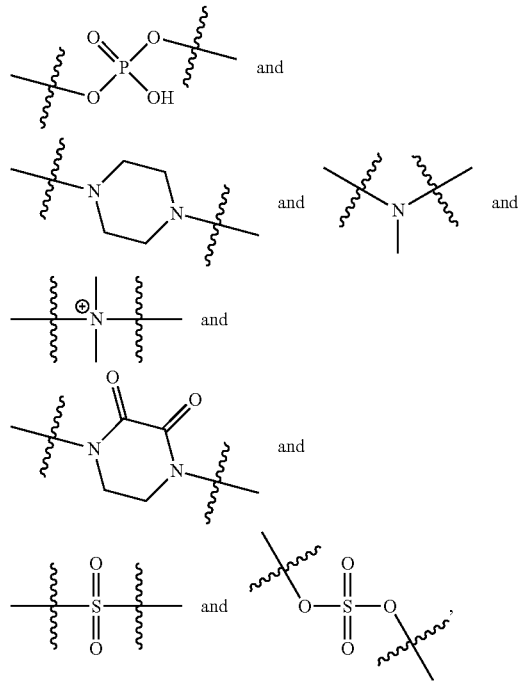

each tt, tt', and tt" is independently selected from 0 and 1, each $X^{21}$ and $X^{22}$ is independently selected from O, S, $NR^{67}$, $H_2$, and $C(R^{67})R^{68}$, wherein $R^{67}$ and $R^{68}$ are independently selected from H and optionally substituted $C_{1-3}$ alkyl or $C_{1-3}$ heteroalkyl, and $R^{66}$ is selected from H, COOH, $CO_2Me$, OH, OMe, $NR^{69}R^{70}$, $NR^{69}C(O)CH_3$, SH, SMe,

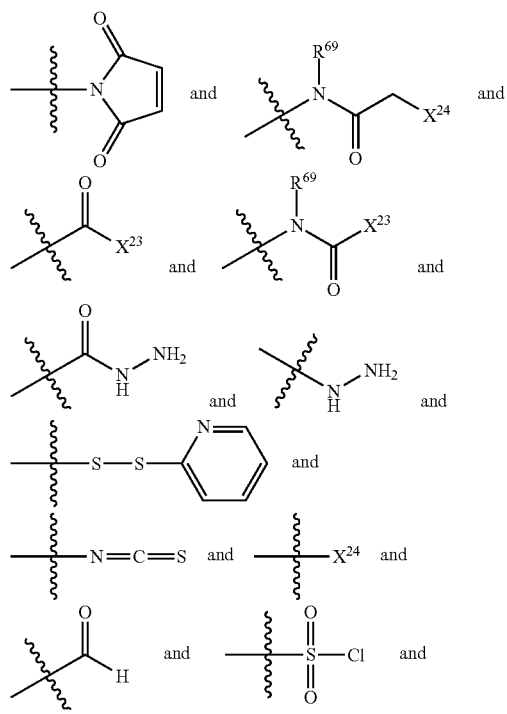

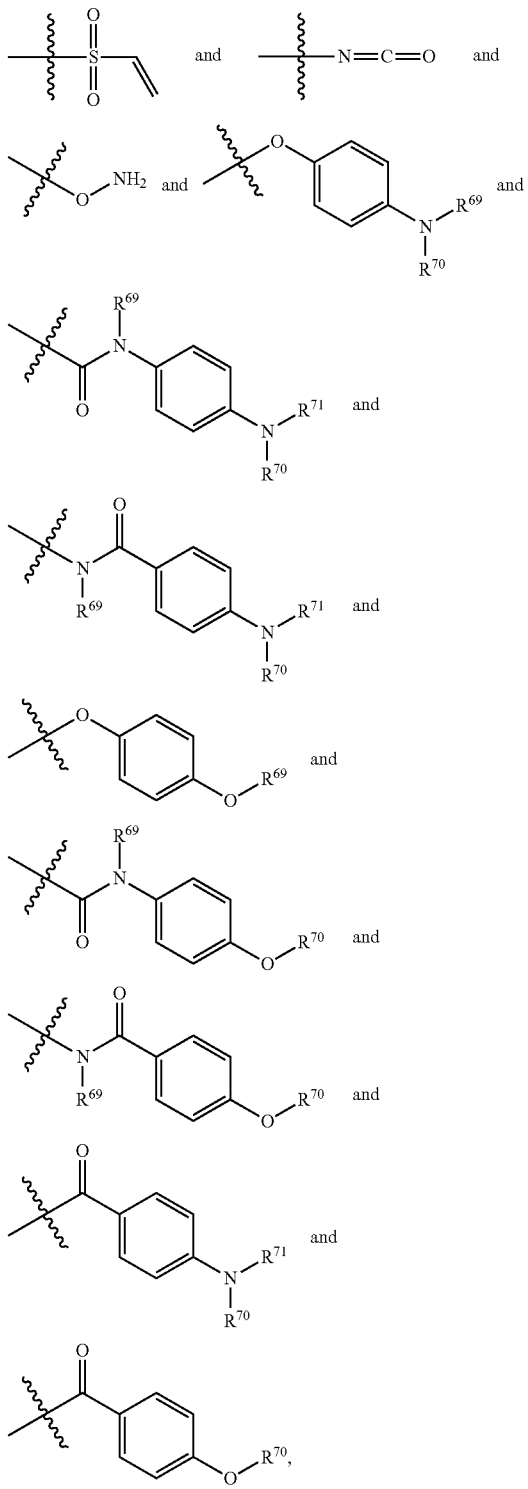

wherein $X^{23}$ is selected from halide, hydroxy, $OC(O)R^{bb}$, and $OC(O)OR^{bb}$, or $C(O)-X^{23}$ is an active ester, $X^{24}$ is selected from halide, mesyloxy, triflyloxy, and tosyloxy, $R^{bb}$ is selected from optionally substituted $C_{1-10}$ alkyl, $C_{1-10}$ heteroalkyl, $C_{3-10}$ cycloalkyl, $C_{1-10}$ heterocycloalkyl, $C_{5-10}$ aryl, and $C_{1-10}$ heteroaryl, and $R^{69}$, $R^{70}$, and $R^{71}$ are independently selected from methyl and H.

In a further embodiment, the moiety DB3 may for example be
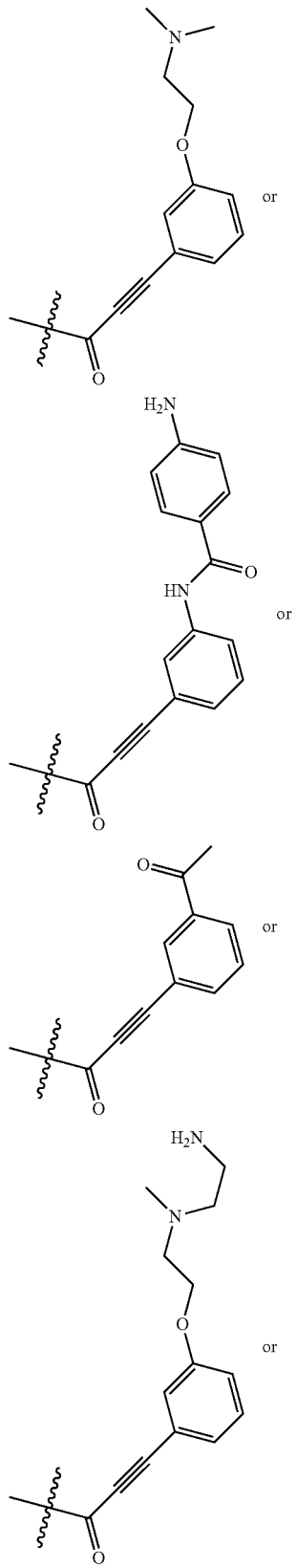
-continued
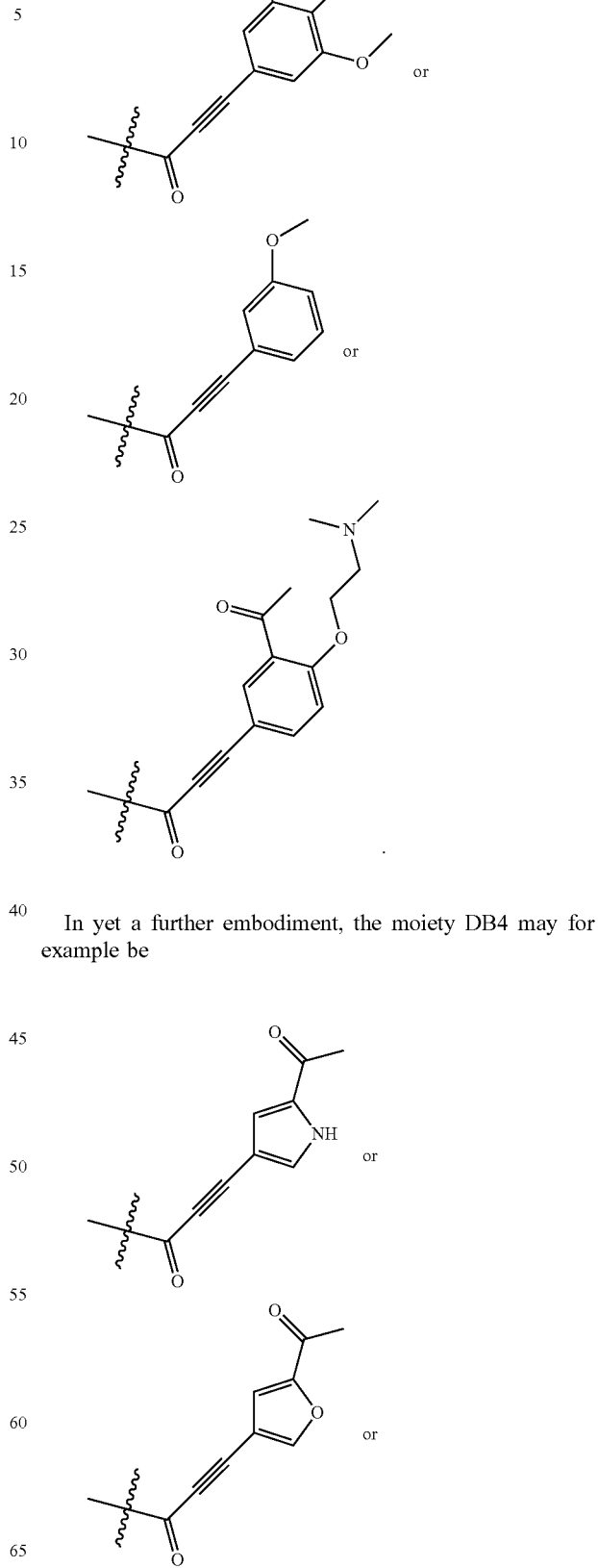
In yet a further embodiment, the moiety DB4 may for example be

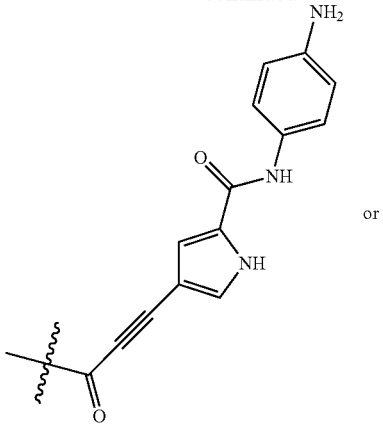

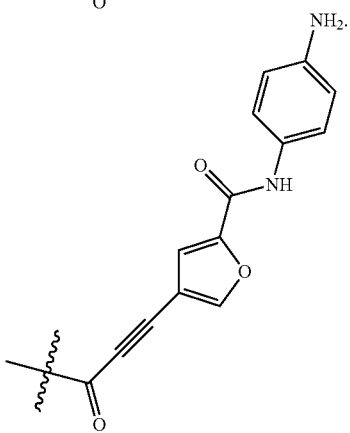

In another aspect of this invention, a compound of formula (I) or (II) has a DNA-binding unit of formula DB5. This moiety comprises structures that are built up of a 5-membered or 6-membered ring coupled to an optionally substituted vinyl moiety. The 5-membered or 6-membered ring may be aromatic or non-aromatic. In the latter case it may be either unsaturated or completely saturated. Polar substituents or heteroatoms in the ring and/or polar substituents on the vinyl group may provide for increased water solubility and favorably affect the pharmacological properties of a compound of formula (I) or (II). Aromatic substituents on the ring or vinyl moiety may increase the binding affinity. The presence of a vinyl moiety in DNA-binding unit DB5 may provide for a handle that allows detoxification by means of for example oxidation or hydration.

The moiety DB5 may for example be

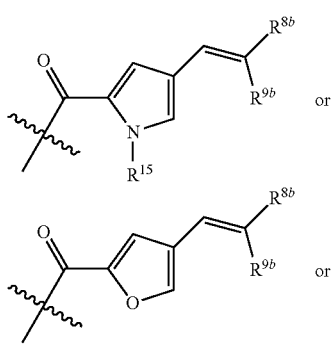

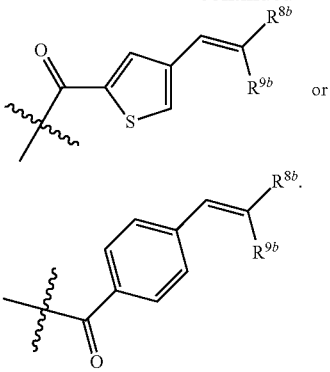

In the exemplary structures of DB5, $R^{8b}$, $R^{9b}$, and $R^{15}$ may for example each independently be selected to be H, be or contain another moiety selected from structures DB1-DB9 or a derivative thereof, or be

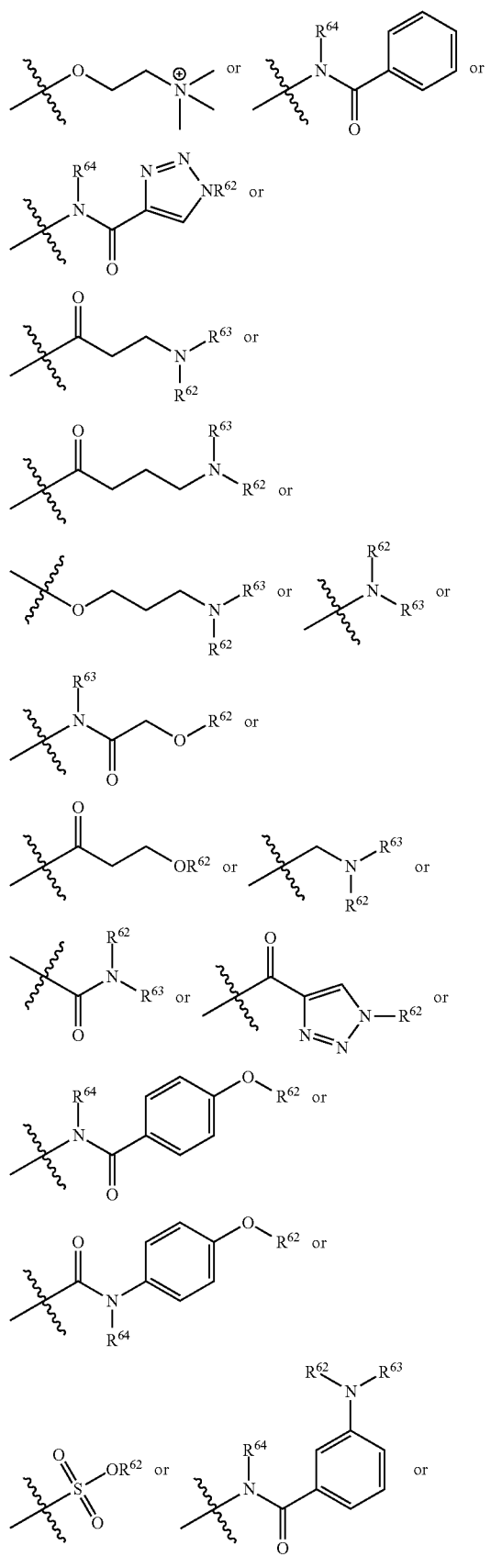
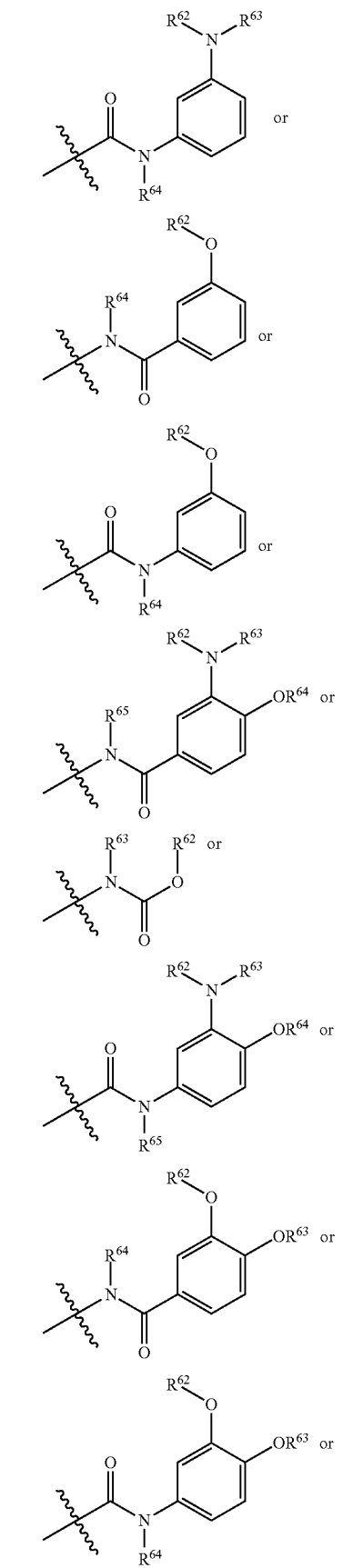

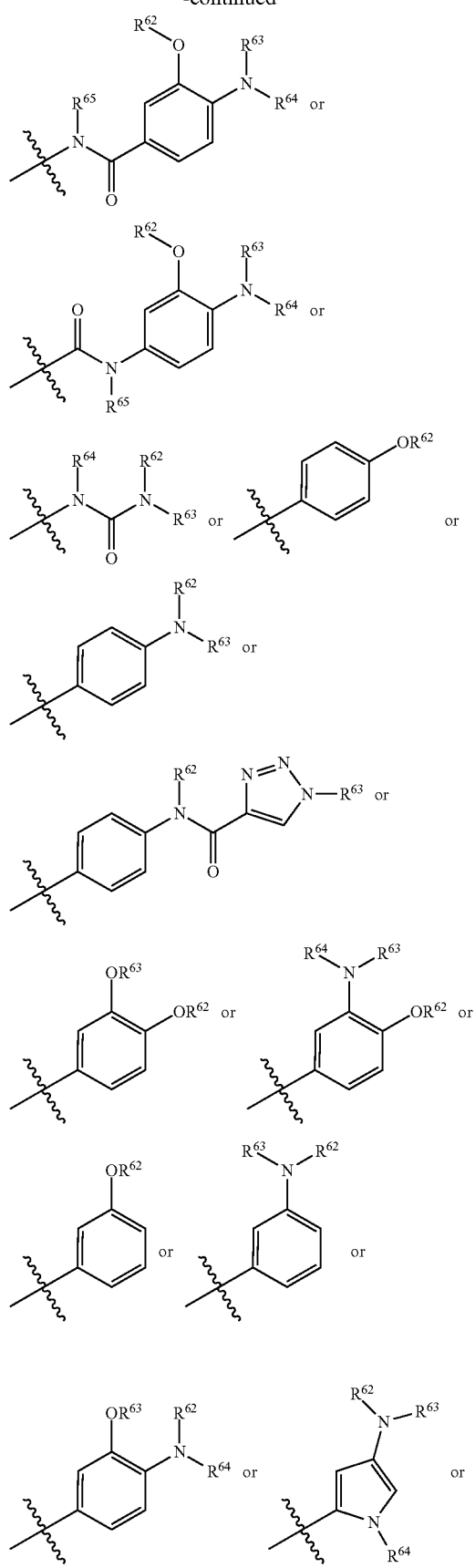
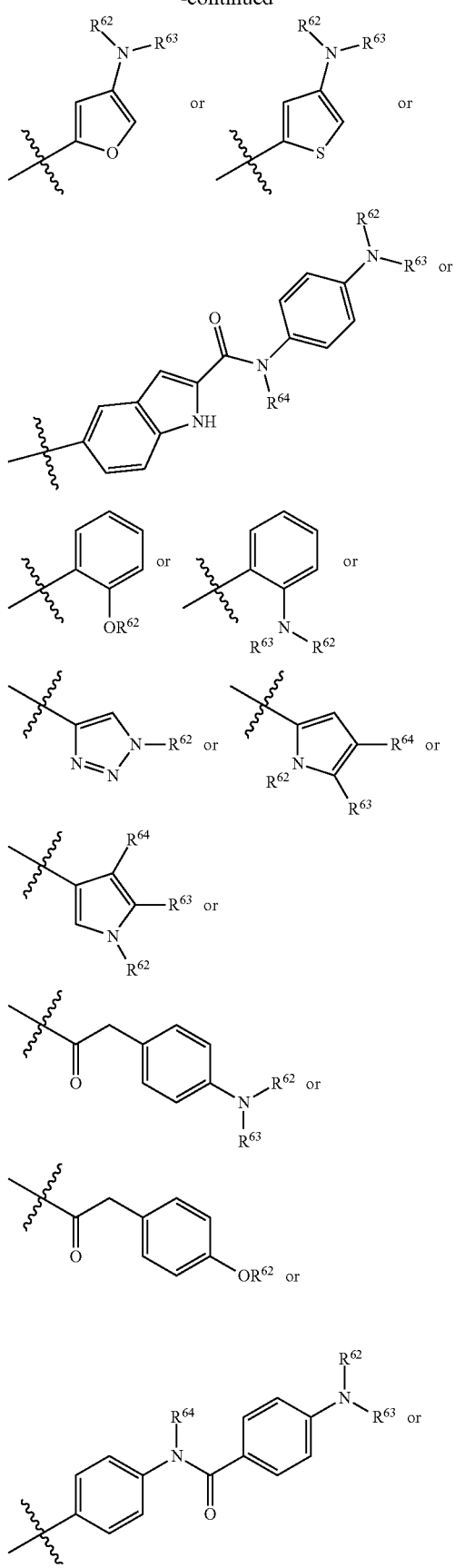

201
-continued
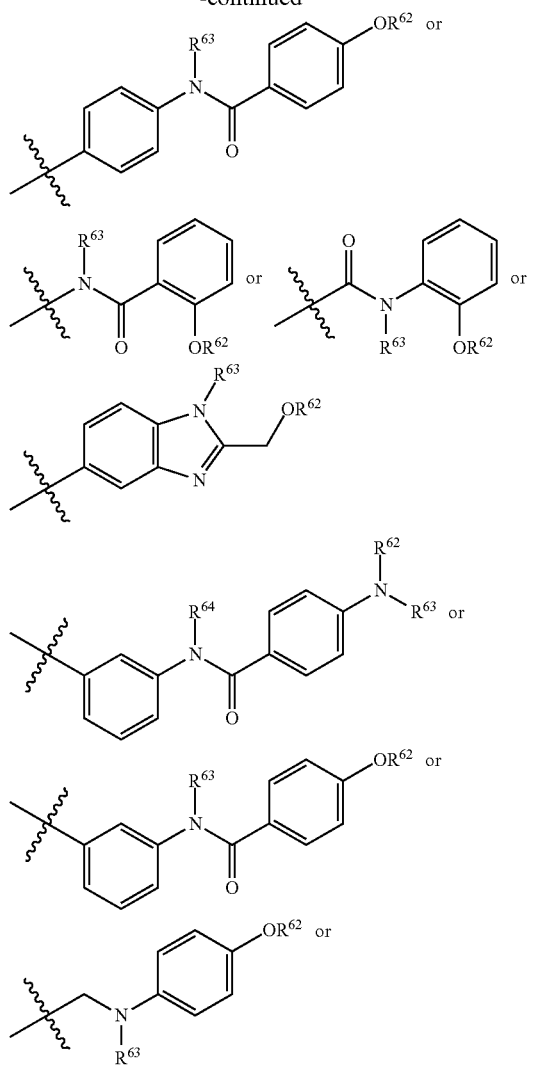
202
-continued
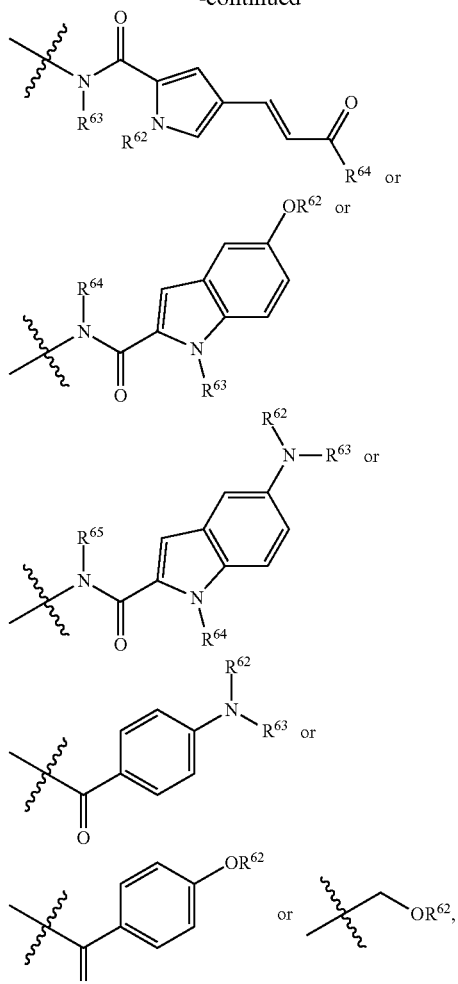
wherein $R^{62}$, $R^{63}$, $R^{64}$, and $R^{65}$ are independently selected from H, $C_{1-3}$ alkyl, and
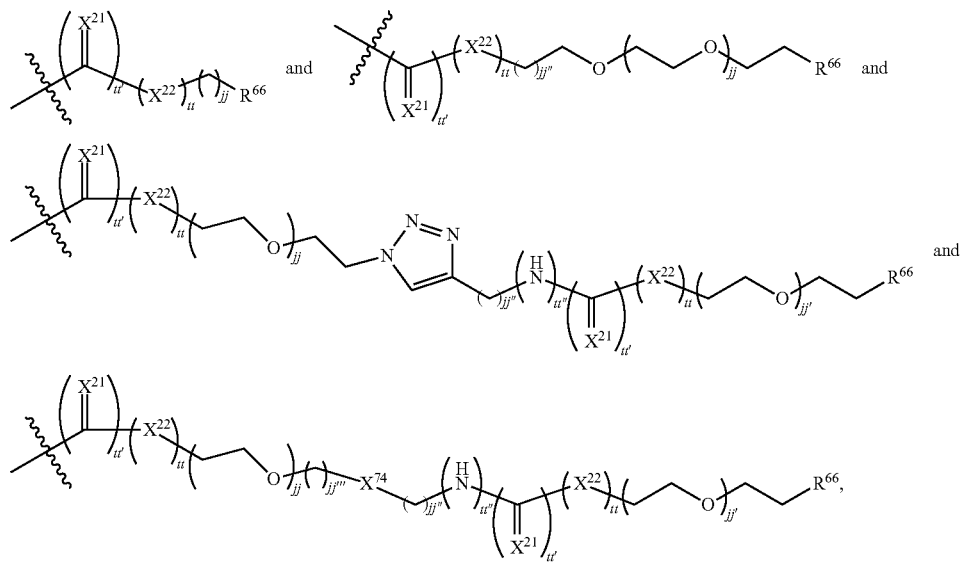

wherein jj, jj', jj", and jj'" are independently selected from 0 to 8, $X^{74}$ is selected from

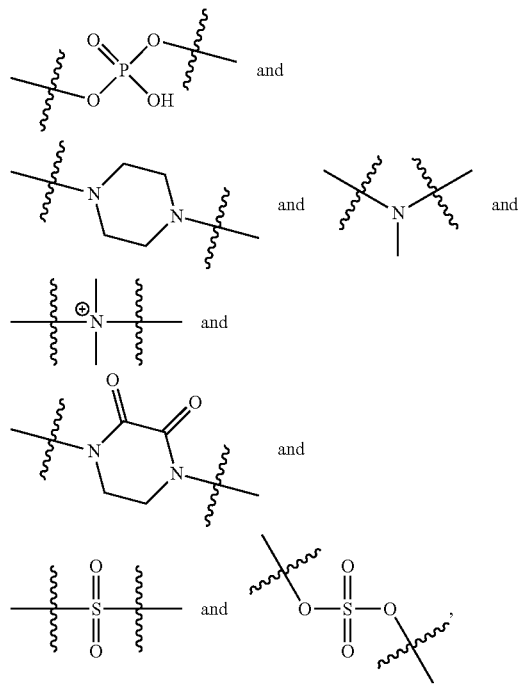

each tt, tt', and tt" is independently selected from 0 and 1, each $X^{21}$ and $X^{22}$ is independently selected from O, S, $NR^{67}$, $H_2$, and $C(R^{67})R^{68}$, wherein $R^{67}$ and $R^{68}$ are independently selected from H and optionally substituted $C_{1-3}$ alkyl or $C_{1-3}$ heteroalkyl, and $R^{66}$ is selected from H, COOH, $CO_2Me$, OH, OMe, $NR^{69}R^{70}$, $NR^{69}C(O)CH_3$, SH, SMe,

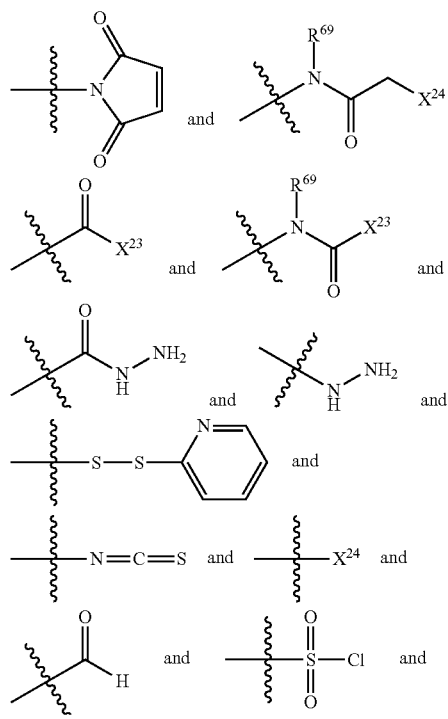

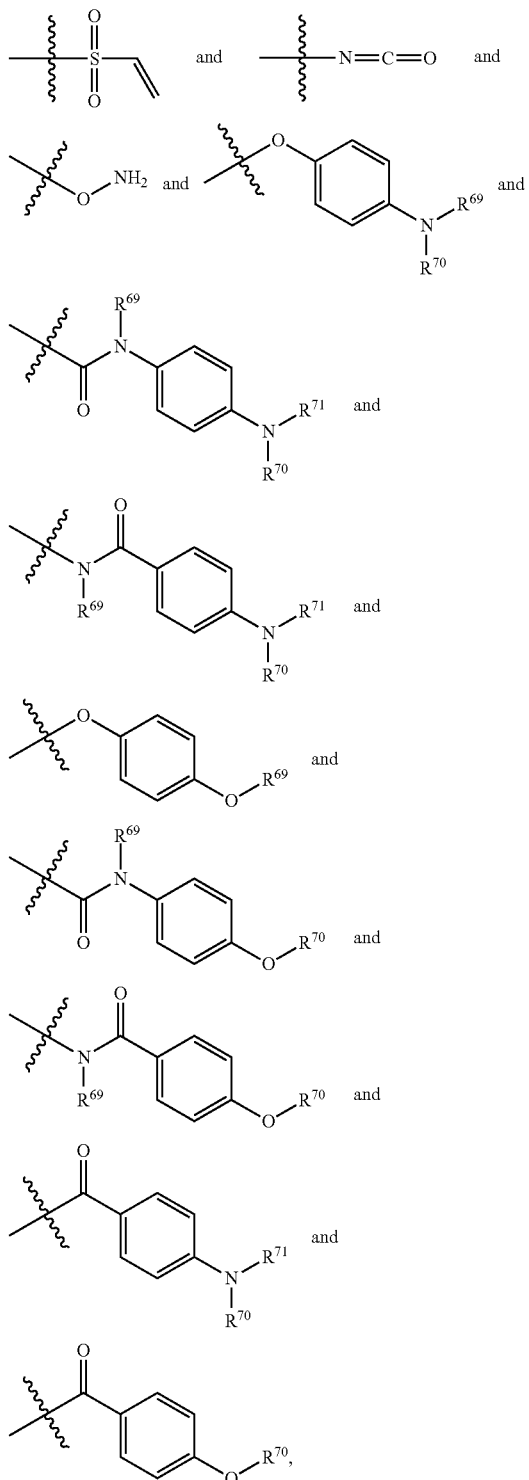

wherein $X^{23}$ is selected from halide, hydroxy, $OC(O)R^{bb}$, and $OC(O)OR^{bb}$, or $C(O)-X^{23}$ is an active ester, $X^{24}$ is selected from halide, mesyloxy, triflyloxy, and tosyloxy, $R^{bb}$ is selected from optionally substituted $C_{1-10}$ alkyl, $C_{1-10}$ heteroalkyl, $C_{3-10}$ cycloalkyl, $C_{1-10}$ heterocycloalkyl, $C_{5-10}$ aryl, and $C_{1-10}$ heteroaryl, and $R^{69}$, $R^{70}$, and $R^{71}$ are independently selected from methyl and H.

In a further embodiment, the moiety DB5 may for example be

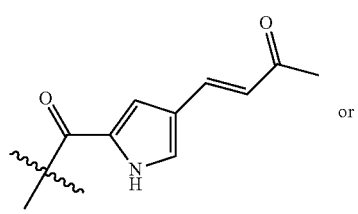

or

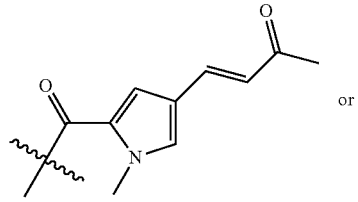

or

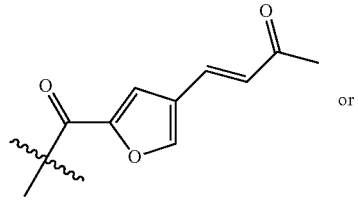

or

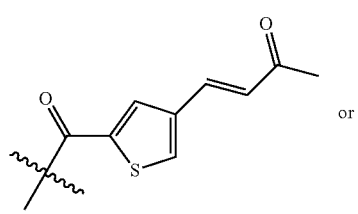

or

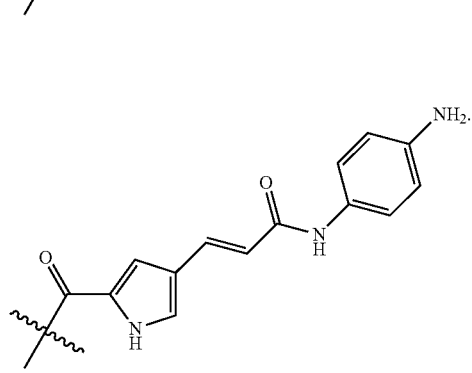

In another aspect of this invention, a compound of formula (I) or (II) has a DNA-binding unit of formula DB6 or DB7. These two moieties comprise structures that are built up of two 5- or 6-membered rings that are connected together via a direct single bond. These rings may each independently be aromatic or non-aromatic. In the latter case, they may be either unsaturated or completely saturated. Furthermore, ring B may be fused to one or more other rings to form an aromatic or non-aromatic ring system, which is preferably flat. This may increase the DNA binding affinity. Either polar substituents or heteroatoms in one or more of the rings may provide for increased water solubility and may favorably affect the pharmacological properties of a compound of formula (I) or (II).

The moiety DB6 may for example be

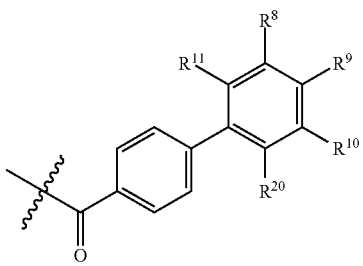

or

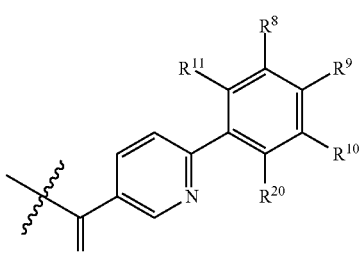

or

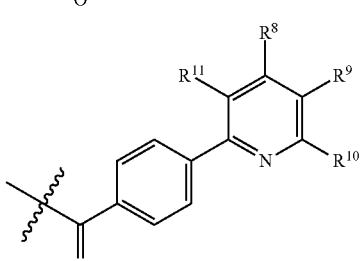

or

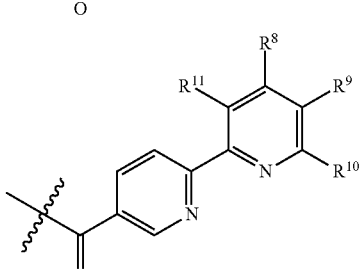

or

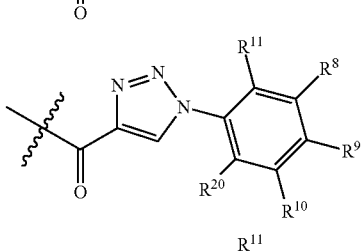

or

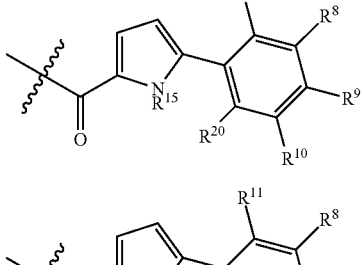

or

207
-continued
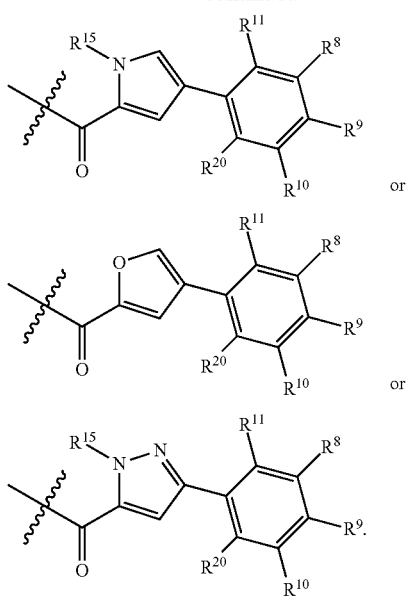
The moiety DB7 may for example be
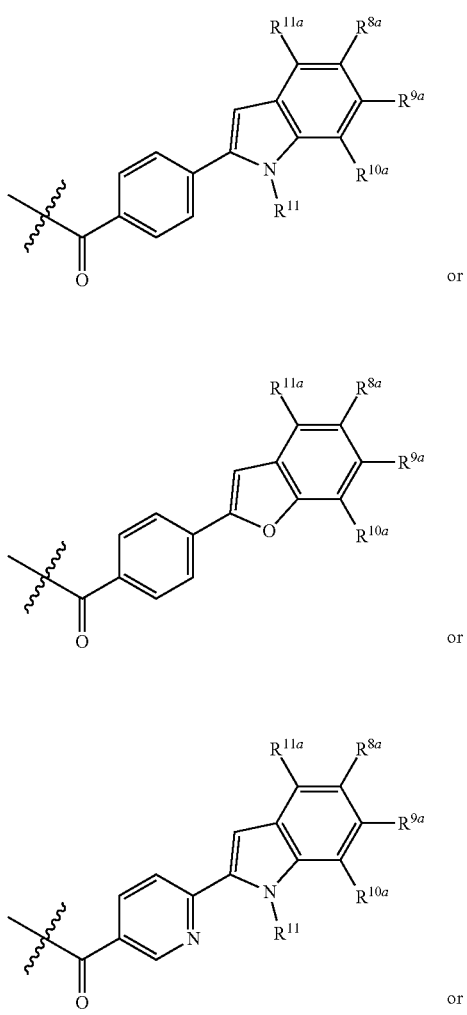
208
-continued
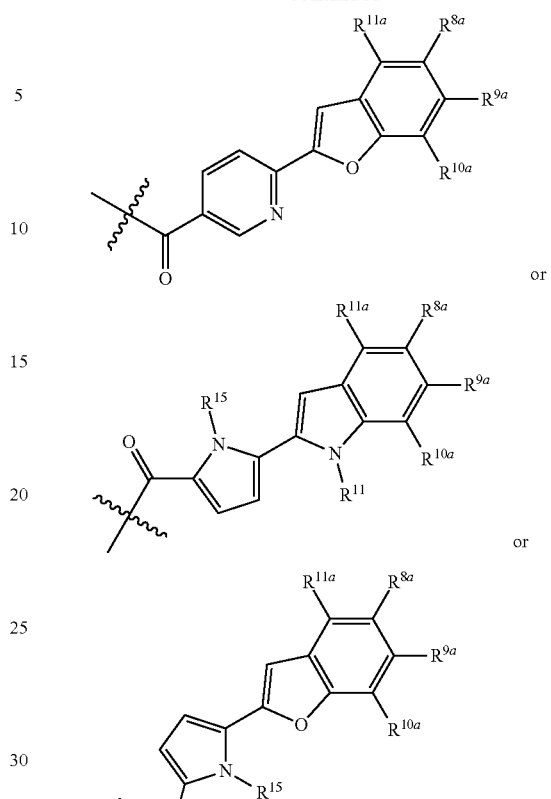

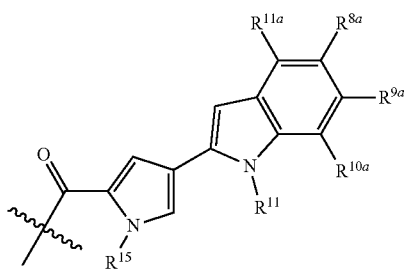
or
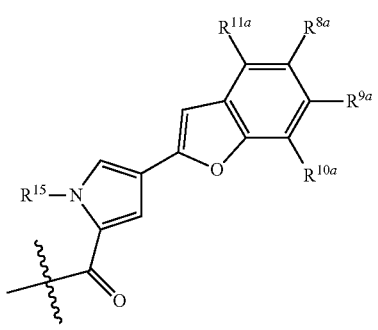
or
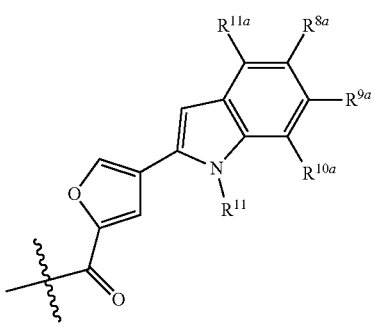
or
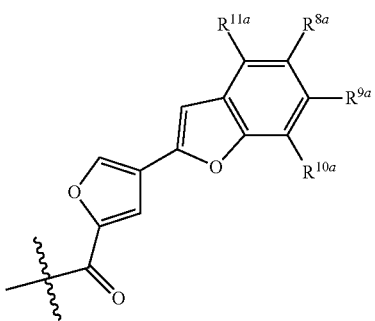
or
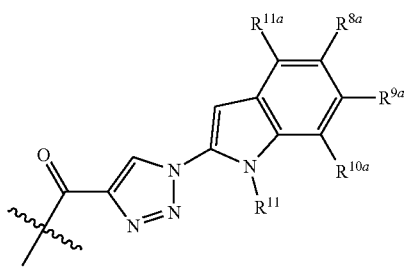
or
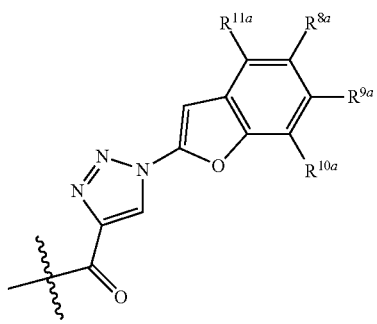
or
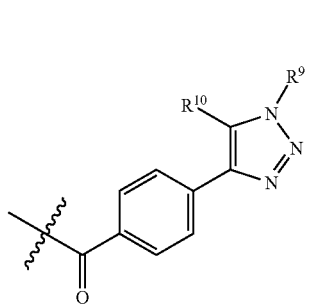
or
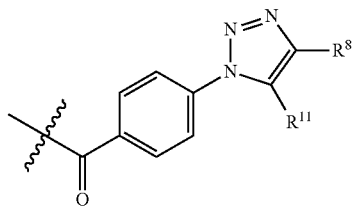
or
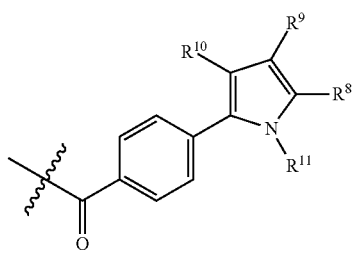
or
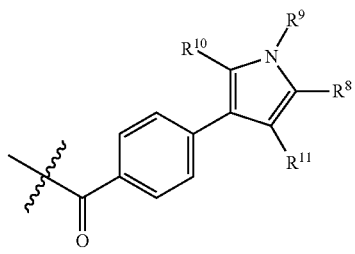
or
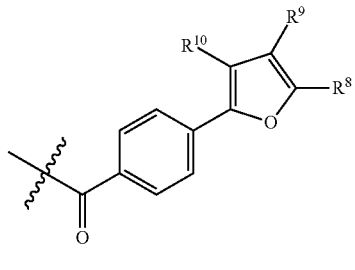
or 211
-continued
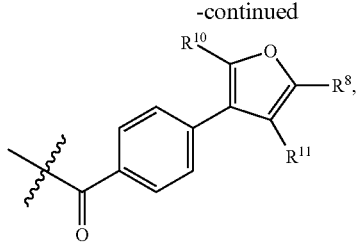
wherein $R^{8a}$, $R^{9a}$, $R^{10a}$, and $R^{11a}$ have the same meaning as defined for $R^8$, $R^9$, $R^{10}$, and $R^{11}$, respectively, and are independently selected.
In a more specific embodiment, moiety DB6 may for example be
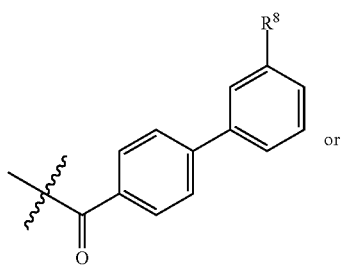
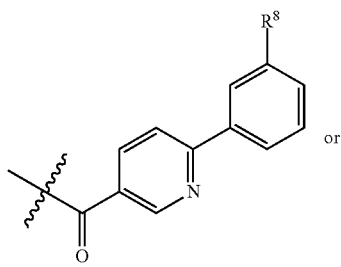

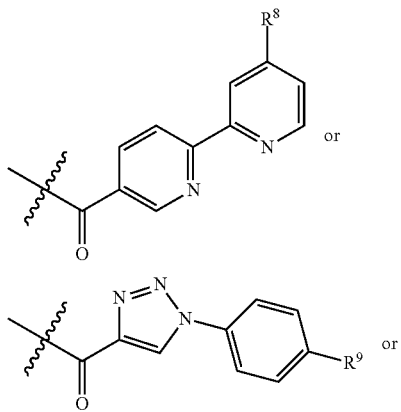
212
-continued
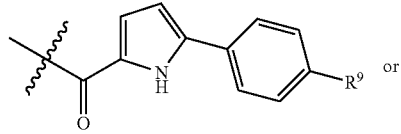
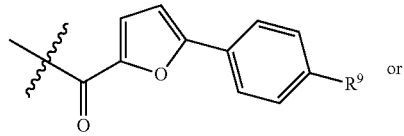
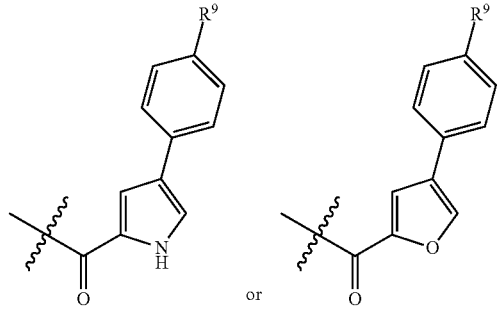
In a more specific embodiment, moiety DB7 may for example be
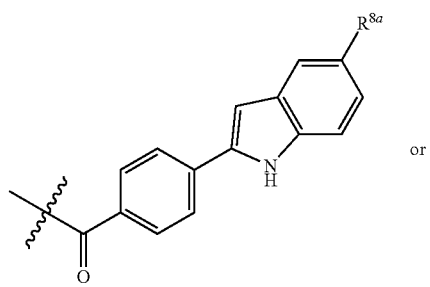

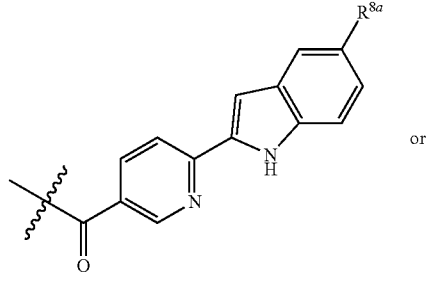

-continued
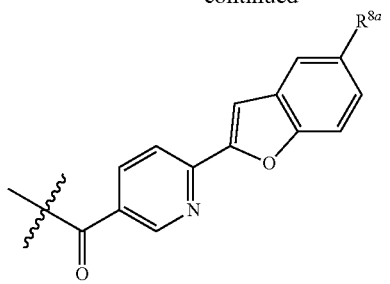
or
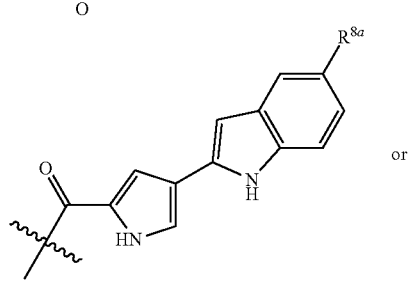
or
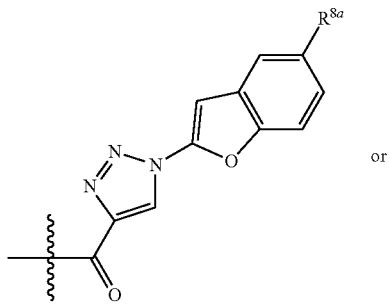
or
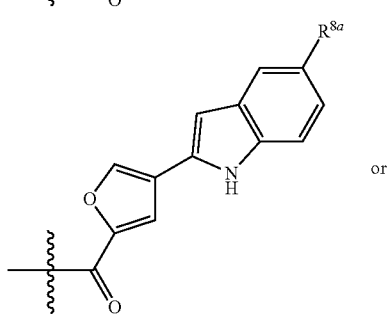
or
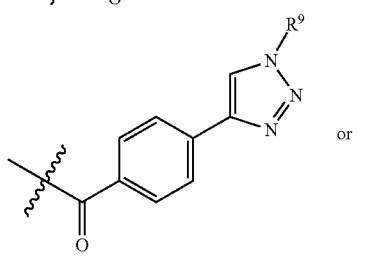
or
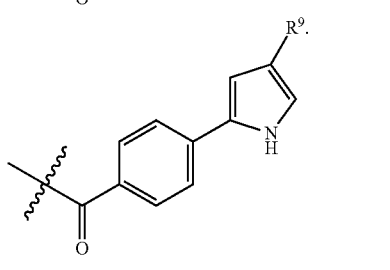
In the exemplary structures of DB6 and DB7, $R^8$, $R^{8a}$, $R^9$, $R^{9a}$, $R^{10}$, $R^{10a}$, $R^{11}$, $R^{11a}$, $R^{15}$ and $R^{20}$ may for example each independently be selected to be H, be or contain another moiety selected from structures DB1-DB9 or a derivative thereof, or be
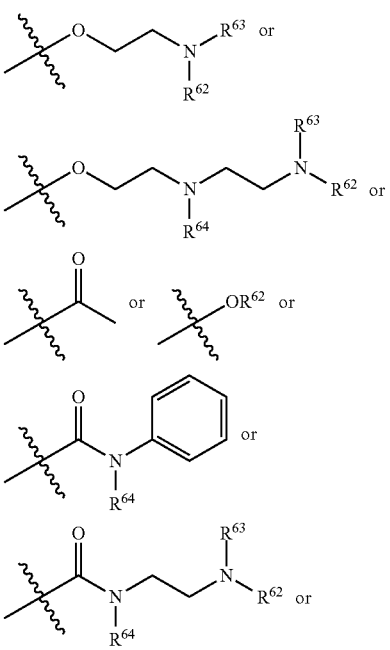
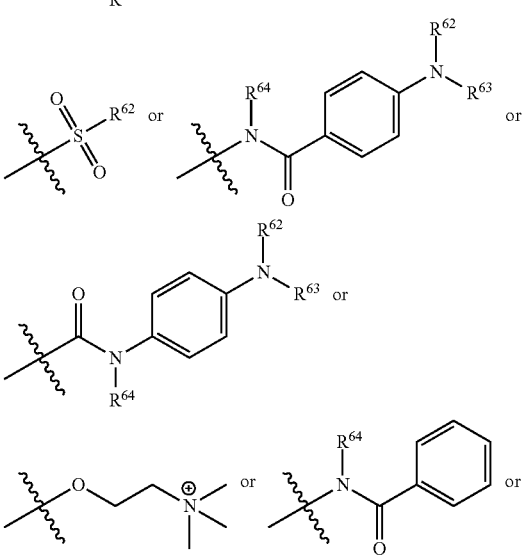
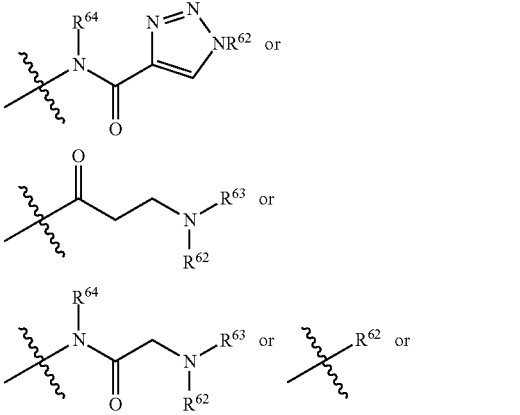

215
-continued
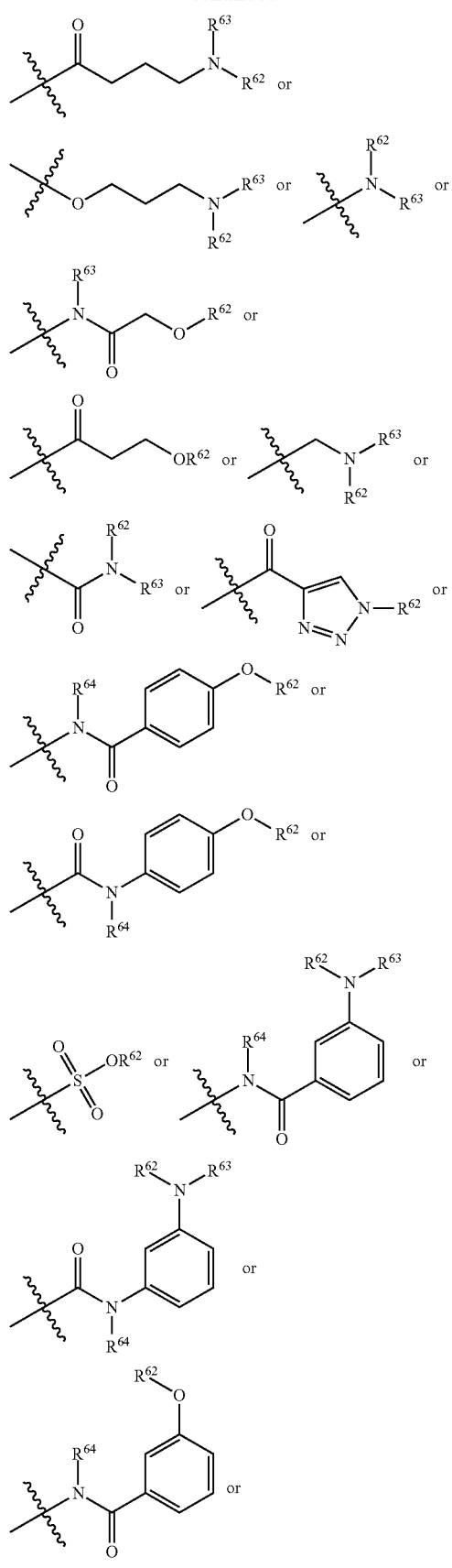
216
-continued
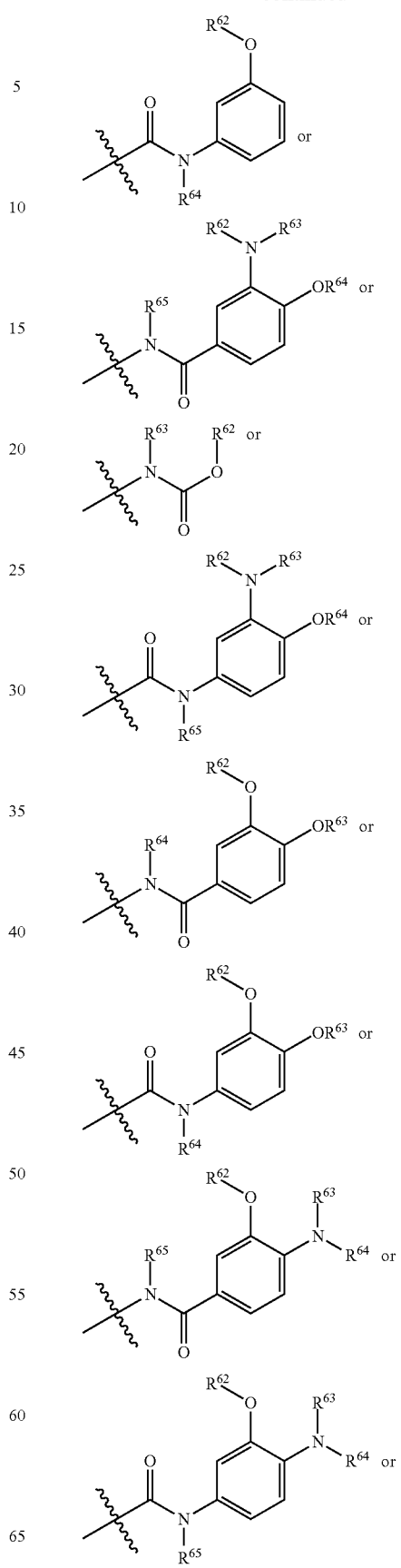

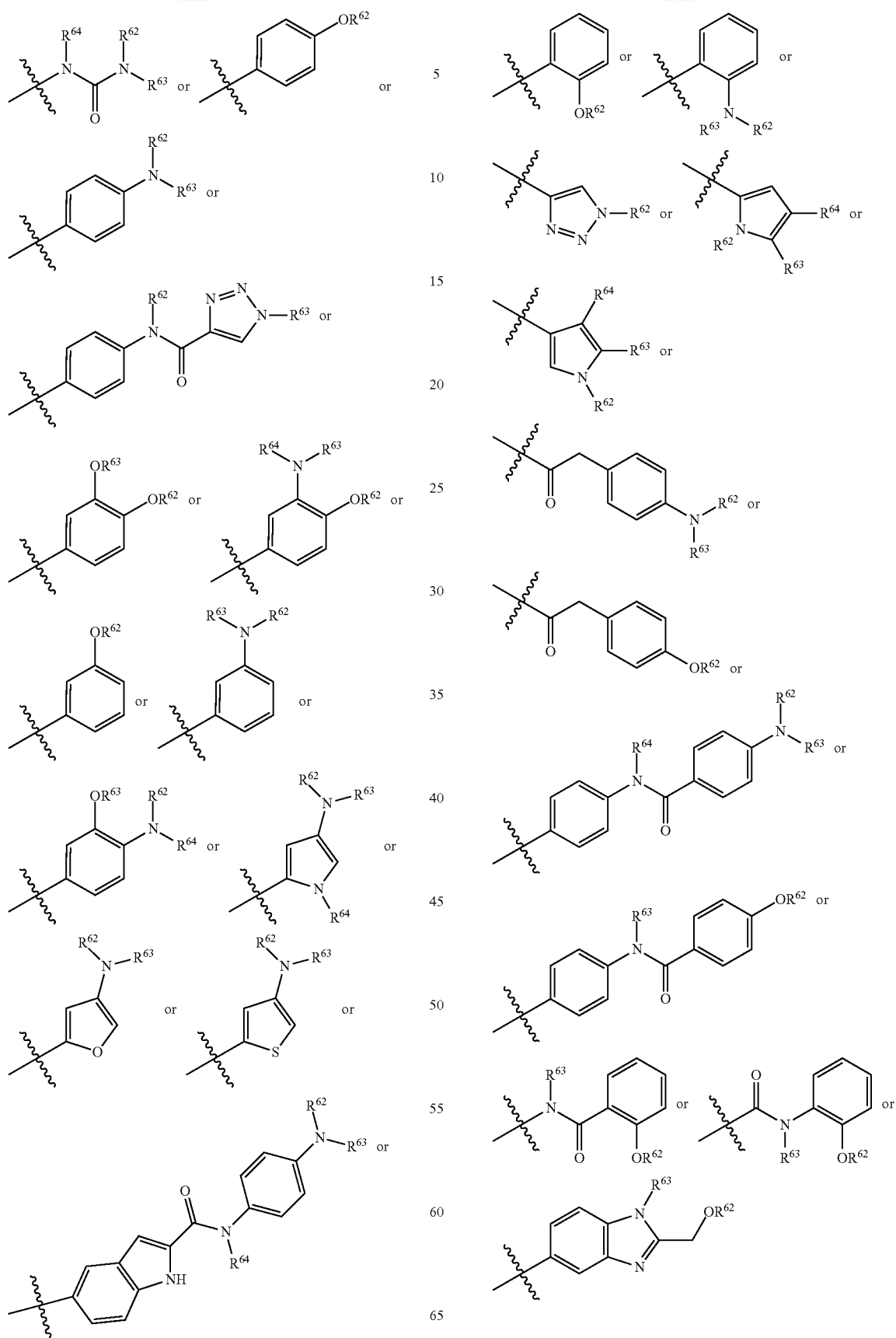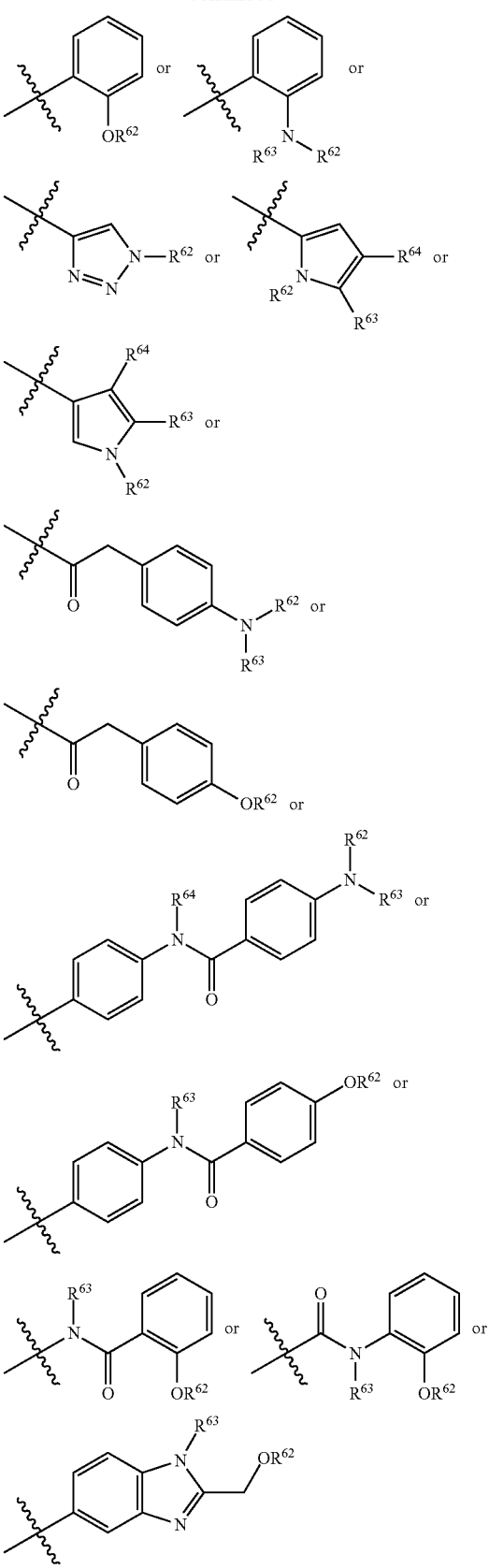

-continued
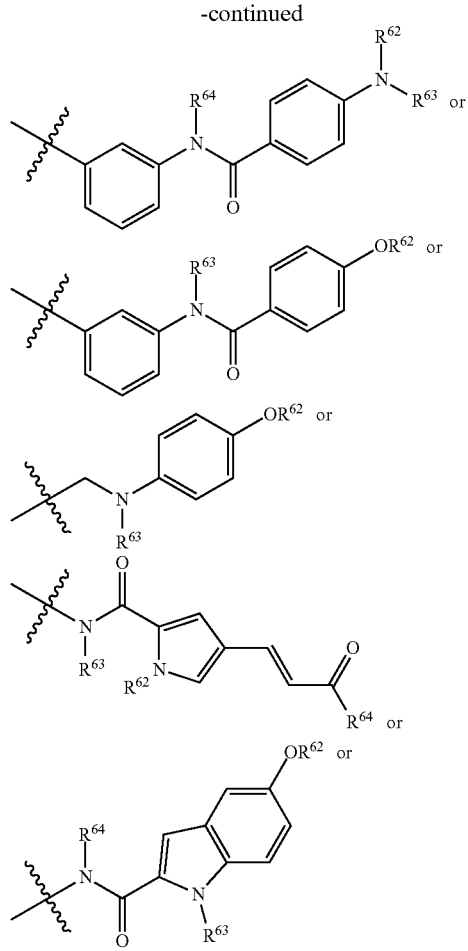
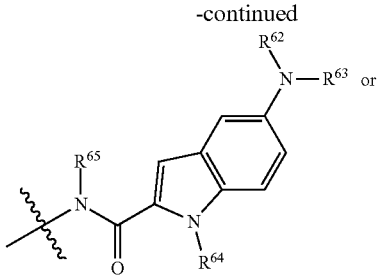
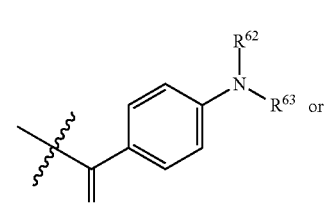
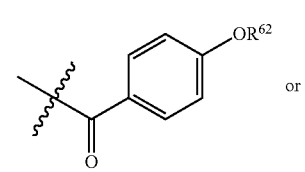
wherein $R^{62}$, $R^{63}$, $R^{64}$ and $R^{65}$ are independently selected from H, $C_{1-3}$ alkyl, and
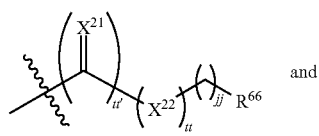 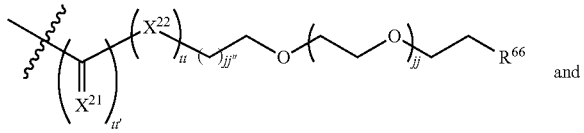
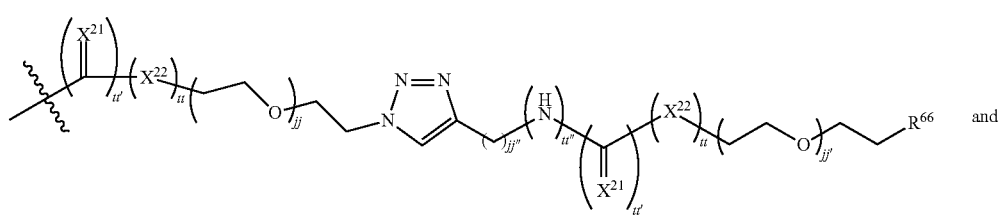
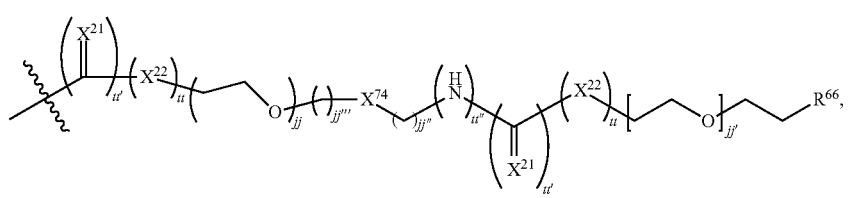

wherein jj, jj', jj", and jj'" are independently selected from 0 to 8, $X^{74}$ is selected from

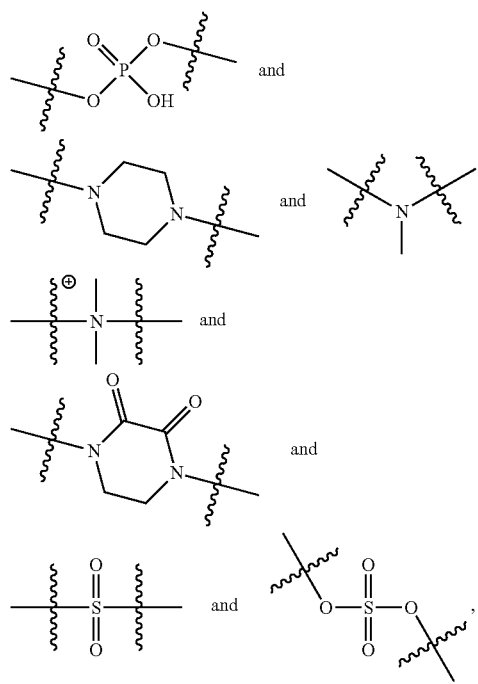

each tt, tt', and tt" is independently selected from 0 and 1, each $X^{21}$ and $X^{22}$ is independently selected from O, S, $NR^{67}$, $H_2$, and $C(R^{67})R^{68}$, wherein $R^{67}$ and $R^{68}$ are independently selected from H and optionally substituted $C_{1-3}$ alkyl or $C_{1-3}$ heteroalkyl, and $R^{66}$ is selected from H, COOH, $CO_2Me$, OH, OMe, $NR^{69}R^{70}$, $NR^{69}C(O)CH_3$, SH, SMe,

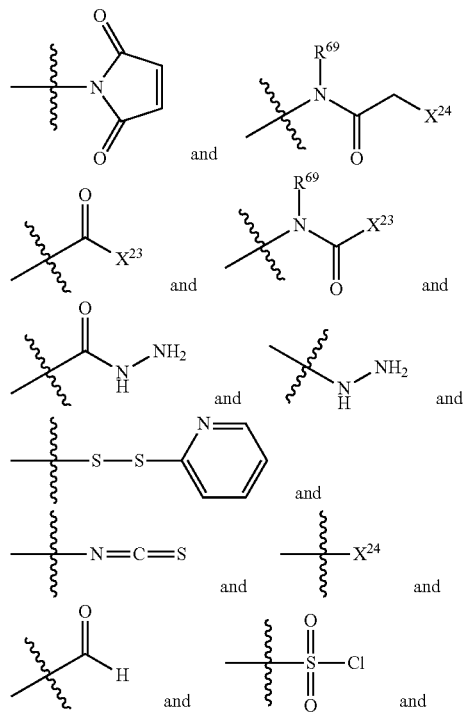

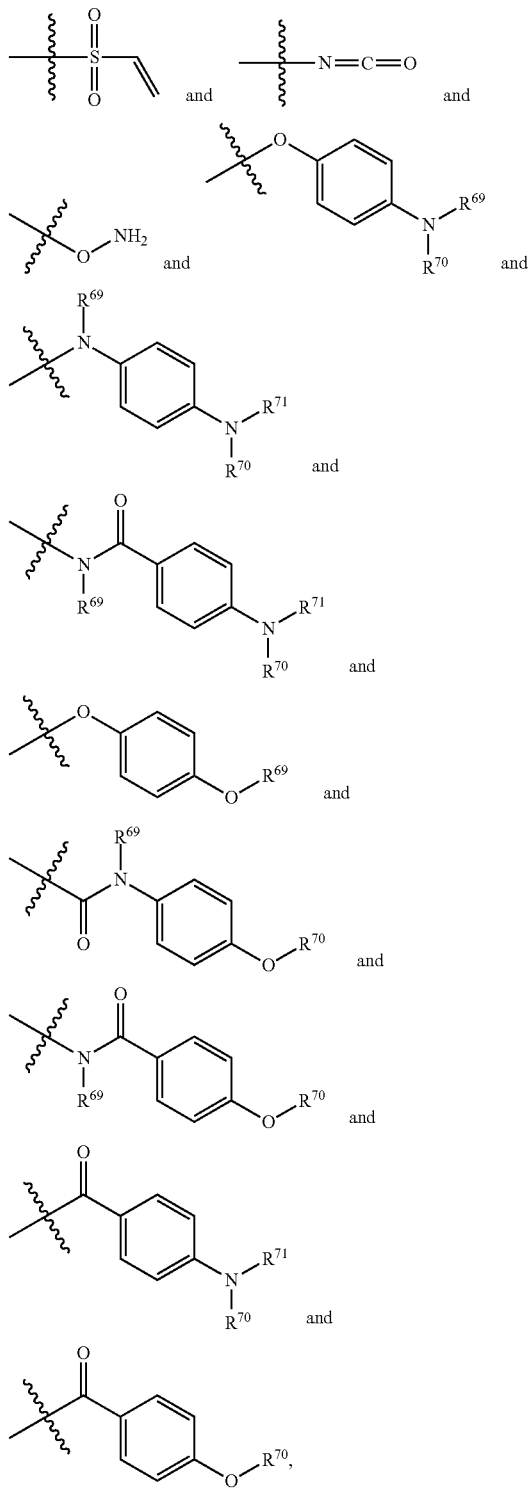

wherein $X^{23}$ is selected from halide, hydroxy, $OC(O)R^{bb}$, and $OC(O)OR^{bb}$, or $C(O)$—$X^{23}$ is an active ester, $X^{24}$ is selected from halide, mesyloxy, triflyloxy, and tosyloxy, $R^{bb}$ is selected from optionally substituted $C_{1-10}$ alkyl, $C_{1-10}$ heteroalkyl, $C_{3-10}$ cycloalkyl, $C_{1-10}$ heterocycloalkyl, $C_{5-10}$ aryl, and $C_{1-10}$ heteroaryl, and $R^{69}$, $R^{70}$, and $R^{71}$ are independently selected from methyl and H.

In a further embodiment, moiety DB6 may for example be
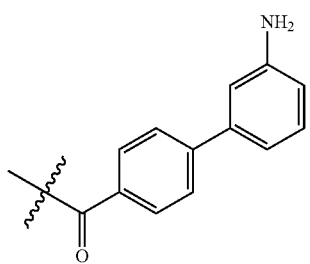
or
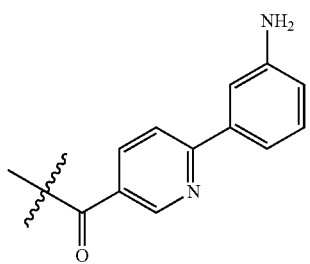
or
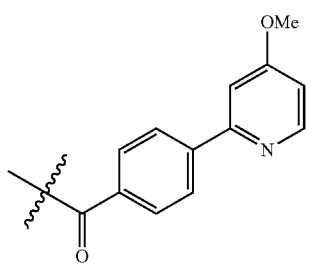
or
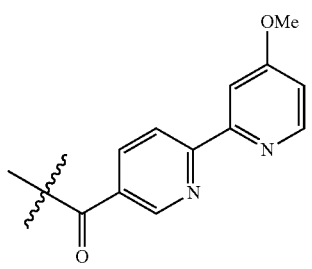
or
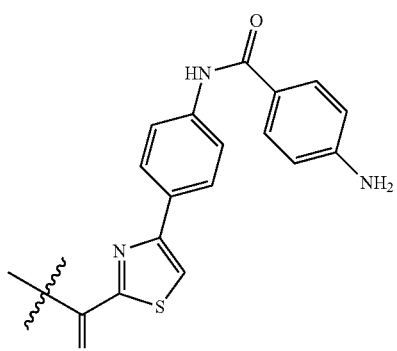
or
-continued
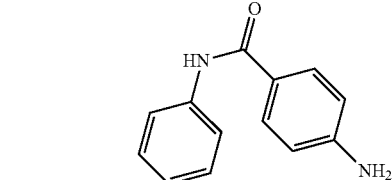
or
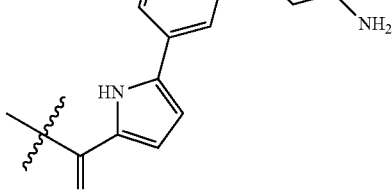
or
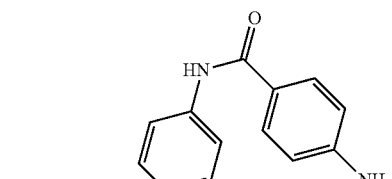
or
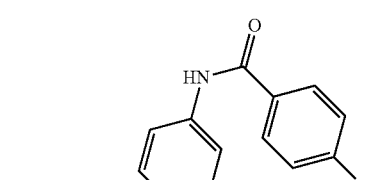
or

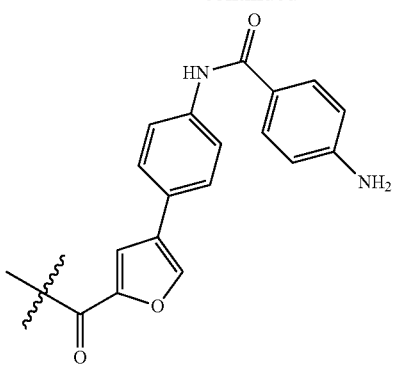
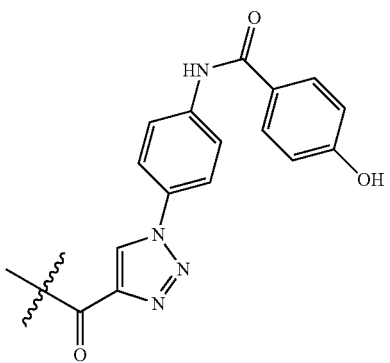
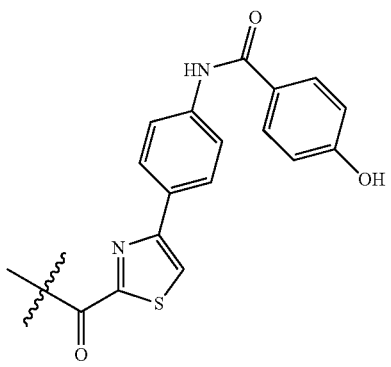
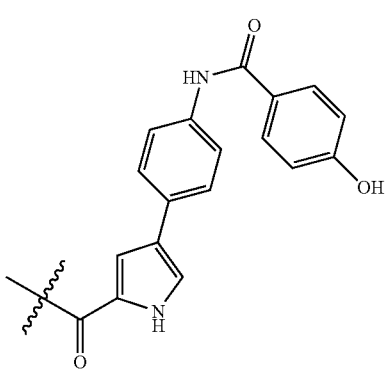
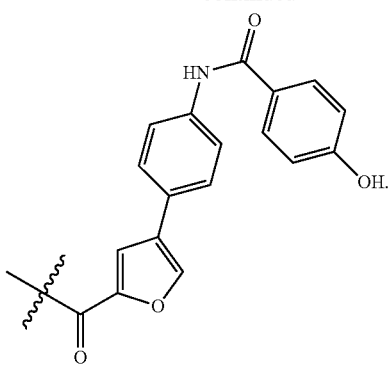
or
In another further embodiment, moiety DB7 may for example be
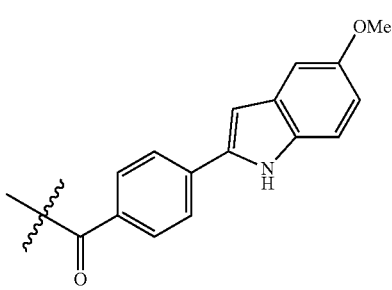
or
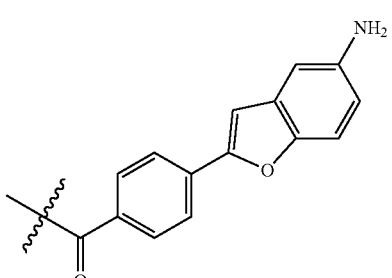
or
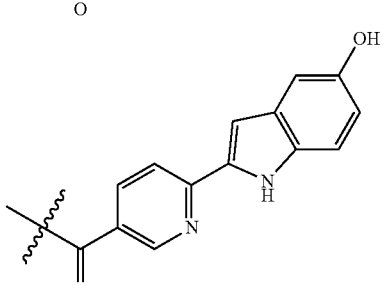
or
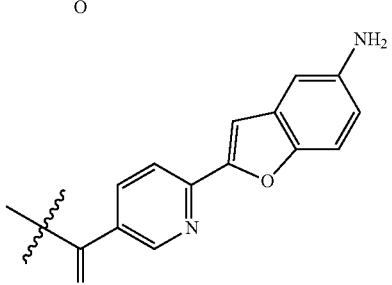
or 227
-continued

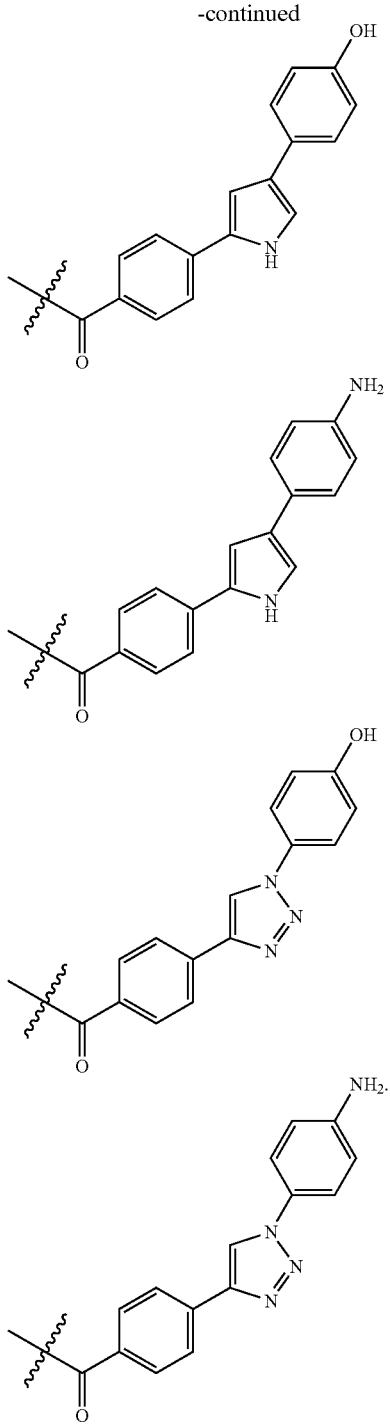

228

The moiety DB8 may for example be

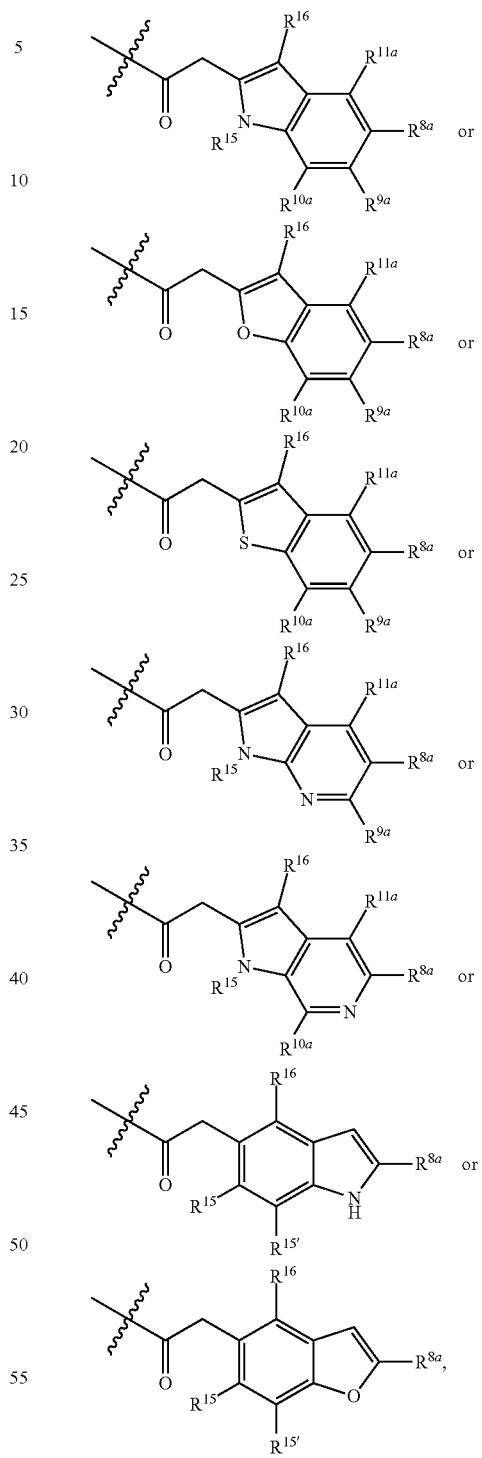

In another aspect of this invention, a compound of formula (I) or (II) has a DNA-binding unit of formula DB8. This moiety comprises structures that are built up of a monocyclic or multicyclic ring system coupled to the DNA-alkylating unit via a methylene unit. Preferably, the DB8 moiety comprises a bicyclic ring system. The ring system may be aromatic or non-aromatic. In the latter case it may be either unsaturated or completely saturated. Either polar substituents or heteroatoms in one or more of the rings may provide for increased water solubility and may favorably affect the pharmacological properties of a compound of formula (I) or (II).

wherein $R^{8a}$, $R^{9a}$, $R^{10a}$, and $R^{11a}$ have the same meaning as defined for $R^8$, $R^9$, $R^{10}$, and $R^{11}$, respectively, and are independently selected.

In the exemplary structures of DB8, $R^{8a}$, $R^{9a}$, $R^{10a}$, $R^{11a}$, $R^{15}$, $R^{15'}$, and $R^{16}$ may for example each independently be selected to be H, be or contain another moiety selected from structures DB1-DB9 or a derivative thereof, or be

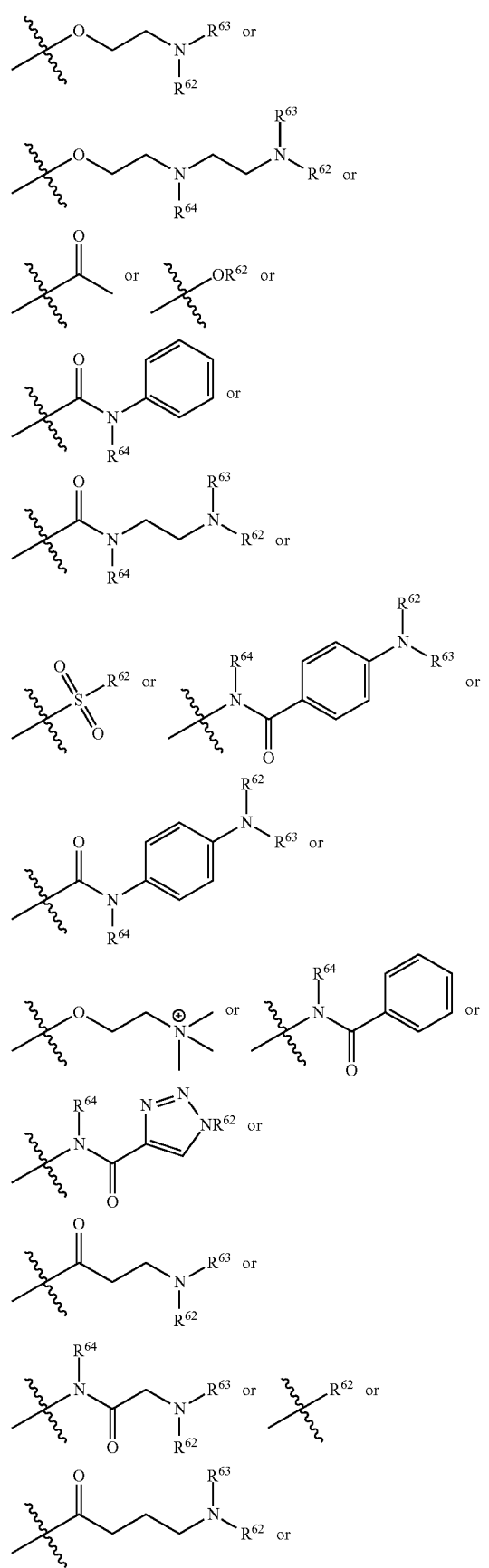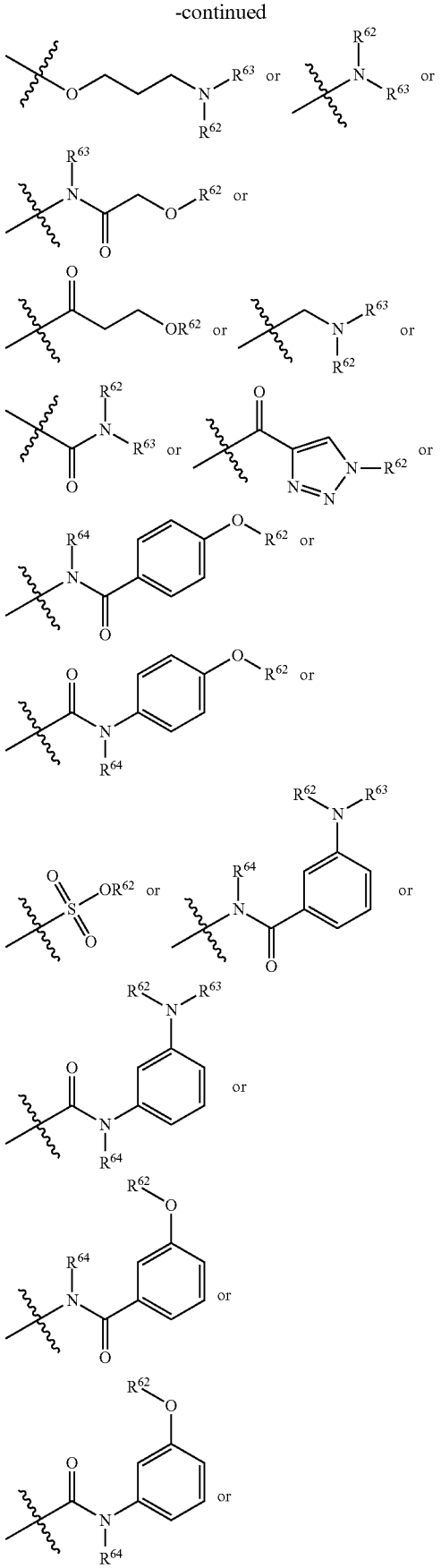

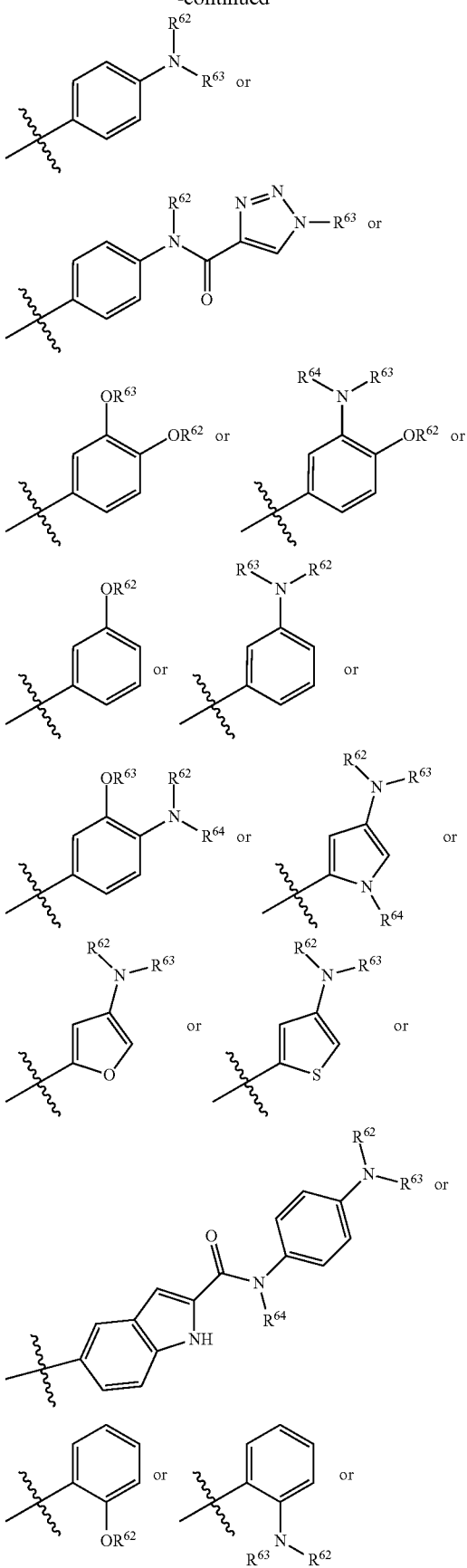

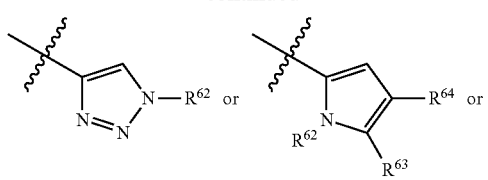 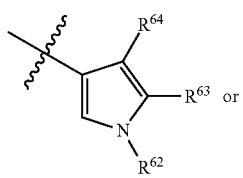 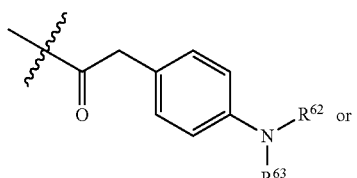 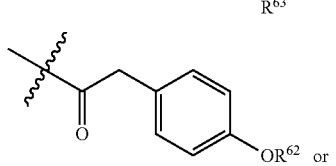 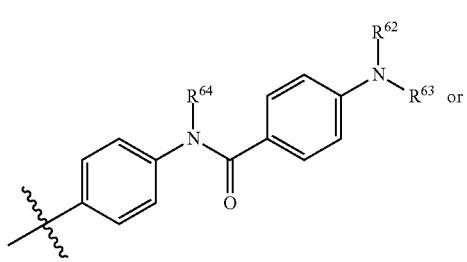 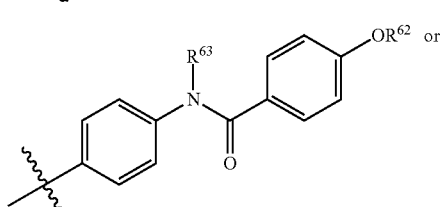 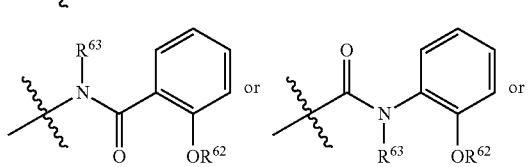 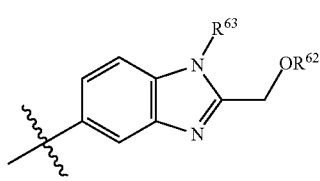 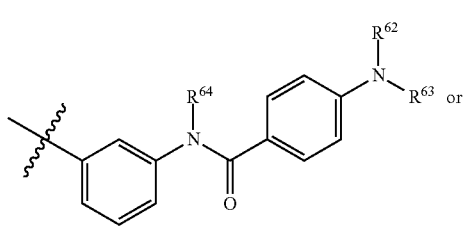
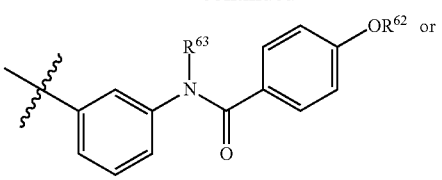 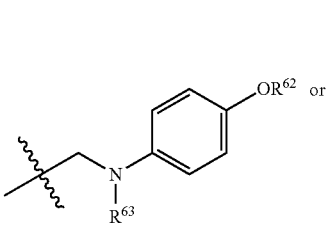 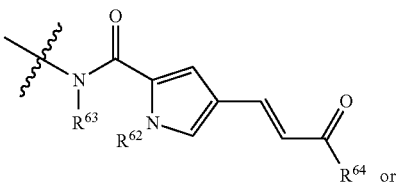 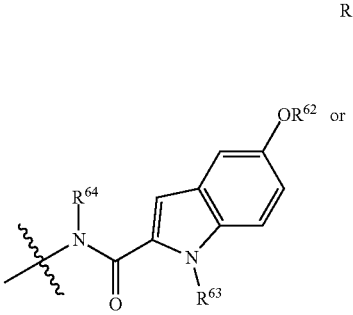 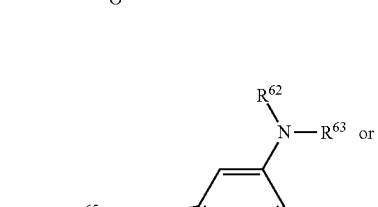 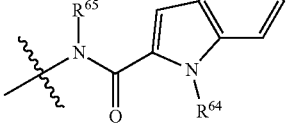 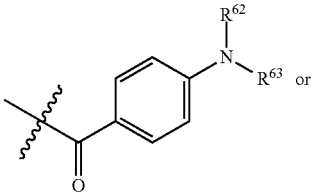 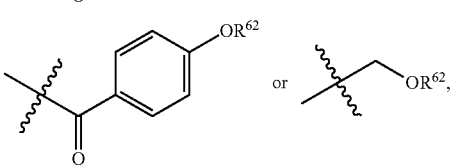
wherein $R^{62}$, $R^{63}$, $R^{64}$ and $R^{65}$ are independently selected from H, $C_{1-3}$ alkyl, and

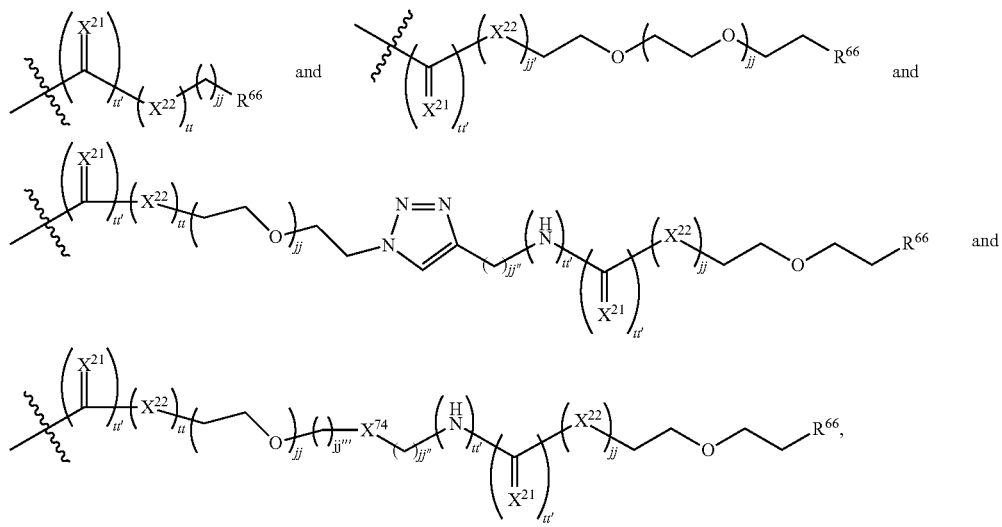

wherein jj, jj', jj'', and jj''' are independently selected from 0 to 8, X is selected from

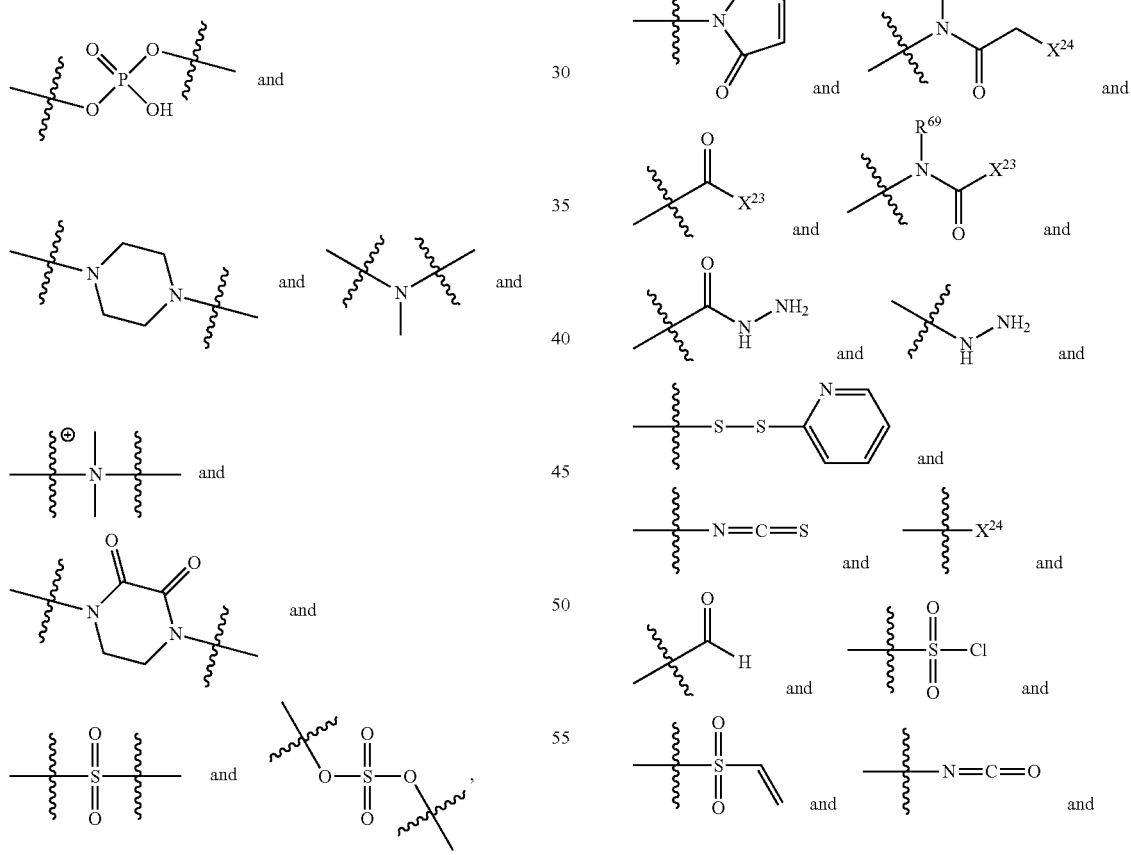

each tt, tt', and tt'' is independently selected from 0 and 1, each $X^{21}$ and $X^{22}$ is independently selected from O, S, $NR^{67}$, $H_2$, and $C(R^{67})R^{68}$, wherein $R^{67}$ and $R^{68}$ are independently selected from H and optionally substituted $C_{1-3}$ alkyl or $C_{1-3}$ heteroalkyl, and $R^{66}$ is selected from H, COOH, $CO_2Me$, OH, OMe, $NR^{69}R^{70}$, $NR^{69}C(O)CH_3$, SH, SMe, -continued

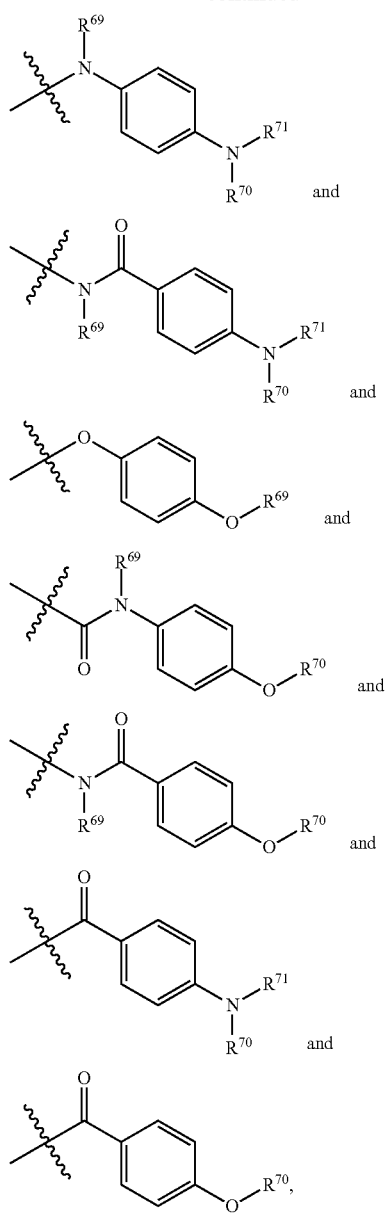

wherein $X^{23}$ is selected from halide, hydroxy, $OC(O)R^{bb}$, and $OC(O)OR^{bb}$, or $C(O)-X^{23}$ is an active ester, $X^{24}$ is selected from halide, mesyloxy, triflyloxy, and tosyloxy, $R^{bb}$ is selected from optionally substituted $C_{1-10}$ alkyl, $C_{1-10}$ heteroalkyl, $C_{3-10}$ cycloalkyl, $C_{1-10}$ heterocycloalkyl, $C_{5-10}$ aryl, and $C_{1-10}$ heteroaryl, and $R^{69}$, $R^{70}$, and $R^{71}$ are independently selected from methyl and H.

In a further embodiment, moiety DB8 may for example be

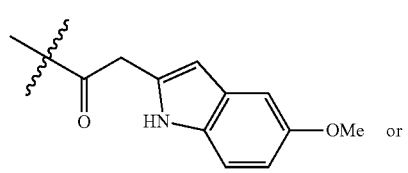

-continued

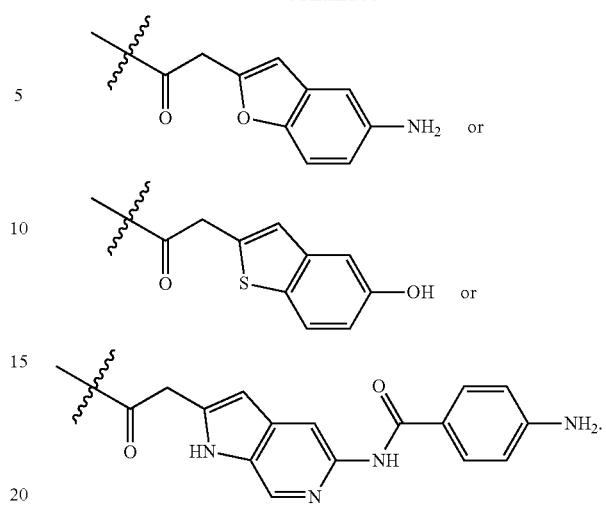

In another aspect of this invention, a compound of formula (I) or (II) has a DNA-binding unit of formula DB9. This moiety comprises structures that are built up of a 5-membered ring that is directly connected to the nitrogen atom of the DNA-alkylating unit via a single bond. The 5-membered ring may be connected or fused to one or more other rings to form a multicyclic ring system, which is preferably flat. This may increase the DNA binding affinity. The ring system may be aromatic or non-aromatic. In the latter case it may be either unsaturated or completely saturated. Either polar substituents or heteroatoms in one or more of the rings may provide for increased water solubility and may favorably affect the pharmacological properties of a compound of formula (I) or (II). In one embodiment, the DB9 moiety contains at least two ring heteroatoms.

The moiety DB9 may for example be

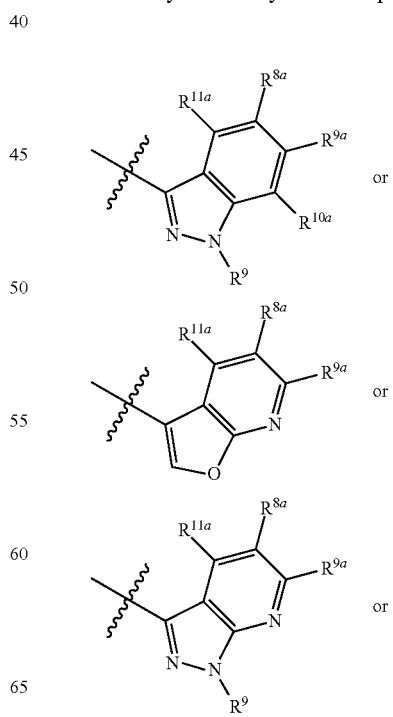

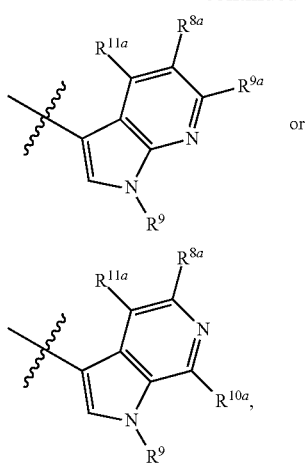
wherein $R^{8a}$, $R^{9a}$, $R^{10a}$, and $R^{11a}$ have the same meaning as defined for $R^8$, $R^9$, $R^{10}$, and $R^{11}$, respectively, and are independently selected.
In the exemplary structures of DB9, $R^{8a}$, $R^{9a}$, $R^{10a}$, $R^{11a}$, and $R^9$ may for example each independently be selected to be H, be or contain another moiety selected from structures DB1-DB9 or a derivative thereof, or be
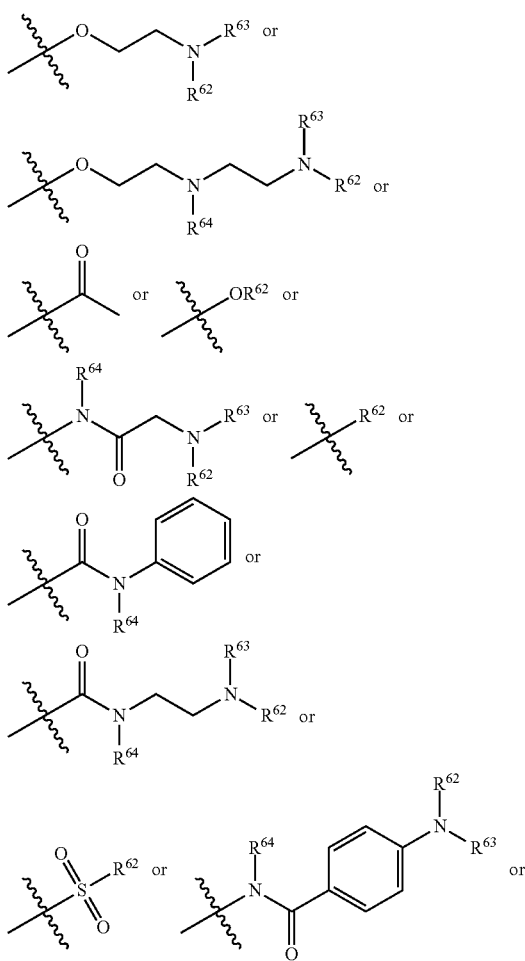
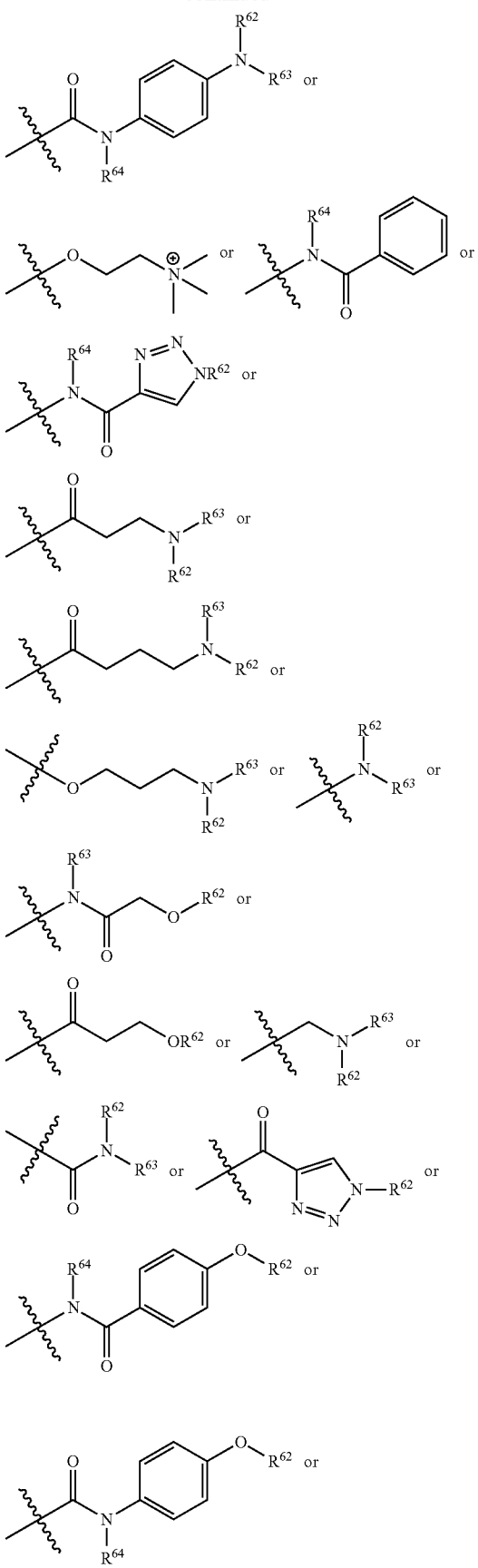

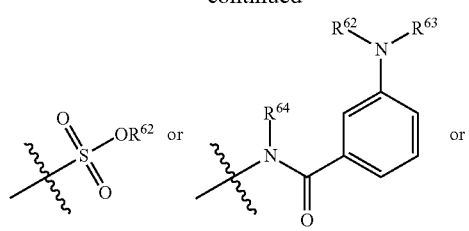 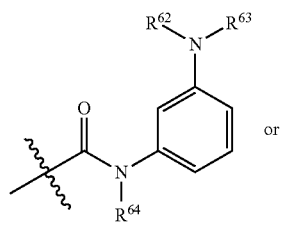 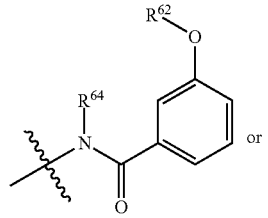 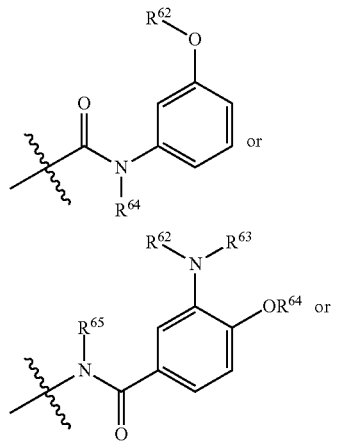 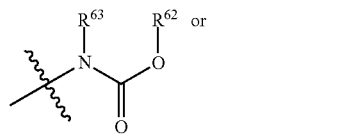  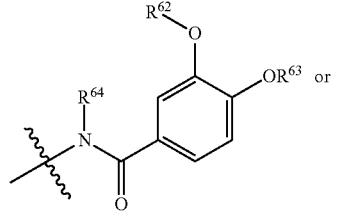 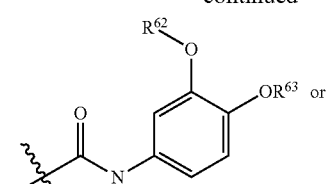 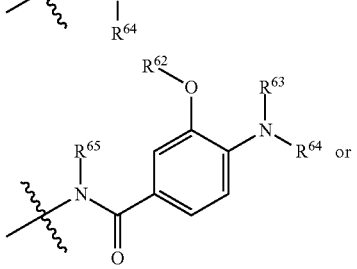 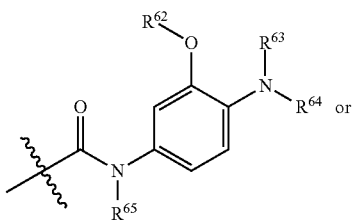 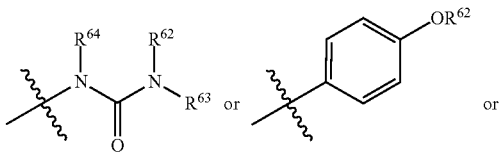 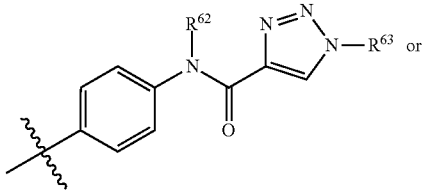 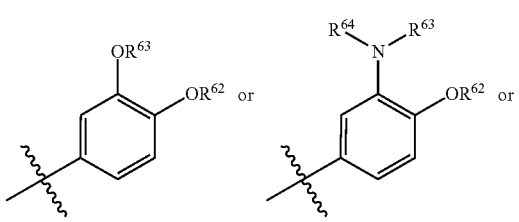 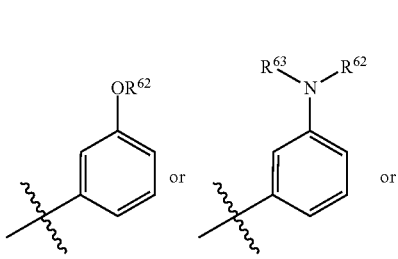

243
-continued
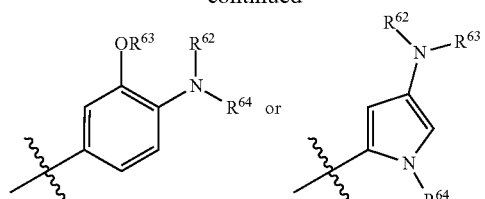
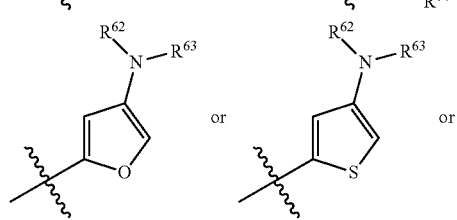
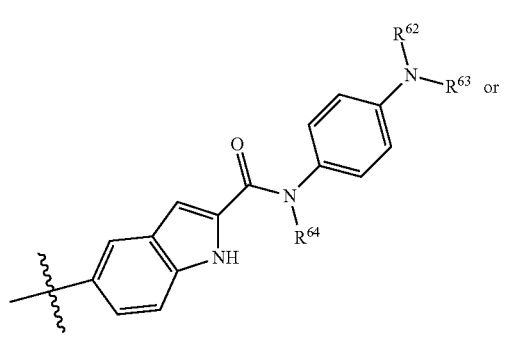
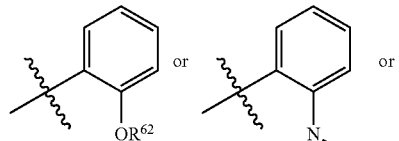
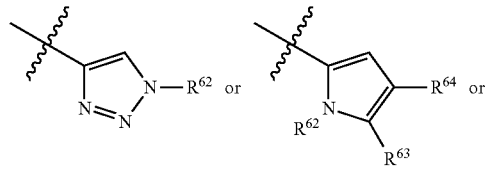
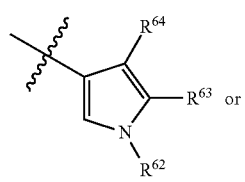
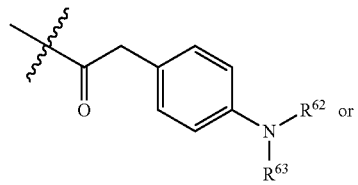
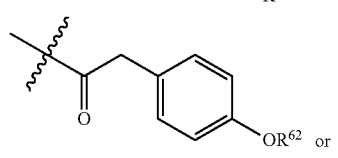
244
-continued
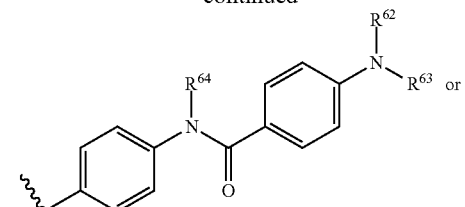
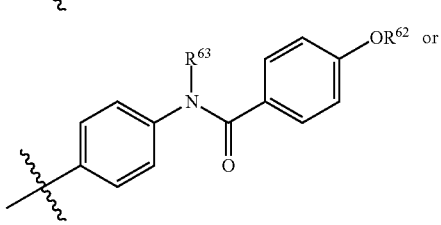
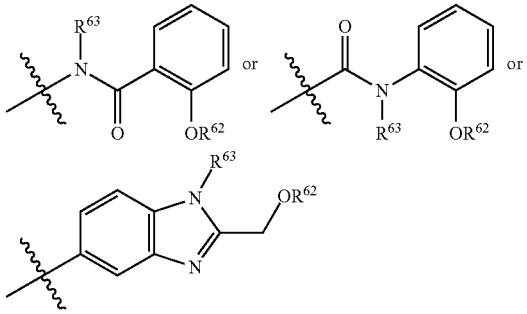
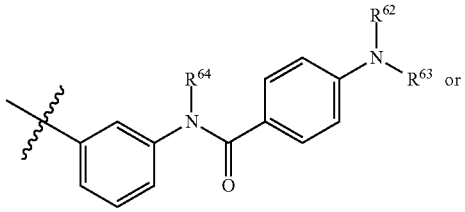
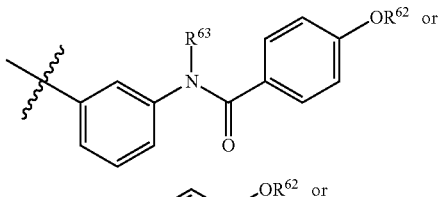
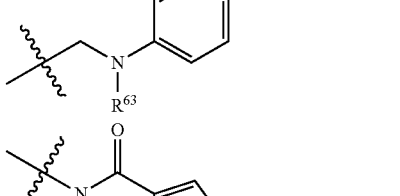
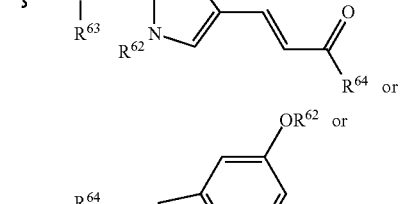
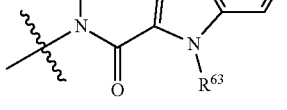

-continued

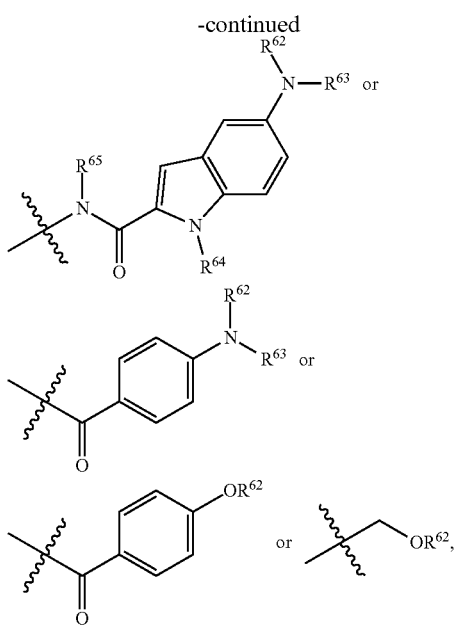

wherein $R^{62}$, $R^{63}$, $R^{64}$, and $R^{65}$ are independently selected from H, $C_{1-3}$ alkyl, and -continued

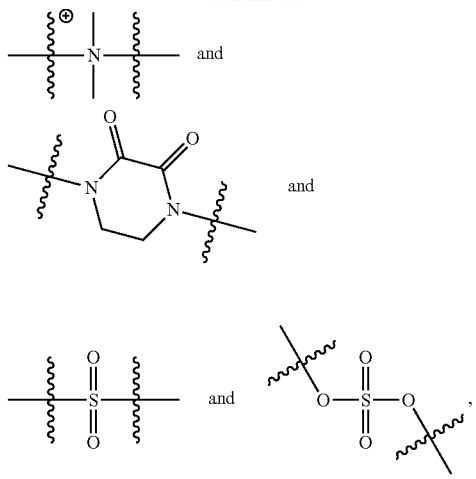

each tt, tt', and tt" is independently selected from 0 and 1, each $X^{21}$ and $X^{22}$ is independently selected from O, S, $NR^{67}$, $H_2$, and $C(R^{67})R^{68}$, wherein $R^{67}$ and $R^{68}$ are independently selected from H and optionally substituted $C_{1-3}$ alkyl or $C_{1-3}$ heteroalkyl, and $R^{66}$ is selected from H, COOH, $CO_2Me$, OH, OMe, $NR^{69}R^{70}$, $NR^{69}C(O)CH_3$, SH, SMe,

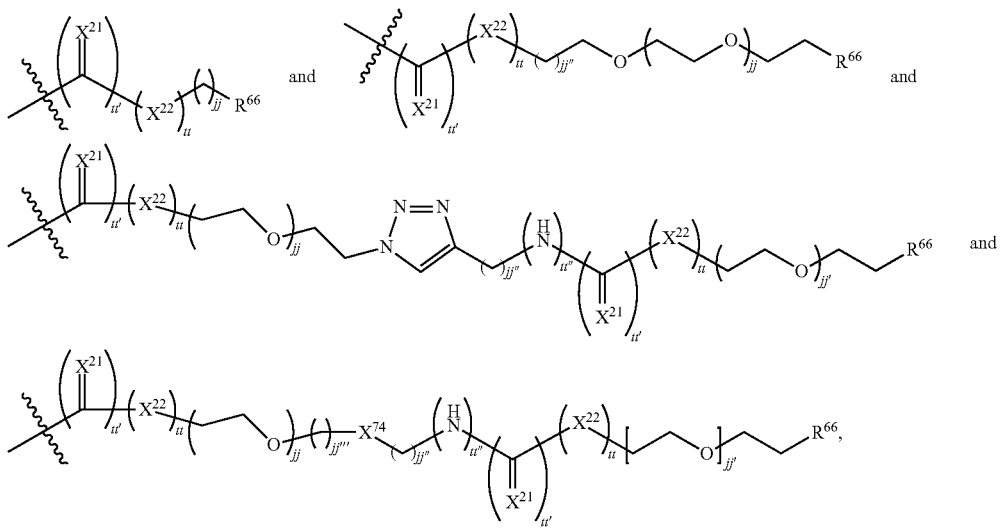

wherein jj, jj', jj", and jj''' are independently selected from 0 to 8, $X^{74}$ is selected from

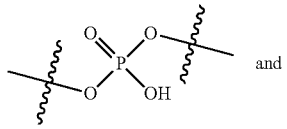

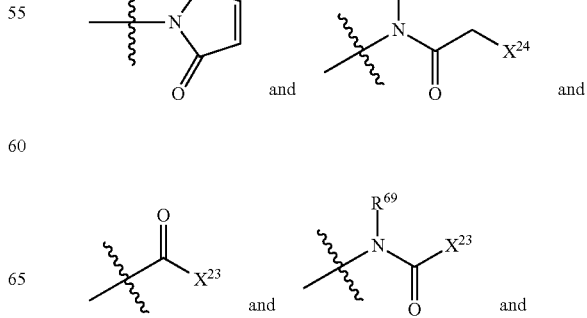

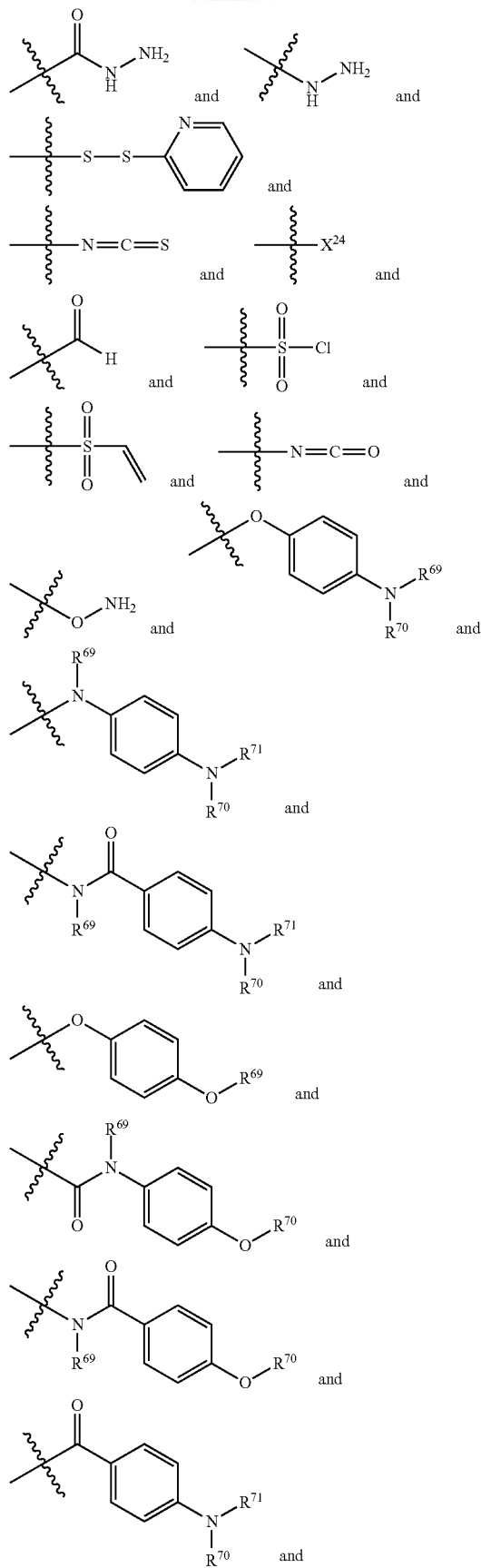

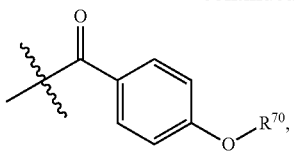

wherein $X^{23}$ is selected from halide, hydroxy, $OC(O)R^{bb}$, and $OC(O)OR^{bb}$, or $C(O)$—$X^{23}$ is an active ester, $X^{24}$ is selected from halide, mesyloxy, triflyloxy, and tosyloxy, $R^{bb}$ is selected from optionally substituted $C_{1-10}$ alkyl, $C_{1-10}$ heteroalkyl, $C_{3-10}$ cycloalkyl, $C_{1-10}$ heterocycloalkyl, $C_{5-10}$ aryl, and $C_{1-10}$ heteroaryl, and $R^{69}$, $R^{70}$, and $R^{71}$ are independently selected from methyl and H.

In a further embodiment, moiety DB9 may for example be


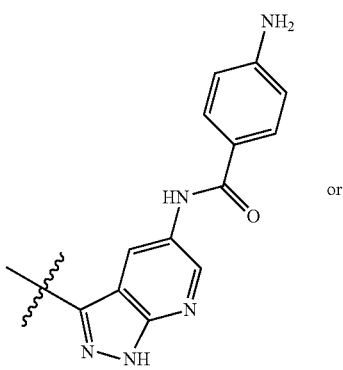


-continued

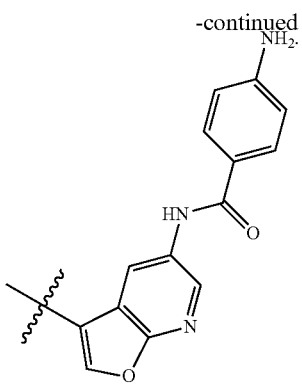

In one embodiment of this invention, the DB unit is DB1. In another embodiment, the DB unit is DB2. In yet another embodiment, the DB unit is DB3. In yet another embodiment, the DB unit is DB4. In yet another embodiment, the DB unit is DB5. In yet another embodiment, the DB unit is DB6. In yet another embodiment, the DB unit is DB7. In yet another embodiment, the DB unit is DB8. In yet another embodiment, the DB unit is DB9. In yet another embodiment, the DB unit is selected from DB1, DB2, DB3, DB4, DB5, DB6, and DB7. In another embodiment, the DB unit is selected from DB1, DB2, DB5, DB6, and DB7. In a further embodiment, DB is selected from DB1, DB2, DB6, and DB7. In yet a further embodiment, DB is selected from DB1 and DB2. In yet a further embodiment, DB is selected from DB6 and DB7.

In one embodiment, $R^5$, $R^{5'}$, $R^6$, $R^{6'}$, $R^7$, and $R^{7'}$ are independently selected from H, OH, SH, $NH_2$, $N_3$, $NO_2$, NO, $CF_3$, CN, $C(O)NH_2$, C(O)H, C(O)OH, halogen, $R^e$, $SR^e$, $S(O)R^e$, $S(O)_2R^e$, $S(O)OR^e$, $S(O)_2OR^e$, $OS(O)R^e$, $OS(O)_2R^e$, $OS(O)OR^e$, $OS(O)_2OR^e$, $OR^e$, $NHR^e$, $N(R^e)R^f$, $^+N(R^e)(R^f)R^g$, $P(O)(OR^e)(OR^f)$, $OP(O)(OR^e)(OR^f)$, $SiR^e R^f R^g$, $C(O)R^e$, $C(O)OR^e$, $C(O)N(R^e)R^f$, $OC(O)R^e$, $OC(O)OR^e$, $OC(O)N(R^e)R^f$, $N(R^e)C(O)R^f$, $N(R^e)C(O)OR^f$, and $N(R^e)C(O)N(R^f)R^g$, wherein $R^e$, $R^f$, and $R^g$ are independently selected from H and optionally substituted $(CH_2CH_2O)_{ee}CH_2CH_2X^{13}R^{e1}$, $C_{1-15}$ alkyl, $C_{1-15}$ heteroalkyl, $C_{3-15}$ cycloalkyl, $C_{1-15}$ heterocycloalkyl, $C_{5-15}$ aryl, or $C_{1-15}$ heteroaryl, wherein ee is selected from 1 to 1000, $X^{13}$ is selected from O, S, and $NR^{f1}$, and $R^{f1}$ and $R^{e1}$ are independently selected from H and $C_{1-3}$ alkyl, two or more of $R^e$, $R^f$, and $R^g$ optionally being joined by one or more bonds to form one or more optionally substituted carbocycles and/or heterocycles, or $R^5+R^{5'}$ and/or $R^6+R^{6'}$ and/or $R^7+R^{7'}$ are independently selected from =O, =S, $=NOR^{e3}$=$C(R^{e3})R^{e4}$, and =$NR^{e3}$, $R^{e3}$ and $R^{e4}$ being independently selected from H and optionally substituted $C_{1-3}$ alkyl, or $R^{5'}+R^{6'}$ and/or $R^{6'}+R^{7'}$ and/or $R^{7'}+R^{14'}$ are absent, resulting in a double bond between the atoms designated to bear $R^{5'}$ and $R^{6'}$, and/or $R^{6'}$ and $R^{7'}$, and/or $R^{7'}$ and $R^{14'}$, respectively, two or more of $R^5$, $R^{5'}$, $R^6$, $R^{6'}$, $R^7$, $R^{7'}$, $R^{14}$, and $R^{14'}$ optionally being joined by one or more bonds to form one or more optionally substituted carbocycles and/or heterocycles.

In another embodiment, $R^8$, $R^{8'}$, $R^9$, $R^{9'}$, $R^{10}$, $R^{10'}$, $R^{11}$, $R^{11'}$, $R^{15}$, $R^{15'}$, $R^{15''}$, $R^{15'''}$, $R^{16}$, $R^{16'}$, $R^{20}$, $R^{20'}$, $R^{21}$, $R^{21'}$, $R^{22}$, and $R^{23}$ are each independently selected from H, OH, SH, $NH_2$, $N_3$, $NO_2$, NO, $CF_3$, CN, $C(O)NH_2$, C(O)H, C(O)OH, halogen, $R^h$, $SR^h$, $S(O)R^h$, $S(O)_2R^h$, $S(O)OR^h$, $S(O)_2OR^h$, $OS(O)R^h$, $OS(O)_2R^h$, $OS(O)OR^h$, $OS(O)_2OR^h$, $OR^h$, $NHR^h$, $N(R^h)R^i$, $^+N(R^h)(R^i)R^j$, $P(O)(OR^h)(OR^i)$, $OP(O)(OR^h)(OR^i)$, $SiR^h R^i R^j$, $C(O)R^h$, $C(O)OR^h$, $C(O)N(R^h)R^i$, $OC(O)R^h$, $OC(O)OR^h$, $OC(O)N(R^h)R^i$, $N(R^h)C(O)R^i$, $N(R^h)C(O)OR^i$, and $N(R^h)C(O)N(R^i)R^j$, wherein $R^h$, $R^i$, and $R^j$ are independently selected from H and optionally substituted $(CH_2CH_2O)_{ee}CH_2CH_2X^{13}R^{e1}$, $C_{1-15}$ alkyl, $C_{1-15}$ heteroalkyl, $C_{3-15}$ cycloalkyl, $C_{1-15}$ heterocycloalkyl, $C_{5-15}$ aryl, or $C_{1-15}$ heteroaryl, two or more of $R^h$, $R^i$, and $R^j$ optionally being joined by one or more bonds to form one or more optionally substituted carbocycles and/or heterocycles, or $R^8+R^{8'}$ and/or $R^9+R^{9'}$ and/or $R^{10}+R^{10'}$ and/or $R^{11}+R^{11'}$ and/or $R^{15}+R^{15'}$ and/or $R^{15}+R^{15'}$ and/or $R^{16}+R^{16'}$ and/or $R^{20}+R^{20'}$ and/or $R^{21}+R^{21'}$ are independently selected from =O, =S, $=NOR^{h1}$, $=C(R^{h1})R^{h2}$, and $=NR^{h1}$, $R^{h1}$ and $R^{h2}$ being independently selected from H and optionally substituted $C_{1-3}$ alkyl, two or more of $R^8$, $R^{8'}$, $R^9$, $R^{9'}$, $R^{10}$, $R^{10'}$, $R^{11}$, $R^{11'}$, $R^{15}$, $R^{15'}$, $R^{15''}$, $R^{15'''}$, $R^{16}$, $R^{16'}$, $R^{20}$, $R^{20'}$, $R^{21}$, $R^{21'}$, $R^{22}$, and $R^{23}$ optionally being joined by one or more bonds to form one or more optionally substituted carbocycles and/or heterocycles.

In another embodiment, $X^3$ is not represented by $—X^{3a}$ and $X^{3b}$.

In a further embodiment, if DB is DB2 in a compound of formula (I) or (II), then $X^1$ is O.

In a further embodiment, if DB is DB2 in a compound of formula (I) or (II) and $X^3$ is represented by $—X^{3a}$ and $X^{3b}—$, then $X^1$ is O.

Any of the substituents present on any of the rings in DB1, DB2, DB3, DB4, DB5, DB6, DB7, DB8, and DB9 may be or comprise another DB1, DB2, DB3, DB4, DB5, DB6, DB7, DB8, or DB9 moiety or any other DNA-binding moiety. Such another DB moiety or DNA-binding moiety may be connected to the first DB moiety via for example an amide or ketone linkage.

In one embodiment, at least one ring in the DNA-binding moiety is aromatic. In another embodiment, at least one ring system is aromatic. In yet another embodiment, all rings in the DNA-binding moiety are aromatic or form an aromatic ring system. In yet another embodiment, the DNA-binding moiety contains at least a bicyclic aromatic moiety.

Substituents $R^1$ to $R^{23}$ may assist in improving the pharmacological properties of a compound of formula (I) or (II) or its conjugate, for example, its water solubility. This may for example be achieved by selecting one or more of the substituents $R^1$, $R^5$, $R^{5'}$, $R^6$, $R^{6'}$, $R^7$, $R^{7'}$, $R^{14}$, $R^{14'}$, $R^8$, $R^{8'}$, $R^9$, $R^{9'}$, $R^{10}$, $R^{10'}$, $R^{11}$, $R^{11'}$, $R^{15}$, $R^{15'}$, $R^{15''}$, $R^{15'''}$, $R^{16}$, $R^{20}$, $R^{20'}$, $R^{21}$, $R^{21'}$, $R^{22}$, and $R^{23}$ to comprise or be an oligoethylene glycol or polyethylene glycol moiety or a triazole moiety. Alternatively or simultaneously, one or more of the substituents may comprise or be a water-soluble group. The presence of a water-soluble group may not only result in enhanced water solubility, but may also prevent a compound of formula (I) or (II) from crossing a biological barrier, especially when it is an apolar barrier, such as a cell membrane. This may be advantageous, especially when a compound of formula (I) or (II) is delivered into a targeted cell through conjugation to a targeting moiety before it is released from the conjugate as the compound of formula (I) or (II) will be unable to leave the cell. Even active transport via for example the P-glycoprotein pump may be (partially) impaired. When a compound of formula (I) or (II) is prematurely released from the conjugate, e.g., in the circulation, it may be unable or only moderately able to enter (non-targeted) cells aspecifically as its membrane translocation capabilities may be impaired by the water-soluble group. This may lead to increased selectivity and therefore to fewer side effects. In addition, at least in some instances, for example when the water-soluble group is positively charged under physiological conditions, the water-soluble group may also improve the binding affinity for DNA by means of favorable electrostatic interactions with the negatively charged phosphate groups.

A water-soluble group is a group that imparts increased solubility on a compound of formula (I) or (II) and/or a conjugate thereof. In one embodiment, water solubility of a compound of this invention carrying a water-soluble group is increased by more than 100% compared to the compound lacking said water-soluble group. In other embodiments, water solubility of a compound of this invention carrying a water-soluble group is increased by more than 75% or 50% or 25% or 10% compared to the compound lacking said water-soluble group. The water-soluble group may also contribute to prevent or reduce aggregation of compounds of this invention or to reduce side effects. Examples of water-soluble groups include, but are not limited to, —NH$_2$, —NH—, —NHR$^s$, —NR$^s$, —N(R$^s$)(R$^t$), —$^+$N(R$^s$)(R$^t$)—, —$^+$N(R$^s$)(R$^t$)(R$^u$), —COOH, —OP(O)(OH)$_2$, —OP(O)(OH)O—, —OP(O)(OR$^s$)O—, —OP(O)(OH)OR$^s$, —OP(O)(OR$^s$)OR$^t$, —P(O)(OH)$_2$, —P(O)(OH)O—, —P(O)(OR$^s$)OH, —P(O)(OR$^s$)O—, —P(O)(OR$^s$)(OR$^t$), —OS(O)$_2$OH, —OS(O)$_2$O—, —OS(O)$_2$OR$^s$, —S(O)$_2$OH, —S(O)$_2$O—, —S(O)$_2$OR$^s$, —OS(O)OH, —OS(O)O—, —OS(O)OR$^s$, —S(O)OH, —S(O)O—, —OS(O)—, —S(O)OR$^s$, —OS(O)$_2$—, —OS(O)$_2$R$^s$, —S(O)$_2$—, —S(O)$_2$R$^s$, —OS(O)R$^s$, —S(O)—, —S(O)R$^s$, —(OCH$_2$CH$_2$)$_{v'}$OH, —(OCH$_2$CH$_2$)$_{v'}$O—, —(OCH$_2$CH$_2$)$_{v'}$OR$^s$, a sugar moiety, a mono-, di-, or oligosaccharide moiety, and an oligopeptide moiety, or a protonated or deprotonated form thereof and further any combination thereof, wherein R$^s$, R$^t$, and R$^u$ are independently selected from H and optionally substituted C$_{1-3}$ alkyl, two or more of R$^s$, R$^t$, and R$^u$ optionally being joined by one or more bonds to form one or more carbocycles and/or heterocycles, and v' is an integer selected from 2 to 1000. The water-soluble group may be at any position within a substituent or may constitute the whole substituent. The water-soluble group may for example be located at any interior position, be part of the main chain, be part of a ring structure, be a functional group pending to the main chain or a ring, or be placed at the position at which the substituent is attached to the remainder of the agent.

In one embodiment, at least one of R$^1$, R$^5$, R$^{5'}$, R$^6$, R$^{6'}$, R$^7$, R$^{7'}$, R$^{14}$, R$^{14'}$, R$^8$, R$^{8'}$, R$^9$, R$^{9'}$, R$^{10}$, R$^{10'}$, R$^{11}$, R$^{11'}$, R$^{15}$, R$^{15'}$, R$^{15''}$, R$^{15'''}$, R$^{16}$, R$^{16'}$, R$^{20}$, R$^{20'}$, R$^{21}$, R$^{21'}$, R$^{22}$, and R$^{23}$ contains a water-soluble group.

In another embodiment, at least one of R$^6$, R$^7$, R$^{14}$, R$^8$, R$^9$, and R$^{10}$ contains a water-soluble group.

In yet other embodiments, R$^8$ or R$^9$ or R$^{10}$ or R$^6$ or R$^7$ or R$^{14}$ contains a water-soluble group.

In one embodiment, the water-soluble group is a carboxylic acid group.

In another embodiment, the water-soluble group is an amino group.

In further embodiments, the water-soluble group is a primary or secondary or tertiary or quaternary amino (ammonium) group. In other embodiments, the water-soluble group is a primary or secondary or tertiary or quaternary aliphatic amino (ammonium) group.

In other embodiments, the water-soluble group is a phosphonate group or a phosphate group or a sulfonate group or a sulfate group or a glycol group or an oligoethylene glycol group or an polyethylene glycol group.

A compound of formula (I) or (II) may not have a reactive moiety incorporated in its structure. On the other hand, as becomes clear from the above, a reactive moiety may be present in its structure that allows for reaction of a compound of formula (I) or (II) with another moiety. For example, a compound of formula (I) or (II) may be reacted with a targeting moiety or a linker-targeting moiety construct, e.g., an antibody or an antibody fragment, or an antibody-linker construct or an antibody fragment-linker construct, to prepare a targeting moiety-agent conjugate in one or more steps, which may or may not be a conjugate of formula (III). Such a targeting moiety-agent conjugate may either be cleavable or non-cleavable. The formation of a targeting moiety-agent conjugate may not only be carried out through chemical synthesis, but may also occur in situ, i.e., upon administration of a compound of formula (I) or (II) in vivo. The compound of formula (I) or (II) may for example bind to endogenous proteins, e.g., albumin, upon administration.

In one embodiment, a compound of formula (I) or (II) is

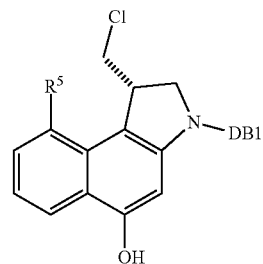

or an isomer thereof, or a mixture of isomers.

In a further embodiment, a compound of formula (I) or (II) is

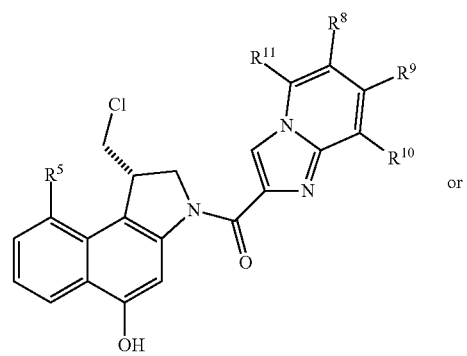

or

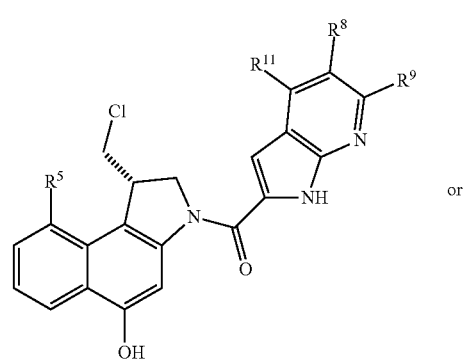

or

253
-continued
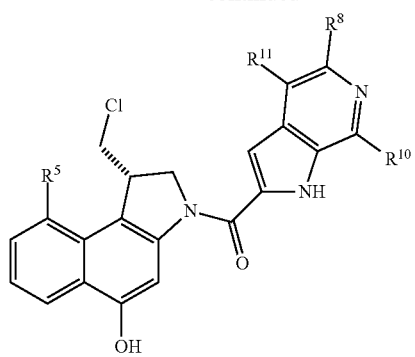
or an isomer of one of these, or a mixture of isomers.
In a further embodiment, a compound of formula (I) or (II) is
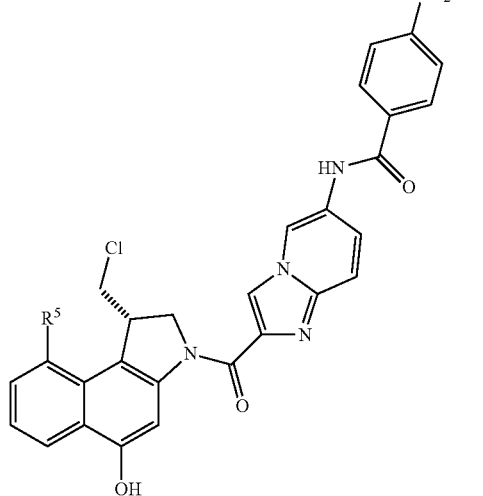
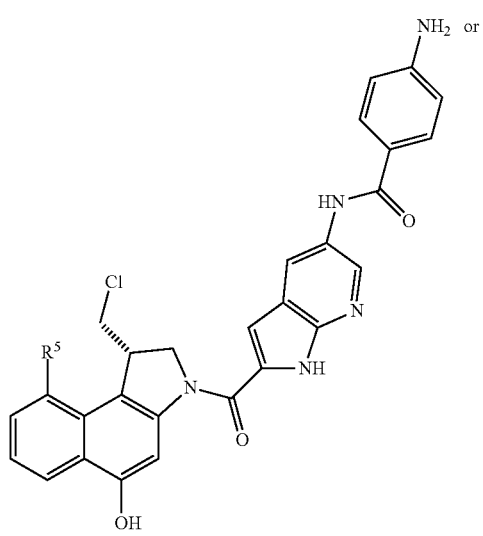
254
-continued
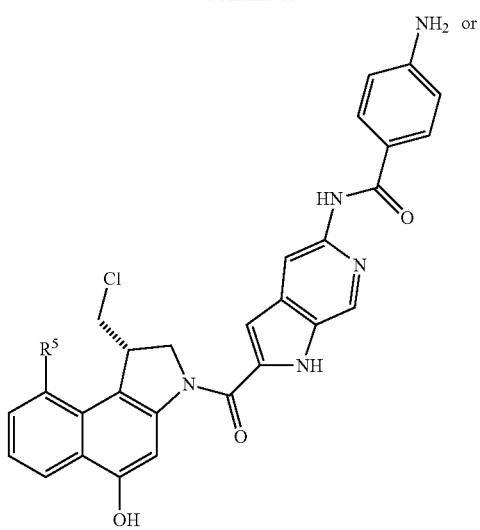
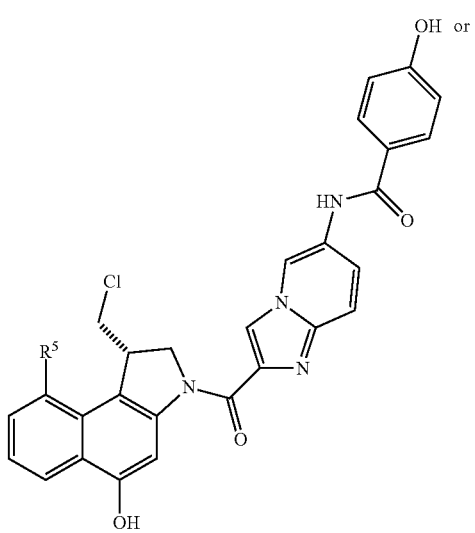
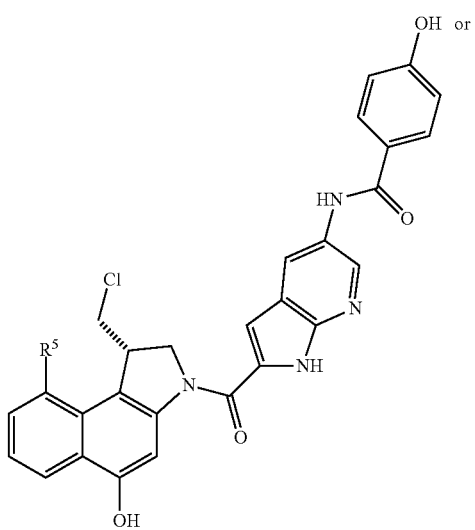

255
-continued
256
-continued
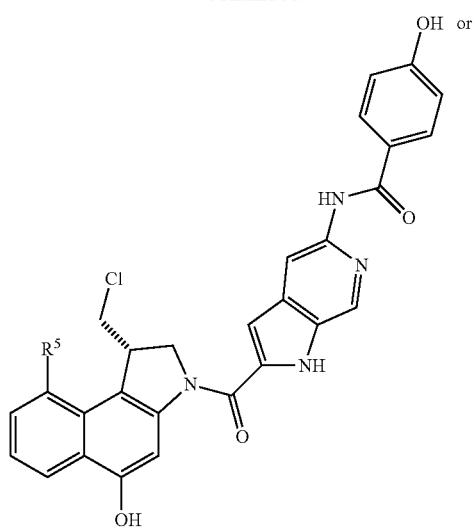
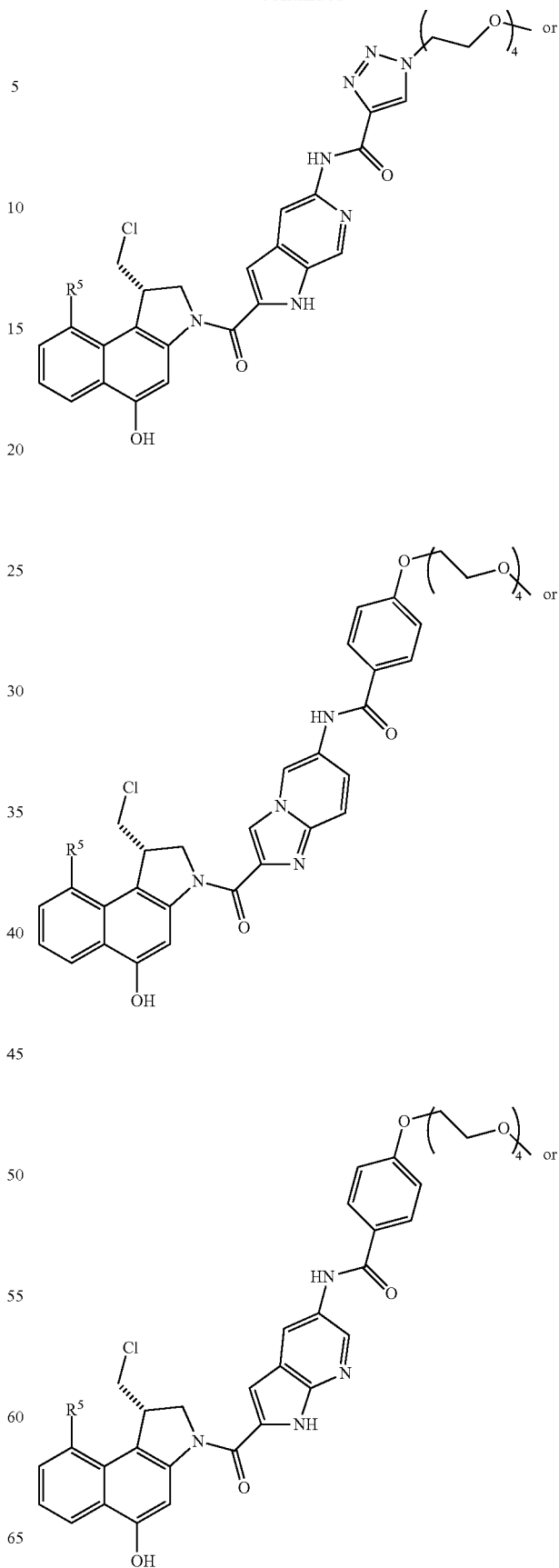

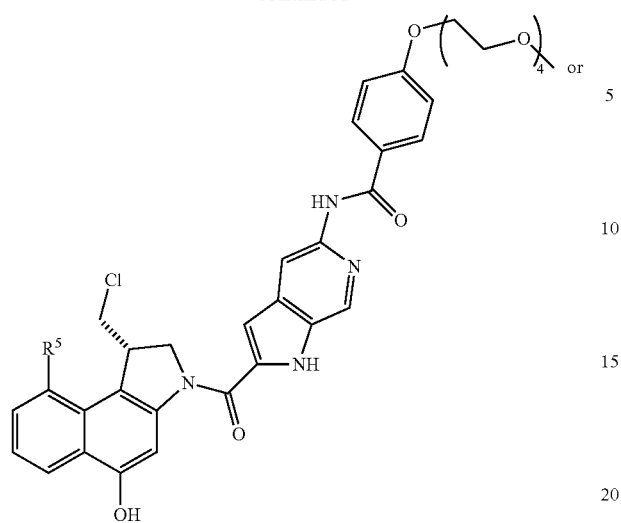
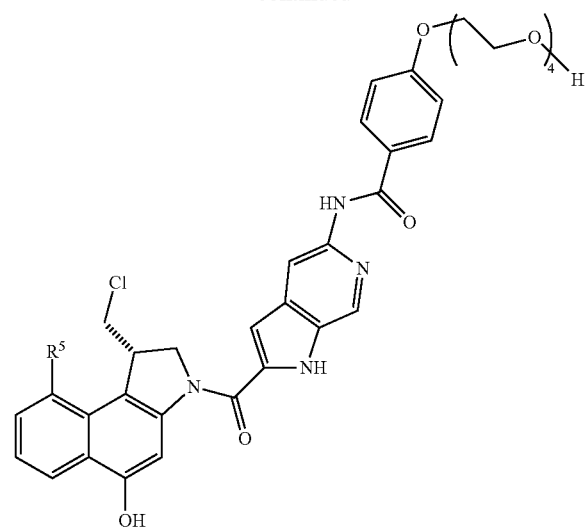
or an isomer of one of these, or a mixture of isomers.
In yet a further embodiment, a compound of formula (I) or (II) is
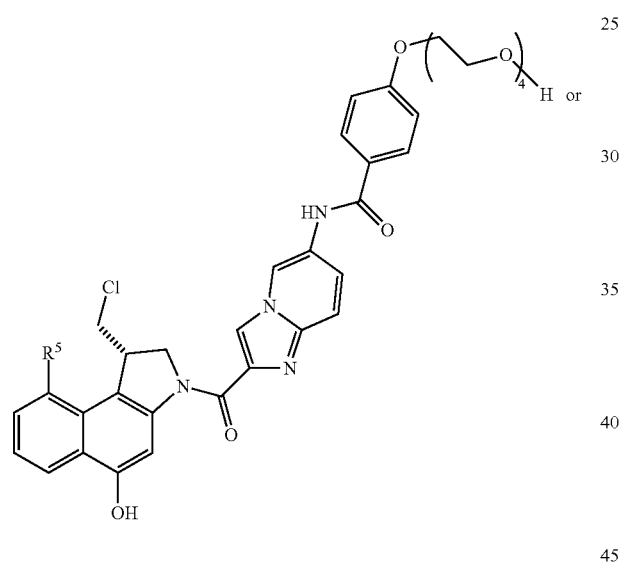
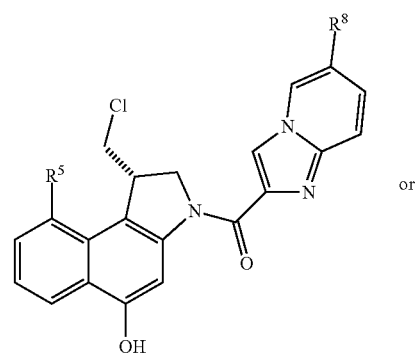
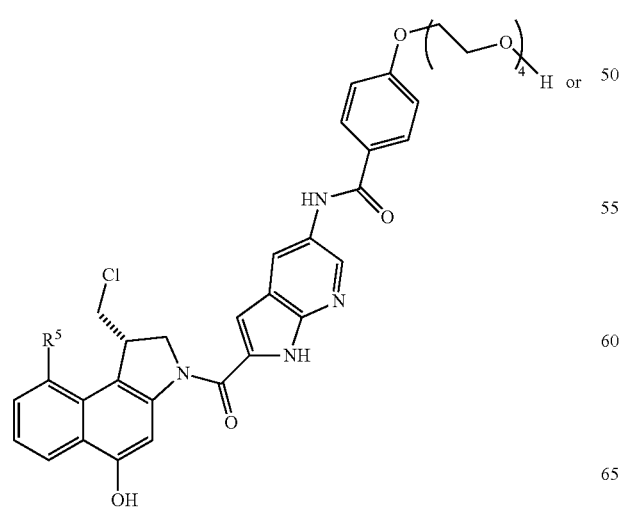
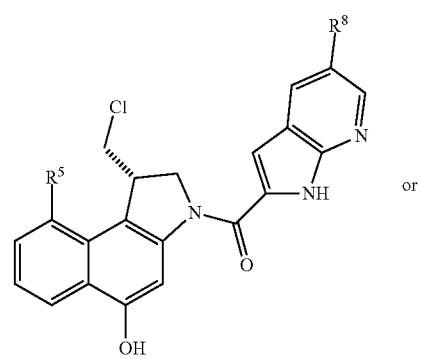

259
-continued
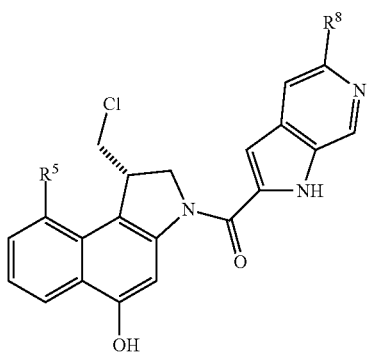
or an isomer of one of these, or a mixture of isomers.
In yet a further embodiment, a compound of formula (I) or (II) is
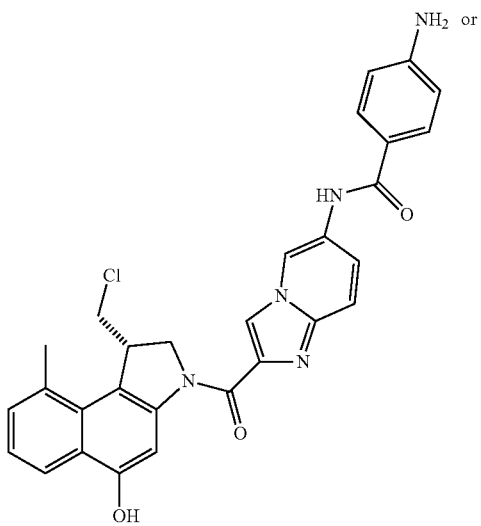
260
-continued
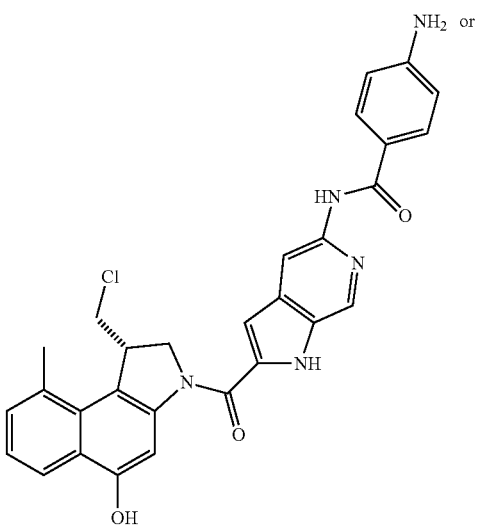
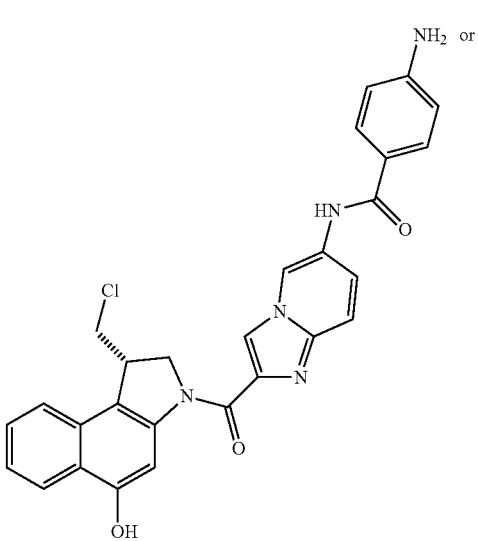
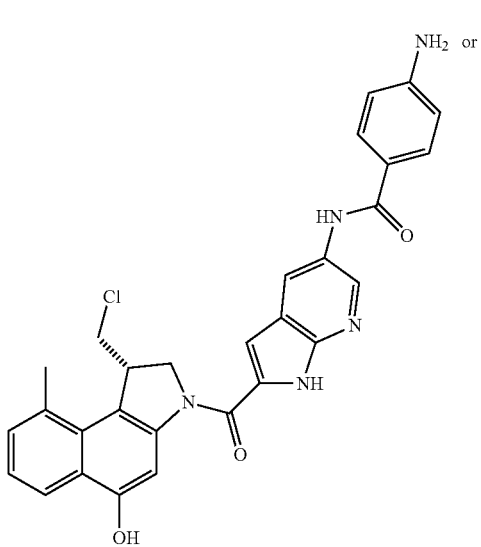
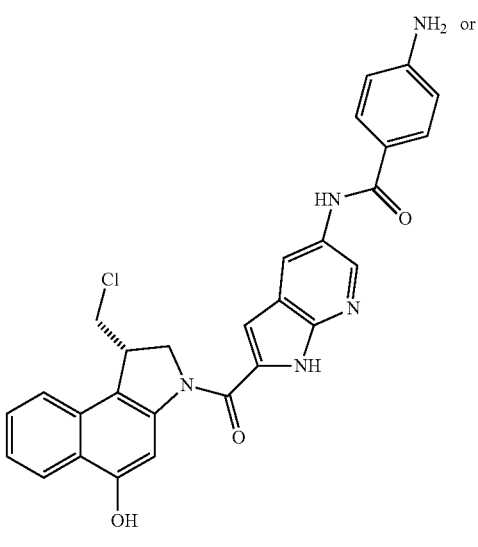

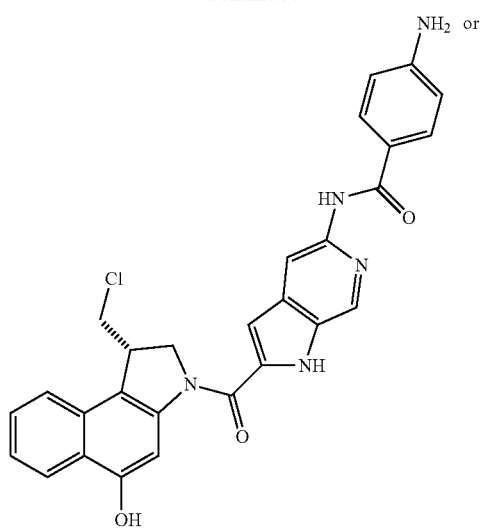
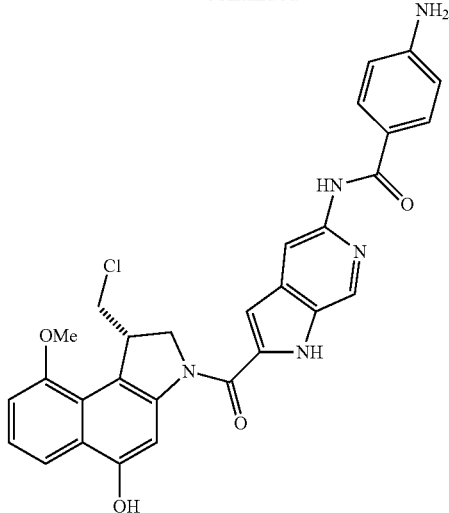
or an isomer of one of these, or a mixture of isomers.
In yet a further embodiment, a compound of formula (I) or (II) is 263
-continued
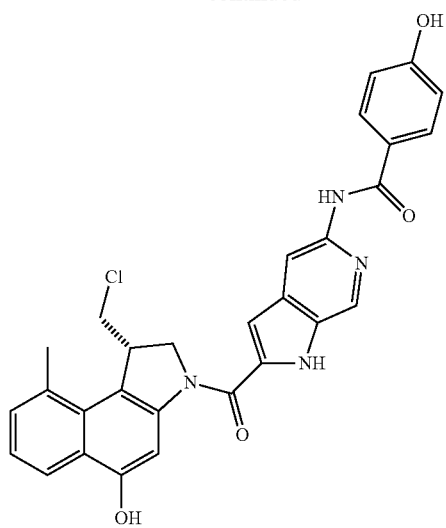
or
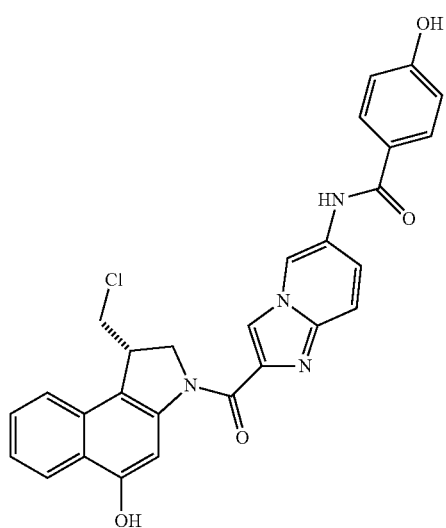
or
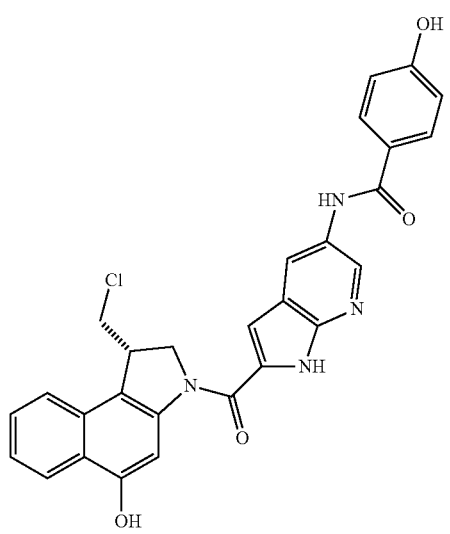
or
264
-continued
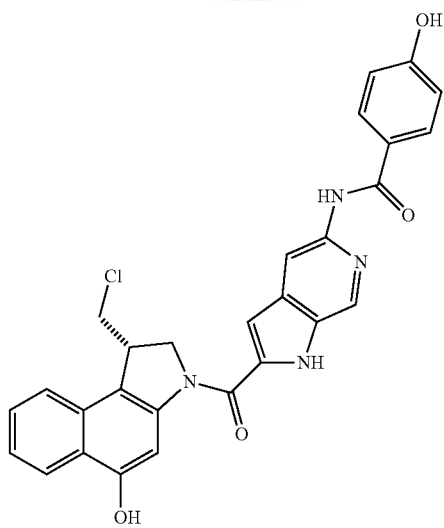
or
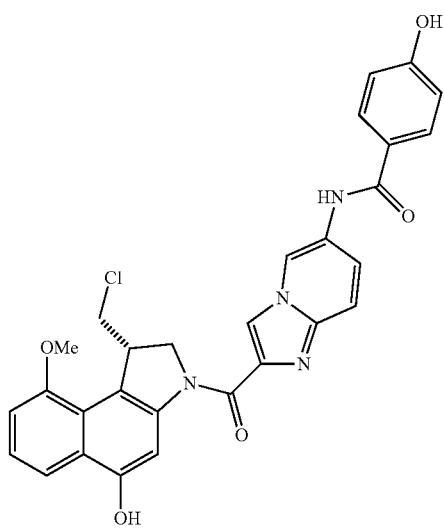
or
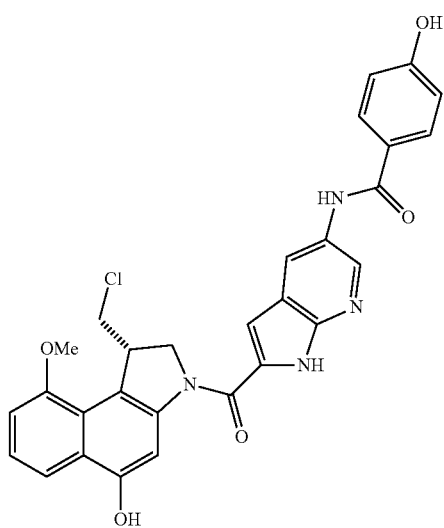
or 265
-continued
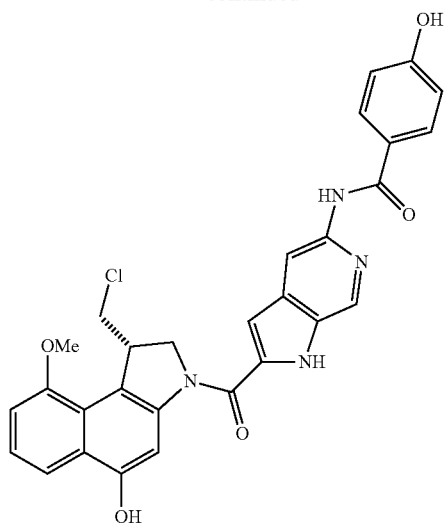
or an isomer of one of these, or a mixture of isomers.
In yet a further embodiment, a compound of formula (I) or (II) is
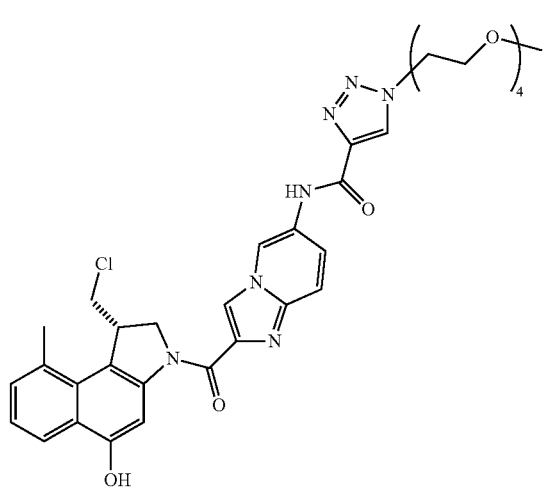
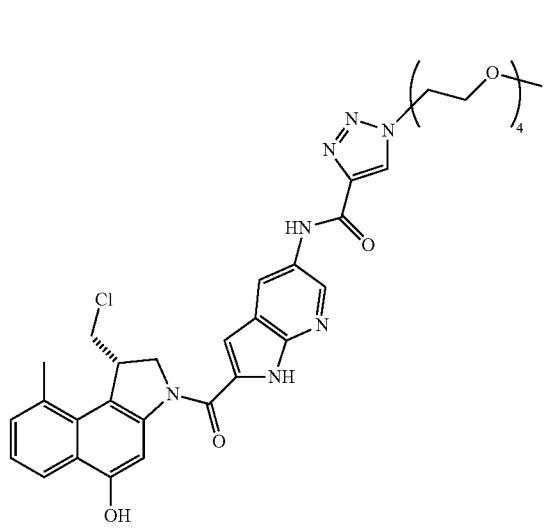
266
-continued
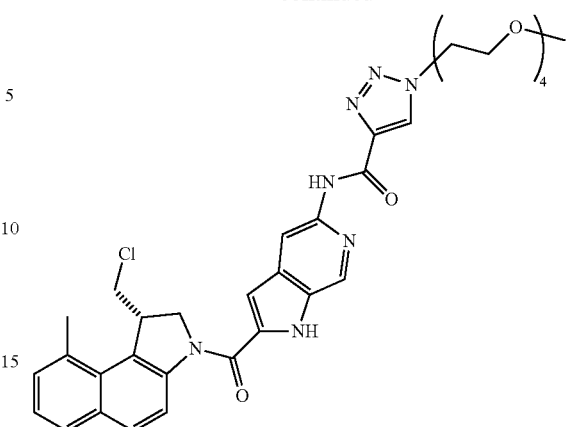
or 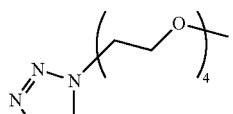
or 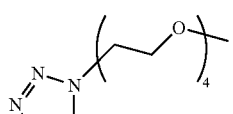
or 

267
-continued
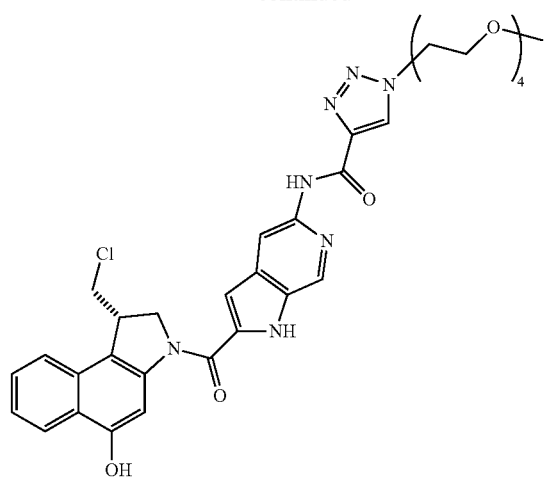
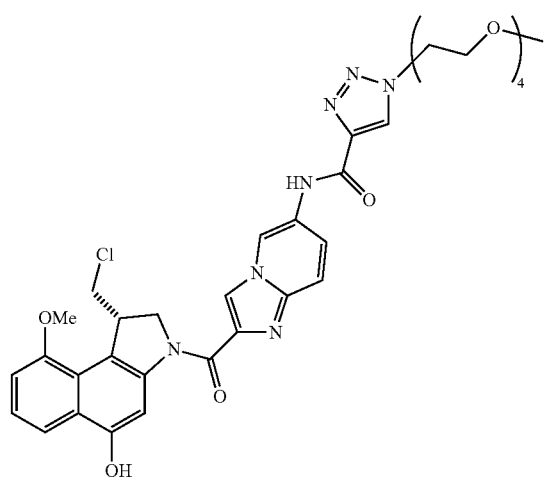
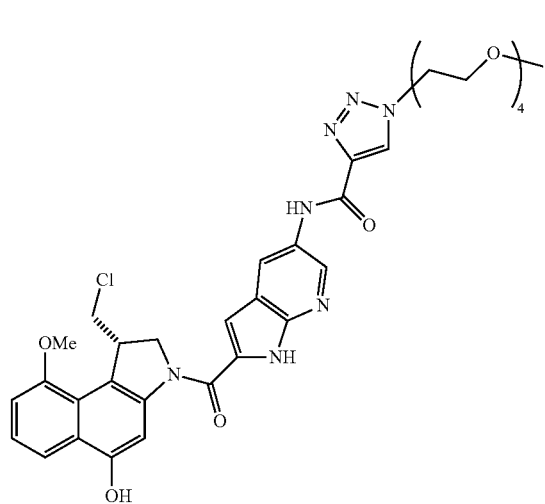
268
-continued
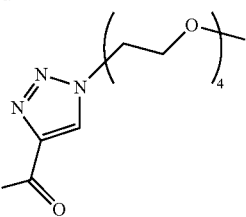
or an isomer of one of these, or a mixture of isomers.
In yet a further embodiment a compound of formula (I) or (II) is

269
-continued
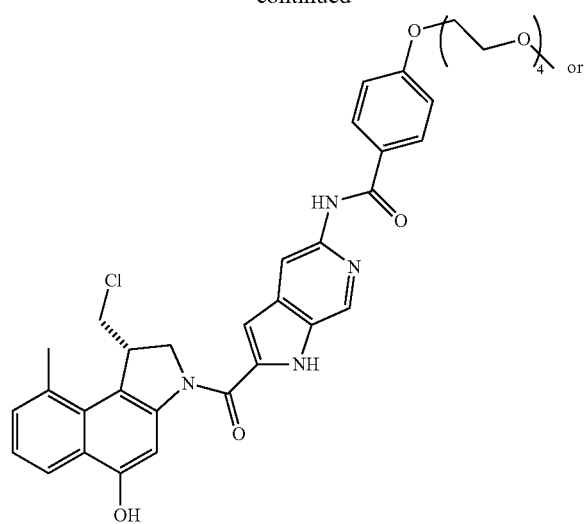
270
-continued
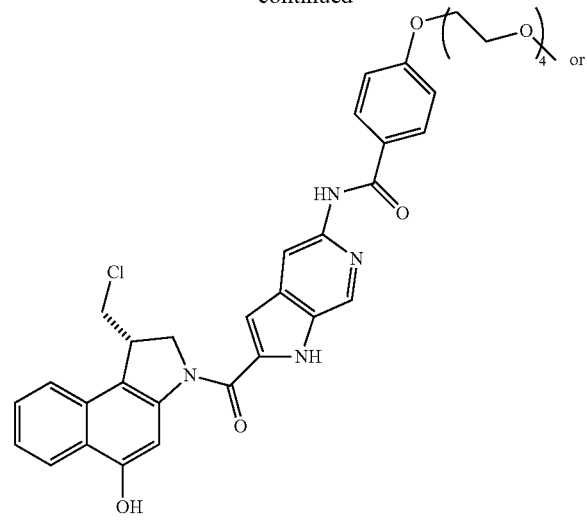

271
-continued
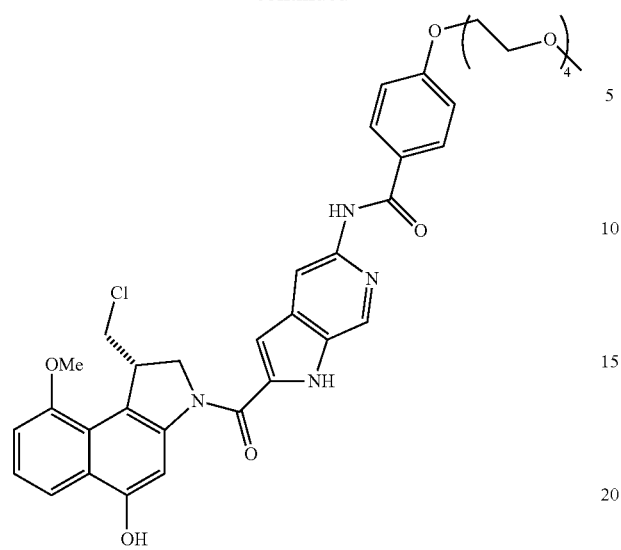
or an isomer of one of these, or a mixture of isomers.
In yet a further embodiment, a compound of formula (I) or (II) is
272
-continued
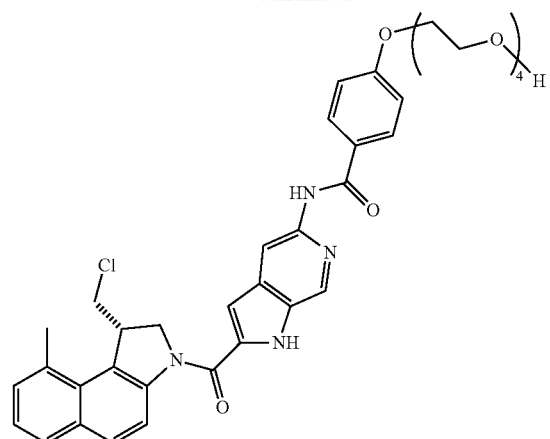
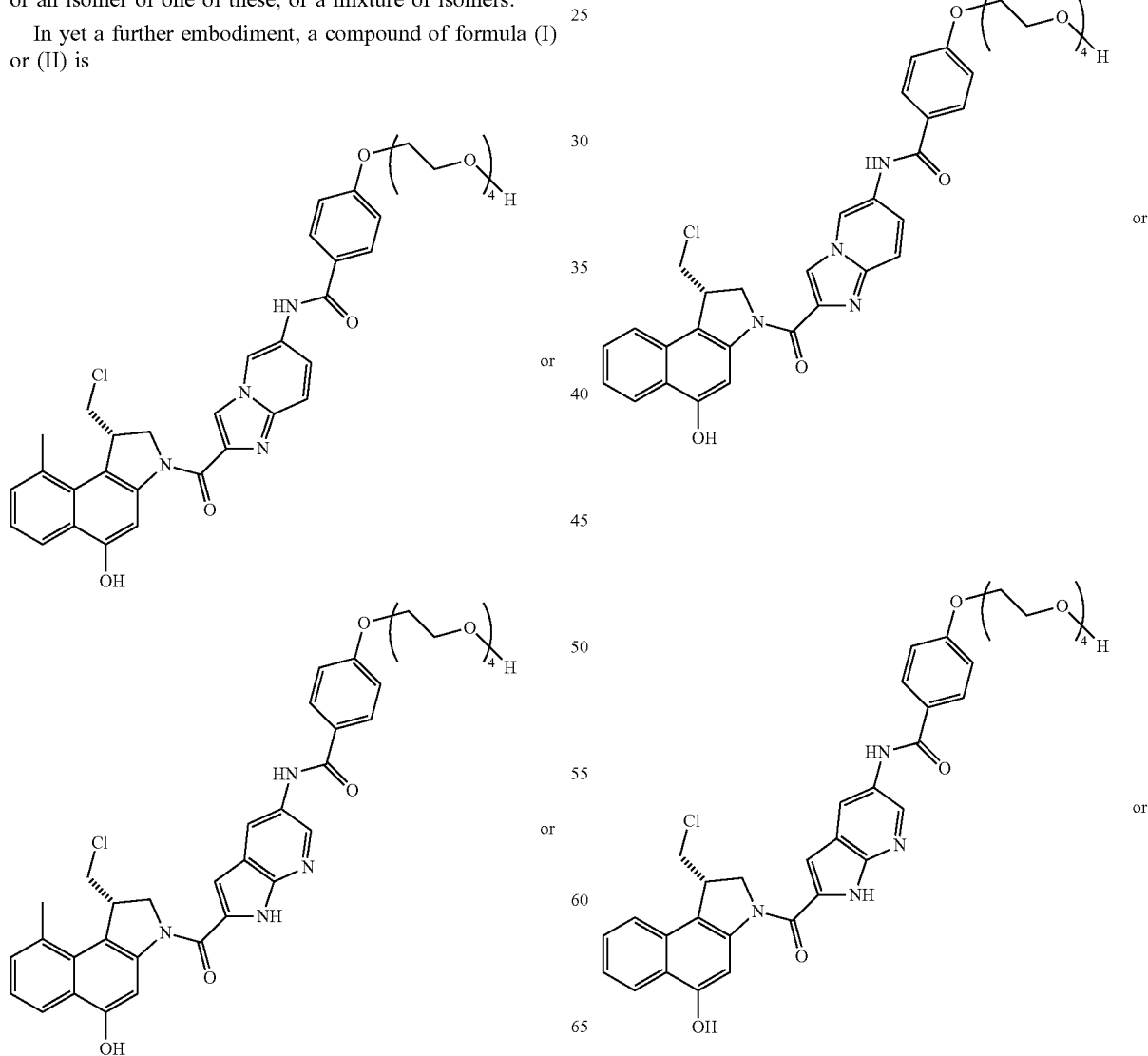

273
-continued
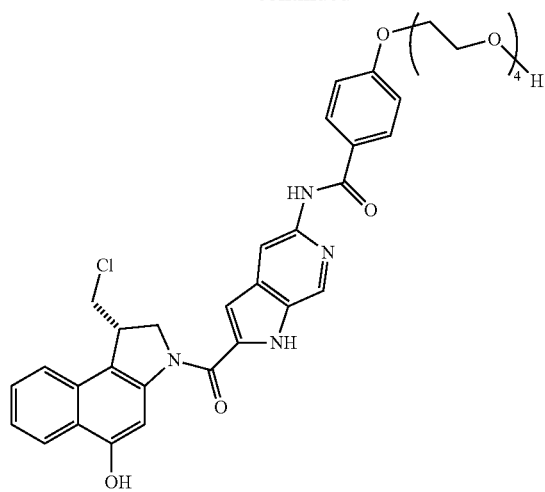
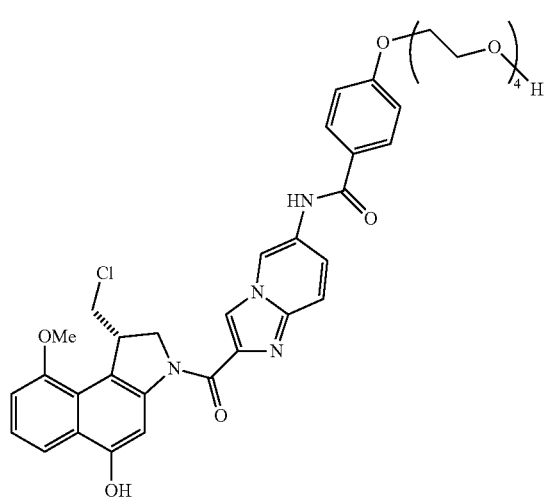
274
-continued
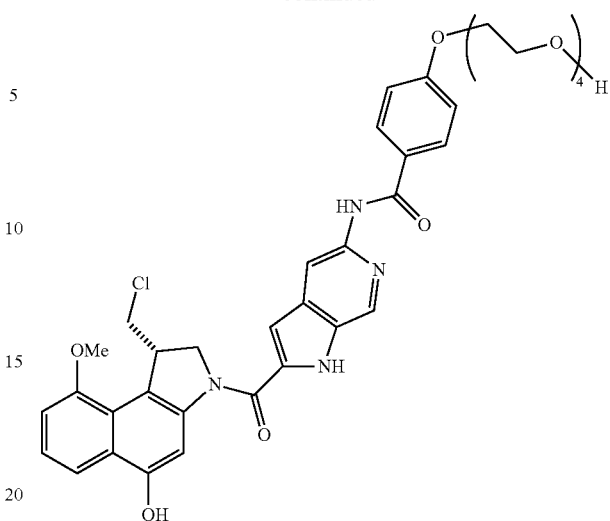
or an isomer of one of these, or a mixture of isomers.
In yet a further embodiment, a compound of formula (I) or (II) is
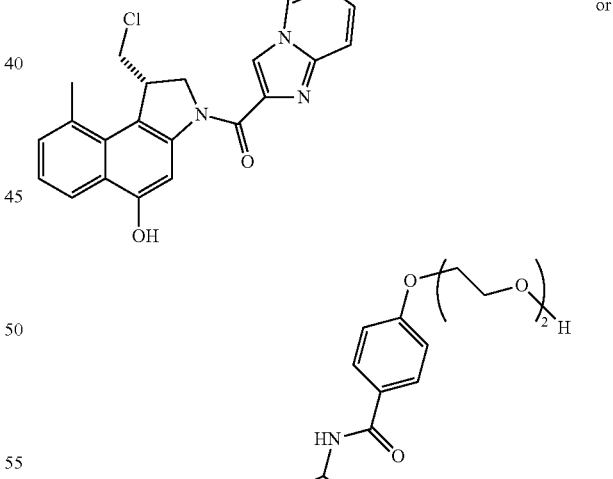
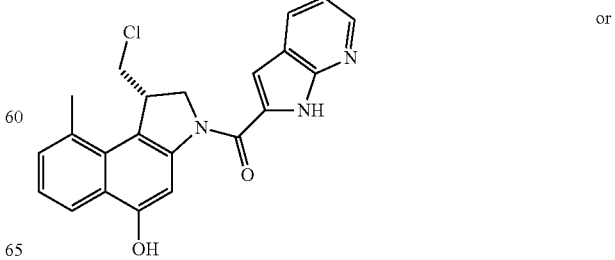

275
-continued
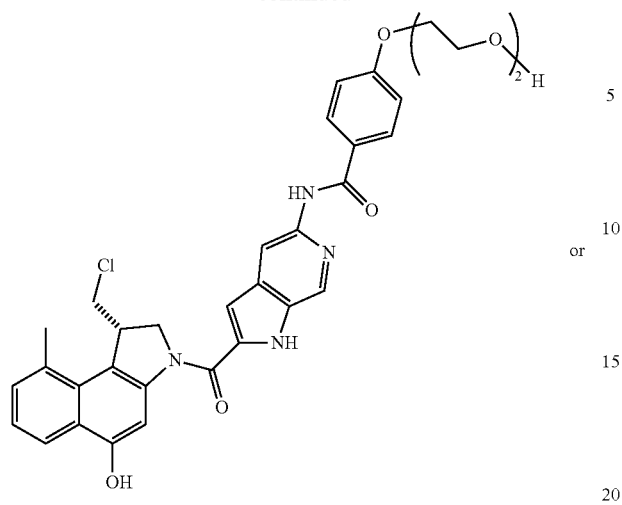
276
-continued
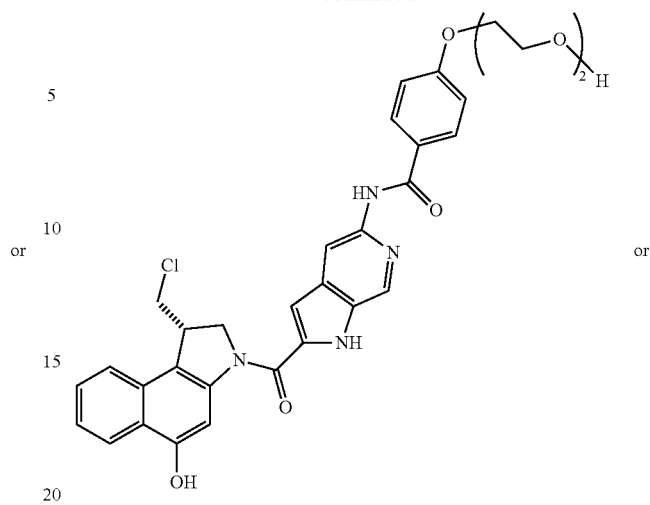
or
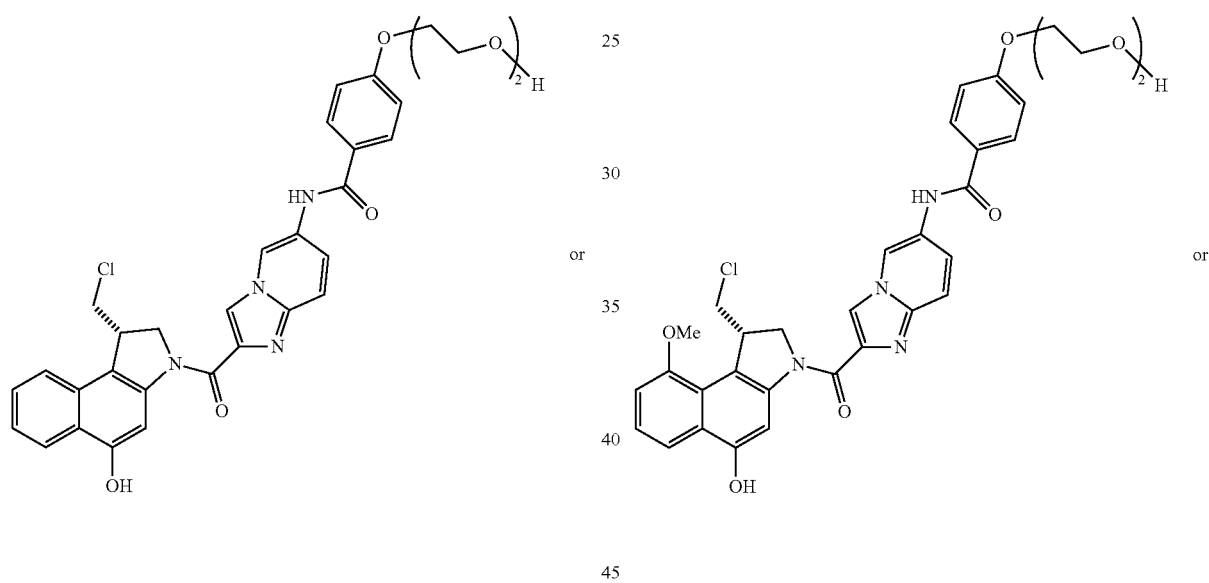
or
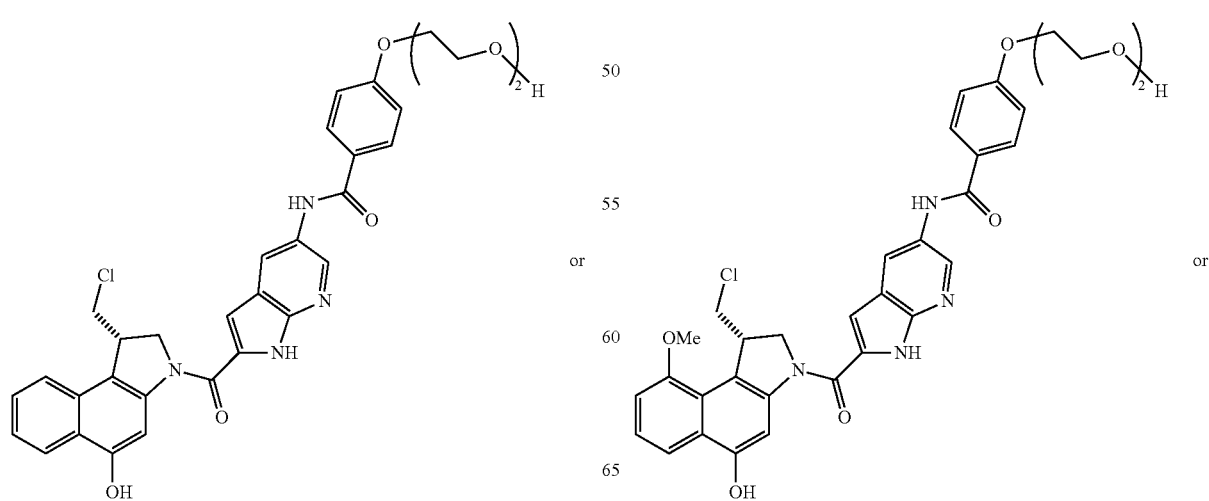
or 277
-continued

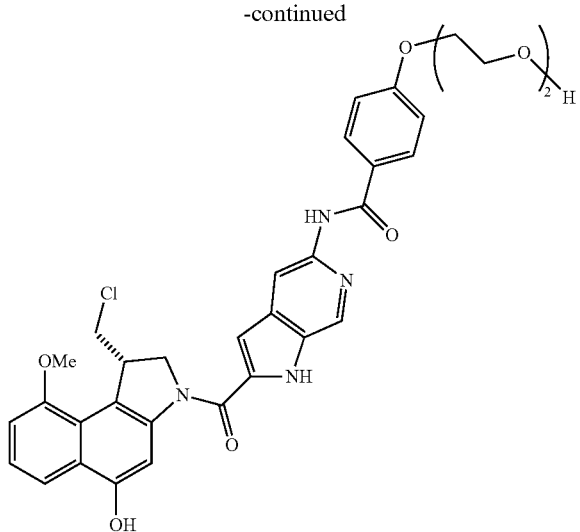

or an isomer of one of these, or a mixture of isomers.

Conjugates, Linker-Agent Conjugates and Bifunctional Linkers

In another aspect, this invention relates to a conjugate of a compound of formula (I) or (II) that can be converted in vivo in one or more steps to a compound of formula (I) or (II), respectively. The conjugate may also be converted to a derivative of a compound of formula (I) or (II) in which a part of the promoiety attached to a compound of formula (I) or (II) in the conjugate remains attached to the compound of formula (I) or (II) after in vivo conversion. An alternative way of looking at this is that the remaining moiety of the linker is part of the compound of formula (I) or (II).

These conjugates may favorably affect the pharmacological properties and other characteristics of a compound of formula (I) or (II). In one embodiment, this invention relates to a conjugate comprising a compound of formula (I) or (II) conjugated to at least one promoiety. In another embodiment, this invention relates to a conjugate comprising a compound of formula (I) or (II) conjugated to a promoiety.

In a further embodiment, this invention relates to a compound of formula (III):

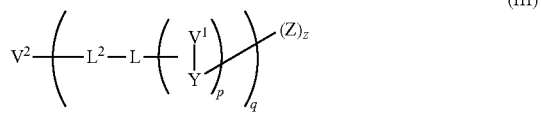
(III)

or a pharmaceutically acceptable salt, hydrate, or solvate thereof, wherein $V^2$ is either absent or a functional moiety;

each $L^2$ is independently absent or a linking group linking $V^2$ to L;

each L is independently absent or a linking group linking $L^2$ to one or more $V^1$ and/or Y;

each $V^1$ is independently absent or a conditionally-cleavable or conditionally-transformable moiety, which can be cleaved or transformed by a chemical, photochemical, physical, biological, or enzymatic process;

each Y is independently absent or a self-eliminating spacer system which is comprised of 1 or more self-elimination spacers and is linked to $V^1$, optionally L, and one or more Z;

278 each p and q are numbers representing a degree of branching and are each independently a positive integer;

z is a positive integer equal to or smaller than the total number of attachment sites for Z;

each Z is independently a compound of formula (I), (II), (I'), or (II') as defined hereinabove wherein one or more of $X^1$, $R^5$, $R^{5'}$, $R^6$, $R^{6'}$, $R^7$, $R^{7'}$, $R^{14}$, $R^{14'}$, $R^8$, $R^{8'}$, $R^9$, $R^{9'}$, $R^{10}$, $R^{10'}$, $R^{11}$, $R^{11'}$, $R^{15}$, $R^{15'}$, $R^{15''}$, $R^{15'''}$, $R^{16}$, $R^{16'}$, $R^{20}$, $R^{20'}$, $R^{21}$, $R^{21'}$, $R^{22}$, and $R^{23}$ may optionally in addition be substituted by or be a substituent of formula (V):

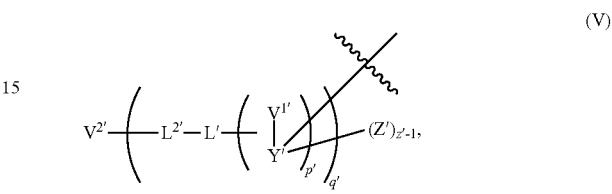
(V)

wherein each $V^{2'}$, $L^{2'}$, $L'$, $V^{1'}$, $Y'$, $Z'$, $p'$, $q'$, and $z'$ has the same meaning as defined for $V^2$, $L^2$, L, $V^1$, Y, Z, p, q, and z, respectively, and is independently selected, the one or more substituents of formula (V) being independently connected via $Y'$ to one or more of $X^1$, $R^5$, $R^{5'}$, $R^6$, $R^{6'}$, $R^7$, $R^{7'}$, $R^{14}$, $R^{14'}$, $R^8$, $R^{8'}$, $R^9$, $R^{9'}$, $R^{10}$, $R^{10'}$, $R^{11}$, $R^{11'}$, $R^{15}$, $R^{15'}$, $R^{15''}$, $R^{15'''}$, $R^{16}$, $R^{16'}$, $R^{20}$, $R^{20'}$, $R^{21}$, $R^{21'}$, $R^{22}$, $R^{23}$, and/or to one or more atoms bearing these R substituents;

each Z is independently connected to Y through either $X^1$, an atom in $R^5$, $R^{5'}$, $R^6$, $R^{6'}$, $R^7$, $R^{7'}$, $R^{14}$, $R^{14'}$, $R^8$, $R^{8'}$, $R^9$, $R^{9'}$, $R^{10}$, $R^{10'}$, $R^{11}$, $R^{11'}$, $R^{15}$, $R^{15'}$, $R^{15''}$, $R^{15'''}$, $R^{16}$, $R^{16'}$, $R^{20}$, $R^{20'}$, $R^{21}$, $R^{21'}$, $R^{22}$, $R^{23}$, or an atom bearing any of these R substituents; and at least $V^2$ or a $V^1$ is present.

In a further aspect, this invention relates to a compound of formula (III), wherein $V^2$ is present and selected to be a targeting moiety and there is at least one group of formula (V) that contains a $V^1$ moiety and either comprises a $V^{2'}$, $L^{2'}$, or $L'$ moiety that contains a $X^{14}(CH_2CH_2O)_{gg}CH_2CH_2X^{14}$ moiety, wherein gg is selected from 3 to 1000 and each $X^{14}$ is independently selected from

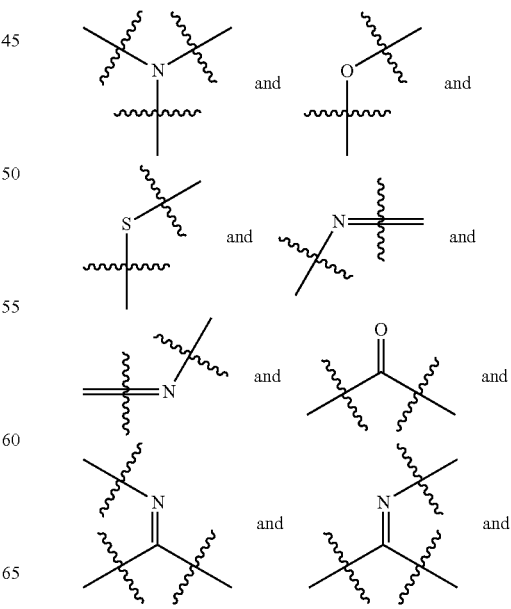

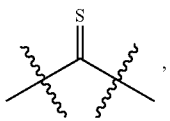

or said same group of formula (V) comprises at least 2 $X^{14}CH_2CH_2OCH_2CH_2X^{14}$ moieties, in which each $X^{14}$ is independently selected.

In a further aspect, this invention relates to a compound of formula (III) that contains at least one $X^{14}(CH_2CH_2O)_{ff}CH_2CH_2X^{14}$ moiety, wherein ff is selected from 1 to 1000 and each $X^{14}$ is independently selected from

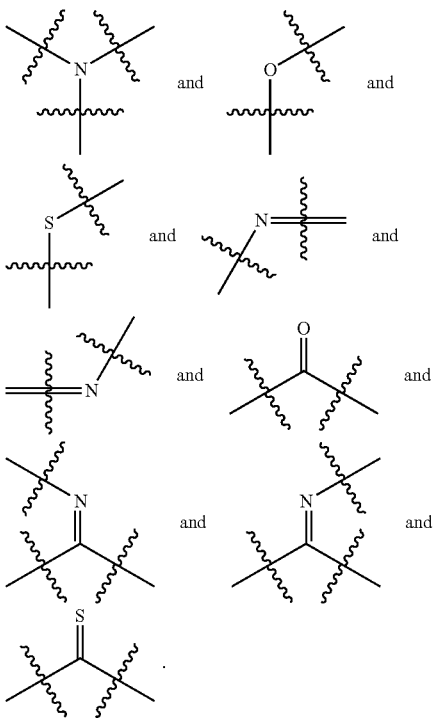

It should be understood from formula (III) that L can be connected to $V^1$ and/or to Y. If L is connected to Y, this means that both $V^1$ and L, as well as one or more Z, are connected to Y. If L is connected to $V^1$, this means that $V^1$ and one or more Z are connected to Y. L may also be connected to both $V^1$ and Y at the same time. If Y is absent, L is connected to $V^1$ or, if $V^1$ is absent, L is directly connected to Z.

The $V^2(-L^2-L(-(V^1-Y))_p)_q(Z)_{z-1}$ and one or more $V^{2'}(-L^{2'}-L'(-(V^{1'}-Y'))_{p'})_{q'}(Z')_{z'-1}$ moieties, wherein $L(-(V^1-Y))_p$ indicates that L can be connected to $V^1$ and/or to Y, connected to Z are herein referred to as promoieties.

The present invention also relates to a compound of formula (IV):

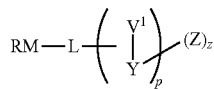

(IV)

or a pharmaceutically acceptable salt, hydrate, or solvate thereof, wherein

RM is a reactive moiety and L, $V^1$, Y, Z, p, and z are as defined hereinabove, except that L is now linking RM to one or more $V^1$ and/or Y, and $V^1$, Y, and Z may contain protecting groups, and the one or more $V^{2'}-L^{2'}$ moieties optionally present in Z as defined hereinabove may optionally and independently be RM' instead, which is a reactive moiety, and wherein, if there is more than 1 reactive moiety in (IV), some or all reactive moieties are the same or different. These linker-agent conjugates of formula (IV) may or may not be considered intermediates for compounds of formula (III). In a compound of formula (IV), RM must be present while $V^1$ may be either present or absent.

In a further aspect, the present invention relates to a compound of formula (IV), wherein RM is a reactive moiety selected from carbamoyl halide [—N(R)C(O)X], acyl halide [—C(O)X], active ester [—C(O)OR], anhydride [—C(O)OC(O)OR], α-haloacetyl [—C(O)CH$_2$X], α-haloacetamide [—N(R)C(O)CH$_2$X], maleimide, isocyanate [—N=C=O], isothiocyanate [—N=C=S], disulfide [—S—SR], thiol [—SH], hydrazine [—NH$_2$NH$_2$], hydrazide [—C(O)NH$_2$NH$_2$], sulfonyl chloride [—S(O)$_2$Cl], aldehyde [—C(O)H], methyl ketone [—C(O)CH$_3$], vinyl sulfone [—S(O)$_2$—CH=CH$_2$], halomethyl [—CH$_2$Cl], and methyl sulfonate [—CH$_2$OS(O)$_2$R], and wherein at least one group of formula (V), being part of Z, contains a $V^{1'}$ moiety and either comprises a $V^{2'}$, $L^{2'}$, or L moiety that contains a $X^{14}(CH_2CH_2O)_{gg}CH_2CH_2X^{14}$ moiety, wherein gg is selected from 3 to 1000 and each $X^{14}$ is independently selected from

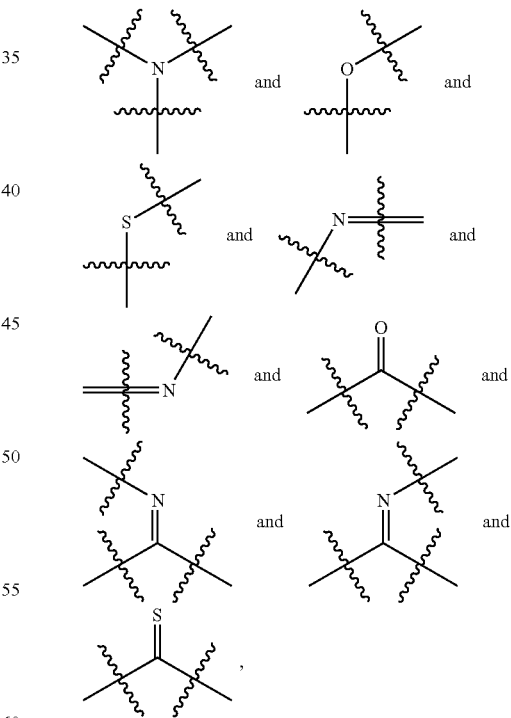

or said same group of formula (V) comprises at least 2 $X^{14}CH_2CH_2OCH_2CH_2X^{14}$ moieties, in which each $X^{14}$ is independently selected. These linker-agent conjugates of formula (IV) may or may not be considered intermediates for compounds of formula (III). In such a compound of formula (IV), RM must be present.

In another embodiment, a compound of formula (IV) contains an RM moiety selected from carbamoyl halide [—N(R)C(O)X], acyl halide [—C(O)X], active ester [—C(O)OR], anhydride [—C(O)OC(O)OR], α-haloacetyl [—C(O)CH$_2$X], α-haloacetamide [—N(R)C(O)CH$_2$X], maleimide, isocyanate [—N=C=O], isothiocyanate [—N=C=S], disulfide [—S—SR], thiol [—SH], hydrazine [—NH$_2$NH$_2$], hydrazide [—C(O)NH$_2$NH$_2$], sulfonyl chloride [—S(O)$_2$Cl], aldehyde [—C(O)H], methyl ketone [—C(O)CH$_3$], vinyl sulfone [—S(O)$_2$—CH=CH$_2$], halomethyl [—CH$_2$Cl], and methyl sulfonate [—CH$_2$OS(O)$_2$R].

The RM-L(-(V$^1$—Y))$_p$(Z)$_{z-1}$ and one or more RM'-L'(-(V$^{1'}$-Y'))$_{p'}$(Z')$_{z'-1}$ moieties, wherein L(-(V$^1$-Y))$_p$ indicates that L can be connected to V$^1$ and/or to Y, connected to Z are herein referred to as promoieties.

In yet a further aspect, this invention relates to novel bifunctional linkers that contain a cleavage site, a self-elimination spacer system and two reactive moieties, one of which can be reacted with a therapeutic or diagnostic moiety, e.g. a compound of formula (II or (II), and the other of which can be reacted with a functional moiety, such as a targeting moiety. These bifunctional linkers can be used to prepare conjugates of formulae (III) and (IV) of this invention or similar compounds with different therapeutic or diagnostic moieties.

More specifically, this invention relates to a compound of formula (VIII):

or a pharmaceutically acceptable salt, hydrate, or solvate thereof, wherein
L, V$^1$, Y, RM, p, and z are as defined for a compound of formula (IV), and RM2 is a reactive moiety or a leaving group. RM and each RM2 are independently selected. These bifunctional linkers of formula (VIII) may or may not be considered intermediates for compounds of formula (III) and (IV). Furthermore, these compounds may be considered to be intermediates for conjugates and linker-agent conjugates similar to compounds of formula (III) and (IV) in which the Z moiety is a therapeutic or diagnostic moiety different from a compound of formula (I), (II), (I'), or (II'), or a promoiety-containing derivative thereof. Therefore, in another aspect, this invention relates to a conjugate of formula (III) in which the one or more Z moieties are independently a therapeutic or diagnostic moiety. In yet another aspect, this invention relates to a linker-agent conjugate of formula (IV) in which the one or more Z moieties are independently a therapeutic or diagnostic moiety.

It is noted that the separate X$^{14}$ moieties in the —CH$_2$CH$_2$X$^{14}$ moieties that may be present in a compound of formula (III), (IV), or (VIII) are independently selected.

It is also noted that z does not represent a degree of polymerization; hence z does not indicate that a number of moieties Z or RM2 are connected to one another.

It is further noted that if Y or Y' is connected to an atom of Z or RM2 bearing a specific R substituent instead of to this R substituent itself, this in fact means that this R substituent is absent if this is necessary to meet valency rules.

It is further noted that if X$^{14}$ in for example —CH$_2$CH$_2$X$^{14}$ represents

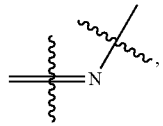

then —CH$_2$CH$_2$X$^{14}$ should be read as —CH$_2$CHX$^{14}$.

It is noted that if a compound of this invention contains an oligoethylene glycol or polyethylene glycol moiety the actual number of ethylene glycol units may vary from molecule to molecule and the variable designating the number of units actually represents the average number of units. Although the average number of ethylene glycol units is generally limited to 1000 in the definitions of compounds of this invention, compounds with a larger average number of ethylene glycol units are also encompassed by this invention.

It should be understood that this invention relates to enantiomerically pure and/or diastereomerically pure compounds of formulae (III), (IV), and (VIII) as well as to enantiomeric and/or diastereomeric mixtures of compounds of formulae (III), (IV), and (VIII).

When a compound of formula (III) or (IV) contains attachment sites in Y for Z that are not coupled to Z, for instance as a consequence of an incomplete coupling reaction with Z during synthesis, these attachment sites are considered to be attached to H, OH, a reactive moiety (e.g., RM2), or a leaving group (e.g., RM2) instead. If all of said attachment sites are connected to Z, then z equals the number of said attachment sites; otherwise, z is lower. Compounds of this invention may exist as a mixture, wherein each component of the mixture has a different z value. For example, the compound may exist as a mixture of two separate compounds, one compound wherein z is 4 and another compound wherein z is 3. Furthermore, for a given z, the compound may exist as a mixture of (constitutional) isomers as Z may be connected to distinct (sets of) attachment sites.

For reasons of clarity, when referring to the connections of one first moiety to other moieties within formula (III), (IV), or (VIII), in general only those said other moieties are mentioned that are directly attached to said first moiety in formula (III), (IV), or (VIII). It should be understood that if one of said other moieties is not present, said first moiety is actually connected to the moiety first in line that is present, unless explicitly stated otherwise. For example, if it is stated that "V$^1$ is cleaved from Y", this phrase actually means "V$^1$ is cleaved from Y, or from Z if Y is absent" and should be read as "V$^1$ is cleaved from Z" when reference is made to a compound lacking Y.

In a compound of formula (III) or (IV), Z may be conjugated to a promoiety through its water-soluble group, e.g., an oligoethylene glycol or polyethylene glycol moiety. In this way, the water-soluble group may contribute less to the water solubility of the compound of formula (III) or (IV), but may contribute again to the water solubility of Z upon removal of said promoiety.

In this document, whenever V$^2$, L$^2$, L, V$^1$, Y, Z, RM, p, q, or z is mentioned, it should be understood that the same can apply for each V$^{2'}$, L$^{2'}$, L', V$^{1'}$, Y', Z', RM', p', q', or z', respectively, unless the context dictates otherwise.

The V$^1$ Moiety

In a compound of formula (III), (IV), or (VIII), the V$^1$ moiety is a group that is conditionally cleavable or transformable. In other words, it is designed to be transformed and/or cleaved from Y by a chemical, photochemical, physical, biological, or enzymatic process upon being brought in or under a certain condition. This condition may for example be bringing a compound of the invention in an aqueous environment, which leads to hydrolysis of $V^1$, or bringing a compound of the invention in an environment that contains an enzyme that recognizes and cleaves $V^1$, or bringing a compound of the invention under reducing conditions, which leads to reduction and/or removal of $V^1$, or bringing a compound of the invention under oxidizing conditions, which leads to oxidation and/or removal of $V^1$, or bringing a compound of the invention in contact with radiation, e.g., UV light, which leads to transformation and/or cleavage, or bringing a compound of the invention in contact with heat, which leads to transformation and/or cleavage, or bringing a compound of the invention under reduced pressure, which leads to transformation, e.g., a retrocycloaddition, and/or cleavage, or bringing a compound of the invention under elevated or high pressure, which leads to transformation and/or cleavage. This condition may be met after administering a compound of this invention to an animal, e.g., a mammal, for example a human: the condition may be met when the compound localizes to for example a specific organ, tissue, cell, subcellular target, or bacterial, viral, or microbial target, for example by the presence of internal factors (e.g., target-specific enzymes or hypoxia) or application of external factors (e.g., radiation, magnetic fields) or the condition may already be met directly upon administration (e.g., ubiquitous enzymes in the circulation).

Cleavage of $V^1$ means that the bond between $V^1$ and Y is broken. Transformation of $V^1$ means that $V^1$ is converted into a different moiety and this event may directly or indirectly lead to self-cleavage of $V^1$ from Y. Alternatively, transformation of $V^1$ may lead to formation of a $V^1$-Y moiety which is a self-immolative linker. In this case, Y only becomes self-immolative after transformation of $V^1$. The transformed $V^1$ moiety actually becomes (partially) part of Y. For example, oxidation of $V^1$ being a hydrogen atom to a hydroxyl group may lead to formation of a para- or ortho-hydroxybenzyloxycarbonyl $V^1$-Y moiety that self-eliminates. As another example, reduction of $V^1$ being a nitro group may lead to formation of a para- or ortho-aminobenzyloxycarbonyl $V^1$-Y moiety that self-eliminates.

Alternatively again, $V^1$ may be absent. In this instance, the promoiety is intended to be non-removable from Z and the whole promoiety or a part thereof (in case of degradation of a compound of formula (III) or (IV) at one or more other sites in the molecule) will stay connected to the one or more moieties Z. One alternative way to look at this is that the part of the promoiety that remains attached to the moiety Z is in fact a part of moiety Z.

A compound of this invention may contain more than one $V^1$ moiety per promoiety (p and/or q>1). These $V^1$ moieties may or may not be the same and may or may not require the same conditions for transformation and/or cleavage.

The rate at which $V^1$ is transformed and/or cleaved may be dependent on the other moieties in a compound of formula (III). For example, use of a shorter L and/or Y moiety may bring the functional moiety and/or Z closer to the cleavage site, which may lead to a reduced rate of transformation and/or cleavage. (Bulky) substituents on the L and/or Y moiety may lead to a reduced rate of transformation and/or cleavage of $V^1$ as well, especially when they are situated close to the site of transformation/cleavage. Other effects, such as hydrogen bonding, neighboring group, and electronic effects, may play a role as well.

In one aspect of this invention, a conjugate is used to target one or more moieties Z to target cells. In this instance, a $V^1$ moiety may for example contain a substrate molecule that is cleaved by an enzyme present in the vicinity of the target cells or inside the target cells, for example tumor cells. $V^1$ can for example contain a substrate that is cleaved by an enzyme present at elevated levels in the vicinity of or inside the target cells as compared to other parts of the body, or by an enzyme that is present only in the vicinity of or inside the target cells.

It is important to recognize that if target site specificity is achieved solely based upon the selective transformation and/or cleavage of said $V^1$ at the target site, the condition causing the cleavage should preferably, at least to a certain degree, be target site-specific, whereas the presence of another target-specific moiety in the compound of the invention, for instance in a $V^2$ moiety, weakens or takes away this requirement. For example, when $V^2$ causes selective internalization into a target cell, an enzyme also present in other cells may transform and/or cleave $V^1$. However, cleavage should preferably not occur at a site distant from the target site. Therefore, the conjugate should not be exposed to enzymes or conditions that can cause cleavage of $V^1$ at sites other than the target site. In one embodiment, transformation and/or cleavage of $V^1$ occur intracellularly. In another embodiment, transformation and/or cleavage of $V^1$ occur extracellularly. In another embodiment, transformation and/or cleavage of $V^1$ occur by a ubiquitous intracellular enzyme. In another embodiment, transformation and/or cleavage of $V^1$ occur by a ubiquitous extracellular enzyme.

In one embodiment, $V^1$ contains a single amino acid, a di-, tri-, tetra-, or oligopeptide, or a peptidomimetic, which consists of an amino acid or amino acid sequence or mimetic thereof recognized and cleavable by a proteolytic enzyme, for example plasmin, a cathepsin, cathepsin B, prostate-specific antigen (PSA), urokinase-type plasminogen activator (u-PA), or a member of the family of matrix metallo-proteinases, present in the vicinity of or inside the target cells, for example tumor cells. In one embodiment, $V^1$ is a peptide. In another embodiment, $V^1$ is a single amino acid. In another embodiment, $V^1$ is a dipeptide. In another embodiment, $V^1$ is a tripeptide. In another embodiment, $V^1$ is a tetrapeptide. In yet another embodiment, $V^1$ is a peptidomimetic. A peptidomimetic may be an amino acid mimic or peptide mimic. An amino acid mimic may for example be a derivative of a natural amino acid in which the amino group has been replaced by a hydroxy group or a triazole group, in which the α-amino group of the amino acid is alkylated, or in which the side chain is connected to the α-amino group instead of to the α-carbon. A peptide mimic may be a peptide that contains one or more of such amino acid mimics.

In another embodiment, $V^1$ contains a β-glucuronide that is recognized by β-glucuronidase present in the vicinity of or inside tumor cells.

In one embodiment, $V^1$ contains a substrate for an enzyme.

In another embodiment, $V^1$ is a substrate for an enzyme.

In one embodiment, $V^1$ contains a substrate for an extracellular enzyme.

In another embodiment, $V^1$ contains a substrate for an intracellular enzyme.

In yet another embodiment, $V^1$ contains a substrate for a lysosomal enzyme.

In yet another embodiment, $V^1$ contains a substrate for the serine protease plasmin.

In yet another embodiment, $V^1$ contains a substrate for one or more of the cathepsins, for example cathepsin B.

In yet another embodiment, $V^1$ contains a substrate for a galactosidase.

In yet another embodiment, $V^1$ contains a substrate for quinone reductase NQO1.

In yet another embodiment, $V^1$ contains a hydrazide, hydrazone or imine moiety that is to be hydrolyzed intracellularly.

In yet another embodiment, $V^1$ contains a disulfide moiety that is to be cleaved intracellularly.

When $V^1$ is cleaved extracellularly, the one or more Z moieties may be released extracellularly. This may provide the advantage that these Z moieties are not only able to affect the cell(s) directly surrounding the site of activation (e.g., target-positive cells), but also cells somewhat further away from the site of activation (e.g., target-negative cells) due to diffusion (bystander effect), provided that the Z moieties are able to penetrate the cell membrane.

An enzyme to cleave $V^1$ can also be transported to the vicinity of or inside target cells or target tissue via for example antibody-directed enzyme prodrug therapy (ADEPT), polymer-directed enzyme prodrug therapy (PDEPT), macromolecular-directed enzyme prodrug therapy (MDEPT), virus-directed enzyme prodrug therapy (VDEPT), or gene-directed enzyme prodrug therapy (GDEPT). In these approaches, the enzyme that needs to cleave $V^1$ is transported to or induced to be produced at the target site before administration of the prodrug, e.g., a compound of formula (III) or (IV). In one embodiment, transformation and/or cleavage of $V^1$ occur through an enzyme linked to an antibody using the ADEPT approach.

In again another embodiment, $V^1$ contains a moiety, for example a nitrobenzyl moiety that can be transformed and/or cleaved by reduction under hypoxic conditions or by reduction by a nitroreductase. After reduction of the nitro group and cleavage of the resulting moiety via self-elimination, self-elimination of the spacer system Y, if present, leads to release of one or more moieties Z.

In one embodiment, the invention relates to a conjugate wherein $V^1$ is a single amino acid, a dipeptide, a tripeptide, a tetrapeptide, or an oligopeptide moiety comprised of natural L amino acids, unnatural D amino acids, or synthetic amino acids, or a peptidomimetic, or any combination thereof. In another embodiment, the invention relates to a compound wherein $V^1$ comprises a tripeptide. The tripeptide may be linked via its C-terminus to Y. In one embodiment, the C-terminal amino acid residue of the tripeptide is selected from alanine, arginine, citrulline, and lysine, the middle amino acid residue of the tripeptide is selected from alanine, valine, leucine, isoleucine, methionine, phenylalanine, cyclohexylglycine, tryptophan, and proline, and the N-terminal amino acid residue of the tripeptide is selected from any natural or unnatural amino acid.

In another embodiment, the invention relates to a compound wherein $V^1$ comprises a dipeptide. The dipeptide may be linked via its C-terminus to Y. In one embodiment, the C-terminal amino acid residue of the dipeptide is selected from alanine, arginine, citrulline, and lysine, and the N-terminal amino acid residue of the dipeptide is selected from any natural or unnatural amino acid.

In yet another embodiment, the invention relates to a compound wherein $V^1$ comprises a single amino acid. The amino acid may be linked via its carboxyl group to Y. In one embodiment, the amino acid is selected from alanine, arginine, citrulline, and lysine.

In one embodiment, when the α-amino group of the N-terminal amino acid of $V^1$ is not coupled to L, this amino acid may be functionalized with a suitable blocking group coupled to the α-amino group or may be an unnatural amino acid such that undesired premature degradation of $V^1$ by for example ubiquitous enzymes, e.g., exopeptidases, is prevented. Such a blocking group may be any group that prevents or considerably retards premature degradation of $V^1$. Examples of such a blocking group include a D-amino acid, an acetyl group, a tert-butyloxycarbonyl group, and an oligoethylene or polyethylene glycol.

In a further embodiment, $V^1$ is selected from D-alanylphenylalanyllysine, D-valylleucyllysine, D-alanylleucyllysine, D-valylphenylalanyllysine, D-valyltryptophanyllysine, D-alanyltryptophanyllysine, alanylphenylalanyllysine, valylleucyllysine, alanylleucyllysine, valylphenylalanyllysine, valyltryptophanyllysine, alanyltryptophanyllysine, D-alanylphenylalanylcitrulline, D-valylleucylcitrulline, D-alanylleucylcitrulline, D-valylphenylalanylcitrulline, D-valyltryptophanylcitrulline, D-alanyltryptophanylcitrulline, alanylphenylalanylcitrulline, valylleucylcitrulline, alanylleucylcitrulline, valylphenylalanylcitrulline, valyltryptophanylcitrulline, and alanyltryptophanylcitrulline.

In yet another embodiment, $V^1$ is selected from phenylalanyllysine, valyllysine, valylalanine, D-phenylalanylphenylalanyllysine, phenylalanylphenylalanyllysine, glycylphenylalanyllysine, alanyllysine, valylcitrulline, N-methylvalylcitrulline, phenylalanylcitrulline, isoleucylcitrulline, tryptophanyllysine, tryptophanylcitrulline, phenylalanylarginine, phenylalanylalanine, glycylphenylalanylleucylglycine, alanylleucylalanylleucine, alanylarginylarginine, phenylalanyl-$N^9$-tosylarginine, phenylalanyl-$N^9$-nitroarginine, leucyllysine, leucylcitrulline, and phenylalanyl-O-benzoylthreonine.

In a further embodiment, $V^1$ is selected from phenylalanyllysine, valyllysine, and valylcitrulline.

In yet further embodiments, $V^1$ is phenylalanyllysine or valyllysine or valylcitrulline.

Therefore, in one embodiment this invention relates to a compound wherein $V^1$ contains a substrate that can be cleaved by a proteolytic enzyme, plasmin, a cathepsin, cathepsin B, β-glucuronidase, a galactosidase, prostate-specific antigen (PSA), urokinase-type plasminogen activator (u-PA), a member of the family of matrix metalloproteinases, or an enzyme localized by means of directed enzyme prodrug therapy, such as ADEPT, VDEPT, MDEPT, GDEPT, or PDEPT, or wherein $V^1$ contains a moiety that can be cleaved or transformed through reduction under hypoxic conditions, through reduction by a nitroreductase, or through oxidation.

In another aspect of this invention, a conjugate of this invention is used primarily to improve the pharmacological properties of Z. When a promoiety does not need to be selectively removed at a target site, $V^1$ of said promoiety may for example be or contain a group that is cleaved by ubiquitous enzymes, e.g., esterases that are present in the circulation or intracellular enzymes, such as for example proteases and phosphatases, by pH-controlled intramolecular cyclization, or by acid-catalyzed, base-catalyzed, or non-catalyzed hydrolysis, or $V^1$ may for example be or contain a disulfide or form a disulfide with a neighboring moiety. $V^1$ may therefore, optionally together with the connecting atom(s) of L and/or Y, for example form a carbonate, carbamate, ureum, ester, amide, imine, hydrazone, hydrazide, oxime, disulfide, acetal, or ketal group that can be cleaved in vivo. This means that $V^1$, optionally together with the connecting atom(s) of L and/or Y, can for example also represent —OC(O)—, —C(O)O—, —OC(O)O—, —N(R$^v$)C(O)—, —C(O)N(R$^v$)—, —N(R$^v$)C(O)O—, —OC(O)N(R$^v$)—, —N(R$^v$)C(O)N(R$^w$)—, —C(O)—, —OC(R$^v$)(R$^w$)—, —C(R$^v$)(R$^w$)O—, —OC(R$^v$)(R$^w$)O—, —C(R$^w$)(R$^w$)—, —S—, —S—S—, —C=, =C—, —N=, =N—, —C=N—, —N=C—, —O—N=, =N—O—, —C=N—O—, —O—N=C—, —N(R$^v$)—N=, =N—N(R$^v$)—, —N(R$^v$)—N=C—, or —C=N—N(R$^v$)—, wherein R$^v$ and R$^w$ are independently selected from H and optionally substituted C$_{1-10}$ alkyl, C$_{1-10}$ heteroalkyl, C$_{1-10}$ heteroaryl, C$_{3-10}$ cycloalkyl, C$_{1-10}$ heterocycloalkyl, or C$_{5-10}$ aryl, R$^v$ and R$^w$ optionally being joined by one or more bonds to form one or more optionally substituted carbocycles and/or heterocycles.

V$^1$ may therefore for example be or contain, optionally together with the connecting atom(s) of L and/or Y, a peptide, an amino acid, a peptidomimetic, a disulfide, a monosaccharide or disaccharide or a derivative thereof, a nitroaromatic moiety, an imine, a hydrazide, or a hydrazone moiety.

If V$^1$ or V$^1$-Y represents a whole promoiety or L is connected to Y and not to V$^1$, V$^1$ may for example also be selected from a mono-, di-, or oligosaccharide, R$^P$—[O(R$^{P'}$O)P(O)]$_{pp}$—, R$^P$—C(O)—, R$^P$—OC(O)—, and R$^P$—N(R$^{P'}$)C(O)—, wherein pp is selected from 1 to 3 and each R$^P$ and R$^{P'}$ is independently selected from H and optionally substituted C$_{1-15}$ alkyl, C$_{1-15}$ heteroalkyl, C$_{3-15}$ cycloalkyl, C$_{1-15}$ heterocycloalkyl, C$_{5-15}$ aryl, or C$_{1-15}$ heteroaryl, R$^P$ and R$^{P'}$ optionally being joined by one or more bonds to form one or more optionally substituted carbocycles and/or heterocycles.

In one embodiment, V$^1$ is selected from phosphono, phenylaminocarbonyl, 4-(piperidin-1-yl)piperidin-1-ylcarbonyl, piperazin-1-ylcarbonyl, piperidin-1-ylcarbonyl, pyrrolidin-1-ylcarbonyl, and 4-methylpiperazin-1-ylcarbonyl.

V$^1$ itself may contribute to favorable pharmacological properties of the conjugate, for example through the presence of polar functional groups in V$^1$.

If a conjugate of this invention contains more than 1 promoiety, one of these promoieties may be used to target the conjugate to a target site (targeting promoiety), whereas another promoiety is used to improve the pharmacological properties. In this instance, the V$^1$ moiety in the targeting promoiety is preferably cleaved at the target site, for example through a target site-specific process such as an enzymatic cleavage by an enzyme predominantly present at the target site or through a more generic intracellular process which can only occur after target cell-selective internalization of the conjugate, whereas the promoiety that helps to improve the pharmacological properties may be cleaved either at the target site or systemically, for example by ubiquitous enzymes.

It should be noted that V$^1$, either in the form of an amino acid, a di-, tri-, tetra-, or oligopeptide, or in any other form, may contain protecting groups. Compounds of the invention comprising such a protected V$^1$ may not release any Z moiety when put under conditions that will transform and/or cleave the corresponding unprotected V$^1$. However, when said compounds are deprotected, such compounds will release one or more Z moieties when put under the appropriate conditions. Compounds comprising such a protected V$^1$ also fall under the scope of this invention. In one aspect the above can be envisioned for compounds of formula (IV). Suitable protecting groups for functional groups, in particular for amino acids, are well-known to the organic chemist and may for example be found in T. W. Greene, *Protective Groups in Organic Synthesis*, John Wiley & Sons, New York, 1981. In another aspect, the protecting group or protecting moiety may be present in a compound of formula (III) and this compound may be administered as such. This means that deprotection should occur in vivo before release of any Z can occur through transformation and/or cleavage of V$^1$. In vivo deprotection of the protected V$^1$ moiety in a compound of formula (III) may occur by, for example, hydrolysis or enzymatic conversion. This deprotection may occur at the target site or aspecifically.

Compounds of formulae (III) and (IV) can be designed to eventually release a compound of formula (I) or (II), or a compound of formula (I') or (II'), after transformation and/or cleavage of the one or more V$^1$ and V$^{1'}$ moieties. Release of a compound of formula (I) or (II), a compound of formula (I') or (II'), or a derivative thereof (for example due to only partial degradation of the promoiety) from a conjugate of this invention via another mechanism is however not excluded from this invention.

In another aspect of this invention, a compound of formula (III) represents an intermediate for the preparation of a compound of formula (I) or (II) or another compound of formula (III). In this instance, for example, V$^2$, L$^2$, L, and Y are absent, p, q, and z all are 1, and the V$^1$ moiety may be a protecting group. There may or may not be one or more V$^{2'}$(-L$^{2'}$-L'(-(V$^1$-Y'))$_{p'}$)$_q$(Z')$_{z'-1}$ moieties present, in which V$^{2'}$, L$^{2'}$, L', and Y' may or may not be absent, and p', q', and z' all may or may not be 1. In one embodiment, a compound of formula (III) is a compound of formula (I) or (II) to which a V$^1$ moiety is attached. In another embodiment, a compound of formula (III) is a compound of formula (I) or (II) to which a V$^1$ moiety and a V$^{2'}$(-L$^{2'}$-L'(-(V$^1$-Y'))$_{p'}$)$_q$(Z')$_{z'-1}$ moiety are attached. In yet another embodiment, a compound of formula (III) is a compound of formula (I) or (II) to which a V$^1$ moiety and a V$^1$ moiety are attached.

In one embodiment, V$^1$ is not a protecting group.

In another embodiment, V$^2$, L$^2$, L, and Y are absent, and p, q, and z all are 1.

In a further embodiment, V$^1$ is a chemically removable group.

In yet a further embodiment, V$^1$ is a chemically removable group connected to Z via X$^1$.

In yet another further embodiment, V$^1$ is a benzyl group connected to Z via X$^1$.

In another embodiment, V$^1$ is tert-butoxycarbonyl(methylamino)ethyl(methylamino)carbonyl.

In another embodiment, V$^1$ is 4-(tert-butoxycarbonyl)piperazine-1-carbonyl.

In one embodiment, V$^1$ is connected to L via more than one functional group on V$^1$.

In another embodiment, V$^1$ is connected to L via one functional group on V$^1$.

In another embodiment, V$^1$ is connected to L via a functional group in the side chain of one of the natural or unnatural amino acids of V$^1$.

In another embodiment, the N-terminal amino acid of V$^1$ is connected via its α amino group to L.

In another embodiment, V$^1$ is absent.

The Self-Eliminating Spacer System Y

The self-elimination spacer system Y, if present, links V$^1$ and optionally L to one or more moieties Z, or RM2 in case of a compound of formula (VIII).

A self-elimination spacer system Y may be incorporated in a conjugate of this invention for example to improve the properties of Z or the conjugate in general, to provide for suitable coupling chemistries, and/or to create space between V$^1$ and Z.

A compound of this invention may contain more than one spacer system Y per promoiety. These moieties Y may or may not be the same.

After cleavage or transformation of $V^1$, the left-hand side of Y may become unblocked or a $V^1$-Y self-elimination moiety may be formed, which results in eventual release of one or more moieties Z. The self-elimination spacer systems may for example be those described in WO 02/083180 and WO 2004/043493, which are incorporated herein by reference in their entirety, the ones described in this section, as well as other self-elimination spacers known to a person skilled in the art.

Moiety Y may, in addition to providing suitable coupling chemistries and creation of space between the cleavage site and Z, help improve the pharmacological properties of the conjugate. For example, the presence of a water-soluble moiety or substituent, such as a polyethylene glycol moiety or a substituent that is charged, at least partly, at physiological pH may contribute to the water solubility and/or increase the storage stability and/or plasma stability of the conjugate.

In one aspect the invention is related to compounds wherein Y is

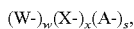

wherein
W and X are each a single-release 1,2+2n electronic cascade spacer (n≥1), being the same or different;
A is an ω-amino aminocarbonyl cyclization spacer that forms a cyclic ureum derivative upon cyclization;
s is 0 or 1;
w and x are numbers representing degree of polymerization and are independently an integer from 0 (included) to 5 (included).

In one embodiment, w+x is 0, 1, or 2. In another embodiment, s is 0. In yet another embodiment, s is 1. In yet another embodiment, w+x is 1 or 2 and s is 1. In yet another embodiment, w+x is 1 and s is 1. In yet another embodiment, w is 1, x is 0, and s is 1.

According to a further embodiment of this invention, the 1,2+2n electronic cascade spacers W and X are independently a moiety having the formula:

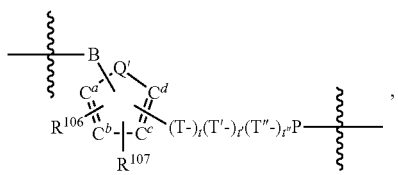

wherein
Q' is selected from —$R^{110}C$=$CR^{111}$—, S, O, $NR^{111}$, —$R^{111}C$=N—, and —N=$CR^{111}$—;
B is selected from $NR^{112}$, O, and S;
P is $C(R^{108})(R^{109})Q$;
$R^{106}$, $R^{107}$, B, and (T-)$_t$(T'-)$_{t'}$(T"-)$_{t"}$P are connected to $C^a$, $C^b$, $C^c$, and $C^d$ in such a way that B and (T-)$_t$(T'-)$_{t'}$(T"-)$_{t"}$P are connected to two adjacent carbon atoms or to $C^a$ and $C^d$, respectively;
Q is absent or —O—C(O)—;
t, t', and t" are numbers representing degree of polymerization and are independently an integer from 0 (included) to 5 (included);
T, T', and T" are independently selected from moieties having the formula:

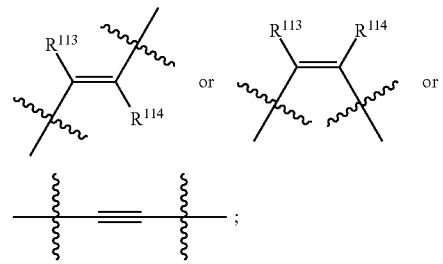

$R^{106}$, $R^{107}$, $R^{108}$, $R^{109}$, $R^{110}$, $R^{111}$, $R^{112}$, $R^{113}$, and $R^{114}$ are independently selected from H, OH, SH, $NH_2$, $N_3$, $NO_2$, NO, $CF_3$, CN, $C(O)NH_2$, C(O)H, C(O)OH, halogen, $R^y$, $SR^y$, $S(O)R^y$, $S(O)_2R^y$, $S(O)OR^y$, $S(O)_2OR^y$, $OS(O)R^y$, $OS(O)_2R^y$, $OS(O)OR^y$, $OS(O)_2OR^y$, $OR^y$, $NHR^y$, $N(R^y)R^{y1}$, $^+N(R^y)(R^{y1})R^{y2}$, $P(O)(OR^y)(OR^{y1})$, $OP(O)(OR^y)(OR^{y1})$, $C(O)R^y$, $C(O)OR^y$, $C(O)N(R^{y1})R^y$, $OC(O)R^y$, $OC(O)OR^y$, $OC(O)N(R^y)R^{y1}$, $N(R^{y1})C(O)R^y$, $N(R^{y1})C(O)OR^y$, and $N(R^{y1})C(O)N(R^{y2})R^y$, wherein $R^y$, $R^{y1}$, and $R^{y2}$ are independently selected from H and optionally substituted $(CH_2CH_2O)_{ee}CH_2CH_2X^{13}R^{e1}$, $C_{1-20}$ alkyl, $C_{1-20}$ heteroalkyl, $C_{3-20}$ cycloalkyl, $C_{1-20}$ heterocycloalkyl, $C_{5-20}$ aryl, or $C_{1-20}$ heteroaryl, wherein ee is selected from 1 to 1000, $X^{13}$ is selected from O, S, and $NR^{f1}$, and $R^{f1}$ and $R^{e1}$ are independently selected from H and $C_{1-3}$ alkyl, two or more of $R^y$, $R^{y1}$, and $R^{y2}$ optionally being joined by one or more bonds to form one or more optionally substituted carbocycles and/or heterocycles, two or more of the substituents $R^{106}$, $R^{107}$, $R^{108}$, $R^{109}$, $R^{110}$, $R^{111}$, $R^{112}$, $R^{113}$, and $R^{114}$ optionally being joined by one or more bonds to form one or more optionally substituted carbocycles and/or heterocycles.

In the formulae above, Q may be O—C(O), but it may also be absent. For example, a compound with a benzyl ether linkage between self-elimination spacer and the group that leaves, the oxycarbonyl moiety thus being absent (Q is absent), has been reported to undergo self-elimination[9].

In one embodiment, t, t' and t" are 0.

Substituents $R^{108}$ and $R^{109}$ can be used to tune the degree of shielding of the linkage to the moiety attached to Q (e.g., A or Z). They may also be used to tune the rate at which the 1,2+2n electronic cascade spacers W and X self-eliminate. In one embodiment, both $R^{108}$ and $R^{109}$ are H. In another embodiment, $R^{108}$ is not H. In yet another embodiment, both $R^{108}$ and $R^{109}$ are not H.

Substituents $R^{106}$, $R^{107}$, $R^{110}$, and $R^{111}$ can be used to tune the degree of shielding of the linkage between $V^1$ and Y and may thus be used to tune the cleavage rate of a compound of formula (III) or (IV). Furthermore, these substituents can be used to introduce additional water solubility into a compound of this invention. In some embodiments, the 1,2+2n electronic cascade spacer W or X is

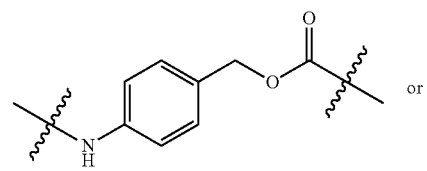

-continued

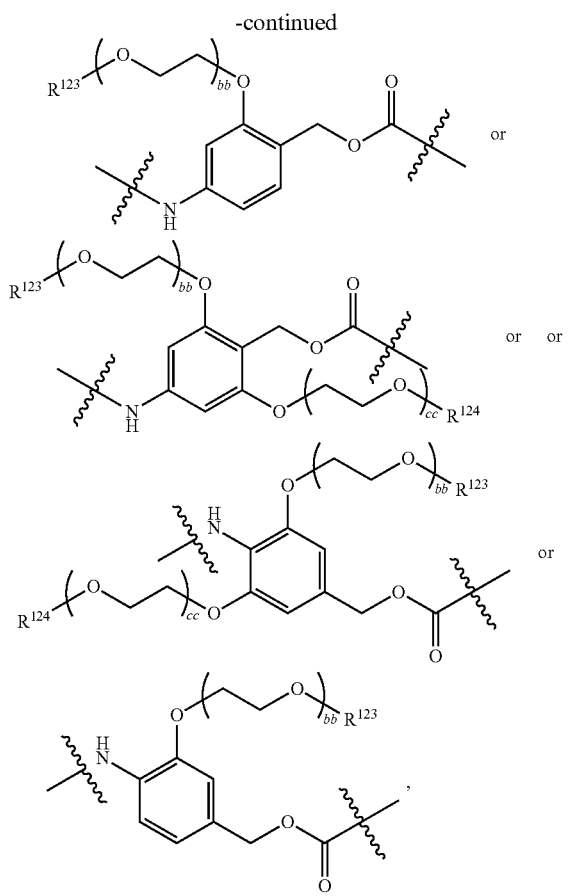

wherein bb and cc are independently an integer from 0 to 10 and $R^{123}$ and $R^{124}$ are independently selected from H and methyl.

In another embodiment, the 1,2+2n electronic cascade spacer W or X is

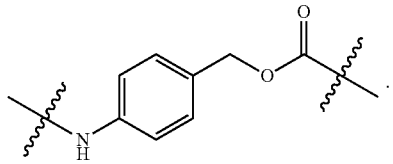 [SMILES: *Nc1ccc(COC(*)=O)cc1]

According to a further embodiment of this invention, the ω-amino aminocarbonyl cyclization elimination spacer A is a moiety having the formula:

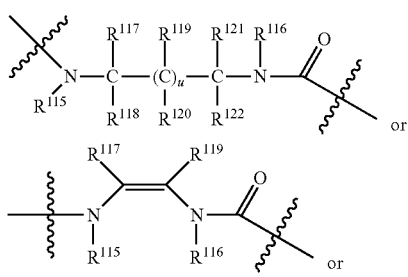

-continued

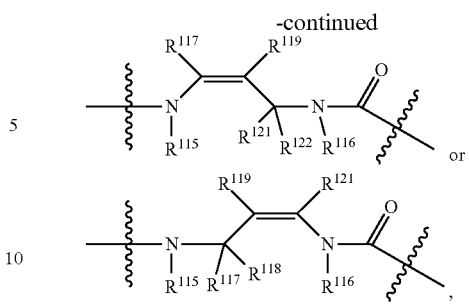

wherein
u is an integer of 0 or 1;
$R^{115}$, $R^{116}$, $R^{117}$, $R^{118}$, $R^{119}$, $R^{120}$, $R^{121}$, and $R^{122}$ are independently selected from H, OH, SH, $NH_2$, $N_3$, $NO_2$, NO, $CF_3$, CN, $C(O)NH_2$, $C(O)H$, $C(O)OH$, halogen, $R^z$, $SR^z$, $S(O)R^z$, $S(O)_2R^z$, $S(O)OR^z$, $S(O)_2OR^z$, $OS(O)R^z$, $OS(O)_2R^z$, $OS(O)OR^z$, $OS(O)_2OR^z$, $OR^z$, $NHR^z$, $N(R^z)R^{z1}$, $^+N(R^z)(R^{z1})R^{z2}$, $P(O)(OR^z)(OR^{z1})$, $OP(O)(OR^z)(OR^{z1})$, $C(O)R^z$, $C(O)OR^z$, $C(O)N(R^{z1})R^z$, $OC(O)R^z$, $OC(O)OR^z$, $OC(O)N(R^z)R^{z1}$, $N(R^{z1})C(O)R^z$, $N(R^{z1})C(O)OR^z$, and $N(R^{z1})C(O)N(R^{z2})R^z$, wherein $R^z$, $R^{z1}$, and $R^{z2}$ are independently selected from H and optionally substituted $(CH_2CH_2O)_{ee}CH_2CH_2X^1R^{e1}$, $C_{1-20}$ alkyl, $C_{1-20}$ heteroalkyl, $C_{3-20}$ cycloalkyl, $C_{1-20}$ heterocycloalkyl, $C_{5-20}$ aryl, or $C_{1-20}$ heteroaryl, wherein ee is selected from 1 to 1000, $X^{13}$ is selected from O, S, and $NR^{f1}$, and $R^{f1}$ and $R^{e1}$ are independently selected from H and $C_{1-3}$ alkyl, two or more of $R^z$, $R^{z1}$, and $R^{z2}$ optionally being joined by one or more bonds to form one or more optionally substituted carbocycles and/or heterocycles, two or more of the substituents $R^{115}$, $R^{116}$, $R^{117}$, $R^{118}$, $R^{119}$, $R^{120}$, $R^{121}$, and $R^{122}$ optionally being joined by one or more bonds to form one or more optionally substituted carbocycles and/or heterocycles.

$R^{115}$ and $R^{116}$ are substituent groups that are located on the nitrogen atoms that are part of the connecting linkages to the moieties adjacent to the ω-amino aminocarbonyl cyclization elimination spacer in a compound of formula (III), (IV), or (VIII). The nitrogen bearing $R^{116}$ is connected to Z or RM2 via a carbonyl moiety. The nitrogen atom bearing $R^{115}$ is connected to W, X, $V^1$, or L. The size and nature of substituents $R^{115}$ and $R^{116}$ may, in addition to affecting pharmacological properties of a compound of formula (III), (IV), or (VIII) in general, especially affect the stability of said connecting linkages. For example, choosing $R^{116}$ to be a small substituent may in general cause the linkage to Z to be less stable to hydrolysis or enzymatic degradation than when $R^{116}$ is a more bulky substituent (e.g., a substituent that is branched at the carbon a or 3 to the nitrogen atom). The nature of the $R^{116}$ substituent, e.g., whether polar or apolar or whether or not charged at physiological pH, may affect the stability of the linkage to Z as well, because the substituent may affect the substrate properties of the connecting linkage for specific enzymes or retard or increase the rate of hydrolysis. If the connecting linkage is susceptible to enzymes that are ubiquitously present, for example enzymes present in the circulation, this may cause premature degradation of the conjugate. The same holds for substituent $R^{115}$ with regard to the connecting linkage to W, X, $V^1$, or L. Similarly, the substituents on the carbons directly attached to the nitrogen atoms ($R^{117}$, $R^{118}$, $R^{119}$, $R^{121}$, and $R^{122}$) may contribute to the stability of the connecting linkages.

Substituents $R^{115}$ and $R^{116}$ may also affect the cyclization rate of the ω-amino aminocarbonyl cyclization elimination spacer A. Bulky substituents may hinder cyclization and thus generally reduce the cyclization rate. Small substituents may therefore in general be favorable for fast cyclization rates. However, other properties of the substituent, such as electronegativity, polarity, and availability of hydrogen bond donor and/or acceptor groups, may also affect the cyclization rate. Furthermore, if only one of $R^{115}$ and $R^{116}$ is a bulky substituent, the cyclization rate may be enhanced with respect to cyclization spacers containing two non-bulky substituents, possibly because of B-strain. The cyclization rate may also be affected by the other substituents on the ω-amino aminocarbonyl cyclization elimination spacer. Properties of these substituents such as polarity, electronegativity, and hydrogen bonding capabilities, may have an effect on the cyclization rate. Furthermore, the presence of geminal substituents on one of the carbons in between the two nitrogen atoms may enhance the cyclization rate as well (Thorpe-Ingold effect). The joinder of substituents to form one or more rings may also have an effect on the cyclization rate. In this respect, every modification that may bring the two nitrogen atoms closer together or that reduces entropy may have an accelerating effect on the cyclization rate.

Effects on the cyclization rate may be pH dependent and the order of the cyclization rate of two ω-amino aminocarbonyl cyclization elimination spacers may be reversed going from for example pH 7 to pH 5.

Although it may be beneficial in some cases for a conjugate of this invention to have an ω-amino aminocarbonyl cyclization elimination spacer with a fast cyclization rate, thus releasing the active drug shortly after cleavage of $V^1$, in other cases it may be more beneficial to have an r-amino aminocarbonyl cyclization elimination spacer that has a slow cyclization rate or a cyclization rate that lies between two predetermined limits or that preferably cyclizes at a fast rate only within certain pH limits. This may cause the cyclization spacer-drug intermediate to survive for a certain amount of time as a prodrug that will release the drug slowly or after a certain condition has been met.

In one embodiment, $R^{115}$ and $R^{116}$ are independently selected from $R^z$, wherein $R^z$ is selected from H and optionally substituted $(CH_2CH_2O)_{ee}CH_2CH_2X^{13}R^{e1}$, $C_{1-20}$ alkyl, $C_{1-20}$ heteroalkyl, $C_{3-20}$ cycloalkyl, $C_{1-20}$ heterocycloalkyl, $C_{5-20}$ aryl, and $C_{1-20}$ heteroaryl, wherein ee is selected from 1 to 1000, $X^{13}$ is selected from O, S, and $NR^{f1}$, and $R^{f1}$ and $R^{e1}$ are independently selected from H and $C_{1-3}$ alkyl.

In another embodiment, both $R^{115}$ and $R^{116}$ are not H. In another embodiment, both $R^{115}$ and $R^{116}$ are not methyl. In yet another embodiment, both $R^{115}$ and $R^{116}$ are not H and at least one of $R^{115}$ and $R^{116}$ is not methyl. In yet another embodiment, both $R^{115}$ and $R^{116}$ are not H and $R^{116}$ is not methyl. In yet another embodiment, at least one of $R^{115}$ and $R^{116}$ is not H or methyl. Such cyclization spacers incorporated in a compound of formula (III) or (IV) have been shown to have improved properties with respect to cyclization spacers in which $R^{115}$ and $R^{116}$ are both selected from only H and methyl. For example, the rate of self-elimination, the rate of drug release, conjugate stability, and/or conjugate polarity may be improved.

In one embodiment, $R^{115}$ and $R^{116}$ are independently selected from optionally substituted $(CH_2CH_2O)_{ee}CH_2CH_2X^{13}R^{e1}$, $C_{1-6}$ alkyl, $C_{1-6}$ heteroalkyl, $C_{3-6}$ cycloalkyl, $C_{1-6}$ heterocycloalkyl, $C_{5-6}$ aryl, and $C_{1-6}$ heteroaryl, wherein ee is selected from 1 to 9, $X^{13}$ is selected from O, S, and $NR^{f1}$, and $R^{f1}$ and $R^{e1}$ are independently selected from H and $C_{1-3}$ alkyl.

In another embodiment, $R^{115}$ and $R^{116}$ are independently selected from H, methyl, ethyl, isopropyl, tert-butyl, phenyl, $(CH_2CH_2O)_{ee}CH_2CH_2X^{13}R^{e1}$,

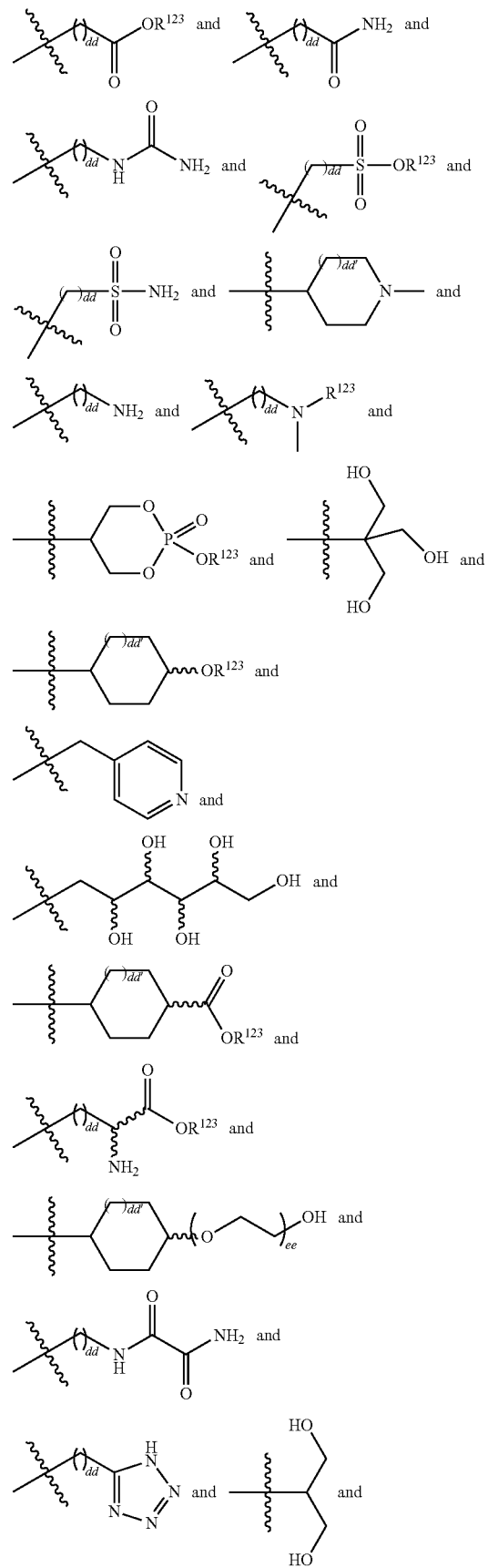

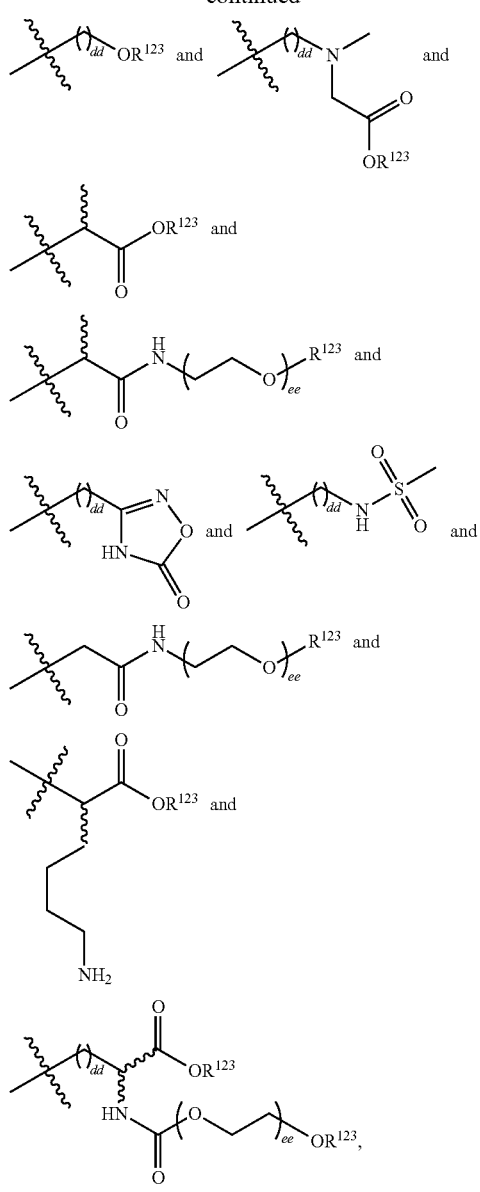
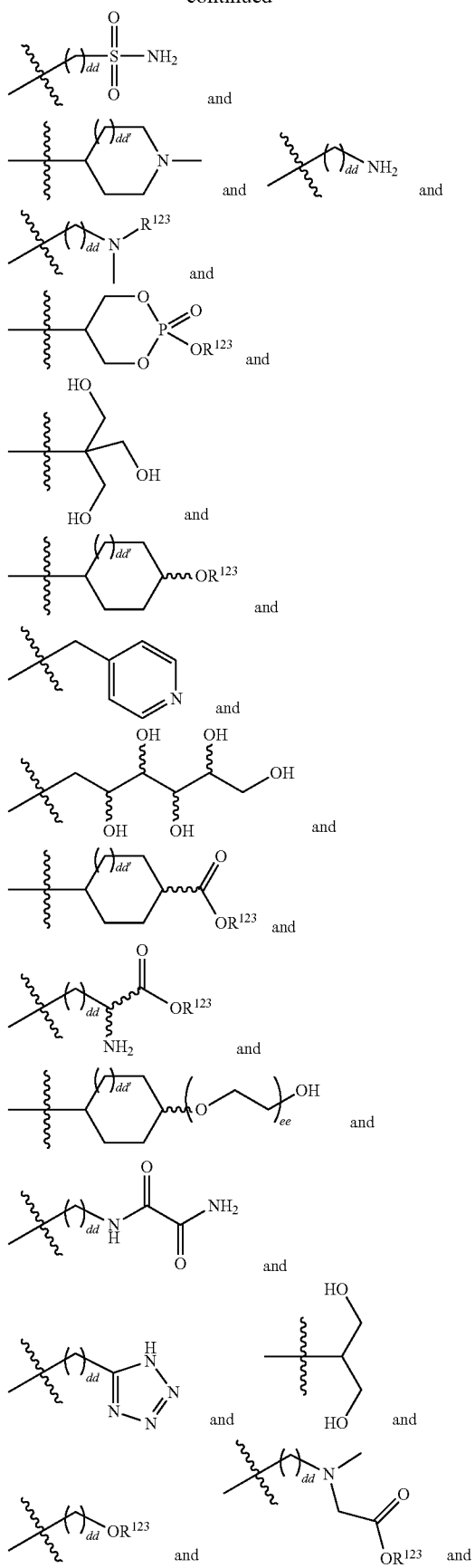

wherein dd is selected from 0 to 10, dd' is selected from 0 and 1, each $R^{123}$ is independently selected from H and methyl, ee is selected from 1 to 1000, $X^{13}$ is selected from O, S, and $NR^{f1}$, and $R^{f1}$ and $R^1$ are independently selected from H and $C_{1-3}$ alkyl.

In further embodiments, $R^{115}$ and $R^{116}$ are independently selected from H, methyl, ethyl, isopropyl, tert-butyl, phenyl, $(CH_2CH_2O)_{ee}CH_2CH_2X^{13}R^{e1}$,

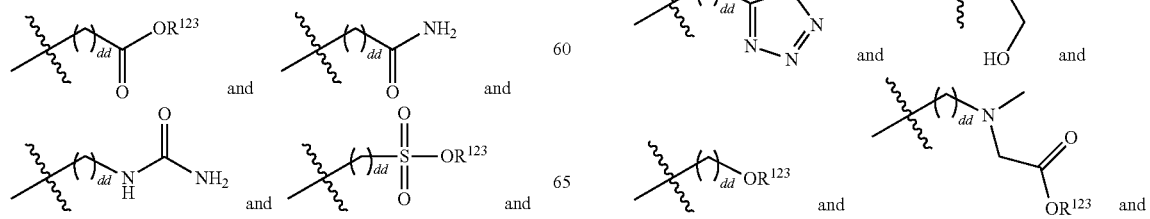

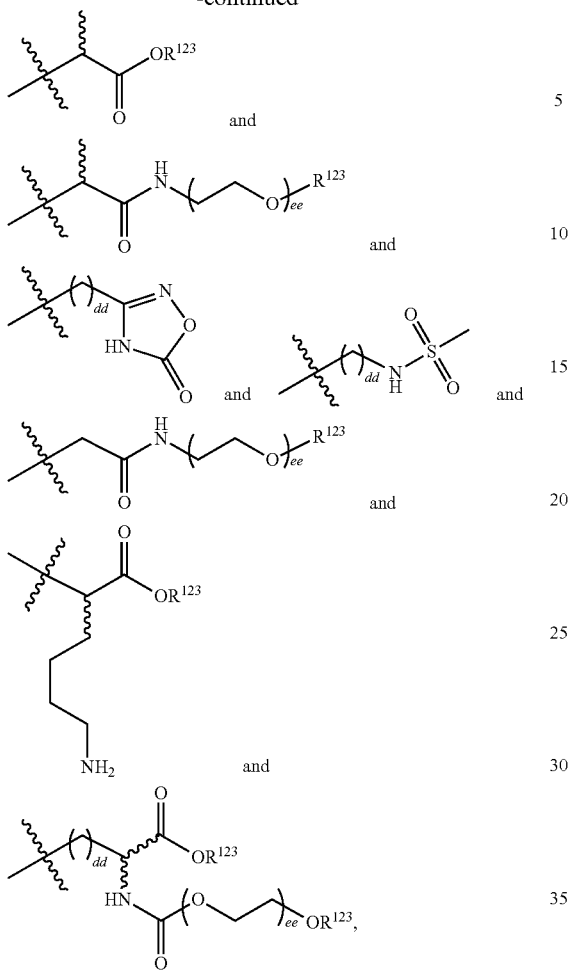
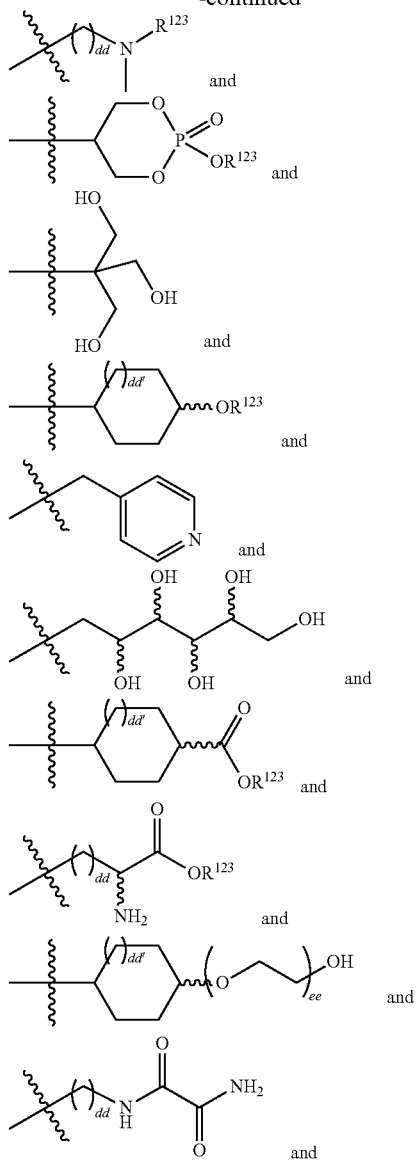
wherein dd' is selected from 0 and 1, each $R^{123}$ is independently selected from H and methyl, $X^{13}$ is selected from O, S, and $NR^{f1}$, $R^{f1}$ and $R^{e1}$ are independently selected from H and $C_{1-3}$ alkyl, dd is 1 or 2 or 3 or 4 or 5, and ee is 1 or 2 or 3 or 4 or 5 or 6 or 7 or 8.
In another embodiment, $R^{115}$ is methyl and $R^{116}$ is selected from H, methyl, ethyl, isopropyl, tert-butyl, phenyl, $(CH_2CH_2O)_{ee}CH_2CH_2X^{13}R^{e1}$,
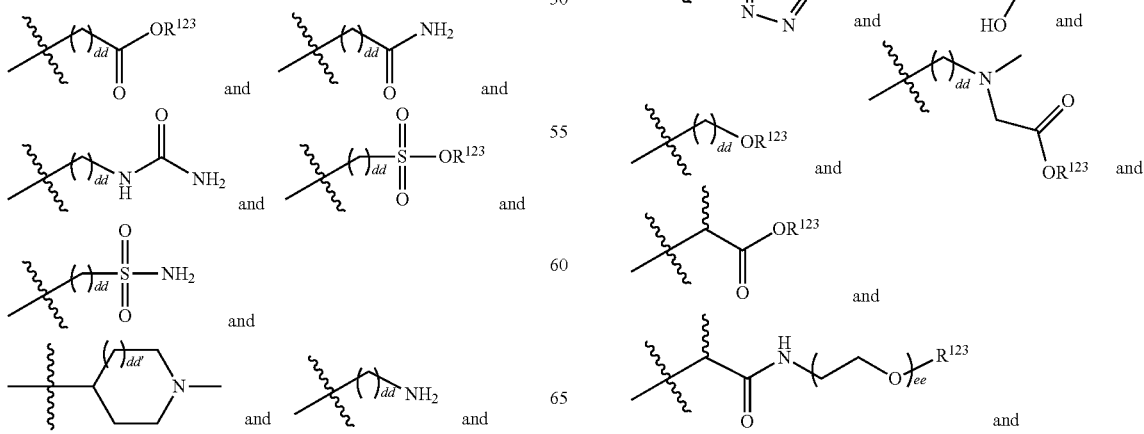

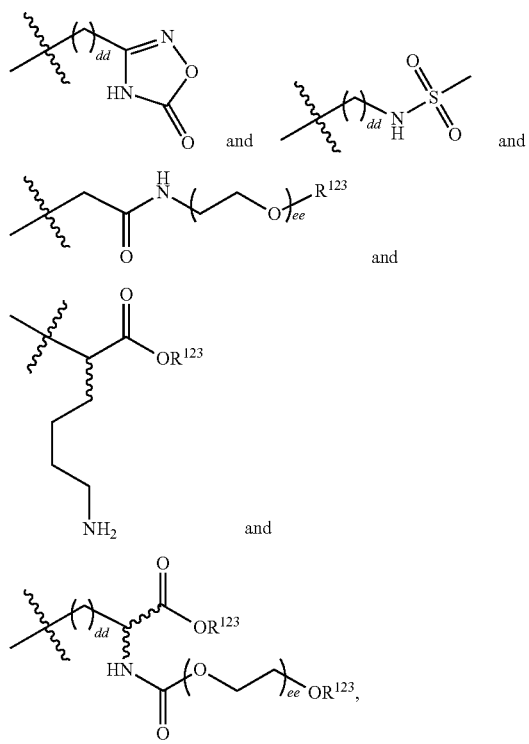
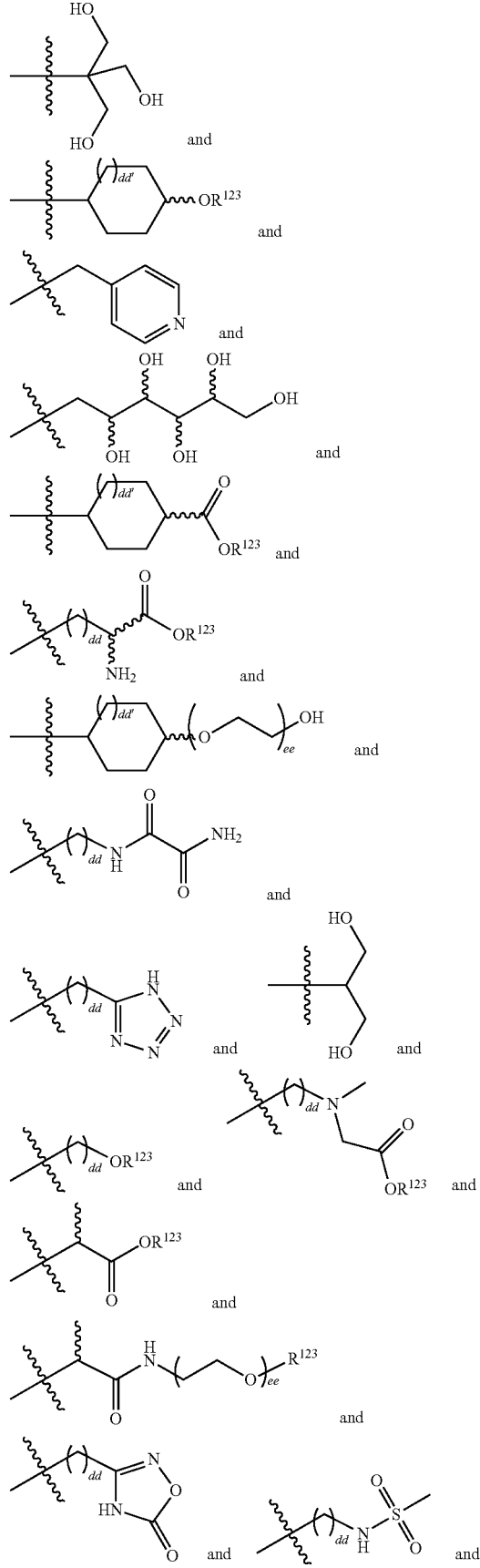
wherein dd is selected from 0 to 10, dd' is selected from 0 and 1, each $R^{123}$ is independently selected from H and methyl, $X^{13}$ is selected from O, S, and $NR^{f1}$, and $R^{f1}$ and $R^{e1}$ are independently selected from H and $C_{1-3}$ alkyl, and ee is selected from 1 to 1000.
In another embodiment, $R^{115}$ is methyl and $R^{116}$ is selected from ethyl, isopropyl, tert-butyl, phenyl, $(CH_2CH_2O)_{ee}CH_2CH_2X^{13}R^{e1}$,
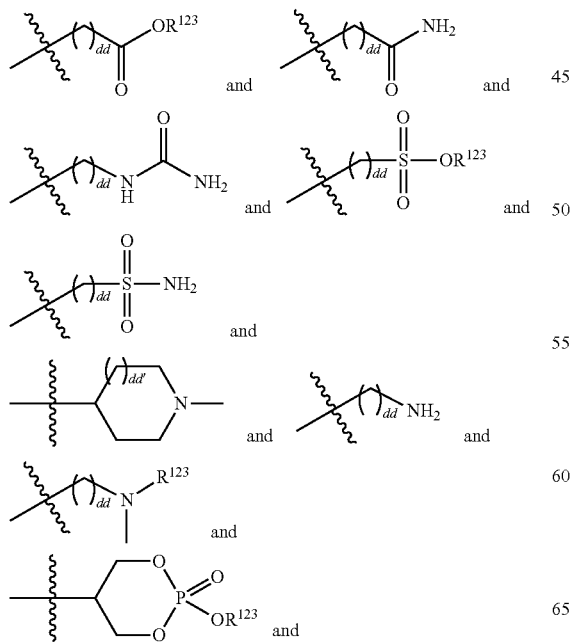

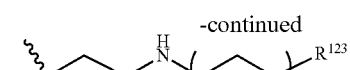

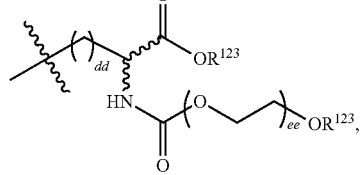

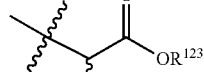

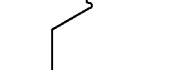

wherein dd is selected from 0 to 10, dd' is selected from 0 and 1, each $R^{123}$ is independently selected from H and methyl, $X^{13}$ is selected from O, S, and $NR^{f1}$, and $R^{f1}$ and $R^{e1}$ are independently selected from H and $C_{1-3}$ alkyl, and ee is selected from 1 to 1000.

In yet another embodiment, $R^{116}$ is methyl and $R^{115}$ is selected from H, methyl, ethyl, isopropyl, tert-butyl, phenyl, $(CH_2CH_2O)_{ee}CH_2CH_2X^{13}R^{e1}$,

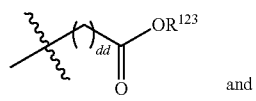 and 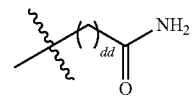 and

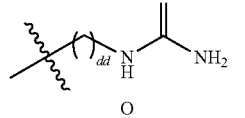 and 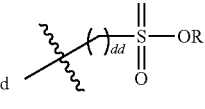 and

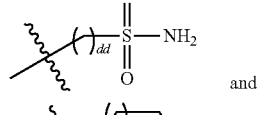 and

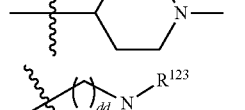 and  and

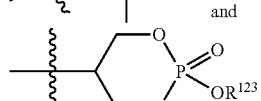 and

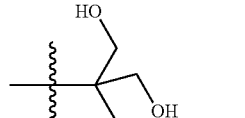 and

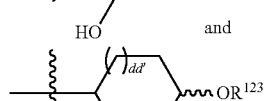 and

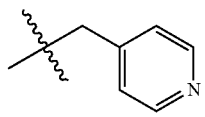 and

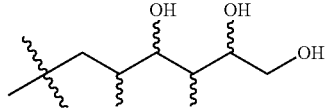 and

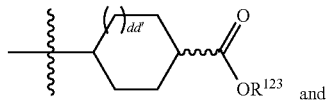 and

 and

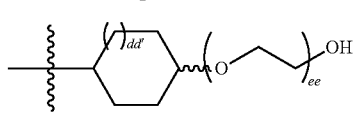 and

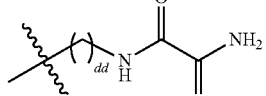 and 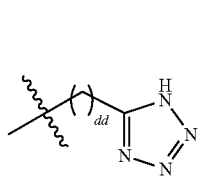 and

 and 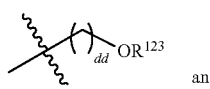 and

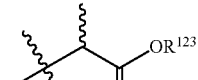 and

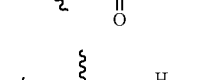 and

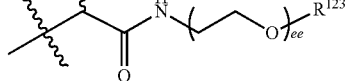 and

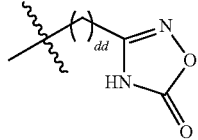 and

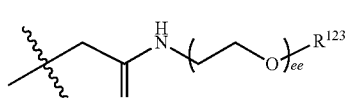 and

-continued

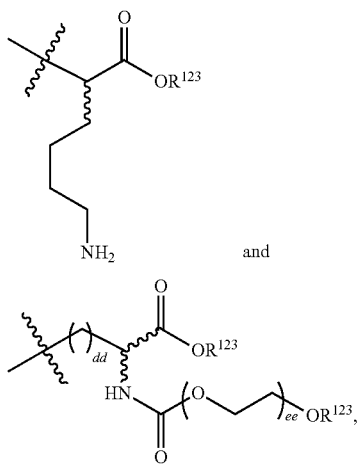

and wherein dd is selected from 0 to 10, dd' is selected from 0 and 1, each $R^{123}$ is independently selected from H and methyl, $X^{13}$ is selected from O, S, and $NR^{f1}$, and $R^{f1}$ and $R^{e1}$ are independently selected from H and $C_{1-3}$ alkyl, and ee is selected from 1 to 1000.

In yet a further embodiment, $R^{115}$ and $R^{116}$ are independently selected from H, methyl, ethyl, isopropyl, tert-butyl, phenyl,

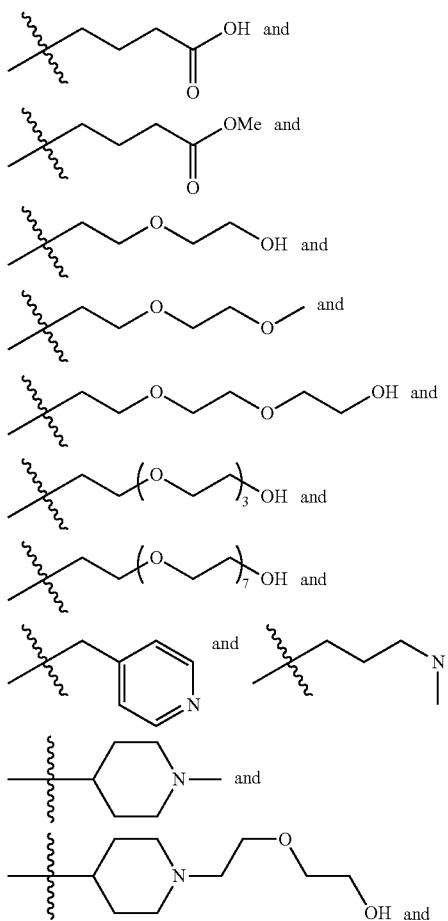

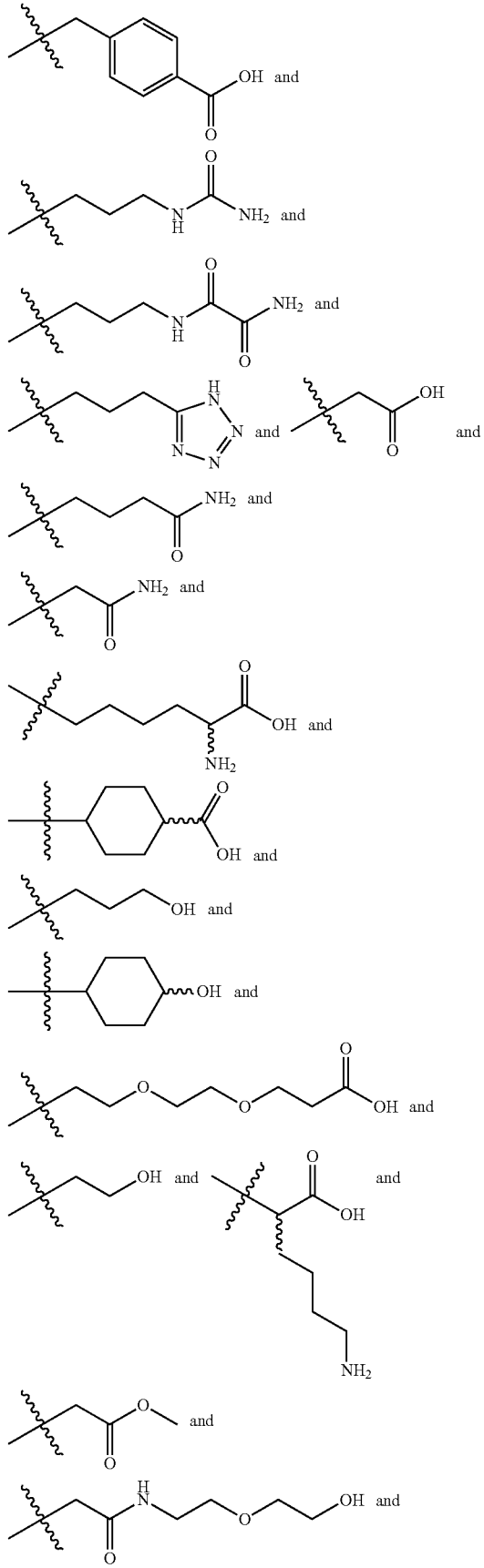

In yet a further embodiment, $R^{115}$ and $R^{116}$ are independently selected from H, methyl, ethyl, isopropyl, tert-butyl phenyl

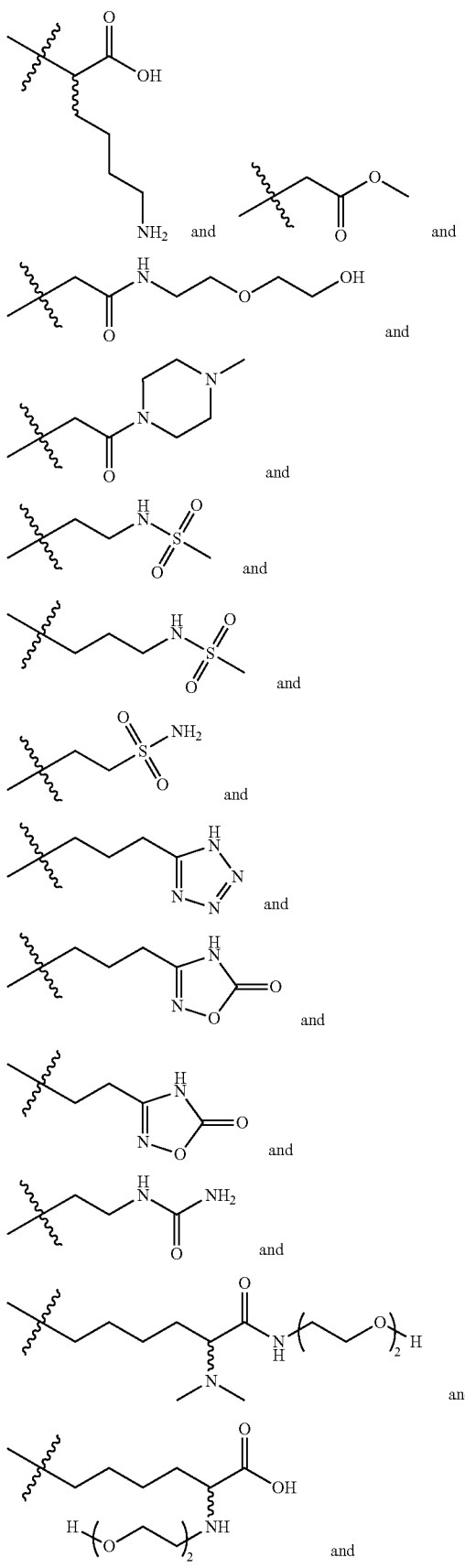
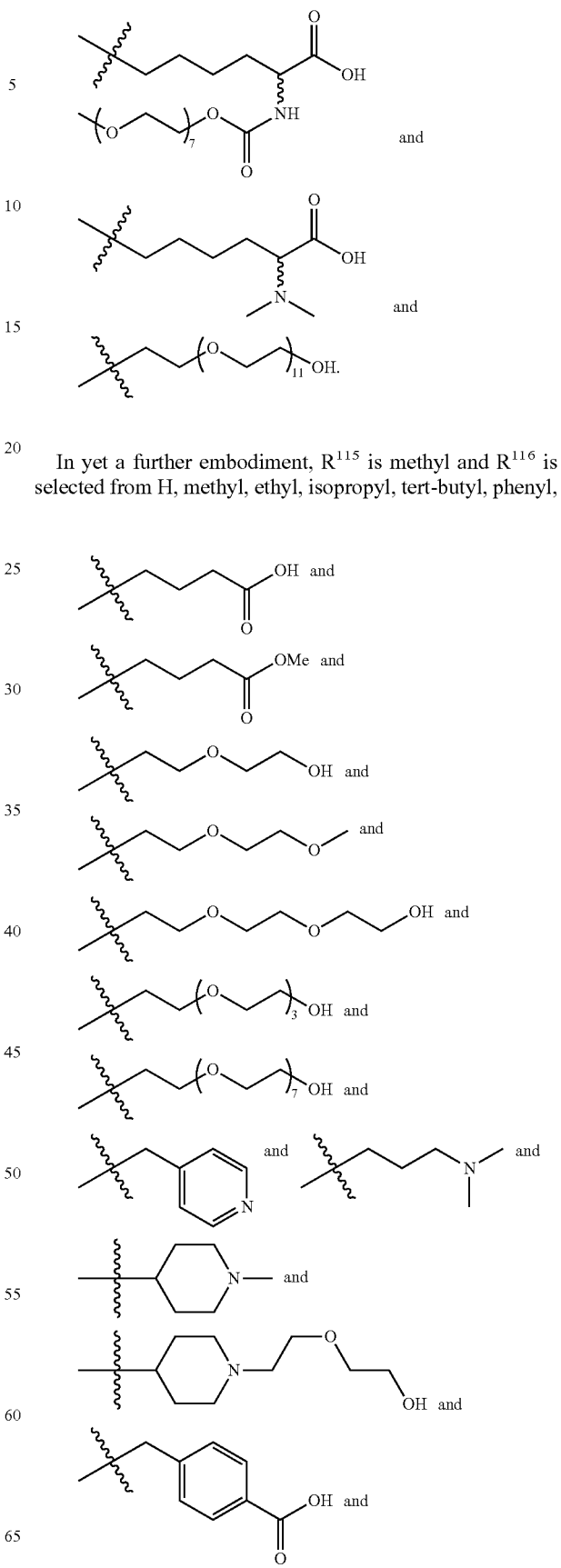
In yet a further embodiment, $R^{115}$ is methyl and $R^{116}$ is selected from H, methyl, ethyl, isopropyl, tert-butyl, phenyl, -continued
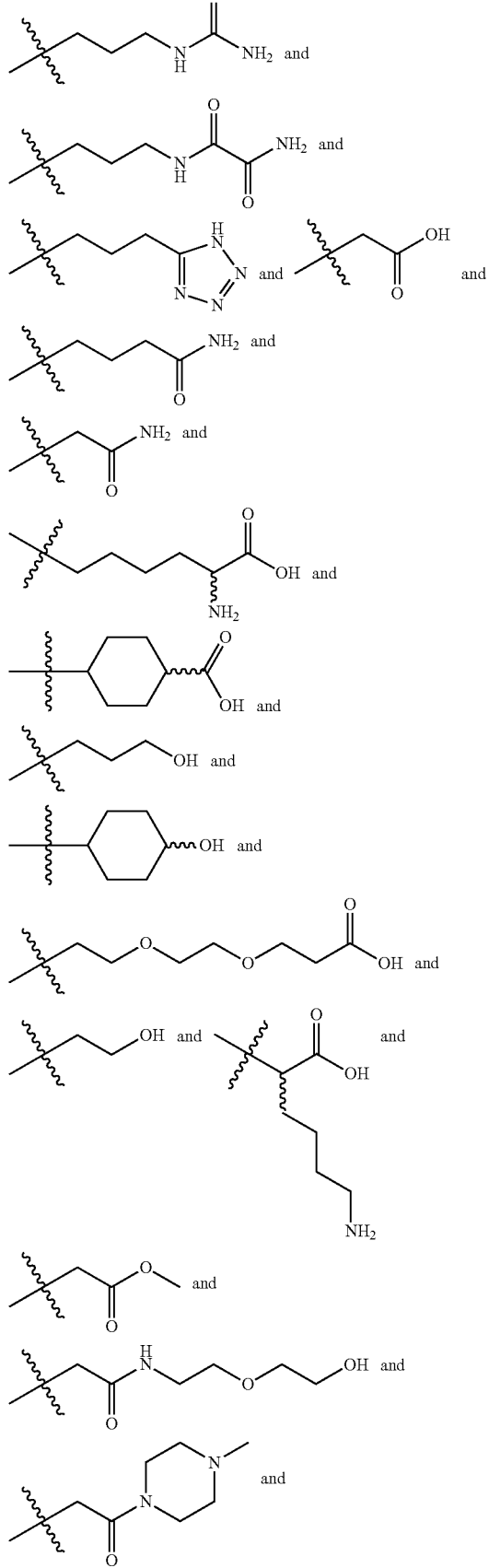
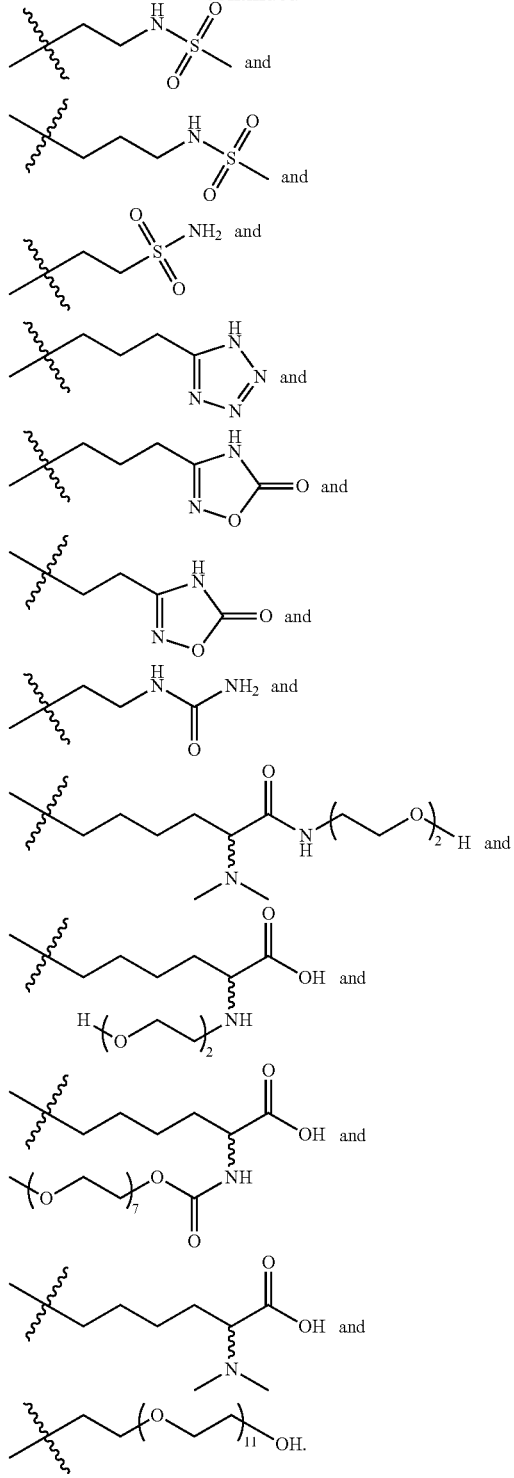
In yet a further embodiment, $R^{116}$ is methyl and $R^{115}$ is selected from H, methyl, ethyl, isopropyl, tert-butyl, phenyl,
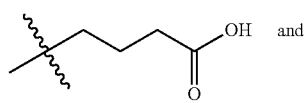

311
-continued
312
-continued
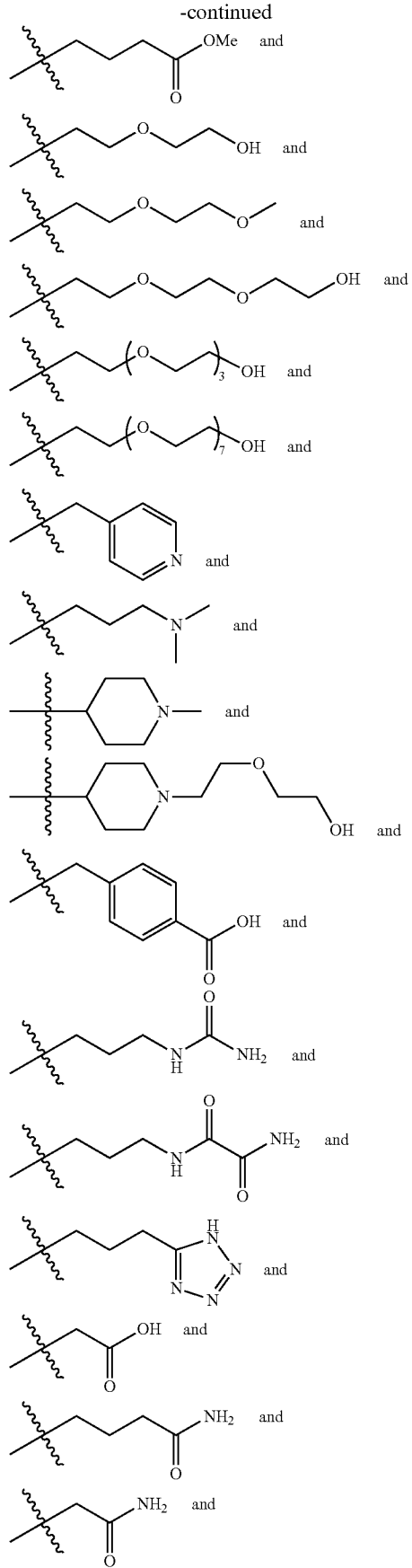
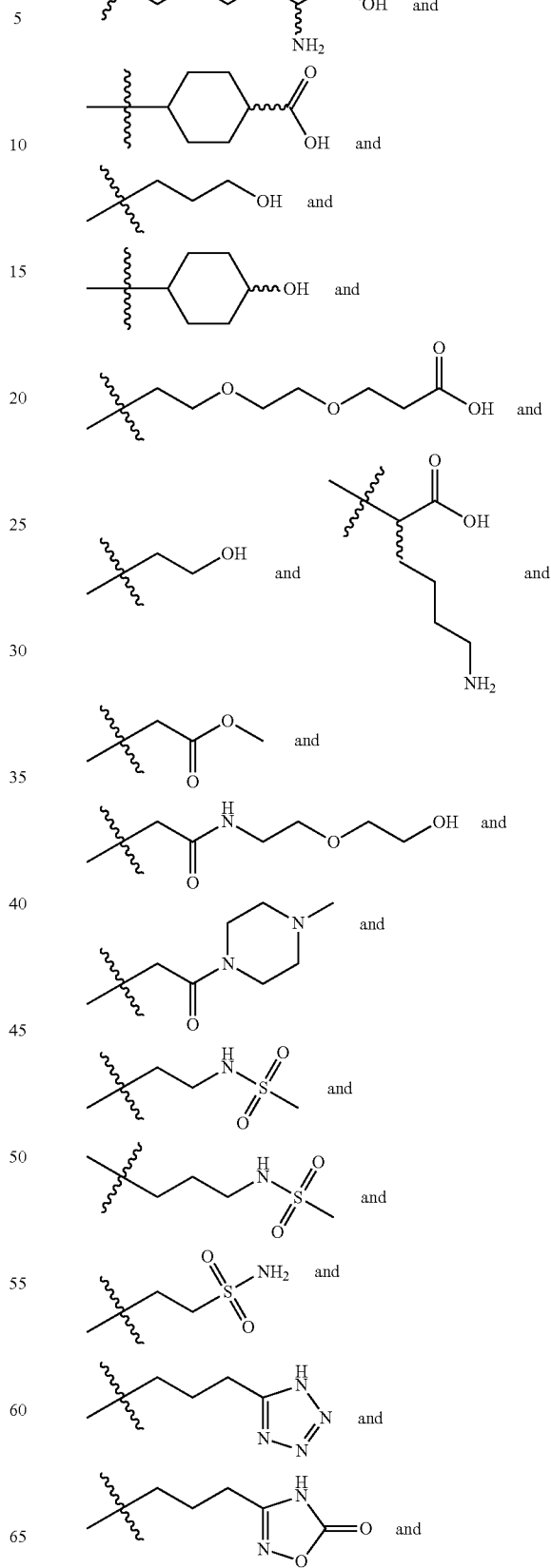

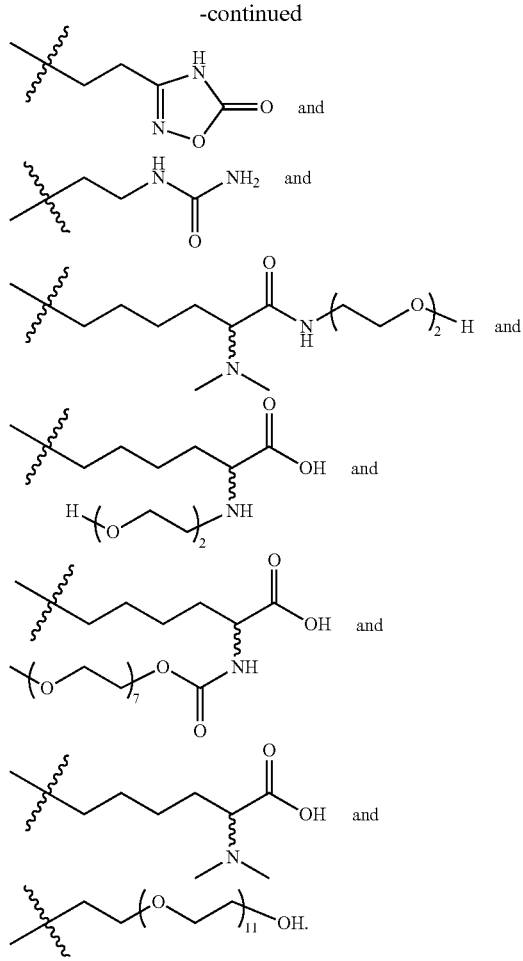

In yet another embodiment, $R^{115}$ or $R^{116}$ is joined with one of $R^{117}$, $R^{118}$, $R^{119}$, $R^{120}$, $R^{121}$, and $R^{122}$ to form a saturated or unsaturated ring. In a further embodiment, $R^{115}$ or $R^{116}$ is joined with one of $R^{117}$, $R^{118}$, $R^{119}$, $R^{120}$, $R^{121}$, and $R^{122}$ to form a saturated or unsaturated 5- or 6-membered ring. In yet a further embodiment, $R^{115}$ is joined with one of $R^{117}$, $R^{118}$, $R^{119}$, $R^{120}$, $R^{121}$, and $R^{122}$ to form a saturated or unsaturated 5- or 6-membered ring. In yet a further embodiment, $R^{116}$ is joined with one of $R^{117}$, $R^{118}$, $R^{119}$, $R^{120}$, $R^{121}$, and $R^{122}$ to form a saturated or unsaturated 5- or 6-membered ring.

In another embodiment, two of $R^{117}$, $R^{118}$, $R^{119}$, $R^{120}$, $R^{121}$, and $R^{122}$ are joined to form a saturated or unsaturated ring. In yet another embodiment, two of $R^{117}$, $R^{118}$, $R^{119}$, $R^{120}$, $R^{121}$, and $R^{122}$ not being connected to the same carbon atom are joined to form a saturated or unsaturated 5- or 6-membered ring.

In one embodiment, the cyclization spacer A is selected from

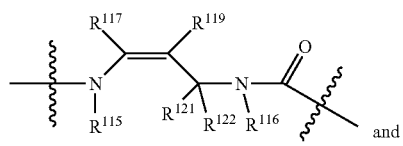

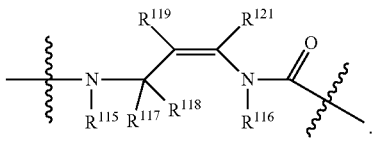

In a further embodiment, the cyclization spacer A is selected from

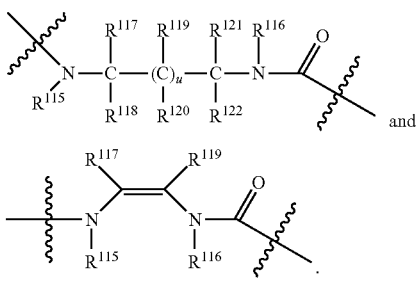

In a further embodiment, the cyclization spacer A is selected from

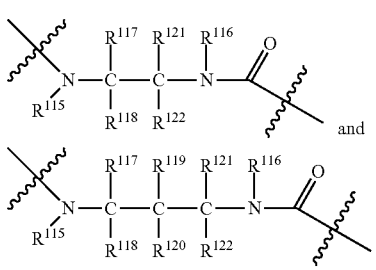

In a further embodiment, the cyclization spacer A is

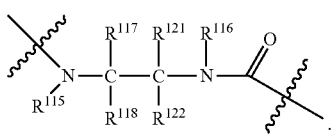

In a further embodiment, the cyclization spacer A is selected from

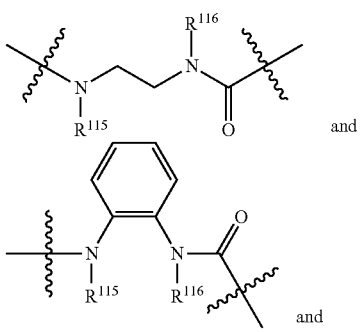

-continued
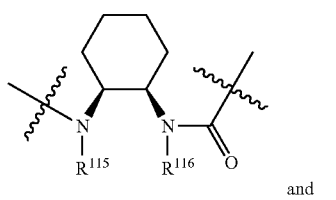
and
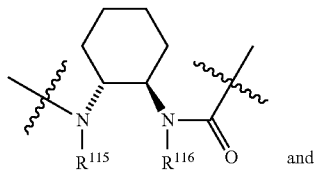
and
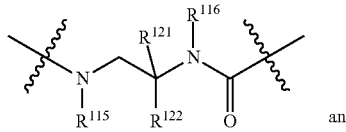
and
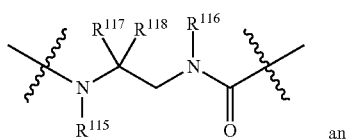
and
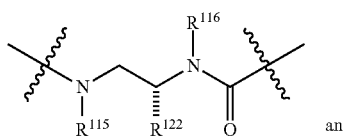
and
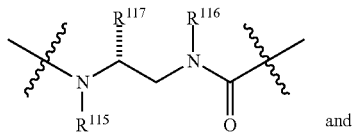
and
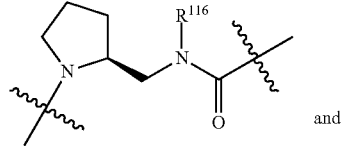
and
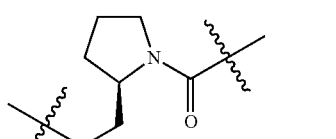
and
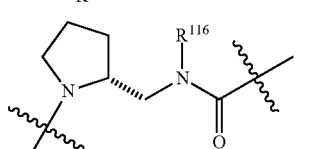
and
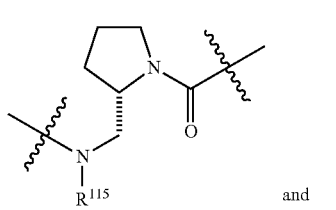
and
-continued
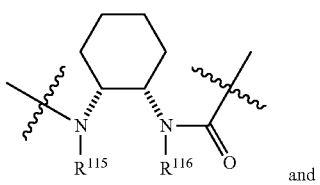
and
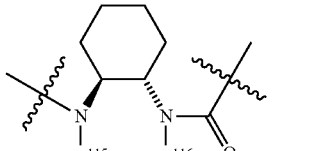
and
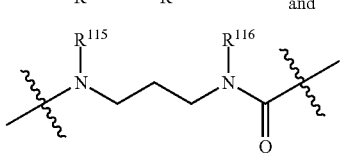
and
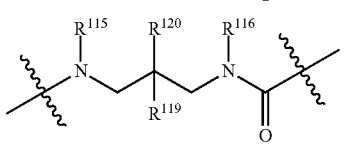
and
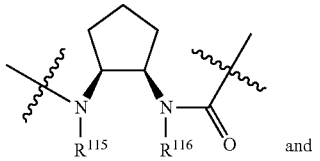
and
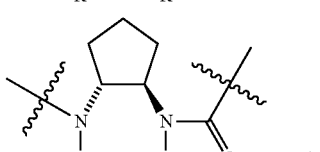
and
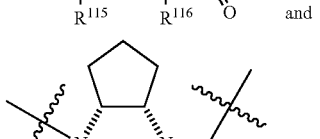
and
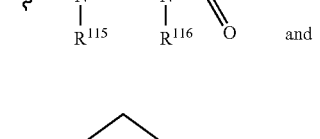
and
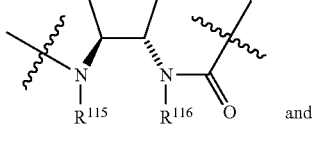
and
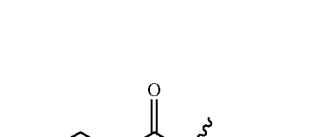
and
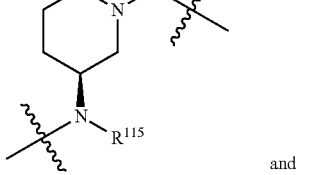
and 317
-continued

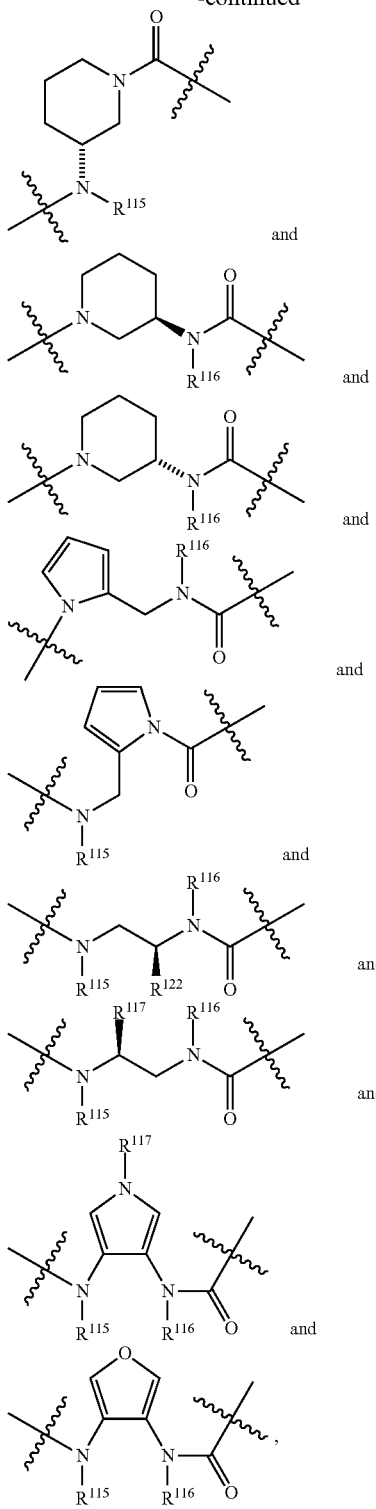

wherein $R^{115}$, $R^{116}$, $R^{117}$, $R^{118}$, $R^{119}$, $R^{120}$, $R^{121}$, and $R^{122}$ are independently selected from H, OH, SH, $NH_2$, $N_3$, $NO_2$, NO, $CF_3$, CN, $C(O)NH_2$, $C(O)H$, $C(O)OH$, halogen, $R^z$, $SR^z$, $S(O)R^z$, $S(O)_2R^z$, $S(O)OR^z$, $S(O)_2OR^z$, $OS(O)R^z$, $OS(O)_2R^z$, $OS(O)OR^z$, $OS(O)_2OR^z$, $OR^z$, $NHR^z$, $N(R^z)R^{z1}$, $N(R^z)(R^{z1})R^{z2}$, $P(O)(OR^z)(OR^{z1})$, $OP(O)(OR^z)(OR^{z1})$, $C(O)R^z$, $C(O)OR^z$, $C(O)N(R^{z1})R^z$, $OC(O)R^z$, $OC(O)OR^z$, $OC(O)N(R^z)R^{z1}$, $N(R^{z1})C(O)R^z$, $N(R^{z1})C(O)OR^z$, and $N(R^{z1})C(O)$

318

$N(R^{z2})R^z$, wherein $R^z$, $R^{z1}$, and $R^{z2}$ are independently selected from H and optionally substituted $(CH_2CH_2O)_{ee}CH_2CH_2X^{13}R^{e1}$, $C_{1-20}$ alkyl, $C_{1-20}$ heteroalkyl, $C_{3-20}$ cycloalkyl, $C_{1-20}$ heterocycloalkyl, $C_{5-20}$ aryl, or $C_{1-20}$ heteroaryl, wherein ee is selected from 1 to 1000, $X^{13}$ is selected from O, S, and $NR^{f1}$, and $R^{f1}$ and $R^{e1}$ are independently selected from H and $C_{1-3}$ alkyl, two or more of $R^z$, $R^{z1}$, and $R^{z2}$ optionally being joined by one or more bonds to form one or more optionally substituted carbocycles and/or heterocycles, two or more of the substituents $R^{115}$, $R^{116}$, $R^{117}$, $R^{118}$, $R^{119}$, $R^{120}$, $R^{121}$, and $R^{122}$ optionally being joined by one or more bonds to form one or more optionally substituted carbocycles and/or heterocycles.

In yet a further embodiment, the cyclization spacer A is selected from

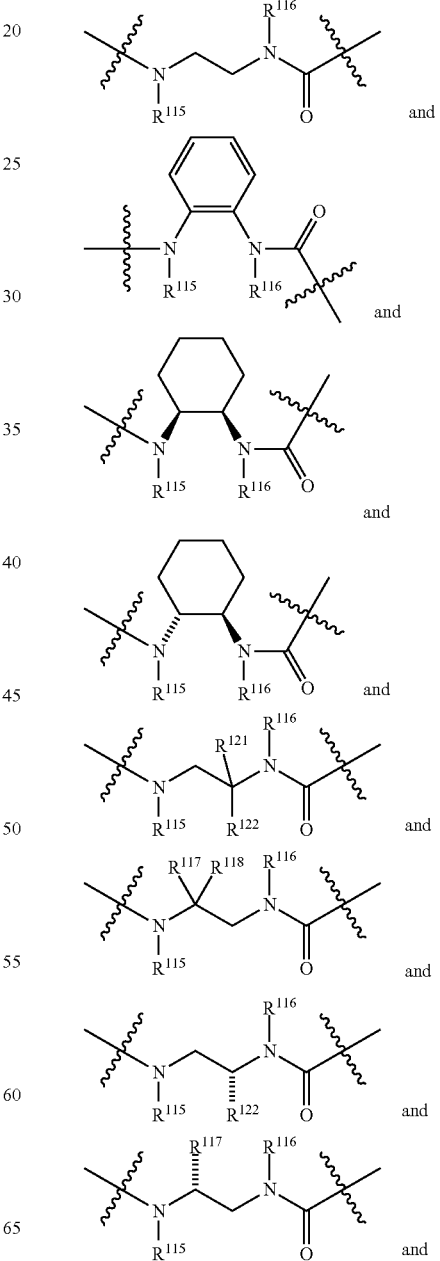

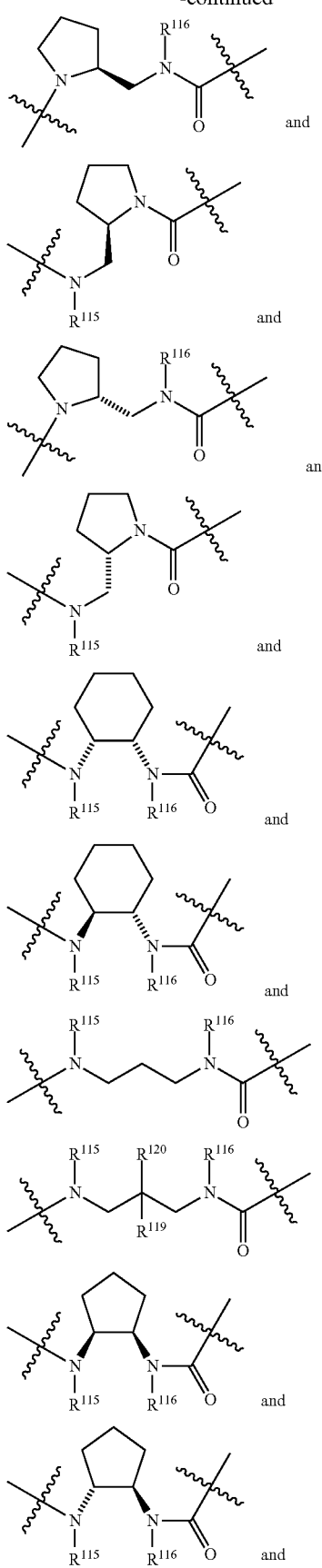

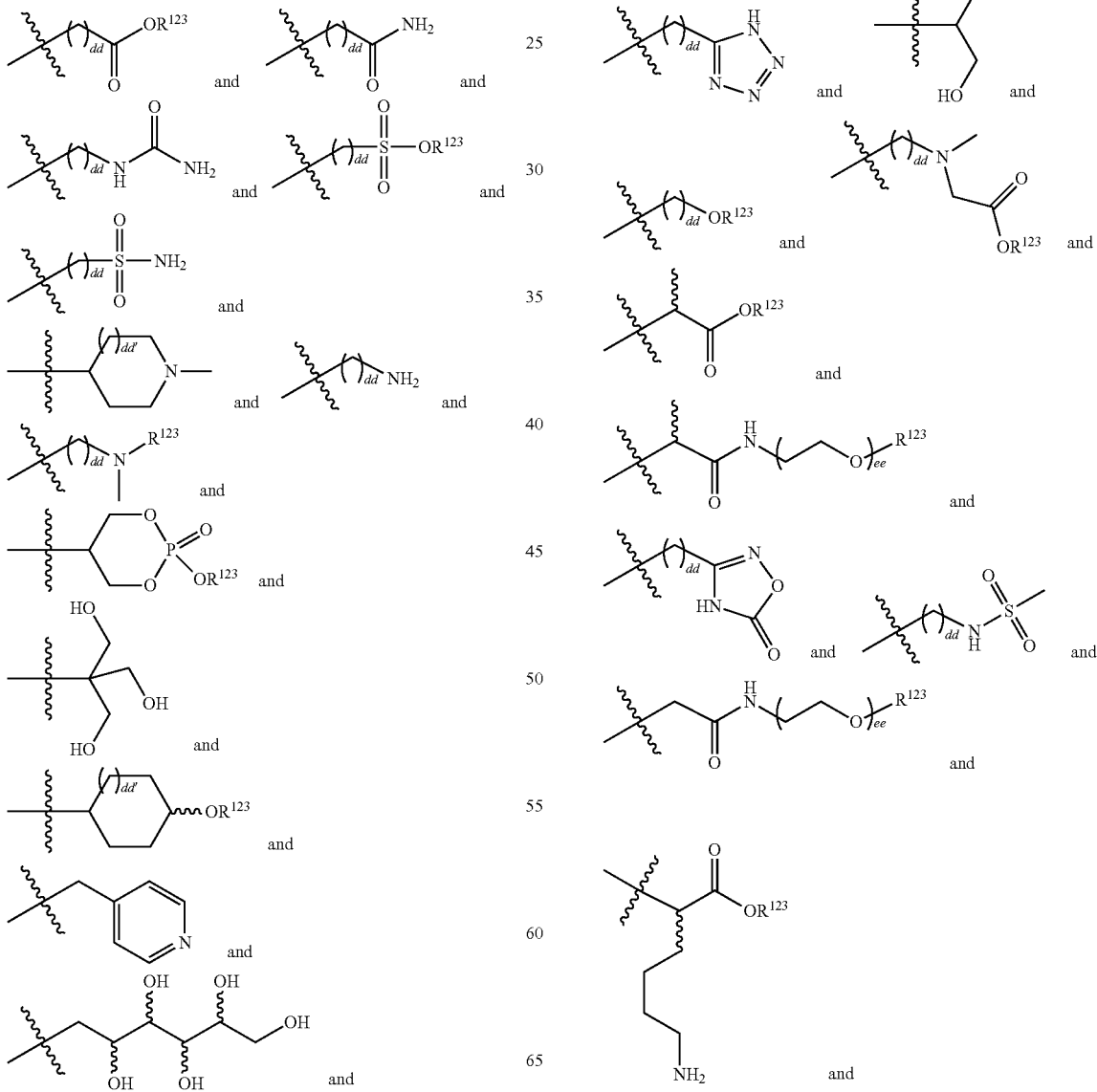
wherein $R^{115}$ and $R^{116}$ are independently selected from H, methyl, ethyl, isopropyl, tert-butyl, phenyl, $(CH_2CH_2O)_{ee}CH_2CH_2X^{13}R^{e1}$, -continued

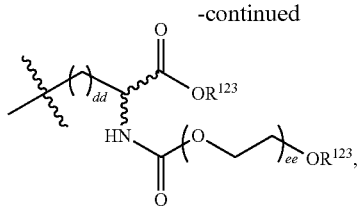

wherein dd is selected from 0 to 10, dd' is selected from 0 and 1, each $R^{123}$ is independently selected from H and methyl, ee is selected from 1 to 1000, $X^{13}$ is selected from O, S, and $NR^{f1}$, and $R^{f1}$ and $R^{e1}$ are independently selected from H and $C_{1-3}$ alkyl, and wherein $R^{117}$, $R^{118}$, $R^{119}$, $R^{120}$, $R^{121}$, and $R^{122}$ are independently selected from H, OH, SH, $NH_2$, $N_3$, $NO_2$, NO, $CF_3$, CN, $C(O)NH_2$, C(O)H, C(O)OH, halogen, $R^z$, $SR^z$, $S(O)R^z$, $S(O)_2R^z$, $S(O)OR^z$, $S(O)_2OR^z$, $OS(O)R^z$, $OS(O)_2R^z$, $OS(O)OR^z$, $OS(O)_2OR^z$, $OR^z$, $NHR^z$, $N(R^z)R^{z1}$, $^+N(R^z)(R^{z1})R^{z2}$, $P(O)(OR^z)(OR^{z1})$, $OP(O)(OR^z)(OR^{z1})$, $C(O)R^z$, $C(O)OR^z$, $C(O)N(R^{z1})R^z$, $OC(O)R^z$, $OC(O)OR^z$, $OC(O)N(R^z)R^{z1}$, $N(R^{z1})C(O)R^z$, $N(R^{z1})C(O)OR^z$, and $N(R^{z1})C(O)N(R^{z2})R^z$, wherein $R^z$, $R^{z1}$, and $R^{z2}$ are independently selected from H and optionally substituted $(CH_2CH_2O)_{ee}CH_2CH_2X^{13}R^{e1}$, $C_{1-20}$ alkyl, $C_{1-20}$ heteroalkyl, $C_{3-20}$ cycloalkyl, $C_{1-20}$ heterocycloalkyl, $C_{5-20}$ aryl, or $C_{1-20}$ heteroaryl, wherein ee is selected from 1 to 1000, $X^{13}$ is selected from O, S, and $NR^{f1}$, and $R^{f1}$ and $R^{e1}$ are independently selected from H and $C_{1-3}$ alkyl.

In yet a further embodiment the cyclization spacer A is selected from

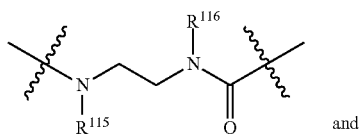

and

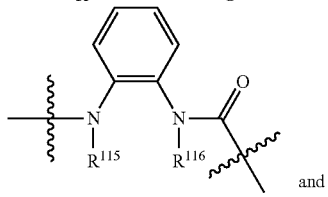

and

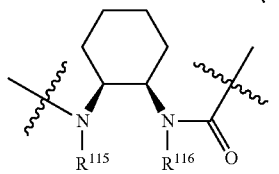

and

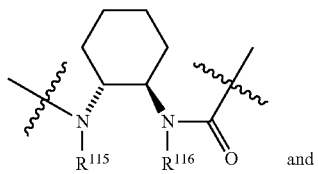

and

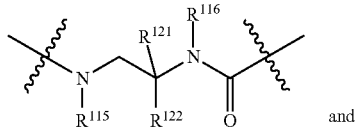

and

-continued

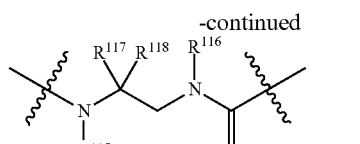

and

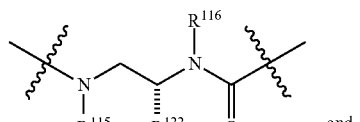

and

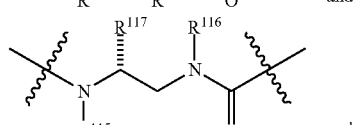

and

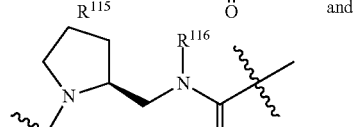

and

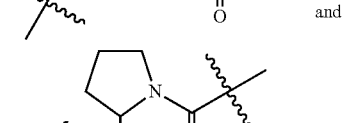

and

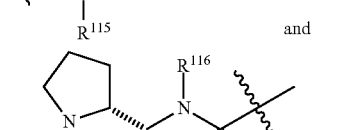

and

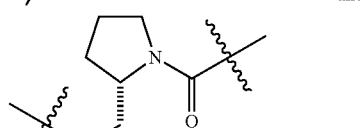

and

and

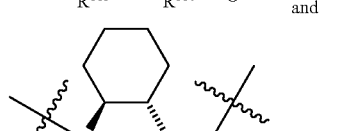

and

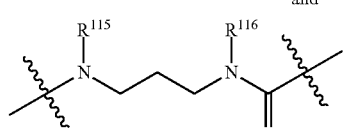

and

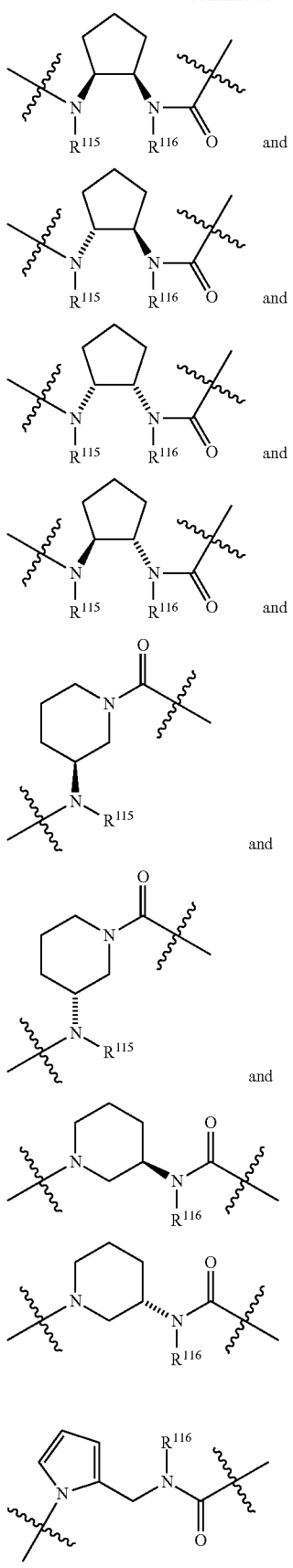
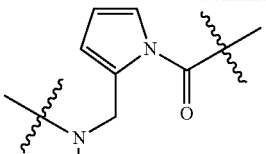
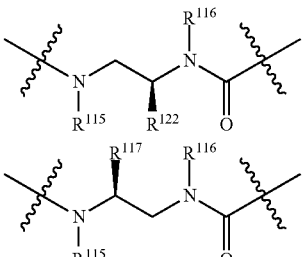
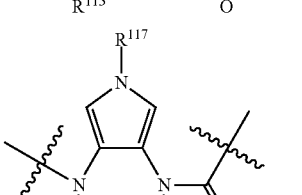
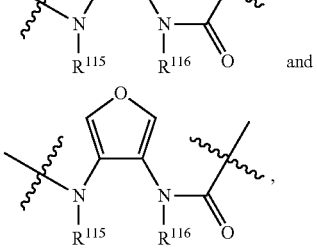
wherein $R^{115}$ and $R^{116}$ are independently selected from H, methyl, ethyl, isopropyl, tert-butyl, phenyl,
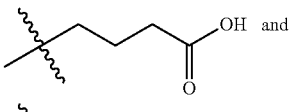
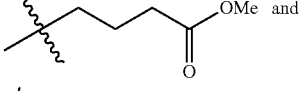
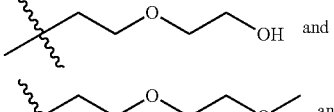
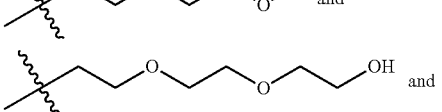
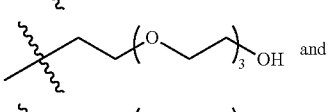
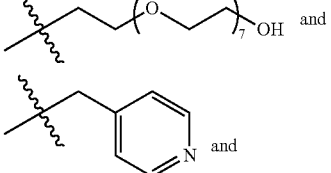

327
-continued
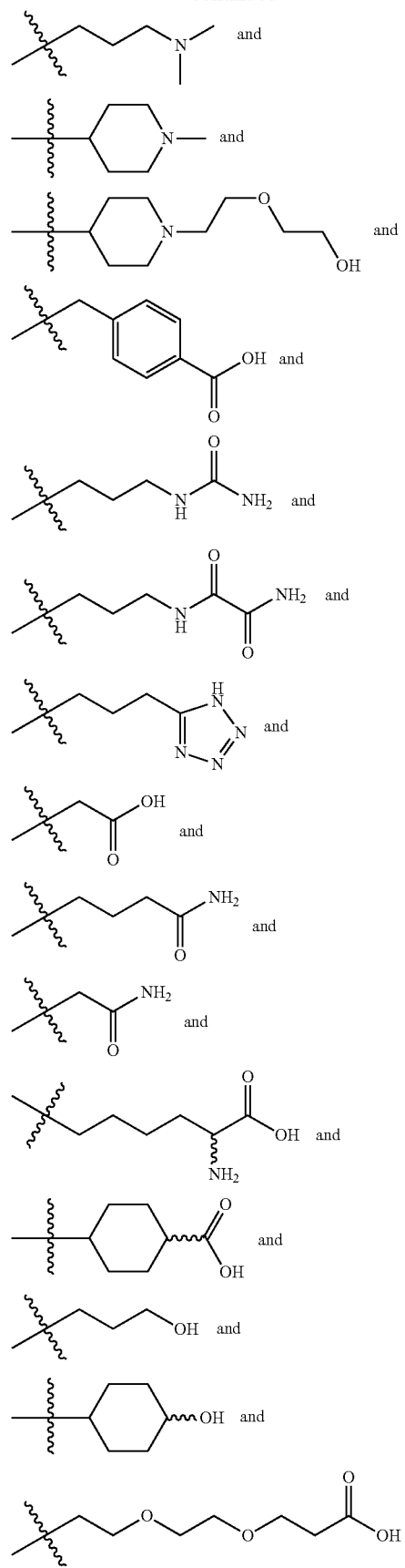
328
-continued
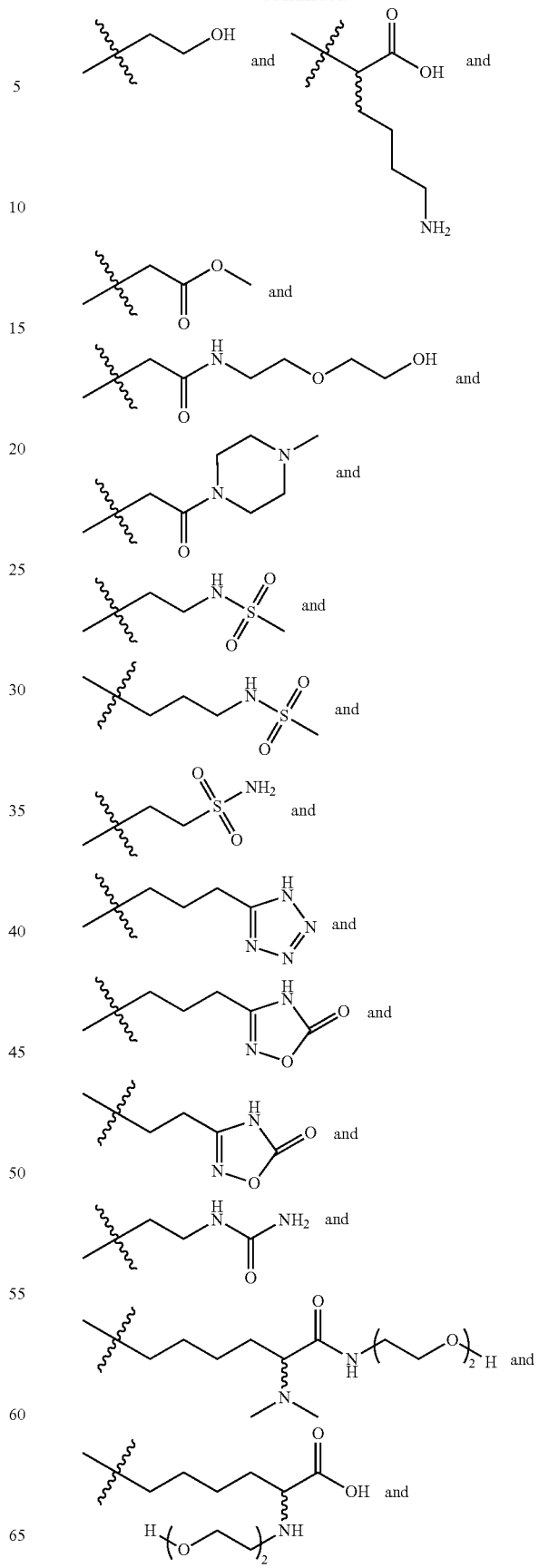

-continued

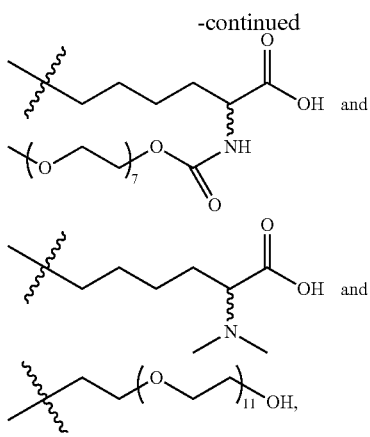

and wherein $R^{117}$, $R^{118}$, $R^{119}$, $R^{120}$, $R^{121}$, and $R^{122}$ are independently selected from H, OH, SH, $NH_2$, $N_3$, $NO_2$, NO, $CF_3$, CN, $C(O)NH_2$, C(O)H, C(O)OH, halogen, $R^z$, $SR^z$, $S(O)R^z$, $S(O)_2R^z$, $S(O)OR$, $S(O)_2OR^z$, $OS(O)R^z$, $OS(O)_2R^z$, $OS(O)OR^z$, $OS(O)_2OR^z$, $OR^z$, $NHR^z$, $N(R^z)R^{z1}$, $^+N(R^z)(R^{z1})R^{z2}$, $P(O)(OR^z)(OR^{z1})$, $OP(O)(OR^z)(OR^{z1})$, $C(O)R^z$, $C(O)OR^z$, $C(O)N(R^{z1})R^z$, $OC(O)R^z$, $OC(O)OR^z$, $OC(O)N(R^z)R^{z1}$, $N(R^{z1})C(O)R^z$, $N(R^{z1})C(O)OR^z$, and $N(R^{z1})C(O)N(R^{z2})R^z$, wherein $R^z$, $R^{z1}$, and $R^{z2}$ are independently selected from H and optionally substituted $(CH_2CH_2O)_{ee}CH_2CH_2X^{13}R^{e1}$, $C_{1-20}$ alkyl, $C_{1-20}$ heteroalkyl, $C_{3-20}$ cycloalkyl, $C_{1-20}$ heterocycloalkyl, $C_{5-20}$ aryl, or $C_{1-20}$ heteroaryl, wherein ee is selected from 1 to 1000, $X^{13}$ is selected from O, S, and $NR^{f1}$, and $R^{f1}$ and $R^{e1}$ are independently selected from H and $C_{1-3}$ alkyl.

In another embodiment, the cyclization spacer A is

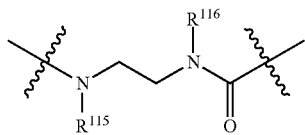

wherein $R^{115}$ and $R^{116}$ are independently selected from H, methyl, ethyl, isopropyl, tert-butyl, phenyl, $(CH_2CH_2O)_{ee}CH_2CH_2X^{13}R^{e1}$,

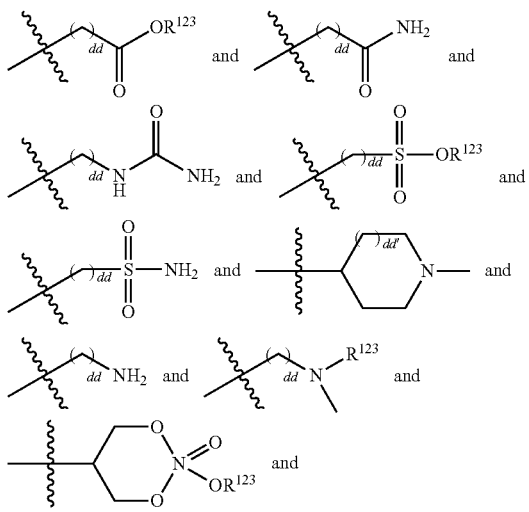

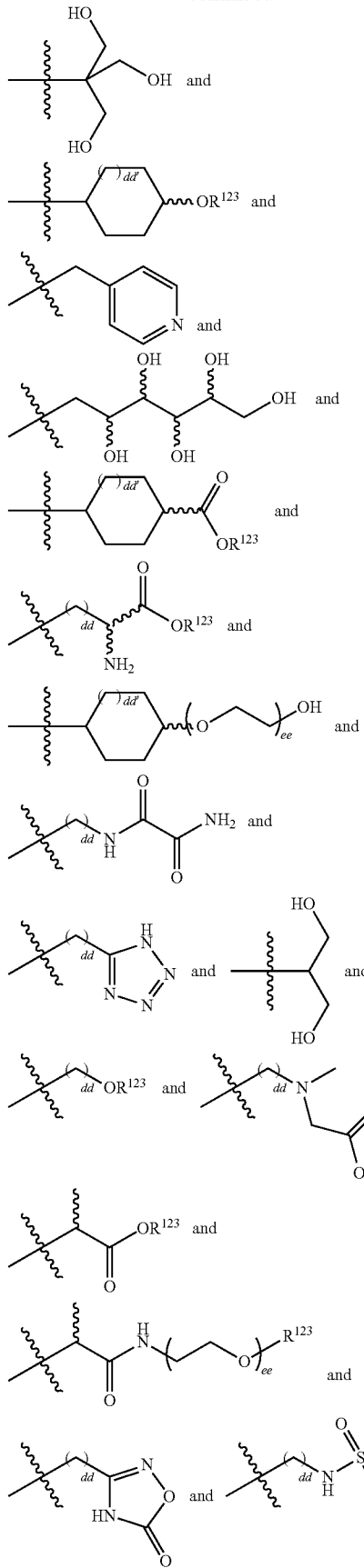

-continued

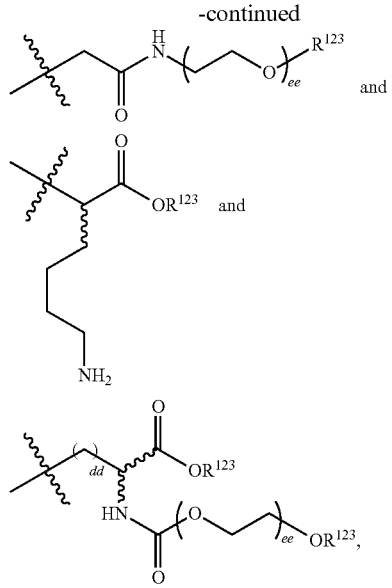
and

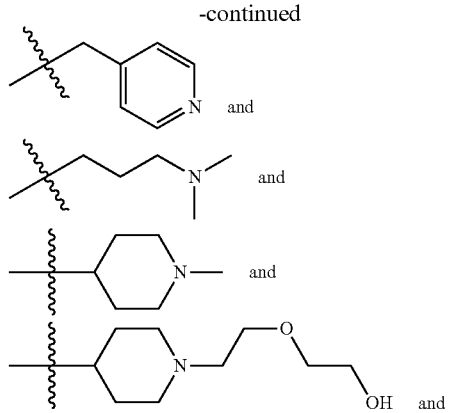
and wherein dd is selected from 0 to 10, dd' is selected from 0 and 1, each $R^{123}$ is independently selected from H and methyl, ee is selected from 1 to 1000, $X^{13}$ is selected from O, S, and $NR^{f1}$, and $R^{f1}$ and $R^{e1}$ are independently selected from H and $C_{1-3}$ alkyl.

In another embodiment, the cyclization spacer A is

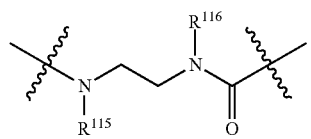

wherein $R^{115}$ and $R^{116}$ are independently selected from H, methyl, ethyl, isopropyl, tert-butyl, phenyl,

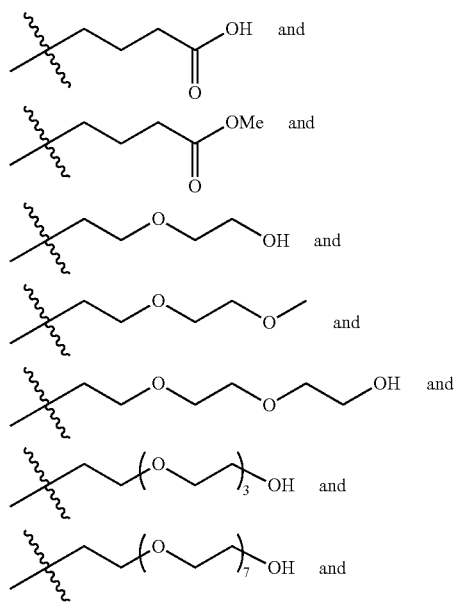

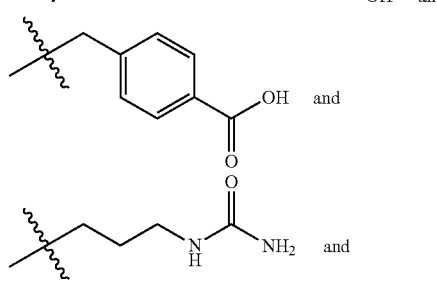
and

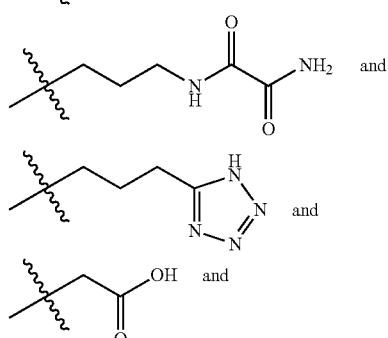
and

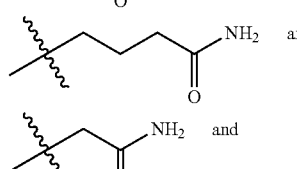
and

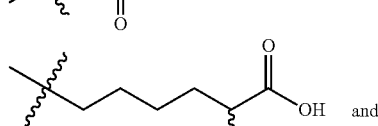
and

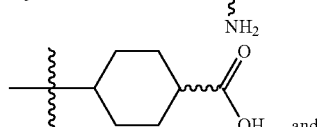
and

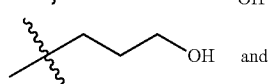
and

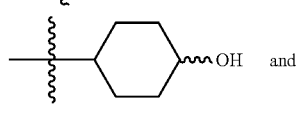
and

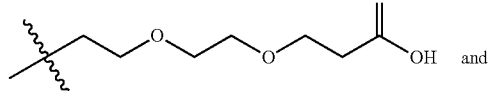
and

-continued
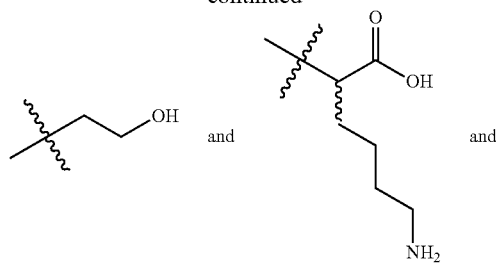 and
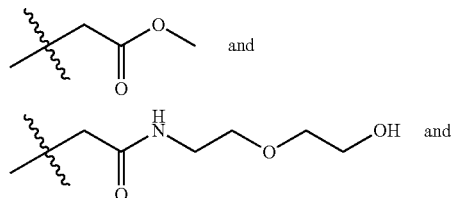 and
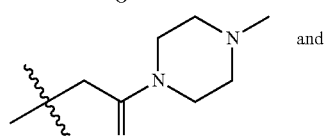 and
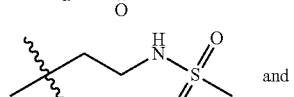 and
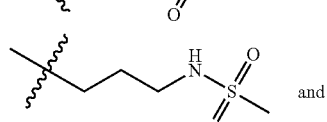 and
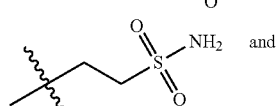 and
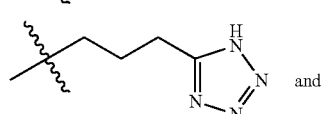 and
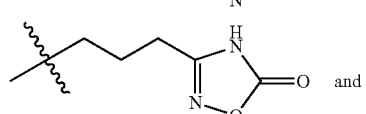 and
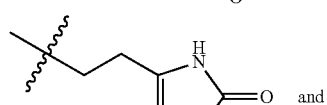 and
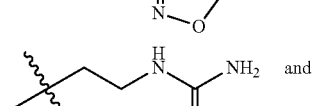 and
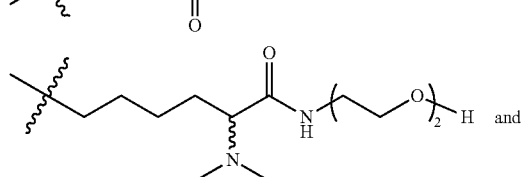 and
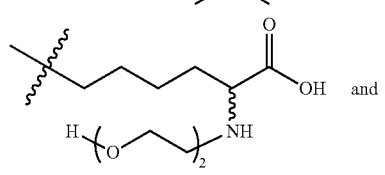
-continued
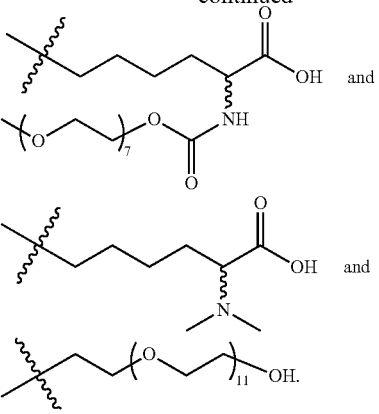
In another embodiment, the cyclization spacer A is
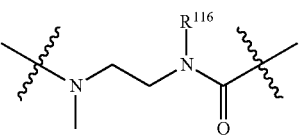
wherein $R^{116}$ is selected from methyl, ethyl, isopropyl, tert-butyl, phenyl,
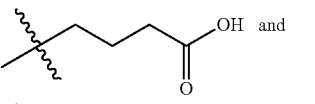 and
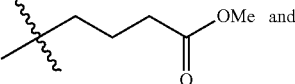 and
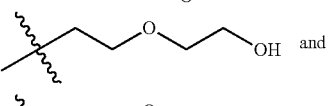 and
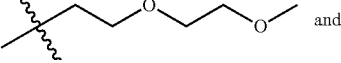 and
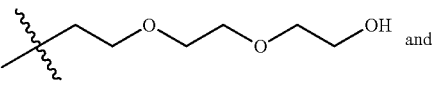 and
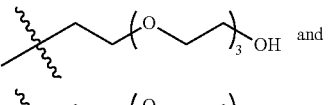 and
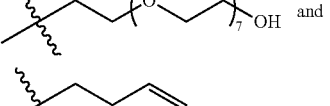 and
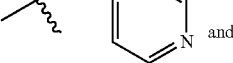 and
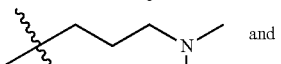 and
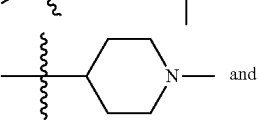 and 335
-continued
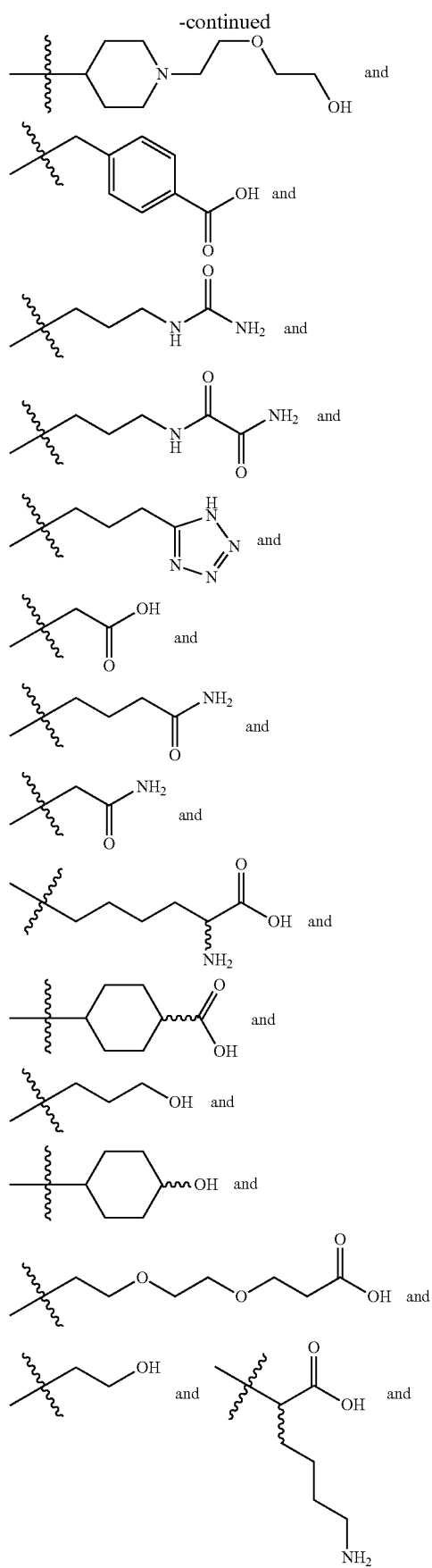
336
-continued
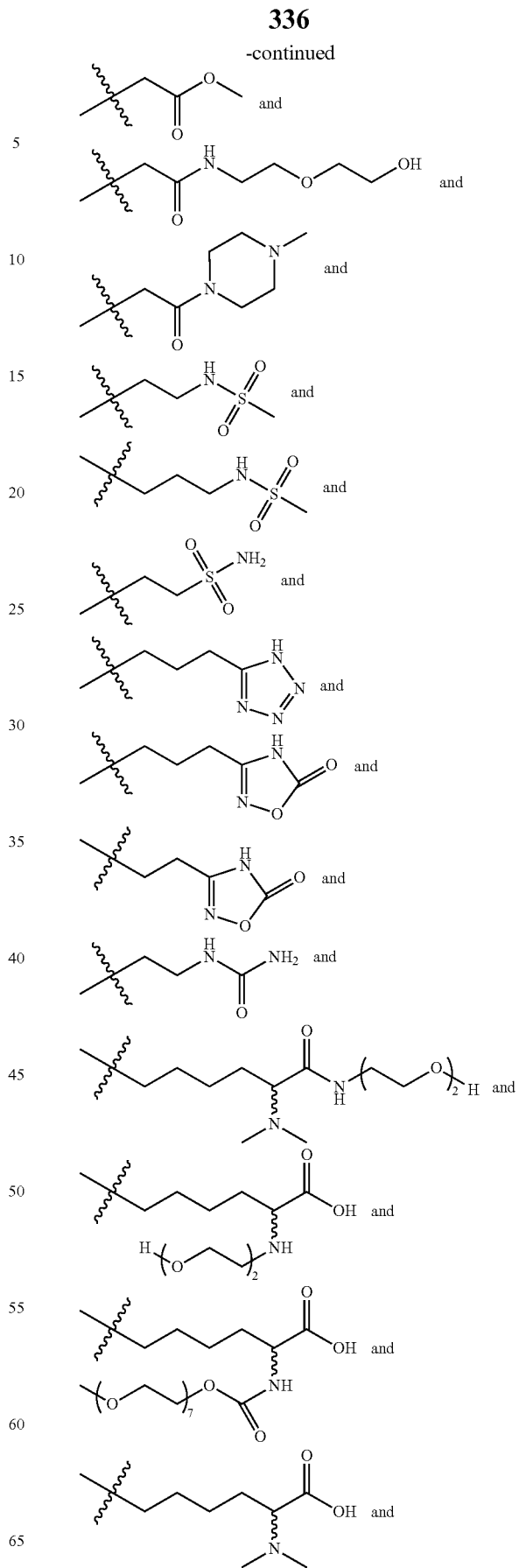

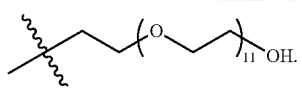
In another embodiment, the cyclization spacer A is
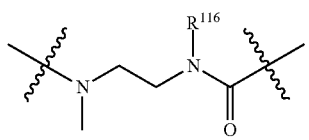
wherein $R^{116}$ is selected from ethyl, isopropyl, tert-butyl, phenyl,
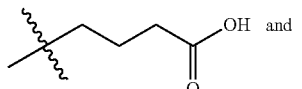
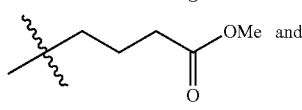
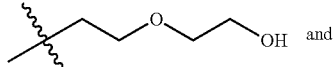
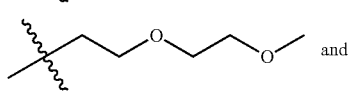
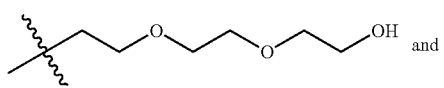
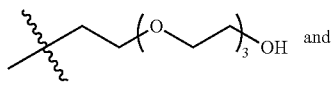
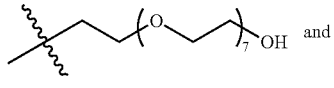
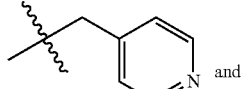
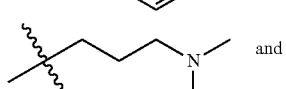
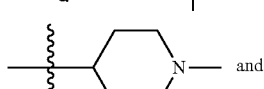
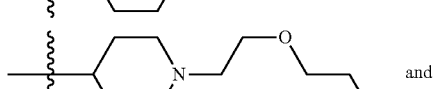
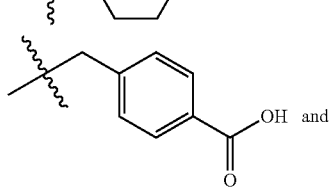
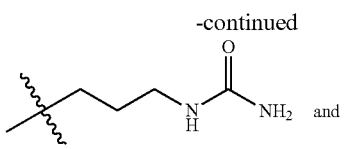
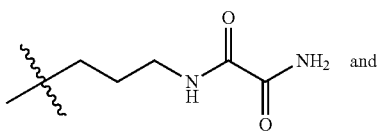
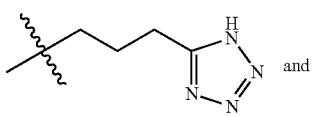
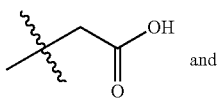
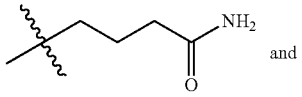
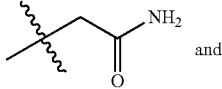
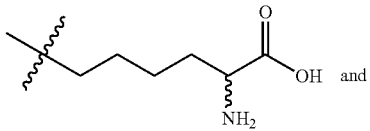
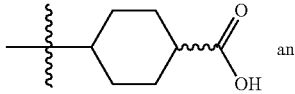
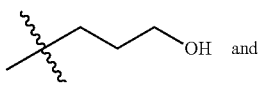
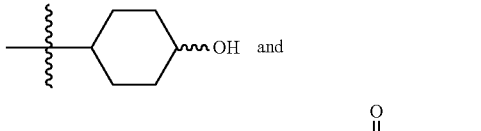
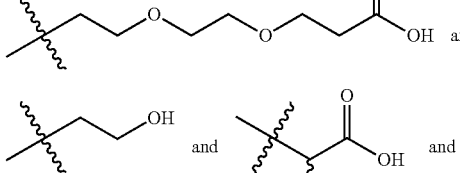
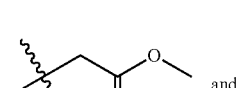
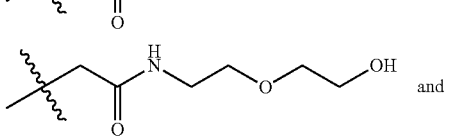

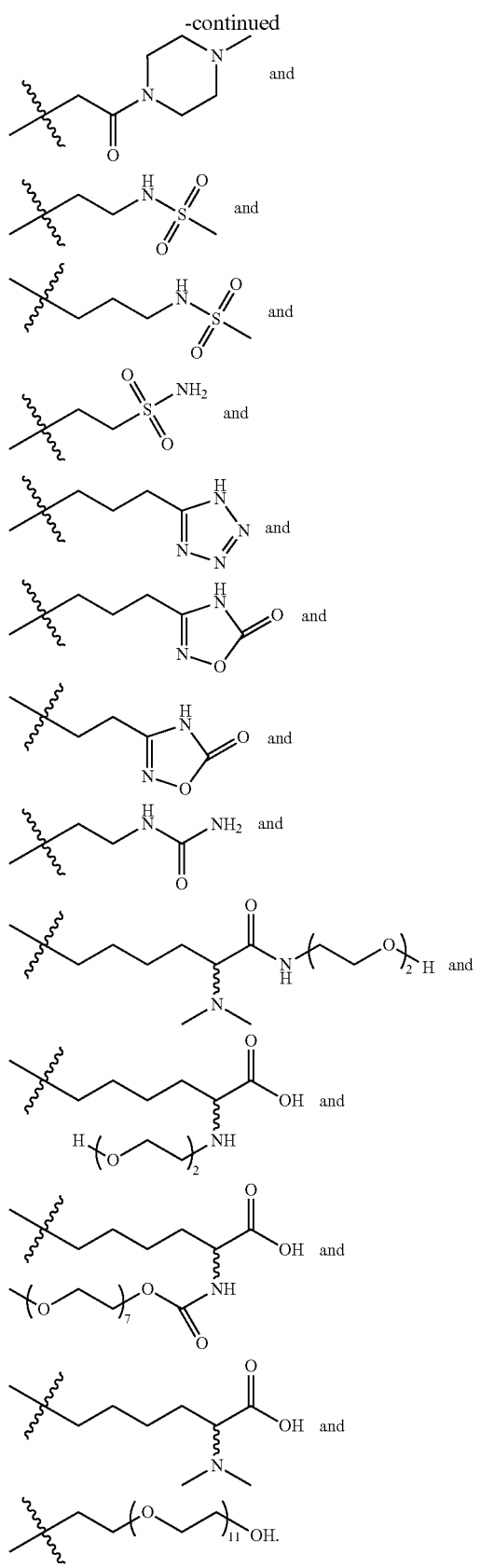
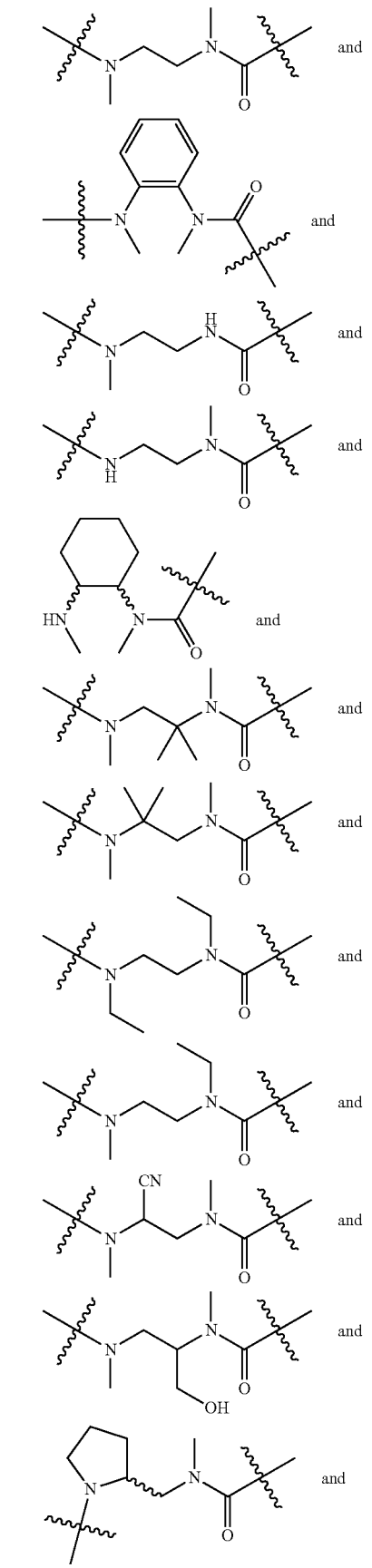
In another embodiment, the cyclization spacer A is selected from

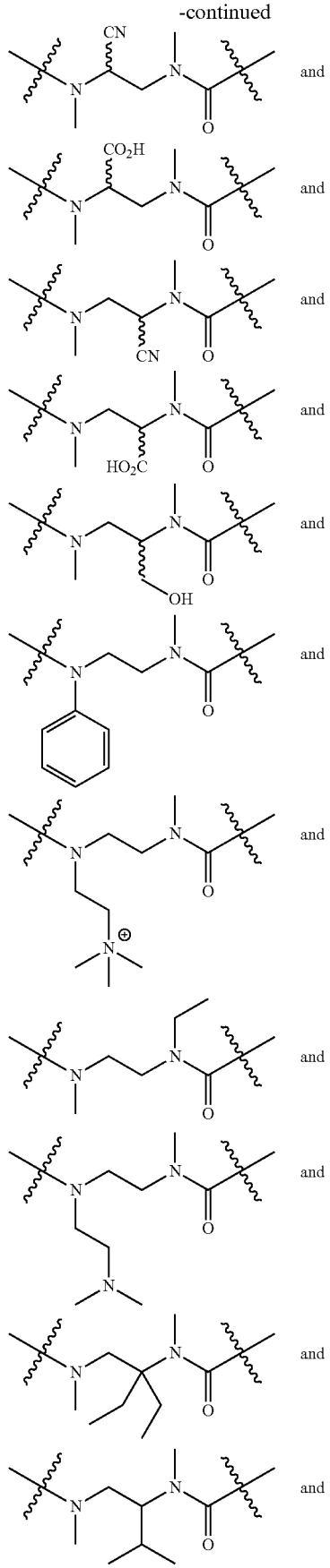
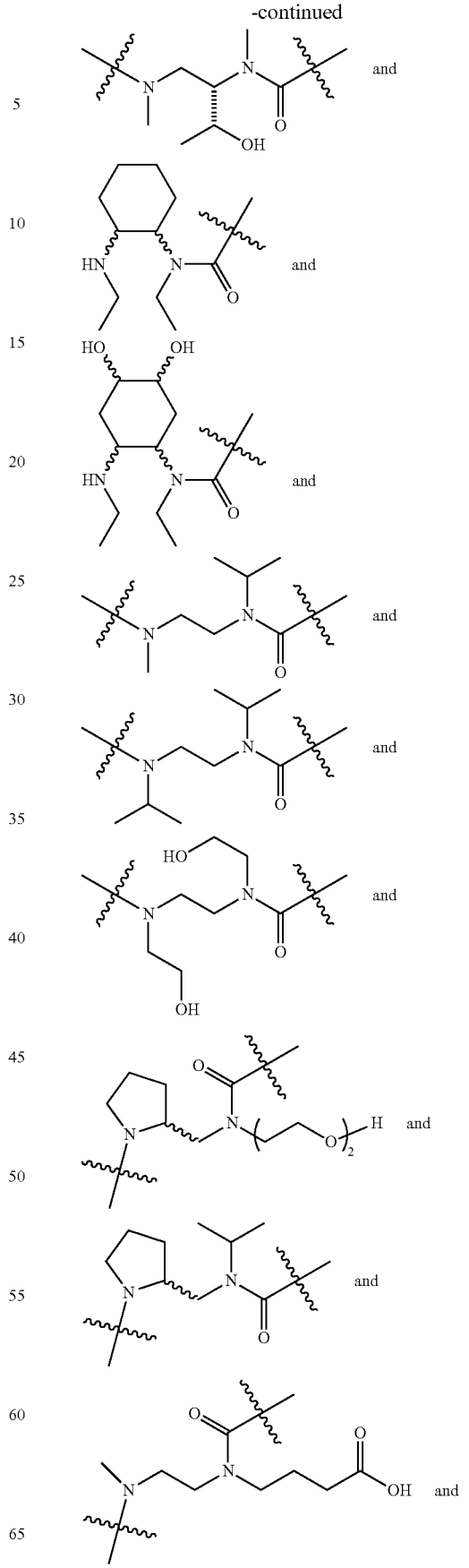

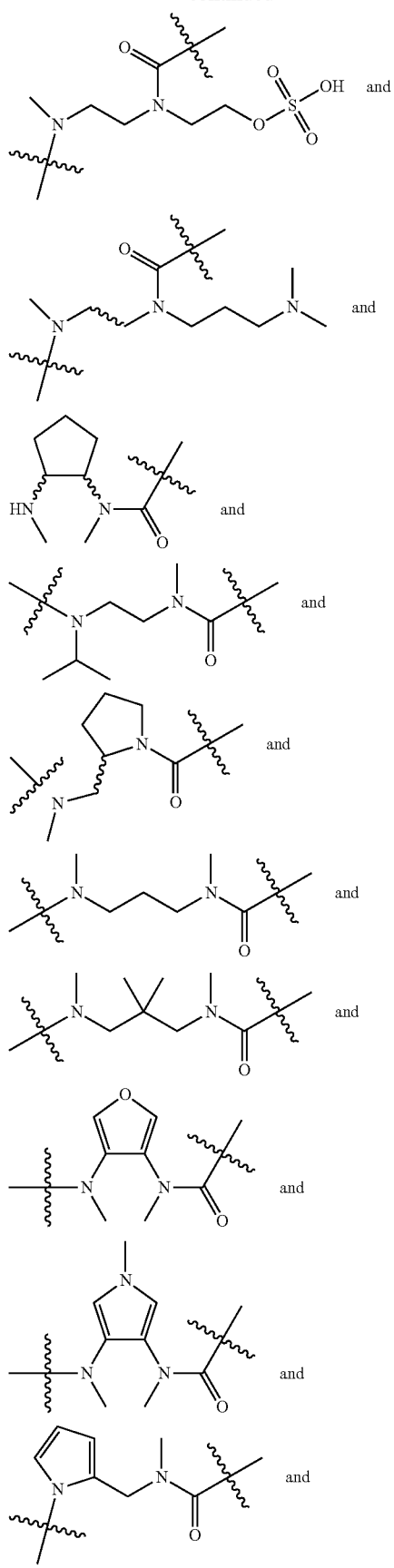
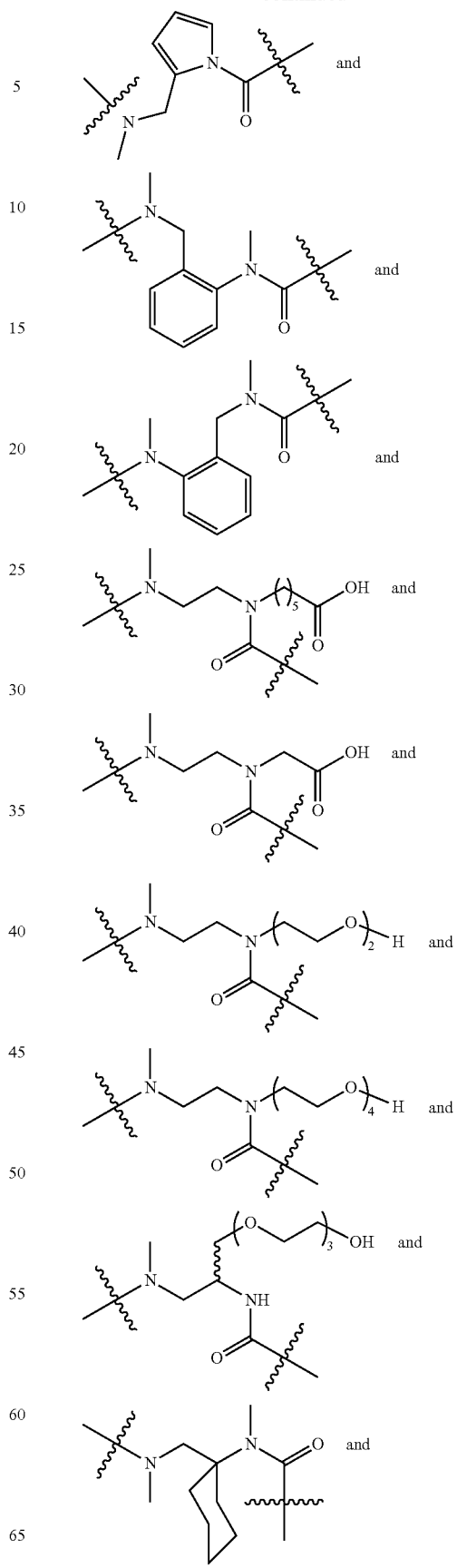

345
-continued
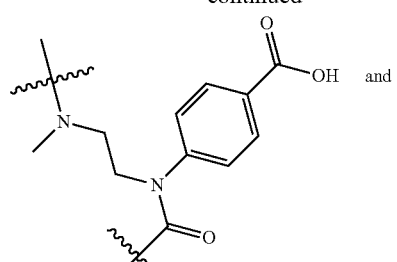 and
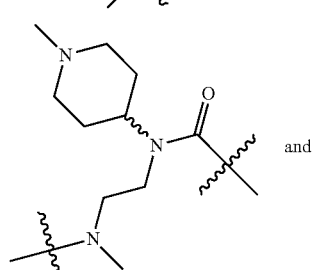 and
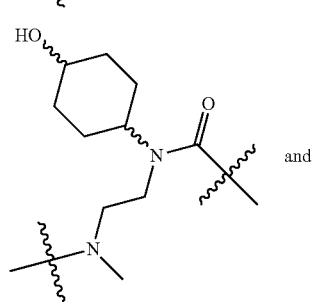 and
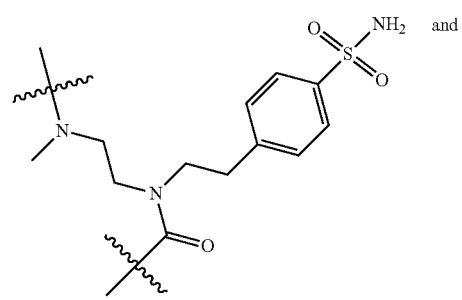 and
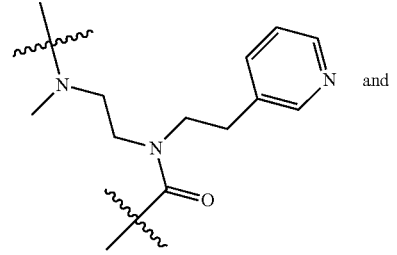 and
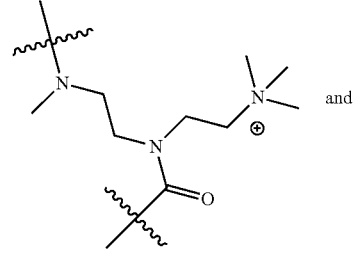 and
346
-continued
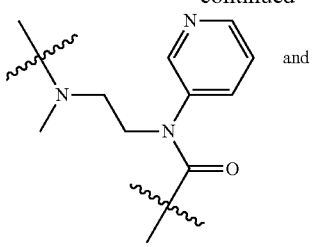 and
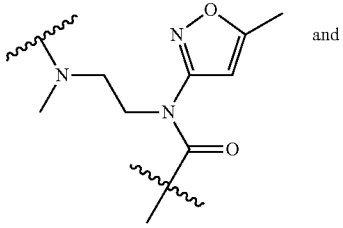 and
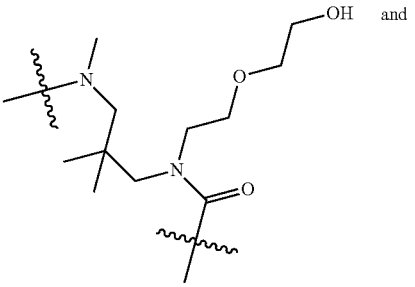 and
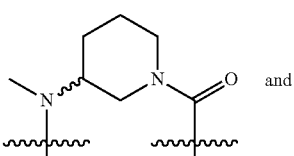 and
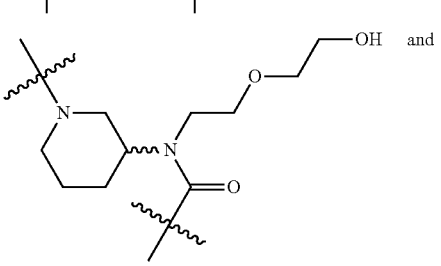 and
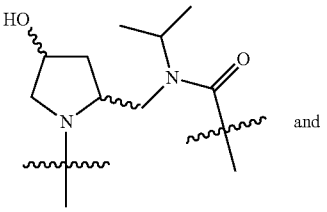 and
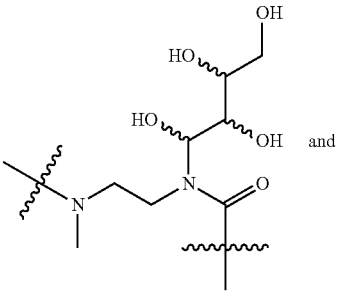 and

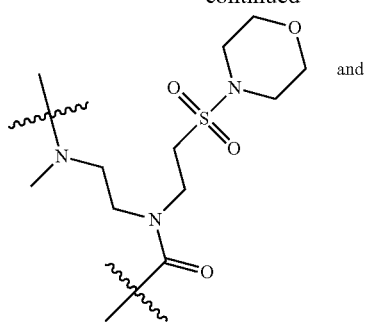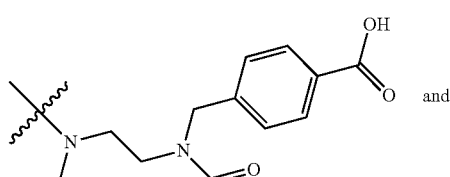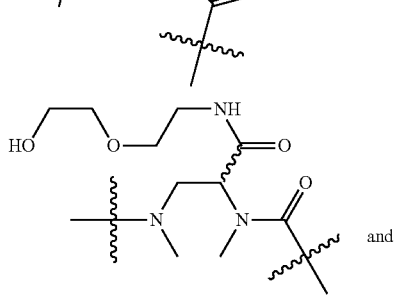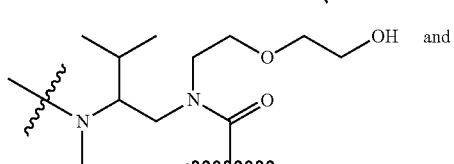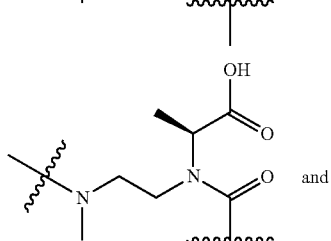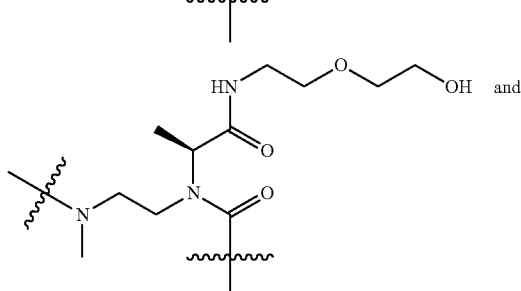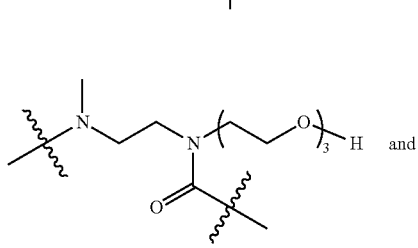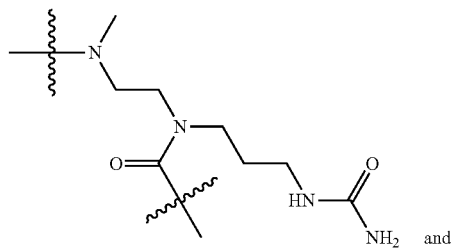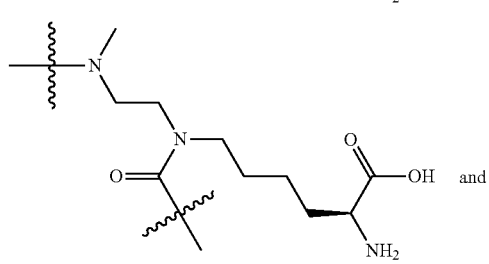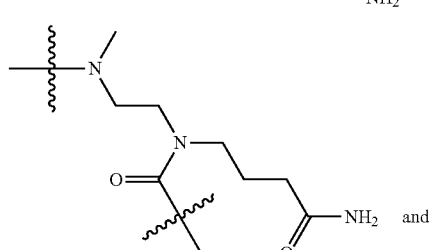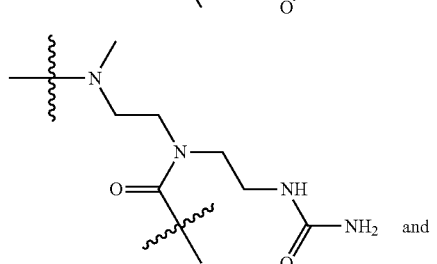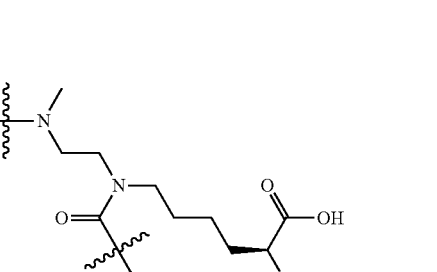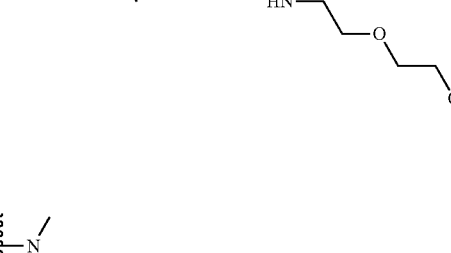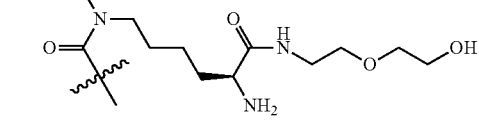

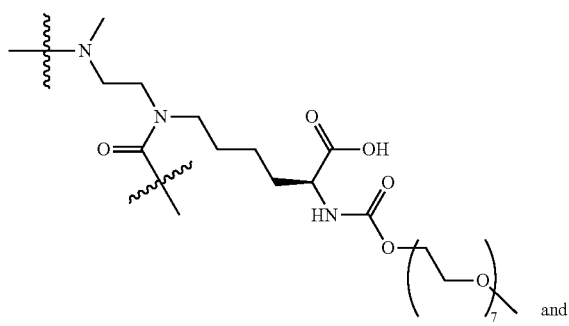 and
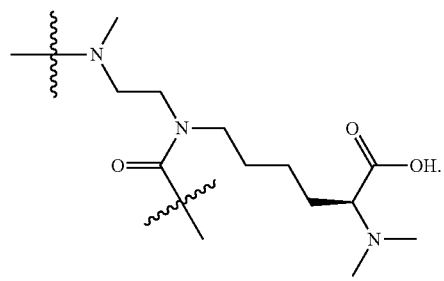
In another embodiment, cyclization linker A is selected from
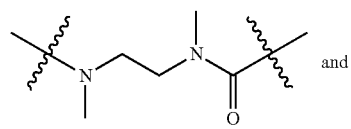 and
 and
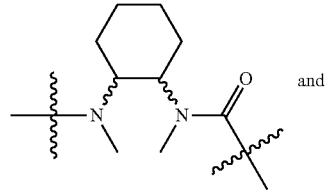 and
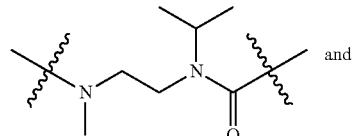 and
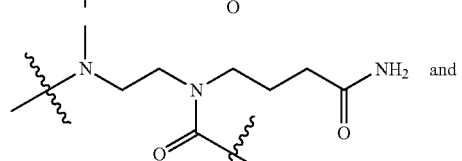 and
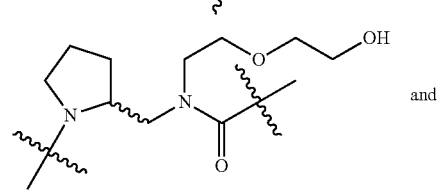 and
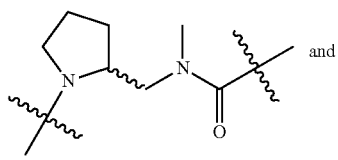 and
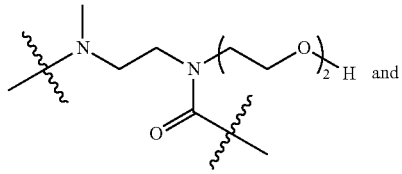 and
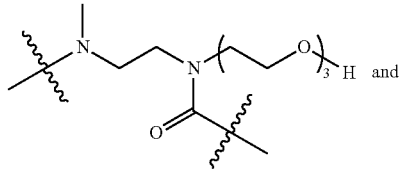 and
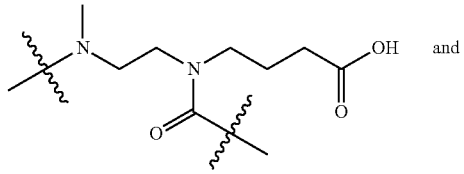 and
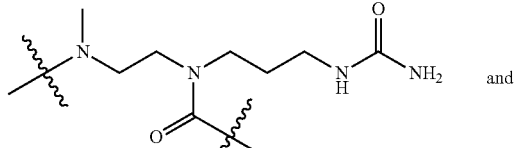 and
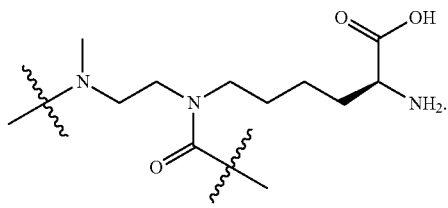
In other embodiments, the cyclization linker A is
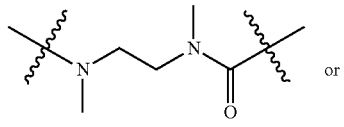 or
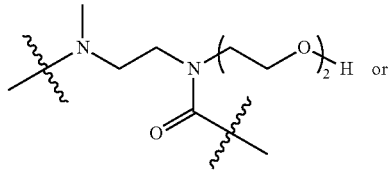 or
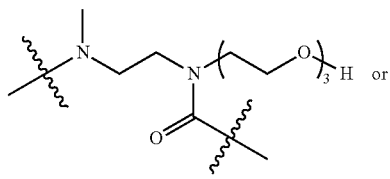 or

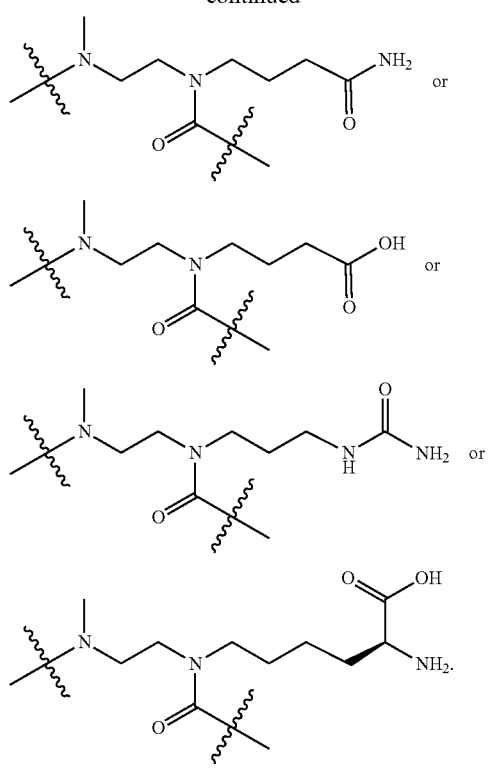
In other embodiments, the cyclization linker A is
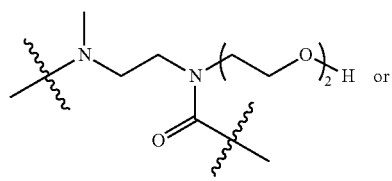
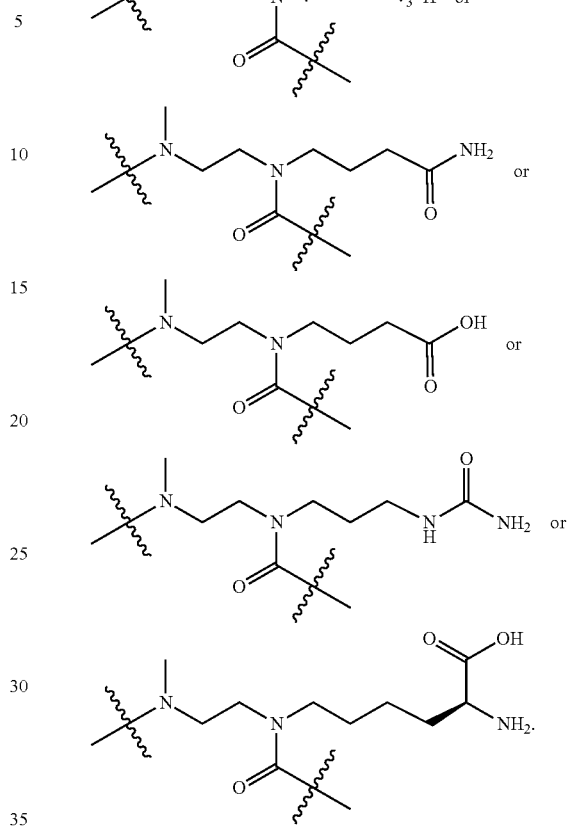
In one embodiment, Y is absent.
In another embodiment, this invention relates to a compound of formula (III) or (IV) wherein $X^1$ is O and Y is connected to $X^1$ via an w-amino aminocarbonyl cyclization spacer being part of Y.
In one embodiment, the spacer system Y is selected from
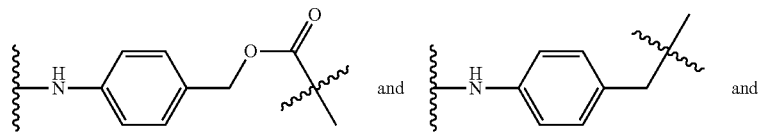
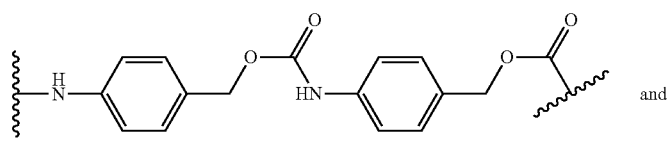
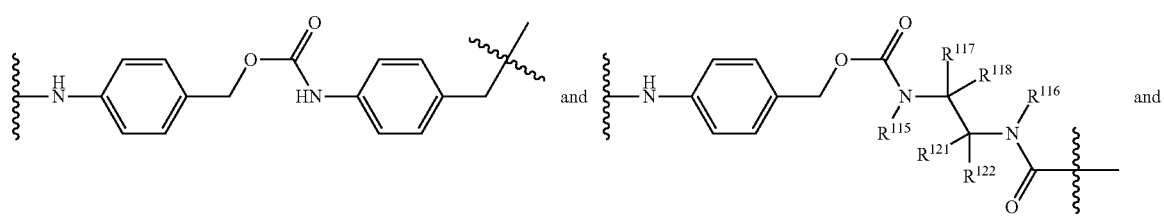

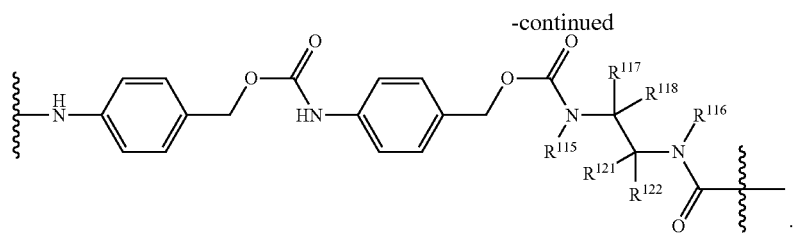
In another embodiment, the spacer system Y is
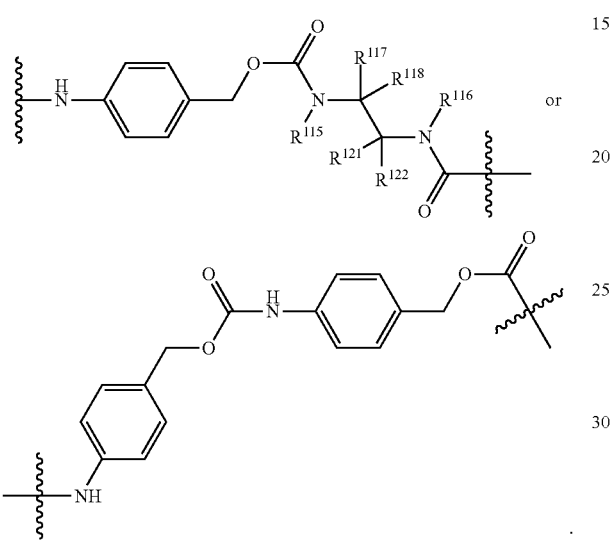
In another embodiment, the spacer system Y is
In a further embodiment, the spacer system Y is
wherein A is selected from
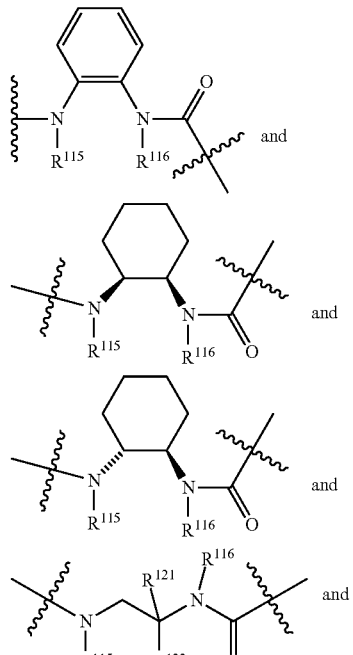
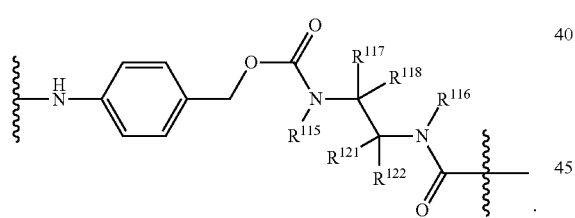 and
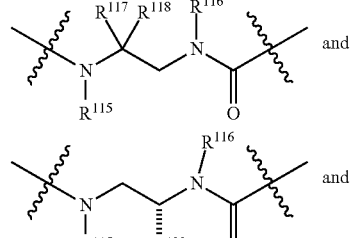 and
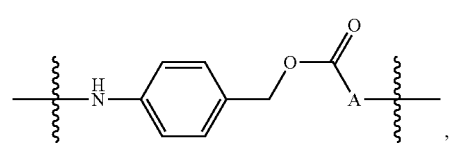 and
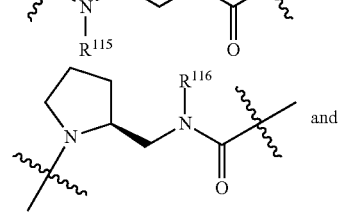 and
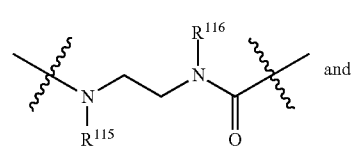 and
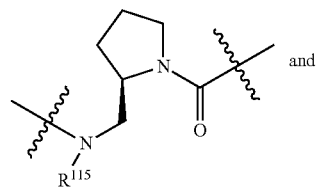 and

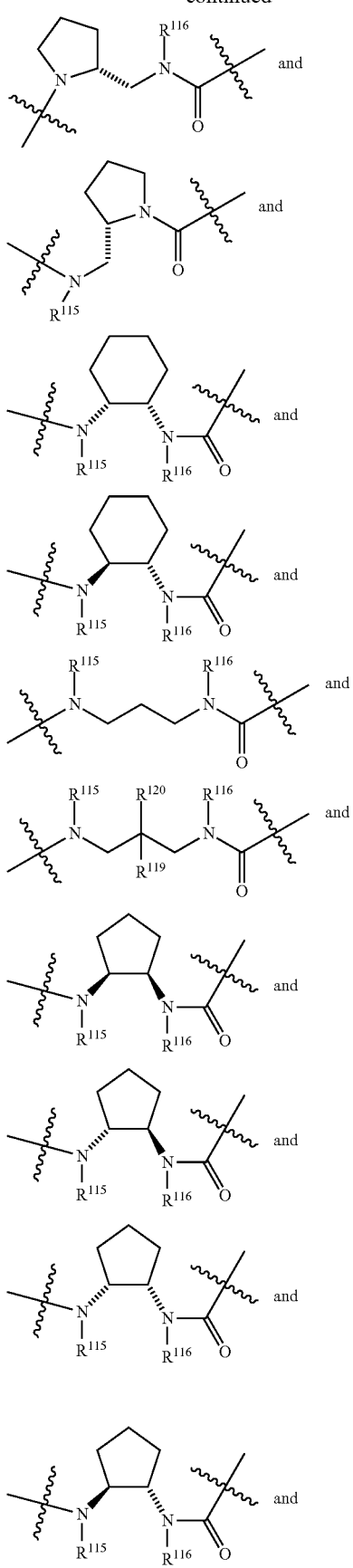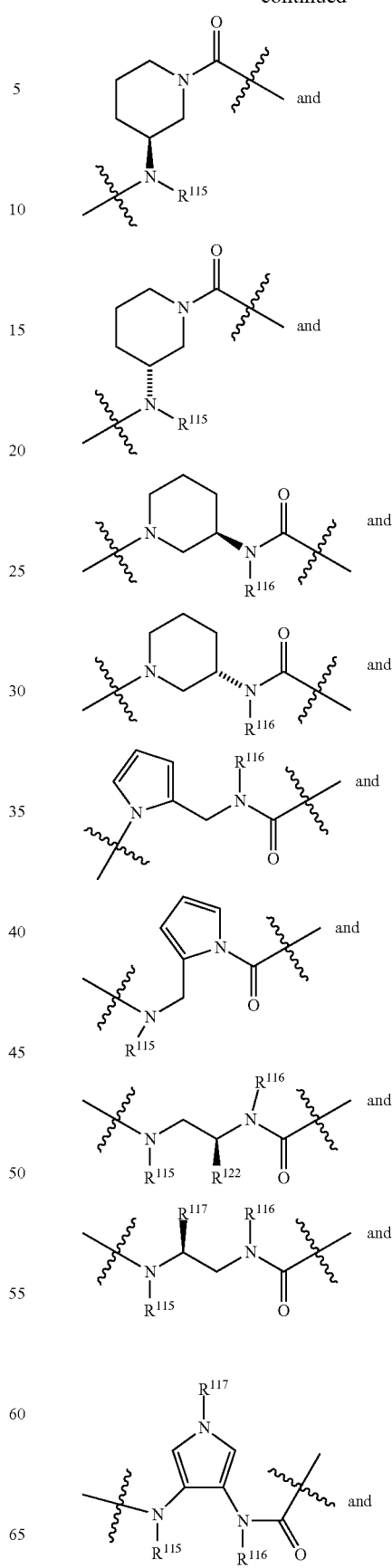

357

-continued

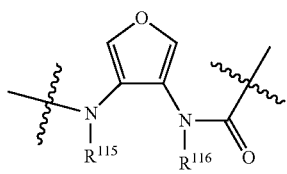

wherein $R^{115}$ and $R^{116}$ are independently selected from H methyl, ethyl, isopropyl, tert-butyl phenyl, $(CH_2CH_2O)_{ee}$ $CH_2CH_2X^{13}R^{e1}$,

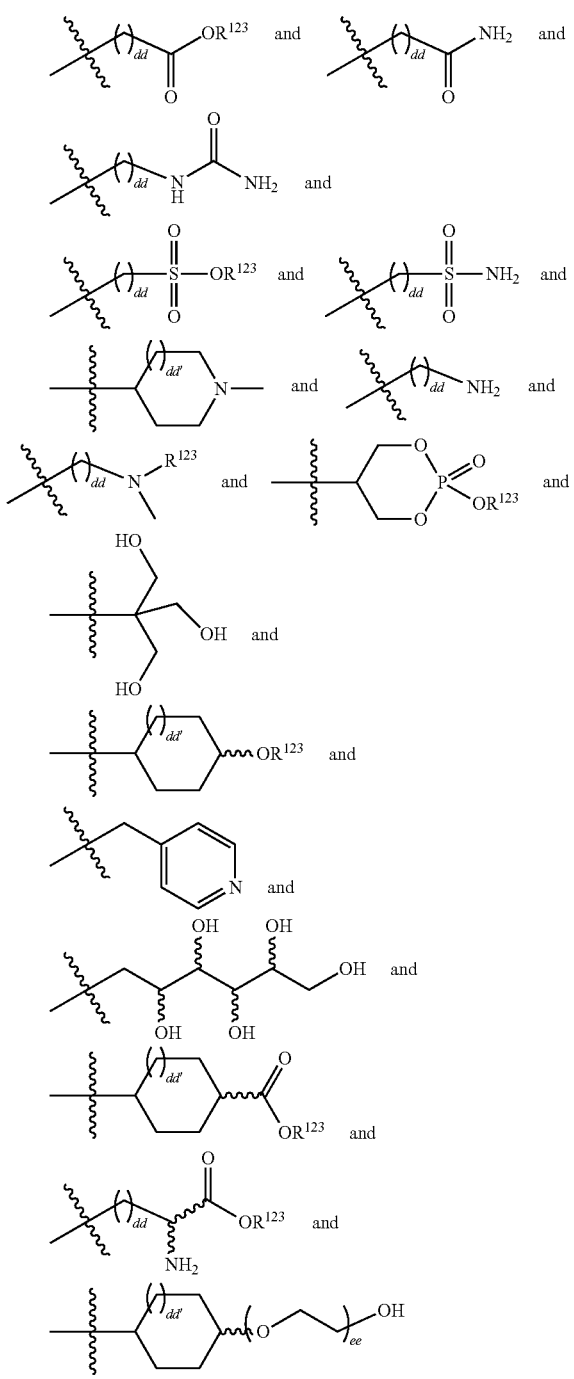

358

-continued

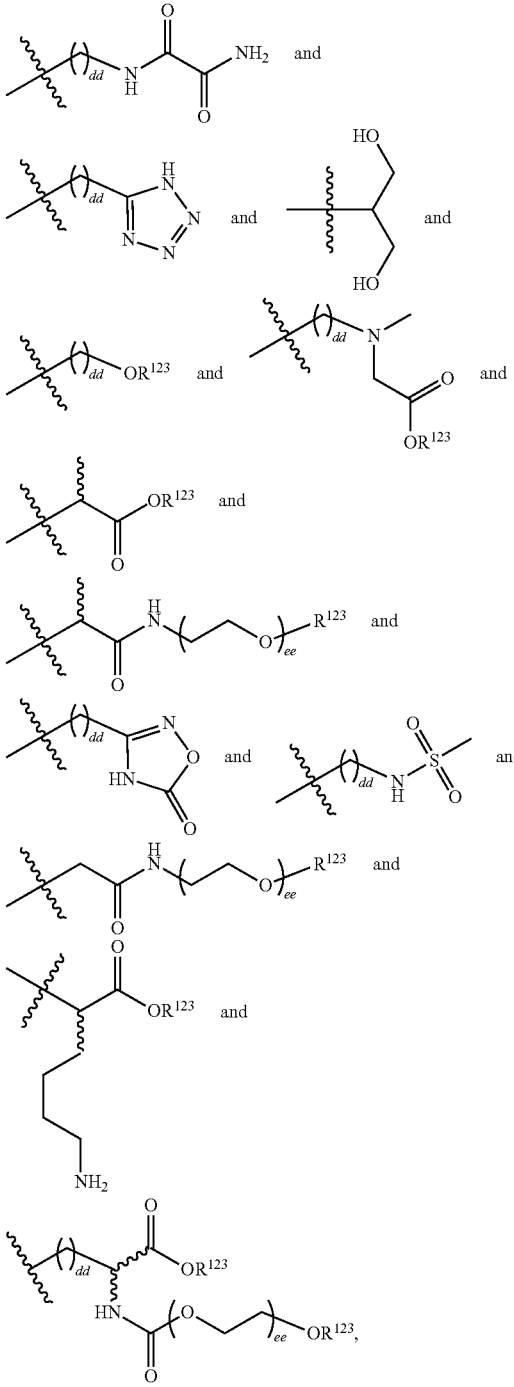

wherein dd is selected from 0 to 10, dd' is selected from 0 and 1, each $R^{123}$ is independently selected from H and methyl, ee is selected from 1 to 1000, $X^{13}$ is selected from O, S, and $NR^{f1}$, and $R^{f1}$ and $R^{e1}$ are independently selected from H and $C_{1-3}$ alkyl, and wherein $R^{117}$, $R^{118}$, $R^{119}$, $R^{120}$, $R^{121}$, and $R^{122}$ are independently selected from H, OH, SH, $NH_2$, $N_3$, $NO_2$, NO, $CF_3$, CN, $C(O)NH_2$, $C(O)H$, $C(O)OH$, halogen, $R^z$, $SR^z$, $S(O)R^z$, $S(O)_2R^z$, $S(O)OR^z$, $S(O)_2OR^z$, $OS(O)R^z$, $OS(O)_2R^z$, $OS(O)OR^z$, $OS(O)_2OR^z$, $OR^z$, $NHR^z$, $N(R^z)R^{z1}$, $^+N(R^z)(R^{z1})R^{z2}$, $P(O)(OR^z)(OR^{z1})$, $OP(O)(OR^z)(OR^{z1})$, $C(O)R^z$, $C(O)OR^z$, $C(O)N(R^{z1})R^z$, $OC(O)R^z$, $OC(O)OR^z$, OC(O)N(R$^{z}$)R$^{z1}$, N(R$^{z1}$)C(O)R$^{z}$, N(R$^{z1}$)C(O)OR$^{z}$, and N(R$^{z1}$)C(O)N(R$^{z2}$)R$^{z}$, wherein R$^{z}$, R$^{z1}$, and R$^{z2}$ are independently selected from H and optionally substituted (CH$_2$CH$_2$O)$_{ee}$CH$_2$CH$_2$X$^{13}$R$^{e1}$, C$_{1-20}$ alkyl, C$_{1-20}$ heteroalkyl, C$_{3-20}$ cycloalkyl, C$_{1-20}$ heterocycloalkyl, C$_{5-20}$ aryl, or C$_{1-20}$ heteroaryl, wherein ee is selected from 1 to 1000, X$^{13}$ is selected from O, S, and NR$^{f1}$, and R$^{f1}$ and R$^{e1}$ are independently selected from H and C$_{1-3}$ alkyl.

In a further embodiment, the spacer system Y is

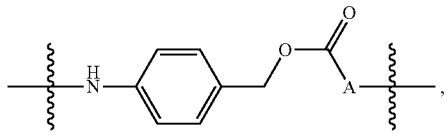

wherein A is selected from

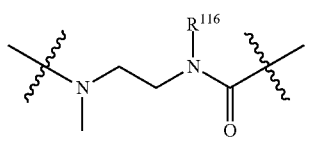

wherein R$^{116}$ is selected from methyl, ethyl, isopropyl, tert-butyl, phenyl,

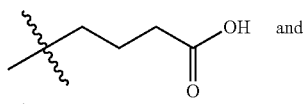
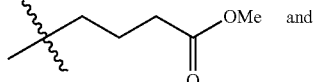
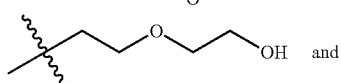
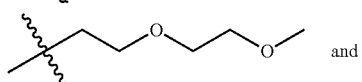
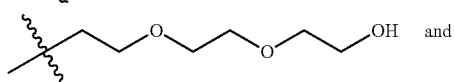
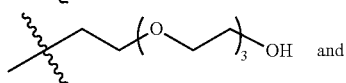
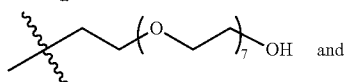
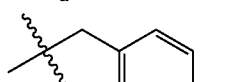
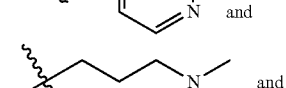
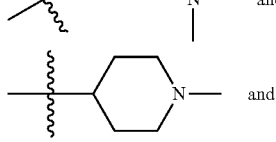

-continued

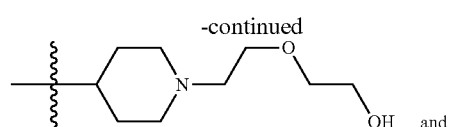
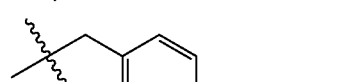
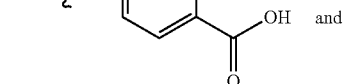
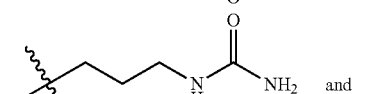
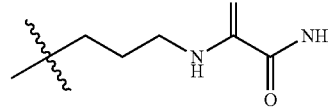
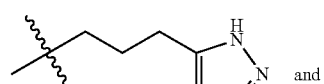
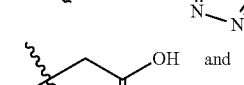
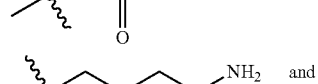
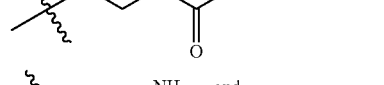
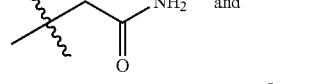
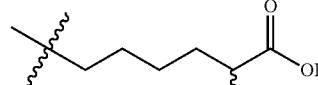
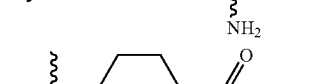
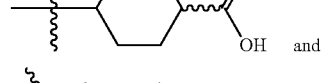
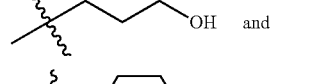
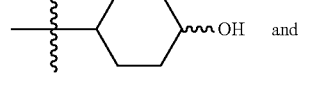
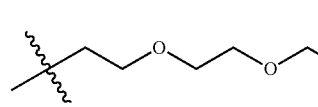
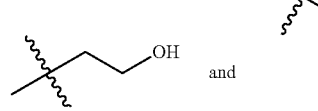

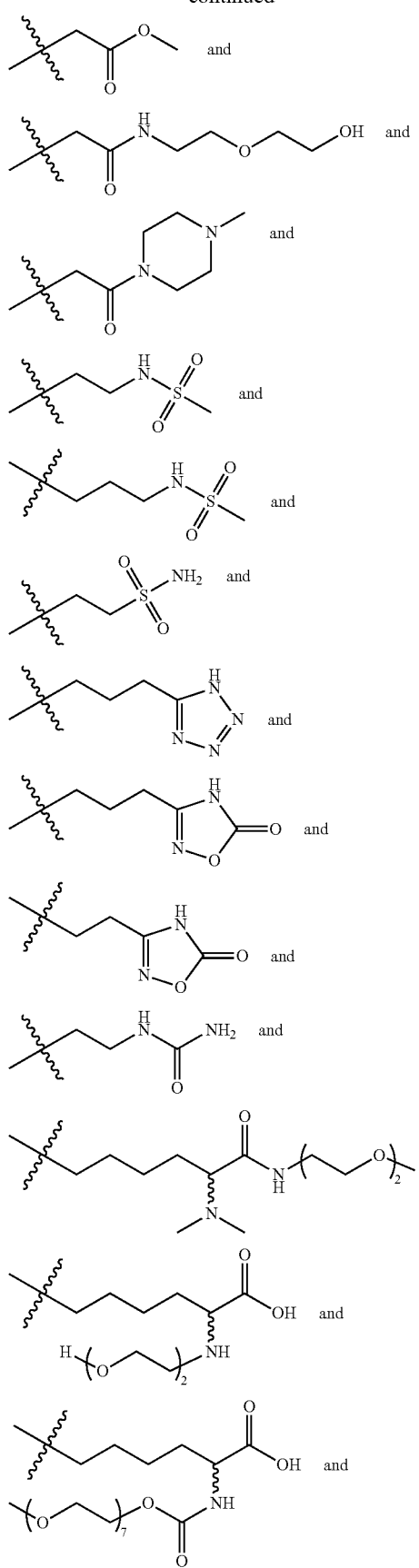
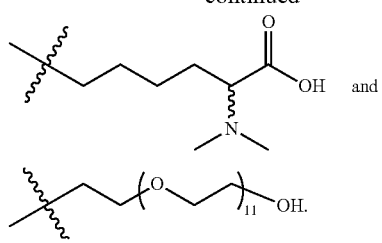
In a further embodiment, the spacer system Y is
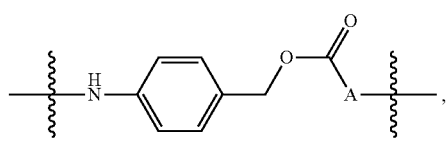
wherein A is selected from
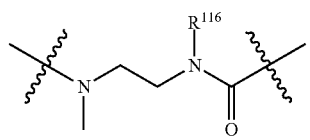
wherein $R^{116}$ is selected from ethyl, isopropyl, tert-butyl, phenyl,
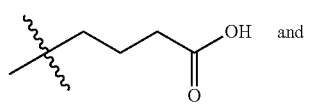
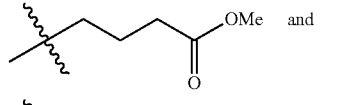
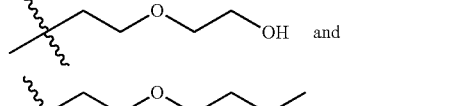
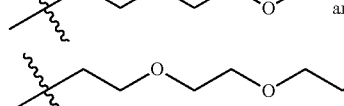
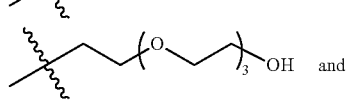
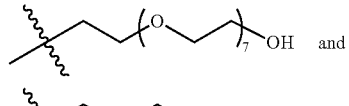
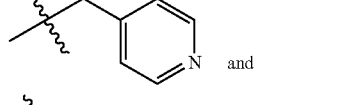

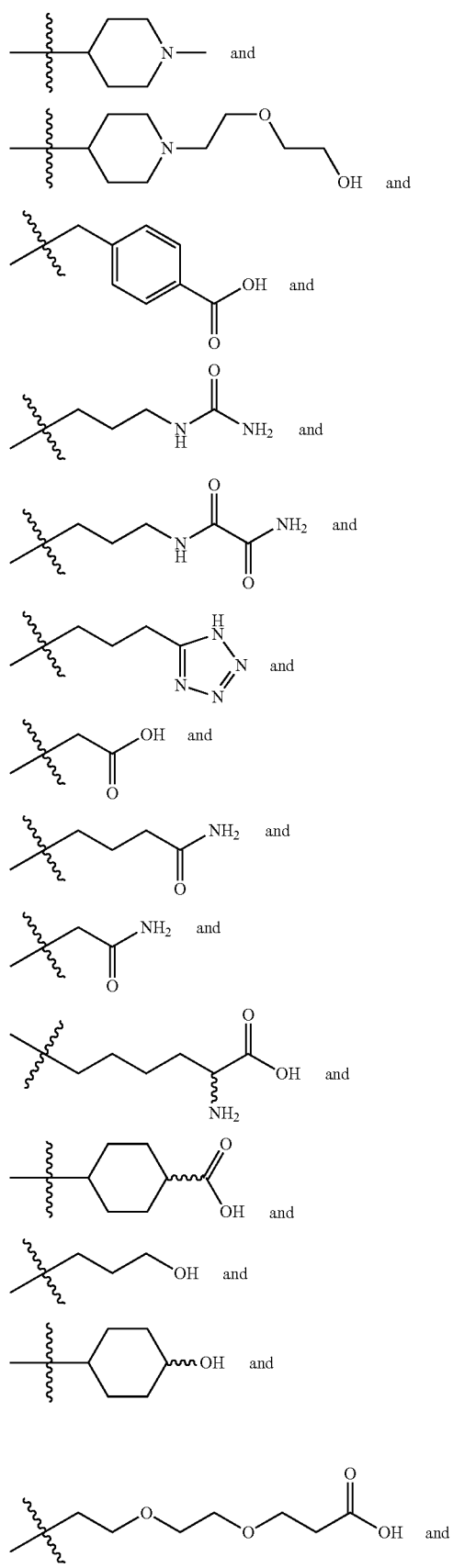
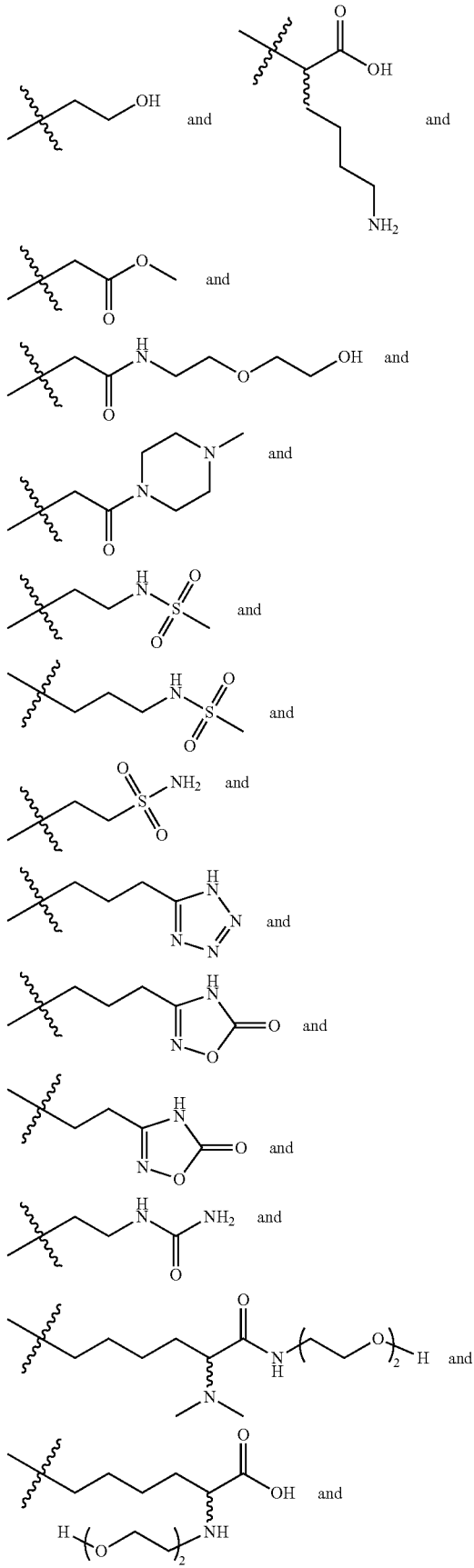

-continued

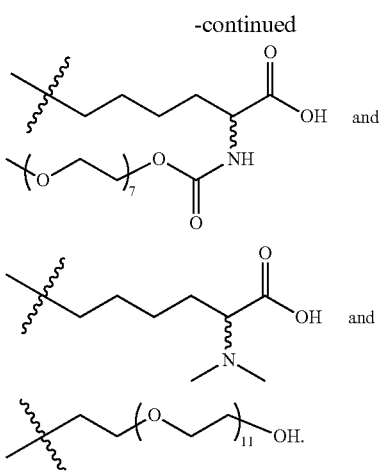

In a further embodiment, the spacer system Y is

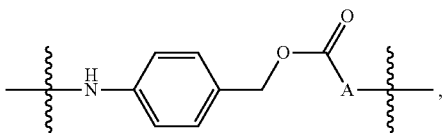

wherein A is selected from

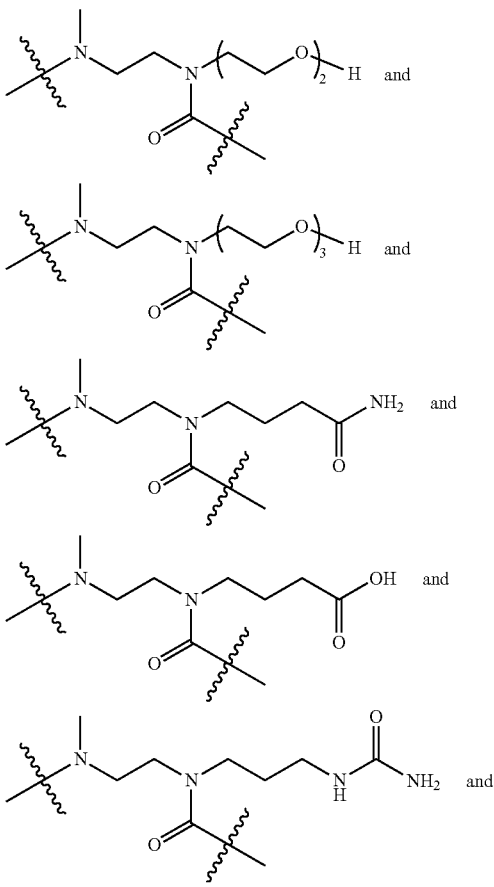

-continued

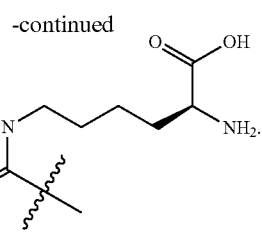

In another embodiment, at least one of $R^{115}$ and $R^{116}$ is not H or methyl when the to nitrogen atoms of the ω-amino aminocarbonyl cyclization spacer are connected via an unsubstituted ethylene bridge.

Other examples of self-eliminating spacers include, but are not limited to, other spacers that can undergo cyclization[10], such as optionally substituted 4-aminobutyric acid amides, appropriately substituted bicyclo[2.2.1] and bicyclo[2.2.2] ring systems, 2-aminophenylpropionic acid amides, and "trimethyl-lock" cyclization spacers[11]. A glycine spacer in which an amine-containing leaving group is connected at the α-position is another useful spacer for the compounds of the invention.[12]

In a conjugate of this invention, a spacer system Y may be connected to more than one $V^1$ moiety. In this case, transformation and/or cleavage of one of these $V^1$ moieties may trigger the release of one or more Z moieties. When $V^1$ moieties that are transformed or cleaved under different conditions are connected to the same Y, release of one or more Z moieties may occur when a conjugate of this invention is brought under one of several distinct conditions if Y can undergo self-elimination in multiple ways. Alternatively, a spacer system Y may be used that requires to be triggered twice or even more times in order to self-eliminate. An example of such a self-elimination spacer is a bicine spacer.[13] When such a spacer is used in combination with different, selectively cleavable $V^1$ moieties connected to said spacer, selectivity of release of Z may be increased as two different conditions must be met before Z is released.

The Linking Group L

The linking group L links one or more $V^1$ and/or Y moieties to $L^2$ or RM. Synthesis may be more straightforward when L is connected to $V^1$ instead of Y and the compound may be less prone to premature degradation as $V^1$ may be more shielded. Connection of L to Y may have the advantage that $V^1$ may be transformed and/or cleaved with more ease. Other reasons to connect L to Y may for example be that (part of) Y remains bound to L upon cleavage of $V^1$, which prevents the release of reactive small molecules, and that the compound may display improved pharmacological properties, solubility, or aggregation behavior. L may be absent, which means that $V^1$ or Y is directly connected to either $L^2$ or RM. In another aspect, however, L is a linking group that functionally links or spaces the one or more $V^1$ and/or Y moieties and the $L^2$ or RM moiety. In a compound of formula (IV), spacing may make the reactive moiety RM more accessible to the reaction partner, for example when the functional moiety $V^2$ is being coupled. In a compound of formula (III), spacing may provide for a better accessibility of $V^1$, because $V^2$ is further away, which, especially in the case of enzymatic cleavage or transformation of $V^1$, may improve the rate at which $V^1$ is transformed and/or cleaved. However, it was found that a relatively short L moiety may improve in vivo efficacy of a compound of formula (III) compared to similar compounds with a relatively long L moiety, provided that $V^1$ can still be transformed and/or cleaved at the target site.

The linking group L must contain suitable functional groups at both of its ends to provide for selective coupling with the one or more $V^1$ and/or Y moieties and $L^2$ or RM.

The linking group L may be a water-soluble moiety or contain one or more water-soluble moieties or water-soluble functional groups, such that L contributes to the water solubility of a compound of formula (III) or (IV). L may also be a moiety or contain one or more moieties that reduce(s) aggregation of a compound of formula (III) or (IV), which may or may not be a moiety/moieties that also increase(s) the water solubility of a compound of formula (III) or (IV). Furthermore, L may also contain or be a moiety that causes a compound of formula (III) or (IV) to be less susceptible to an immune response or increased efflux from cells by multidrug resistance-associated transporter proteins. The L moiety may contain an oligoethylene glycol or polyethylene glycol moiety or a derivative thereof. This moiety may for example improve the water solubility, reduce aggregation, reduce the immune response, and/or reduce the efflux from cells of a compound of formula (III) or (IV). L may for example contain a —$(CH_2CH_2O)_{ff}CH_2CH_2X^{13}$— or —$(CH_2CH_2O)_{ee}CH_2CH_2X^{13}R^{e1}$ moiety, wherein ff is selected from 1 to 1000, $X^{13}$ is selected from O, S, and $NR^{f1}$, and $R^{f1}$ and $R^{e1}$ are independently selected from H and $C_{1-3}$ alkyl. In one embodiment, such a moiety is part of a substituent attached to the main chain of L that connects RM or $L^2$ to $V^1$ and not present in the main chain of L itself in order to keep the length of the main chain relatively short. The L moiety may also contain polar groups and/or groups that are charged, at least partly, at physiological pH in order to improve the pharmacological properties of a compound of formula (III) or (IV).

In one aspect, the L moiety is a linear, branched, or dendritic moiety, so that it can be connected to one or more $V^1$ and/or Y moieties. Branching can occur via one or more cyclic structures or at one or more branching atoms that may for example be carbon, nitrogen, silicon, or phosphorus.

The number of branches in L that are connected to $V^1$ and/or Y does not necessarily equal the total number of branches as in the coupling reaction with $V^1$ and/or Y not all branches may be coupled to $V^1$ and/or Y moieties due to incomplete chemical conversion. This means that L may contain branches that are not coupled to $V^1$ or Y, but instead end in for example a functional group, H, OH, or a leaving group.

Therefore, when L is branched, compounds of this invention may exist as a mixture, wherein each component of the mixture has a different p value. For example, the compound may exist as a mixture of two separate compounds, one compound wherein p is 2 and another compound wherein p is 3. Furthermore, for a given p, the compound may exist as a mixture of (constitutional) isomers as $V^1$ and/or Y may be connected to distinct (sets of) branches on L.

In one embodiment, L is absent.

In another embodiment, L is a linear linker.

In another embodiment, the chain of atoms linking $L^2$ or RM to $V^1$ consists of less than 19 atoms.

In another embodiment, the chain of atoms linking $L^2$ or RM to $V^1$ consists of less than 15 atoms.

In another embodiment, the chain of atoms linking $L^2$ or RM to $V^1$ consists of less than 10 atoms.

In another embodiment, the chain of atoms linking $L^2$ or RM to $V^1$ consists of less than 5 atoms.

In another embodiment, L is a linear linker containing a 1,2,3-triazole moiety. Such a linker may be built up through a cycloaddition reaction between a molecule containing an azide group and one containing an acetylene group.

In another embodiment, L is a linear linker containing a water-soluble group. In another embodiment, L is a linear linker that comprises an oligoethylene glycol or polyethylene glycol or a derivative thereof. In a further embodiment, L is a linear linker that contains a functional group that is charged, at least partly, at physiological pH.

In another embodiment, L is a branched linker.

In another embodiment, L is a dendritic linker. The dendritic structure may for example be built up through cycloaddition reactions between molecules containing one or more azide groups and ones containing one or more acetylene groups.

In one embodiment, p is 1.

In other embodiments, p is 2 or 3 or 4 or 6 or 8 or 9.

In another embodiment, L is represented by the formula:

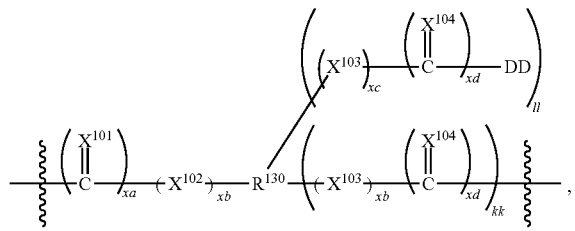

wherein
$X^{101}$ and $X^{102}$ are each independently O, $NR^{131}$, or S;
Each $X^{103}$ and $X^{104}$ is independently O, $NR^{132}$, or S;
Each xa, xb, xc, and xd is independently 0 or 1;
kk is a number representing a degree of branching and is an integer selected from 1 (included) to 128 (included);
ll is a number representing a degree of branching and is an integer selected from 0 (included) to 127 (included);

$kk+ll \leq 128$;

Each DD is independently H, OH, or a leaving group;
$R^{130}$ is either a dendritic, branched, or unbranched multivalent moiety and selected from optionally substituted alkylene, oligoalkylene, or polyalkylene, and optionally substituted heteroalkylene, oligoheteroalkylene, or polyheteroalkylene, and optionally substituted arylene, oligoarylene, or polyarylene, and optionally substituted heteroarylene, oligoheteroarylene, or polyheteroarylene, and optionally substituted cycloalkylene, oligocycloalkylene, or polycycloalkylene, and optionally substituted heterocycloalkylene, oligoheterocycloalkylene, or polyheterocycloalkylene, and —$(CH_2CH_2O)_v$—, -alkylene-$(CH_2CH_2O)_v$—, —$(CH_2CH_2O)_v$-alkylene-, -alkylene-$(CH_2CH_2O)_v$-alkylene-, -heteroalkylene-$(CH_2CH_2O)_v$—, —$(CH_2CH_2O)_v$-heteroalkylene-, -heteroalkylene-$(CH_2CH_2O)_v$-alkylene-, -heteroalkylene-$(CH_2CH_2O)_v$-heteroalkylene-, -alkylene-$(CH_2CH_2O)_v$-heteroalkylene-, $X^{14}(CH_2CH_2O)_{ff}CH_2CH_2X^{14}$, a dendritic structure, a sugar residue, and an oligopeptide, or any combination of two or more of the above, wherein optional substituents may for example be selected from $C_{1-8}$ alkyl, $C_{1-8}$ heteroalkyl, $C_{5-8}$ aryl, $C_{1-8}$ heteroaryl, $X^{14}(CH_2CH_2O)_{ee}CH_2CH_2X^{13}R^{e1}$, —$(CHOR^{133})_{vv}$—$R^{133}$, a sugar residue, and charged substituents selected from $SO_3^-$, $OPO_3^{2-}$, $PO_3^{2-}$, $CO_2^-$, and $NR^{133}R^{133'}R^{133''}$, or from any combination thereof;
$R^{131}$, $R^{132}$, $R^{133}$, $R^{133'}$, and $R^{133''}$ are independently selected from H, $C_{1-8}$ alkyl, and $C_{1-8}$ heteroalkyl;
$X^{13}$ is selected from O, S, and $NR^{f1}$;
$R^{f1}$ and $R^{e1}$ are independently selected from H and $C_{1-3}$ alkyl;
ee and ff are independently selected from 1 to 1000;

Each $X^{14}$ is independently selected from
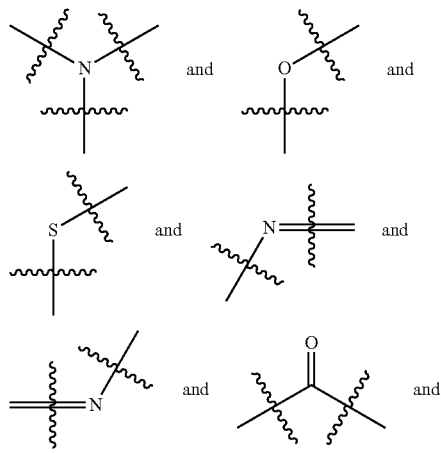
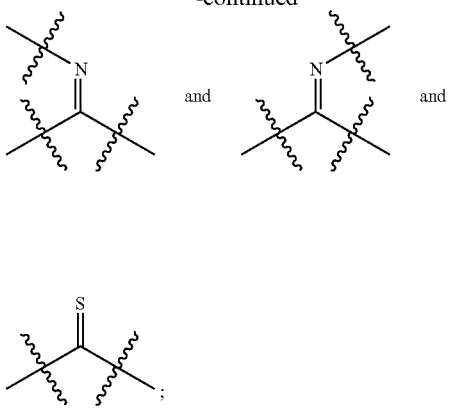
$v$ is selected from 1 (included) to 1000 (included);
$vv$ is selected from 1 to 10.
In another embodiment, L is selected from
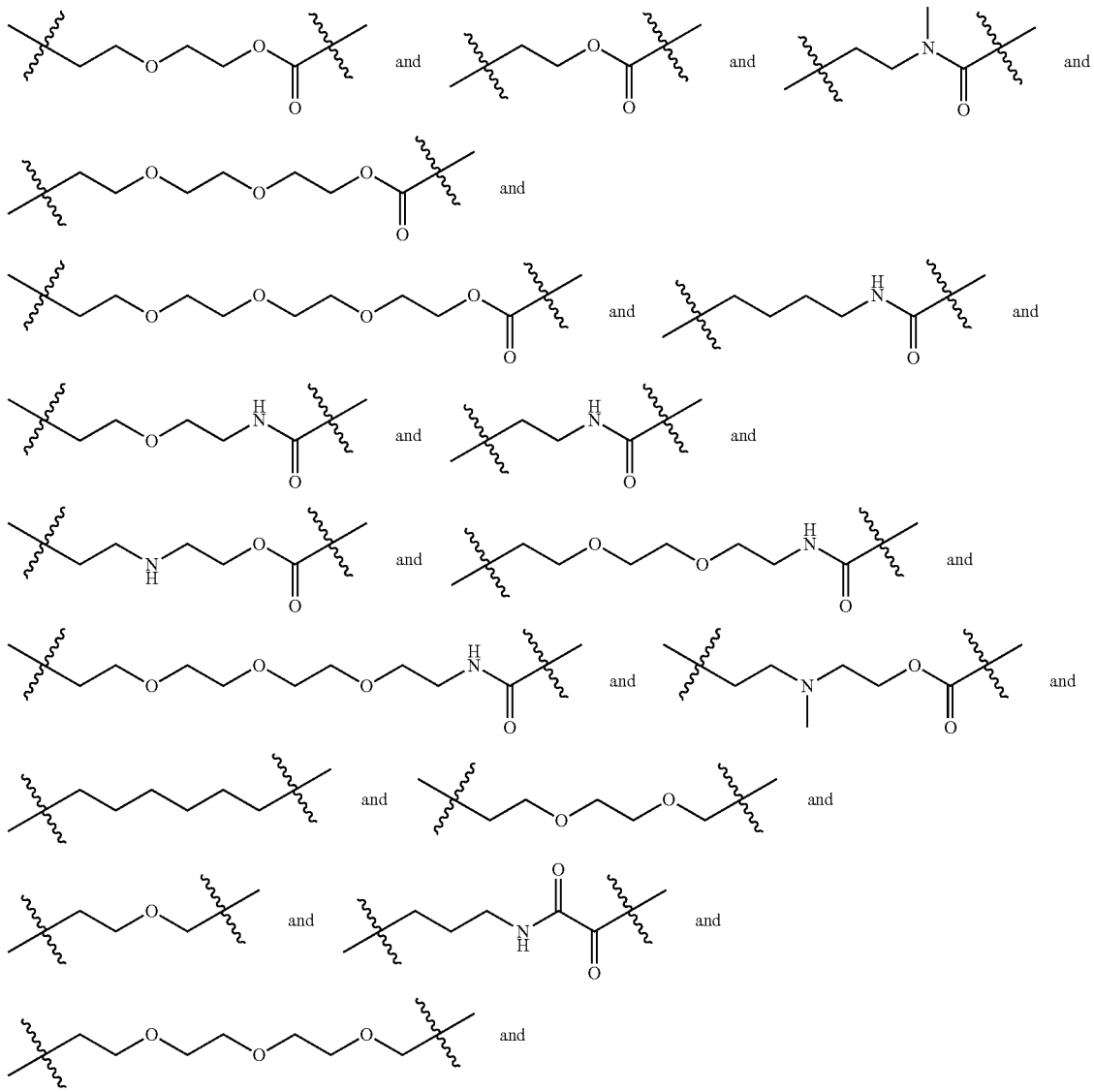

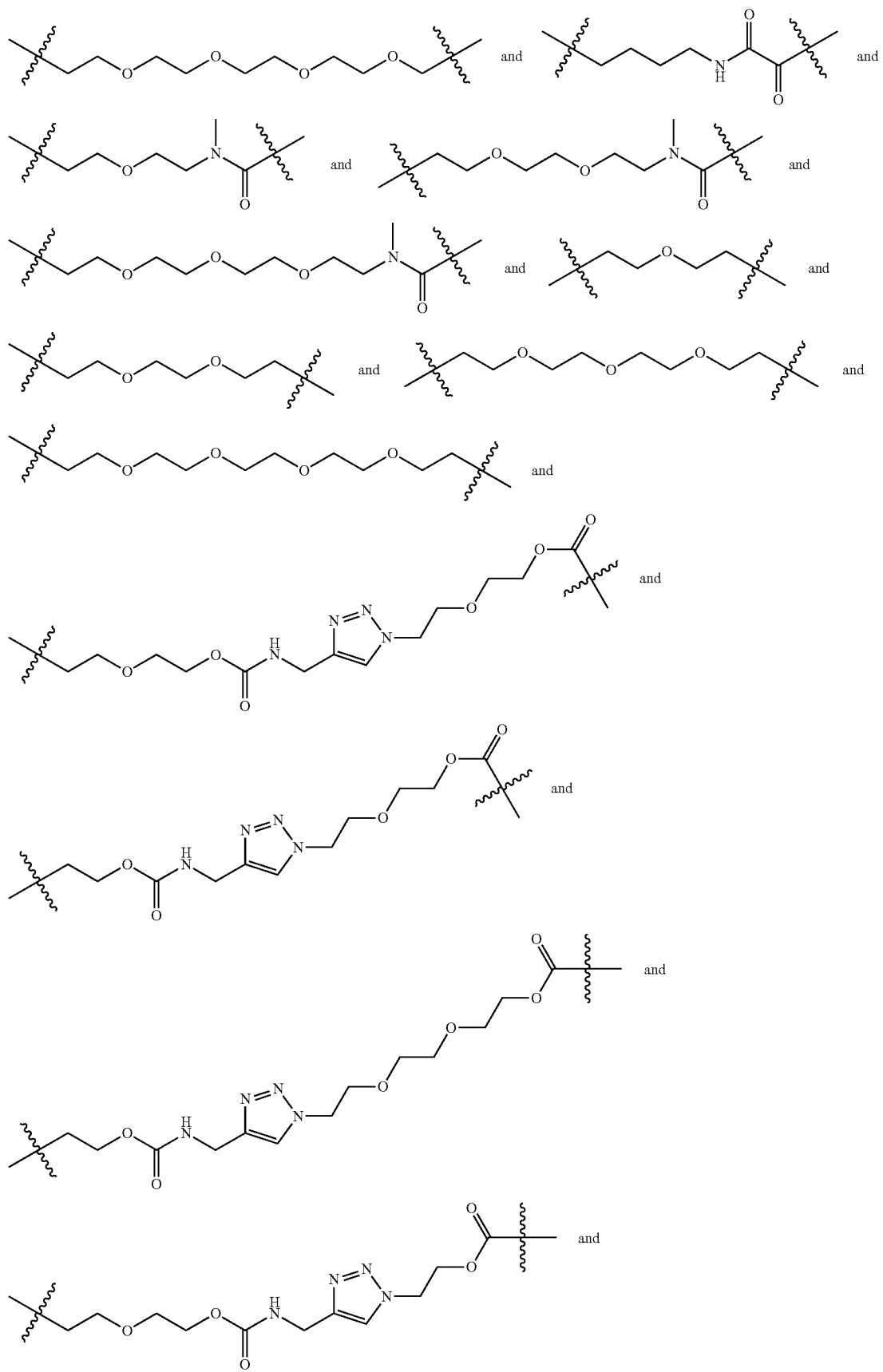

-continued
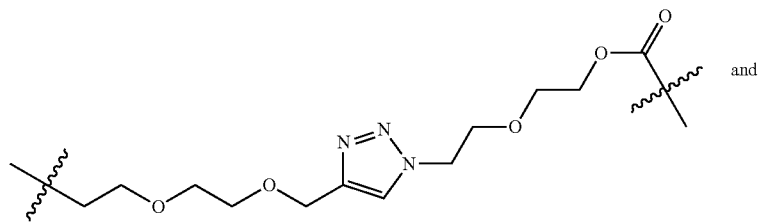 and
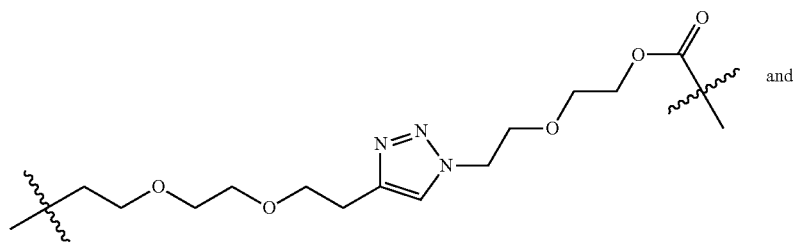 and
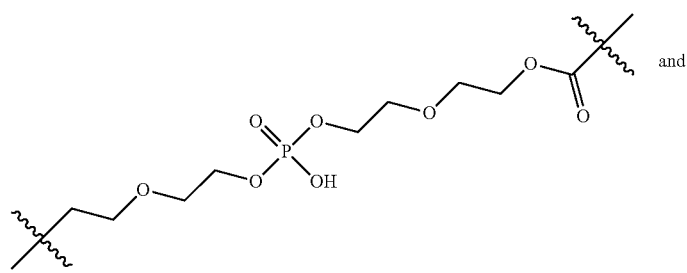 and
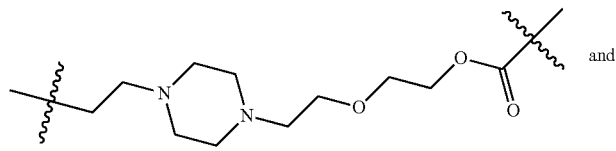 and
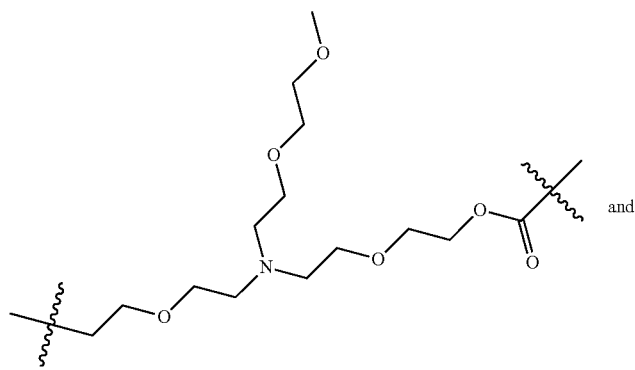 and
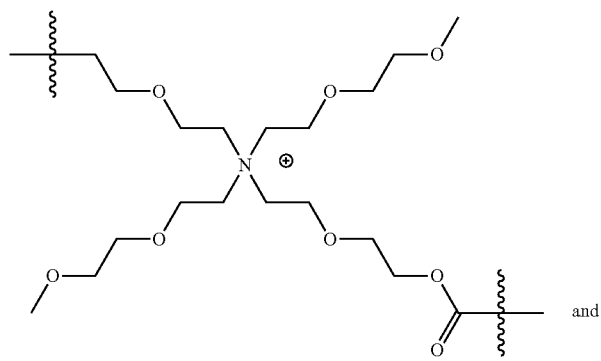 and -continued
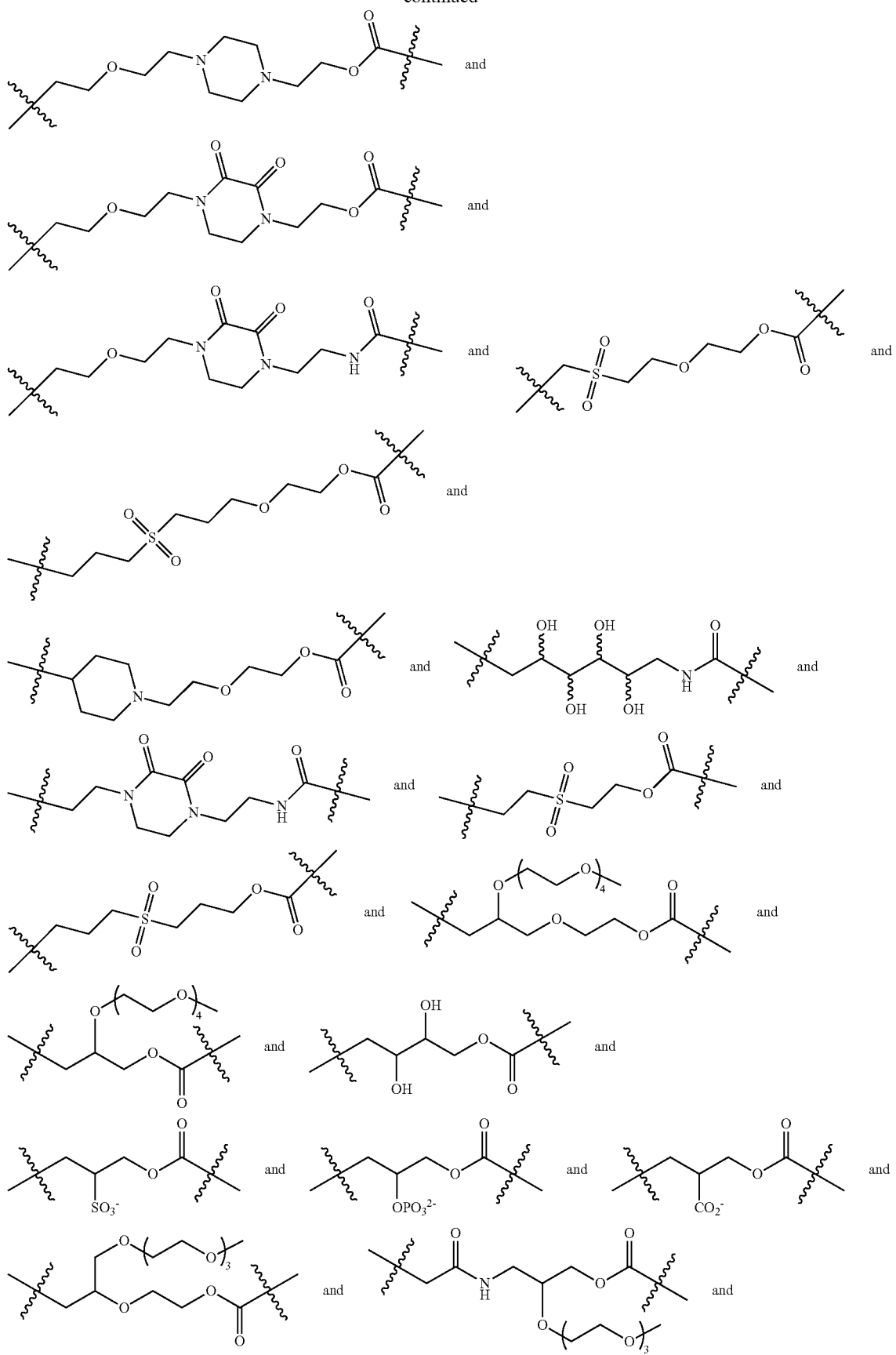

-continued
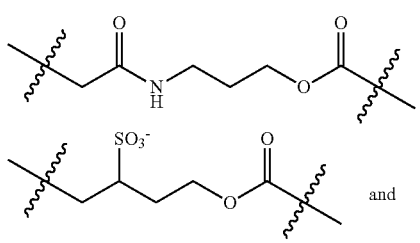 and 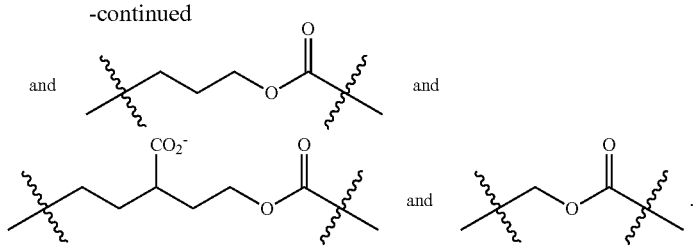
In yet another embodiment, L is selected from
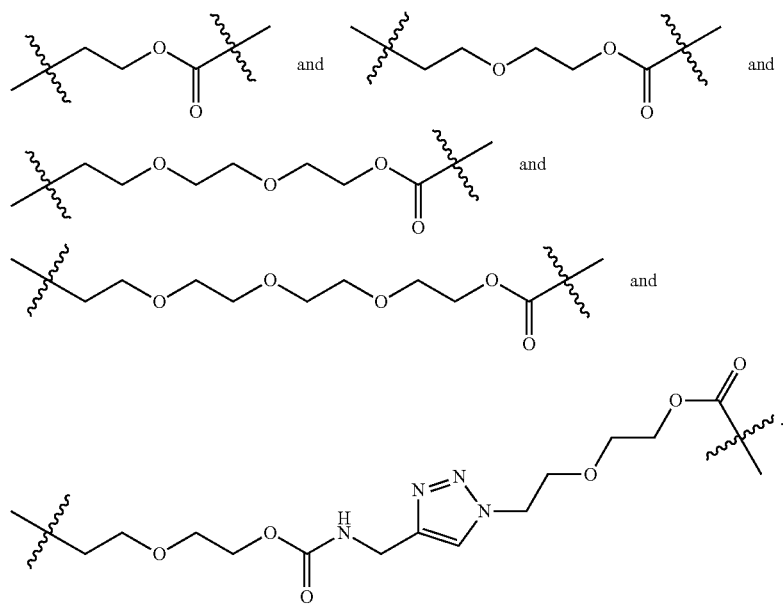
In yet another embodiment, L is selected from
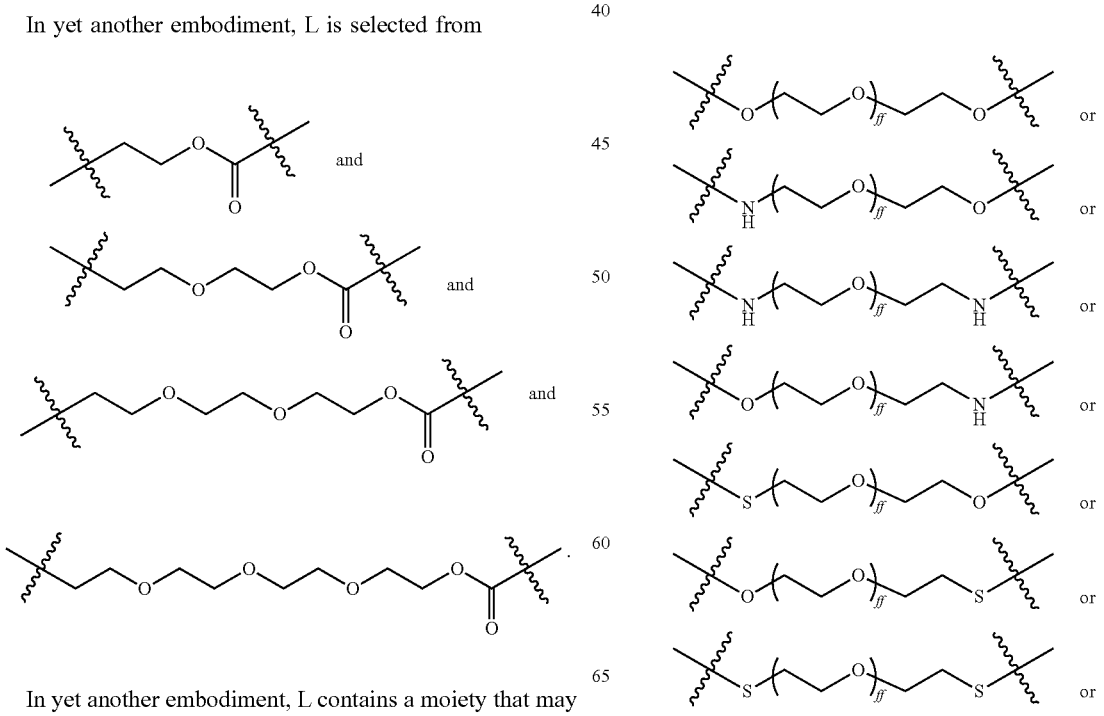
In yet another embodiment, L contains a moiety that may for example be

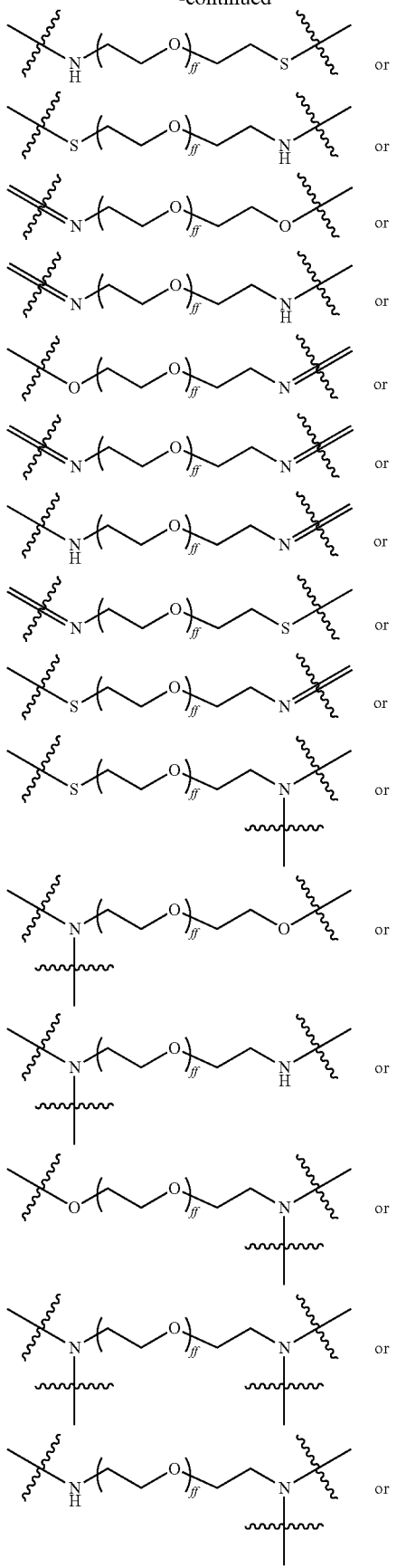
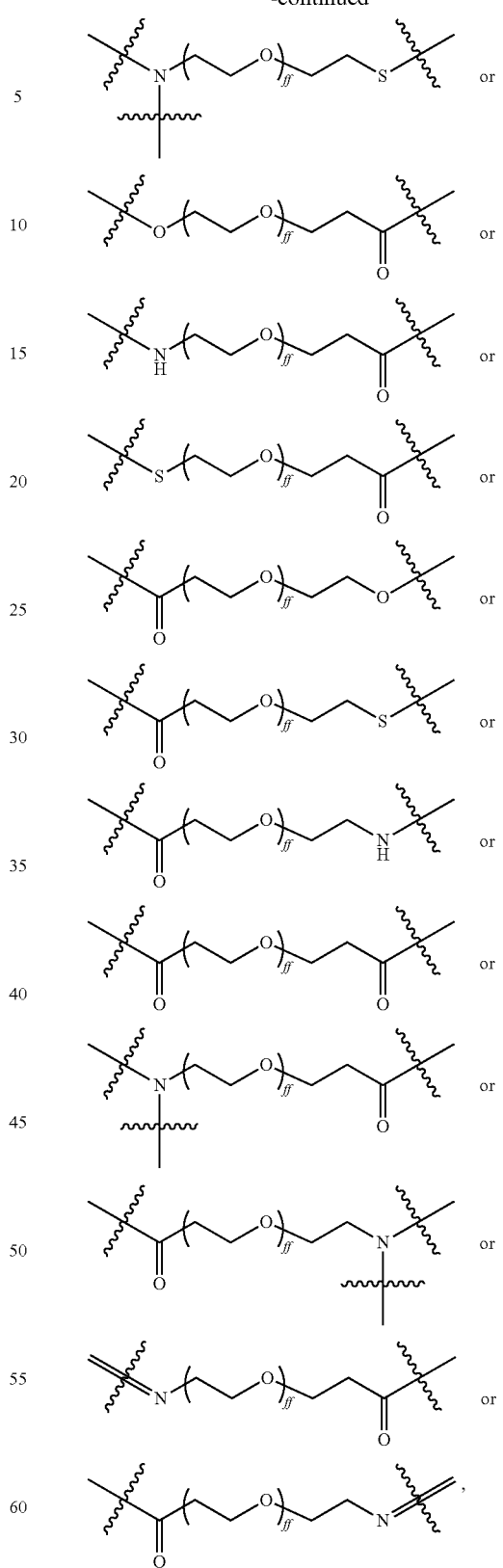
wherein ff is selected from 1 to 1000. In other embodiments, ff is selected from 3 to 1000 or 500 or 100 or 50 or 10. In other embodiments, ff is selected to be 1 or 2 or 3 or 4 or 5.

In yet another embodiment, L is selected from
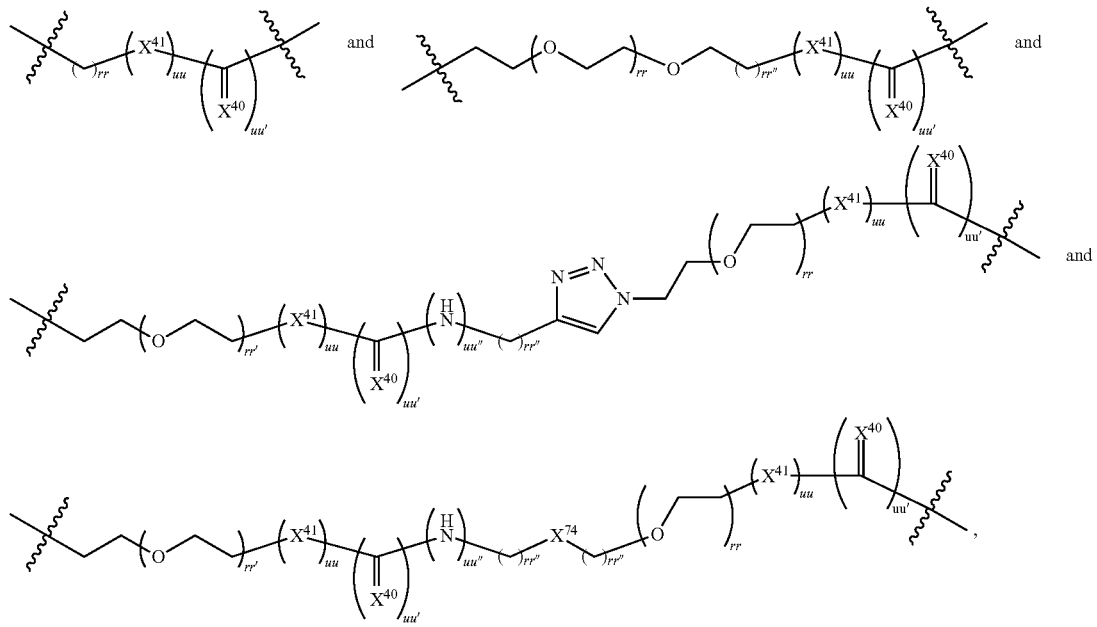
wherein rr, rr', rr", and rr''' each independently range from 0 to 8, $X^{74}$ is selected from
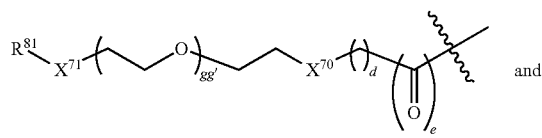
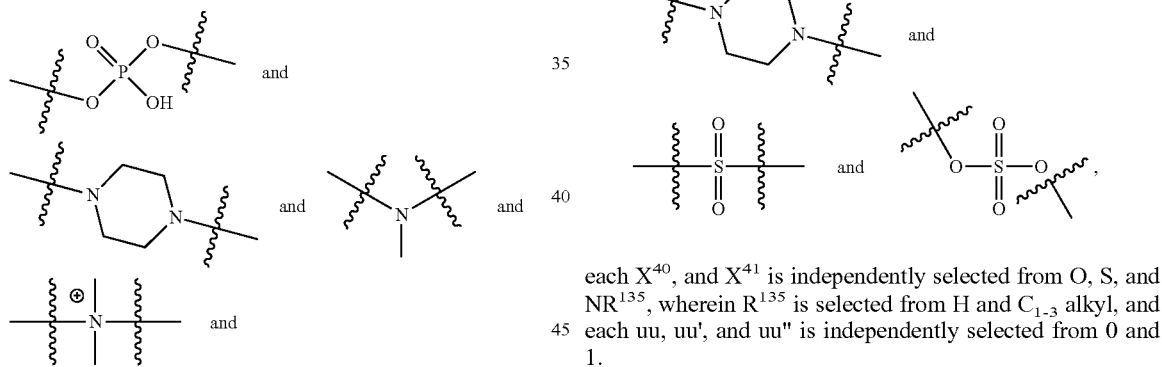
each $X^{40}$, and $X^{41}$ is independently selected from O, S, and $NR^{135}$, wherein $R^{135}$ is selected from H and $C_{1-3}$ alkyl, and each uu, uu', and uu" is independently selected from 0 and 1.
In another embodiment, L is selected from
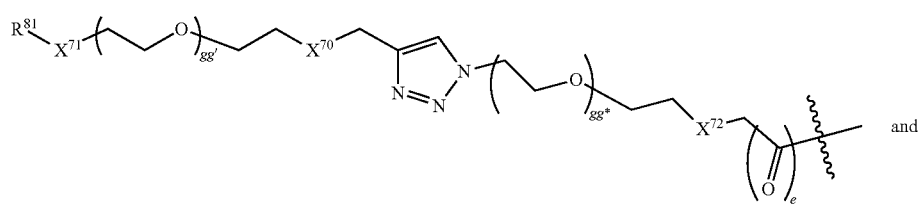

-continued

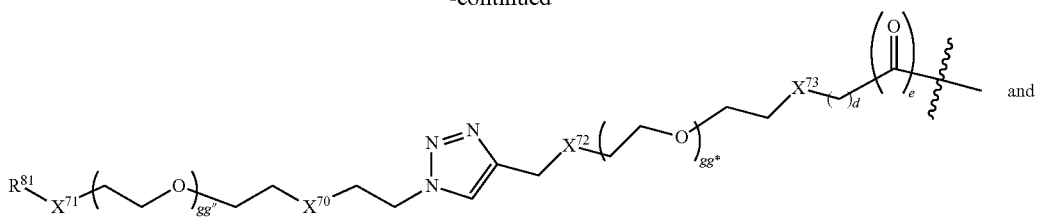

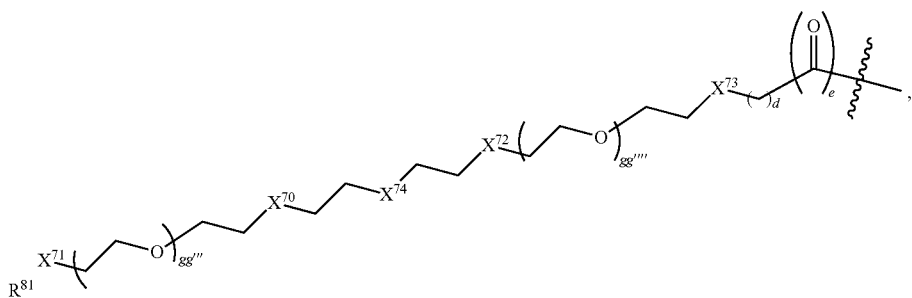

wherein $X^{70}$, $X^{71}$, $X^{72}$, and $X^{73}$ are independently selected from O, S, and $NR^{82}$, $X^{74}$ is selected from

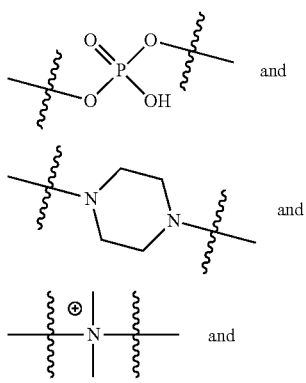

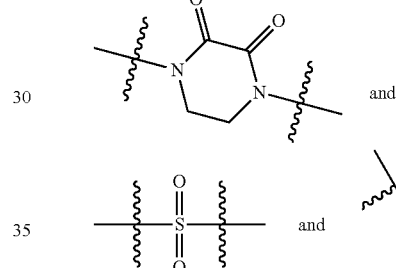

d is selected from 0 to 8, e is 0 or 1, gg', gg'', gg''', gg'''', and gg* are independently selected from 0 to 1000, and $R^{81}$ and $R^{82}$ are independently selected from H and optionally substituted $C_{1-3}$ alkyl. In other embodiments, gg', gg'', gg''', gg'''', and gg* are independently selected from 3 to 1000 or 500 or 100 or 50 or 10.

In yet another embodiment, L is not

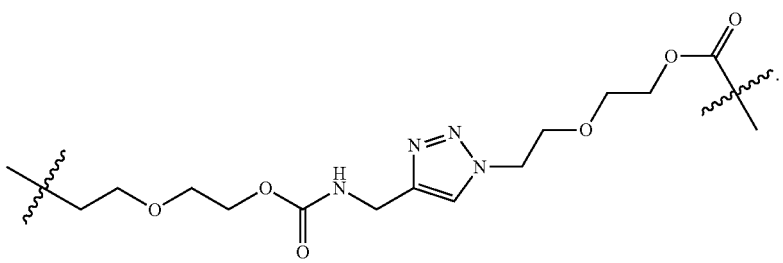 [SMILES: *CCOCCOC(=O)NCc1cn(CCOCCOC(*)=O)nn1]

The linkage between L and $V^1$ or Y may for example be an amide, a ureum, a carbonate, or a carbamate linkage. In one embodiment, the linkage between L and $V^1$ is a ureum, carbonate, or carbamate linkage. Alternatively, when $V^1$ is a peptide in which the N-terminal amino acid is an amino acid mimic that carries an α-azido group instead of an α-amino group, the linkage between L and $V^1$ may be a triazole group formed through reaction of an acetylene group being part of L and the α-azido group of $V^1$.

The Reactive Moiety RM and the Linking Group $L^2$

The reactive moiety RM in a compound of formula (IV) is connected to the linking group L and is able to react with a suitable functional group on a reaction partner.

In one embodiment of this invention, the reactive moiety RM is designed to react with a functional group on the moiety $V^2$, which results in formation of a compound of formula (III). In this reaction, the moiety RM is transformed into the moiety $L^2$. In another embodiment, the reactive moiety RM is designed to react with a complementary moiety in situ, e.g., in vivo, for example with serum albumin, to give a compound that may or may not be a compound of formula (III).

In one aspect of this invention, the reactive moiety RM contains an electrophilic group that reacts with a nucleophilic group on the reaction partner, for example $V^2$, e.g., a thiol group, an amino group, or a hydroxy group.

In another aspect of this invention, the reactive moiety RM contains a nucleophilic group that reacts with an electrophilic group on the reaction partner, for example $V^2$, e.g., an aldehyde group.

In another aspect of the invention, the reactive moiety RM contains a cycloaddition partner moiety, e.g., an alkene, a diene, a 1,3-dipole, or a 1,3-dipolarophile, that reacts with a suitable complementary cycloaddition partner moiety on the reaction partner, for example $V^2$, e.g., a diene, an alkene, a 1,3-dipolarophile, or a 1,3-dipole.

In another aspect of the invention, the reactive moiety RM contains a group that can be coupled with a suitable complementary group on the reaction partner, for example $V^2$, under metal-catalyzed, biocatalyzed, or enzyme-catalyzed conditions, e.g., palladium-catalyzed conditions.

In one aspect of the invention, the reactive moiety RM is, without limitation,

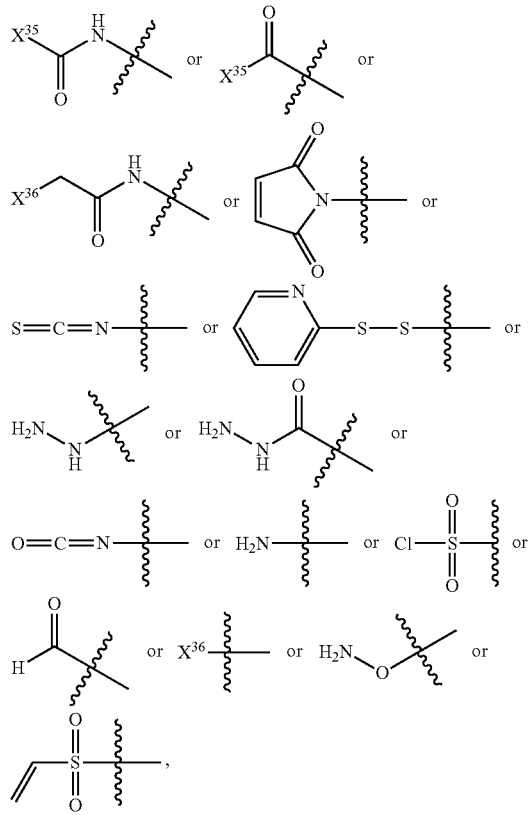

wherein $X^{35}$ is selected from halide, hydroxy, $OC(O)R^{dd}$, and $OC(O)OR^{dd}$, or $C(O)-X^{35}$ is an active ester, $X^{36}$ is selected from halide, mesyloxy, triflyloxy, and tosyloxy, and $R^{dd}$ is selected from optionally substituted $C_{1-10}$ alkyl, $C_{1-10}$ heteroalkyl, $C_{3-10}$ cycloalkyl, $C_{1-10}$ heterocycloalkyl, $C_{5-10}$ aryl, and $C_{1-10}$ heteroaryl.

In one embodiment, the moiety RM is selected from

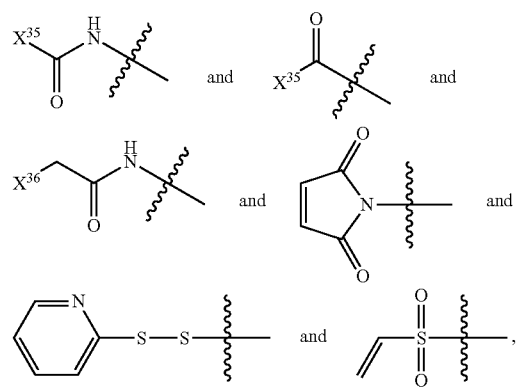

which makes it able to react with a thiol group on the reaction partner, for example moiety $V^2$.

In another embodiment, the moiety RM is

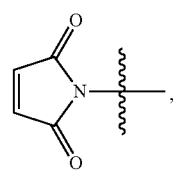 [SMILES: *N1C(=O)C=CC1=O]

which makes it able to react with a thiol group on the reaction partner, for example moiety $V^2$.

In another embodiment, the moiety RM is

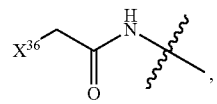

wherein $X^{36}$ is Br, which makes it able to react with a thiol group on the reaction partner, for example moiety $V^2$.

In another embodiment, the moiety RM is selected from

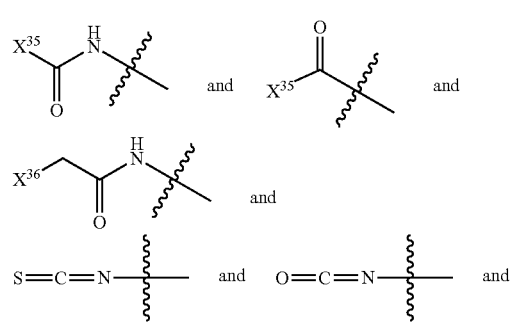

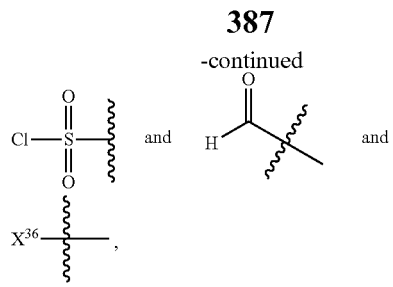

which makes it able to react with an amino group, e.g., a primary or secondary amino group, on the reaction partner, for example moiety $V^2$.

In another embodiment, the moiety RM is selected from

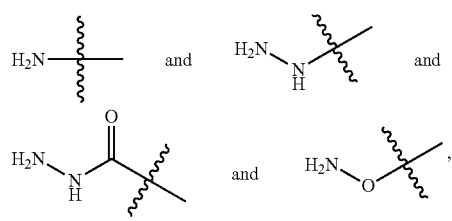

which makes it able to react with an aldehyde group on the reaction partner, for example moiety $V^2$.

The linking group $L^2$ in a compound of formula (III) represents the remainder of RM when the reactive moiety RM has reacted with $V^2$. This group then links the moiety $V^2$ with L. The group that remains may be a bond, meaning that $L^2$ is absent. Typically, however, $L^2$ is a linking group. When a compound of formula (III) is formed other than via a compound of formula (IV), $L^2$ does not represent the remainder of RM, but may represent a similar or the same moiety and in addition be selected from for example optionally substituted $C_{1-10}$ alkylene, $C_{1-10}$ heteroalkylene, $C_{3-10}$ cycloalkylene, $C_{1-10}$ heterocycloalkylene, $C_{5-10}$ arylene, and $C_{1-10}$ heteroarylene. The $L^2$ moiety may optionally comprise a $X^{14}(CH_2CH_2O)_{gg}CH_2CH_2X^{14}$ moiety.

In one embodiment, the moiety $L^2$ is absent.

In another embodiment, the moiety $L^2$ is, without limitation,

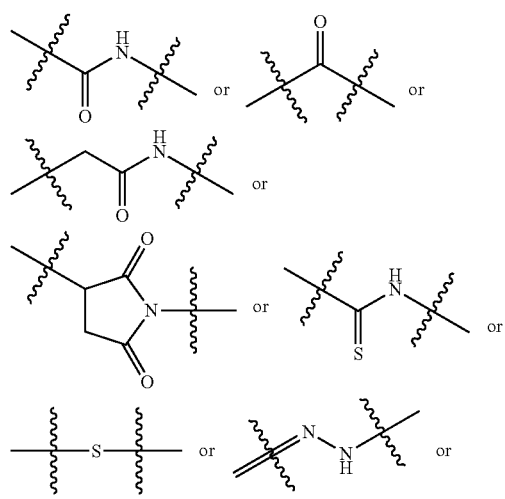

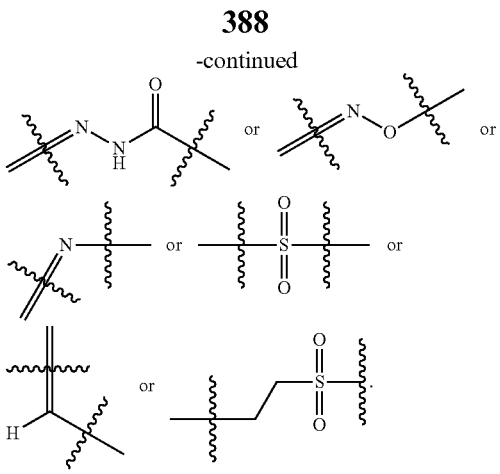

In a further embodiment, the moiety $L^2$ is

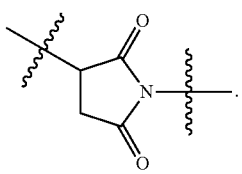 [SMILES: *C1CC(=O)N(*)C1=O]

In yet a further embodiment, the moiety $L^2$ is

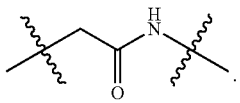 [SMILES: *CC(=O)N*]

The RM2 Moiety

RM2 may be a reactive moiety or a leaving group.

If RM2 is a reactive moiety, it is preferably different from the RM reactive moiety. In this way, reactions with the bifunctional linker may be carried out selectively and individually with each of the reactive moieties. When RM2 is a reactive moiety, this means that after reaction with a therapeutic or diagnostic moiety or a promoiety-containing derivative thereof, the RM2 moiety (or what remains of it after reaction) may become part of said therapeutic or diagnostic moiety or a promoiety-containing derivative thereof optionally together with any part of Y which may not self-eliminate because of a limited or absent leaving capability of therapeutic or diagnostic moiety-conjugated RM2.

In one embodiment, the RM2 may be connected to Y and be

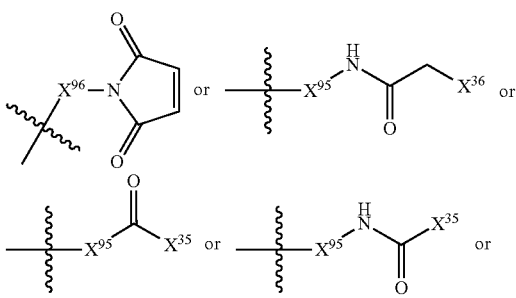

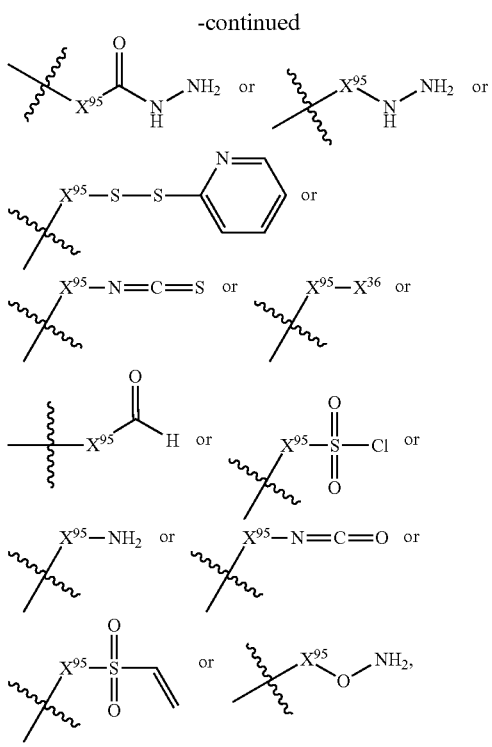

wherein
$X^{35}$ is selected from halide, hydroxy, $OC(O)R^{dd}$, and $OC(O)OR^{dd}$, or $C(O)$—$X^{35}$ is an active ester, $X^{36}$ is selected from halide, mesyloxy, triflyloxy, and tosyloxy, $X^{95}$ is either absent or selected from O, S, $NR^{95}$, $C_{1-3}$ alkyl, and $C_{1-3}$ heteroalkyl, $R^{dd}$ is selected from optionally substituted $C_{1-10}$ alkyl, $C_{1-10}$ heteroalkyl, $C_{3-10}$ cycloalkyl, $C_{1-10}$ heterocycloalkyl, $C_{5-10}$ aryl, and $C_{1-10}$ heteroaryl, and $R^{95}$ is selected from H and $C_{1-3}$ alkyl.

RM2 may also be a leaving group. In this case, RM2 is replaced by the therapeutic or diagnostic moiety or a pro-moiety-containing derivative thereof in a reaction of a compound of formula (VIII) with such a therapeutic or diagnostic moiety or a derivative thereof and this therapeutic or diagnostic moiety or a derivative thereof becomes directly attached to Y.

In one embodiment, RM2 is selected from a halide (fluoride, chloride, bromide, and iodide), azide, a sulfonate (e.g., an optionally substituted $C_{1-6}$ alkanesulfonate, such as methanesulfonate, trifluoromethanesulfonate, and trifluoroethanesulfonate, or an optionally substituted benzenesulfonate, such as p-toluenesulfonate and nosylate), imidazole, a cyclic imide thione, succinimide-N-oxide, phtalimide-N-oxide, p-nitrophenoxide, o-nitrophenoxide, pentafluorophenoxide, tetrafluorophenoxide, 1,3,5-trichlorophenoxide, 1,3,5-trifluorophenoxide, a carboxylate, an aminocarboxylate (carbamate), an alkoxycarboxylate (carbonate), and an alkoxy group that together with the carbonyl group of Y can be referred to as an active ester group. Such alkoxy groups include, but are not limited to, succinimide-N-oxide, p-nitrophenoxide, pentafluorophenoxide, tetrafluorophenoxide, 1-hydroxybenzotriazole, and 1-hydroxy-7-azabenzotriazole, and groups with comparable leaving capability.

The Moiety $V^2$

The moiety $V^2$ is a functional moiety, which means that it adds additional functionality to a compound of the invention.

In one embodiment, $V^2$ is a targeting moiety. In another embodiment, the $V^2$ moiety is a moiety that improves the pharmacological properties of a compound of the invention. In yet another embodiment, the $V^2$ moiety is a moiety that causes accumulation of a compound of the invention at a target site. In yet another embodiment, the $V^2$ moiety is a moiety that improves the aqueous solubility of a compound of the invention. In yet another embodiment, the $V^2$ moiety is a moiety that increases the hydrophobicity of a compound of the invention. In yet another embodiment, the $V^2$ moiety is a moiety that reduces extravasation of a compound of the invention. In yet another embodiment, the $V^2$ moiety is a moiety that reduces excretion of a compound of the invention. In yet another embodiment, the $V^2$ moiety is a moiety that reduces the immunogenicity of a compound of the invention. In yet another embodiment, the $V^2$ moiety is a moiety that enhances the circulation time of a compound of the invention. In yet another embodiment, the $V^2$ moiety is a moiety that enhances the ability of a compound of the invention to cross a biological barrier, e.g., a membrane, cell wall, or the blood-brain barrier. In yet another embodiment, the $V^2$ moiety is a moiety that enhances the ability of a compound of the invention to internalize. In yet another embodiment, the $V^2$ moiety is a moiety that enables a compound of the invention to internalize. In yet another embodiment, the $V^2$ moiety is a moiety that causes the compounds of the invention to aggregate. In yet another embodiment, the $V^2$ moiety is a moiety that reduces aggregation of a compound of the invention. In yet another embodiment, the $V^2$ moiety is a moiety that causes a compound of the invention to form micelles or liposomes. In yet another embodiment, the $V^2$ moiety is a moiety that causes complexation of a compound of the invention to another molecule, e.g., a biomolecule. In yet another embodiment, the $V^2$ moiety is a polynucleotide moiety that complexes with a complementary nucleotide sequence, for example RNA or DNA. In yet another embodiment, the $V^2$ moiety is a moiety that causes a compound of the invention to bind, associate, interact, or complex to another moiety, for example a (functionalized) surface or solid support.

In another embodiment, $V^2$ exhibits two or more different functions. The $V^2$ moiety may for example be a targeting moiety and at the same time improve the pharmacological properties, including water solubility.

In one aspect of the invention, the moiety $V^2$ includes within its scope any unit that binds or reactively associates or complexes with a receptor, a receptor complex, antigen, or other moiety associated with a given target cell population. $V^2$ can be any molecule that binds to, complexes with, or reacts with a moiety of a cell population sought to be therapeutically or otherwise biologically modified. The $V^2$ moiety acts to deliver the one or more moieties Z to the particular target cell population with which $V^2$ reacts or to which $V^2$ binds. Such $V^2$ moieties include, but are not limited to, aptamers, full-length antibodies and antibody fragments and derivatives thereof, lectins, biologic response modifiers, enzymes, vitamins, growth factors, steroids, nutrients, sugar residues, oligosaccharide residues, hormones, and any derivatives thereof, or any combination of any of these. Upon binding, reactively associating, or complexing, the compounds of the invention may or may not be internalized. If internalization occurs, transformation and/or cleavage of $V^1$ preferably occur inside the target cell.

Useful non-immunoreactive protein, polypeptide, or peptide $V^2$ moieties include, but are not limited to, transferrin, epidermal growth factors ("EGF"), bombesin, gastrin and its derivatives, gastrin-releasing peptide, platelet-derived growth factor, IL-2, IL-6, transforming growth factors ("TGF"), such as TGF-a and TGF-P, tumor growth factors, vaccinia growth factor ("VGF"), insulin and insulin-like growth factors I and II, lectins, and apoprotein from low density lipoprotein.

Useful polyclonal antibody $V^2$ moieties are heterogeneous populations of antibody molecules. Various procedures well-known in the art may be used for the production of polyclonal antibodies to an antigen-of-interest.

Useful monoclonal antibody $V^2$ moieties are homogeneous populations of antibodies to a particular antigen (e.g., a cancer cell antigen). A monoclonal antibody (mAb) to an antigen-of-interest can be prepared by using any technique known in the art which provides for the production of monoclonal antibody molecules.

Useful monoclonal antibody $V^2$ moieties include, but are not limited to, human monoclonal antibodies, humanized monoclonal antibodies, or chimeric human-mouse (or other species) monoclonal antibodies. Monoclonal antibodies may be made by any of numerous techniques known in the art.

The $V^2$ moiety can also be a bispecific antibody. Methods for making bispecific antibodies are known in the art.

The $V^2$ moiety can be a functionally active fragment, derivative, or analog of an antibody that immunospecifically binds to an antigen on a target cell, e.g., a cancer cell antigen. In this regard, "functionally active" means that the fragment, derivative, or analog is able to elicit anti-anti-idiotype antibodies that recognize the same antigen that the antibody from which the fragment, derivative, or analog is derived, recognizes.

Other useful $V^2$ moieties comprise fragments of antibodies including, but not limited to, F(ab')$_2$ fragments, which contain the variable region, the light chain constant region, and the CH1 domain of the heavy chain, which can be produced by pepsin digestion of the antibody molecule, and Fab fragments, which can be generated by reducing the disulfide bridges of the F(ab')$_2$ fragments. Other useful $V^2$ moieties are heavy chain and light chain dimers of antibodies, or any minimal fragment thereof such as Fvs or single chain antibodies (SCAs), domain antibodies, anticalins, affibodies, nanobodies, and any other molecules with the same, similar, or comparable specificity as the parent antibody.

Additionally, recombinant antibodies, such as chimeric and humanized monoclonal antibodies, comprising both human and non-human portions, which can be made using standard recombinant DNA techniques, are useful $V^2$ moieties. A chimeric antibody is a molecule in which different portions are derived from different animal species, such as those having a variable region derived from a murine monoclonal and a human immunoglobulin constant region. Humanized antibodies are antibody molecules from non-human species having one or more complementarity determining regions (CDRs) from the non-human species and a framework region from a human immunoglobulin molecule.

Completely human antibodies are particularly desirable as $V^2$ moieties. Such antibodies can for example be produced using transgenic mice that are incapable of expressing endogenous immunoglobulin heavy and light chains genes, but which can express human heavy and light chain genes.

In other embodiments, the $V^2$ moiety is a fusion protein of an antibody, or a functionally active fragment or derivative thereof, for example one in which the antibody is fused via a covalent bond (e.g., a peptide bond) at either the N-terminus or the C-terminus to an amino acid sequence of another protein (or portion thereof, preferably at least a 10, 20, or 50 amino acid portion of the protein) that is not the antibody. Preferably, the antibody or fragment thereof is covalently linked to the other protein at the N-terminus of the constant domain.

The $V^2$ moiety antibodies include analogs and derivatives that are modified, i.e., by the covalent attachment of any type of molecule as long as such covalent attachment permits the antibody to retain its antigen-binding immunospecificity. For example, but not by way of limitation, derivatives and analogs of antibodies include those that have been further modified, e.g., by glycosylation, acetylation, pegylation, disulfide reduction, phosphylation, amidation, derivatization by known protecting or blocking groups, proteolytic cleavage, linkage to another protein, etc. Additionally, the analog or derivative can contain one or more unnatural amino acids.

The $V^2$ moiety antibodies include antibodies having modifications (e.g., substitutions (for example cysteine to serine or serine to cysteine), deletions, or additions). In particular, they include antibodies having modifications in amino acid residues identified as involved in the interaction between the Fc domain and the FcRn receptor. Modifications may also be introduced to be able to couple the antibody to linker-agent conjugates at specific positions on the antibody.

In a specific embodiment, an antibody immunospecific for a cancer or tumor antigen is used as a $V^2$ moiety in accordance with the compounds, compositions, and methods of the invention.

Antibodies immunospecific for a cancer cell antigen can be obtained commercially or produced by any method known to one of skill in the art, such as chemical synthesis or recombinant expression techniques. The nucleotide sequences encoding antibodies immunospecific for a cancer cell antigen can be obtained, e.g., from the GenBank database or a database like it, a commercial or other source, literature publications, or by routine cloning and sequencing.

Examples of antibodies available for the treatment of cancer that may be useful for incorporation into conjugates of this invention as a $V^2$ moiety include, but are not limited to, HERCEPTIN (trastuzumab), which is a humanized anti-HER$^2$ monoclonal antibody for the treatment of patients with metastatic breast cancer; RITUXAN (rituximab), which is a chimeric anti-CD20 monoclonal antibody for the treatment of patients with non-Hodgkin's lymphoma; OvaRex (oregovomab), which is a murine antibody for the treatment of ovarian cancer; Panorex (edrecolomab), which is a murine IgG$_{2a}$ antibody for the treatment of colorectal cancer; IMC-BEC2 (mitumomab), which is a murine IgG antibody for the treatment of lung cancer; IMC-C225 (erbitux), which is a chimeric IgG antibody for the treatment of head and neck cancer; Vitaxin, which is a humanized antibody for the treatment of sarcoma; Campath I/H (alemtuzumab), which is a humanized IgG$_1$ antibody for the treatment of chronic lymphocytic leukemia (CLL); SGN-70, which is a humanized anti-CD70 antibody for the treatment of hematologic malignancies; Smart MI95, which is a humanized IgG antibody for the treatment of acute myeloid leukemia (AML); J591, which is a humanized antibody against prostate specific membrane antigen; LymphoCide (epratuzumab), which is a humanized IgG antibody for the treatment of non-Hodgkin's lymphoma; SGN-33, which is a humanized anti-CD33 antibody for the treatment of acute myeloid leukemia; Smart ID 10, which is a humanized antibody for the treatment of non-Hodgkin's lymphoma; Oncolym, which is a murine antibody for the treatment of non-Hodgkin's lymphoma; Allomune, which is a humanized anti-CD2 mAb for the treatment of Hodgkin's disease or non-Hodgkin's lymphoma; Avastin (bevacizumab), which is a humanized anti-VEGF antibody for the treatment of lung and colorectal cancers; SGN-40, which is a humanized anti-CD40 antibody for the treatment of multiple myeloma; SGN-30, which is a chimeric anti-CD30 antibody for the treatment of Hodgkin's disease; CEAcide, which is a humanized anti-CEA antibody for the treatment of colorectal cancer; IMC-1C11, which is an anti-KDR chimeric antibody for the treatment of colorectal cancer, lung cancers, and melanoma; and Cetuximab, which is an anti-EGFR chimeric antibody for the treatment of epidermal growth factor positive cancers.

Other antibodies that may be useful for incorporation into conjugates of this invention as a $V^2$ moiety include, but are not limited to, antibodies against the following antigens: CA125, CA9, CA6, CA15-3, CA19-9, $L^6$, Lewis Y, Lewis X, Lewis A, alpha fetoprotein, CA 242, placental alkaline phosphatase, prostate specific antigen (PSA), prostate specific membrane antigen (PSMA), prostatic acid phosphatase, epidermal growth factor receptors, interleukin receptors, integrins, insulin-like growth factor receptors, CanAg, DAF, PEM, IRTA-2, IRTA-4, AFP, HER$^2$, EGFR, VEGFR1, VEGFR2, MAGE-1, LUCA1, LUCA2, MAGE-2, MAGE-3, MAGE-4, ED-B, MADCAM, CEACAMS, MCP-1, Cripto, TAT226, VLA-4, C3B, anti-transferrin receptor, endosialin, E-selectin, GCC, GP-75, Syndecan-1, GPNMB, ROBO4, STEAP-1, CMET, EGP-1, Kim-1, Tim-1, Eph receptor tyrosine kinases, HMW-MAA, TMEFF2, PSCA, CLL-1, TNF-α, FAP-α, IFN-α, EphA2, EphB2, EphB3, EphB4, EGFL-7, DLL-4, RS7, 4-1BB, TENB2, FLT3, p97, FGF19, FGFR$^2$, glypican-3, P53, $L^{53}$, RON, MN, GFR-α3, FDF03, TSLPR, MUC1-KLH, Tag 72, MUC18, B7H4, PTK7, RG-1, MUC16, CSAP, PDGF, PSMA, 5T4, EpCAM, SGA-1M, SGA-56M, SGA-72M, IGF1R, CCR$^2$, CCR$^5$, CTLA4, CLCA-1, ELAM1, DR$^5$, CEA, CXCR-4, GD2, gp100, GD3 ganglioside, $L^{243}$, HMGB1, GPC-3, MART1, IL-2 receptor, CD2, CD3, CD303, CD4, CD20, CD43, CD44, CD30, CD55, CD151, CD154, CD19, CD21, CD23, CD79, CD52, CD25, CD45, CD46, CD56, CD59, CD7, CD137, CD138, CD74, CD133, CD80, CD63, CD64, CD66, CD140b, CD32, CD33, CD37, CD22, CD27, Apo-2, ERBB4, HLA-DR, HLA-DR10, human chorionic gonadotropin, CD38, CD40, CD70, mucin, P21, a cancer stem cell-specific receptor, MPG, and Neu oncogene product. Many other internalizing or non-internalizing antibodies that bind to tumor-associated antigens can be used in this invention as a $V^2$ moiety, some of which have been reviewed[14].

In one embodiment, the anti-Her2 antibody trastuzumab is selected as the $V^2$ moiety. In another embodiment, an epitope-binding functional fragment or derivative of trastuzumab is selected as the $V^2$ moiety. In yet another embodiment, an anti-Her2 antibody or a functional fragment or derivative thereof is selected as the $V^2$ moiety. In yet another embodiment, an anti-Her2 antibody or functional fragment or derivative thereof that has improved properties with respect to trastuzumab is selected as the $V^2$ moiety; improved properties may for example be increased binding, longer circulation half-life, increased internalization rate, higher binding specificity for tumor tissue compared to non-tumor tissue, and/or reduced immunogenicity.

In yet another embodiment, the anti-PSMA antibody J591 is selected as the $V^2$ moiety. In another embodiment, an epitope-binding functional fragment or derivative of J591 is selected as the $V^2$ moiety. In yet another embodiment, an anti-PSMA antibody or a functional fragment or derivative thereof is selected as the $V^2$ moiety. In yet another embodiment, an anti-PSMA antibody or functional fragment or derivative thereof that has improved properties with respect to J591 is selected as the $V^2$ moiety; improved properties may for example be increased binding, longer circulation half-life, increased internalization rate, higher binding specificity for tumor tissue compared to non-tumor tissue, and/or reduced immunogenicity.

In yet other embodiments, an anti-CD19 antibody or an anti-CD22 antibody or an anti-CD30 antibody or an anti-CD33 antibody or an anti-CD56 antibody or an anti-CD70 antibody or an anti-CD74 antibody or an anti-CD138 antibody or an anti-CLL-1 antibody or an anti-5T4 antibody or an anti-CD303 antibody or an anti-Tag 72 antibody or an anti-Lewis A like carbohydrate antibody or an anti-EphB3 antibody or an anti-HMW-MAA antibody or an anti-CD38 antibody or an anti-Cripto antibody or an anti-EphA2 antibody or an anti-GPNMB antibody or an anti-integrin antibody or an anti-MN antibody is selected as the $V^2$ moiety. In yet other embodiments, an epitope-binding functional fragment or derivative of an anti-CD19 antibody or an anti-CD22 antibody or an anti-CD30 antibody or an anti-CD33 antibody or an anti-CD56 antibody or an anti-CD70 antibody or an anti-CD74 antibody or an anti-CD138 antibody or an anti-CLL-1 antibody or an anti-5T4 antibody or an anti-CD303 antibody or an anti-Tag 72 antibody or an anti-Lewis A like carbohydrate antibody or an anti-EphB3 antibody or an anti-HMW-MAA antibody or an anti-CD38 antibody or an anti-Cripto antibody or an anti-EphA2 antibody or an anti-GPNMB antibody or an anti-integrin antibody or an anti-MN antibody is selected as the $V^2$ moiety. Therefore, in one embodiment, the $V^2$ moiety may be selected from an anti-CD19 antibody, an anti-CD22 antibody, an anti-CD30 antibody, an anti-CD33 antibody, an anti-CD56 antibody, an anti-CD70 antibody, an anti-CD74 antibody, an anti-CD138 antibody, an anti-CLL-1 antibody, an anti-5T4 antibody, an anti-CD303 antibody, an anti-Tag 72 antibody, an anti-Lewis A like carbohydrate antibody, an anti-EphB3 antibody, an anti-HMW-MAA antibody, an anti-CD38 antibody, an anti-Cripto antibody, an anti-EphA2 antibody, an anti-GPNMB antibody, an anti-integrin antibody, an anti-MN antibody, an anti-Her2 antibody, and an anti-PSMA antibody, or from an epitope-binding functional fragment or derivative of any of these.

In some embodiments, the antibody is an anti-nuclear antibody or an antibody that can bind to a receptor or receptor complex expressed on a target cell. The receptor or receptor complex can comprise an immunoglobulin gene superfamily member, an integrin, a chemokine receptor, a TNF receptor superfamily member, a cytokine receptor, a major histocompatibility protein, a complement control protein, or a lectin.

In another specific embodiment, an antibody immunospecific for an antigen associated with an autoimmune disease is used as a $V^2$ moiety in accordance with the compounds, compositions, and methods of the invention. In another specific embodiment, an antibody immunospecific for a viral or microbial antigen is used as a $V^2$ moiety in accordance with the compounds, compositions, and methods of the invention. As used herein, the term "viral antigen" includes, but is not limited to, any viral peptide, polypeptide, protein, saccharide, polysaccharide, or lipid that is capable of eliciting an immune response. As used herein, the term "microbial antigen" includes, but is not limited to, any microbial peptide, polypeptide, protein, saccharide, polysaccharide, or lipid that is capable of eliciting an immune response.

New antibodies are continually being discovered and developed, and the present invention provides that these new antibodies may also be incorporated into a compound of this invention.

$V^2$ can react with the reactive moiety RM via for example a heteroatom on $V^2$. Heteroatoms that may be present on $V^2$ include, without limitation, sulfur (in one embodiment, from a sulfhydryl group), oxygen (in one embodiment, from a carboxyl or hydroxyl group), and nitrogen (in one embodiment, from a primary or secondary amino group). $V^2$ may also react via for example a carbon atom (in one embodiment, from a carbonyl group). These atoms can be present on $V^2$ in $V^2$'s natural state, for example a naturally occurring antibody, or can be introduced into $V^2$ via (chemical) modification.

Free sulfhydryl groups can be generated in an antibody or antibody fragment by reduction of the antibody (fragment) with a reducing agent such as dithiothreitol (DTT) or tris(2-carboxyethyl)phosphine (TCEP). In this way, modified antibodies can be obtained that can have from 1 to about 20 sulfhydryl groups, but typically between about 1 and about 9 sulfhydryl groups.

Alternatively, $V^2$ can have one or more carbohydrate groups that can be chemically modified to contain one or more sulfhydryl groups. As another alternative, sulfhydryl groups can be generated by reaction of amino groups, for example from lysine moieties, on $V^2$ with 2-iminothiolane (Traut's reagent), N-succinimidyl S-acetylthioacetate (SATA), or another sulfhydryl-generating reagent. Such a reagent may also be used to introduce additional functionality. For example, a sulfhydryl-generating reagent may be used that not only introduces a sulfhydryl group onto $V^2$, but at the same time introduces a water-soluble moiety such as an oligoethylene glycol or polyethylene glycol. Such a group may be present as a substituent in the reagent (instead of being part of the main chain) in order to keep the sulfhydryl group close to the $V^2$ moiety. The presence of such a water-soluble moiety may eventually improve the pharmacological properties of a compound of formula (III).

In one embodiment, the $V^2$ moiety is a receptor-binding moiety.

In another embodiment, the $V^2$ moiety is an antibody or an antibody fragment or a derivative thereof.

In another embodiment, the $V^2$ moiety is a monoclonal antibody or a fragment or derivative thereof.

In one embodiment, $V^2$ has one or more sulfhydryl groups and $V^2$ reacts with one or more RM moieties of one or more compounds of formula (IV) via one or more of these sulfhydryl groups' sulfur atoms to form a compound of formula (III) in which one or more compounds of formula (IV) have thus been incorporated.

In yet another embodiment, $V^2$ contains one or more disulfide bonds that can be chemically reduced to sulfhydryl groups (two for each disulfide bond), which can then be reacted with one or more reactive moieties RM to form a compound of formula (III).

In another embodiment, $V^2$ contains about 1 to about 3 sulfhydryl groups, which can be reacted with one or more reactive moieties RM to form a compound of formula (III).

In another embodiment, $V^2$ contains about 2 sulfhydryl groups, which can be reacted with one or more reactive moieties RM to form a compound of formula (III).

In another embodiment, $V^2$ contains about 3 to about 5 sulfhydryl groups, which can be reacted with one or more reactive moieties RM to form a compound of formula (III).

In another embodiment, $V^2$ contains about 4 sulfhydryl groups, which can be reacted with one or more reactive moieties RM to form a compound of formula (III).

In another embodiment, $V^2$ contains about 7 to about 9 sulfhydryl groups, which can be reacted with one or more reactive moieties RM to form a compound of formula (III).

In another embodiment, $V^2$ contains about 8 sulfhydryl groups, which can be reacted with one or more reactive moieties RM to form a compound of formula (III).

In another embodiment, $V^2$ can have one or more carbohydrate groups that can be chemically modified to have one or more sulfhydryl groups. $V^2$ reacts with RM moieties via these one or more sulfhydryl groups' sulfur atoms to form a compound of formula (III).

In another embodiment, $V^2$ can have one or more lysine groups that can be chemically modified to have one or more sulfhydryl groups, which can be reacted with one or more reactive moieties RM to form a compound of formula (III).

Reactive moieties that can react with a sulfhydryl group include, but are not limited to, carbamoyl halide, acyl halide, α-haloacetamide, halomethyl ketone, vinyl sulfone, maleimide, and 2-disulfanylpyridine.

In yet another embodiment, $V^2$ can have one or more carbohydrate groups that can be oxidized to provide one or more aldehyde groups. The corresponding aldehyde(s) can then react with one or more reactive moieties RM to form a compound of formula (III). Reactive moieties that can react with an aldehyde group on $V^2$ include, but are not limited to, hydrazine, hydrazide, amine, and hydroxylamine.

In yet another embodiment, $V^2$ can have one or more amino groups, e.g., from lysine residues, which can be reacted with one or more reactive moieties RM to form a compound of formula (III). Reactive moieties that can react with an amino group include, but are not limited to, carbamoyl halide, α-haloacetamide, acyl halide, aldehyde, sulfonyl chloride, alkyl halide, alkyl sulfonate, isocyanate, and isothiocyanate.

A conjugate of formula (III) may exist as a mixture, wherein each component of the mixture has a different q value. For example, the compound may exist as a mixture of two separate compounds, one compound wherein q is 2 and another compound wherein q is 3. As another example, a compound may exist as a mixture of 5 separate compounds, in which q is 1, 2, 3, 4, and 5, respectively. As yet another example, a compound may exist as a mixture of more than 5 separate compounds. Such mixtures might further be "contaminated" with unconjugated $V^2$. When analyzing the compound of formula (III) it is understood that q may be the (rounded) average number of $L^2$-L(-($V^1$-Y))$_p$(Z)$_{z/q}$ units per $V^2$ moiety. Furthermore, for a given q, the compound may exist as a mixture of (constitutional) isomers as the q $L^2$-L(-($V^1$-Y))$_p$(Z)$_{z/q}$ moieties may be connected to distinct (sets of) functional groups on $V^2$. It should be noted that the number of Z moieties in each unit only equals z/q if all units are the same and/or contain the same number of Z moieties.

In one embodiment, the $V^2$ moiety is connected to $L^2$ via a sulfur atom of $V^2$.

In another embodiment, the $V^2$ moiety is connected to $L^2$ via a sulfur atom and q ranges from about 1 to about 20.

In another embodiment, the $V^2$ moiety is connected to $L^2$ via a sulfur atom and q ranges from about 1 to about 9.

In another embodiment, the $V^2$ moiety is connected to $L^2$ via a sulfur atom and q ranges from about 1 to about 3.

In another embodiment, the $V^2$ moiety is connected to $L^2$ via a sulfur atom and q is about 1.

In another embodiment, the $V^2$ moiety is connected to $L^2$ via a sulfur atom and q is about 2.

In another embodiment, the $V^2$ moiety is connected to $L^2$ via a sulfur atom and q ranges from about 3 to about 5.

In another embodiment, the $V^2$ moiety is connected to $L^2$ via a sulfur atom and q is about 4.

In another embodiment, the $V^2$ moiety is connected to $L^2$ via a sulfur atom and q ranges from about 7 to about 9.

In another embodiment, the $V^2$ moiety is connected to $L^2$ via a sulfur atom and q is about 8.

In one embodiment, a compound of formula (III) exists as a mixture of separate compounds.

In one embodiment, a compound of formula (III) exists as a mixture of separate compounds wherein q for three compounds is 1, 2, and 3, respectively.

In one embodiment, a compound of formula (III) exists as a mixture of separate compounds wherein q for three compounds is 3, 4, and 5, respectively.

In one embodiment, a compound of formula (III) exists as a mixture of separate compounds wherein q for three compounds is 5, 6, and 7, respectively.

In one embodiment, a compound of formula (III) exists as a mixture of separate compounds wherein q for three compounds is 7, 8, and 9, respectively.

In another embodiment, the $V^2$ moiety is connected to $L^2$ via a nitrogen atom of $V^2$.

In yet another embodiment, the $V^2$ moiety is connected to $L^2$ via a carbon atom of $V^2$.

In another aspect of this invention, the $V^2$ moiety includes any unit that causes accumulation of compounds of the invention at the target site or in the vicinity thereof by a mechanism other than binding or reactively associating or complexing with a receptor, antigen, or other receptive moiety associated with a given target site, e.g., a target cell population. One way to achieve this is for example to use a large macromolecule as a $V^2$ moiety, which targets to solid tumor tissue through the enhanced permeability and retention (EPR) effect. Ringsdorf reported use of polymers to target antitumor agents to tumors.[15] Through this EPR effect, macromolecules passively accumulate in solid tumors as a consequence of the disorganized pathology of angiogenic tumor vasculature with its discontinuous endothelium, leading to hyperpermeability to large macromolecules, and the lack of effective tumor lymphatic drainage.

The $V^2$ moiety may for example be a branched or unbranched polymer, such as for example poly[N-(2-hydroxypropyl)methacrylamide] (HPMA), hydroxyethyl starch (HES), poly(2-hydroxyethyl methacrylate) (HEMA), polyglutamic acid or poly-L-glutamic acid (PG), carboxymethyldextran (CMDex), a polyacetal, chitosan, a polypeptide, an oligoethylene glycol or polyethylene glycol (PEG), or a copolymer, such as an HPMA copolymer, an HPMA-methacrylic acid copolymer, a HEMA-methacrylic acid copolymer, a CMDex copolymer, a β-cyclodextrin copolymer, a PEG copolymer, or a poly(lactic-co-glycolic) acid copolymer.[16] In this document both polymer and copolymer are referred to as polymer.

The polymer may be connected to $L^2$ via any suitable functional group, which can be located at one or both ends of the polymer, meaning that in the conjugate q ranges from 1 to 2, or alternatively, the functional groups may (also) be located on groups pendant on the polymer such that $L^2$ is (also) connected to the polymer via these pendant groups with q typically ranging from 1 to about 1000. Optionally, the polymer may also contain an additional targeting group that can bind or reactively associate or complex with a receptive moiety, e.g., an antibody or antibody derivative, bonded to the polymer either via a pendant group or end group, such that improved targeting to the target site is achieved.

Alternatively, the $V^2$ moiety may be a dendrimer or a protein or protein fragment, e.g., serum albumin, which has no targeting properties except for its ability to accumulate at the target site because of its size or molecular weight.

In one embodiment, the $V^2$ moiety contains a polymer.

In another embodiment, the $V^2$ moiety is a polymer.

In another embodiment, the $V^2$ moiety is a polymer and q ranges from 1 to about 1000.

In other embodiments, the $V^2$ moiety is a polymer and q ranges from 1 to about 500 or 400 or 300 or 200 or 100 or less than 100.

In another embodiment, the $V^2$ moiety is a polymer and q ranges from 1 to 2.

In another embodiment, the $V^2$ moiety is a polymer and q is 1.

In a specific embodiment, the $V^2$ moiety is an oligoethylene glycol or a polyethylene glycol or a derivative thereof.

In another embodiment, the $V^2$ moiety is a dendrimer, a protein, or a protein fragment.

In another embodiment, $V^2$ is absent.

In another embodiment, the $V^2$ moiety is a moiety that is able to transport the conjugate across a biological barrier, e.g., a cell membrane, either with or without prior binding, associating, or complexing with a receptor or receptor complex. In one embodiment, the $V^2$ moiety is a Tat peptide or a derivative, fragment, or analog thereof, or a moiety that has similar transmembrane delivery properties. In another embodiment, the $V^2$ moiety is a protein or protein fragment, an antibody or an antibody fragment, a receptor-binding or peptide vector moiety, or a polymeric or dendritic moiety, or any combination thereof, to which is attached a Tat peptide or a derivative, fragment, or analog thereof, or a moiety that has similar transmembrane delivery properties.

Thus, in one aspect of the invention, the moiety $V^2$ is a targeting moiety and is selected from the group consisting of a protein or protein fragment, an antibody or an antibody fragment, a receptor-binding or peptide vector moiety, and a polymeric or dendritic moiety, and any combination or derivative thereof.

In another aspect of the invention, the $V^2$ moiety is a moiety that improves the pharmacological properties of a conjugate of the invention. For example, the moiety $V^2$ can be chosen such that the water solubility of the conjugate is (further) improved. This can be achieved by choosing $V^2$ to be a hydrophilic moiety. Alternatively, the $V^2$ moiety can be used for example to increase the residence time of the compound in the circulation, to reduce extravasation and/or excretion, to reduce aggregation, and/or to reduce the immunogenicity of the compound. This may for example be achieved by choosing $V^2$ to be or contain a polyethylene glycol or oligoethylene glycol or derivative thereof. When the moiety $V^2$ is a moiety that improves the pharmacological properties of a compound of the invention and $V^1$ is a moiety that can be cleaved or transformed aspecifically and there are no $V^{1'}$ and $V^{2'}$ moieties, the compound solely serves to improve the (pharmacological) properties of the one or more Z moieties.

In one embodiment, $V^2$ is a moiety that improves the pharmacological properties and $V^1$ is a moiety that can be cleaved or transformed specifically.

In another embodiment, $V^2$ is an oligoethylene glycol or a polyethylene glycol or a derivative thereof and $V^1$ is a moiety that can be cleaved or transformed specifically.

In another embodiment, $V^2$ is a moiety that improves the pharmacological properties and $V^1$ is a moiety that can be cleaved or transformed aspecifically.

In another embodiment, $V^2$ is an oligoethylene glycol or a polyethylene glycol or a derivative thereof and $V^1$ is a moiety that can be cleaved or transformed aspecifically.

In another embodiment, $V^2$ is an oligoethylene glycol or a polyethylene glycol or a derivative thereof and $V^1$ is a moiety that can be cleaved by ubiquitous enzymes.

In another embodiment, $V^2$ is an oligoethylene glycol or a polyethylene glycol or a derivative thereof and $V^1$ is a hydrolyzable moiety.

In another embodiment, $V^2$ contains a $X^{14}(CH_2CH_2O)_{gg}CH_2CH_2X^{14}$ moiety.

In one aspect of this invention, the $V^2$ moiety is represented by formula (VI):

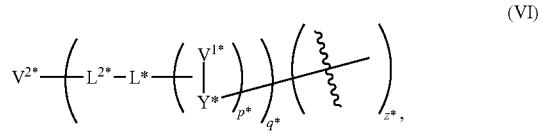

(VI)

wherein $V^{2*}$, $L^{2*}$, $L^*$, $V^1$, $Y^*$, $p^*$, $q^*$, and $z^*$ have the same meaning as $V^2$, $L^2$, $L$, $V^1$, $Y$, $p$, $q$, and $z$, respectively, as defined in this document and are selected independently, except that $Y^*$ is connected to $L^2$. It should be noted that $z^*$ actually equals q, assuming that all $Y^*$ are indeed connected to $L^2$. When a compound of formula (III) contains a $V^2$ moiety represented by formula (VI), the one or more $L^2$ moieties are thus connected to $Y^*$.

Use of a $V^2$ moiety of formula (VI) in a conjugate of formula (III) implicates that two conditionally-cleavable or conditionally-transformable moieties may be present in between the functional moiety $V^{2*}$ and Z, and therefore two separate cleavages/transformations may be required to release Z. The requirement that two different conditions need to have been met—in consecutive order—before one or more Z are released might favorably affect the properties of the conjugate. For instance, it may increase the targeting efficiency and therapeutic index of the conjugate. The two transformations/cleavages may occur at different extracellular/intracellular locations. The moiety to be removed by the second cleavage or as a consequence of the second transformation may for example be used to help transport Z from a first extracellular or intracellular location (where the first cleavage has occurred) to a second extracellular or intracellular location, or to stabilize Z until it is closer to its target, or to (temporarily) increase the water solubility of Z. In order to increase the targeting efficiency and/or therapeutic index using this concept, the second transformation and/or cleavage should only occur after the first transformation and/or cleavage have occurred. If the second transformation and/or cleavage can also occur before the first transformation and/or cleavage have occurred, an improved targeting efficiency and/or an improved therapeutic index due to this concept seems unlikely.

It will be apparent that a $V^2$ moiety of formula (VI) or a promoiety containing such a $V^2$ cannot only be useful in conjugates of a compound of formula (I) or (II), but may be used in similar conjugates of other therapeutic agents, diagnostic moieties, and the like.

A compound of formula (III) containing a $V^2$ moiety of formula (VI) may be prepared from a compound of formula (III) containing a $V^2$ moiety of formula (VII):

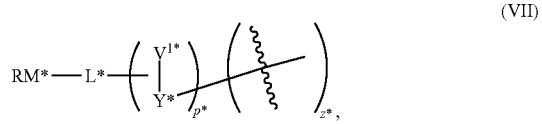

(VII)

wherein RM* has the same meaning as RM and is selected independently.

It should be understood that in this document, whenever $V^2$, $L^2$, L, $V^1$, Y, RM, p, q, or z is mentioned, the same can apply for each $V^{2*}$, $L^{2*}$, $L^*$, $V^{1*}$, $Y^*$, $RM^*$, $p^*$, $q^*$, or $z^*$, respectively, unless the context dictates otherwise.

It should be understood that the functional moiety $V^2$ can have several functional properties combined. For example, $V^2$ can be a moiety that improves the pharmacological properties of a compound of this invention and at the same time be or contain a targeting moiety.

Conjugates of this invention may contain one or more promoieties. These promoieties may be the same or different. The presence of two or more promoieties may favorably affect the properties of the conjugate. For instance, it may improve the water solubility and/or increase the targeting efficiency of the conjugate. Furthermore, if in a targeted conjugate there are two promoieties and the promoiety required for targeting is prematurely cleaved from Z, for example in the circulation, the second promoiety attenuates the cytotoxicity of Z.

In one embodiment, when there are two or more promoieties, said promoieties are different from each other. The two or more different promoieties may have different functions and may be removed under different conditions and at different extracellular/intracellular locations.

In one embodiment, there is one promoiety linked to Z. In another embodiment, there is one promoiety linked to Z via $X^1$. In another embodiment, there are two promoieties linked to Z. In another embodiment, there are two promoieties linked to Z, of which one is connected via $X^1$. In another embodiment, there are two promoieties linked to Z, of which one is connected via $X^1$ and the other to the DNA-alkylating unit. In another embodiment, there are two promoieties linked to Z, of which one is connected via $X^1$ and the other to the DNA-binding unit. In another embodiment, there are two promoieties linked to Z, of which one is connected to the DNA-binding unit and the other to the DNA-alkylating unit. In yet another embodiment, there are three promoieties linked to Z. In yet another embodiment, there are three promoieties linked to Z, of which one is connected via $X^1$.

In another aspect, this invention relates to conjugates and linker-agent conjugates similar to compounds of formulae (III) and (IV) in which the Z moiety is a therapeutic or diagnostic moiety different from a compound of formula (I), (II), (I'), or (II'), or a promoiety-containing derivative thereof. Therapeutic moieties may for example be selected from anthracyclines (e.g., daunorubicin, doxorubicin), antimetabolites (e.g., methotrexate, cytarabine, 6-mercaptopurine), calicheamycins, dolastatins, auristatins, tubulysins, epothilones, taxoids (e.g., paclitaxel, docetaxel), maytansinoids, mitomycins, other alkylating agents (e.g., melphalan, carmustine, chlorambucil, cyclophosphamide), and other tubulin-binding agents (e.g., vincristine, vinblastine). All embodiments for compounds of formulae (III) and (IV) also apply to conjugates and linker-agent conjugates similar to compounds of formulae (III) and (IV) in which the Z moiety is a therapeutic or diagnostic moiety different from a compound of formula (I), (II), (I'), or (II'), or a promoiety-containing derivative thereof, unless the context dictates otherwise.

In one aspect of this invention, a compound of formula (III) comprises at least 2 promoieties. The first promoiety contains at least a targeting moiety and the second comprises at least a $X^{14}(CH_2CH_2O)_{gg}CH_2CH_2X^{14}$ moiety or 2 $X^{14}CH_2CH_2OCH_2CH_2X^{14}$ moieties, and $V^1$ of said same second promoiety is present. Similarly, a compound of formula (IV) may comprise at least 2 promoieties. The first promoiety contains at least a reactive moiety RM and the second comprises at least a $X^{14}(CH_2CH_2O)_{gg}CH_2CH_2X^{14}$ moiety or 2 $X^{14}CH_2CH_2OCH_2CH_2X^{14}$ moieties, and $V^1$ of said same second promoiety is present. Said second promoieties of compounds of formulae (III) and (IV) may for example be represented by

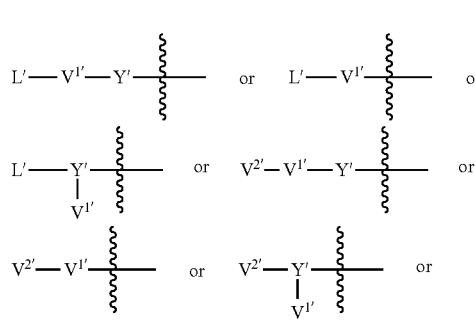

-continued

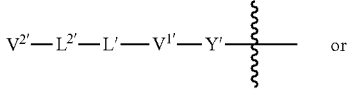  or

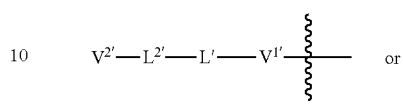  or

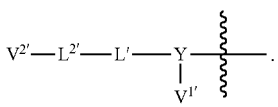.

In one embodiment, said second promoiety is selected from

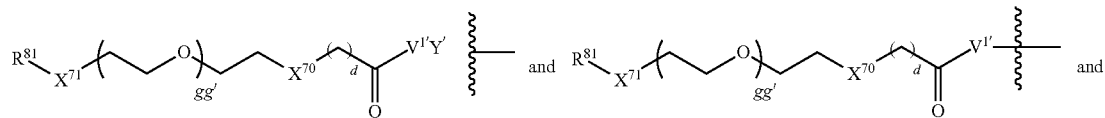

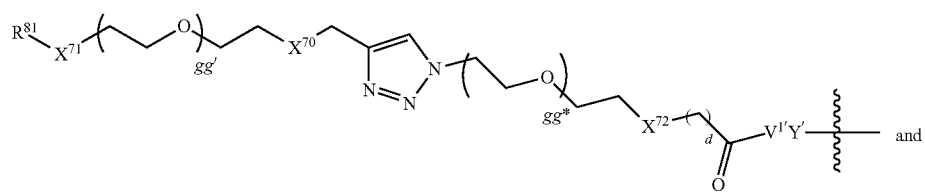

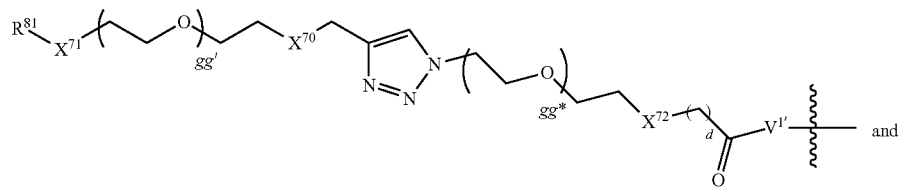

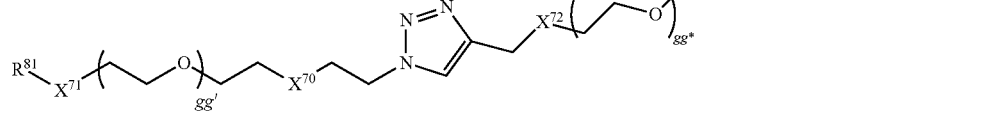

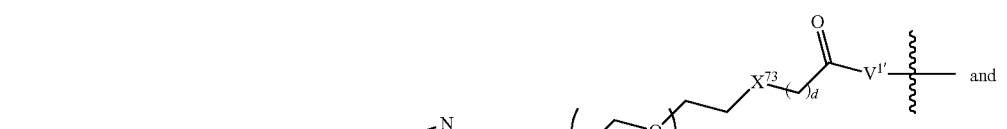

-continued
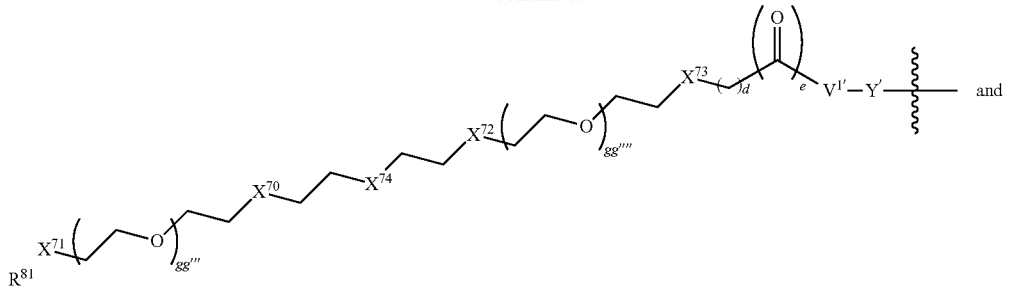
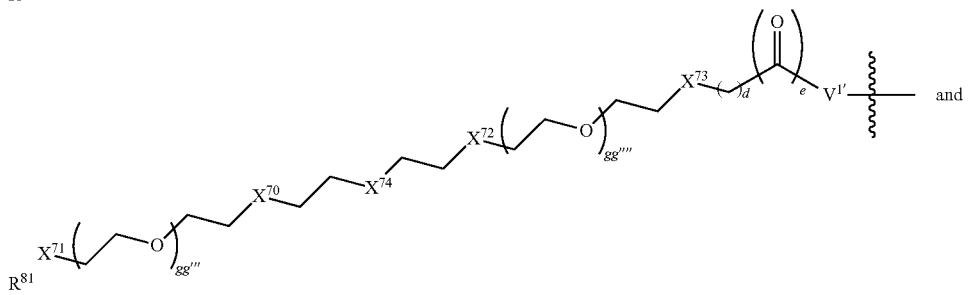
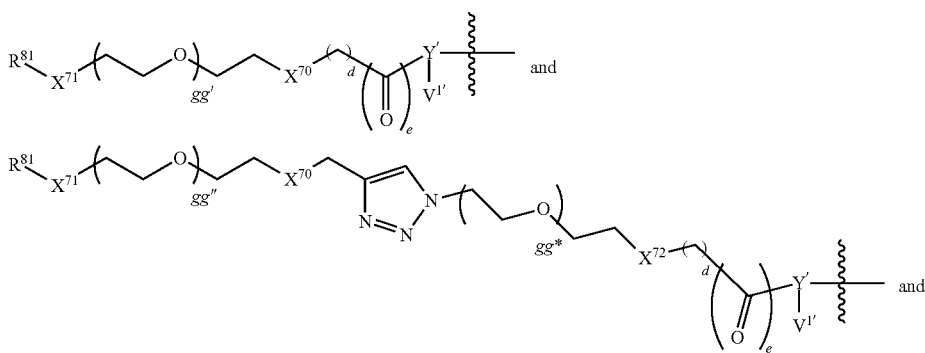
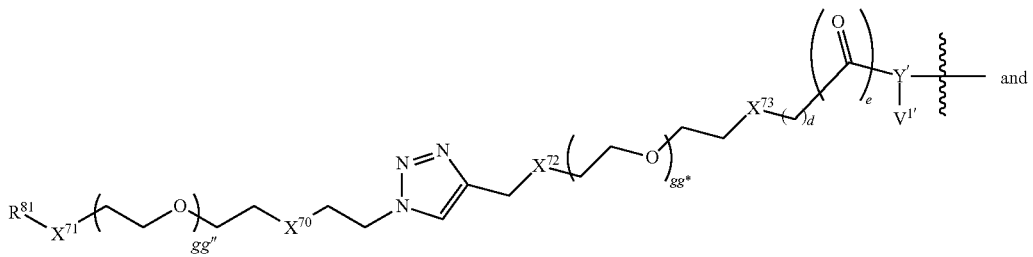
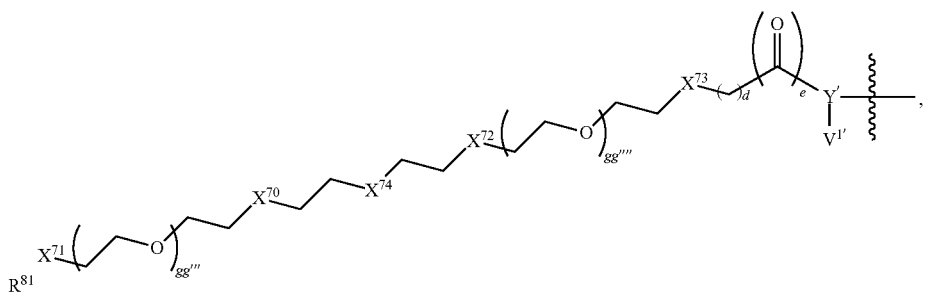

wherein $X^{70}$, $X^{71}$, $X^{72}$, and $X^{73}$ are independently selected from O, S, and $NR^{82}$, $X^{74}$ is selected from

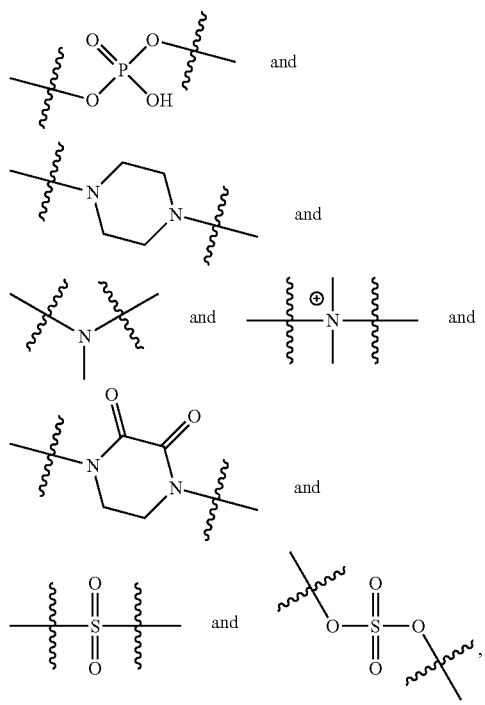

d is selected from 0 to 8, e is 0 or 1, gg', gg'', gg''', gg'''', and gg* are independently selected from 0 to 1000, and $R^{81}$ and $R^{82}$ are independently selected from H and optionally substituted $C_{1-3}$ alkyl. In other embodiments, gg', gg'', gg''', gg'''', and gg* are independently selected from 3 to 1000 or 500 or 100 or 50 or 10.

In another embodiment, said second promoiety is selected from

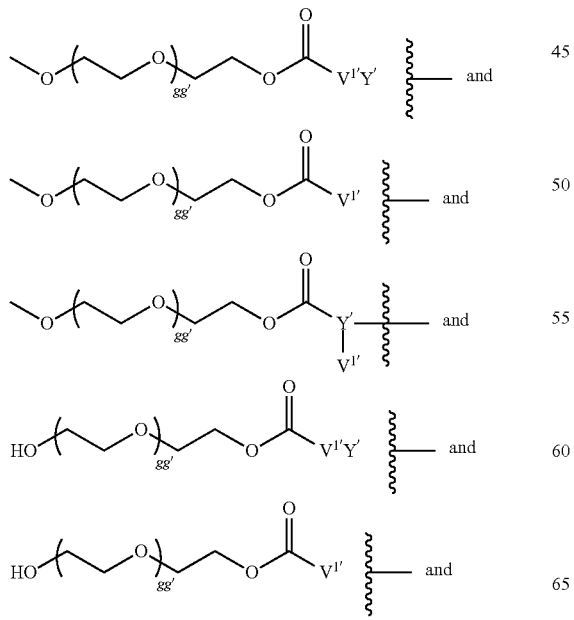

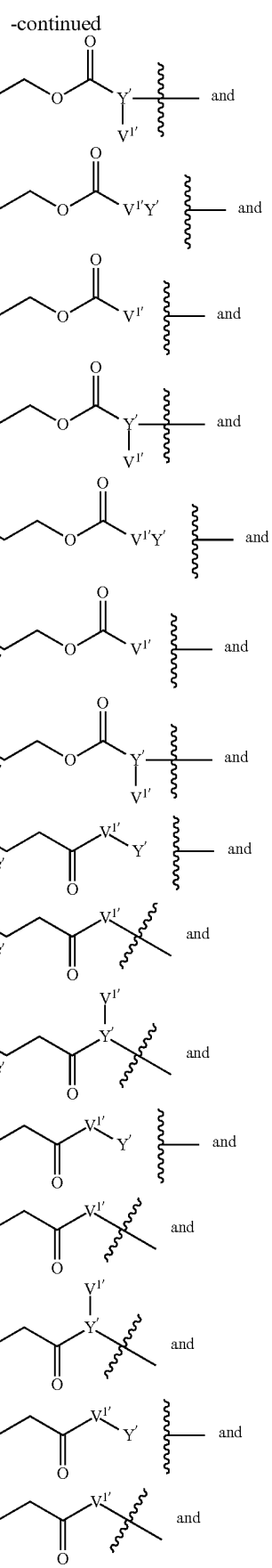

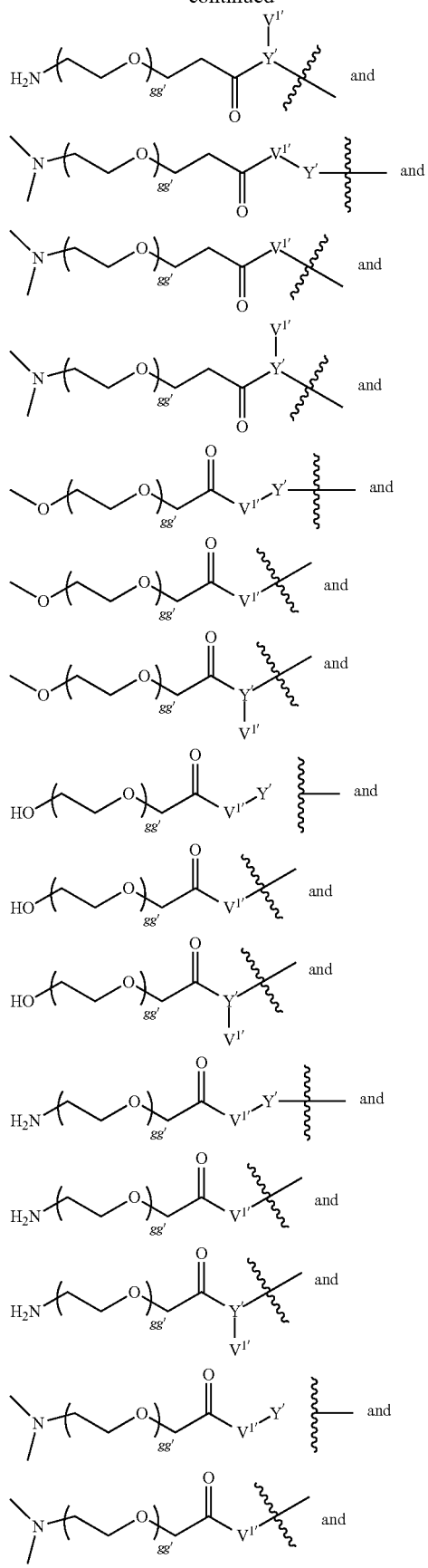
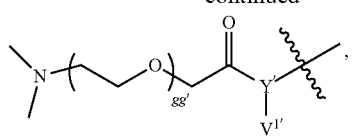
wherein gg' is selected from 0 to 1000. In other embodiments, gg' is selected from 3 to 1000 or 500 or 100 or 50 or 10.
In a further embodiment, said second promoiety is selected from
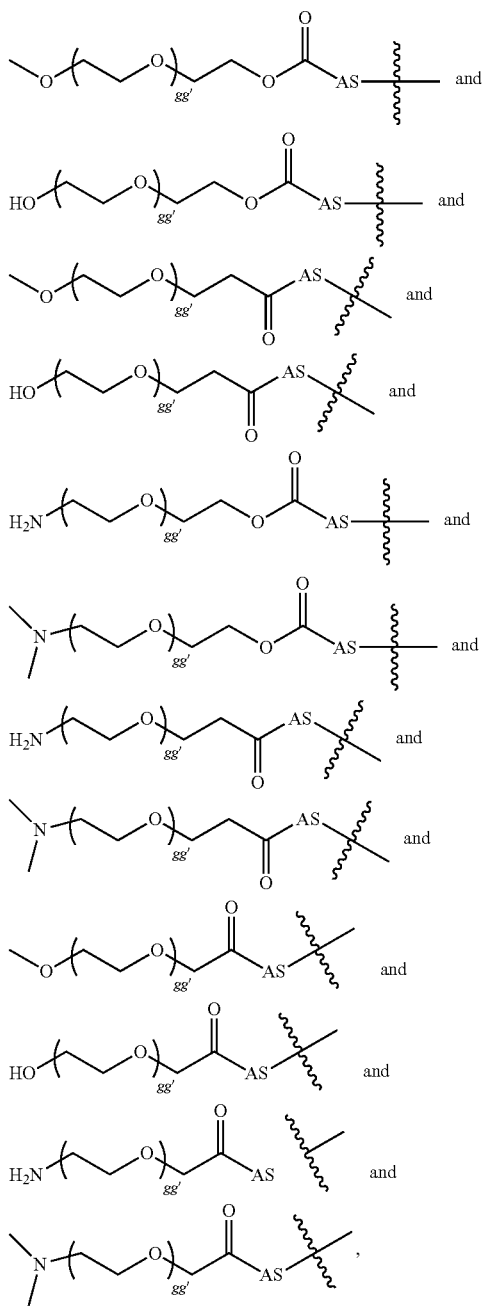

wherein gg' is selected from 0 to 1000, AS is wherein A is $R^{116}$ is selected from methyl, ethyl, isopropyl, tert-butyl, phenyl, f is 0, 1, or 2, g is 0 or 1, and PM is an amino acid or a peptide coupled with its N-terminus to L'.

In other embodiments, gg' is selected from 3 to 1000 or 500 or 100 or 50 or 10 or 5.

In one embodiment, (III) is represented by a compound of formula (III-1) or (III-2):

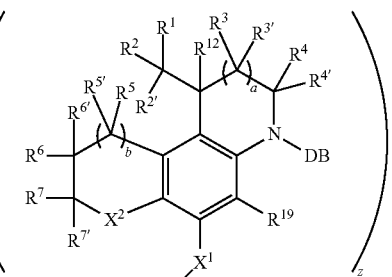
(III-1)

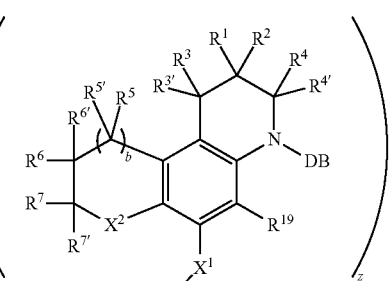
(III-2)

In more specific embodiments, the DB unit in a compound of formula (III-1) or (III-2) is DB1 or DB2 or DB3 or DB4 or DB5 or DB6 or DB7 or DB8 or DB9.

In another embodiment, a compound of formula (III) is represented by a compound of formula (III-3a) or (III-4a), wherein the DNA-binding moiety is DB1:

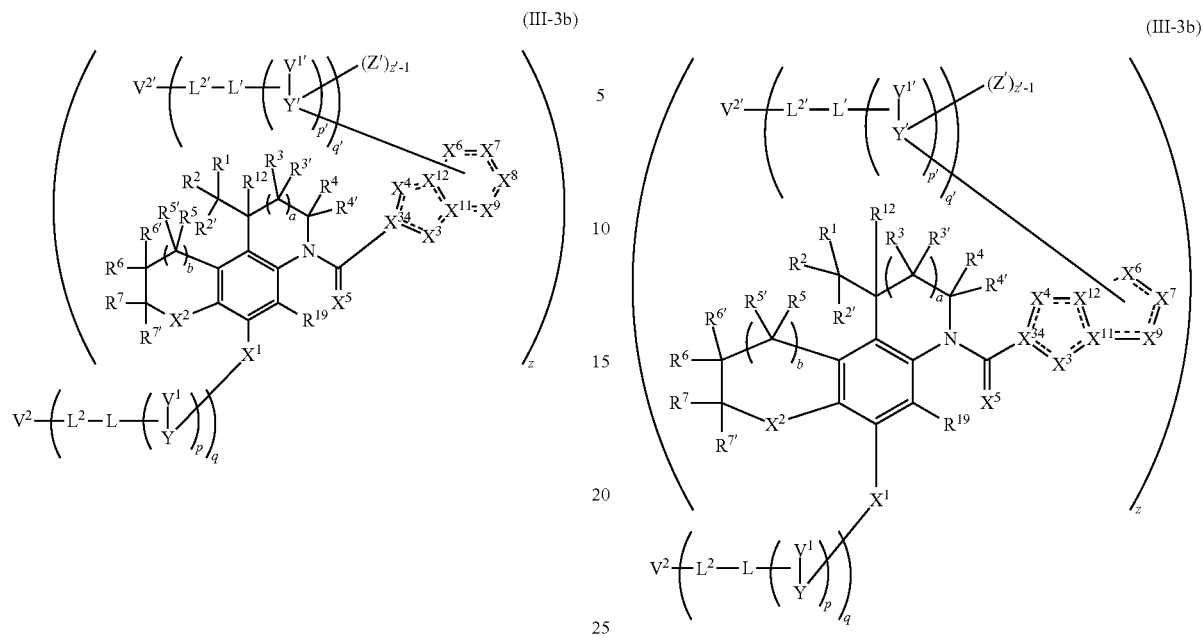

wherein Y' is connected to an atom being part of $X^3$, $X^{34}$, $X^4$, $X^6$, $X^7$, $X^8$, $X^9$, $X^{11}$, or $X^{12}$.

In another embodiment, a compound of formula (III) is represented by a compound of formula (III-3b) or (III-4b), wherein the DNA-binding moiety is DB2:

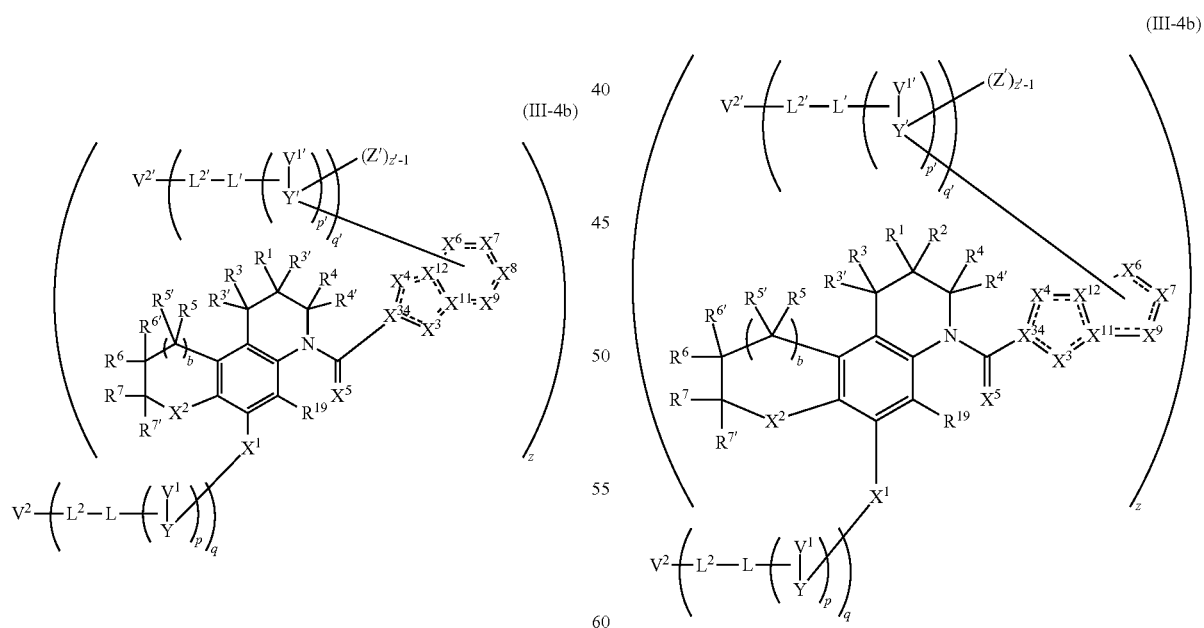

wherein Y' is connected to an atom being part of $X^3$, $X^{34}$, $X^4$, $X^6$, $X^7$, $X^9$ or $X^{11}$, or $X^{12}$.

In another embodiment, a compound of formula (III) is represented by a compound of formula (III-3c) or (III-4c), wherein the DNA-binding moiety is DB3:

(III-3c)

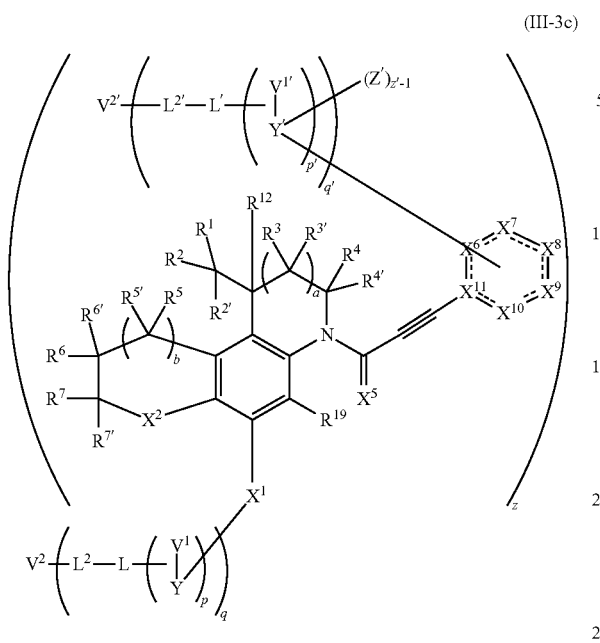

(III-3d)

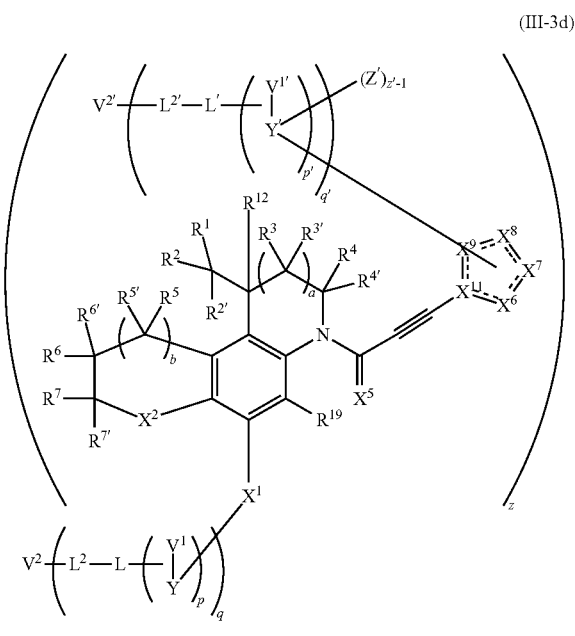

(III-4c)

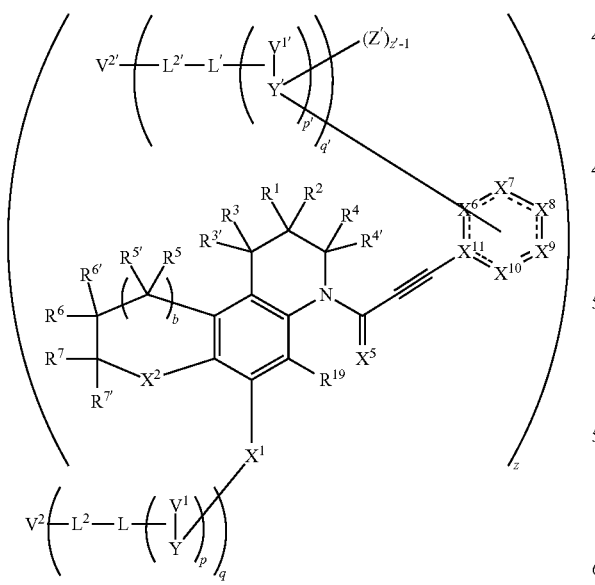

(III-4d)

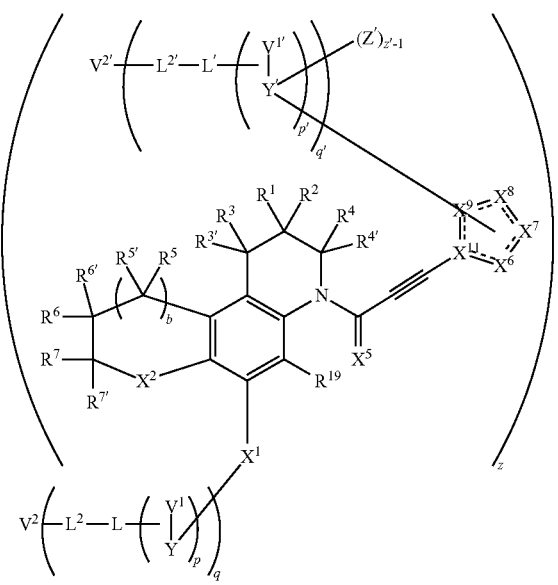

wherein Y' is connected to an atom being part of $X^6$, $X^7$, $X^8$, $X^9$, $X^{10}$, or $X^{11}$.

In another embodiment, a compound of formula (III) is represented by a compound of formula (III-3d) or (III-4d), wherein the DNA-binding moiety is DB4:

wherein Y' is connected to an atom being part of $X^6$, $X^7$, $X^8$, $X^9$, or $X^{11}$.

In another embodiment, a compound of formula (III) is represented by a compound of formula (III-3e) or (III-4e), wherein the DNA-binding moiety is DB5

(III-3e)

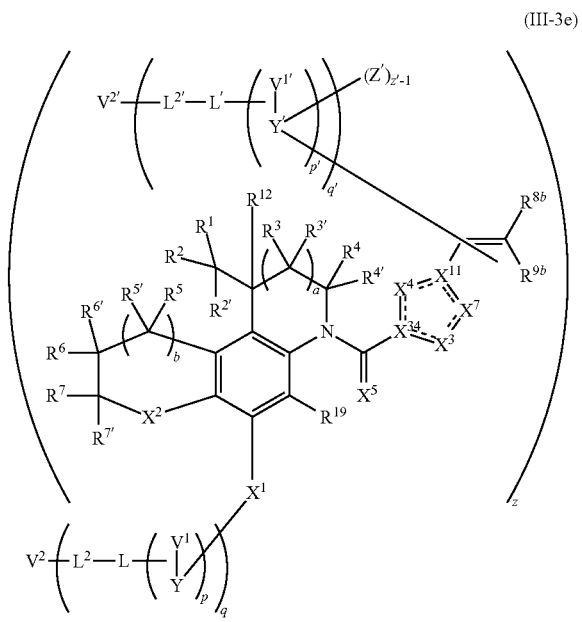

(III-3f)

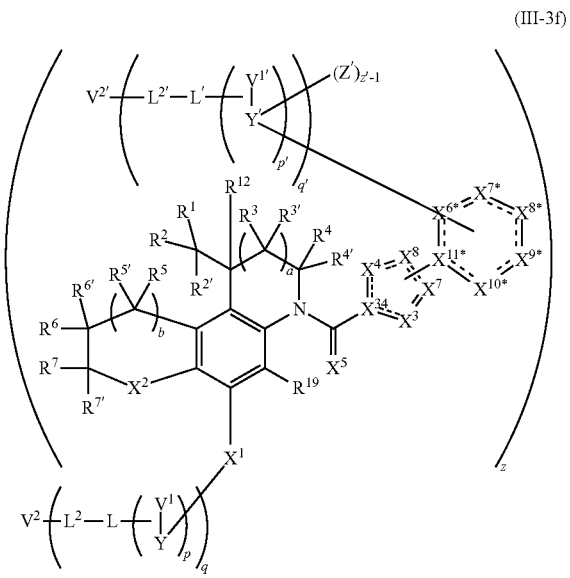

(III-4e)

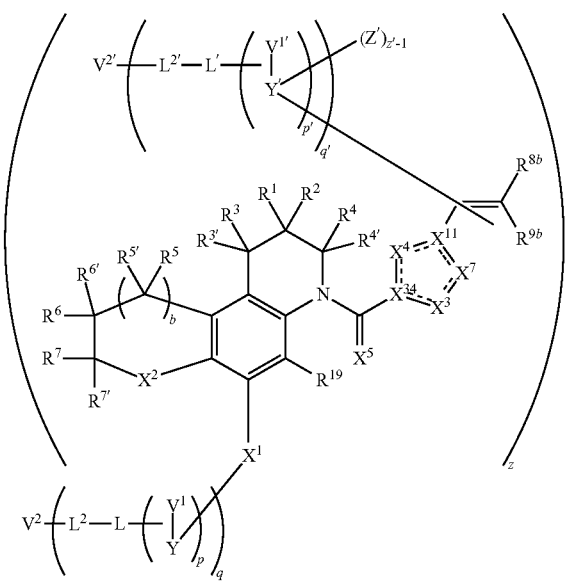

(III-4f)

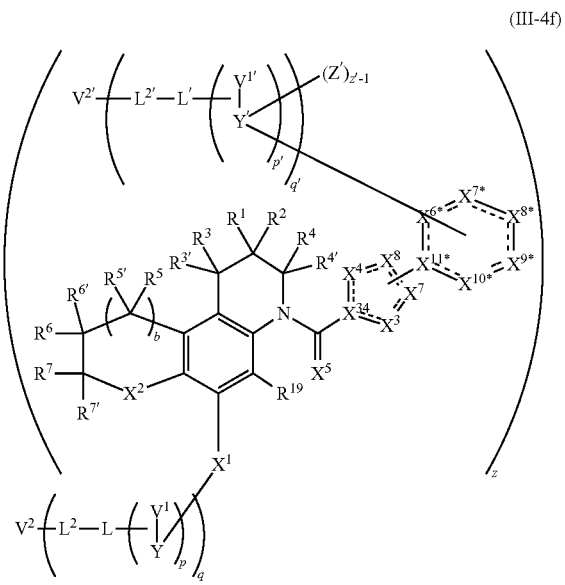

wherein Y' is connected to an atom being part of $R^{8b}$, $R^{9b}$, $X^3$, $X^{34}$, $X^4$, $X^7$, or $X^{11}$.

In another embodiment, a compound of formula (III) is a compound of formula (III-3f) or (III-4f), wherein the DNA-binding moiety is DB6:

wherein Y' is connected to an atom part of $X^3$, $X^{34}$, $X^4$, $X^{6*}$, $X^{7*}$, $X^7$, $X^8$, $X^{8*}$, $X^{9*}$, $X^{10*}$, or $X^{11*}$.

In another embodiment, a compound of formula (III) is a compound of formula (III-3g) or (III-4g), wherein the DNA-binding moiety is DB7:

(III-3g)

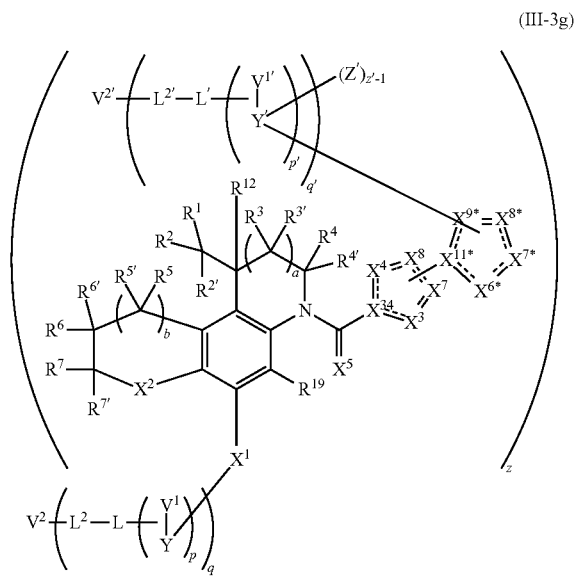

(III-3h)

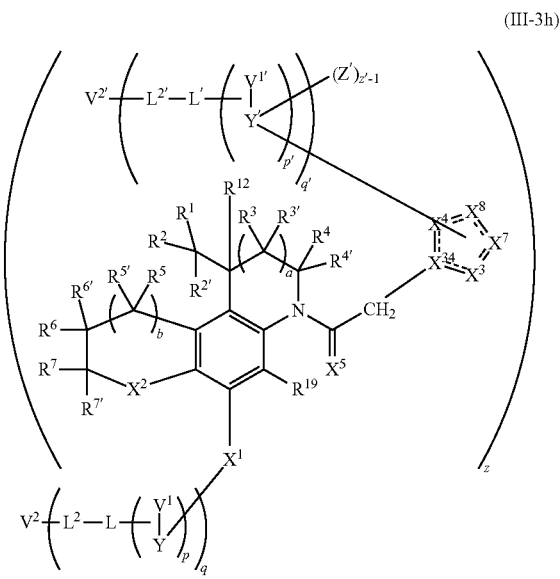

(III-4g)

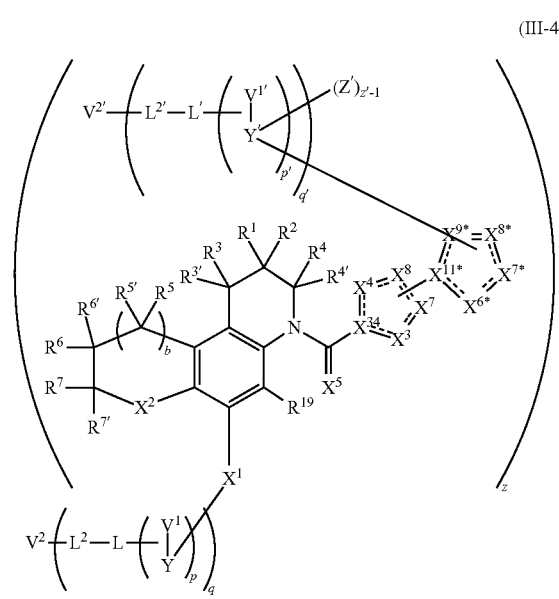

(III-4h)

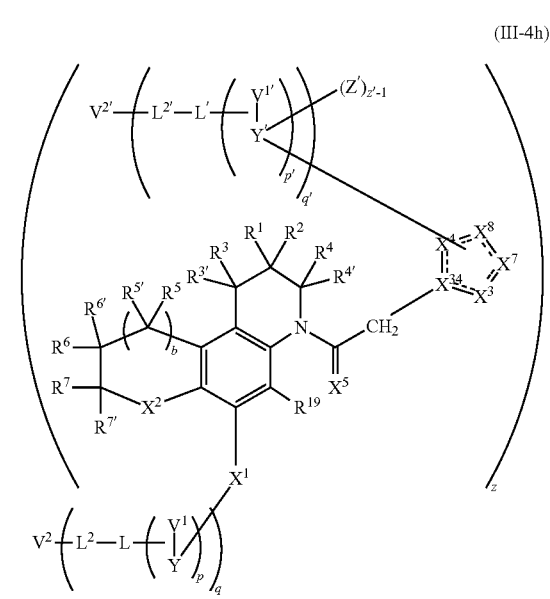

wherein Y' is connected to an atom being part of $X^3$, $X^{34}$, $X^4$, $X^{6*}$, $X^7$, $X^{7'}$, $X^8$, $X^{8*}$, $X^9$, or $X^{11*}$.

In another embodiment, a compound of formula (III) is a compound of formula (III-3h) or (III-4h), wherein the DNA-binding moiety is DB8:

wherein Y' is connected to an atom being part of $X^3$, $X^{34}$, $X^4$, $X^7$, or $X^8$.

In another embodiment, a compound of formula (III) is represented by a compound of formula (III-3i) or (III-4i), wherein the DNA-binding moiety is DB9:

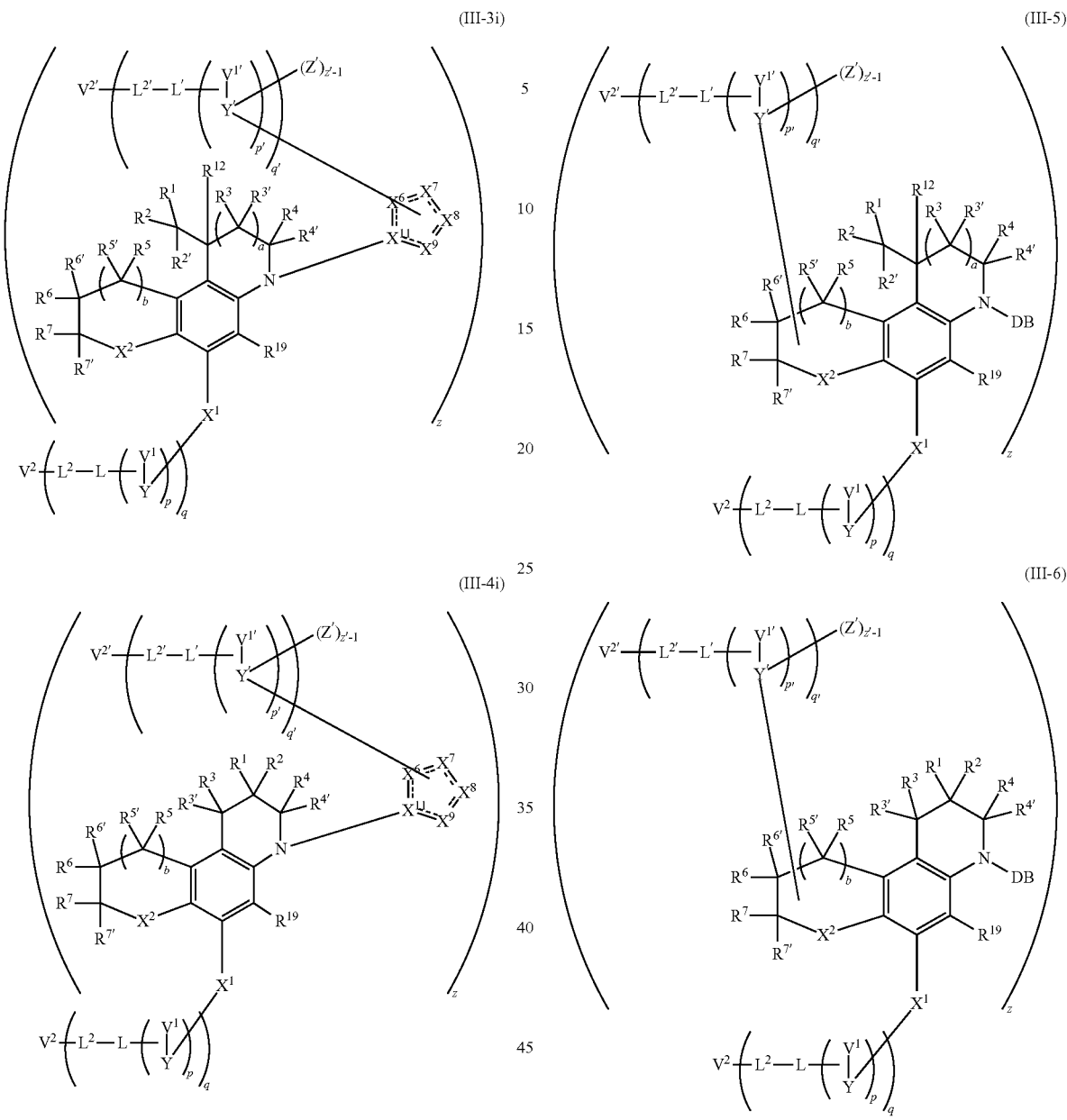

wherein Y' is connected to an atom being part of $X^6$, $X^7$, $X^8$, $X^9$, or $X^{11}$.

This invention further relates to compounds of formulae (III-3j)-(III-3r) and (III-4j)-(III-4r), which are identical to compounds of formulae (III-3a)-(III-3i) and (III-4a)-(III-4i), respectively, except that the two promoieties have switched places, Y now being connected to an atom in the DNA-binding unit and Y' being connected to $X^1$.

It is noted that if in any of compounds of formulae (III-3a)-(III-3i) and (III-4a)-(III-4i) Y' is connected to a ring atom being part of ring A or ring B instead of to an atom in an R substituent connected to said ring atom, this in fact means that such an R substituent is absent if this is necessary to meet valency rules. The same holds for Y in compounds of formulae (III-3j)-(III-3r) and (III-4j)-(III-4r).

In another embodiment, a compound of formula (III) is represented by a compound of formula (III-5) or (III-6):

wherein Y' is connected to an atom being part of $R^5$, $R^{5'}$, $R^6$, $R^{6'}$, $R^7$, $R^{7'}$, $R^{14}$, $R^{14'}$, $X^2$ or to any of the atoms bearing these R substituents.

In more specific embodiments, the DB unit in a compound of formula (III-5) or (III-6) is DB1 or DB2 or DB3 or DB4 or DB5 or DB6 or DB7 or DB8 or DB9.

In a further embodiment, a compound of formula (III) is represented by compounds of formulae (III-7) and (III-8), which are identical to compounds (III-5) and (III-6), respectively, except that the two promoieties have switched places, Y now being connected to an atom in the DNA-alkylating unit and Y' being connected to $X^1$.

In more specific embodiments, the DB unit in a compound of formula (III-7) or (III-8) is DB1 or DB2 or DB3 or DB4 or DB5 or DB6 or DB7 or DB8 or DB9.

When Y' in compounds of formulae (III-5) and (III-6) is connected to a ring atom instead of to an atom in an R substituent connected to said ring atom, this in fact means that such an R substituent is absent if this is necessary to meet valency rules. The same holds for Y in compounds of formulae (III-7) and (III-8).

Similar embodiments can be envisioned for compounds of formula (IV) by replacing $V^2\text{-}L^2$ and/or $V^{2'}\text{-}L^{2'}$ by RM and/or RM', respectively, and removing the parentheses with subscript q and/or q'. Therefore, compounds of formulae (IV-1), (IV-2), (IV-3a)-(IV-3r), (IV-4a)-(IV-4r), (IV-5), (IV-6), (IV-7), and (IV-8) are represented by the structures of compounds of formulae (III-1), (III-2), (III-3a)-(III-3r), (III-4a)-(III-4r), (III-5), (III-6), (III-7), and (III-8), respectively, in which at least one of $V^2\text{-}L^2$ and $V^{2'}\text{-}L^{2'}$ is replaced by RM and RM', respectively.

In one embodiment, the $V^{2'}(\text{-}L^{2'}\text{-}L'(\text{-}(V^{1'}\text{-}Y'))_{p'})_{q'}(Z')_{z'-1}$ moiety in any of compounds of formulae (III-3a)-(III-3r), (III-4a)-(III-4r), (III-5), (III-6), (III-7), and (III-8) or an analogous compound thereof based on a compound of formula (IV) is represented by

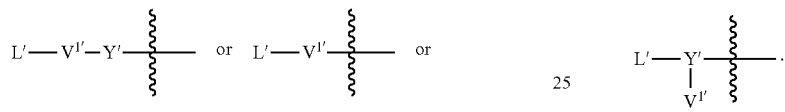

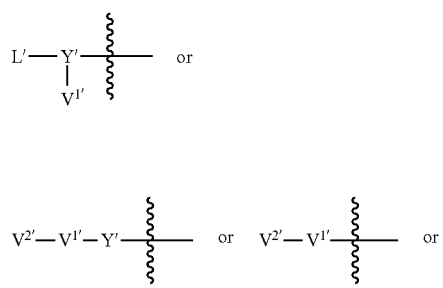

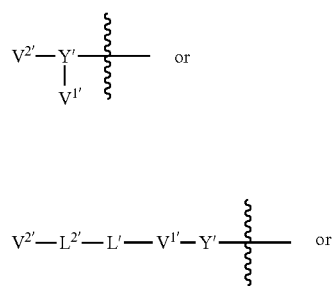

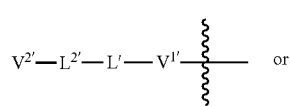

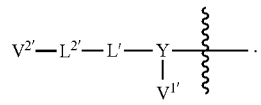

In another embodiment, the $V^{2'}(\text{-}L^{2'}\text{-}L'(\text{-}(V^{1'}\text{-}Y'))_{p'})_{q'}(Z')_{z'-1}$ moiety in any of compounds of formulae (III-3a)-(III-3r), (III-4a)-(III-4r), (III-5), (III-6), (III-7), and (III-8) or an analogous compound thereof based on a compound of formula (IV) is represented by

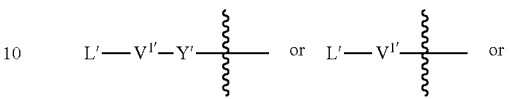

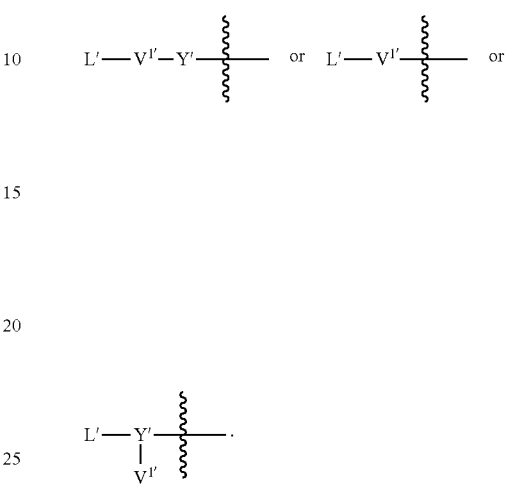

In one embodiment, p is an integer from 1 (included) to 128 (included). In another embodiment, q is an integer from 1 (included) to 1000 (included). In other embodiments, p is an integer from 1 (included) to 64 (included) or 32 (included) or 16 (included) or 8 (included) or 4 (included) or 2 (included), or p is 1. In other embodiments, q is an integer from 1 (included) to 500 (included) or 400 (included) or 300 (included) or 200 (included) or 100 (included) or 16 (included) or 8 (included) or 6 (included) or 4 (included) or 2 (included), or q is 1. In another embodiment, q is selected from 1 to 4.

In one embodiment, if more than 1 promoiety is connected to a first Z and in one of the promoieties there is more than one attachment site for Z moieties, then the other ones of said promoieties connected to said first Z each contain a single attachment site for a Z moiety.

In one embodiment, a compound of formula (III) is represented by

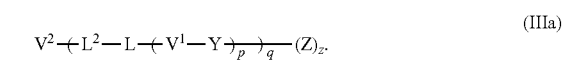 (IIIa)

In one embodiment, p in a compound of formula (IIIa) is 1.

In another embodiment, in a compound of formula (IIIa) p is 1 and z equals q, which reduces formula (IIIa) to:

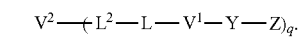

In another embodiment, a compound of formula (IIIa) is represented by

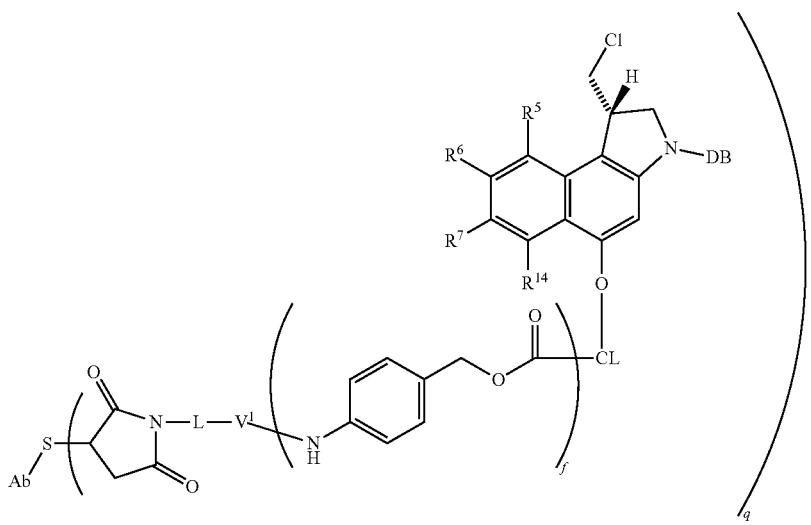
or by an isomer, or by a mixture of isomers, wherein $R^5$, $R^6$, $R^7$, $R^{14}$, and DB are as previously defined, $V^1$ is selected from valylcitrulline, valyllysine, phenylalanyllysine, alanylphenylalanyllysine, and D-alanylphenylalanyllysine, f is 1 or 2, CL is selected from
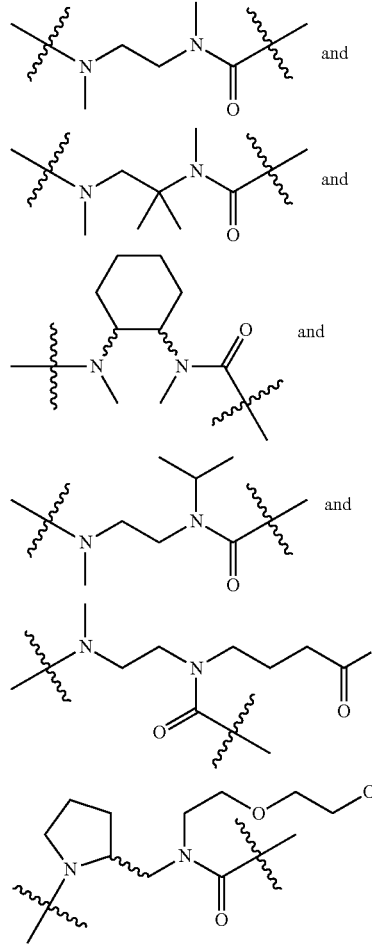
-continued
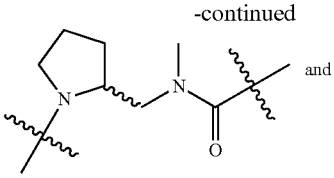
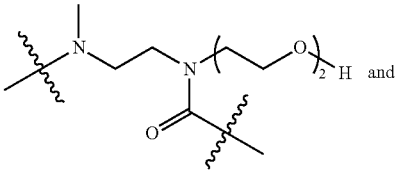
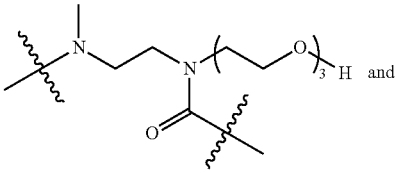
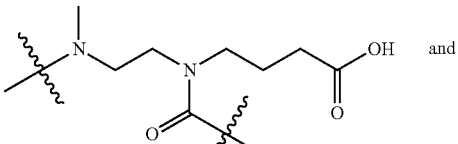
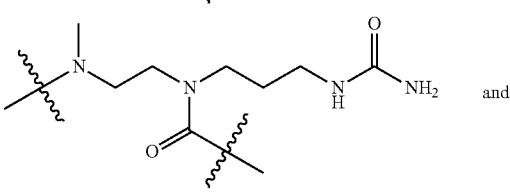
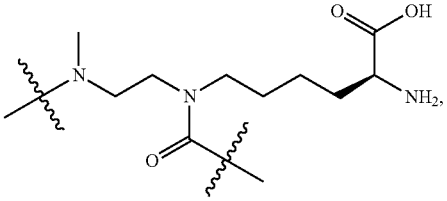

L is selected from

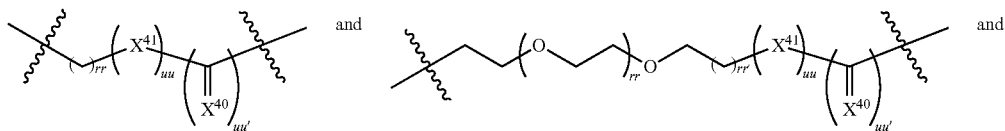

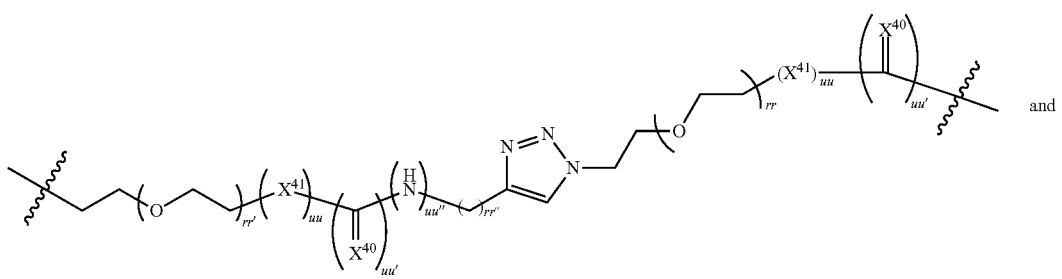

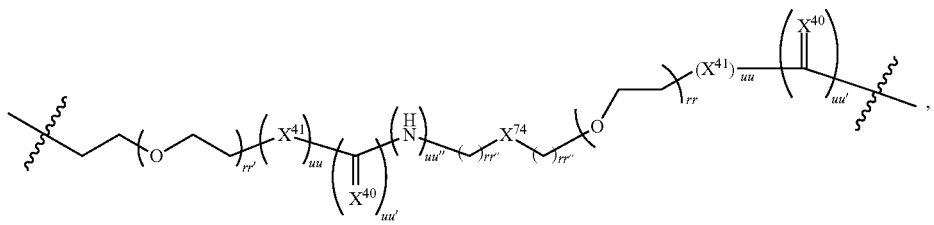

q ranges from 1 to 20, rr, rr', rr", and rr'" each independently range from 0 to 8, $X^{74}$ is selected from

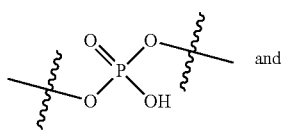

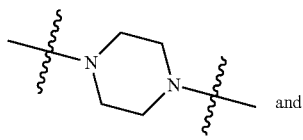

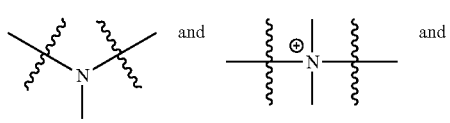

-continued

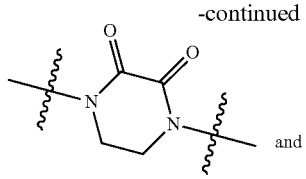

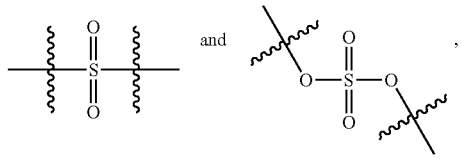

each $X^{40}$ and $X^{41}$ is independently selected from O, S, and $NR^{135}$, wherein $R^{135}$ is selected from H and $C_{1-3}$ alkyl, each uu, uu', and uu" is independently selected from 0 and 1, and Ab is an antibody or a fragment or derivative thereof.

In yet another embodiment, a compound of formula (IIIa) is represented by

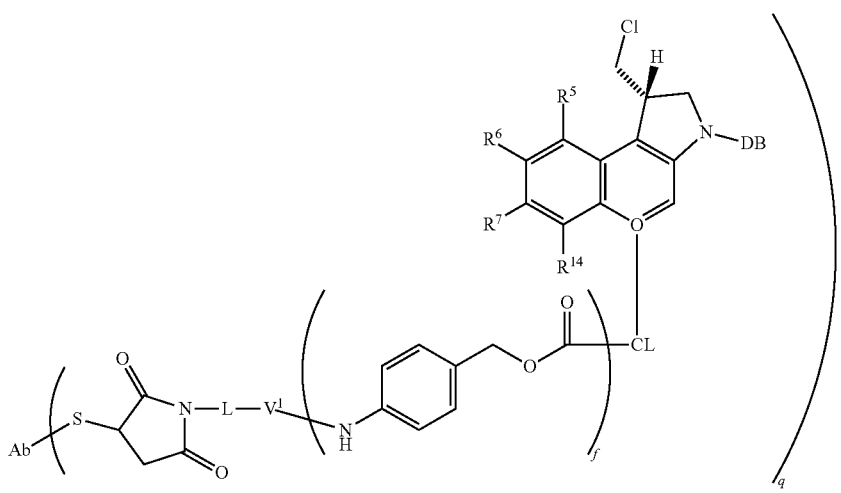
or by an isomer, or by a mixture of isomers, wherein $R^5$, $R^6$, $R^7$, $R^{14}$, and DB are as previously defined, $V^1$ is selected from valylcitrulline, valyllysine, phenylalanyllysine, alanylphenylalanyllysine, and D-alanylphenylalanyllysine, f is 1 or 2, CL is
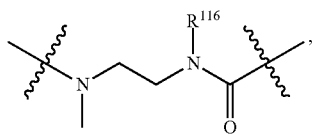
$R^{116}$ is selected from methyl, ethyl, isopropyl, tert-butyl, phenyl,
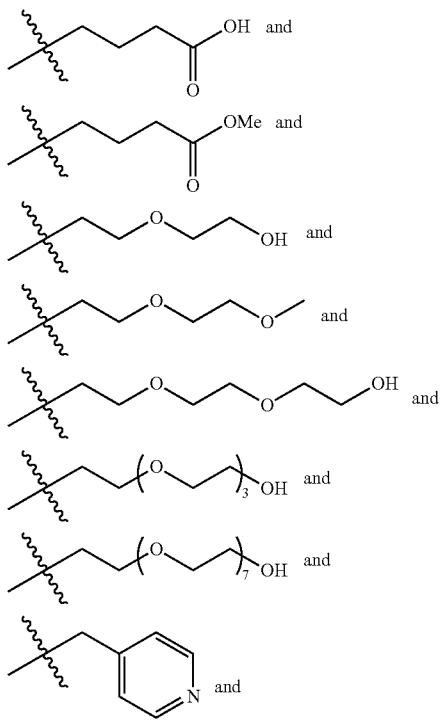
-continued
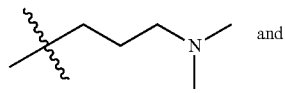
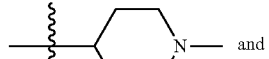
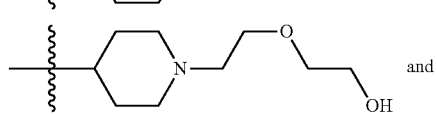
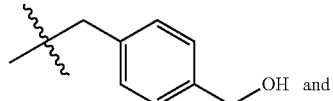
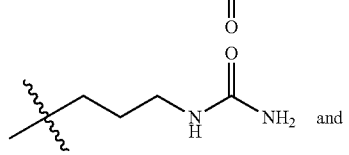
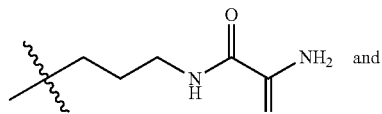
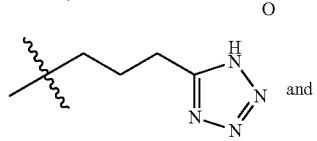
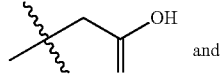
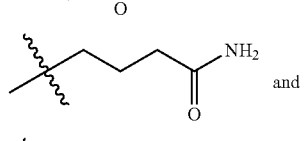
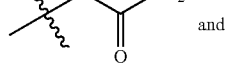

431
-continued
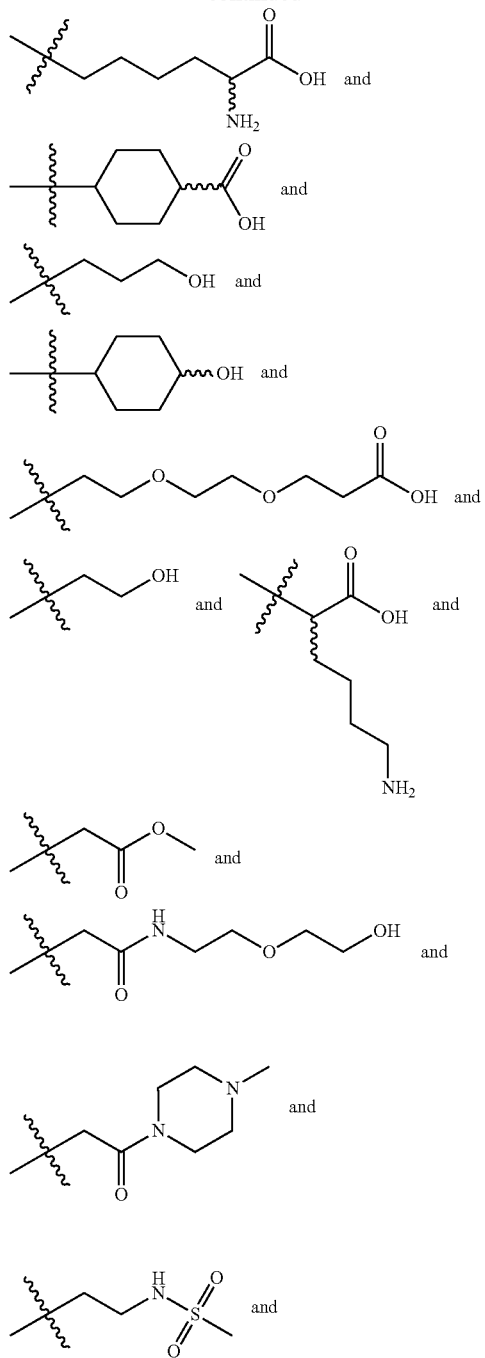
432
-continued
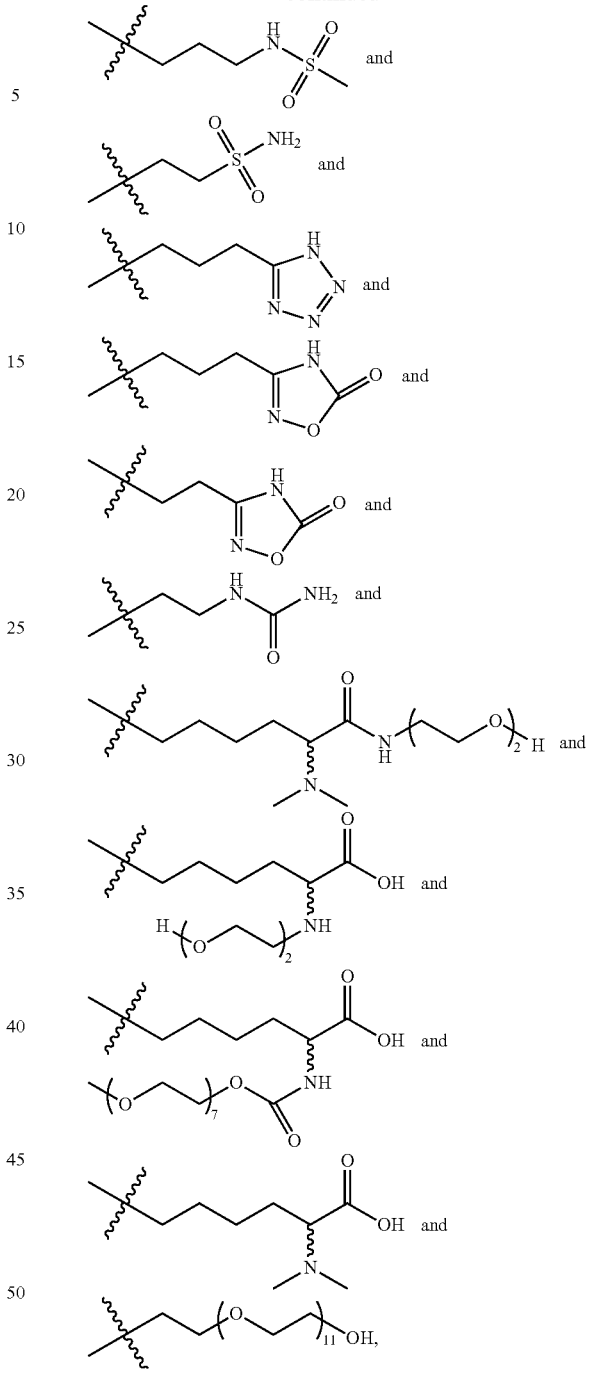
L is selected from
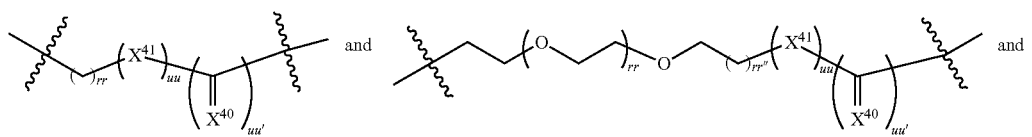

-continued

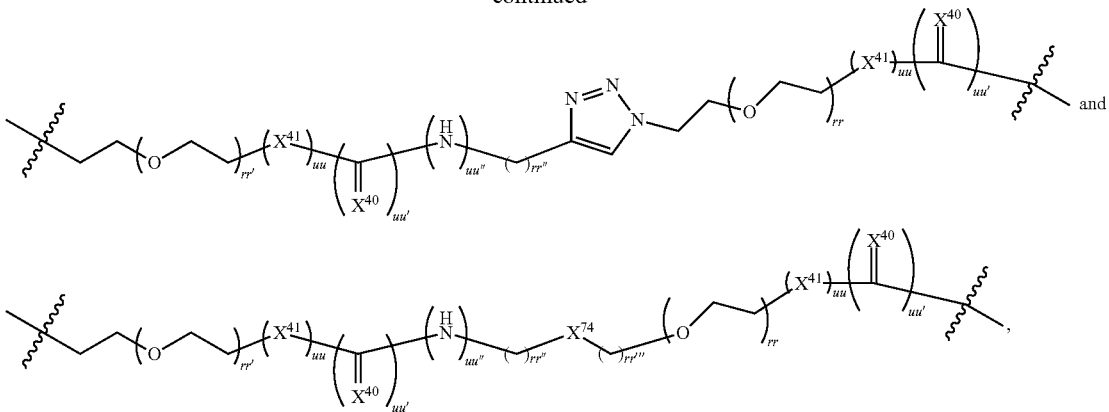

q ranges from 1 to 20, rr, rr', rr", and rr''' each independently range from 0 to 8, $X^{74}$ is selected from

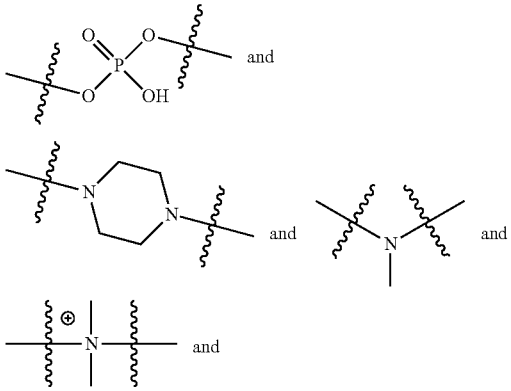

-continued

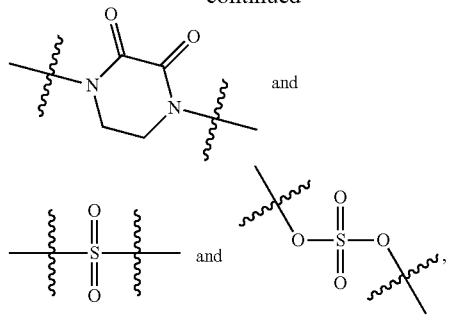

each $X^{40}$ and $X^{41}$ is independently selected from O, S, and $NR^{135}$, wherein $R^{135}$ is selected from H and $C_{1-3}$ alkyl, each uu, uu', and uu" is independently selected from 0 and 1, and Ab is an antibody or a fragment or derivative thereof.

In yet another embodiment, a compound of formula (IIIa) is represented by

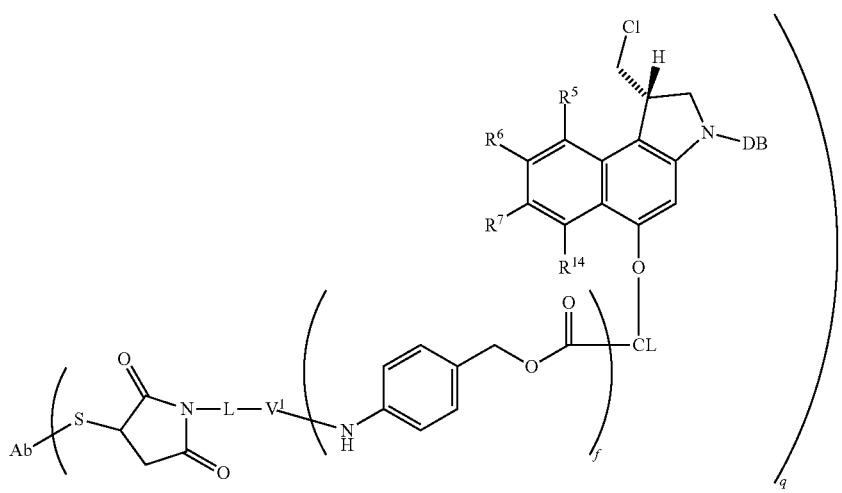

or by an isomer, or by a mixture of isomers, wherein $R^5$, $R^6$, $R^7$, $R^{14}$, and DB are as previously defined, $V^1$ is selected from valylcitrulline, valyllysine, phenylalanyllysine, alanylphenylalanyllysine, and D-alanylphenylalanyllysine, f is 1 or 2, CL is selected from

435
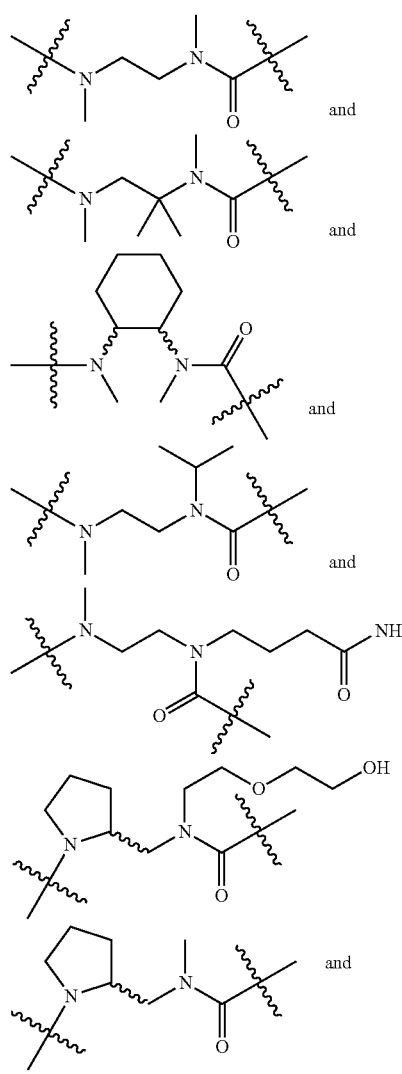 and
436
-continued
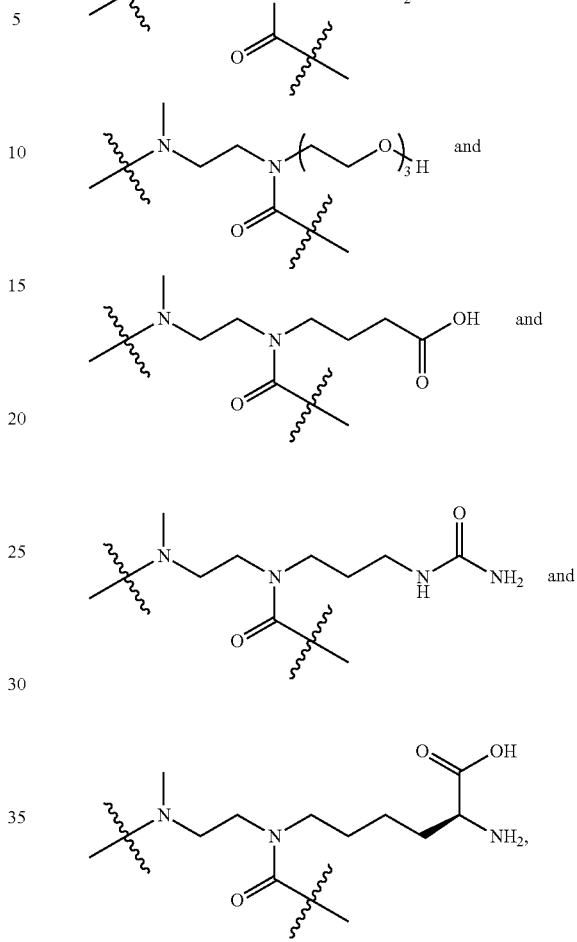
L is selected from
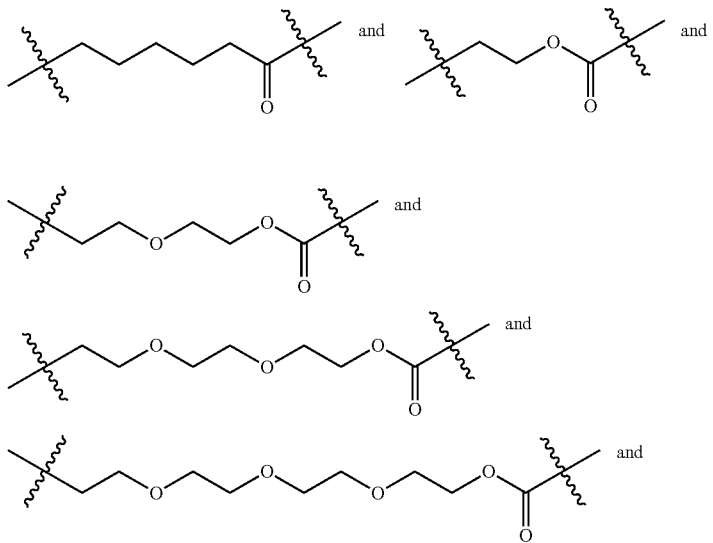

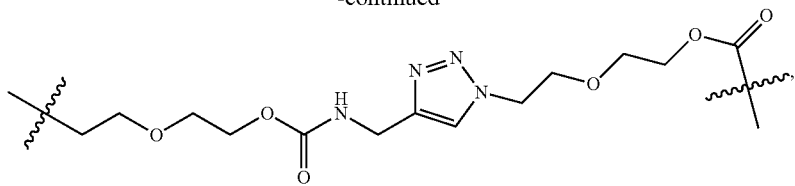

q ranges from 1 to 20, and Ab is an antibody or a fragment or derivative thereof.

In yet another embodiment, a compound of formula (IIIa) is represented by

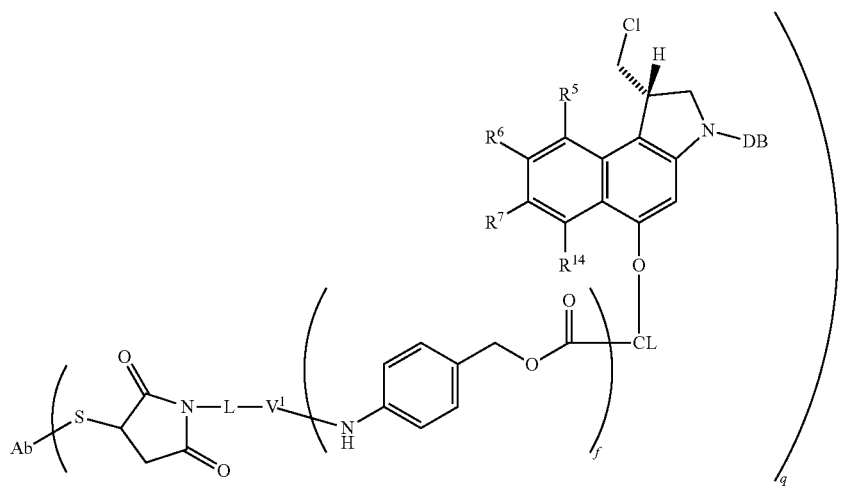

or by an isomer, or by a mixture of isomers, wherein $R^5$ is selected from H, methyl and methoxy, $R^6$, $R^7$, and $R^{14}$ are H, DB is DB1, $V^1$ is selected from valylcitrulline, valyllysine, phenylalanyllysine, alanylphenylalanyllysine, and D-alanylphenylalanyllysine, f is 1 or 2, CL is selected from

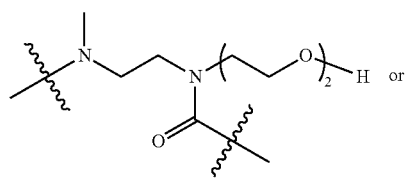 or

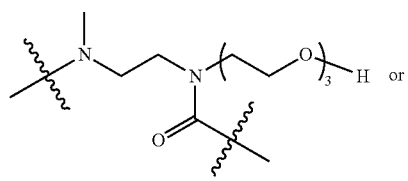 or

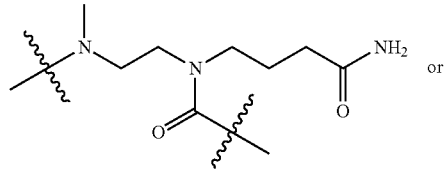 or

-continued

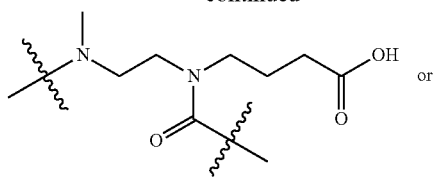 or

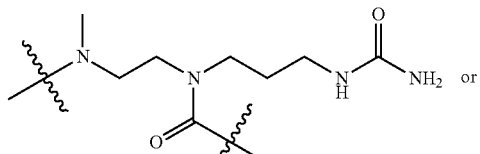 or

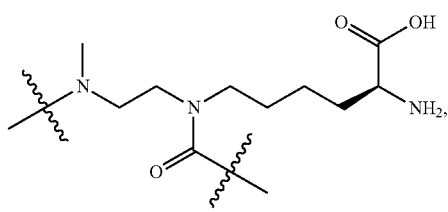 [SMILES: *C(=O)N(CCCC[C@H](N)C(=O)O)CCN(*)C]

L is selected from
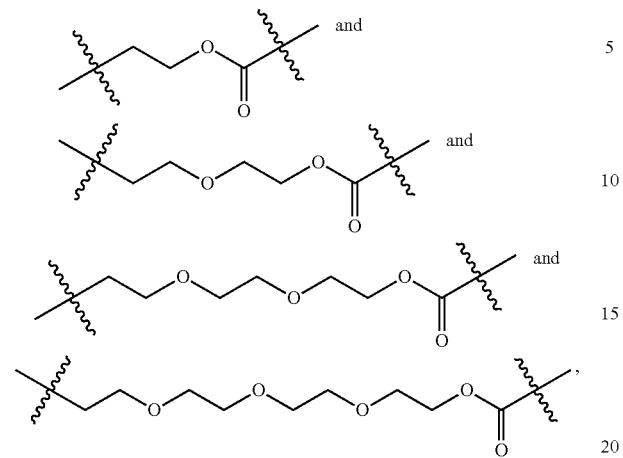
q ranges from 1 to 4, and Ab is an antibody or a fragment or derivative thereof.
In another embodiment, a compound of formula (IIIa) is represented by
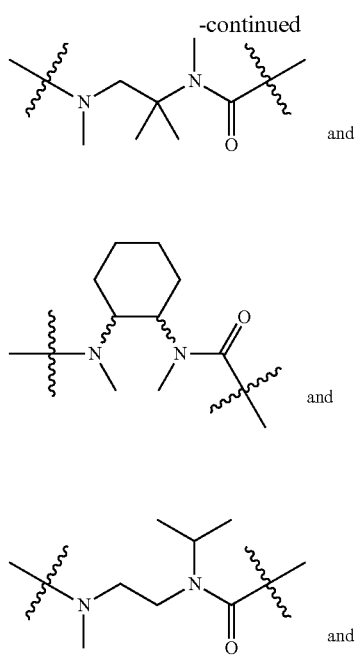
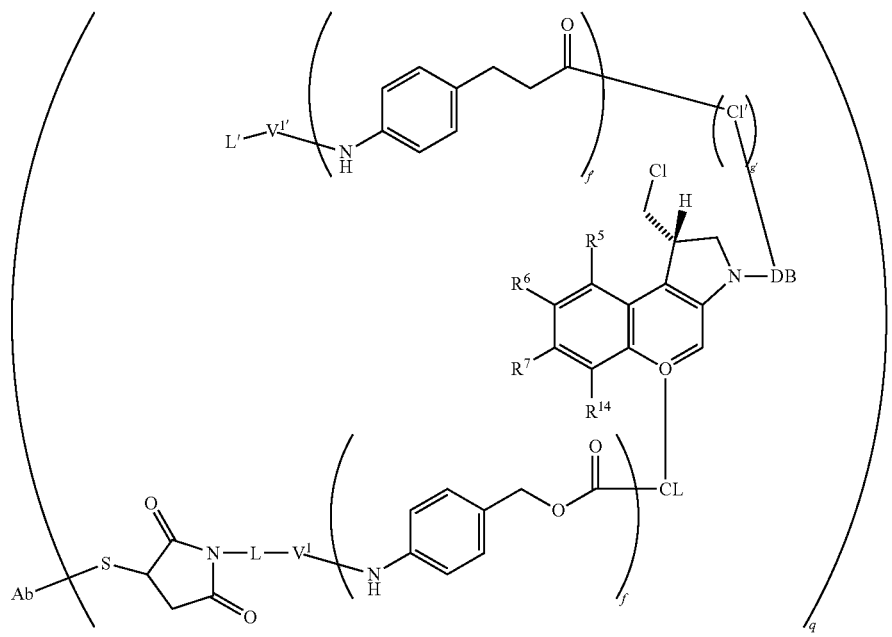
or by an isomer, or by a mixture of isomers, wherein R, $R^6$, R, $R^{14}$, and DB are as previously defined, CL and CL' are independently selected from
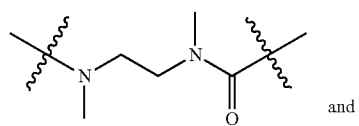
-continued
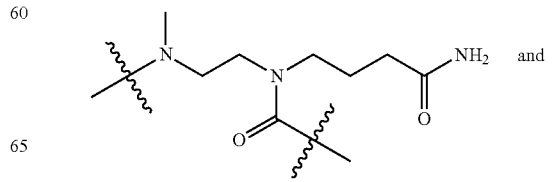

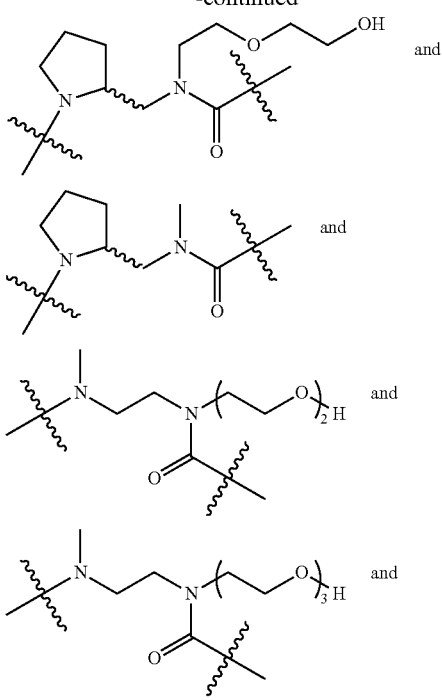

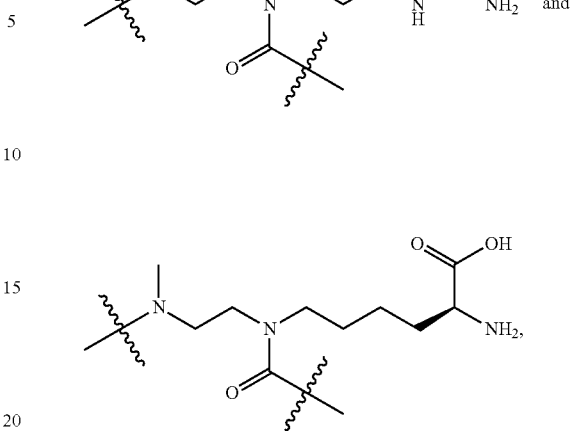

$V^1$ and $V^{1'}$ are independently selected from valylcitrulline, valyllysine, phenylalanyllysine, alanylphenylalanyllysine, and D-alanylphenylalanyllysine, f is 1 or 2, f' is 0, 1, or 2, g' is 0 or 1, the CL' group—or the p-aminobenzyloxycarbonyl group if g' is 0, or the $V^{1'}$ group if f' is 0 as well—is connected to an atom in DB, L is selected from

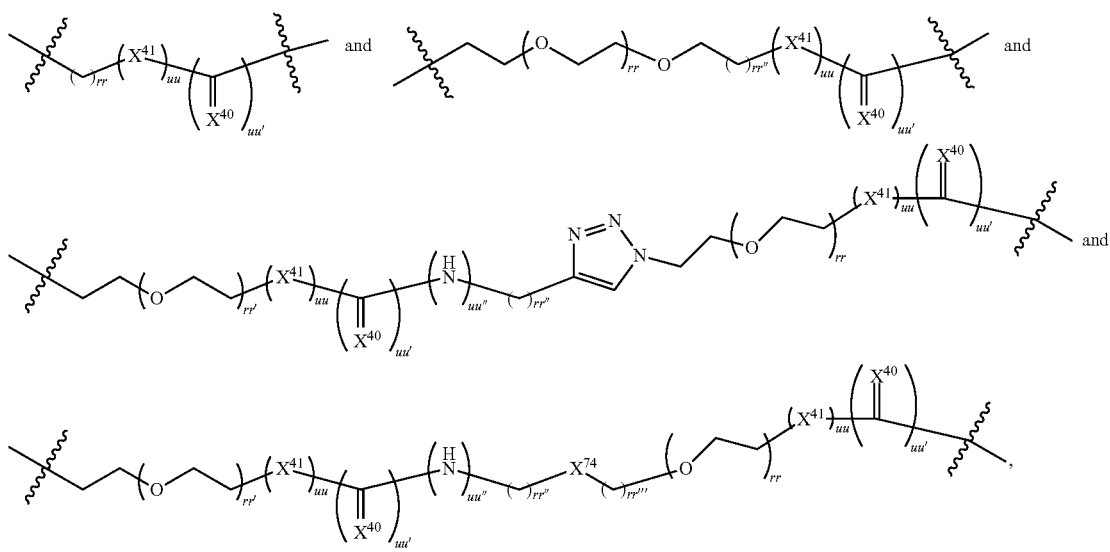

-continued q ranges from 1 to 20, rr, rr', rr", and rr"' each independently range from 0 to 8, $X^{74}$ is selected from

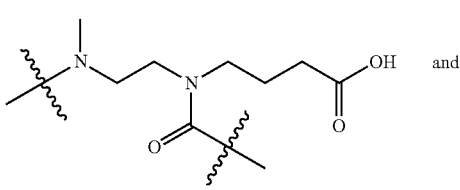

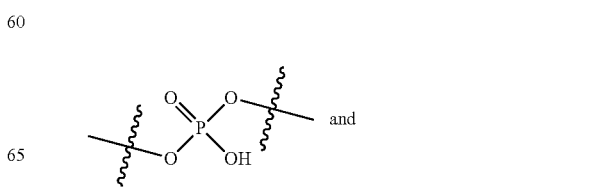

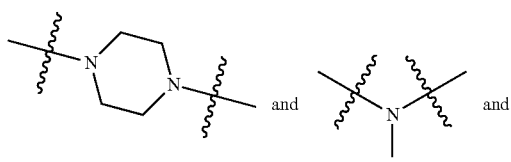 and 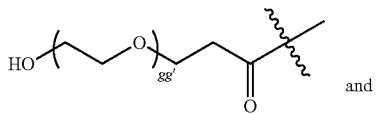 and

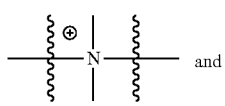 and

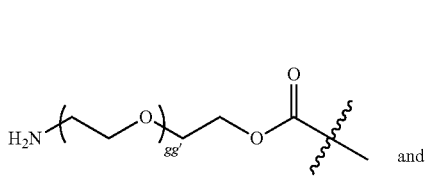 and

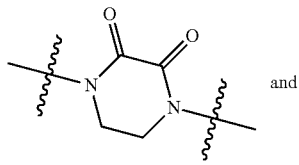 and

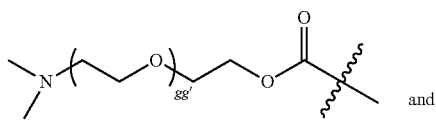 and

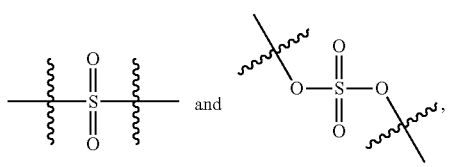

each $X^{40}$ and $X^{41}$ is independently selected from O, S, and $NR^{135}$, wherein $R^{135}$ is selected from H and $C_{1-3}$ alkyl, each uu, uu', and uu" is independently selected from 0 and 1, Ab is an antibody or a fragment or derivative thereof, and L' is selected from

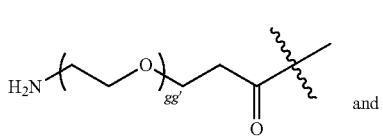 and

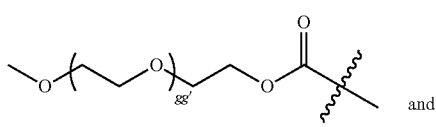 and

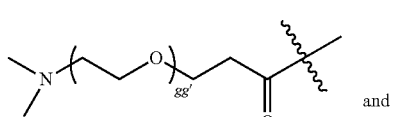 and

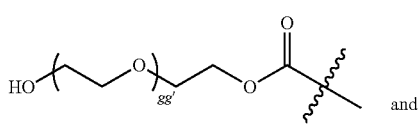 and

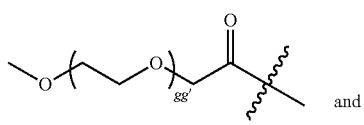 and

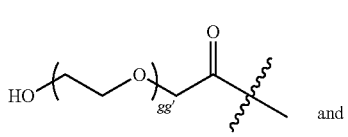 and

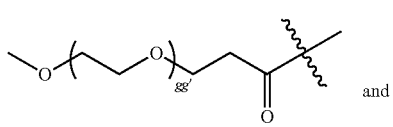 and

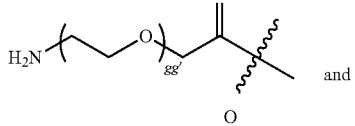 and

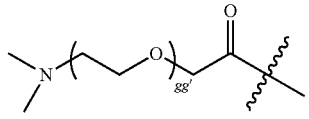

wherein gg' is selected from 0 to 1000.

In another embodiment, a compound of formula (IIIa) is represented by

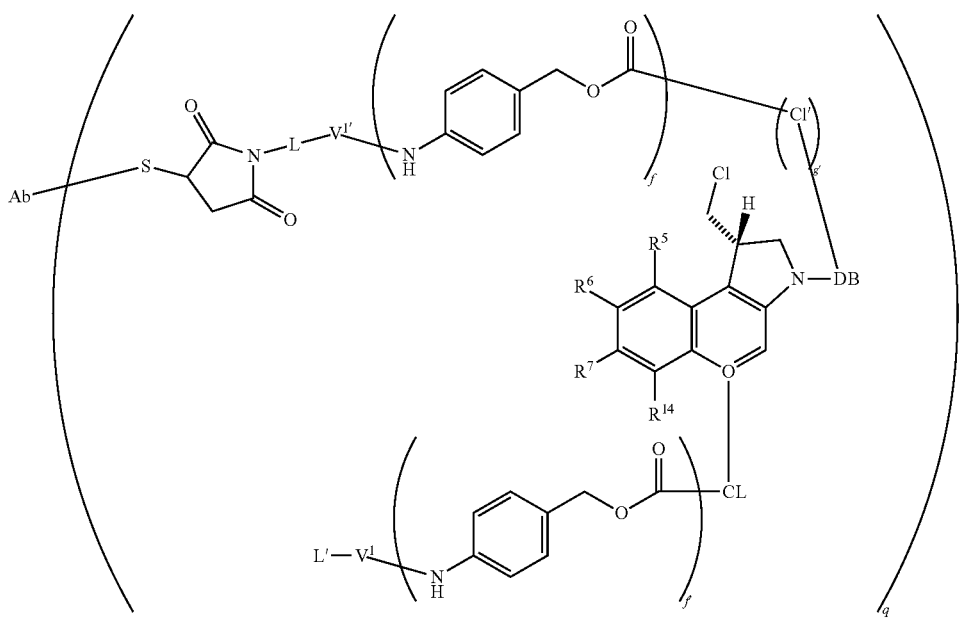
or by an isomer, or by a mixture of isomers, wherein $R^5$, $R^6$, $R^7$, $R^{14}$, and DB are as previously defined, CL and CL' are independently selected from
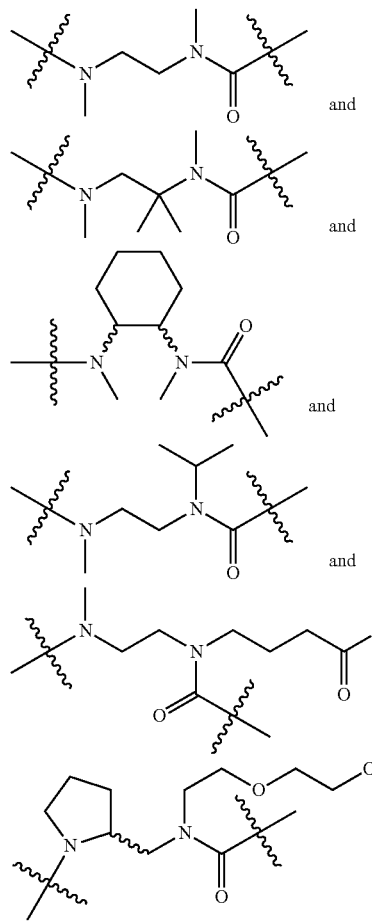
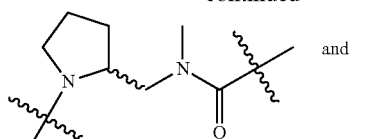

447
-continued

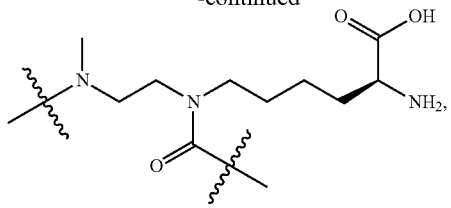

$V^1$ and $V^{1'}$ are independently selected from valylcitrulline, valyllysine, phenylalanyllysine, alanylphenylalanyllysine, and D-alanylphenylalanyllysine, f is 0, 1, or 2, f' is 1, or 2, g is 0 or 1, the CL group—or the p-aminobenzyloxycarbonyl group if g is 0, or the $V^1$ group if f is 0 as well—is connected to an atom in DB, L is selected from

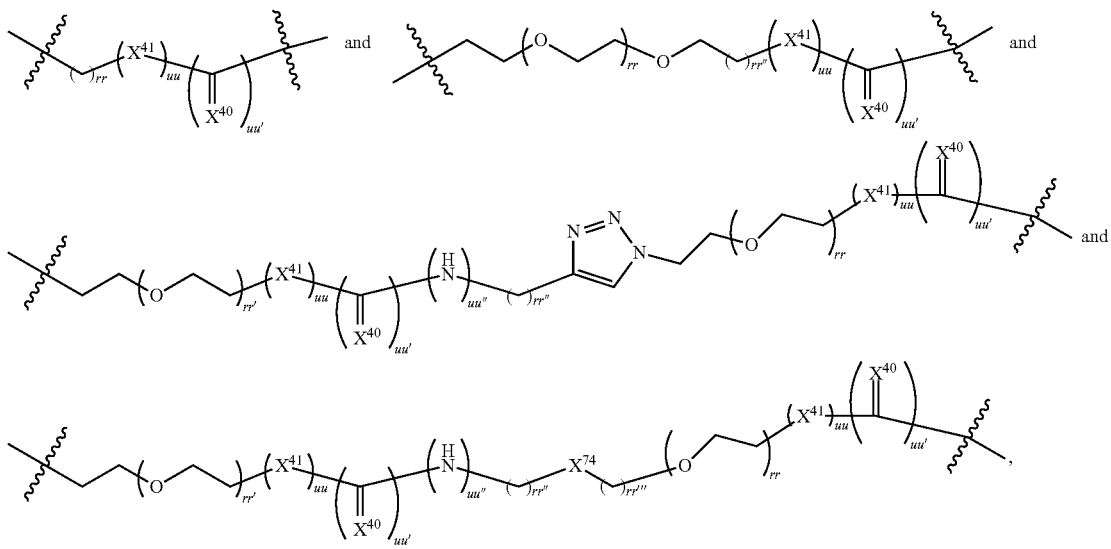

q ranges from 1 to 20, rr, rr', rr", and rr'" each independently range from 0 to 8, $X^{74}$ is selected from

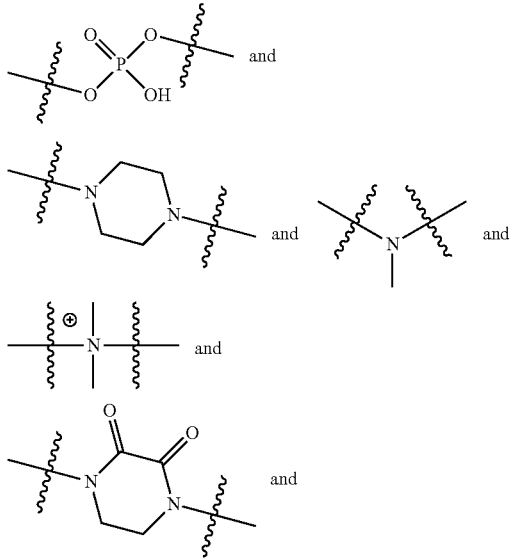

448
-continued

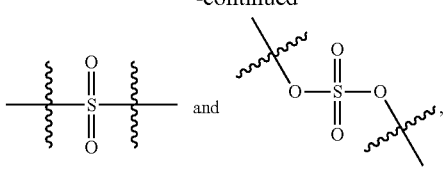

each $X^{40}$ and $X^{41}$ is independently selected from O, S, and $NR^{135}$, wherein $R^{135}$ is selected from H and $C_{1-3}$ alkyl, each uu, uu', and uu" is independently selected from 0 and 1, Ab is an antibody or a fragment or derivative thereof, and L' is selected from

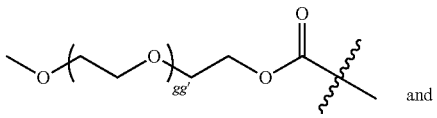

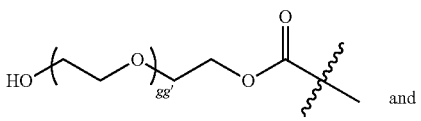

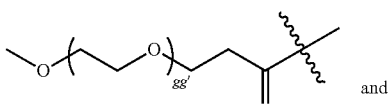

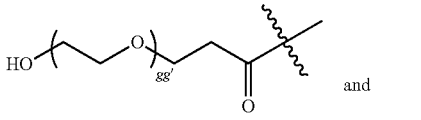

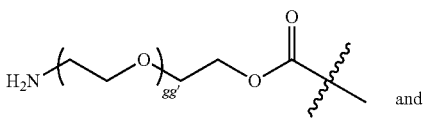

-continued

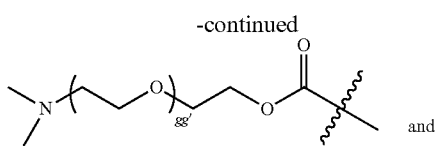 and

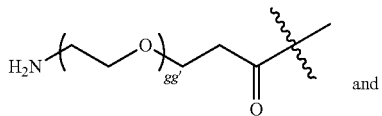 and

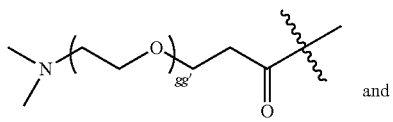 and

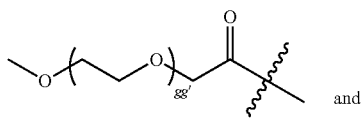 and

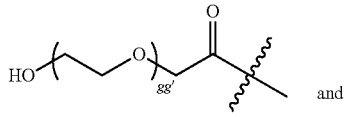 and

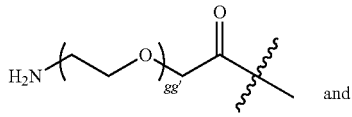 and

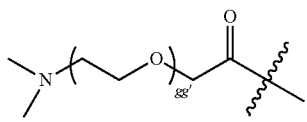

wherein gg' is selected from 0 to 1000.

In another embodiment, a compound of formula (III) is represented by

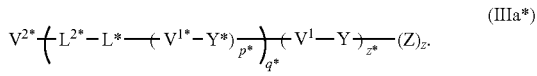 (IIIa*)

In one embodiment, $p^*$ in a compound of formula (IIIa*) is 1.

In another embodiment, in a compound of formula (IIIa*) $p^*$ is 1 and $z^*$ equals $q^*$.

In another embodiment, in a compound of formula (IIIa*) $p^*$ is 1 and $z^*$ as well as z equal $q^*$, which reduces formula (IIIa*) to:

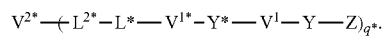

In another embodiment, a compound of formula (III) is represented by

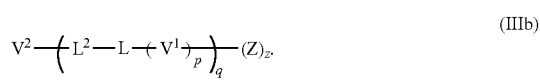 (IIIb)

In one embodiment, p in a compound of formula (IIIb) is 1.

In another embodiment, p in a compound of formula (IIIb) is 1 and z equals q, which reduces formula (IIIb) to:

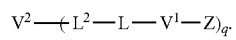

In another embodiment, a compound of formula (III) is represented by

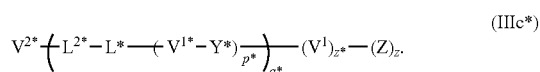 (IIIc*)

In one embodiment, $p^*$ in a compound of formula (IIIc) is 1.

In another embodiment, in a compound of formula (IIIc) $p^*$ is 1 and $z^*$ equals $q^*$.

In yet another embodiment, in a compound of formula (IIIc) $p^*$ is 1 and $z^*$ as well as z equal $q^*$, which reduces formula (IIIc) to:

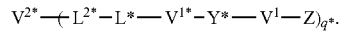

In another embodiment, $V^1$ in a compound of formula (IIIc) is an enzyme-cleavable substrate. In a further embodiment, $V^1$ can be cleaved by an intracellular enzyme. In another embodiment, $V^1$ is an optionally substituted N,N-dialkylaminocarbonyl group wherein the two alkyl groups may be the same or different and optionally be connected to each other to form an optionally substituted heterocycle. In yet another embodiment, $V^1$ is piperazinocarbonyl. Such a $V^1$ group may be cleaved enzymatically, for example by carboxylesterases.

In another embodiment, a compound of formula (IIIc) is represented by

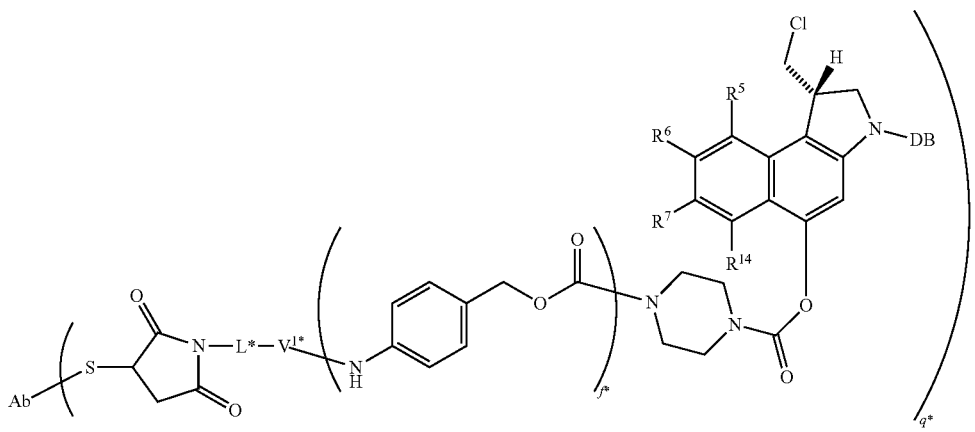

or by an isomer, or by a mixture of isomers, wherein $R^5$, $R^6$, $R^7$, $R^{14}$, and DB are as previously defined, $V^{1*}$ is selected from valylcitrulline, valyllysine, phenylalanyllysine, alanylphenylalanyllysine, and D-alanylphenylalanyllysine, f* is 1 or 2, L* is selected from

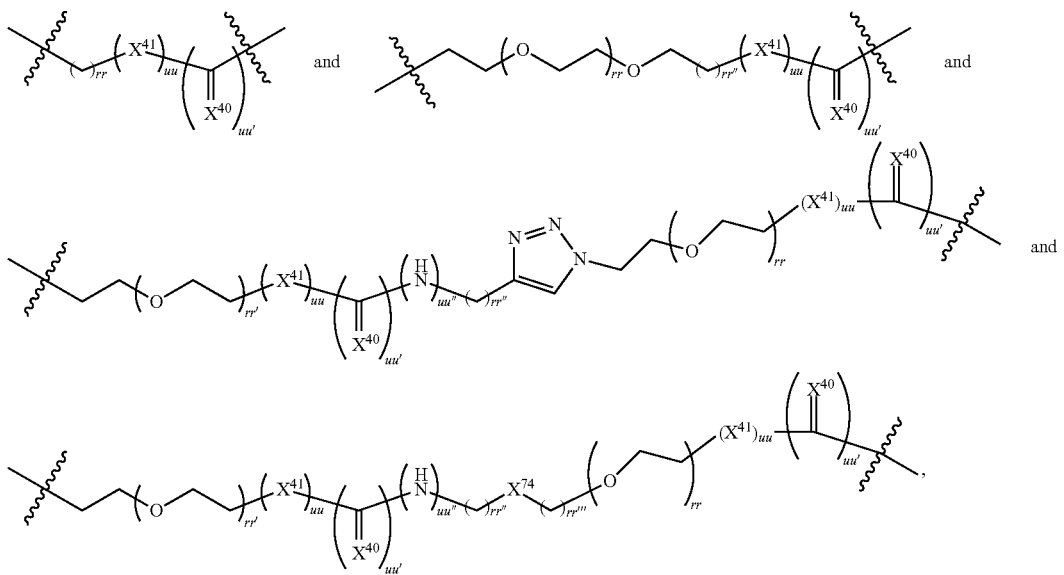

q* ranges from 1 to 20, rr, rr', rr", and rr'" each independently range from 0 to 8, $X^{74}$ is selected from

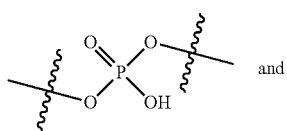

and

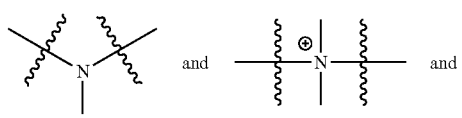

and

-continued

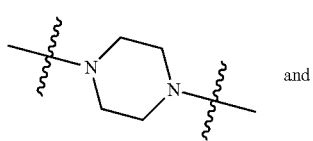

and

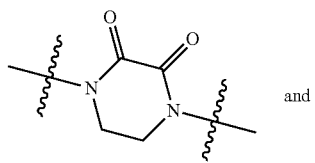

and

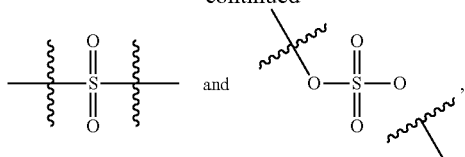 and 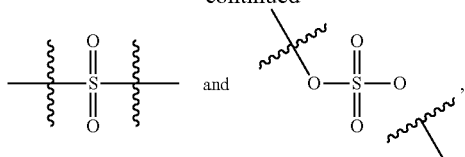, each $X^{40}$ and $X^{41}$ is independently selected from O, S, and $NR^{135}$, wherein $R^{135}$ is selected from H and $C_{1-3}$ alkyl, each uu, uu', and uu" is independently selected from 0 and 1, and Ab is an antibody or a fragment or derivative thereof.

In yet another embodiment, a compound of formula (IIIc) is represented by

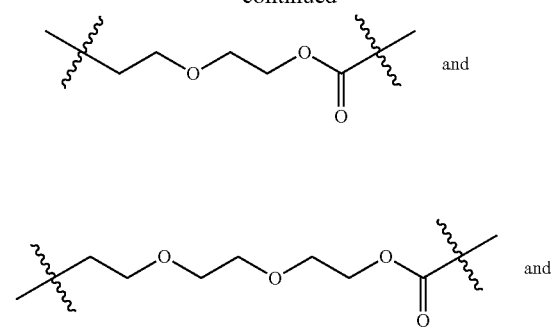

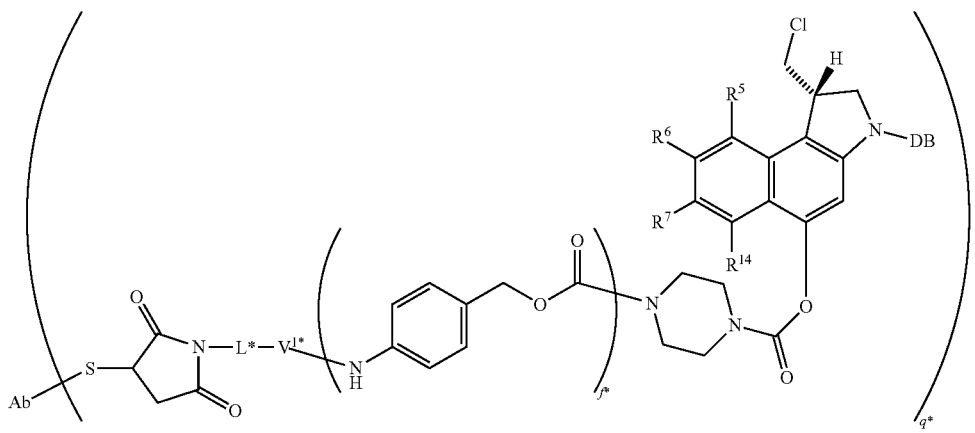

or by an isomer, or by a mixture of isomers, wherein $R^5$, $R^6$, $R^7$, $R^{14}$, and DB are as previously defined, $V^{1*}$ is selected from valylcitrulline, valyllysine, phenylalanyllysine, alanylphenylalanyllysine, and D-alanylphenylalanyllysine, f* is 1 or 2, L* is selected from

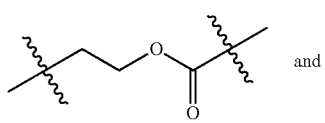 and

-continued

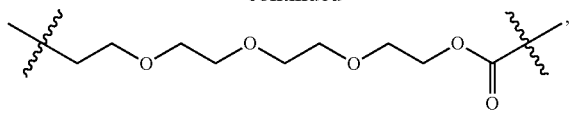, q* ranges from 1 to 20, and Ab is an antibody or a fragment or derivative thereof.

In yet another embodiment, a compound of formula (III) is represented by $$V^1\text{-}Z \qquad (IIId)$$

In one embodiment, a compound of formula (IIId) is represented by

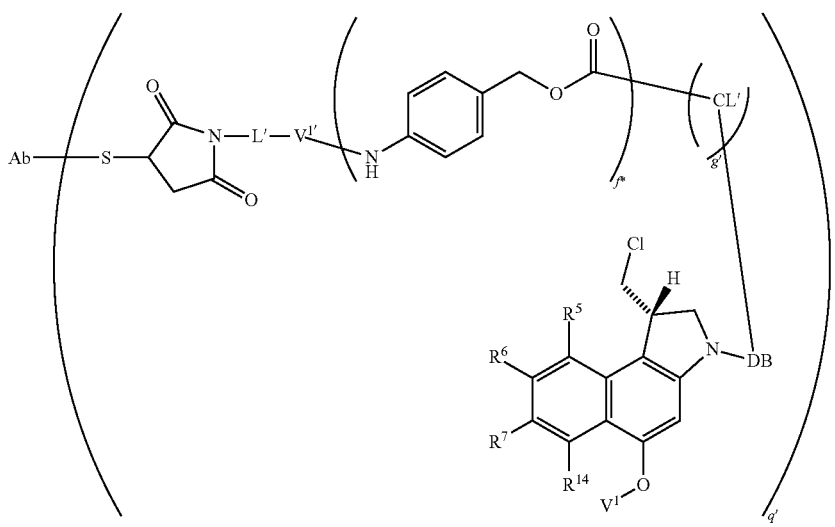
or by an isomer, or by a mixture of isomers, wherein $R^5$, $R^6$, $R^7$, $R^{14}$, and DB are as previously defined, CL' is selected from
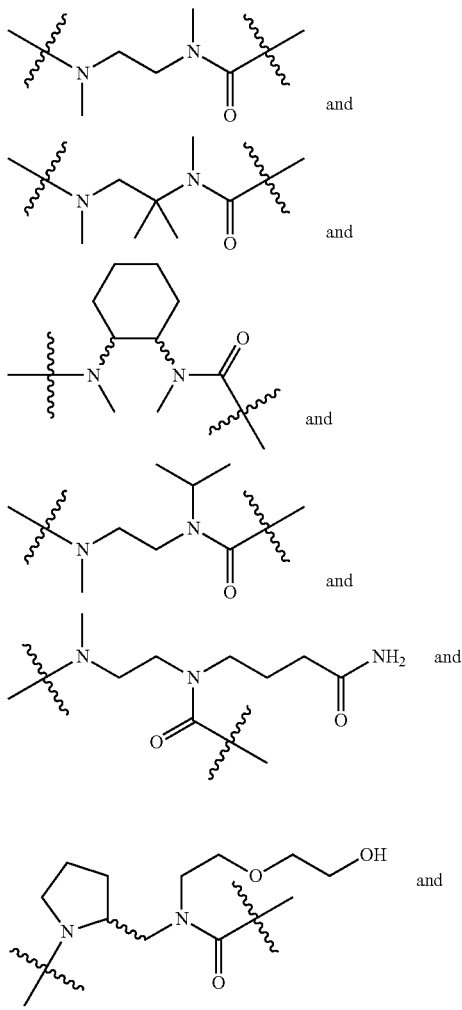
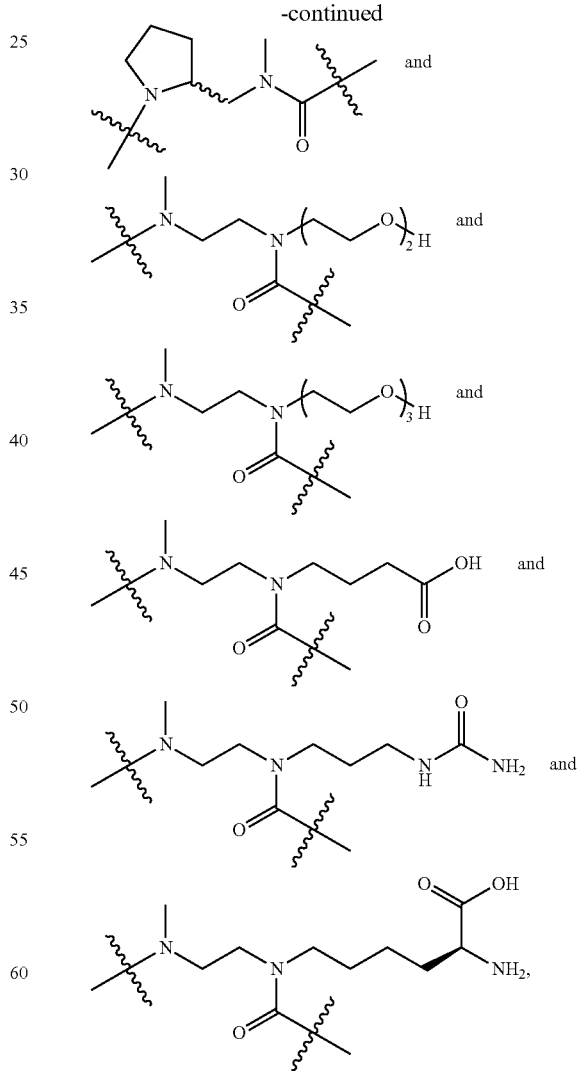
f' is 0, 1, or 2, g' is 0 or 1, $V^{1'}$ is selected from valylcitrulline, valyllysine, phenylalanyllysine, alanylphenylalanyllysine, and D-alanylphenylalanyllysine or is absent, the CL' group—or the p-aminobenzyloxycarbonyl group if g' is 0, or the V¹ group if f' is 0 as well, or the L' group if the V¹ group is absent as well—is connected to an atom in DB, L' is selected from uu, uu', and uu" is independently selected from 0 and 1, Ab is an antibody or a fragment or derivative thereof, and V¹ is selected from a mono-, di-, or oligosaccharide or a reduced, oxidized, or protected derivative thereof and

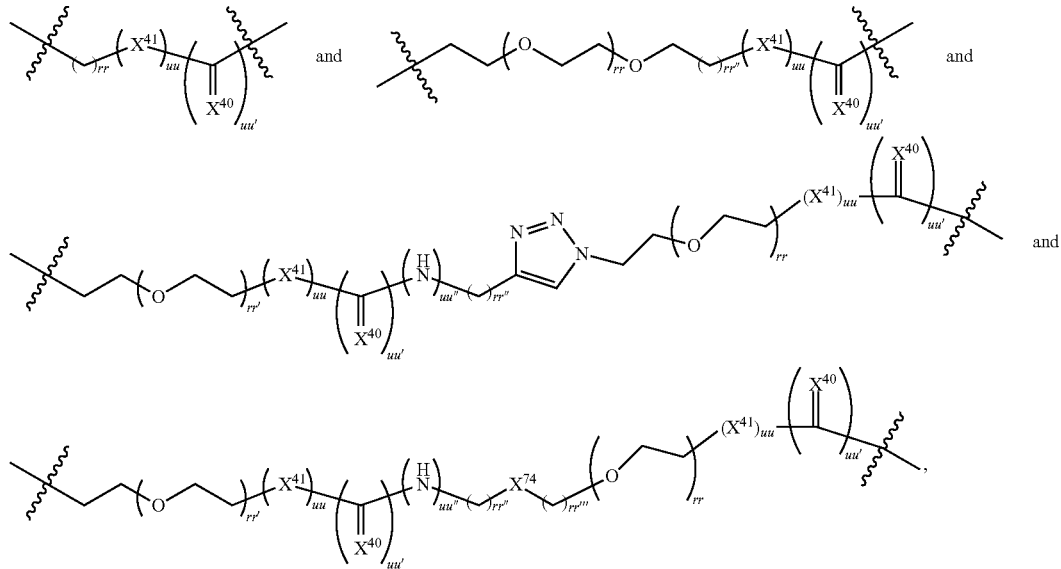

q' ranges from 1 to 20, rr, rr', rr", and rr'" each independently range from 0 to 8, $X^{74}$ is selected from

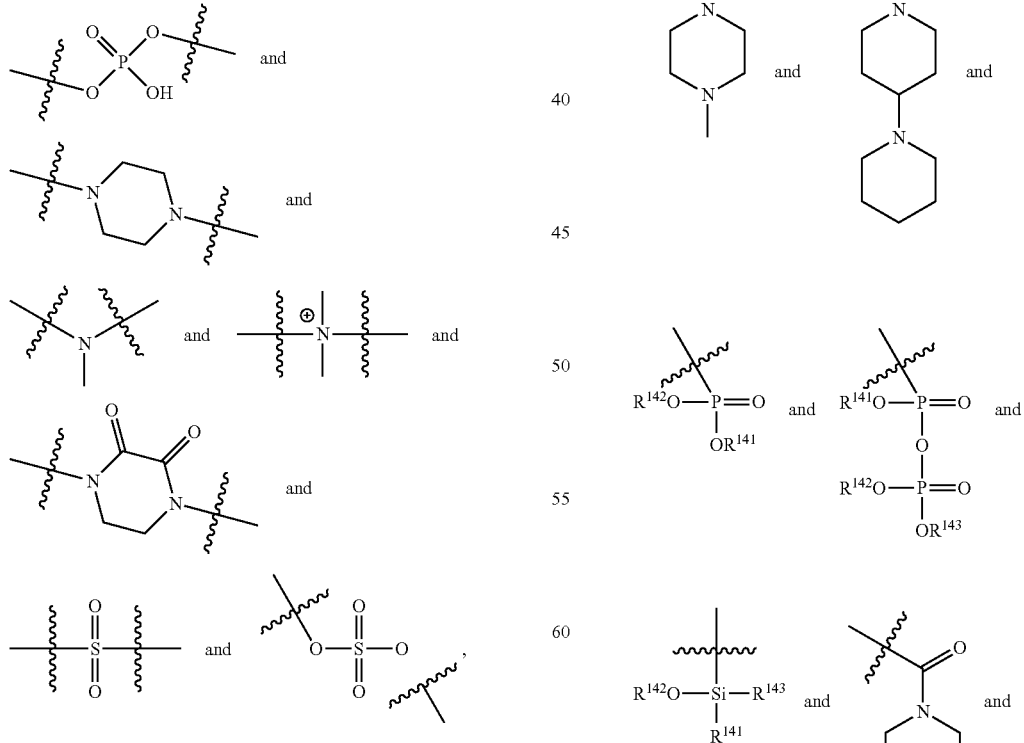

each $X^{40}$ and $X^{41}$ is independently selected from O, S, and $NR^{135}$, wherein $R^{135}$ is selected from H and $C_{1-3}$ alkyl, each -continued

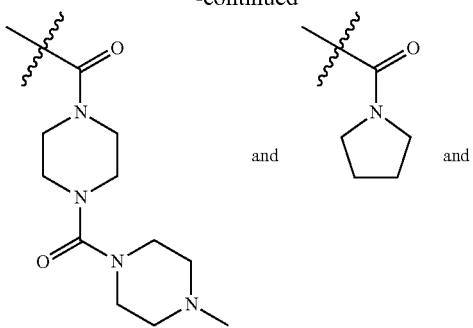
and
and
and

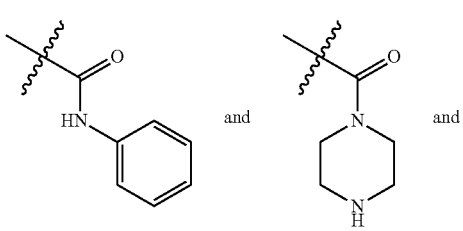
and
and

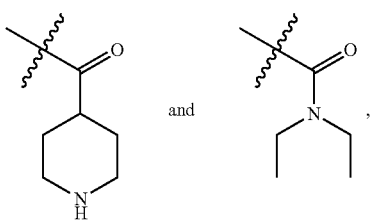
and wherein $R^{141}$, $R^{142}$, and $R^{143}$ are independently selected from H and optionally substituted $C_{1-8}$ alkyl, $C_{1-8}$ heteroalkyl, $C_{3-8}$ cycloalkyl, $C_{1-8}$ heterocycloalkyl, $C_{5-8}$ aryl, or $C_{1-8}$ heteroaryl.

In another embodiment, a compound of formula (IIId) is represented by or by an isomer, or by a mixture of isomers, wherein $R^5$, $R^6$, $R^7$, $R^{14}$, and DB are as previously defined, CL' is

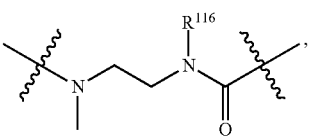, $R^{116}$ is selected from methyl, ethyl, isopropyl, tert-butyl, phenyl,

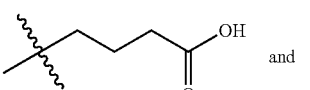 and

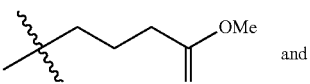 and

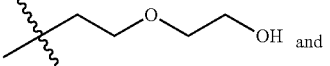 and

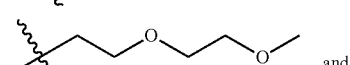 and

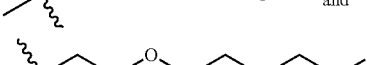 and

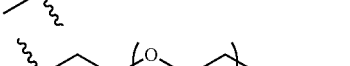 and

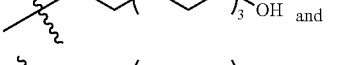 and

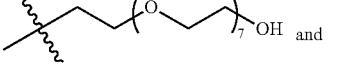 and

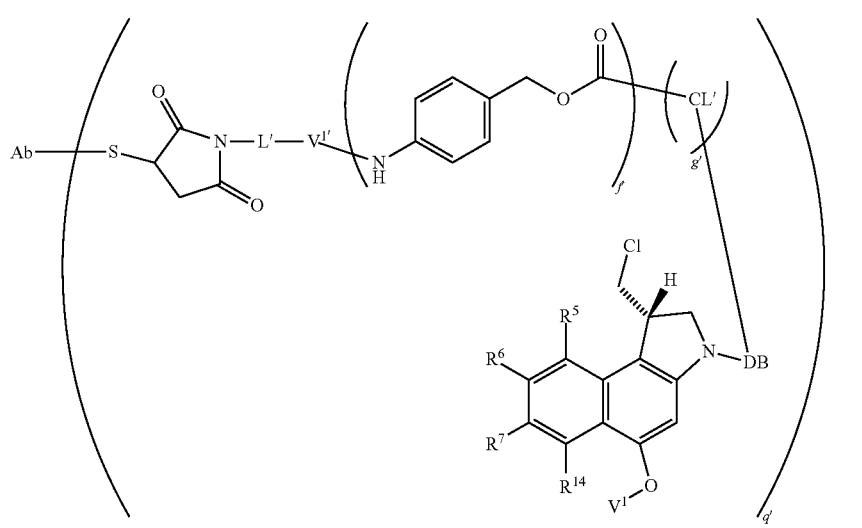

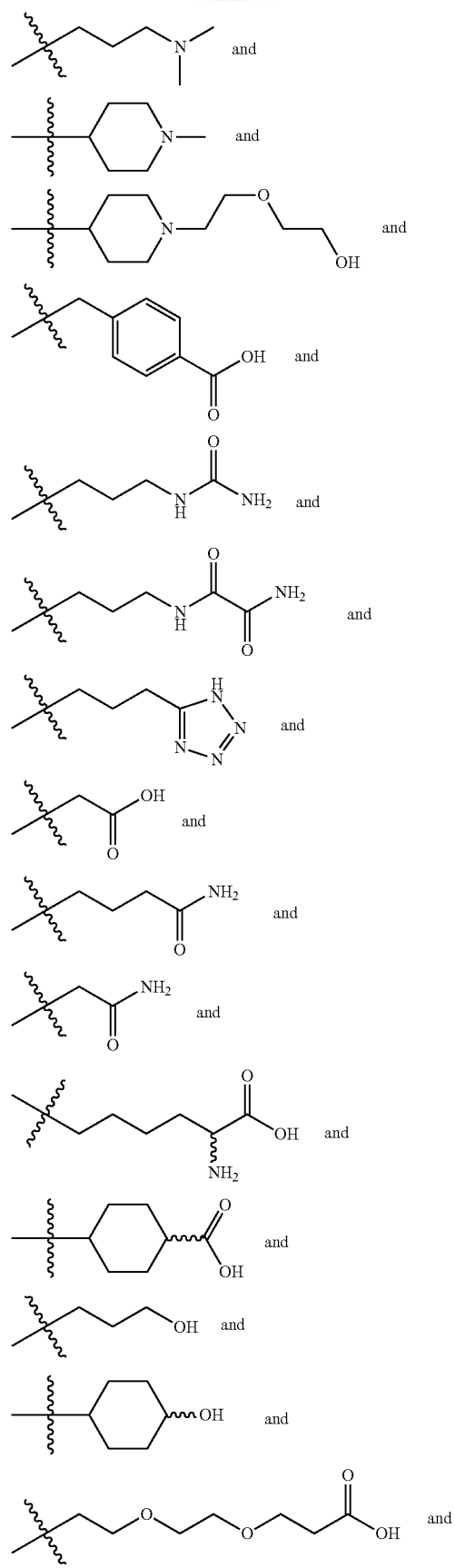
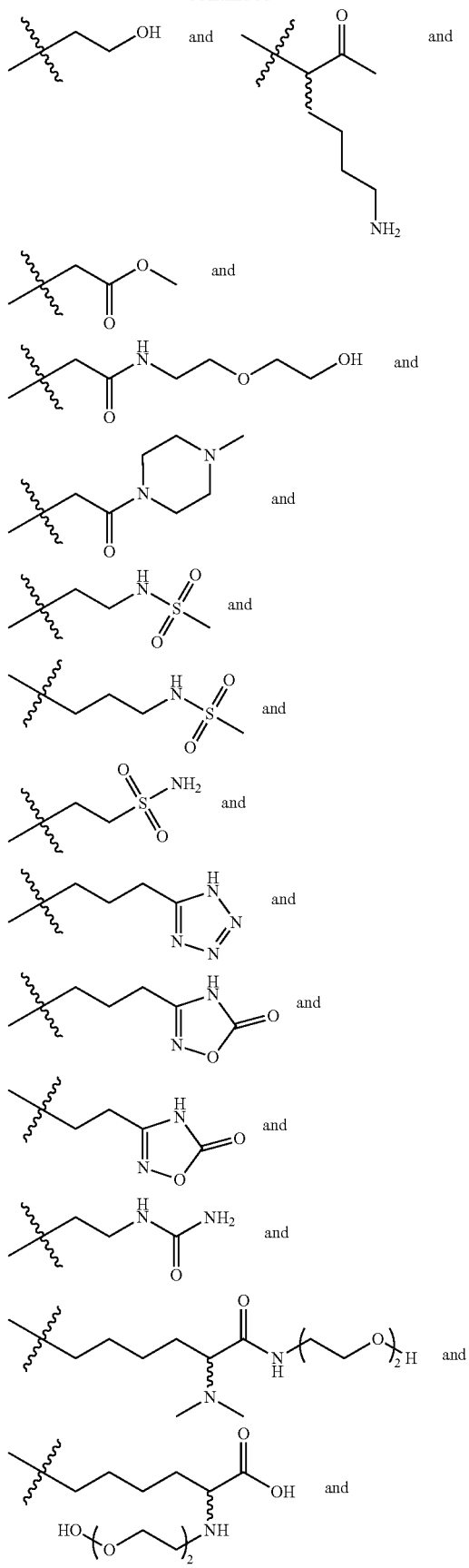

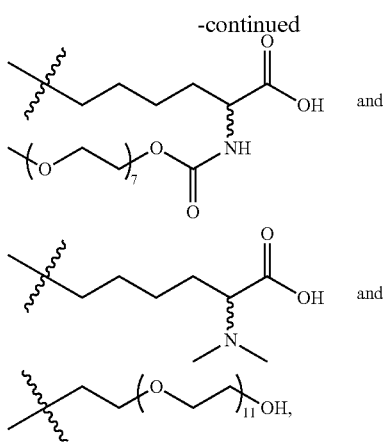 and

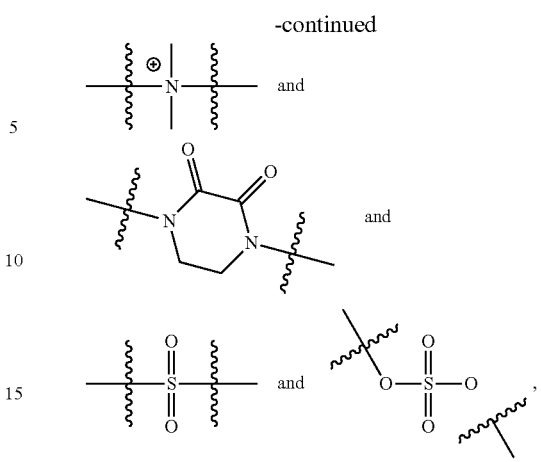 and f' is 0, 1, or 2, g' is 0 or 1, $V^{1'}$ is selected from valylcitrulline, valyllysine, phenylalanyllysine, alanylphenylalanyllysine, and D-alanylphenylalanyllysine or is absent, the CL' group— or the p-aminobenzyloxycarbonyl group if g' is 0, or the $V^{1'}$ group if f' is 0 as well, or the L' group if the $V^{1'}$ group is absent as well—is connected to an atom in DB, L' is selected from each $X^{40}$ and $X^{41}$ is independently selected from O, S, and $NR^{135}$, wherein $R^{135}$ is selected from H and $C_{1-3}$ alkyl, each uu, uu', and uu'' is independently selected from 0 and 1, Ab is an antibody or a fragment or derivative thereof, and $V^1$ is selected from a mono-, di-, or oligosaccharide or a reduced, oxidized, or protected derivative thereof and

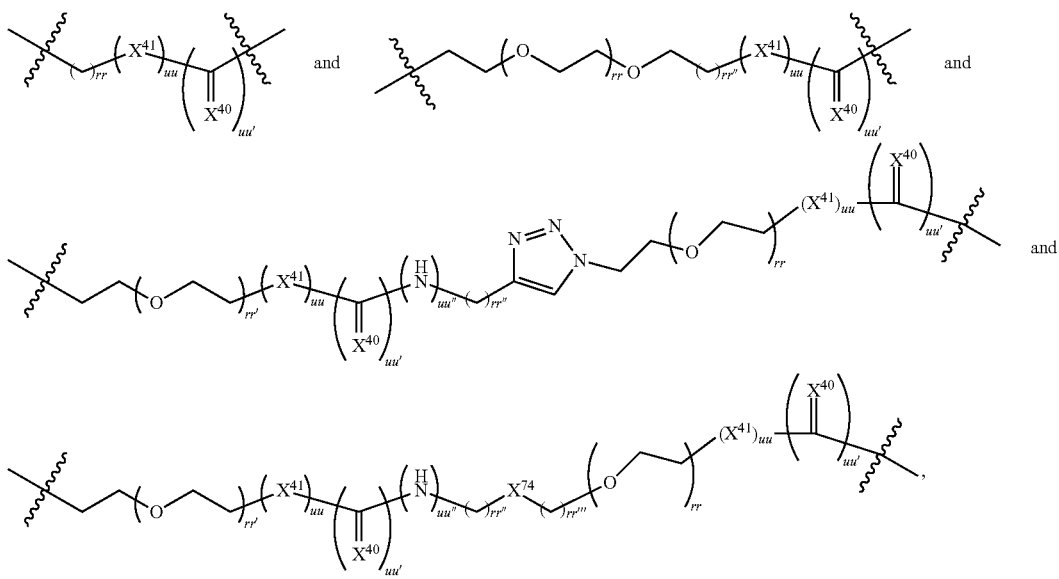

q' ranges from 1 to 20, rr, rr', rr'', and rr''' each independently range from 0 to 8, $X^{74}$ is selected from

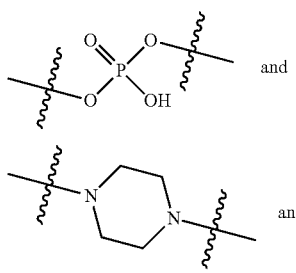 and

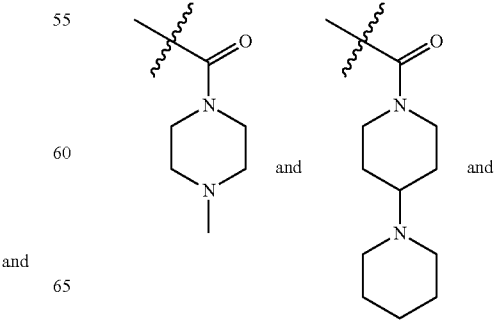 and

465

-continued

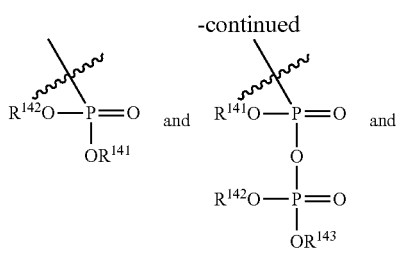

466

-continued

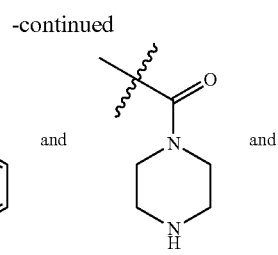

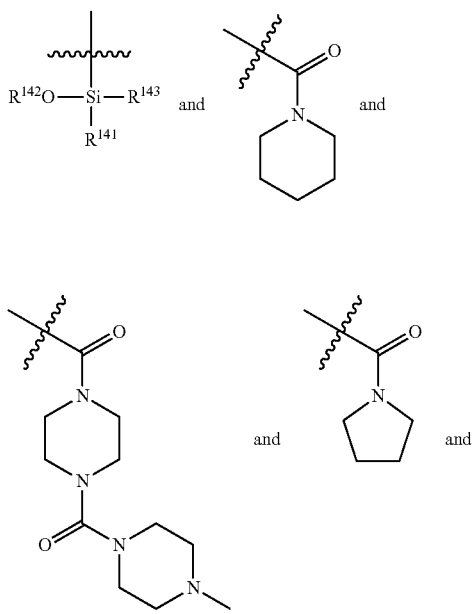

wherein $R^{141}$, $R^{142}$, and $R^{143}$ are independently selected from H and optionally substituted $C_{1-8}$ alkyl, $C_{1-8}$ heteroalkyl, $C_{3-8}$ cycloalkyl, $C_{1-8}$ heterocycloalkyl, $C_{5-8}$ aryl, or $C_{1-8}$ heteroaryl.

In another embodiment, a compound of formula (IIId) is represented by

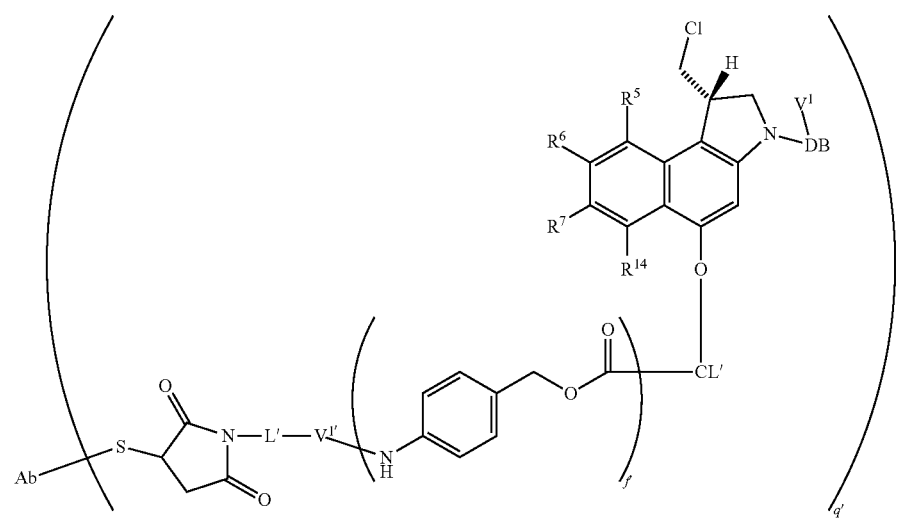

or by an isomer, or by a mixture of isomers, wherein $R^5$, $R^6$, $R^7$, $R^{14}$, and DB are as previously defined, CL' is selected from 467
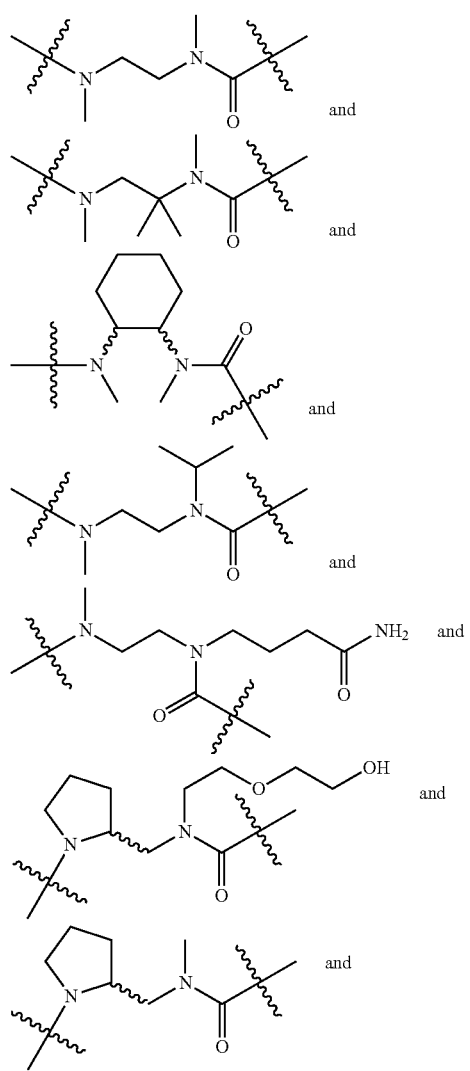
468
-continued
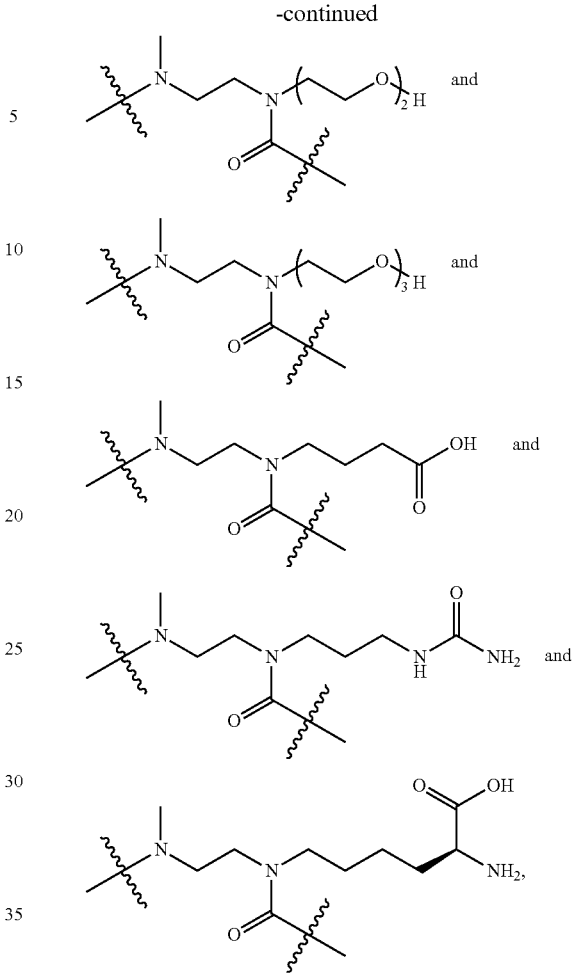
f' is 1 or 2, $V^{1'}$ is selected from valylcitrulline, valyllysine, phenylalanyllysine, alanylphenylalanyllysine, and D-alanylphenylalanyllysine, L' is selected from
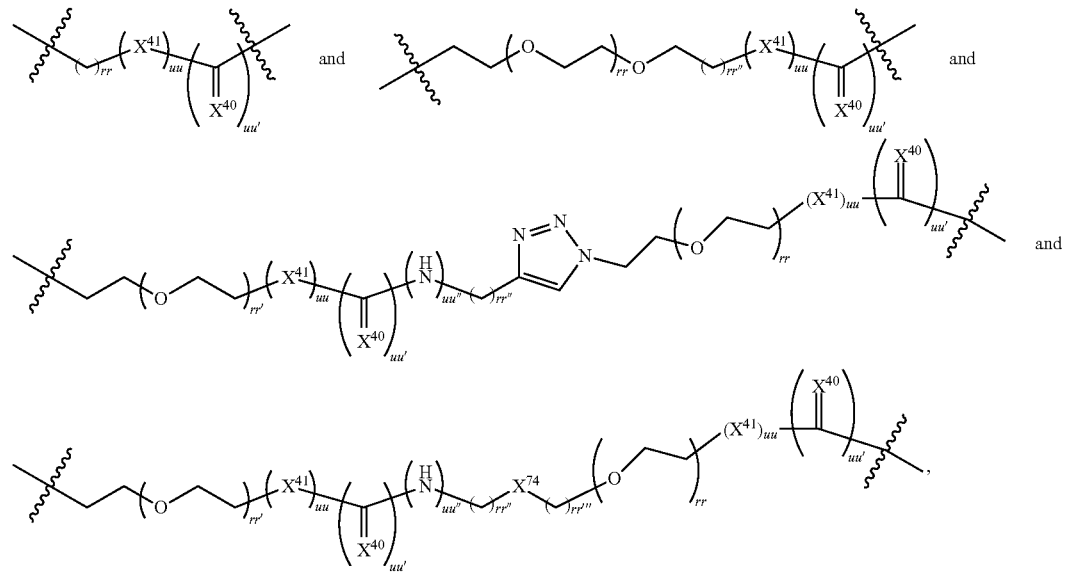

q' ranges from 1 to 20, rr, rr', rr'', and rr''' each independently range from 0 to 8, each $X^{40}$ and $X^{41}$ is independently selected from O, S, and $NR^{135}$, wherein $R^{135}$ is selected from H and $C_{1-3}$ alkyl, each uu, uu', and uu'' is independently selected from 0 and 1, Ab is an antibody or a fragment or derivative thereof, and $V^1$ is coupled to an atom of DB and is selected from a mono-, di-, or oligosaccharide or a reduced, oxidized, or protected derivative thereof and

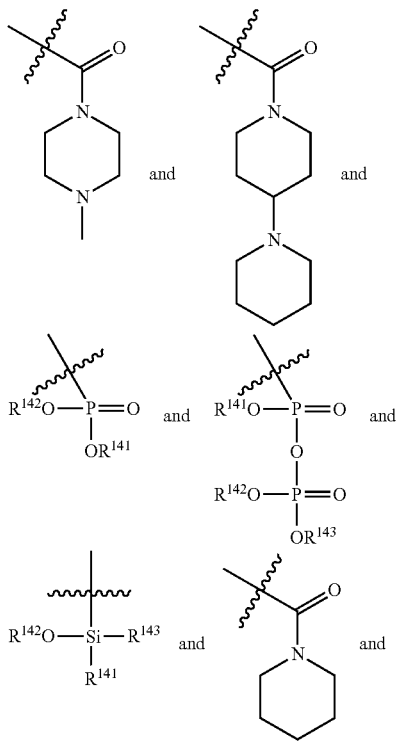

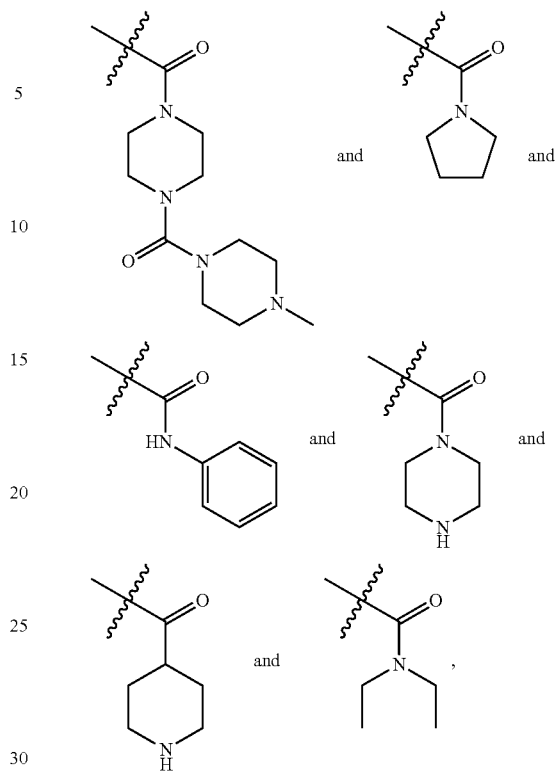

wherein $R^{141}$, $R^{142}$, and $R^{143}$ are independently selected from H and optionally substituted $C_{1-8}$ alkyl, $C_{1-8}$ heteroalkyl, $C_{3-8}$ cycloalkyl, $C_{1-8}$ heterocycloalkyl, $C_{5-8}$ aryl, or $C_{1-8}$ heteroaryl.

In another embodiment, a compound of formula (Id) is represented by

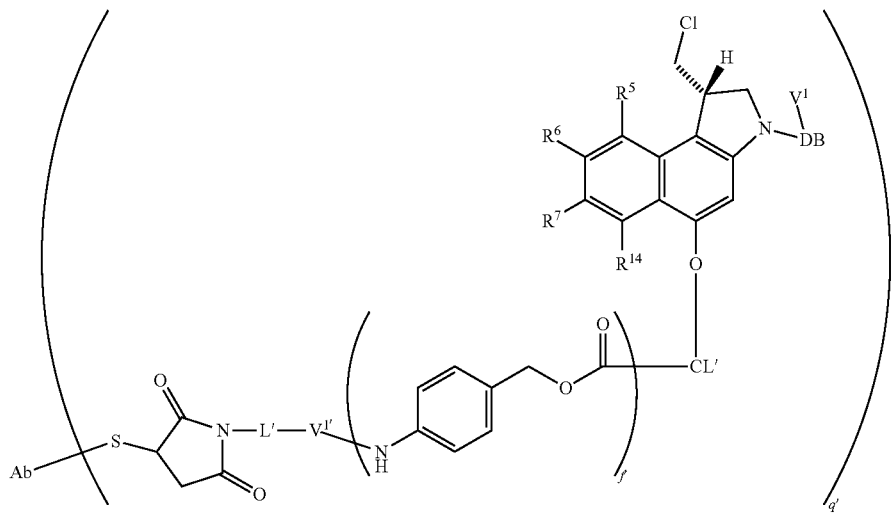

or by an isomer, or by a mixture of isomers, wherein $R^5$, $R^6$, $R^7$, $R^{14}$, and DB are as previously defined, CL' is
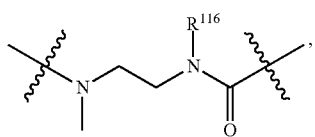
$R^{116}$ is selected from methyl, ethyl, isopropyl, tert-butyl, phenyl,
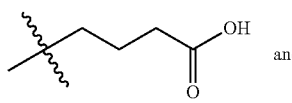 and
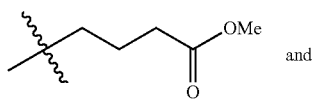 and
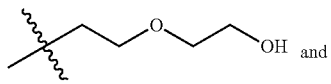 and
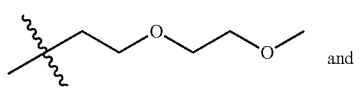 and
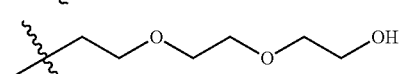 and
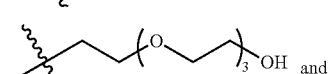 and
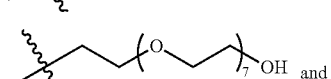 and
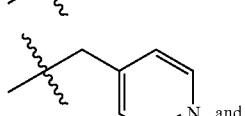 and
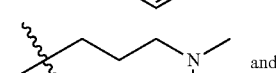 and
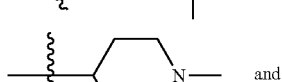 and
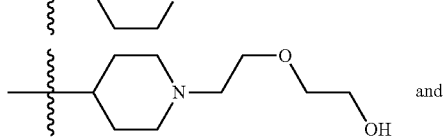 and
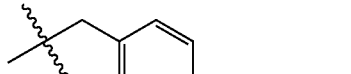 and
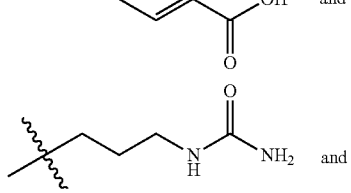 and
-continued
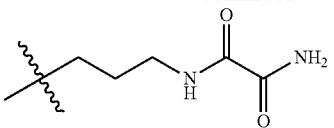 and
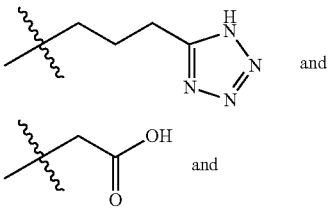 and
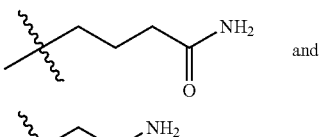 and
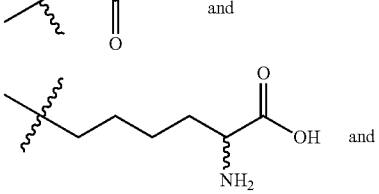 and
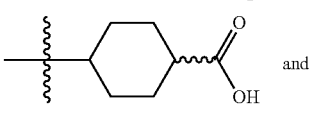 and
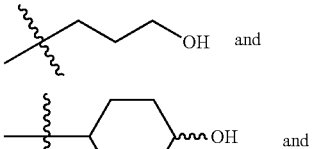 and
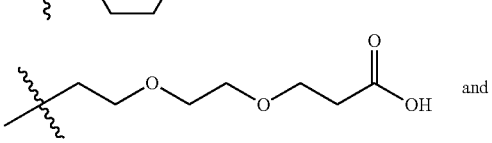 and
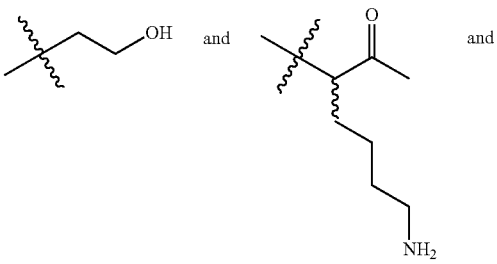 and
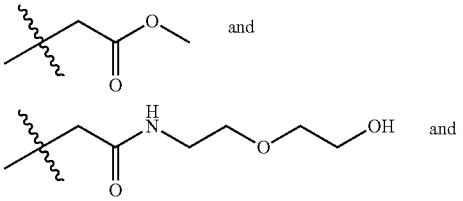 and
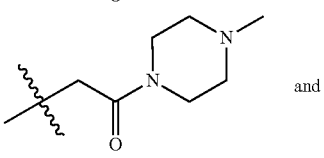 and

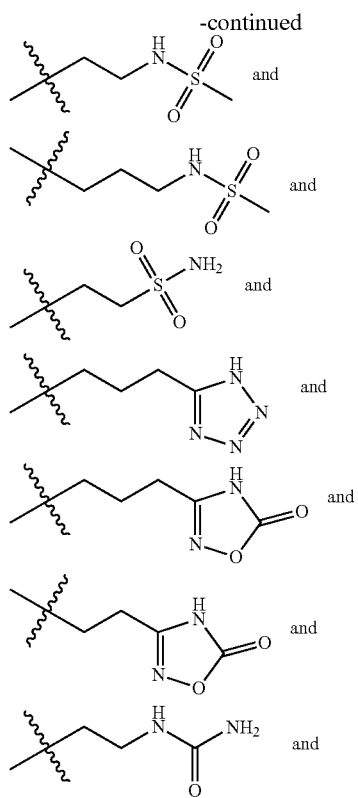

and

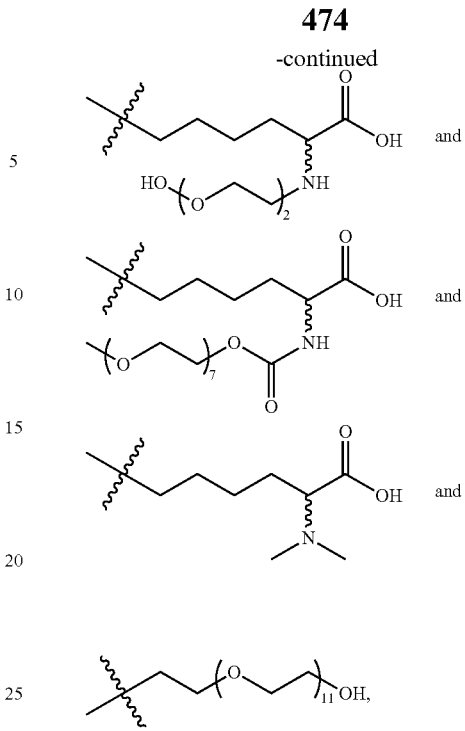

f' is 1 or 2, V¹' is selected from valylcitrulline, valyllysine, phenylalanyllysine, alanylphenylalanyllysine, and D-alanylphenylalanyllysine, L' is selected from

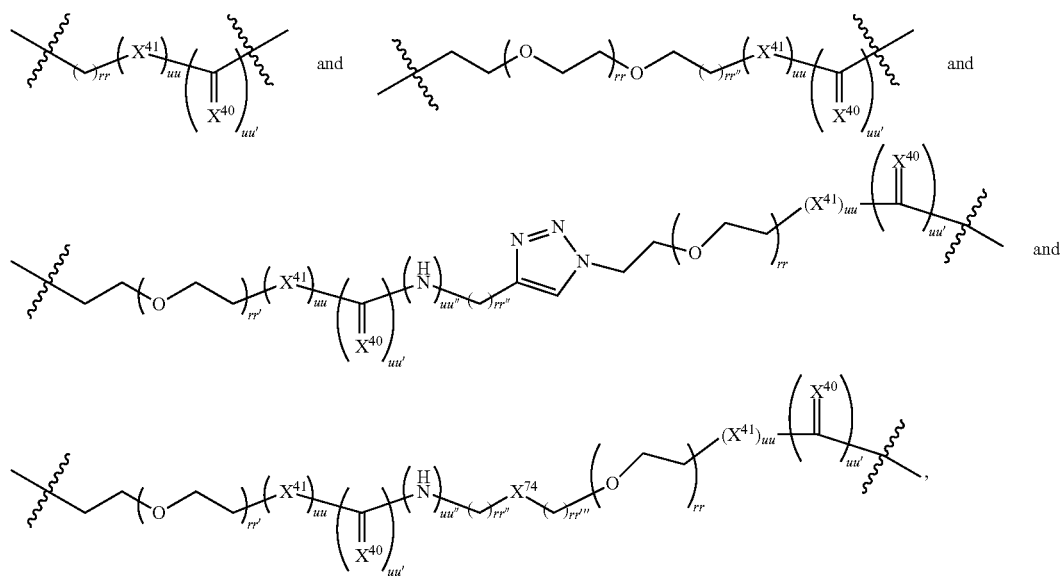

q' ranges from 1 to 20, rr, rr', rr'', and rr''' each independently range from 0 to 8, each $X^{40}$ and $X^{41}$ is independently selected from O, S, and $NR^{135}$, wherein $R^{135}$ is selected from H and $C_{1-3}$ alkyl, each uu, uu', and uu'' is independently selected from 0 and 1, Ab is an antibody or a fragment or derivative thereof, and V¹ is coupled to an atom of DB and is selected from a mono-, di-, or oligosaccharide or a reduced, oxidized, or protected derivative thereof and -continued

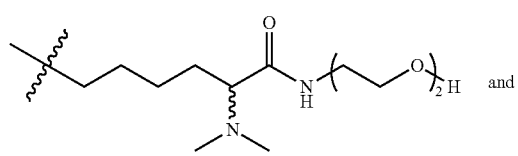

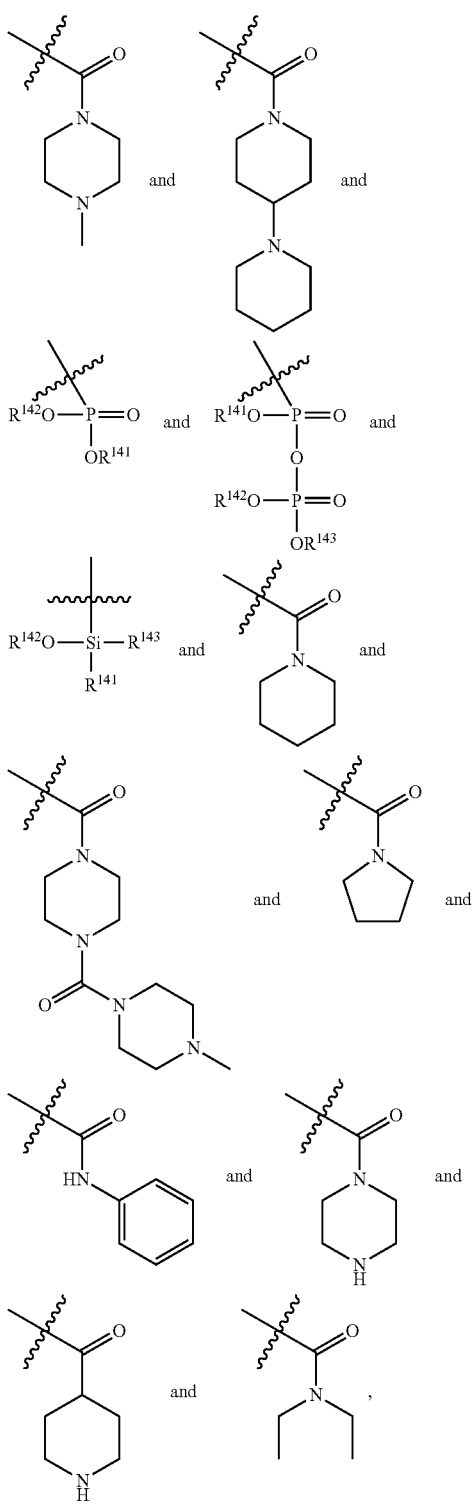

wherein $R^{141}$, $R^{142}$, and $R^{143}$ are independently selected from H and optionally substituted $C_{1-8}$ alkyl, $C_{1-8}$ heteroalkyl, $C_{3-8}$ cycloalkyl, $C_{1-8}$ heterocycloalkyl, $C_{5-8}$ aryl, or $C_{1-8}$ heteroaryl.

In yet another embodiment, a compound of formula (III) is represented by $$V^2\text{-}L^2\text{-}L\text{-}Z \qquad (\text{IIIe})$$

Similar embodiments can be envisioned for compounds of formula (IV) by replacing $V^2$-$L^2$ and/or $V^{2'}$-$L^{2'}$ by RM and/or RM', respectively, and removing the parentheses with subscript q and/or q', or by eliminating Ab-SH from the structures. Therefore, compounds of formulae (IVa)-(IVe) are represented by the structures of compounds of formulae (IIIa)-(IIIe), respectively, in which $V^2$-$L^2$ or $V^{2'}$-$L^{2'}$ is replaced by RM or RM', respectively, and parentheses with subscript q or q' are removed.

In one embodiment, the DB moiety of a Z in a compound of formula (III) is DB1.

In other embodiments, the DB moiety of a Z in a compound of formula (III) is DB2 or DB3 or DB4 or DB5 or DB6 or DB7 or DB8 or DB9.

In another embodiment, the DB moiety of a Z in a compound of formula (IV) is DB1.

In other embodiments, the DB moiety of a Z in a compound of formula (IV) is DB2 or DB3 or DB4 or DB5 or DB6 or DB7 or DB8 or DB9.

In yet another embodiment, the DB moiety of a Z in a compound of formula (III) is

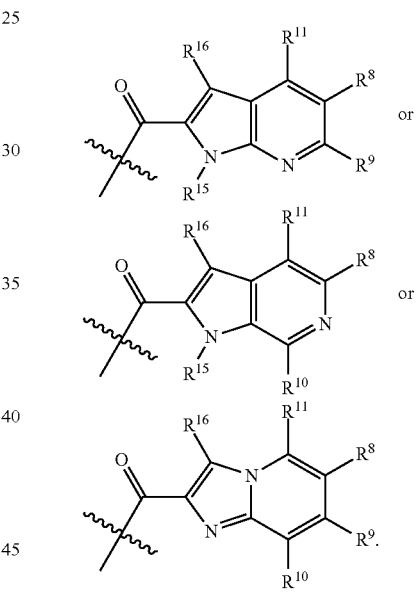

In yet another embodiment, the DB moiety of a Z in a compound of formula (IV) is

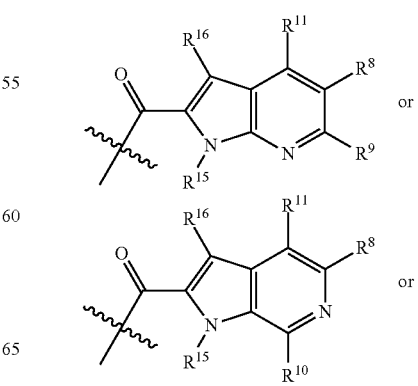

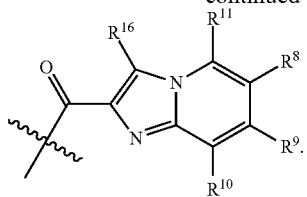
In one embodiment, a compound of formula (IV) is represented by
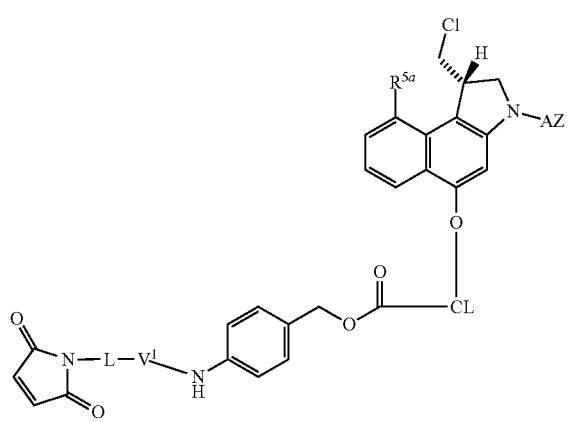
or by an isomer, or by a mixture of isomers, wherein $R^{5a}$ is selected from H, methyl and methoxy, AZ is
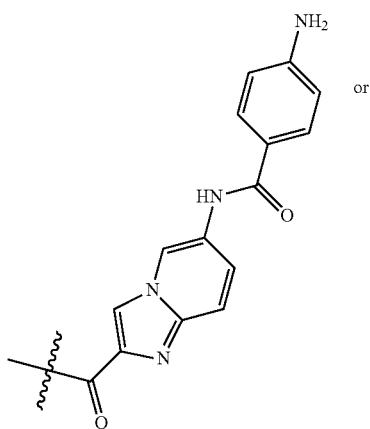
or
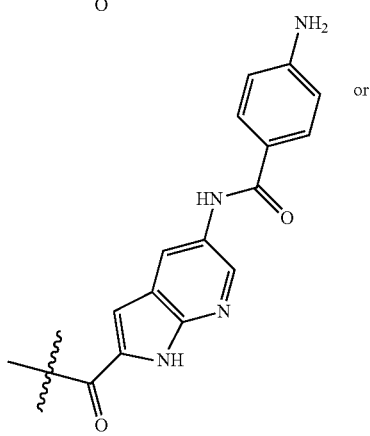
or
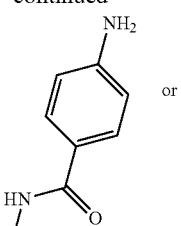
or
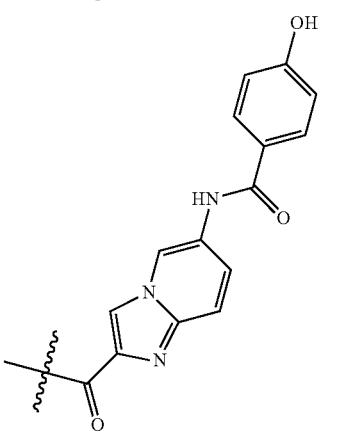
or
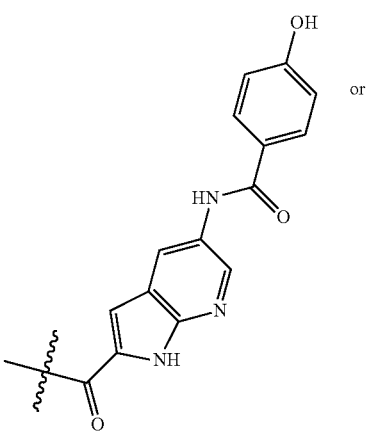
or
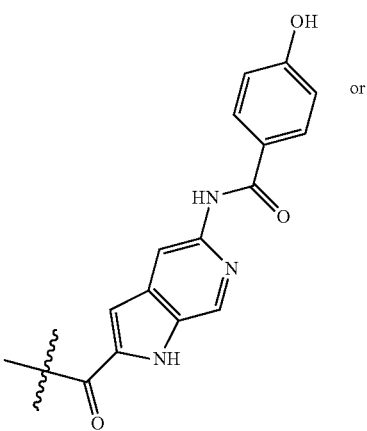
or 479
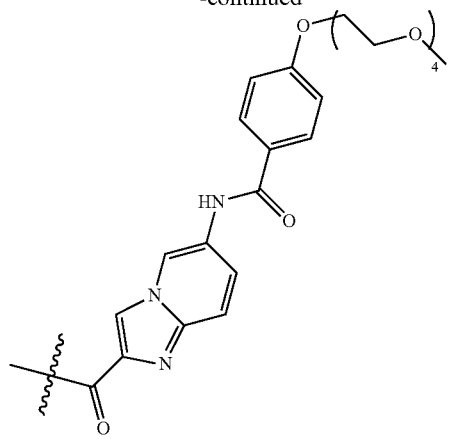 or
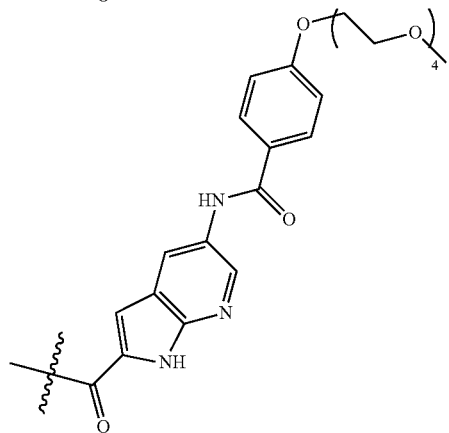 or
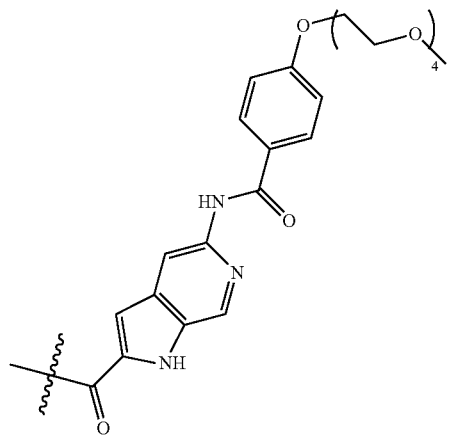 or
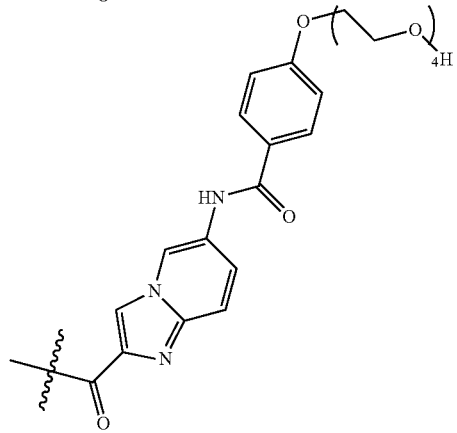 or
480
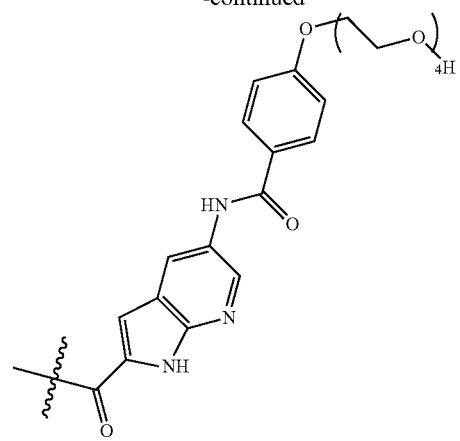 or
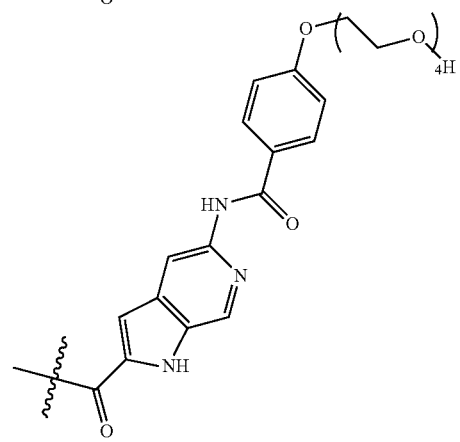 or
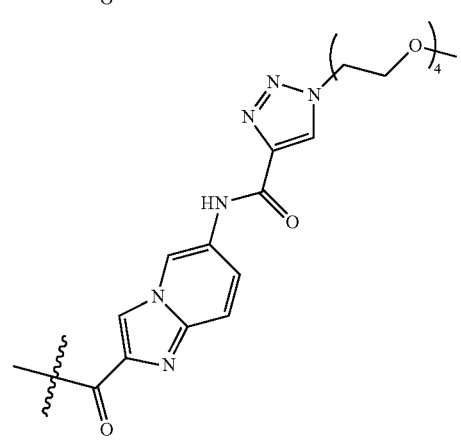 or
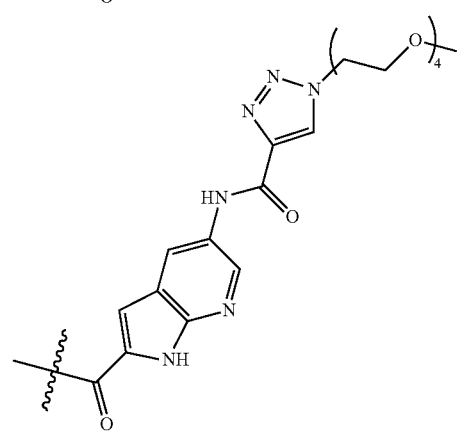 or -continued
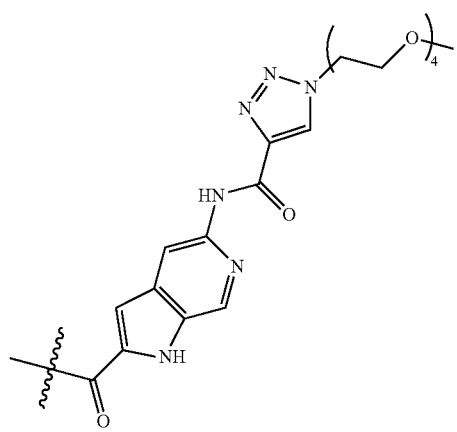
or
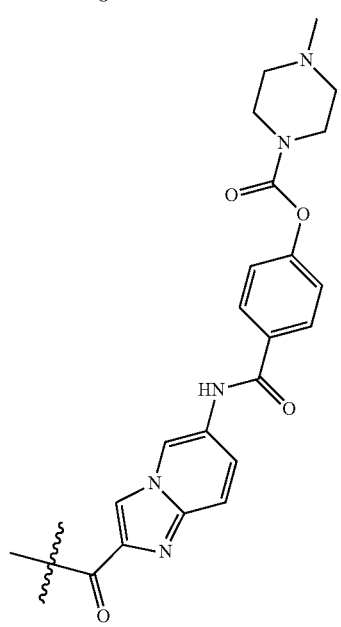
or
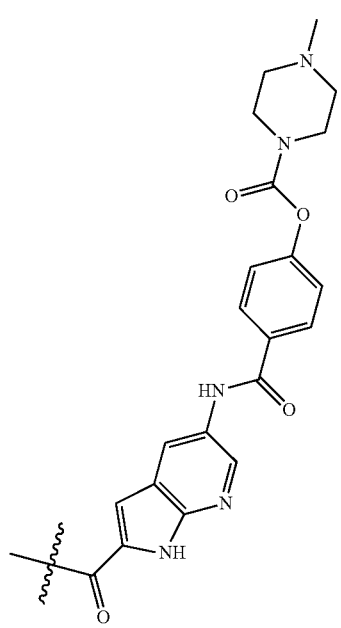
or
-continued
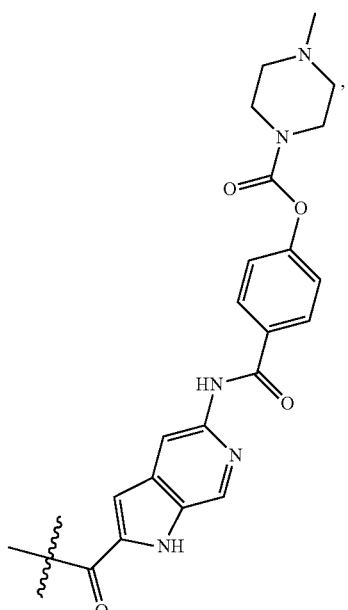
V¹ is selected from valylcitrulline, valyllysine, phenylalanyllysine, alanylphenylalanyllysine, and D-alanylphenylalanyllysine, CL is
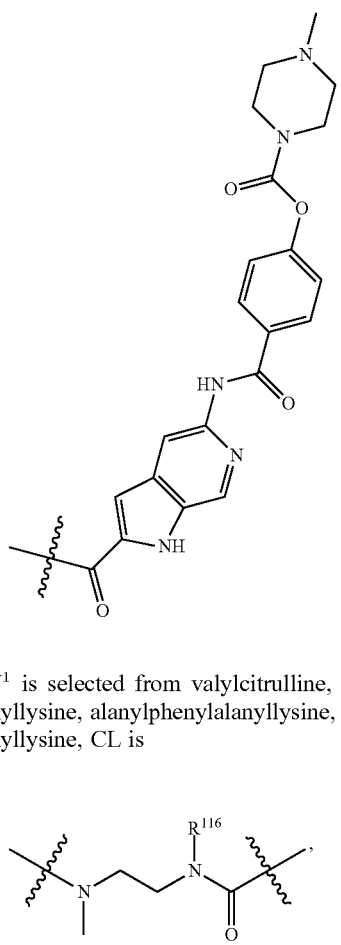
$R^{116}$ is selected from methyl, ethyl, isopropyl, tert-butyl, phenyl,
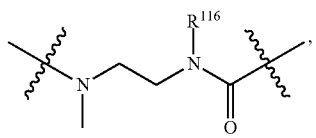 and
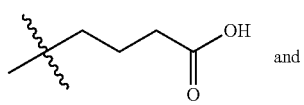 and
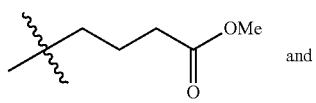 and
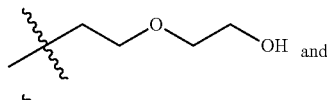 and
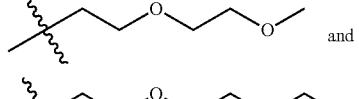 and
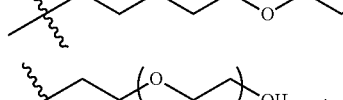 and
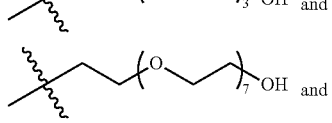 and

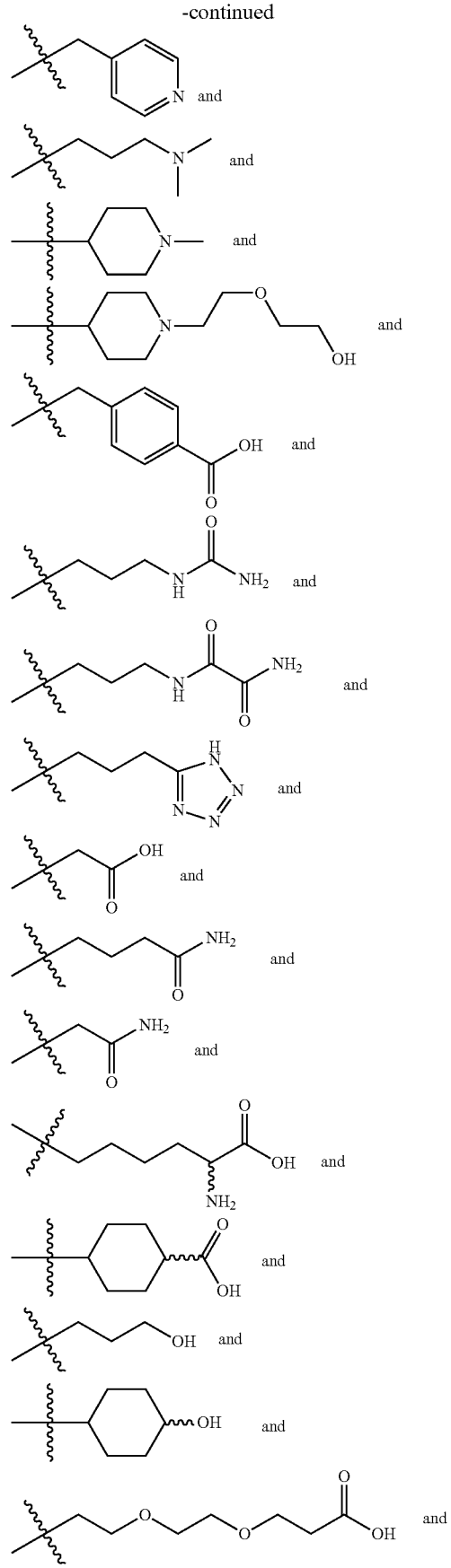
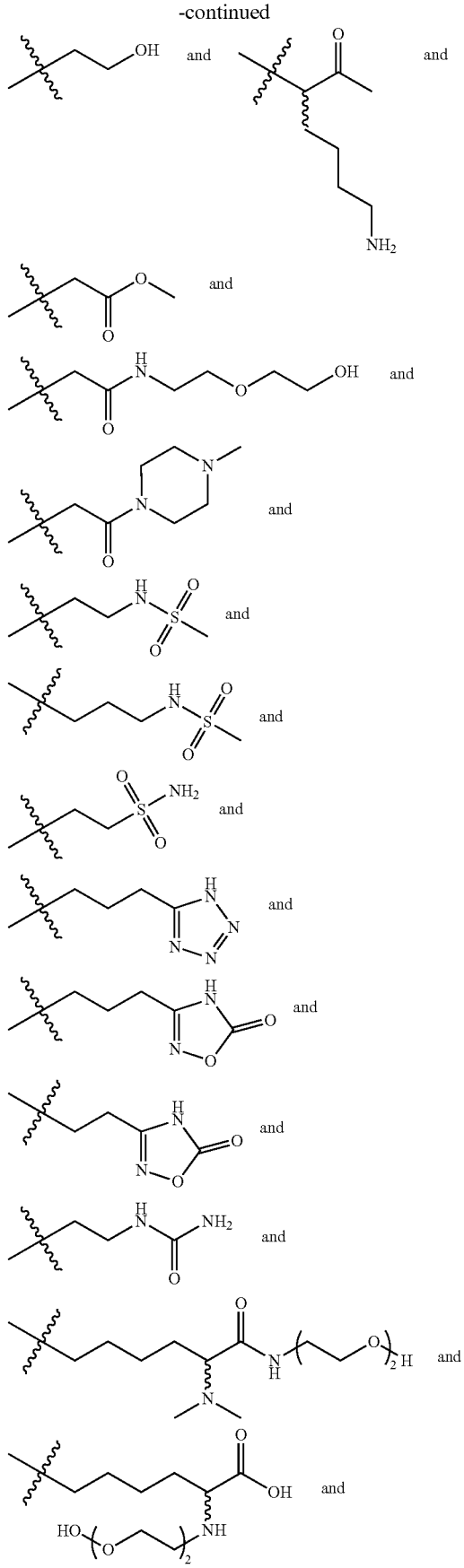

485
-continued
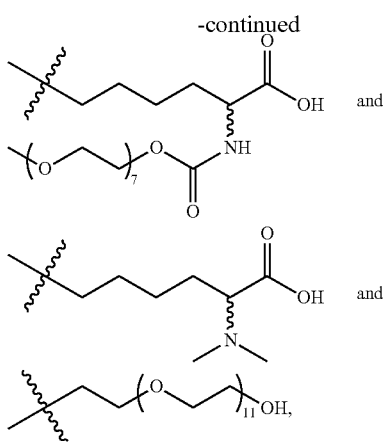
and L is selected from
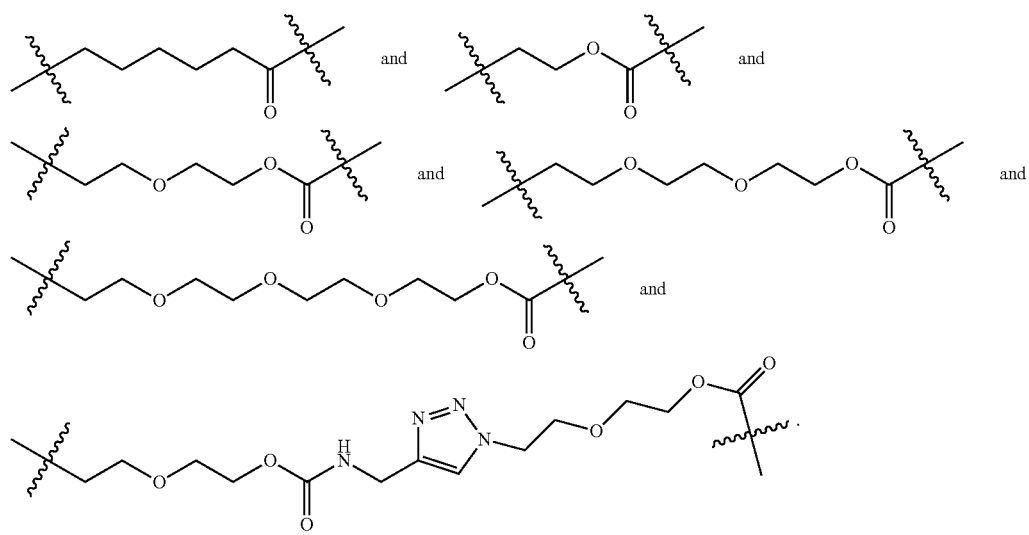
In another embodiment, a compound of formula (IV) is represented by
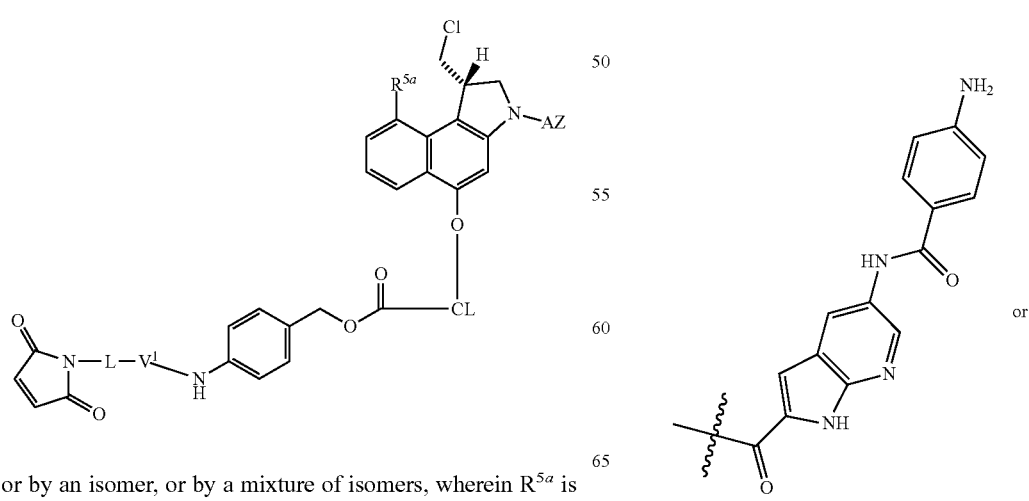
or by an isomer, or by a mixture of isomers, wherein $R^{5a}$ is selected from H, methyl and methoxy, AZ is
486
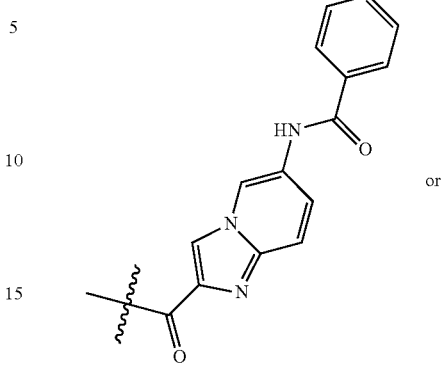
or
-continued 487
-continued
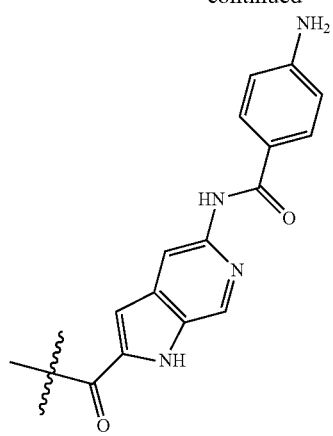
or
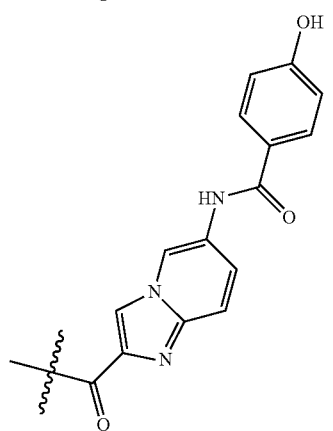
or
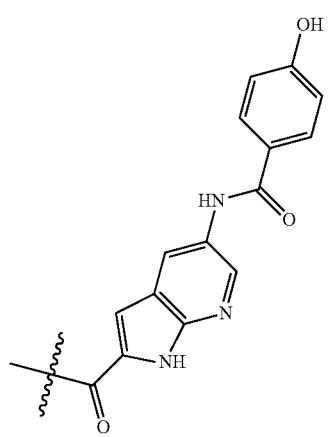
or
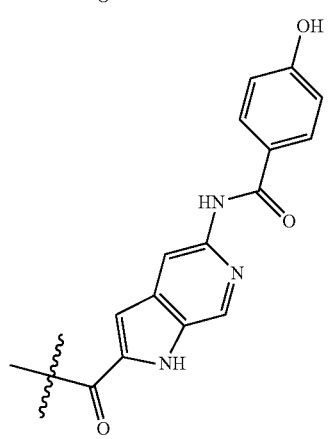
or
488
-continued
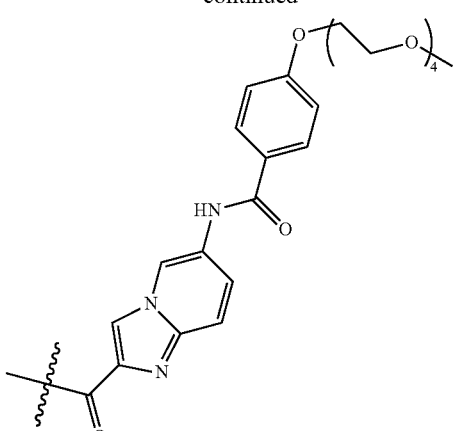
or
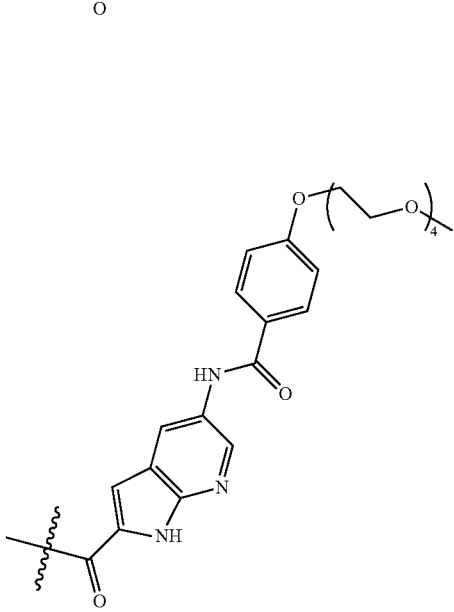
or
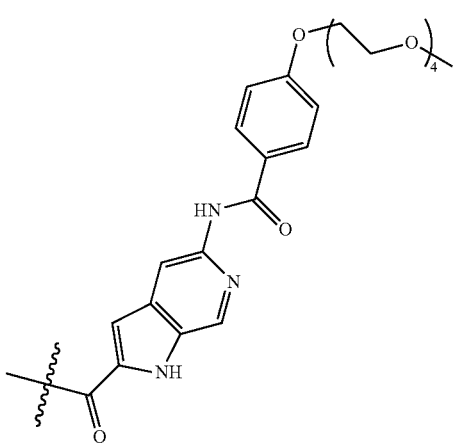
or 489
-continued
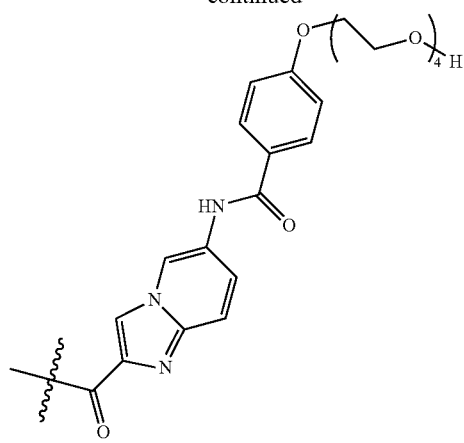
or
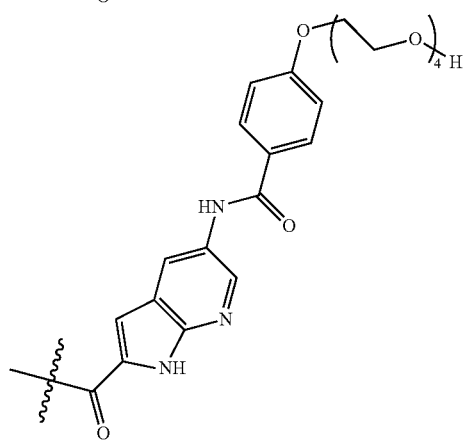
or
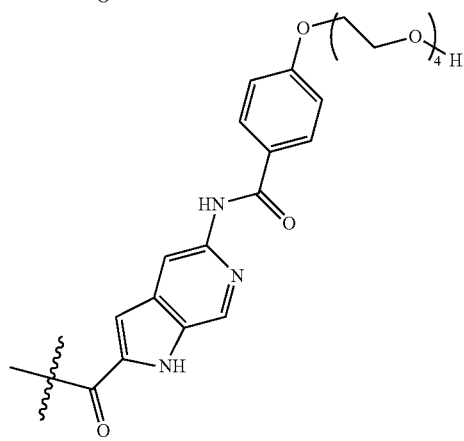
or
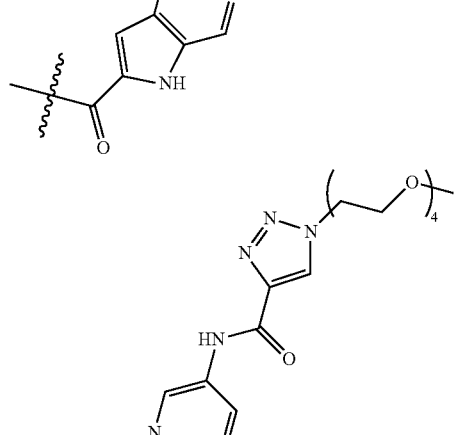
or
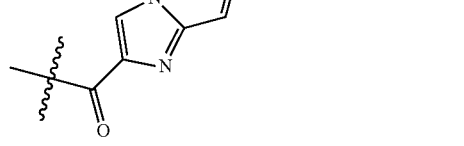
490
-continued
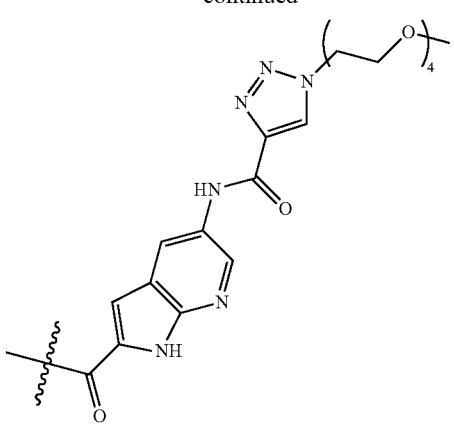
or
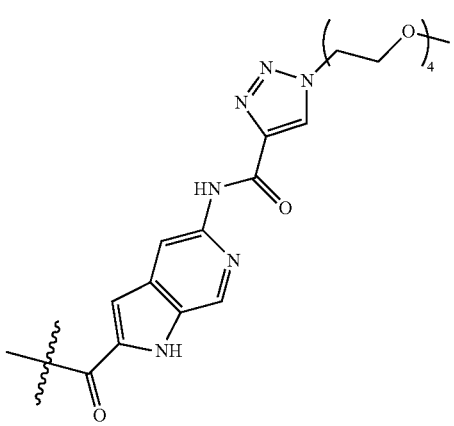
or
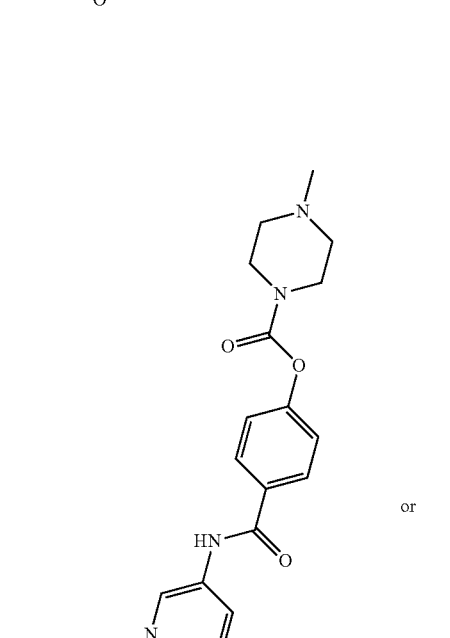
or
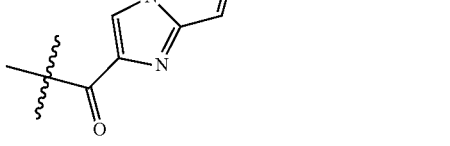

491
-continued
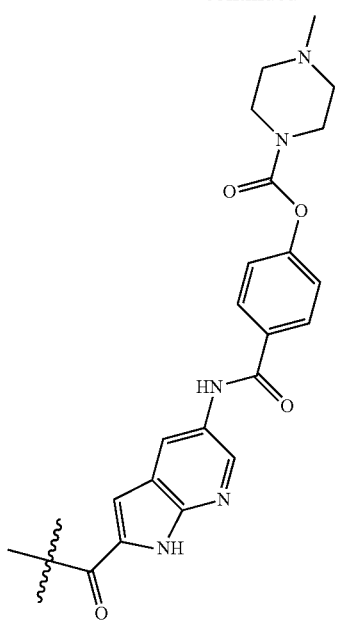
or
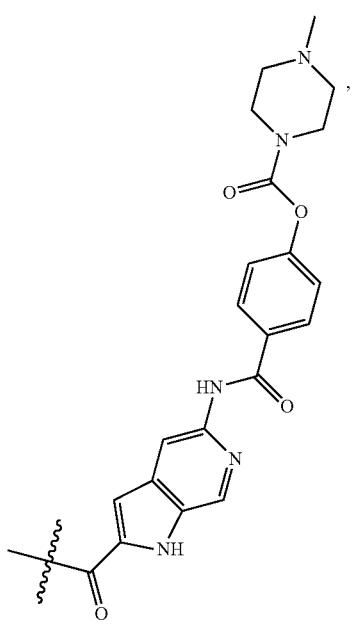
,
V¹ is selected from valylcitrulline, valyllysine, phenylalanyllysine, alanylphenylalanyllysine, and D-alanylphenylalanyllysine, CL is
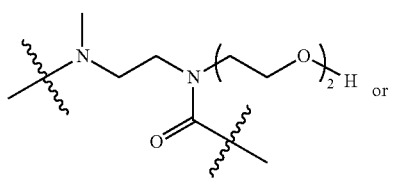
or
492
-continued
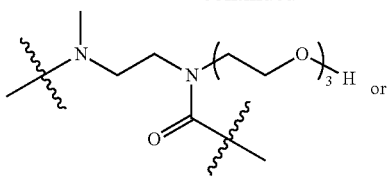
or
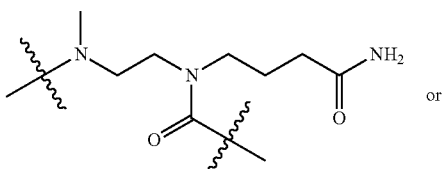
or
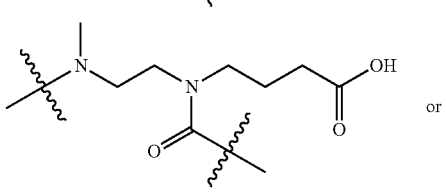
or
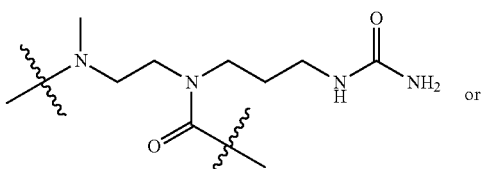
or
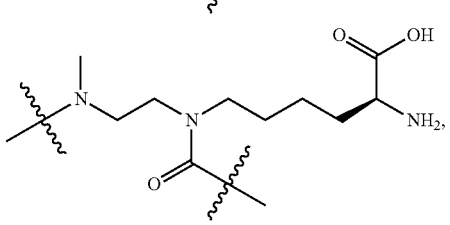
,
and L is selected from
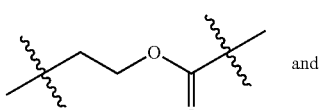
and
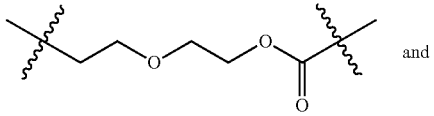
and
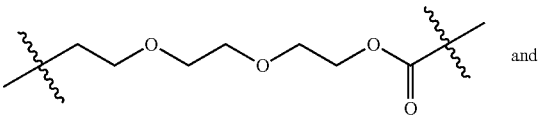
and
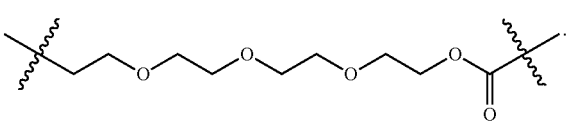
.

In another embodiment, a compound of formula (III) is represented by
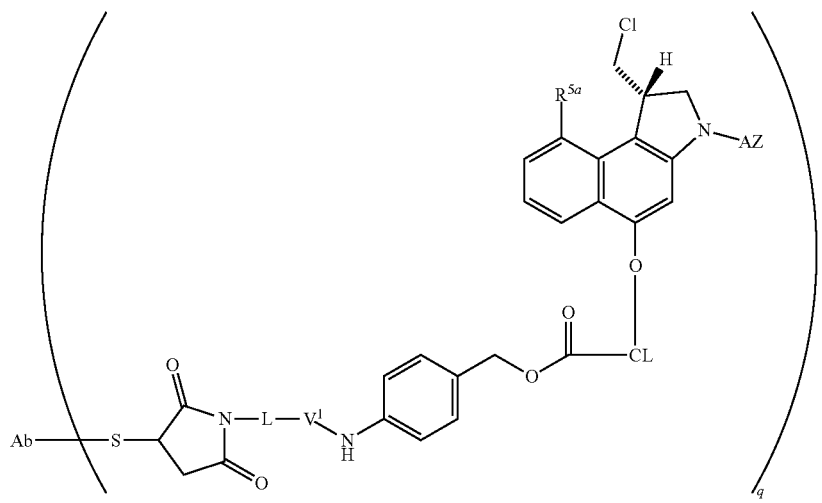
or by an isomer, or by a mixture of isomers, wherein $R^{5a}$ is selected from H, methyl and methoxy, AZ is
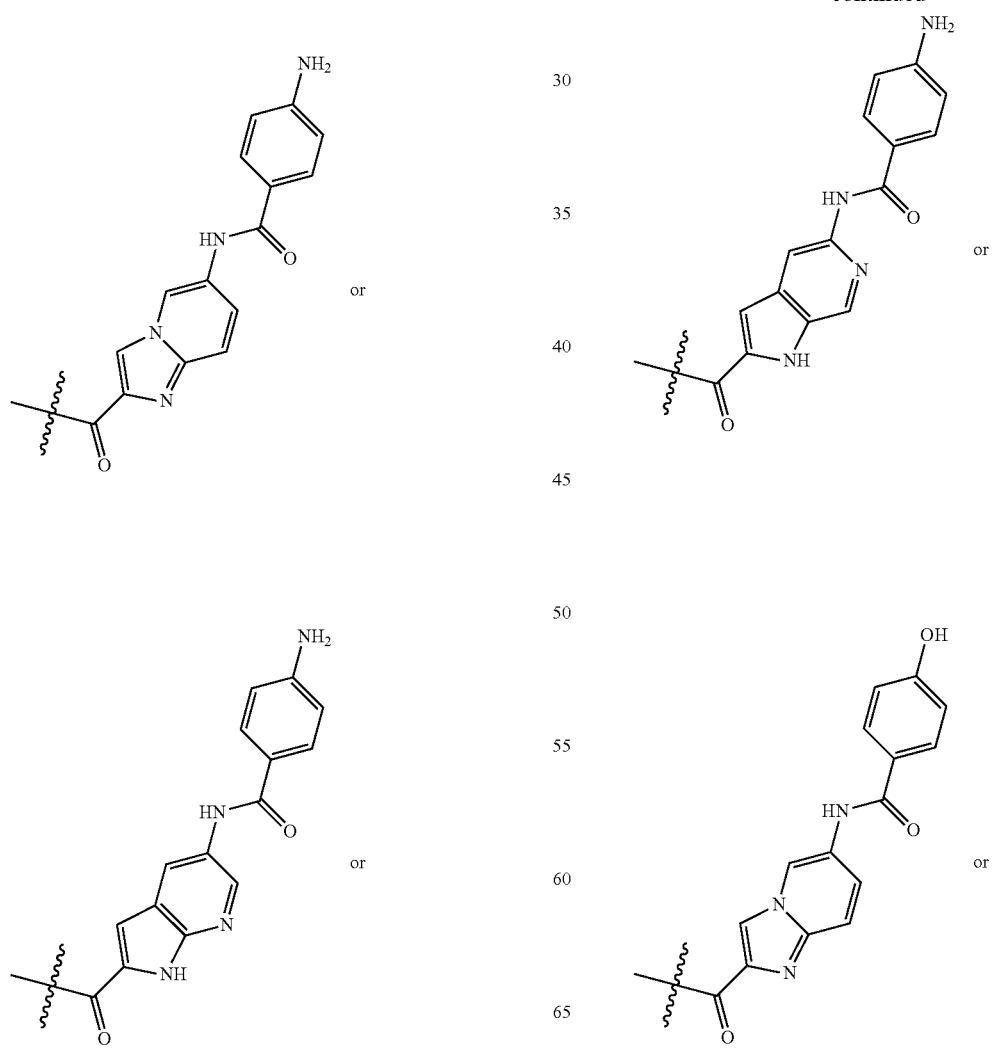

495
-continued
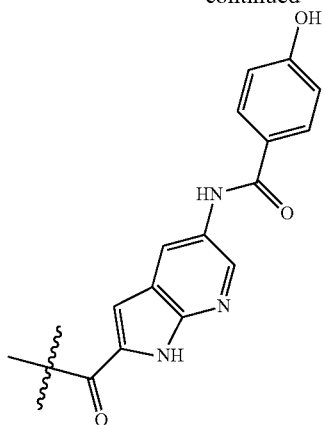
or
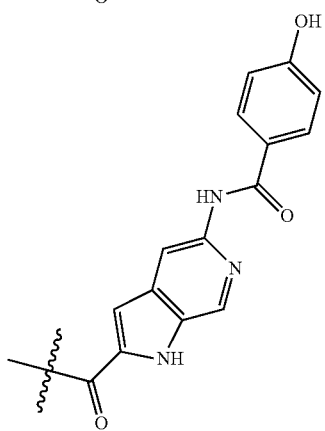
or
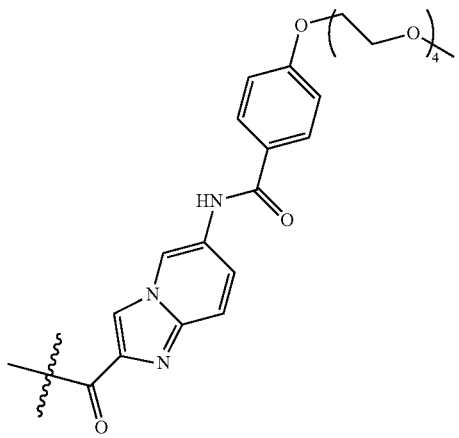
or
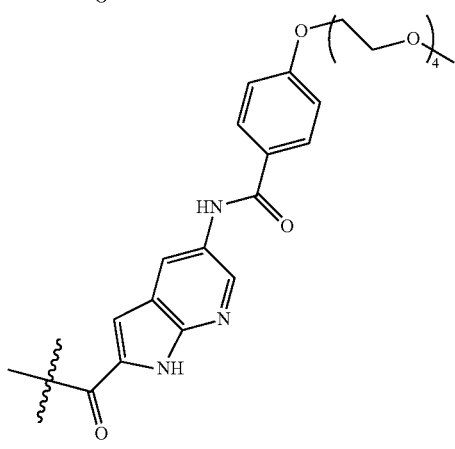
or
496
-continued
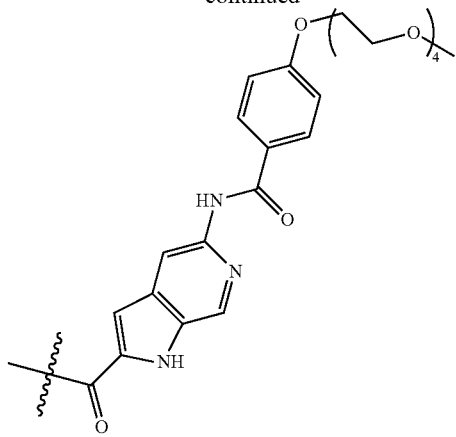
or
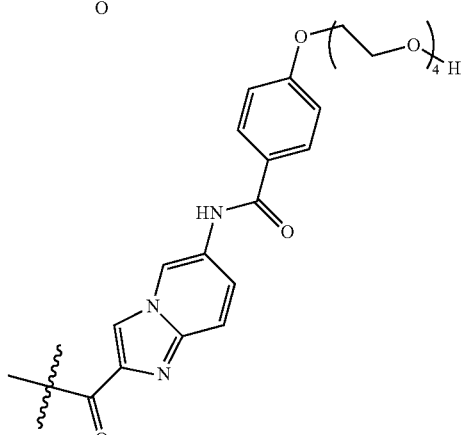
or
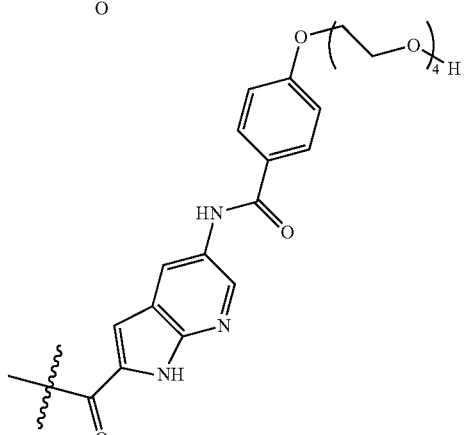
or
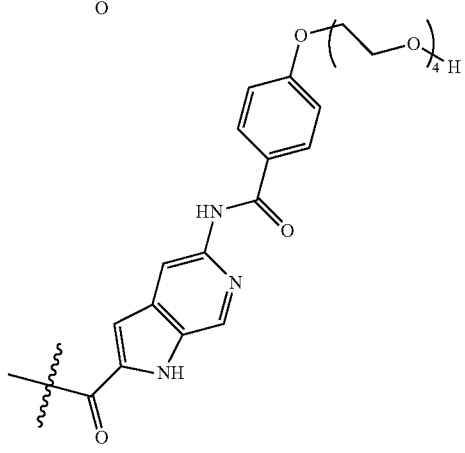
or

497
-continued
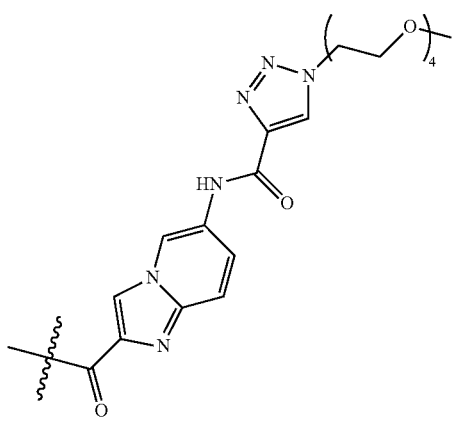
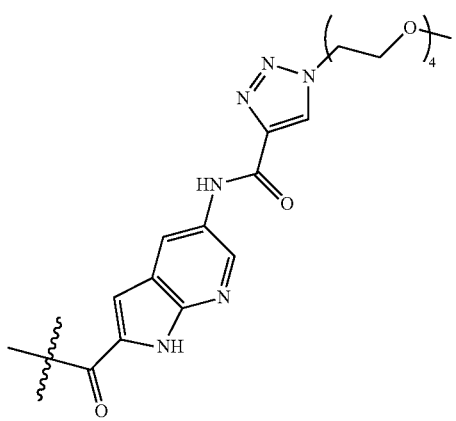
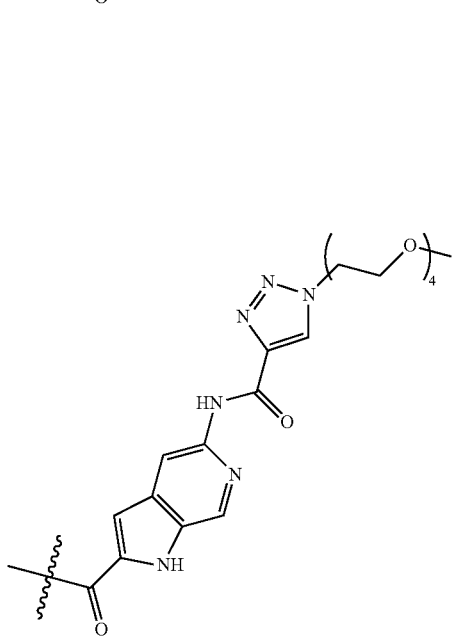
498
-continued
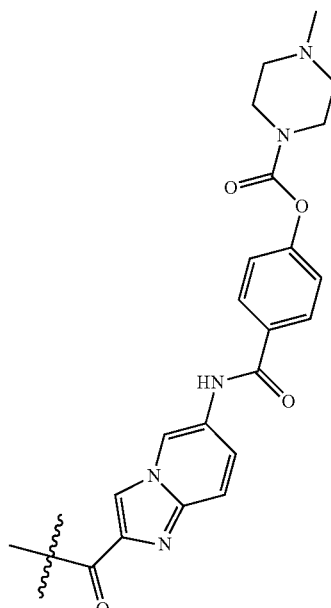
or
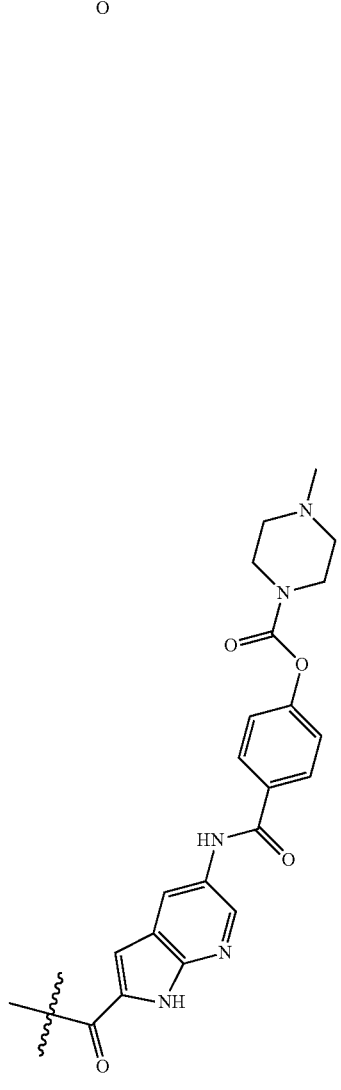
or -continued
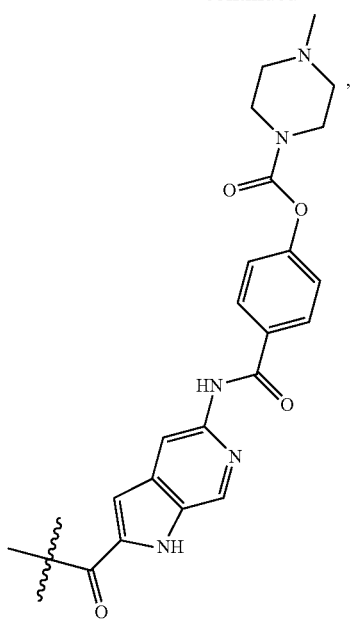
$V^1$ is selected from valylcitrulline, valyllysine phenylalanyllysine, alanylphenylalanyllysine, and D-alanylphenylalanyllysine, CL is
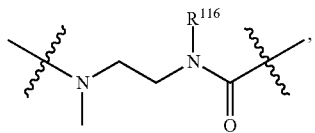
$R^{116}$ is selected from methyl, ethyl, isopropyl, tert-butyl, phenyl,
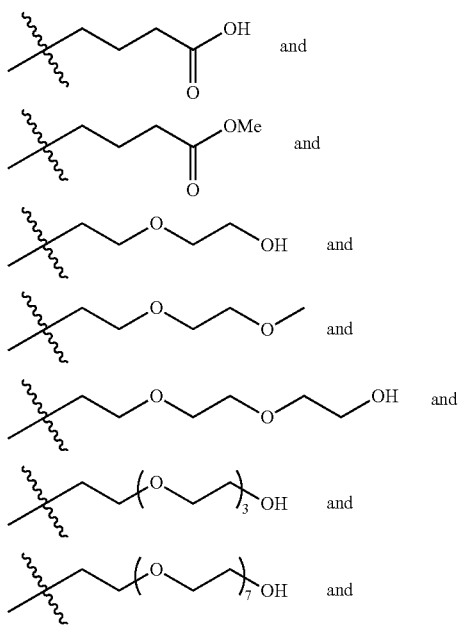
-continued
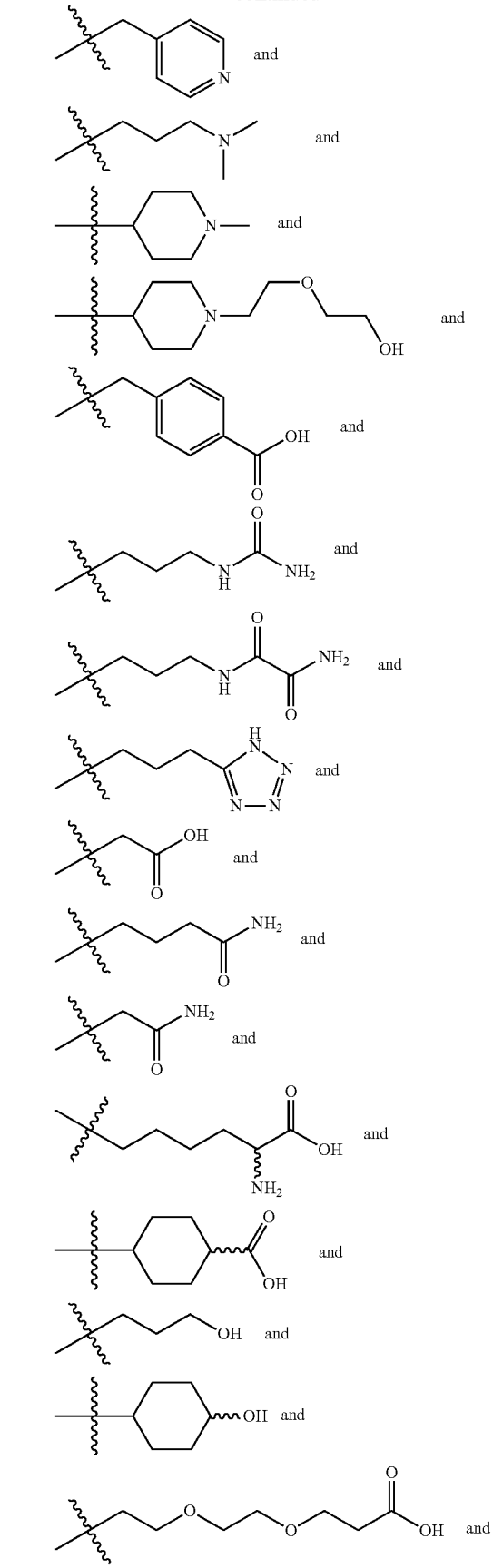

501
-continued
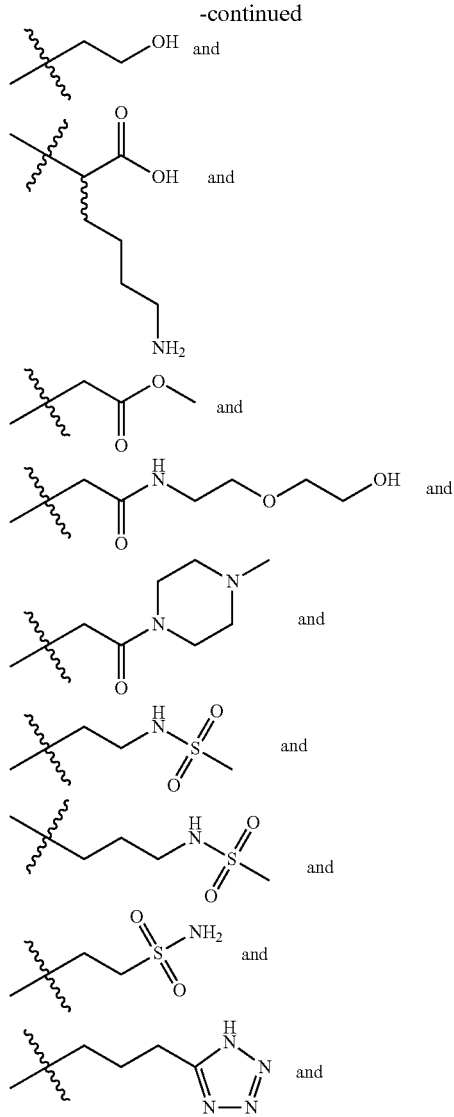
502
-continued
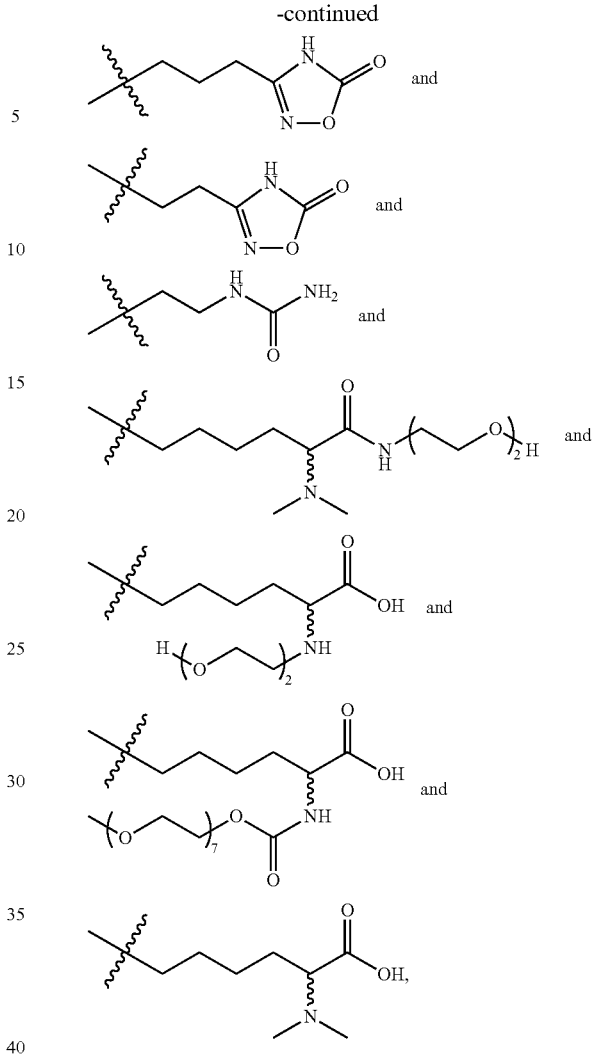
q ranges from 1 to 8, Ab is an antibody or a fragment or derivative thereof, and L is selected from
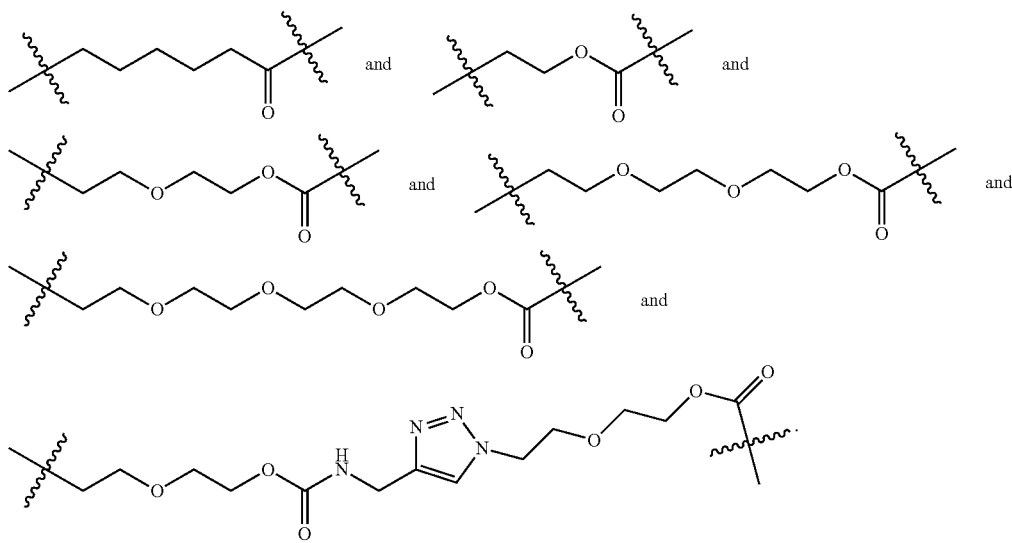

In yet another embodiment, a compound of formula (III) is represented by
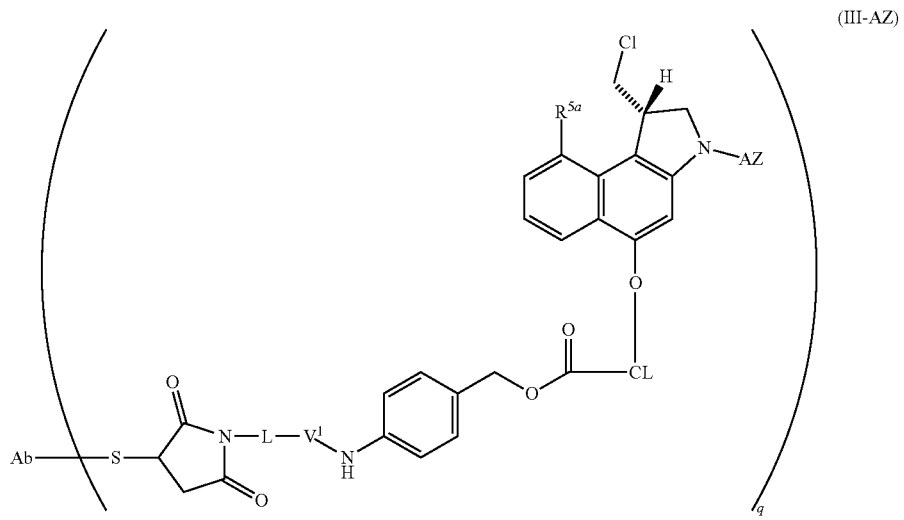
(III-AZ)
or by an isomer, or by a mixture of isomers, wherein $R^{5a}$ is selected from H, methyl and methoxy, AZ is
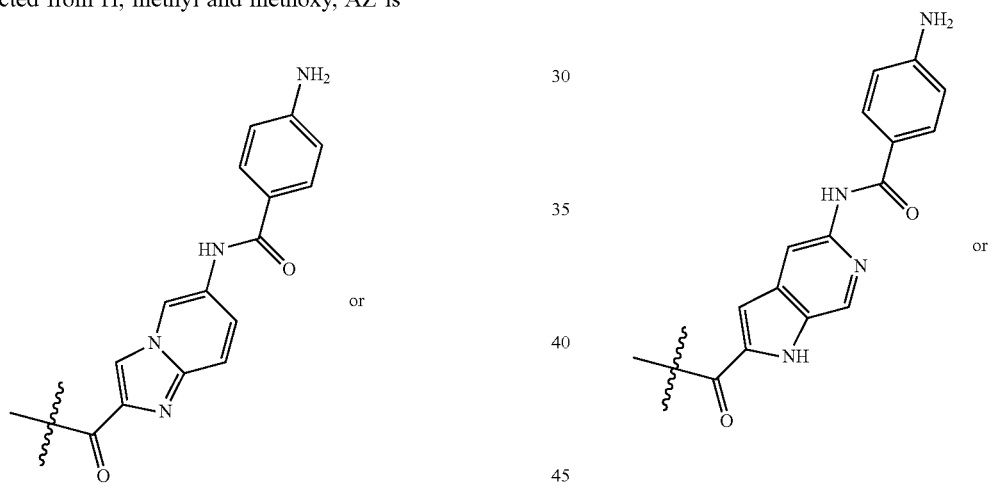
-continued
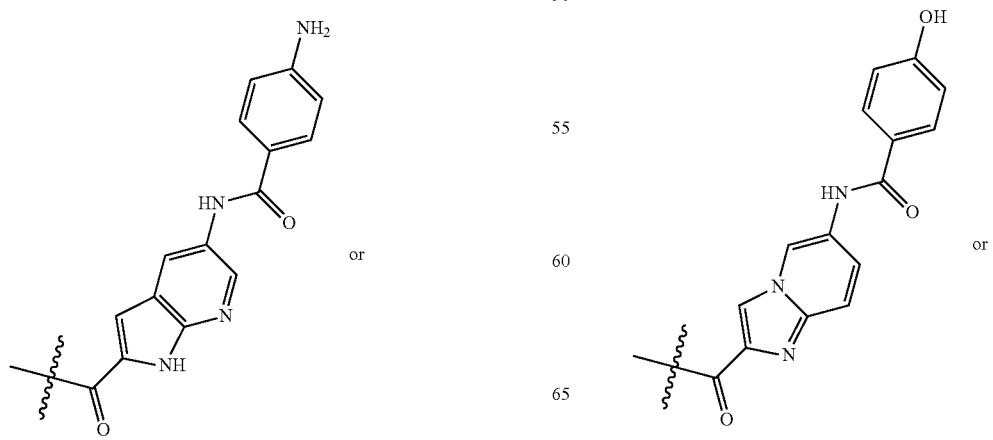

505
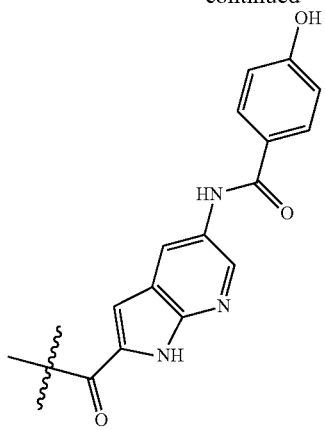
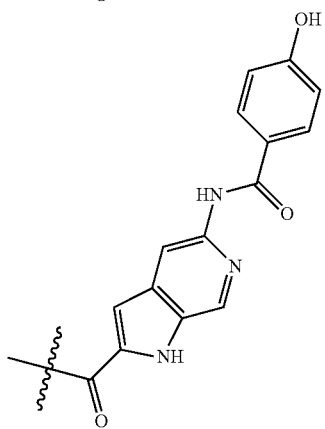
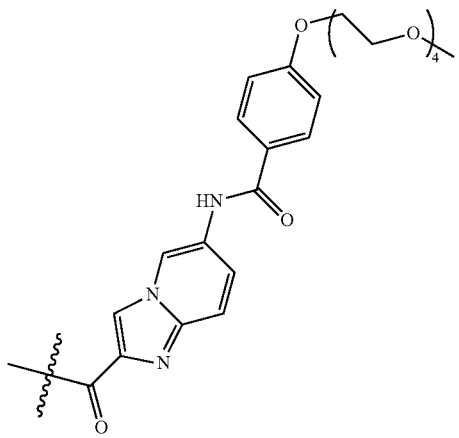
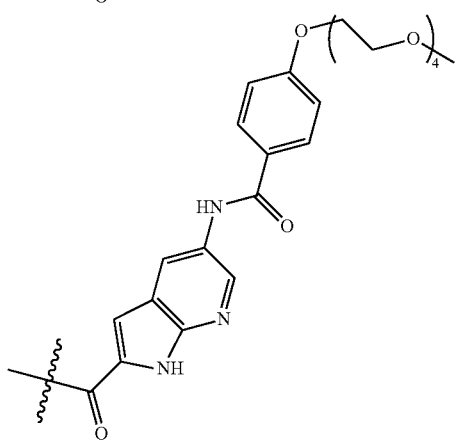
or
or
or
or
506
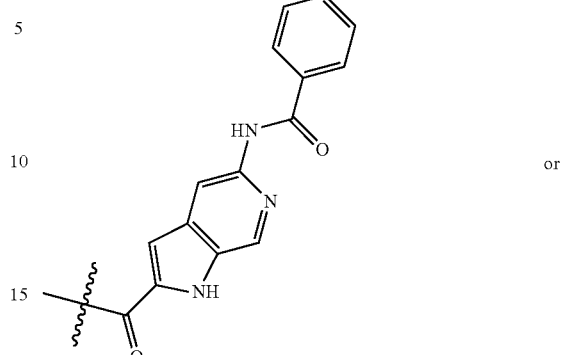
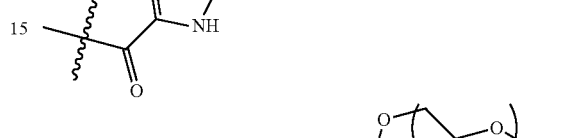
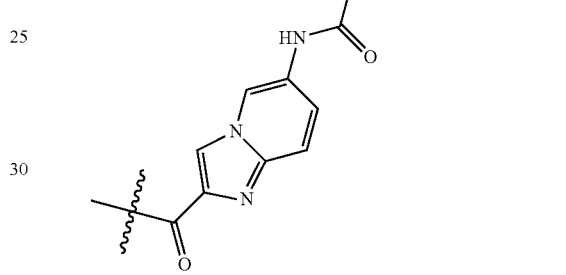
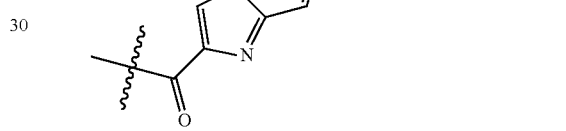
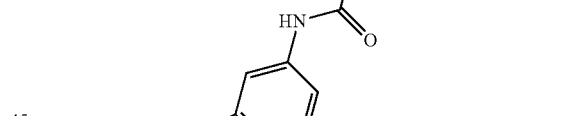
or
or
or
or

507
-continued
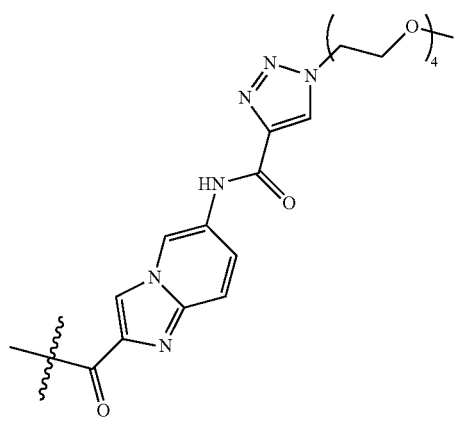
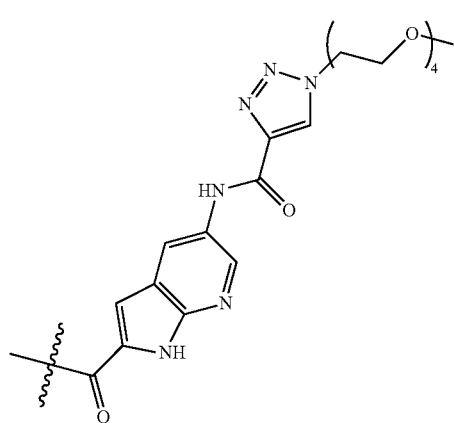
or
or
508
-continued
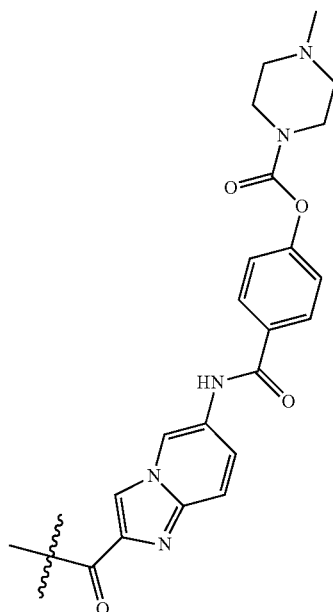
or
or
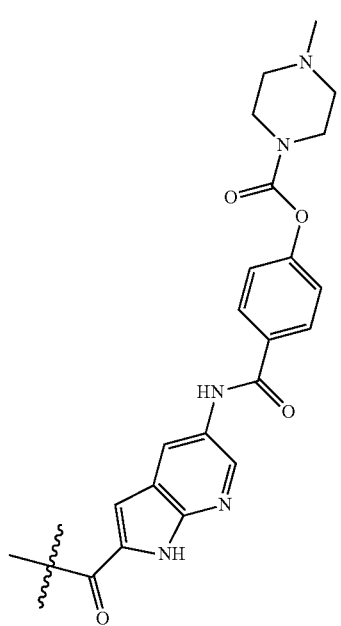

-continued

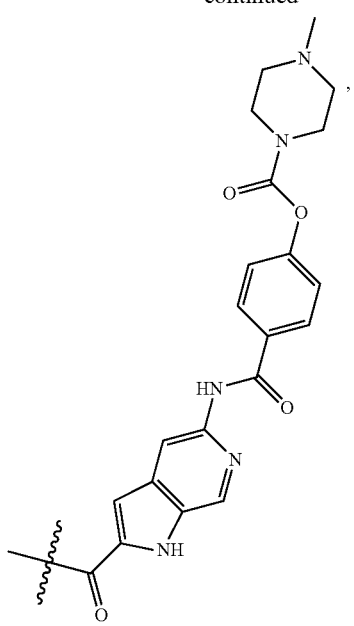

$V^1$ is selected from valylcitrulline, valyllysine, phenylalanyllysine, alanylphenylalanyllysine, and D-alanylphenylalanyllysine, CL is

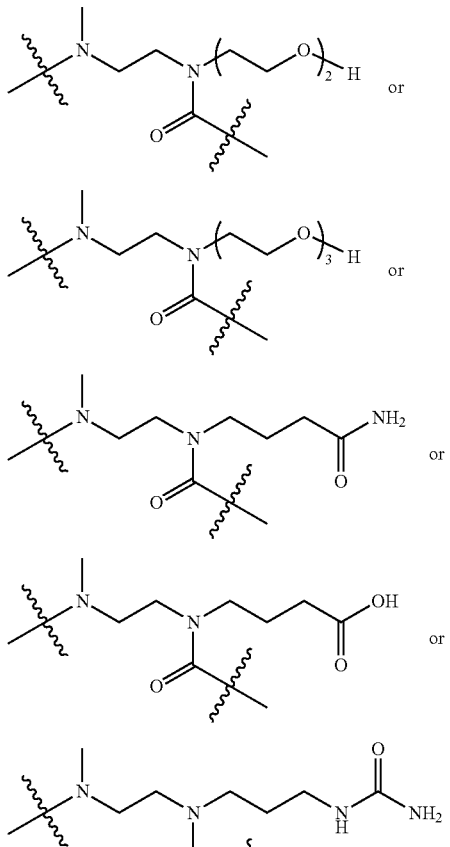

-continued

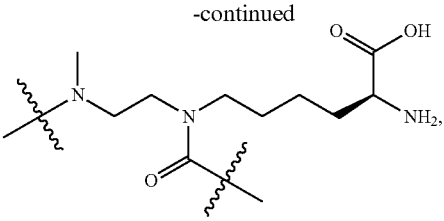

L is selected from

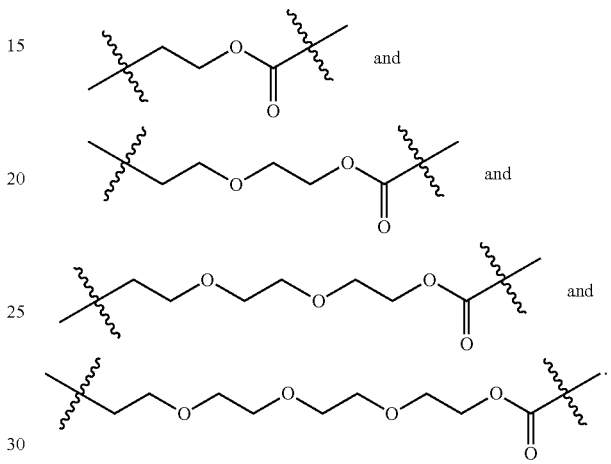

q ranges from 1 to 4, and Ab is an antibody or a fragment or derivative thereof.

A series of compounds (III-AZ) wherein $R^{5a}$ is methyl, AZ is

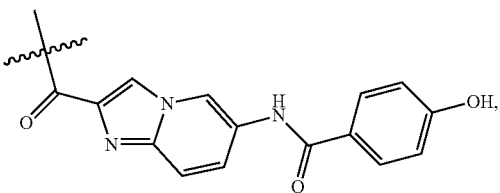 [SMILES: *C(=O)c1cn2cc(NC(=O)c3ccc(O)cc3)ccc2n1]

L is

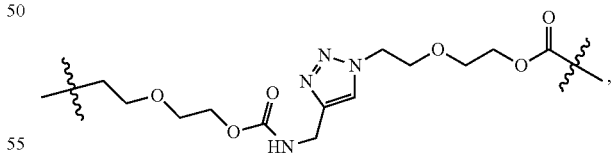

Ab is Trastuzumab, $V^1$ is valylcitrulline, and CL is

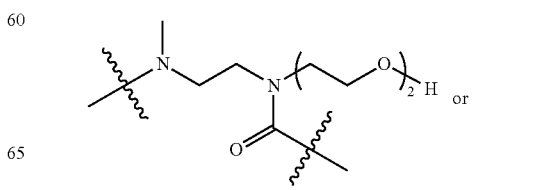

511
-continued

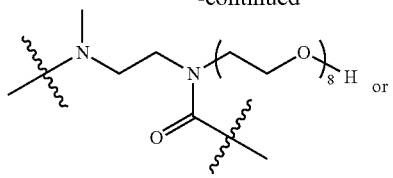 or

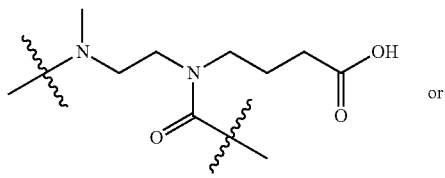 or

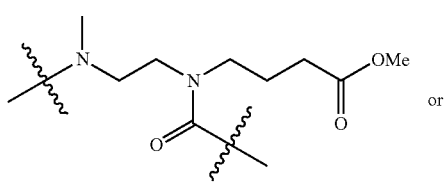 or

512
-continued

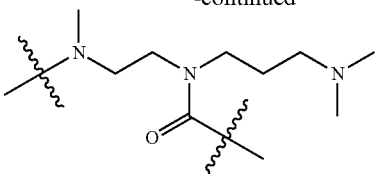

were prepared according to the procedure described in Example 15 and evaluated against the corresponding reference compound in which CL is

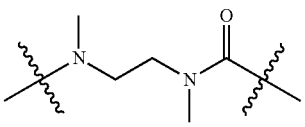 [SMILES: *C(=O)N(C)CCN(*)C]

for amount of aggregate present after the conjugation step. The evaluated compounds had relative aggregate amounts of 33%, 15%, 8%, 58%, and 12%, respectively, compared to that of the reference compound (100%), clearly showing the advantage of the present cyclization spacers.

In one embodiment, a compound of formula (IV) is selected from

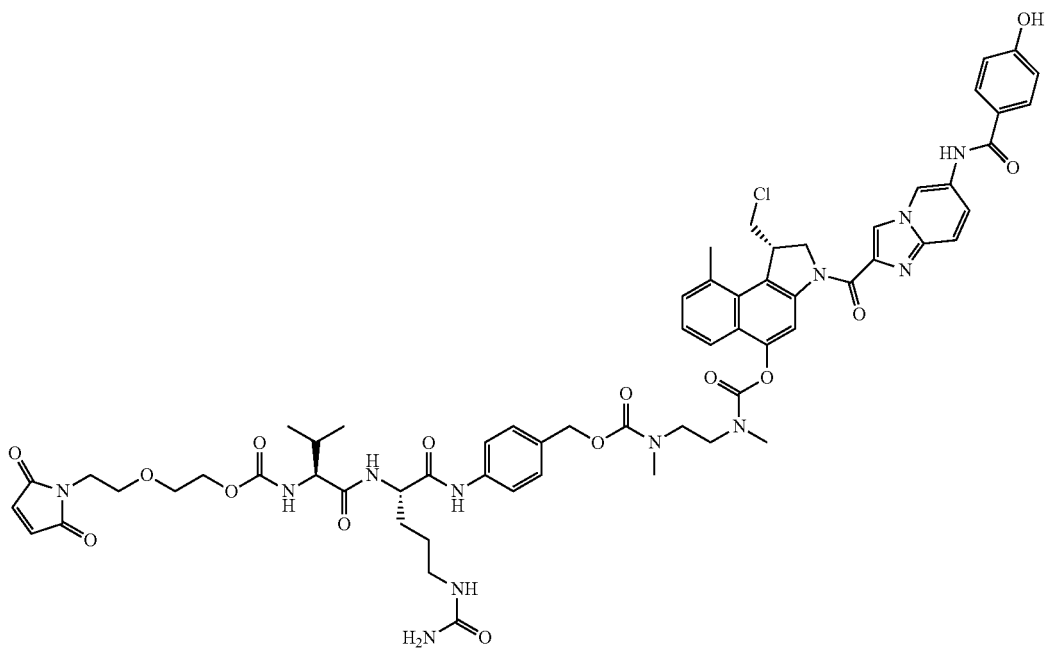

513
514
-continued
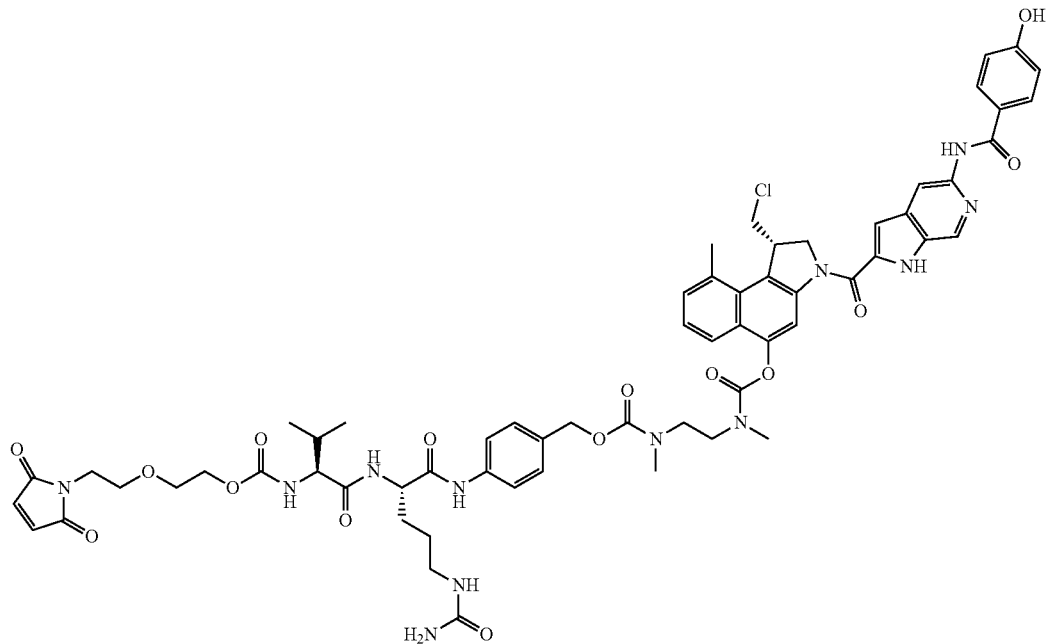
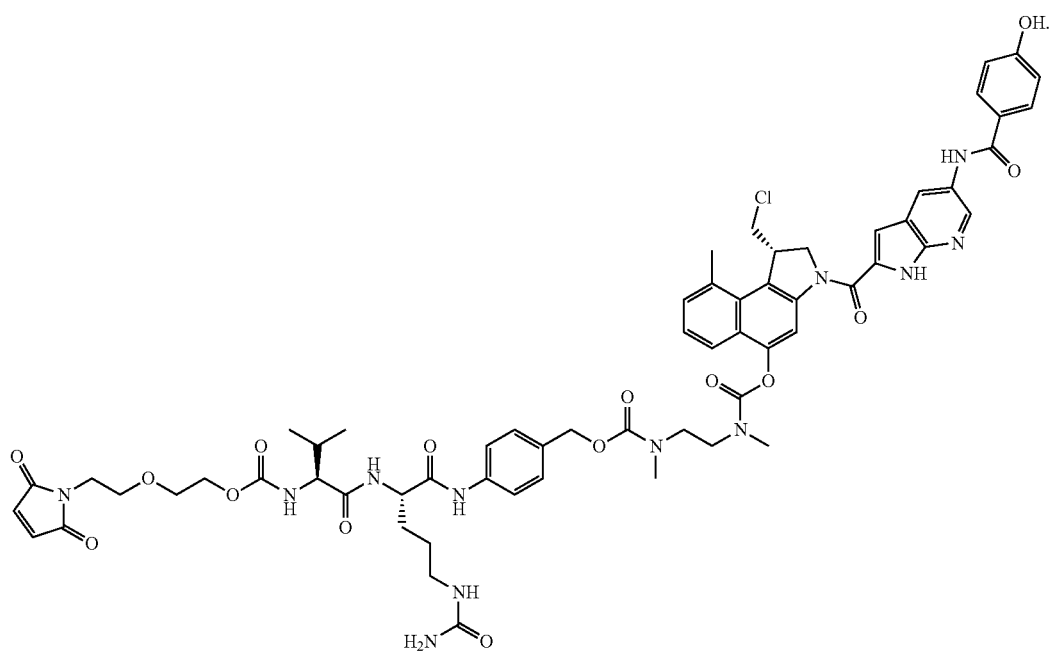 [SMILES: Cc1cccc2c(OC(=O)N(C)CCN(C)C(=O)OCc3ccc(NC(=O)[C@H](CCCNC(N)=O)NC(=O)[C@@H](NC(=O)OCCOCCN4C(=O)C=CC4=O)C(C)C)cc3)cc3c(c12)[C@H](CCl)CN3C(=O)c1cc2cc(NC(=O)c3ccc(O)cc3)cnc2[nH]1]

In another embodiment, a compound of formula (IV) is selected from
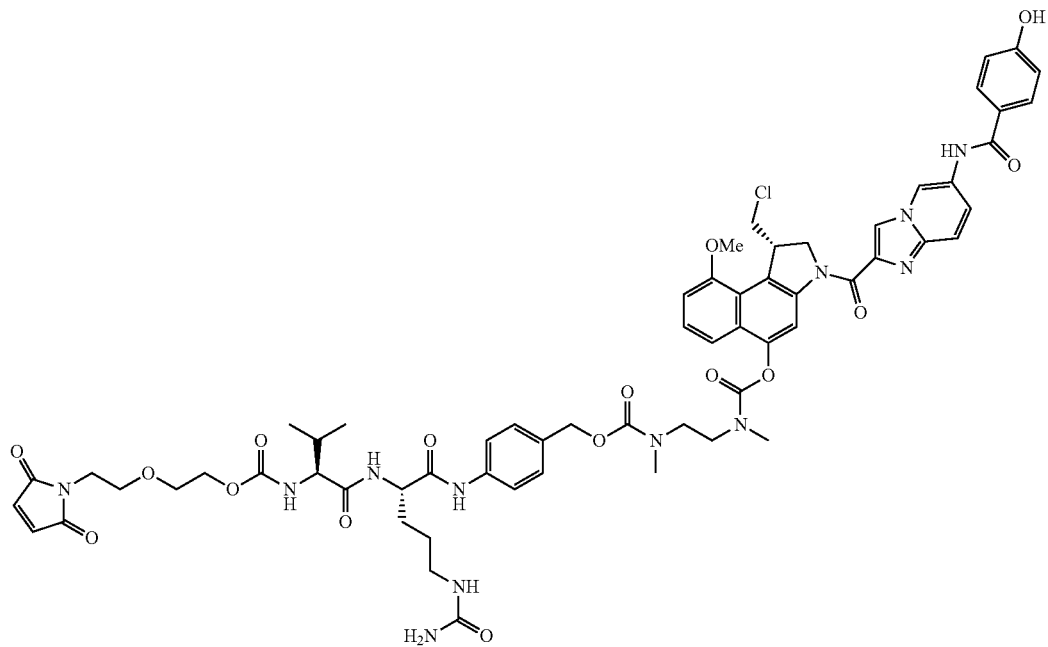
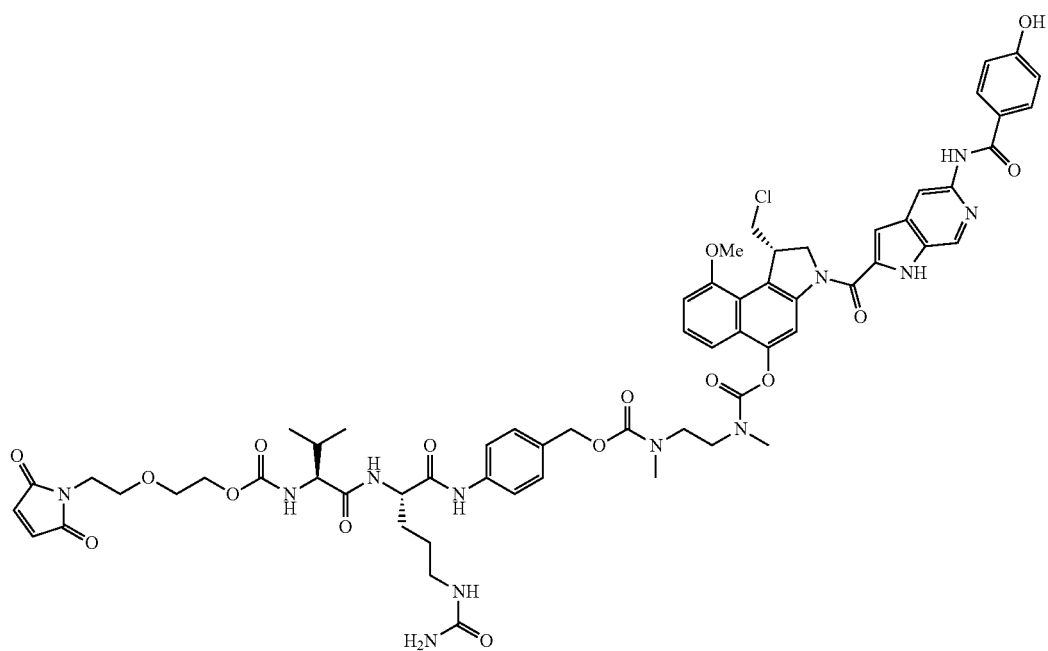 [SMILES: COc1cccc2c(OC(=O)N(C)CCN(C)C(=O)OCc3ccc(NC(=O)[C@H](CCCNC(N)=O)NC(=O)[C@@H](NC(=O)OCCOCCN4C(=O)C=CC4=O)C(C)C)cc3)cc3c(c12)[C@H](CCl)CN3C(=O)c1cc2cc(NC(=O)c3ccc(O)cc3)cnc2[nH]1]

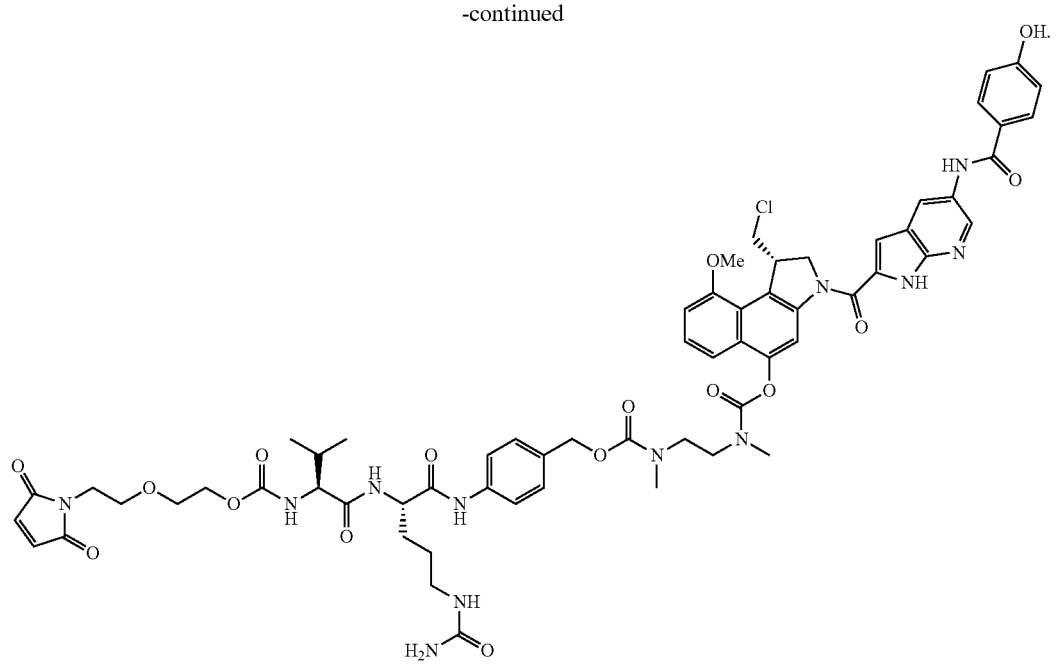
In another embodiment, a compound of formula (IV) is selected from
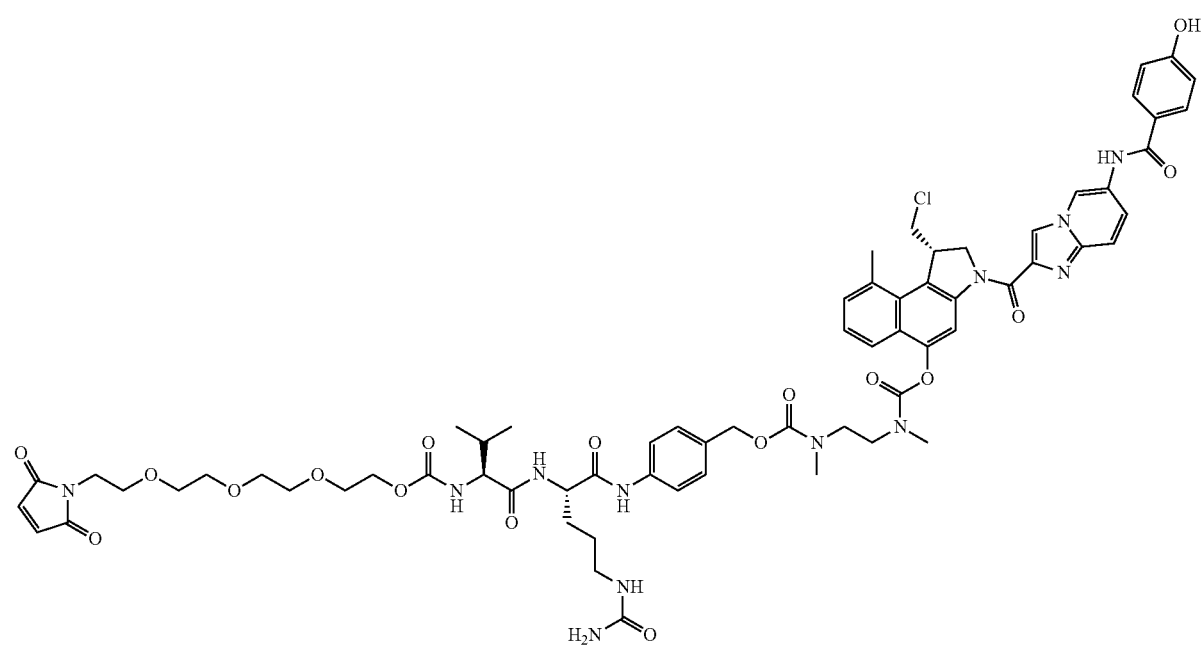

519 520
-continued
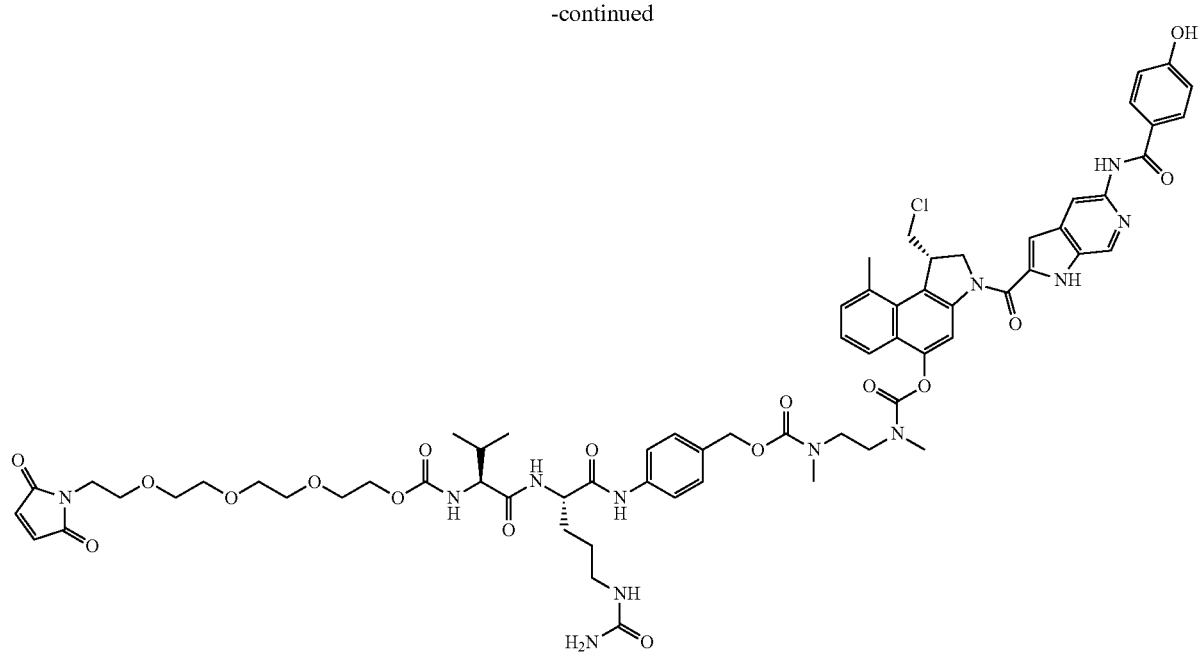
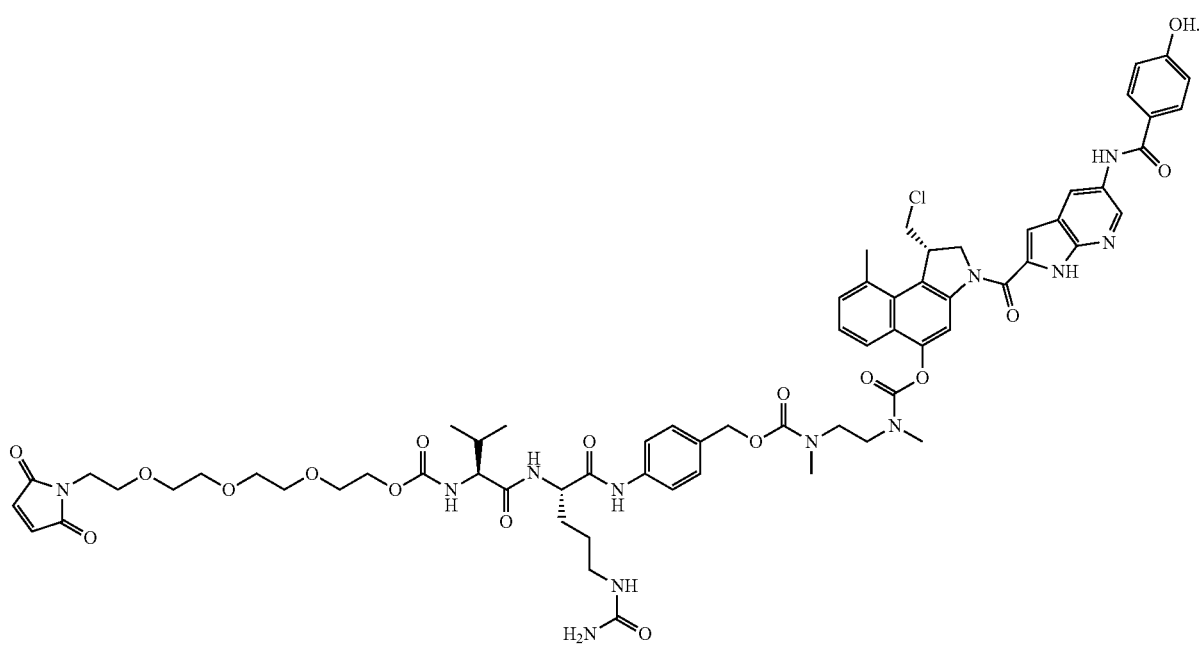 [SMILES: Cc1cccc2c(OC(=O)N(C)CCN(C)C(=O)OCc3ccc(NC(=O)[C@H](CCCNC(N)=O)NC(=O)[C@@H](NC(=O)OCCOCCOCCOCCN4C(=O)C=CC4=O)C(C)C)cc3)cc3c(c12)[C@H](CCl)CN3C(=O)c1cc2cc(NC(=O)c3ccc(O)cc3)cnc2[nH]1]

In another embodiment, a compound of formula (IV) is selected from
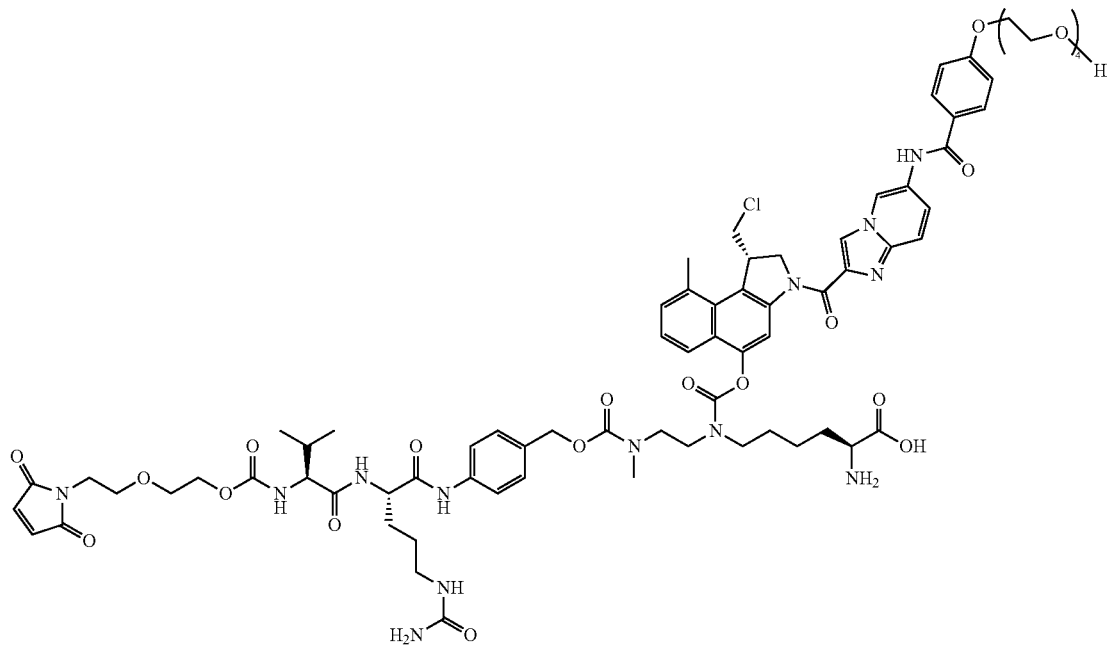
521
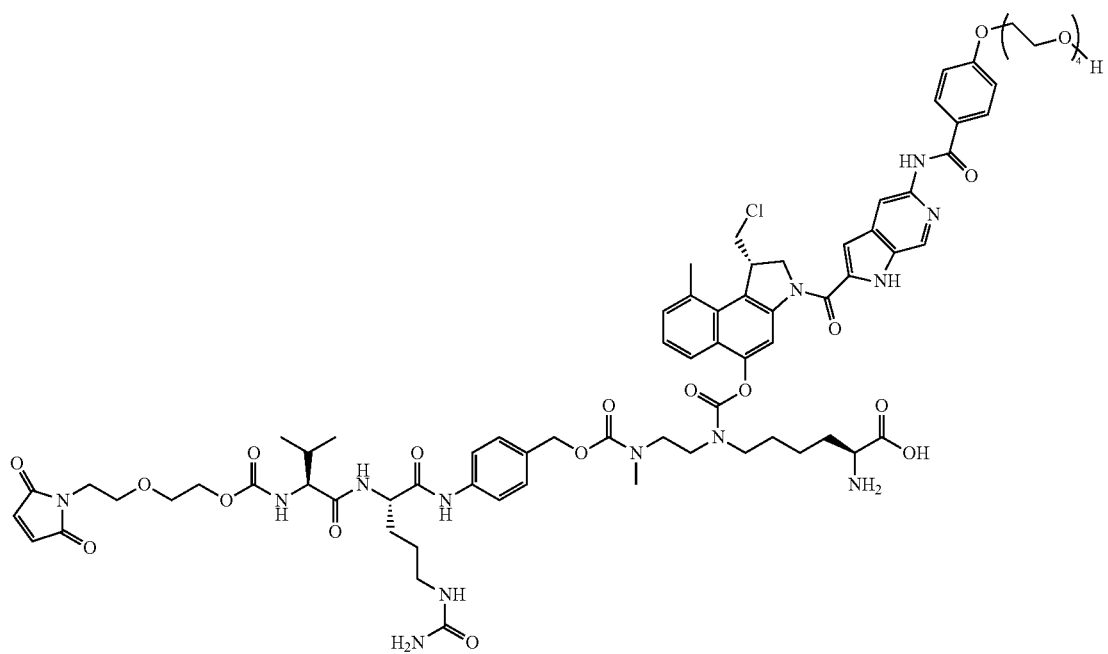
522

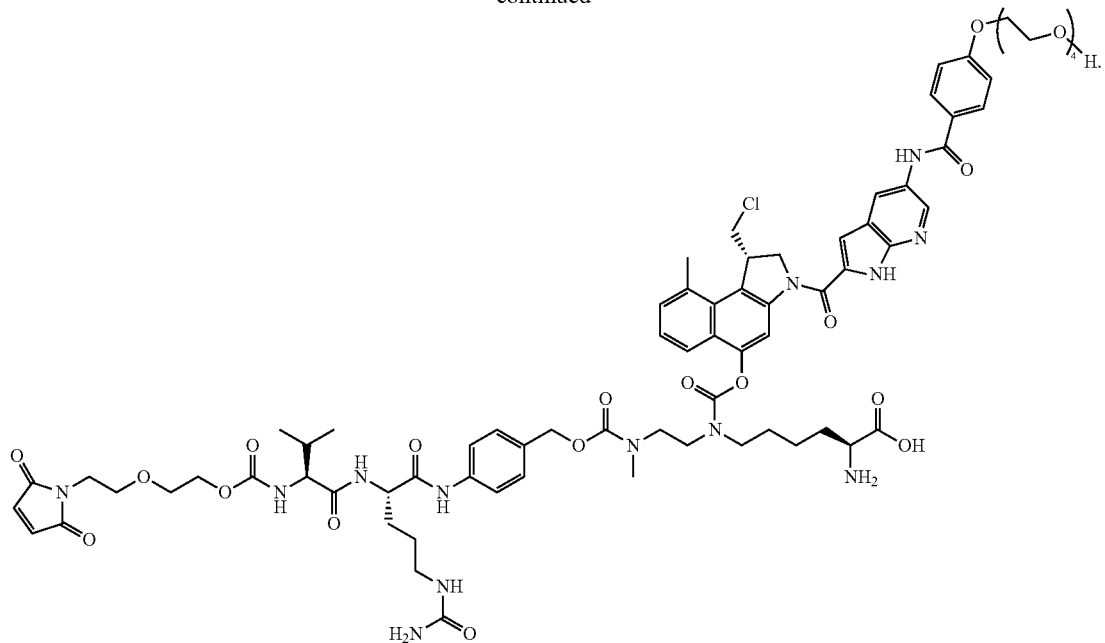
In another embodiment, a compound of formula (IV) is selected from
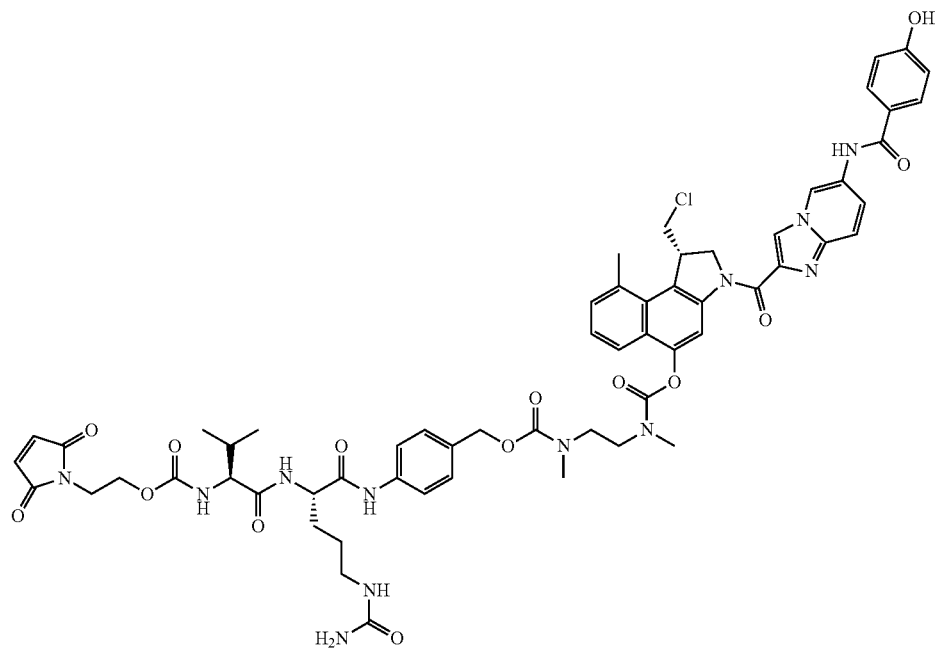

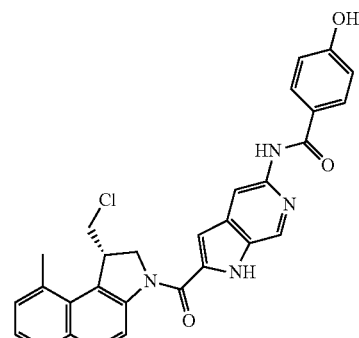
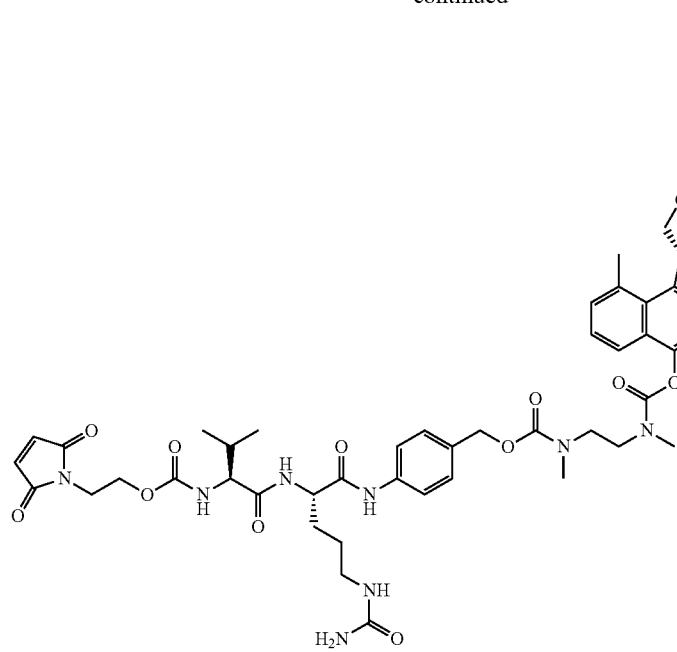
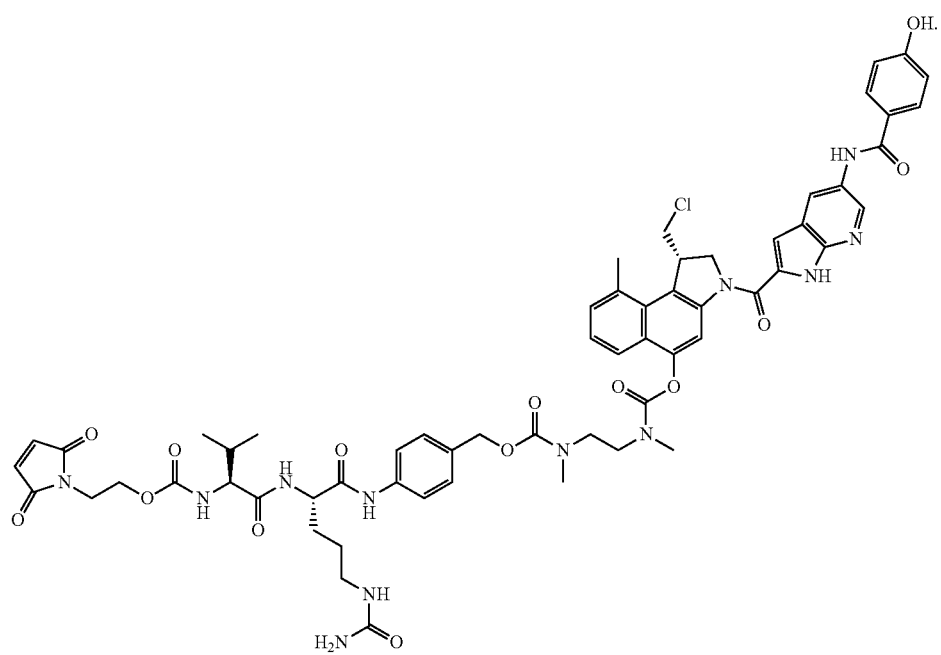 [SMILES: Cc1cccc2c(OC(=O)N(C)CCN(C)C(=O)OCc3ccc(NC(=O)[C@H](CCCNC(N)=O)NC(=O)[C@@H](NC(=O)OCCN4C(=O)C=CC4=O)C(C)C)cc3)cc3c(c12)[C@H](CCl)CN3C(=O)c1cc2cc(NC(=O)c3ccc(O)cc3)cnc2[nH]1]

In another embodiment, a compound of formula (IV) is selected from
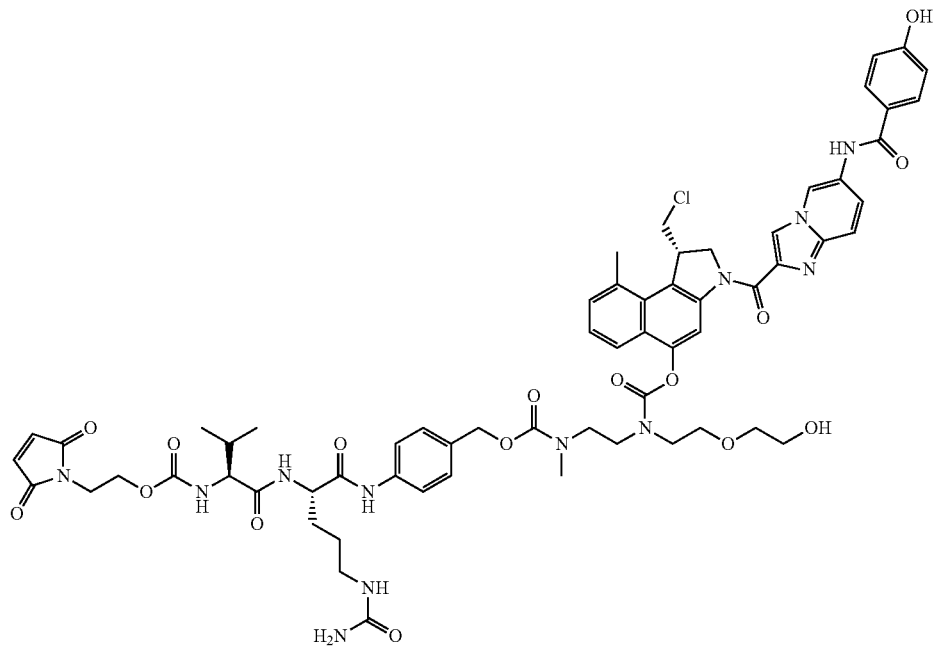
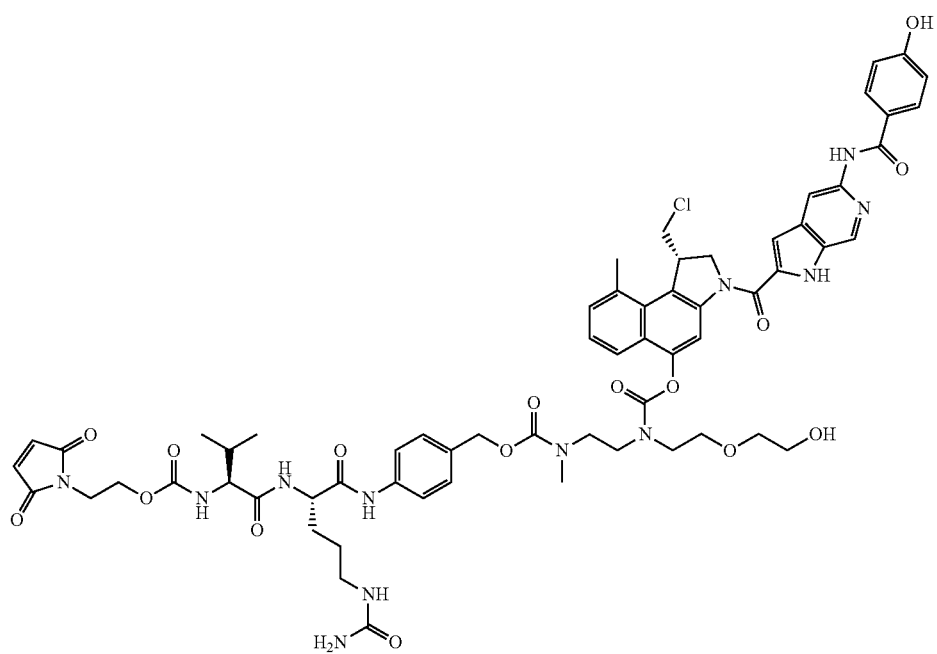 [SMILES: Cc1cccc2c(OC(=O)N(CCOCCO)CCN(C)C(=O)OCc3ccc(NC(=O)[C@H](CCCNC(N)=O)NC(=O)[C@@H](NC(=O)OCCN4C(=O)C=CC4=O)C(C)C)cc3)cc3c(c12)[C@H](CCl)CN3C(=O)c1cc2cc(NC(=O)c3ccc(O)cc3)cnc2[nH]1]

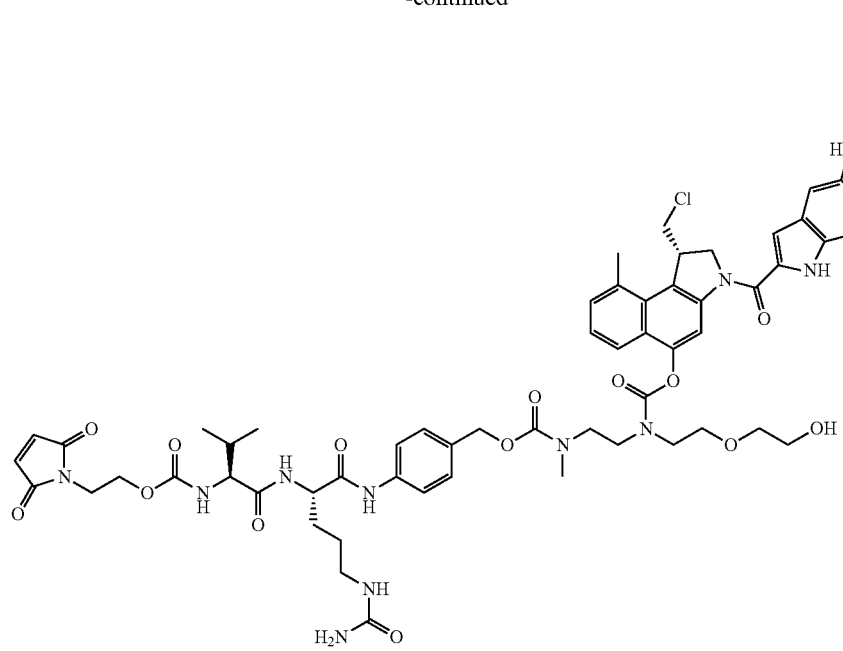
In another embodiment, a compound of formula (IV) is selected from
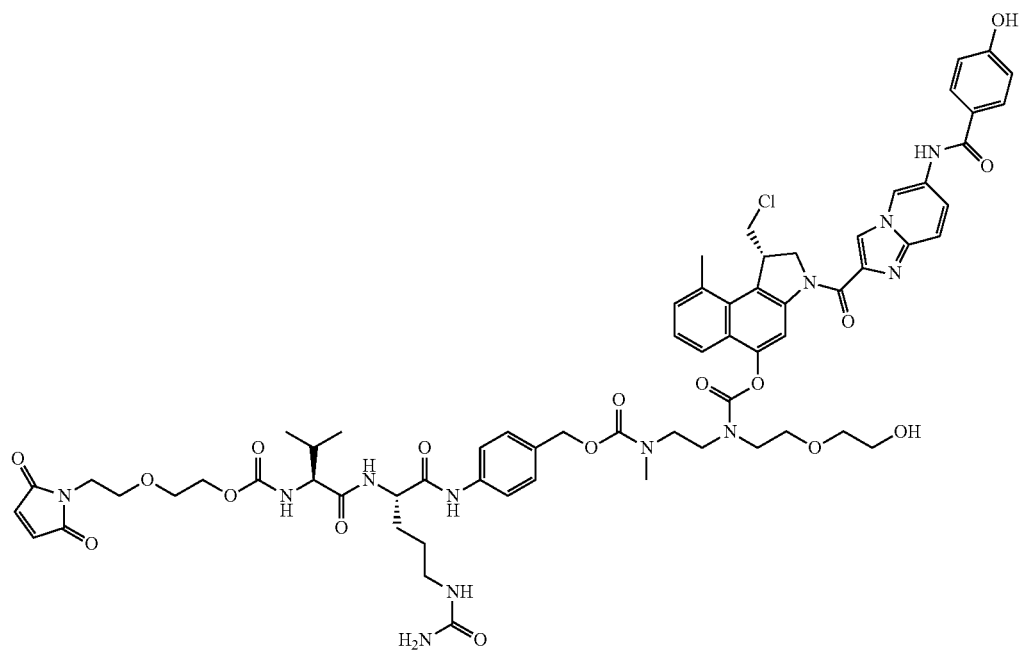

531 532
-continued
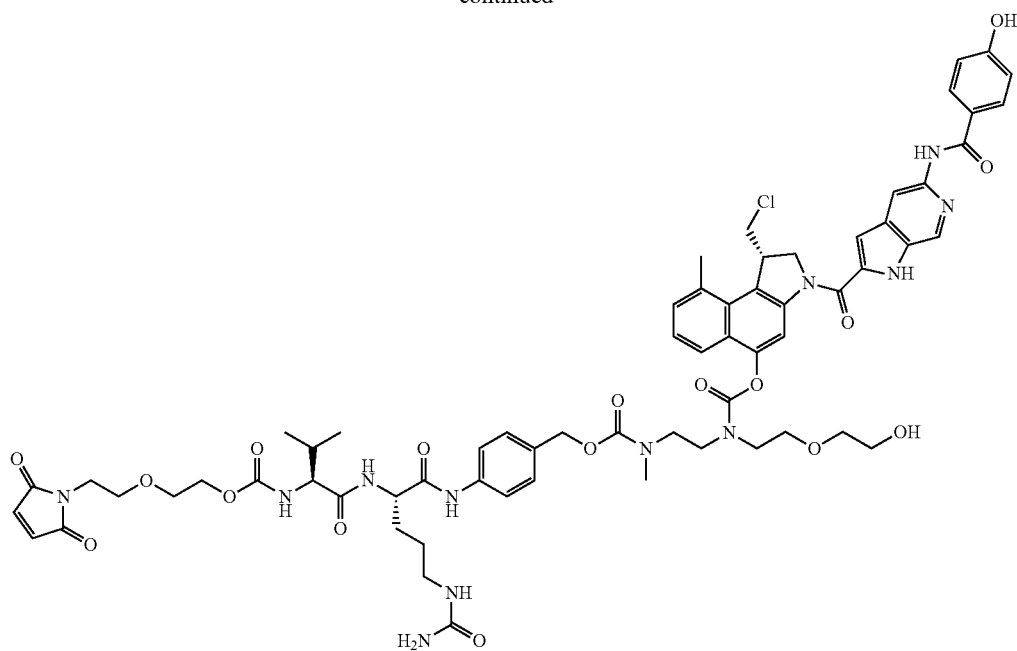
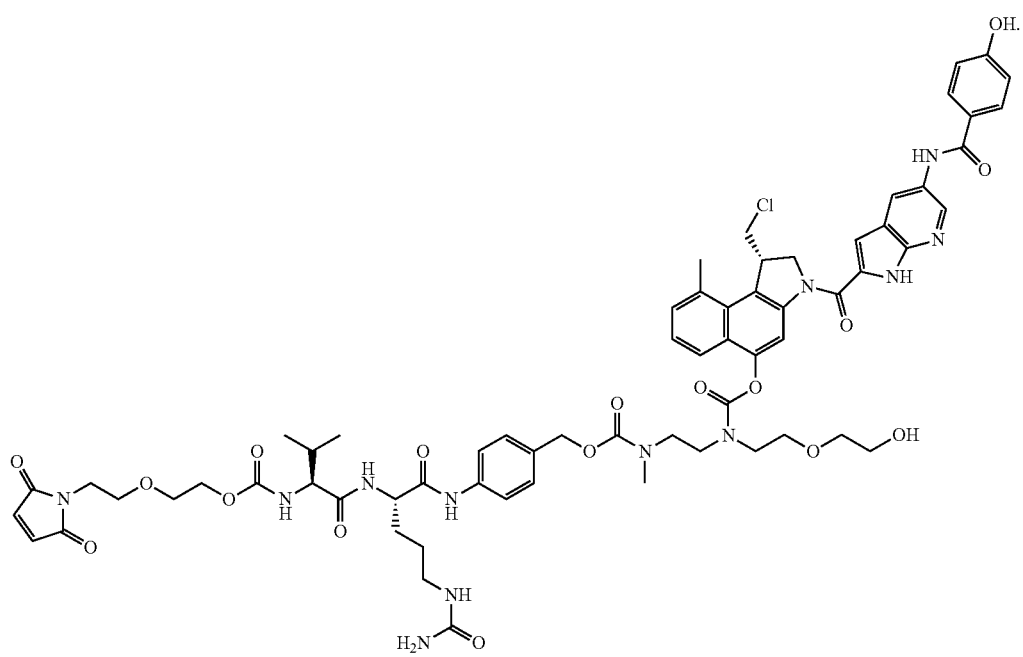 [SMILES: Cc1cccc2c(OC(=O)N(CCOCCO)CCN(C)C(=O)OCc3ccc(NC(=O)[C@H](CCCNC(N)=O)NC(=O)[C@@H](NC(=O)OCCOCCN4C(=O)C=CC4=O)C(C)C)cc3)cc3c(c12)[C@H](CCl)CN3C(=O)c1cc2cc(NC(=O)c3ccc(O)cc3)cnc2[nH]1]

In another embodiment, a compound of formula (IV) is selected from
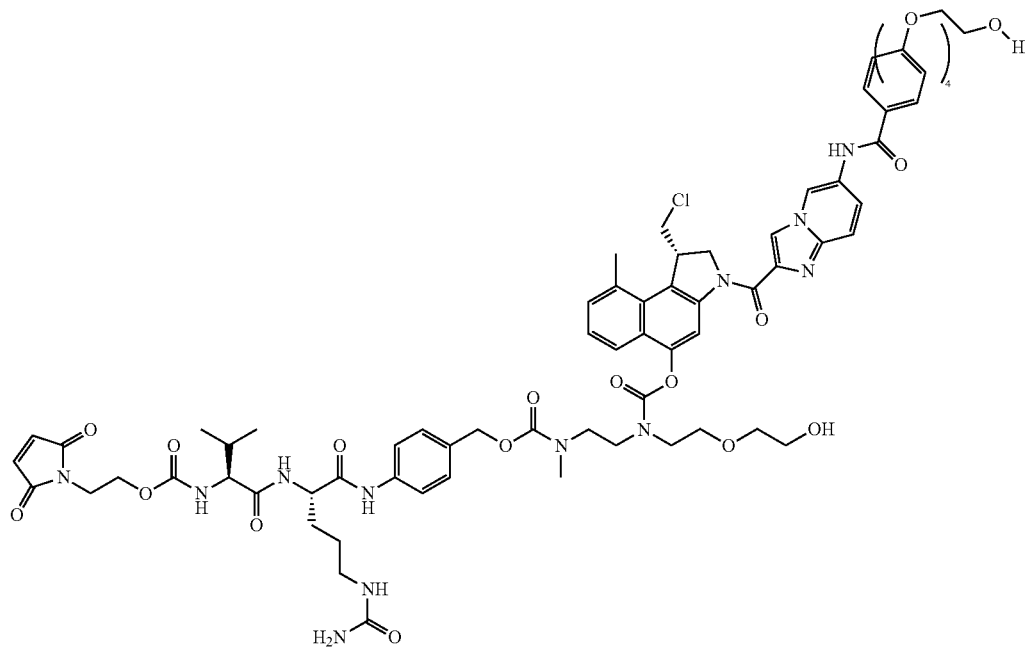
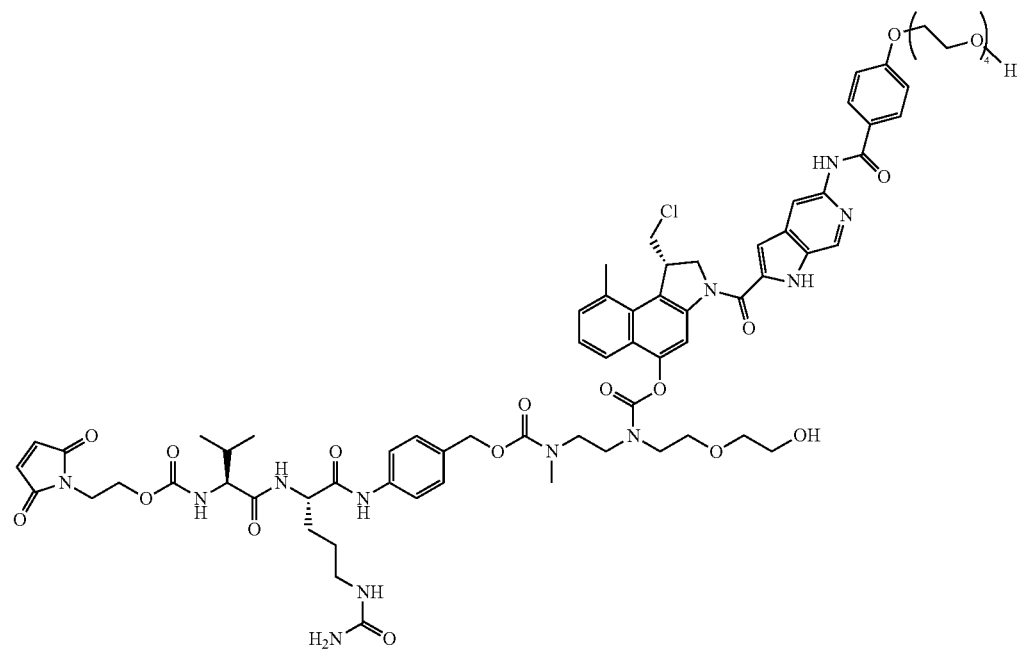

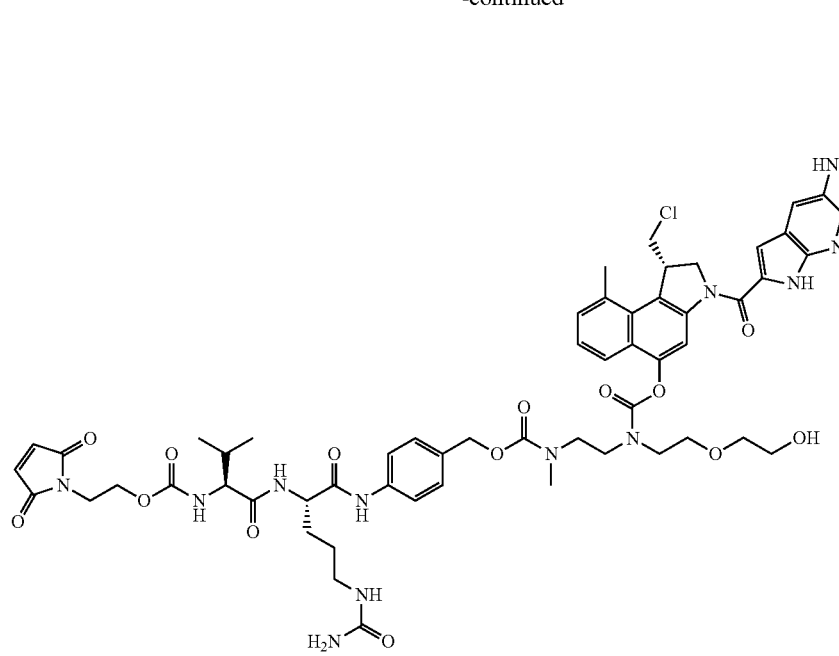
In another embodiment, a compound of formula (IV) is selected from
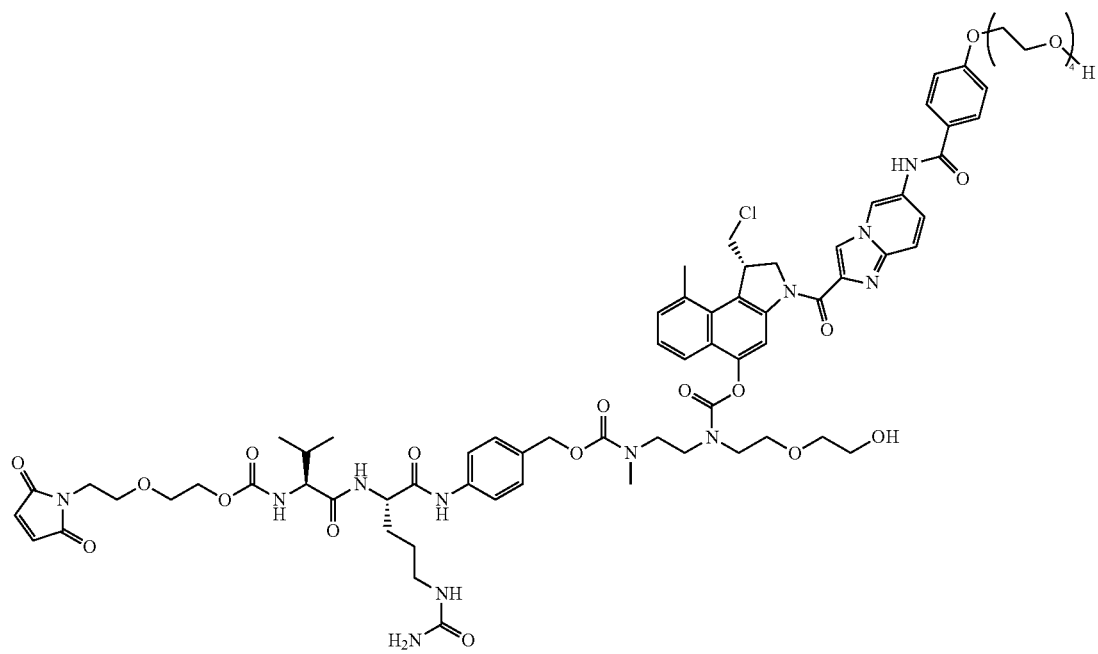

-continued
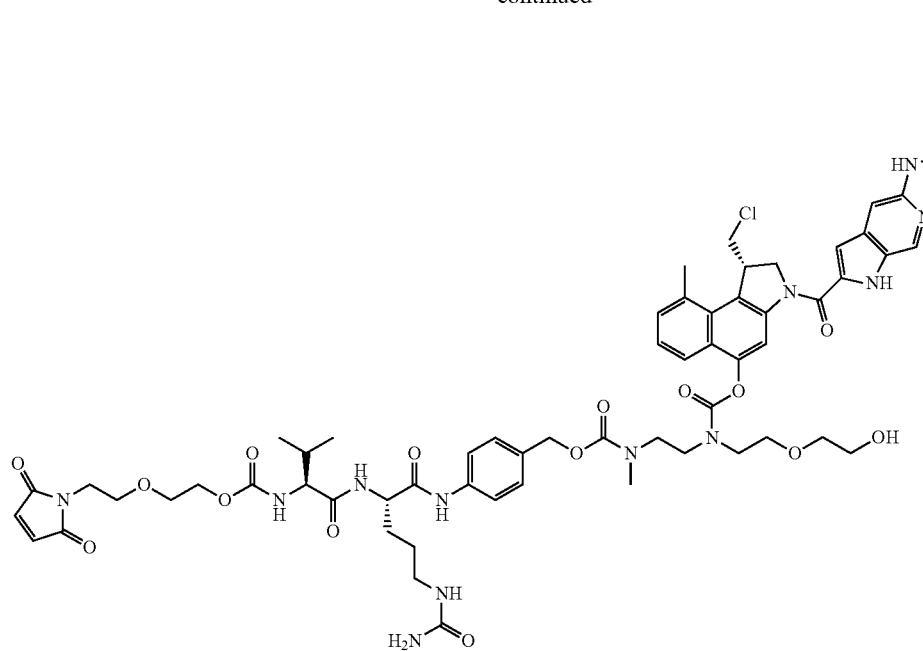
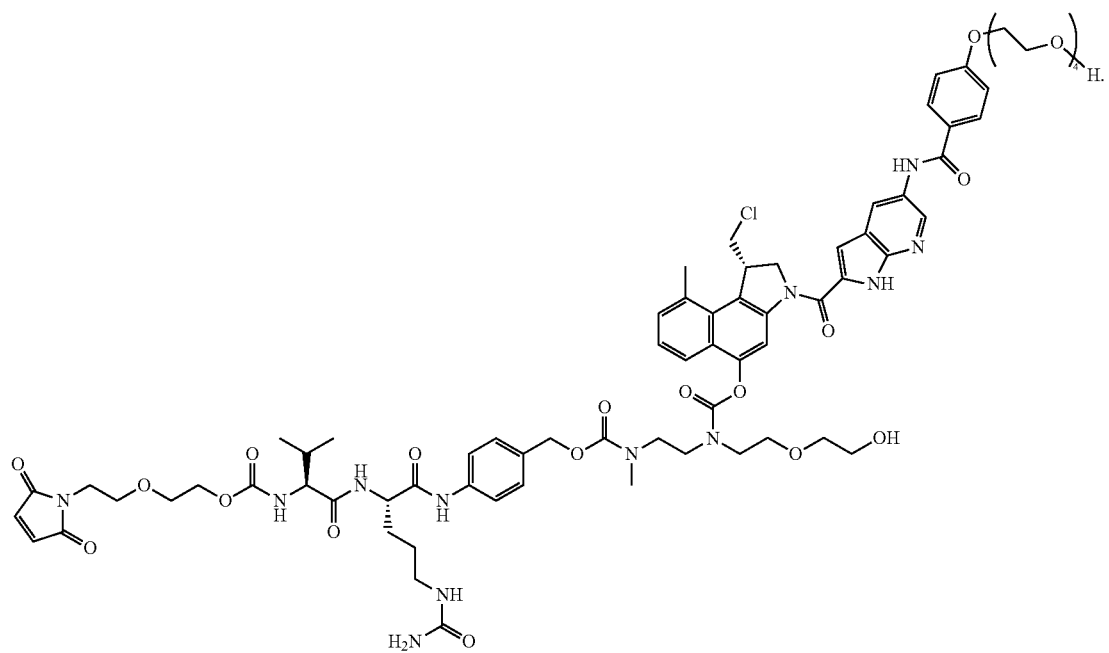

In another embodiment, a compound of formula (IV) is selected from
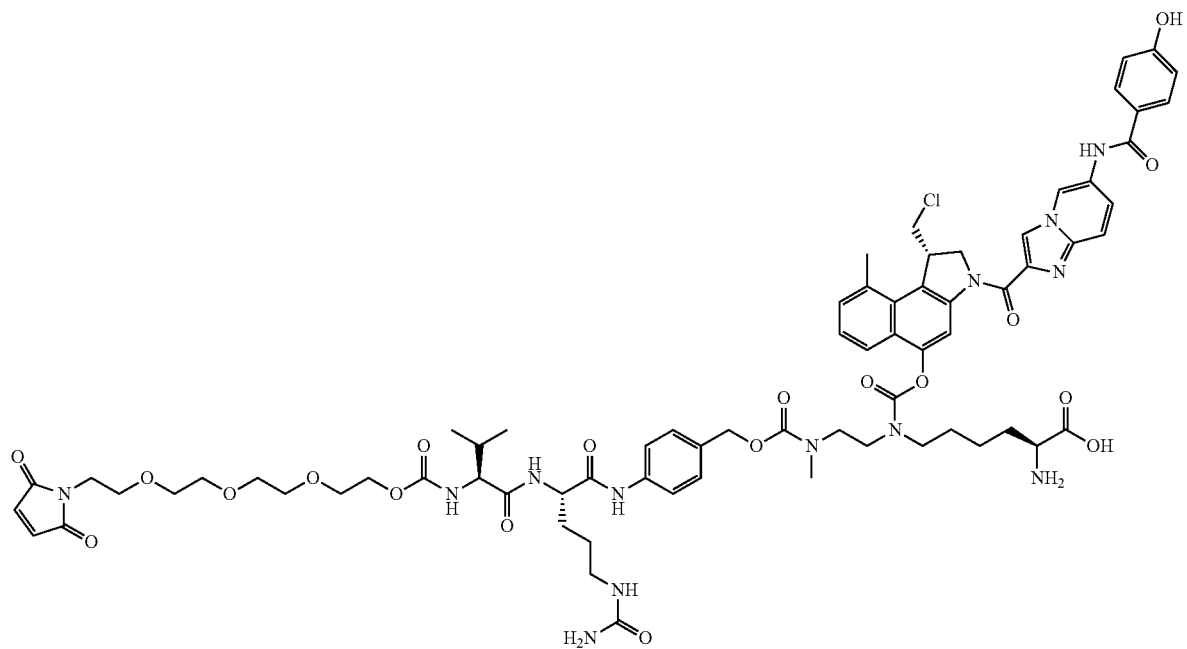 [SMILES: Cc1cccc2c(OC(=O)N(CCCC[C@H](N)C(=O)O)CCN(C)C(=O)OCc3ccc(NC(=O)[C@H](CCCNC(N)=O)NC(=O)[C@@H](NC(=O)OCCOCCOCCOCCN4C(=O)C=CC4=O)C(C)C)cc3)cc3c(c12)[C@H](CCl)CN3C(=O)c1cc2cc(NC(=O)c3ccc(O)cc3)cnc2[nH]1]
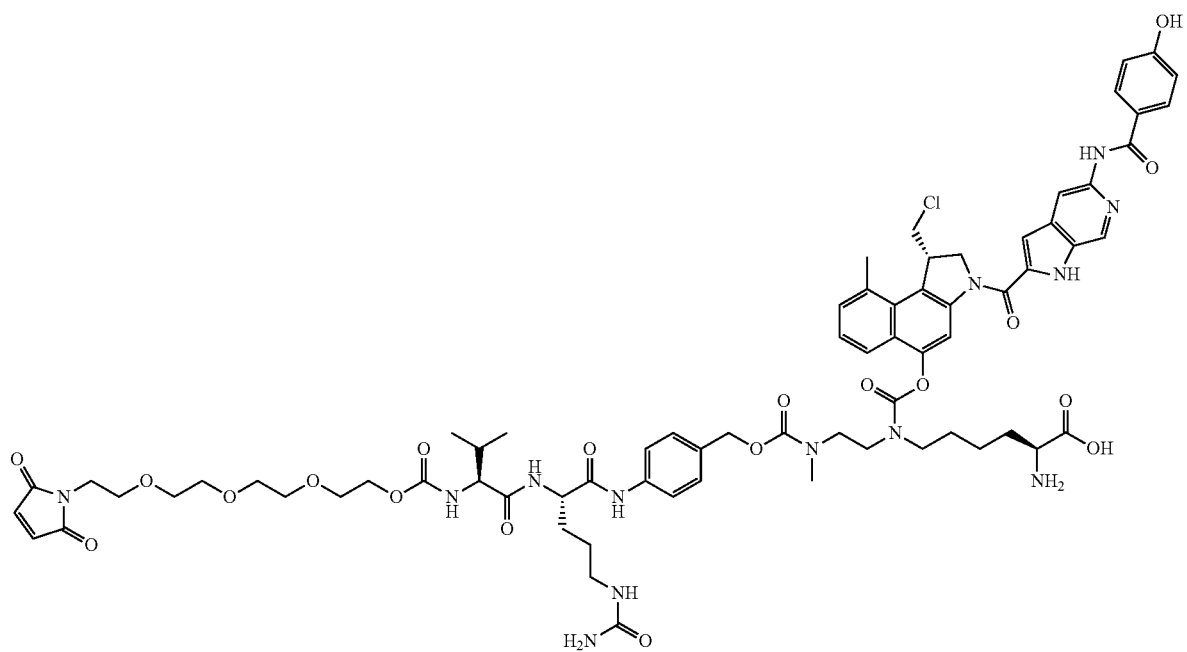

-continued
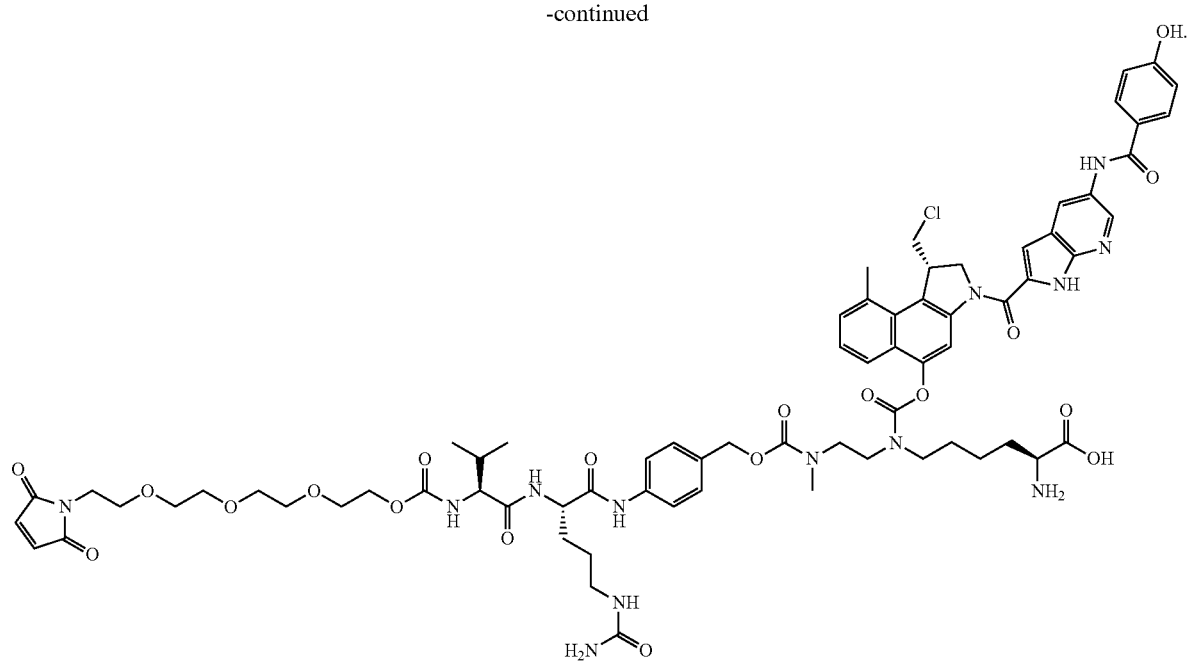
In another embodiment, a compound of formula (IV) is selected from
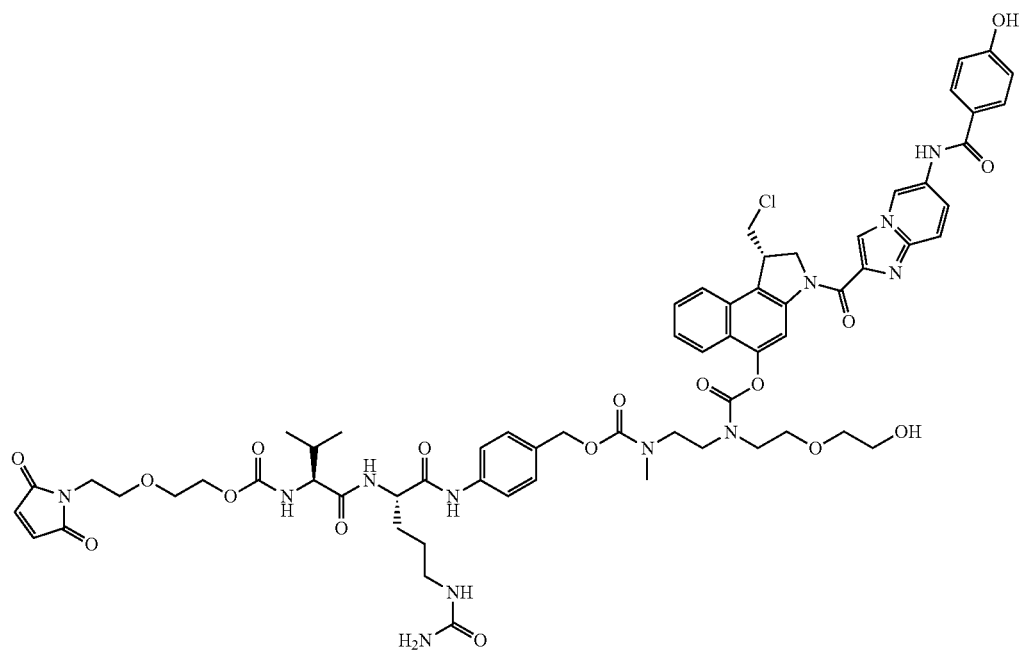

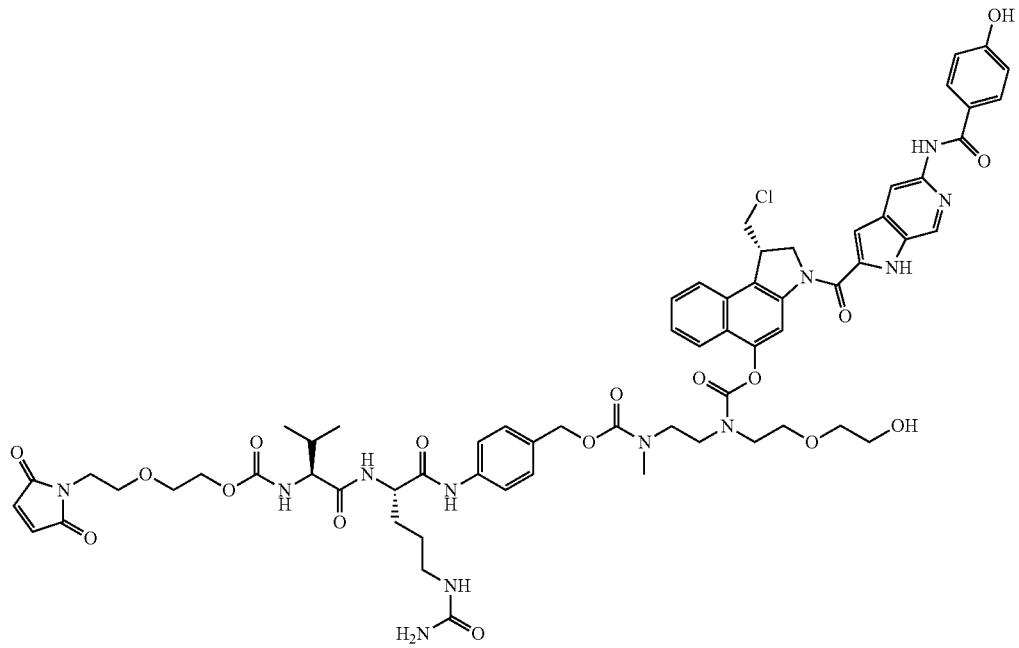
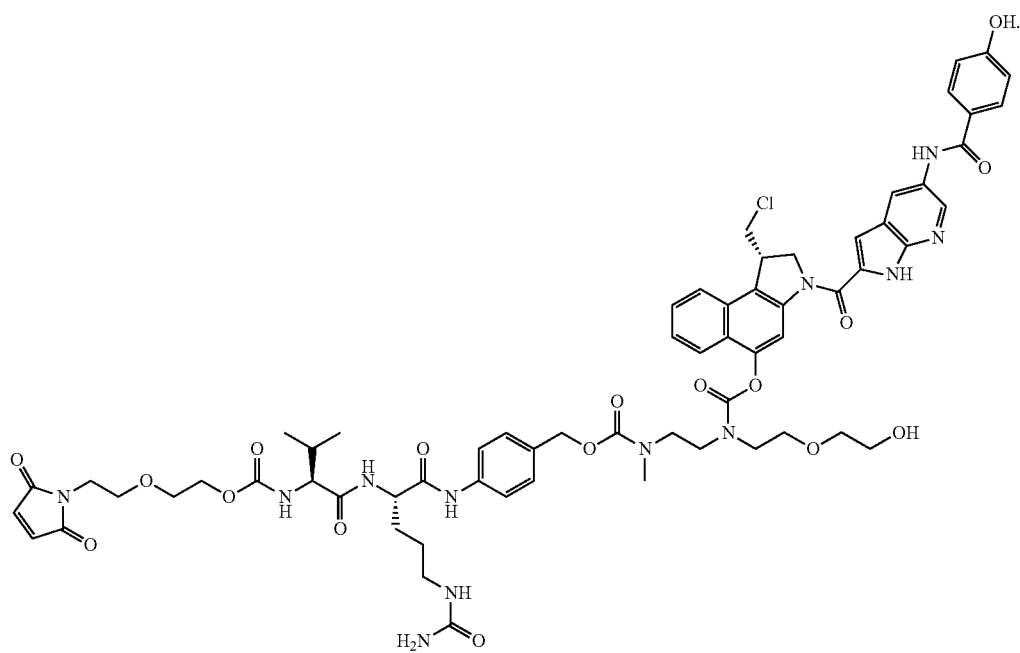 [SMILES: CC(C)[C@H](NC(=O)OCCOCCN1C(=O)C=CC1=O)C(=O)N[C@@H](CCCNC(N)=O)C(=O)Nc1ccc(COC(=O)N(C)CCN(CCOCCO)C(=O)Oc2cc3c(c4ccccc24)[C@H](CCl)CN3C(=O)c2cc3cc(NC(=O)c4ccc(O)cc4)cnc3[nH]2)cc1]

In another embodiment, a compound of formula (IV) is selected from
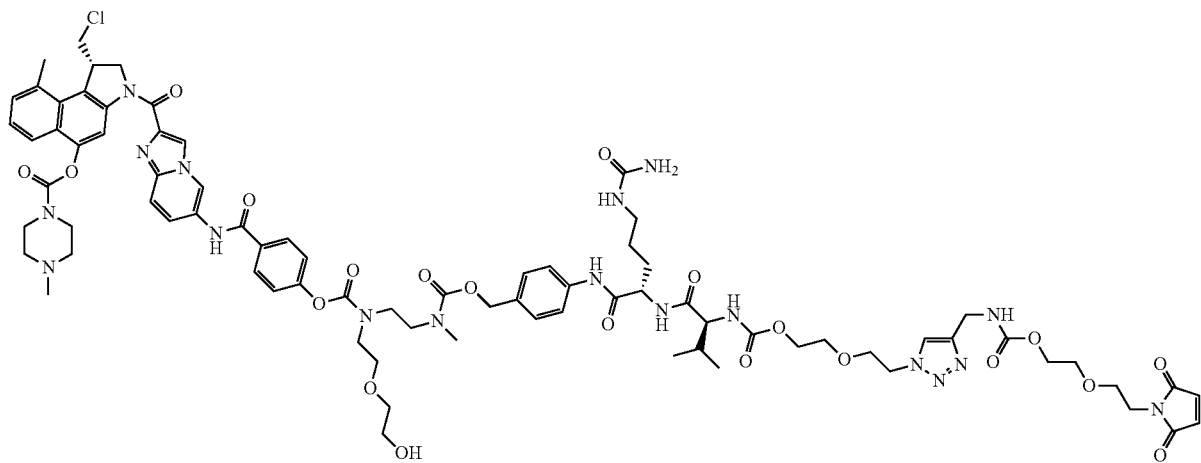
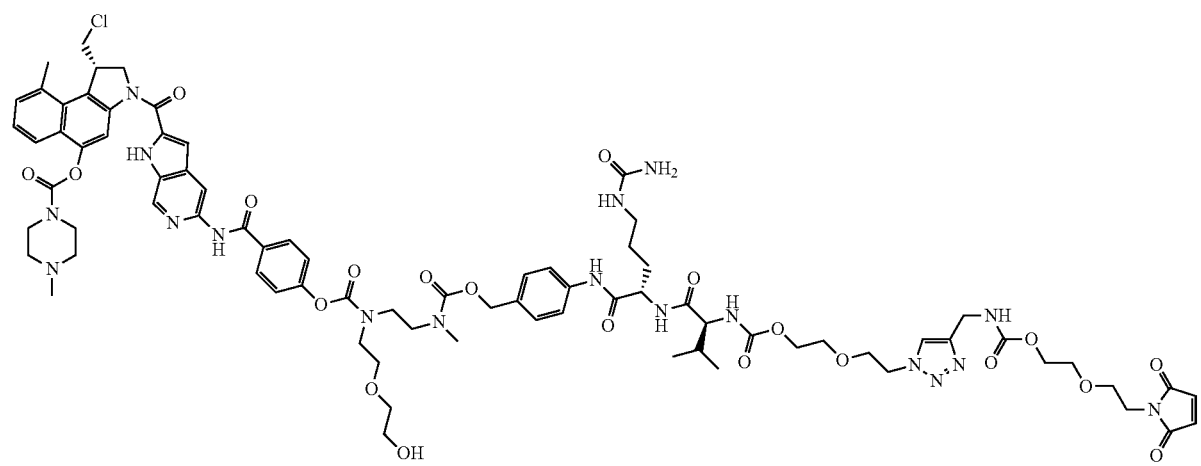
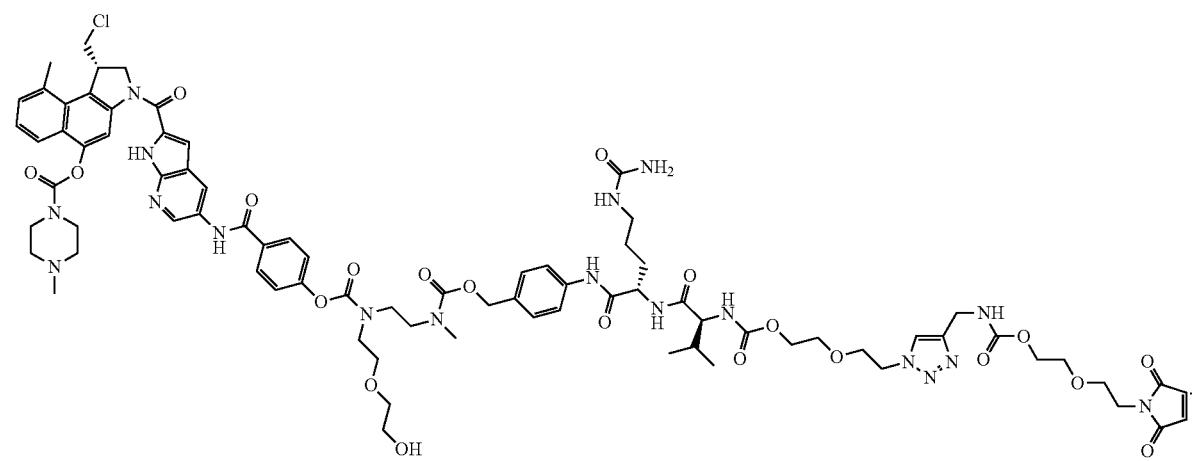 [SMILES: Cc1cccc2c(OC(=O)N3CCN(C)CC3)cc3c(c12)[C@H](CCl)CN3C(=O)c1cc2cc(NC(=O)c3ccc(OC(=O)N(CCOCCO)CCN(C)C(=O)OCc4ccc(NC(=O)[C@H](CCCNC(N)=O)NC(=O)[C@@H](NC(=O)OCCOCCn5cc(CNC(=O)OCCOCCN6C(=O)C=CC6=O)nn5)C(C)C)cc4)cc3)cnc2[nH]1]

In another embodiment, a compound of formula (IV) is selected from
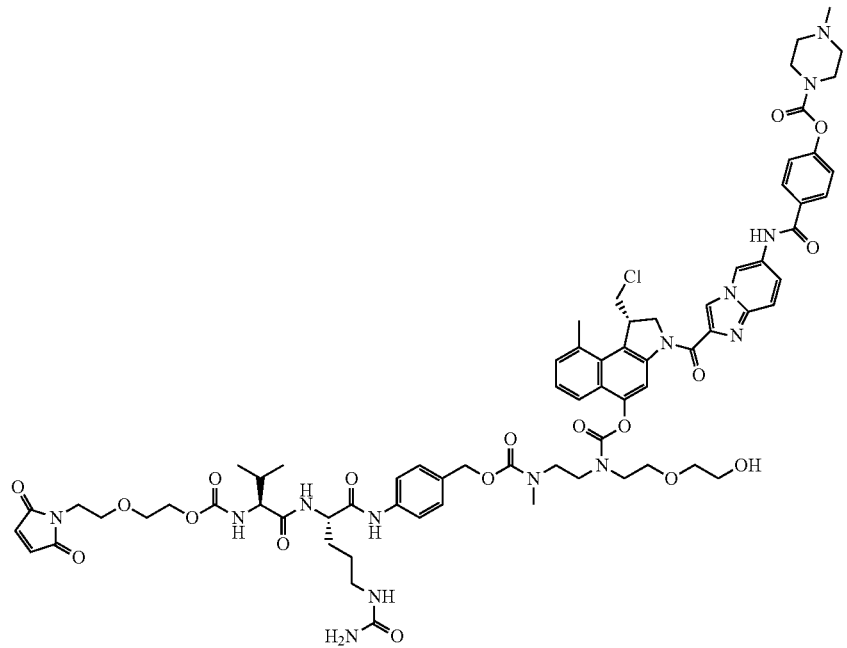
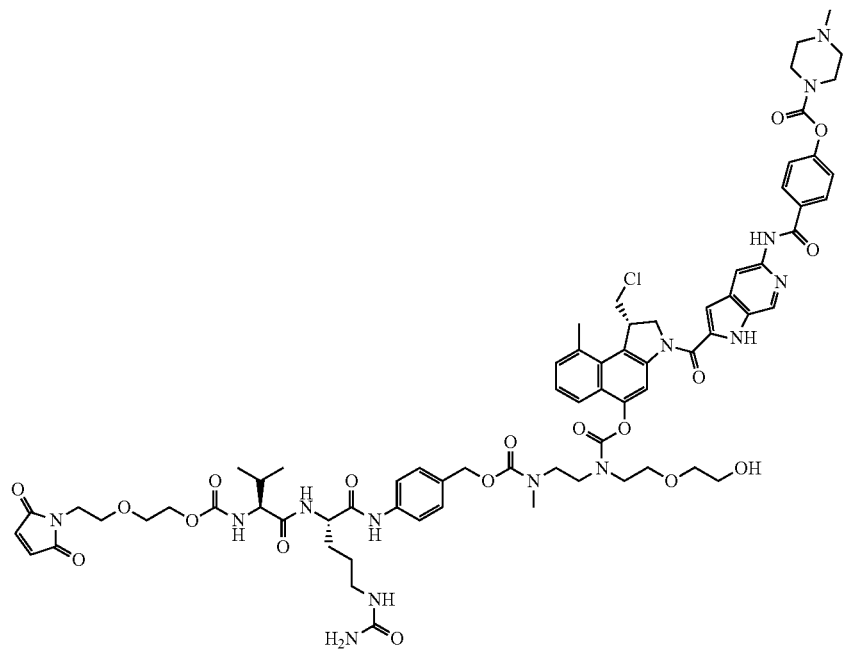 [SMILES: Cc1cccc2c(OC(=O)N(CCOCCO)CCN(C)C(=O)OCc3ccc(NC(=O)[C@H](CCCNC(N)=O)NC(=O)[C@@H](NC(=O)OCCOCCN4C(=O)C=CC4=O)C(C)C)cc3)cc3c(c12)[C@H](CCl)CN3C(=O)c1cc2cc(NC(=O)c3ccc(OC(=O)N4CCN(C)CC4)cc3)cnc2[nH]1]

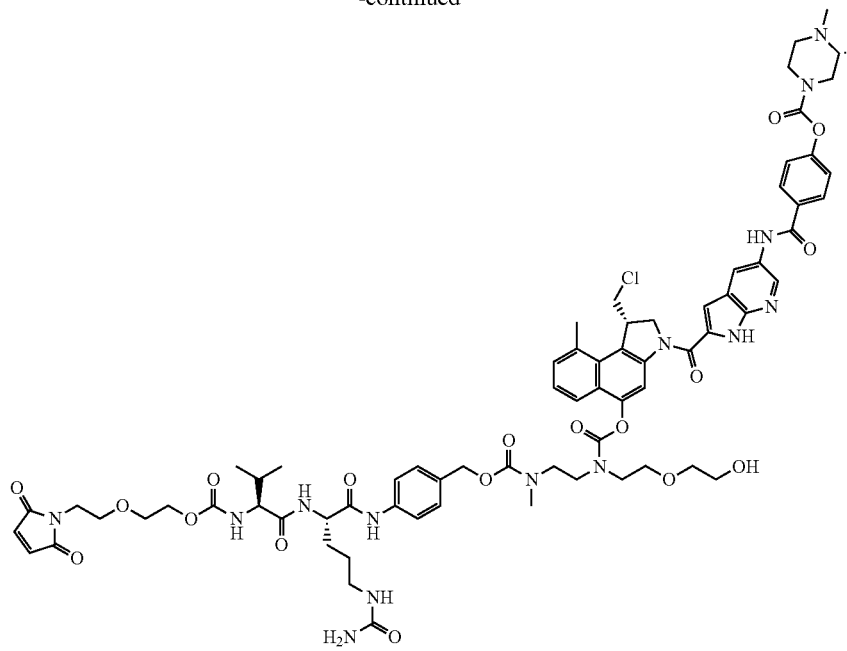
In another embodiment, a compound of formula (IV) is selected from
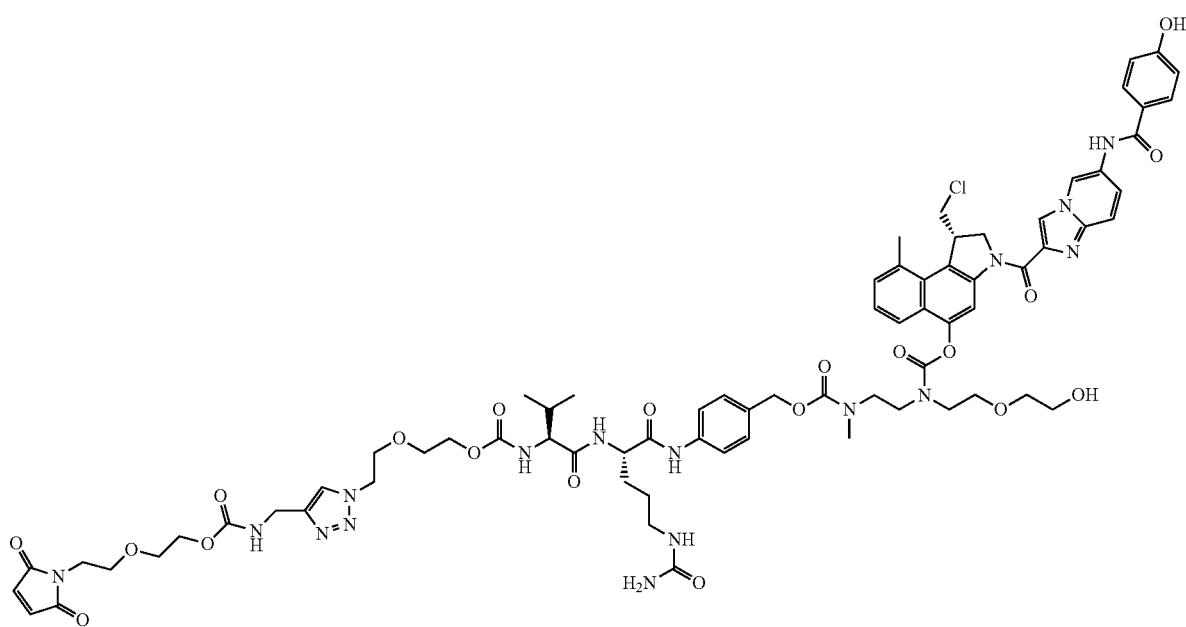

551
552
-continued
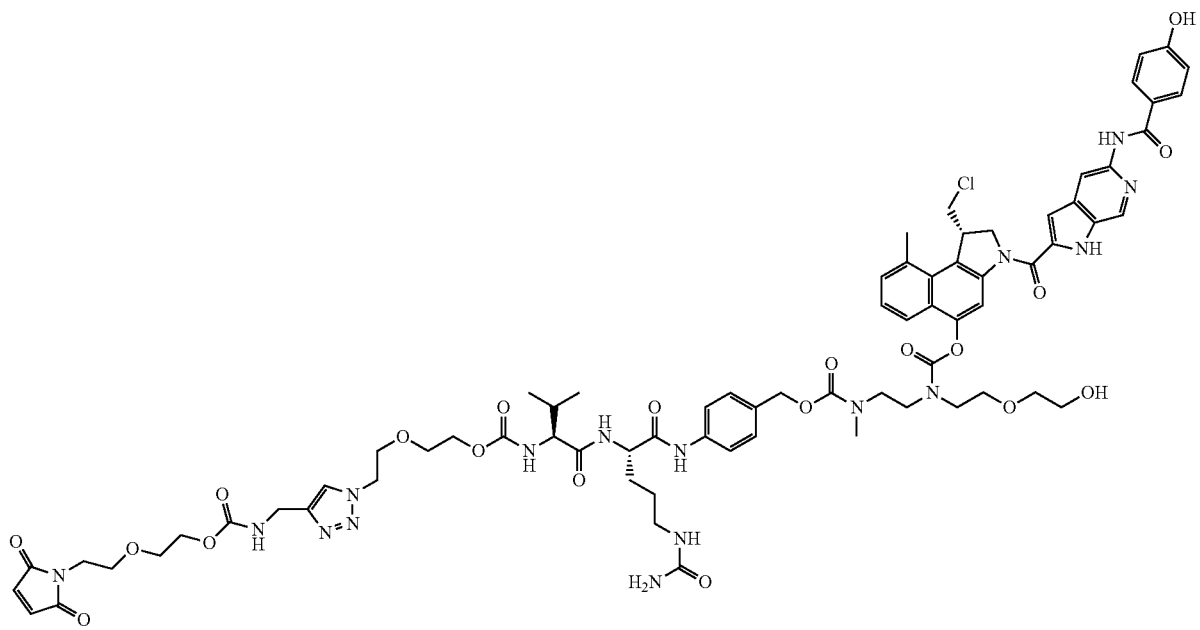
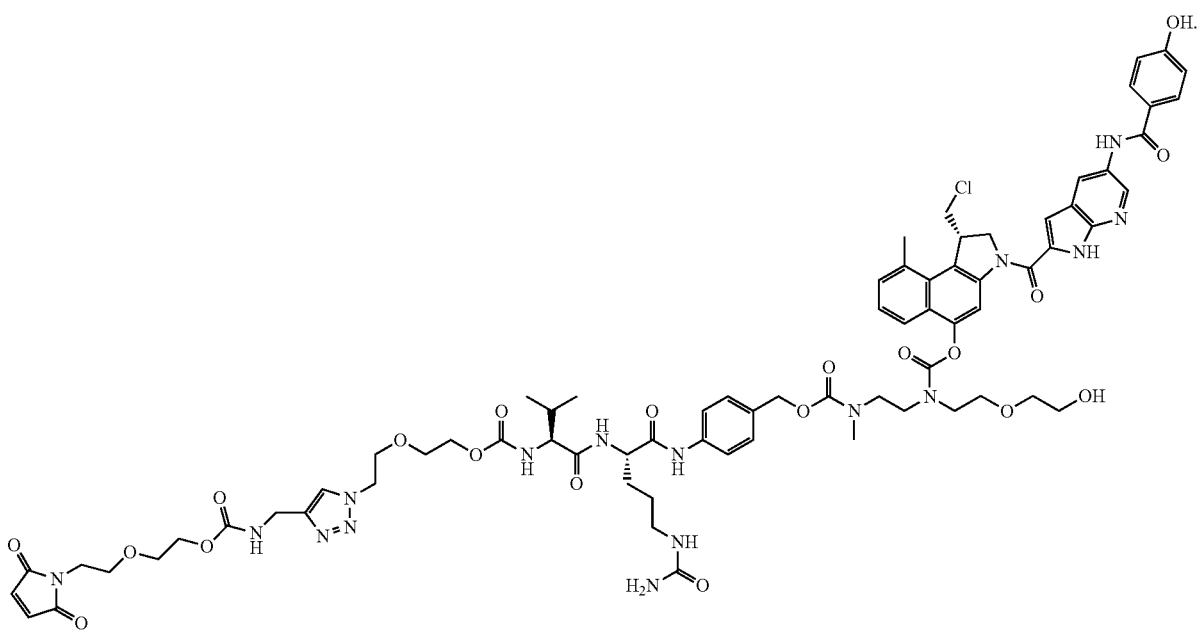 [SMILES: Cc1cccc2c(OC(=O)N(CCOCCO)CCN(C)C(=O)OCc3ccc(NC(=O)[C@H](CCCNC(N)=O)NC(=O)[C@@H](NC(=O)OCCOCCn4cc(CNC(=O)OCCOCCN5C(=O)C=CC5=O)nn4)C(C)C)cc3)cc3c(c12)[C@H](CCl)CN3C(=O)c1cc2cc(NC(=O)c3ccc(O)cc3)cnc2[nH]1]

In another embodiment, a compound of formula (IV) is selected from
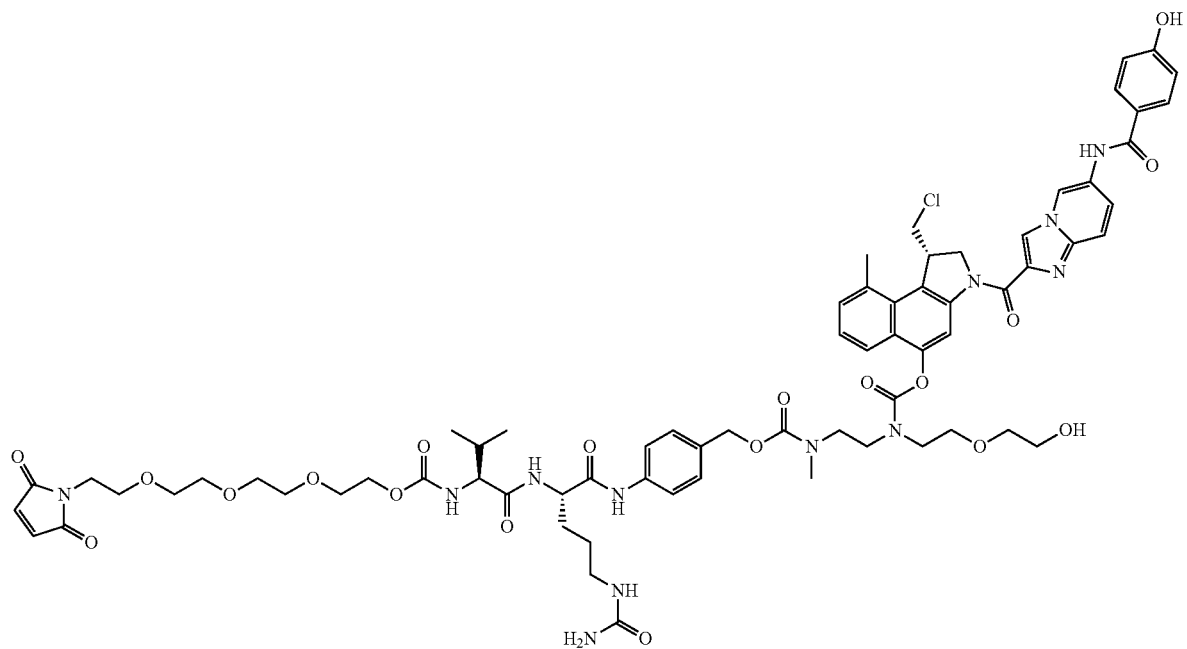
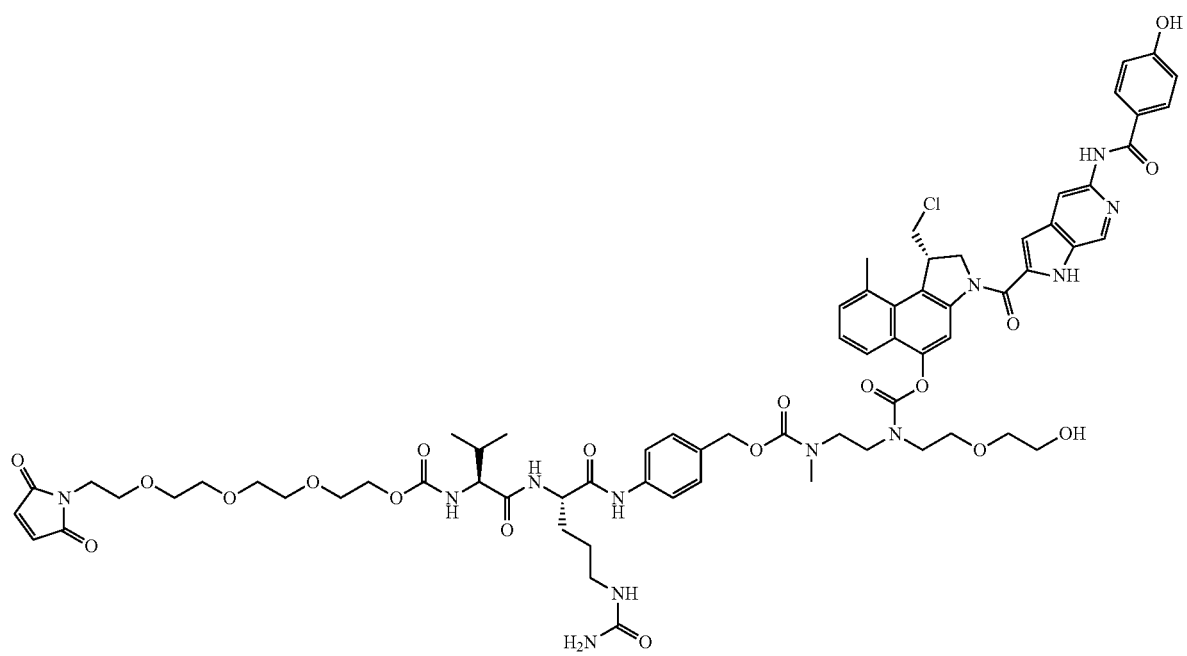 [SMILES: Cc1cccc2c(OC(=O)N(CCOCCO)CCN(C)C(=O)OCc3ccc(NC(=O)[C@H](CCCNC(N)=O)NC(=O)[C@@H](NC(=O)OCCOCCOCCOCCN4C(=O)C=CC4=O)C(C)C)cc3)cc3c(c12)[C@H](CCl)CN3C(=O)c1cc2cc(NC(=O)c3ccc(O)cc3)cnc2[nH]1]

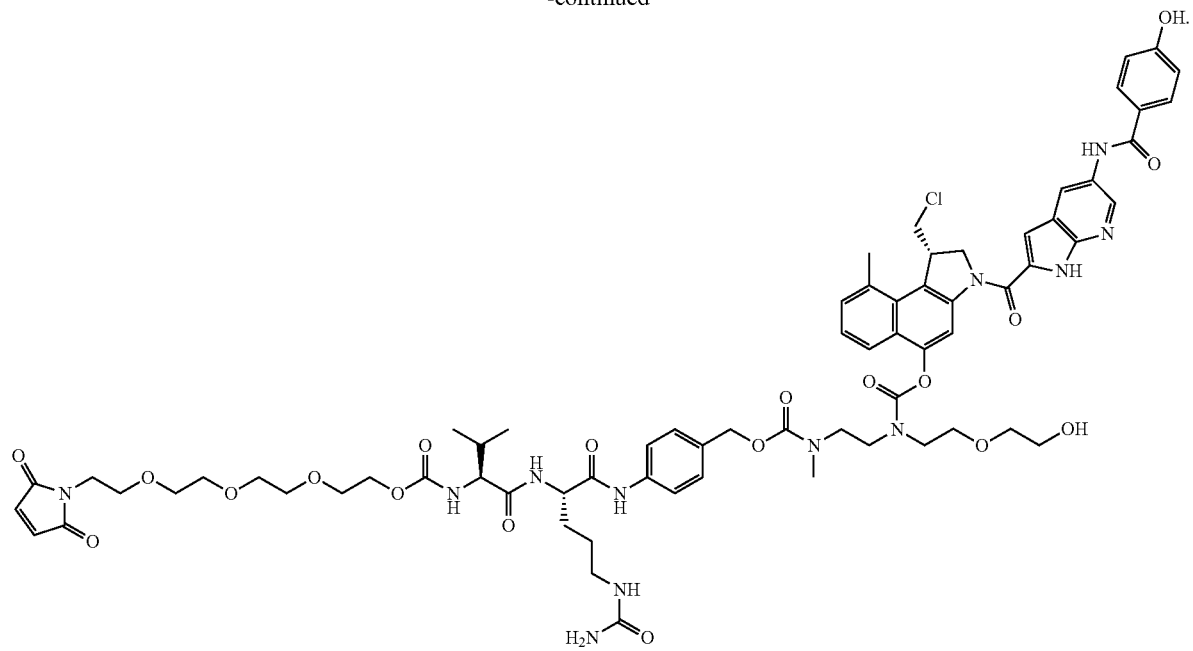
In another embodiment, a compound of formula (IV) is selected from
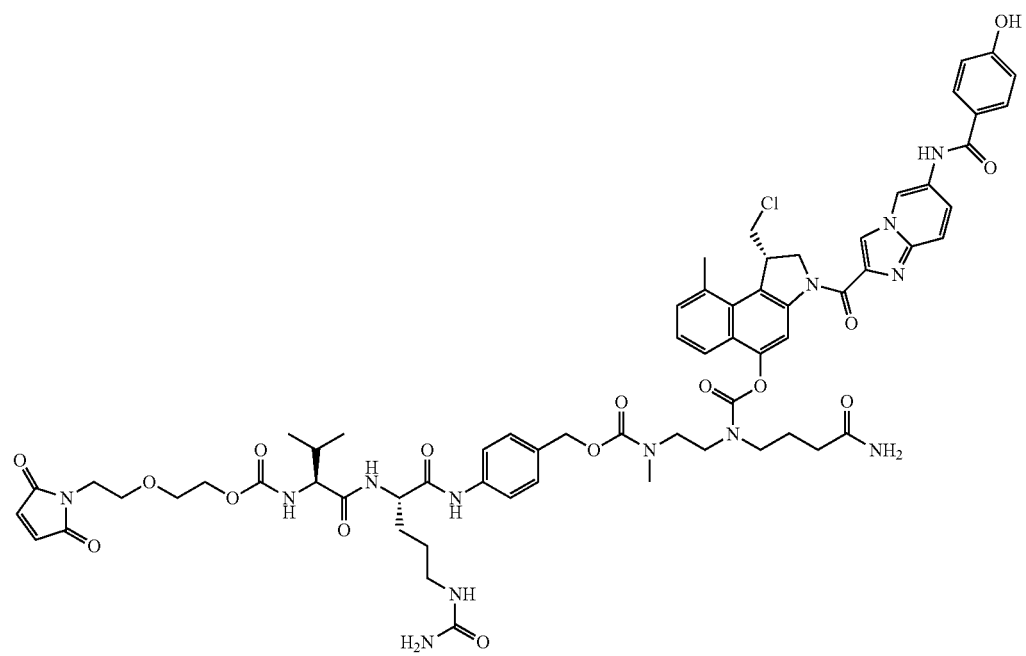

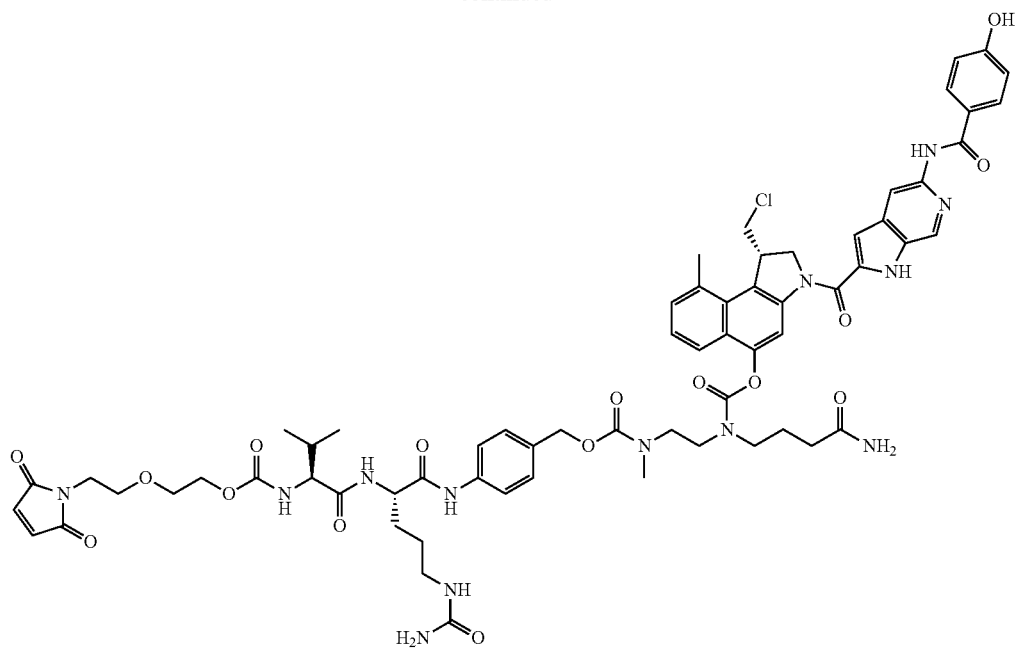 [SMILES: Cc1cccc2c(OC(=O)N(CCCC(N)=O)CCN(C)C(=O)OCc3ccc(NC(=O)[C@H](CCCNC(N)=O)NC(=O)[C@@H](NC(=O)OCCOCCN4C(=O)C=CC4=O)C(C)C)cc3)cc3c(c12)[C@H](CCl)CN3C(=O)c1cc2cc(NC(=O)c3ccc(O)cc3)cnc2[nH]1]
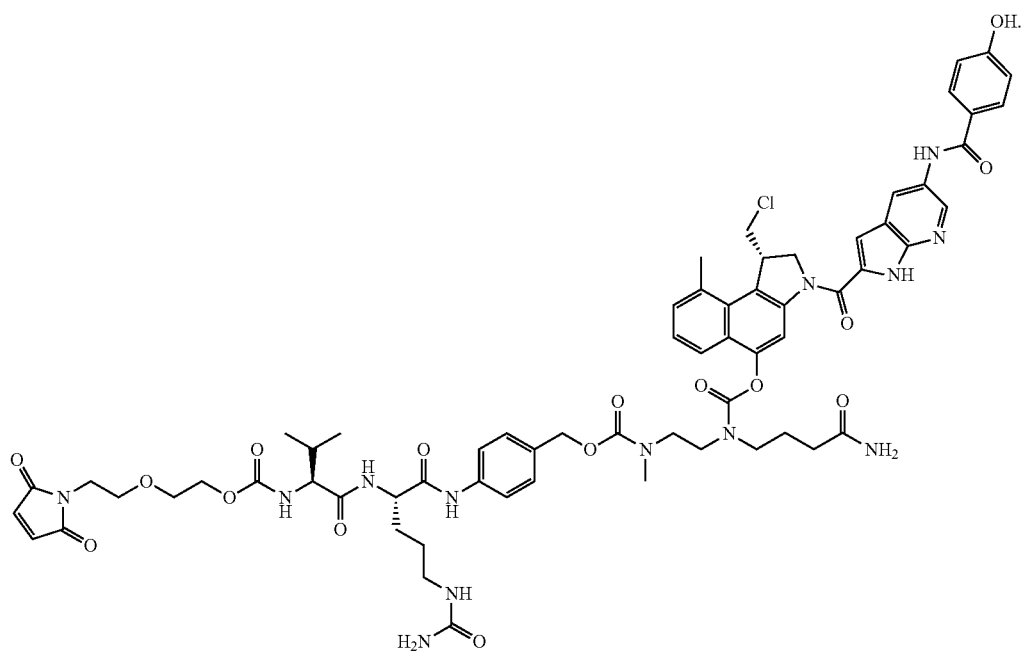

In another embodiment, a compound of formula (IV) is selected from
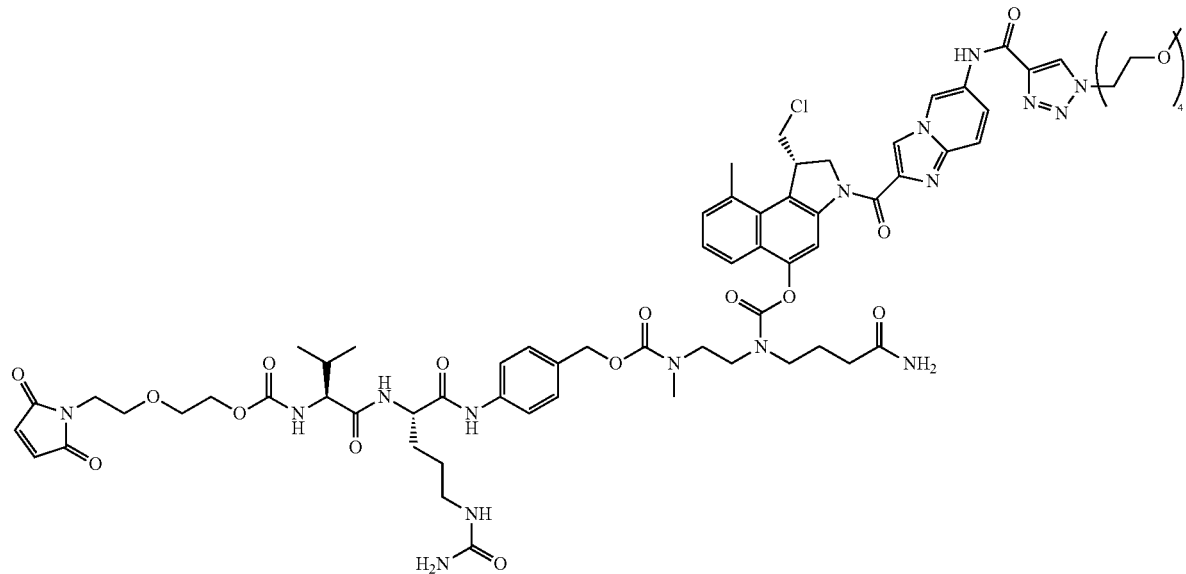
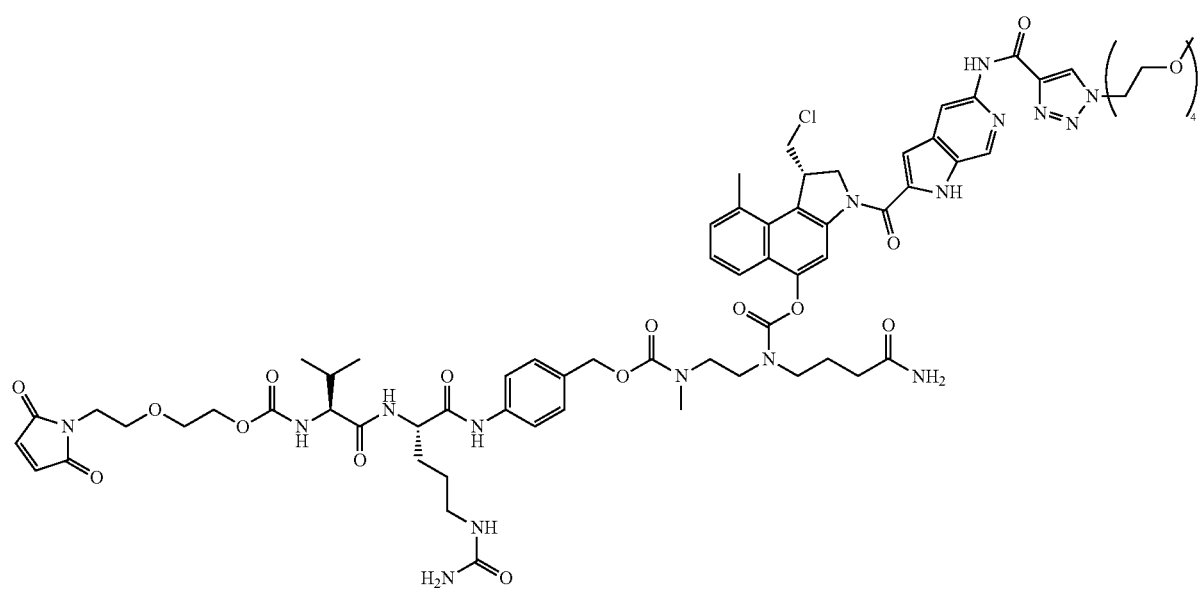

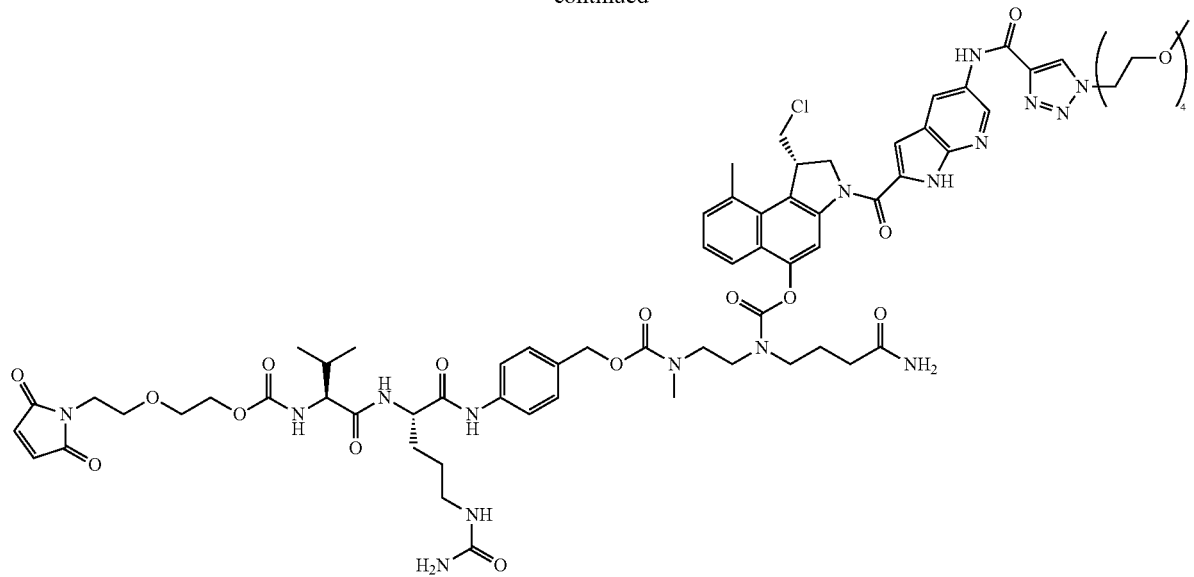
In another embodiment, a compound of formula (IV) is selected from
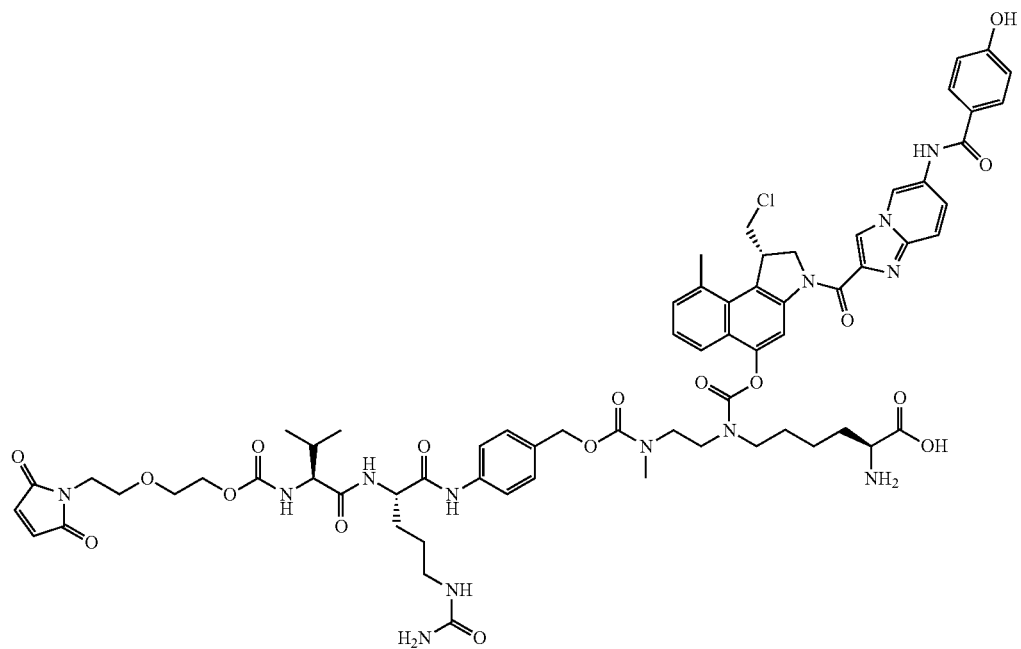

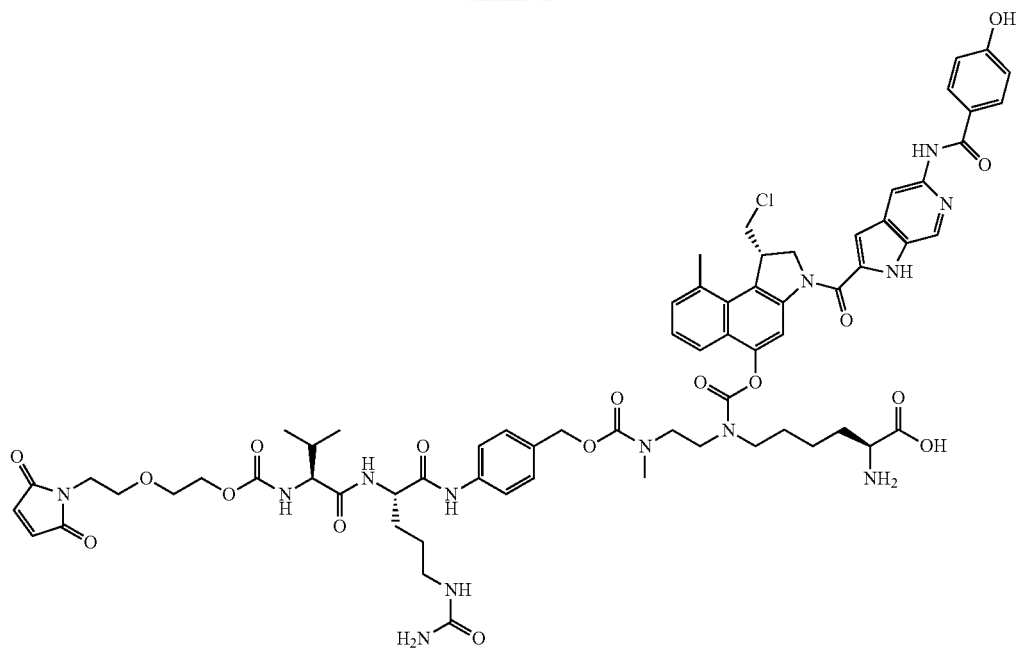
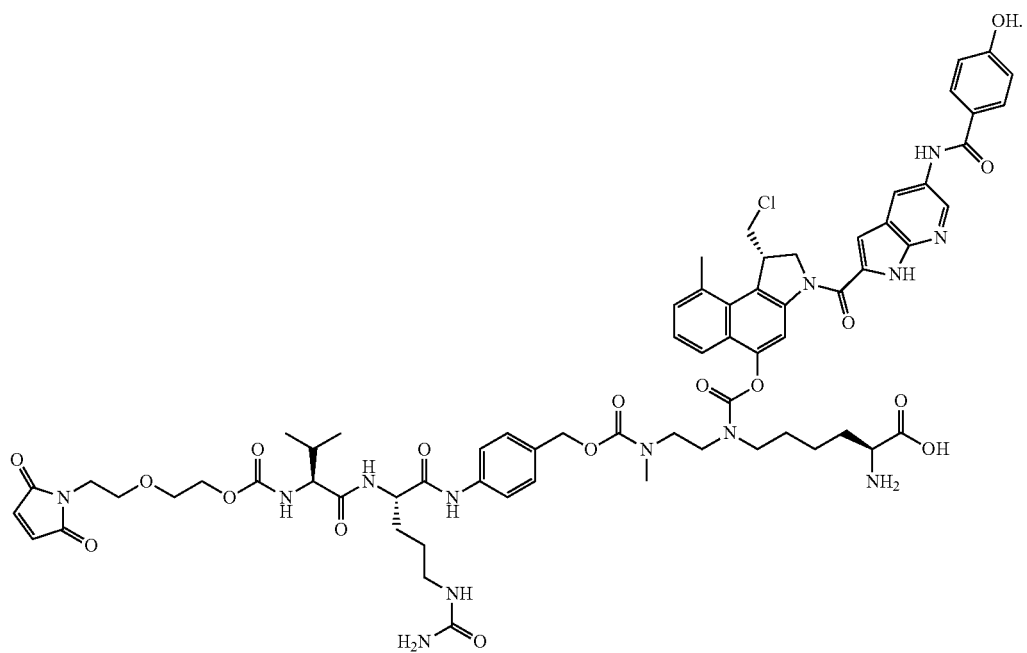 [SMILES: Cc1cccc2c(OC(=O)N(CCCC[C@H](N)C(=O)O)CCN(C)C(=O)OCc3ccc(NC(=O)[C@H](CCCNC(N)=O)NC(=O)[C@@H](NC(=O)OCCOCCN4C(=O)C=CC4=O)C(C)C)cc3)cc3c(c12)[C@H](CCl)CN3C(=O)c1cc2cc(NC(=O)c3ccc(O)cc3)cnc2[nH]1]

In another embodiment, a compound of formula (IV) is selected from
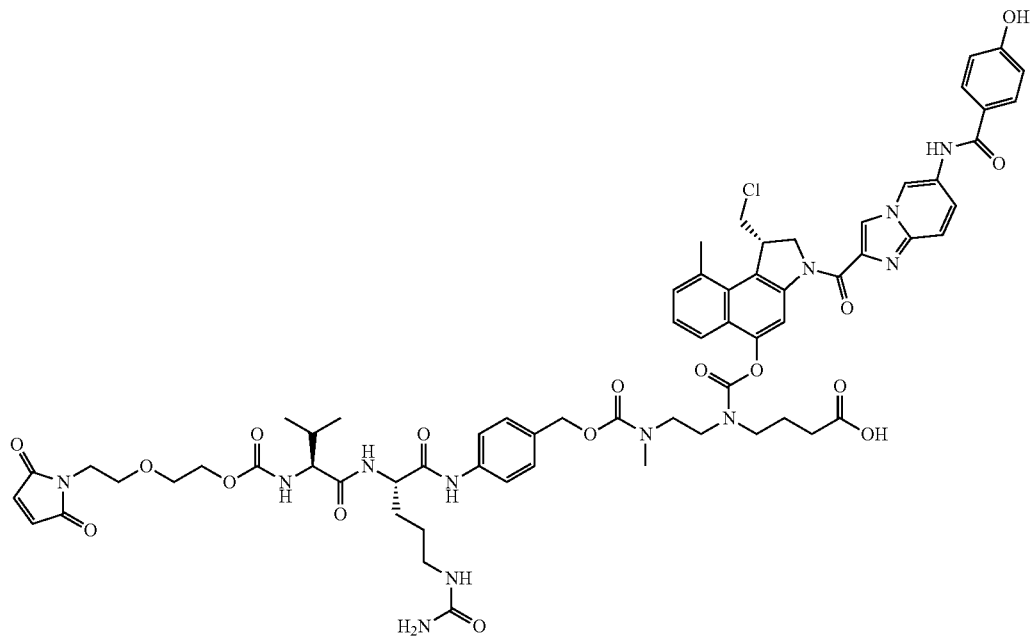 [SMILES: Cc1cccc2c(OC(=O)N(CCCC(=O)O)CCN(C)C(=O)OCc3ccc(NC(=O)[C@H](CCCNC(N)=O)NC(=O)[C@@H](NC(=O)OCCOCCN4C(=O)C=CC4=O)C(C)C)cc3)cc3c(c12)[C@H](CCl)CN3C(=O)c1cc2cc(NC(=O)c3ccc(O)cc3)cnc2[nH]1]
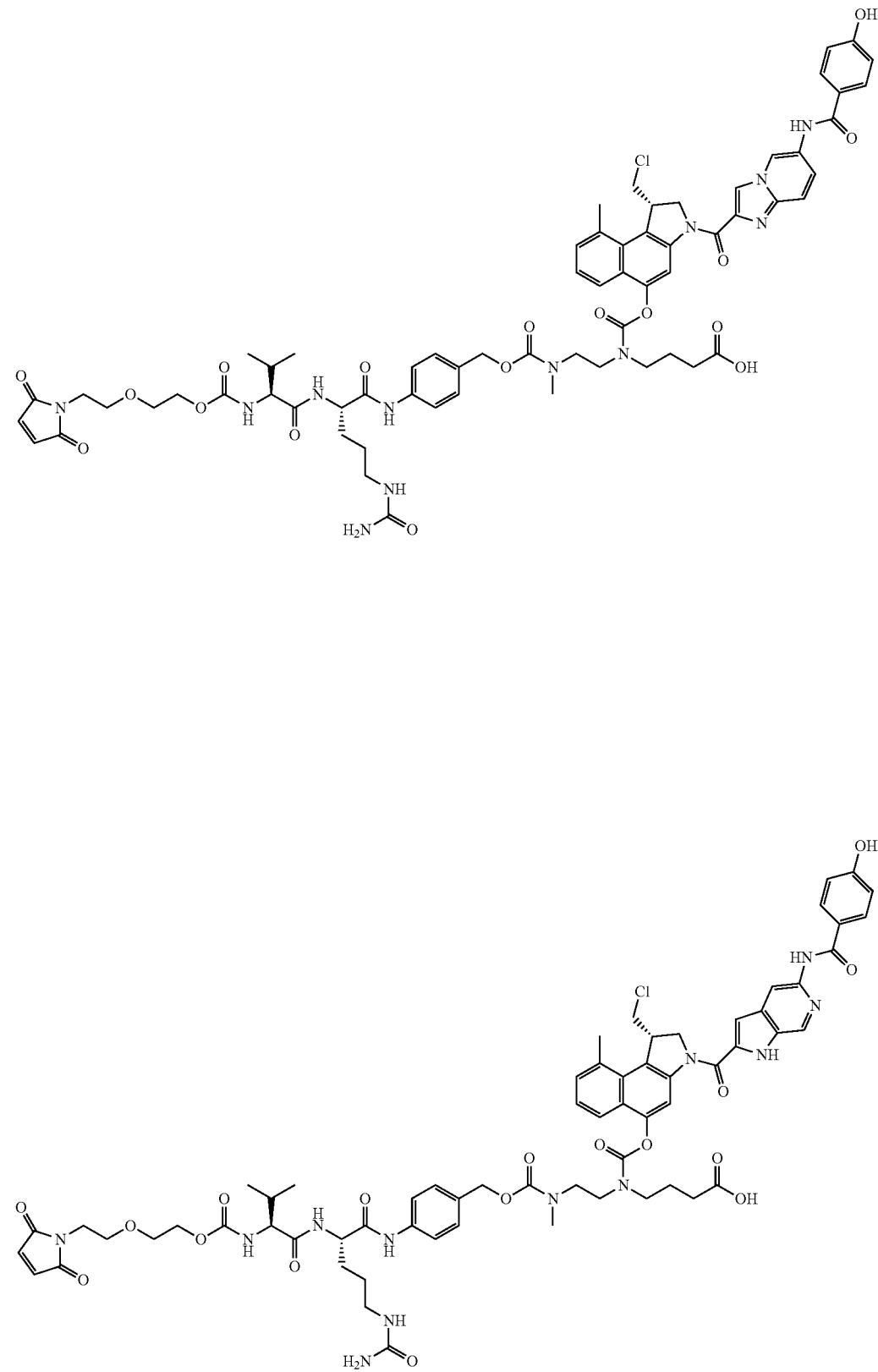

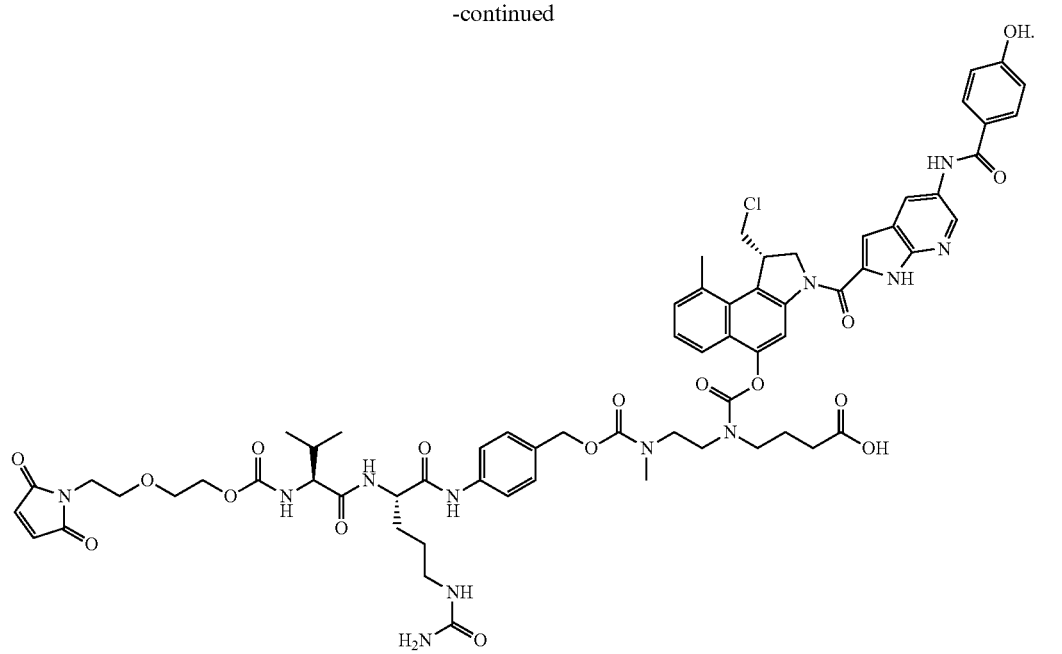
In another embodiment, a compound of formula (IV) is selected from
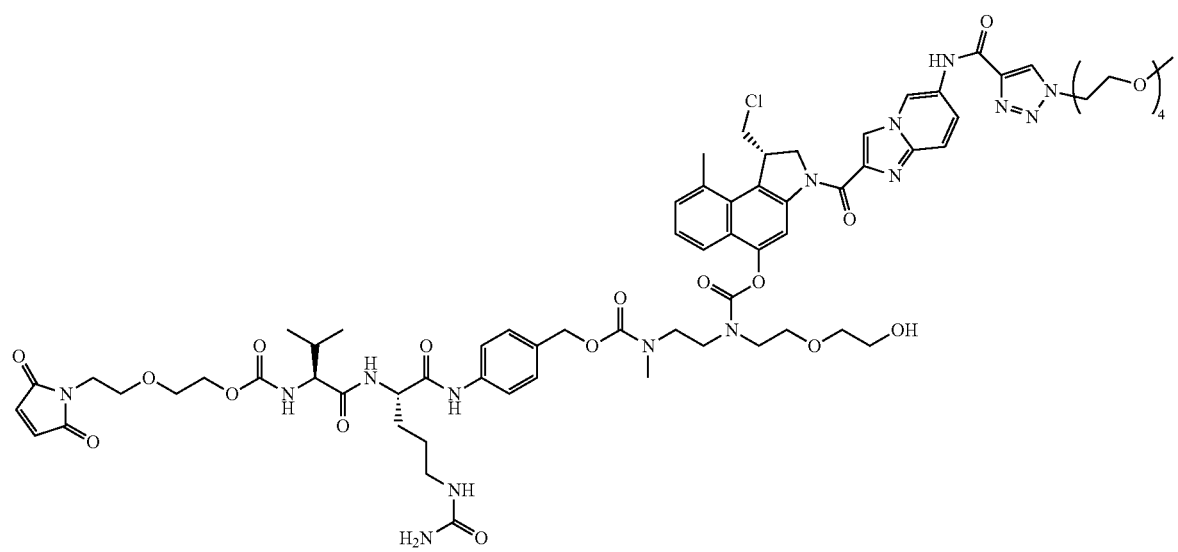

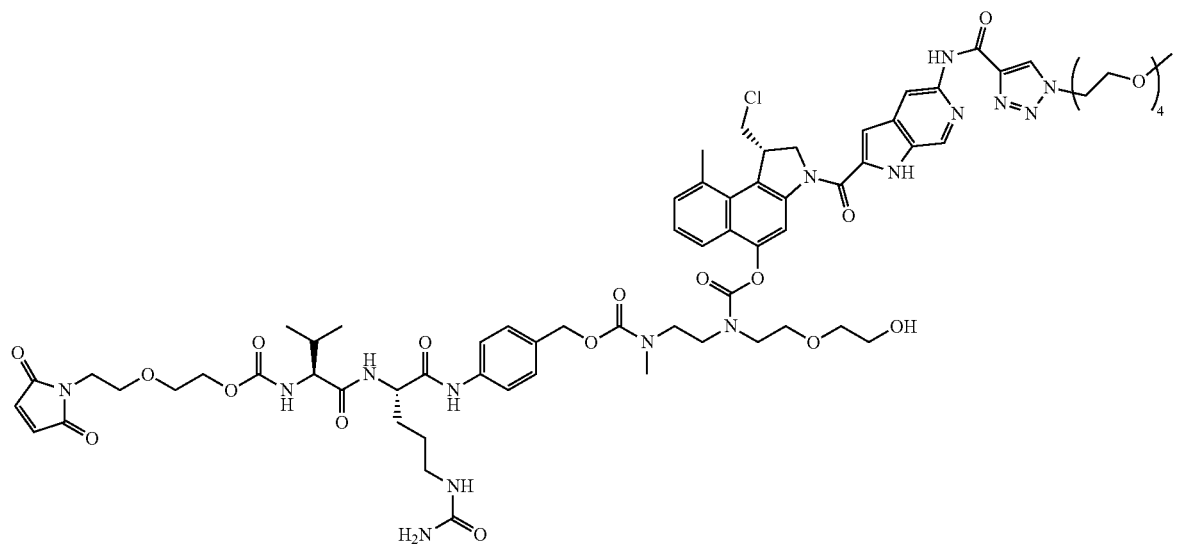
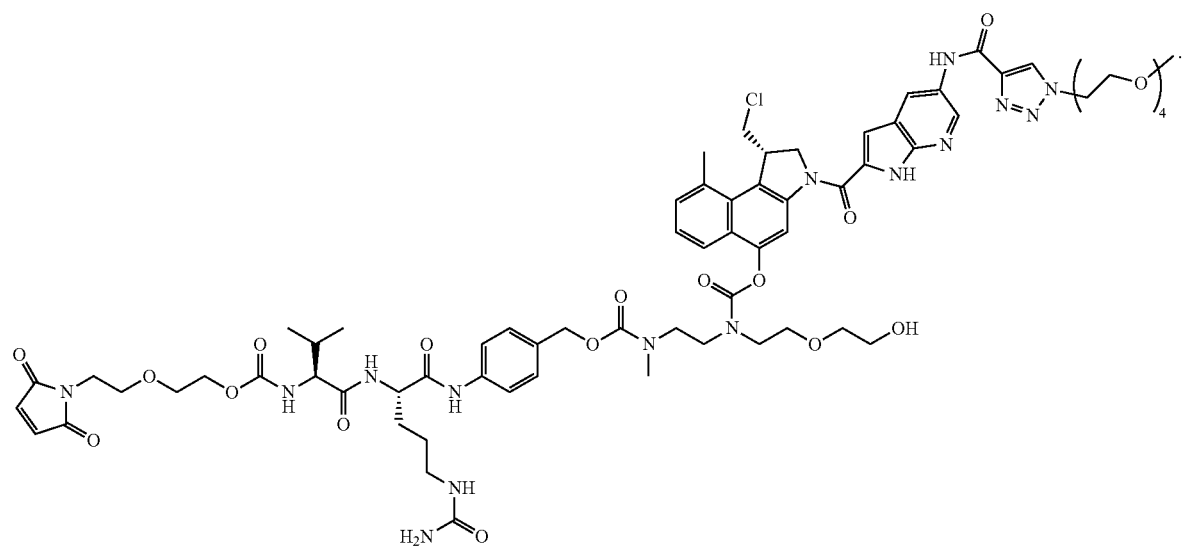

In another embodiment, a compound of formula (IV) is selected from
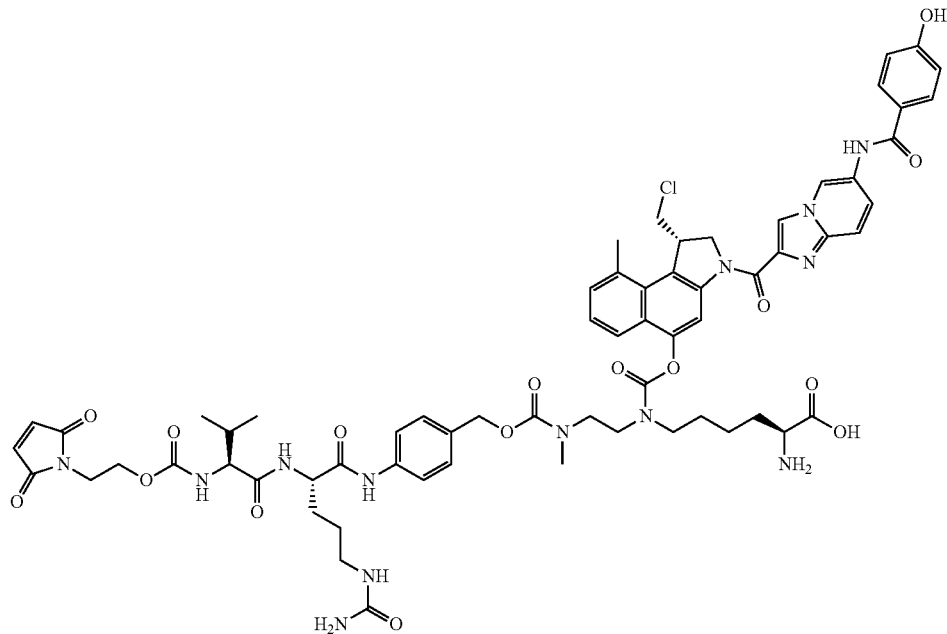 [SMILES: Cc1cccc2c(OC(=O)N(CCCC[C@H](N)C(=O)O)CCN(C)C(=O)OCc3ccc(NC(=O)[C@H](CCCNC(N)=O)NC(=O)[C@@H](NC(=O)OCCN4C(=O)C=CC4=O)C(C)C)cc3)cc3c(c12)[C@H](CCl)CN3C(=O)c1cc2cc(NC(=O)c3ccc(O)cc3)cnc2[nH]1]
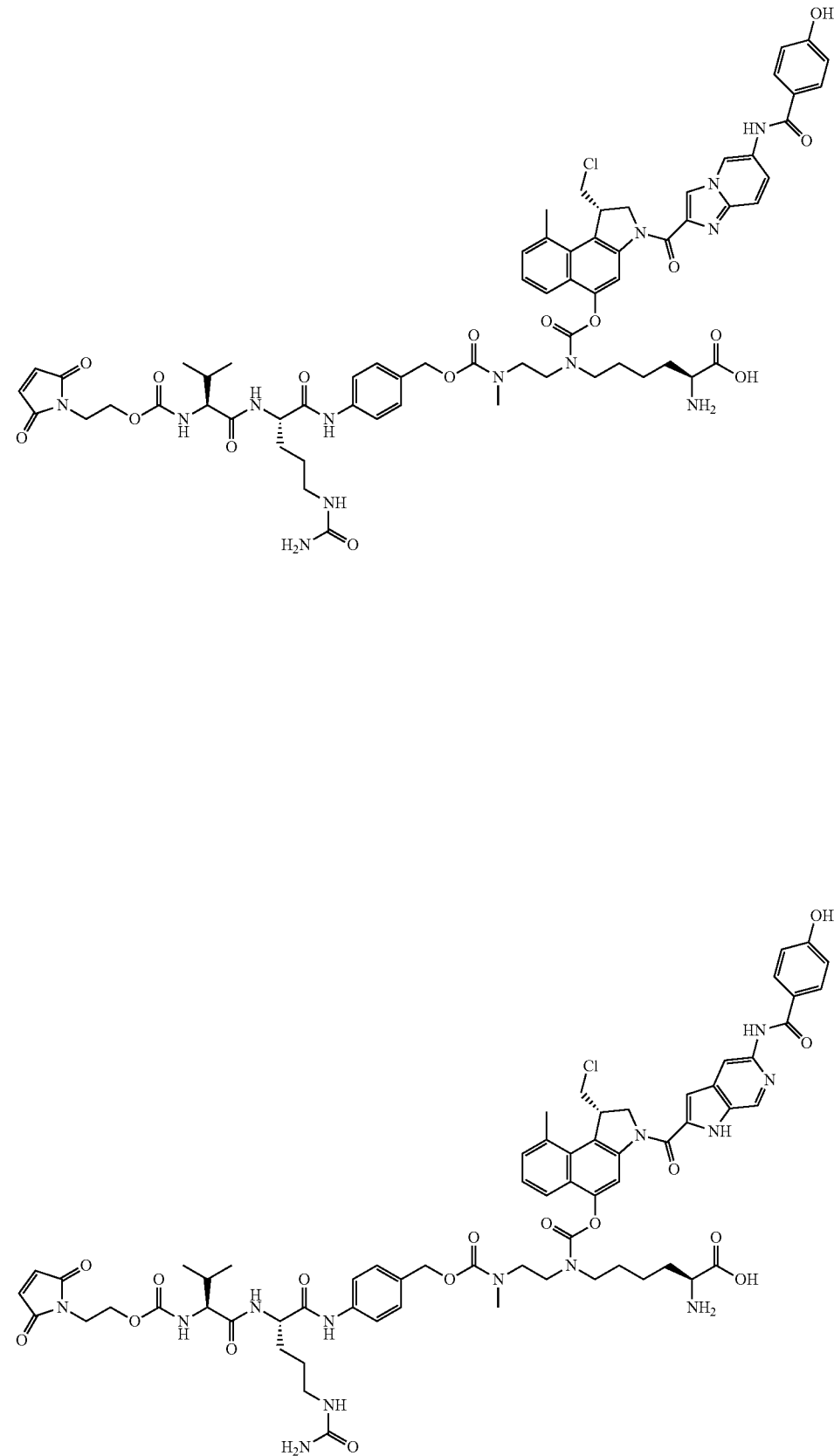

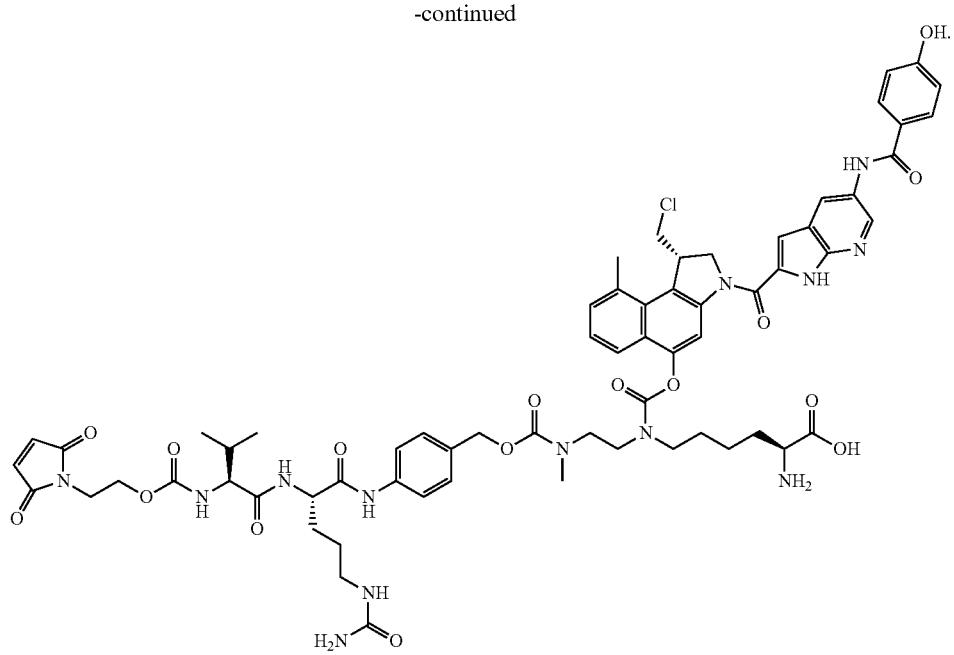
In another embodiment, a compound of formula (IV) is selected from
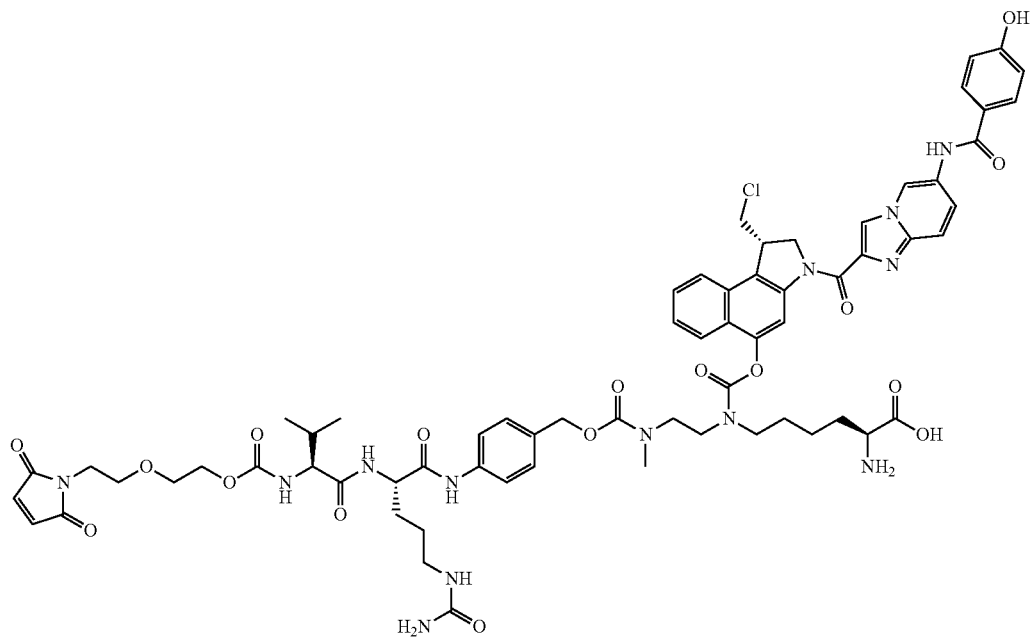

-continued
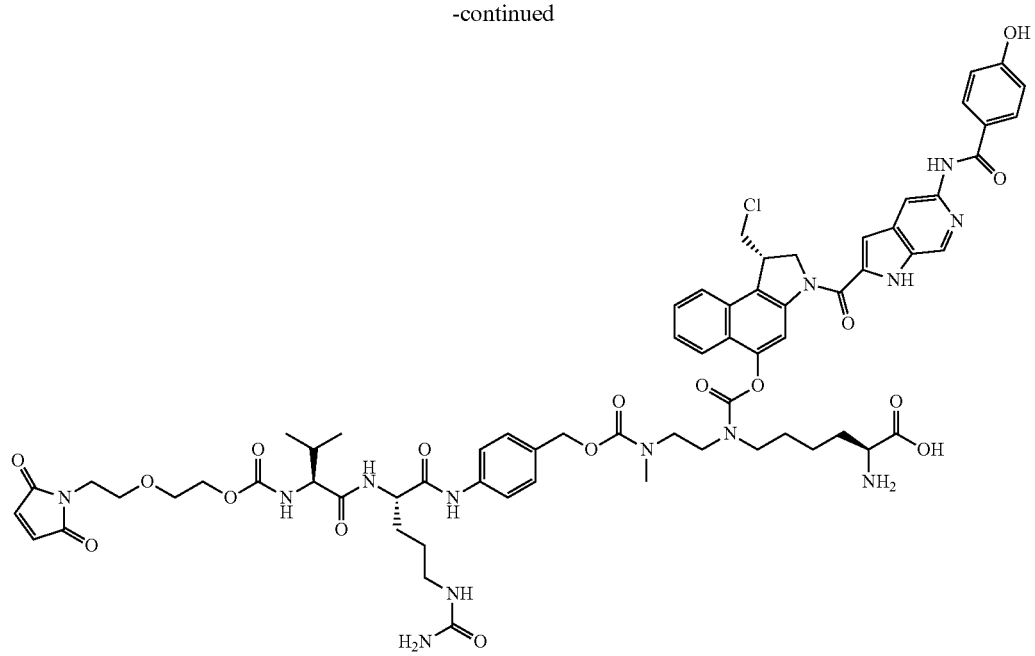
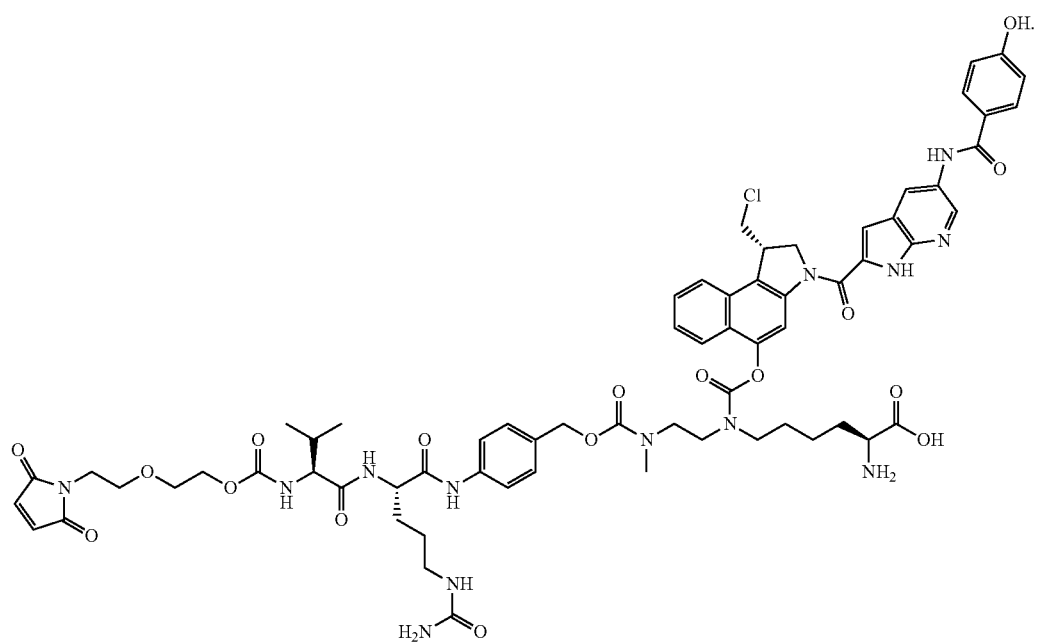 [SMILES: CC(C)[C@H](NC(=O)OCCOCCN1C(=O)C=CC1=O)C(=O)N[C@@H](CCCNC(N)=O)C(=O)Nc1ccc(COC(=O)N(C)CCN(CCCC[C@H](N)C(=O)O)C(=O)Oc2cc3c(c4ccccc24)[C@H](CCl)CN3C(=O)c2cc3cc(NC(=O)c4ccc(O)cc4)cnc3[nH]2)cc1]

In another embodiment, a compound of formula (IV) is selected from
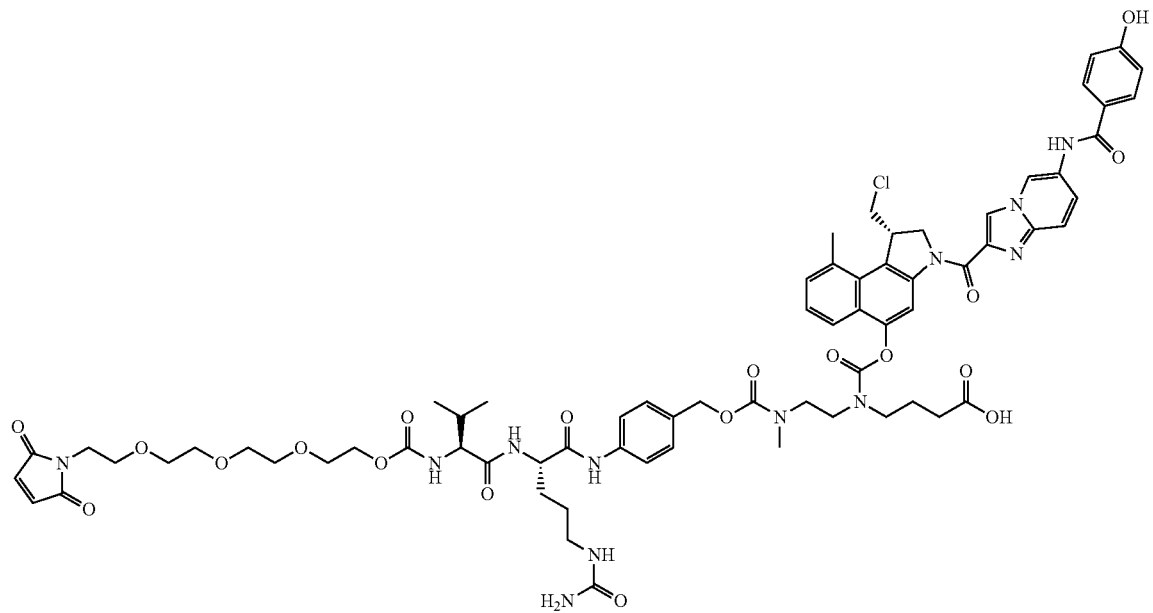
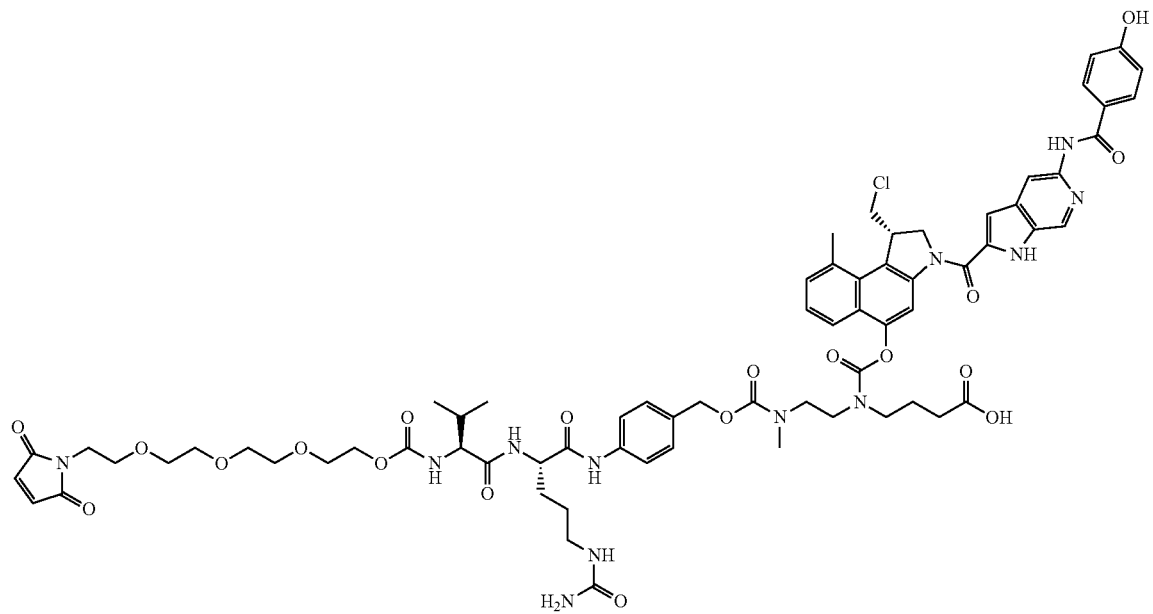 [SMILES: Cc1cccc2c(OC(=O)N(CCCC(=O)O)CCN(C)C(=O)OCc3ccc(NC(=O)[C@H](CCCNC(N)=O)NC(=O)[C@@H](NC(=O)OCCOCCOCCOCCN4C(=O)C=CC4=O)C(C)C)cc3)cc3c(c12)[C@H](CCl)CN3C(=O)c1cc2cc(NC(=O)c3ccc(O)cc3)cnc2[nH]1]

-continued
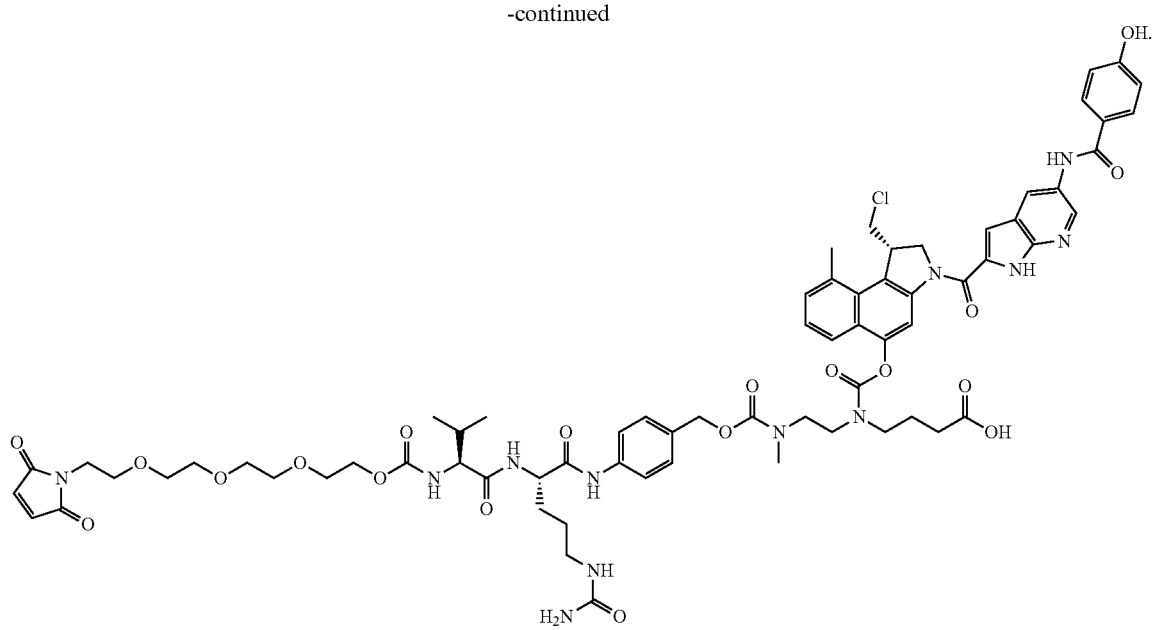
In another embodiment, a compound of formula (IV) is selected from
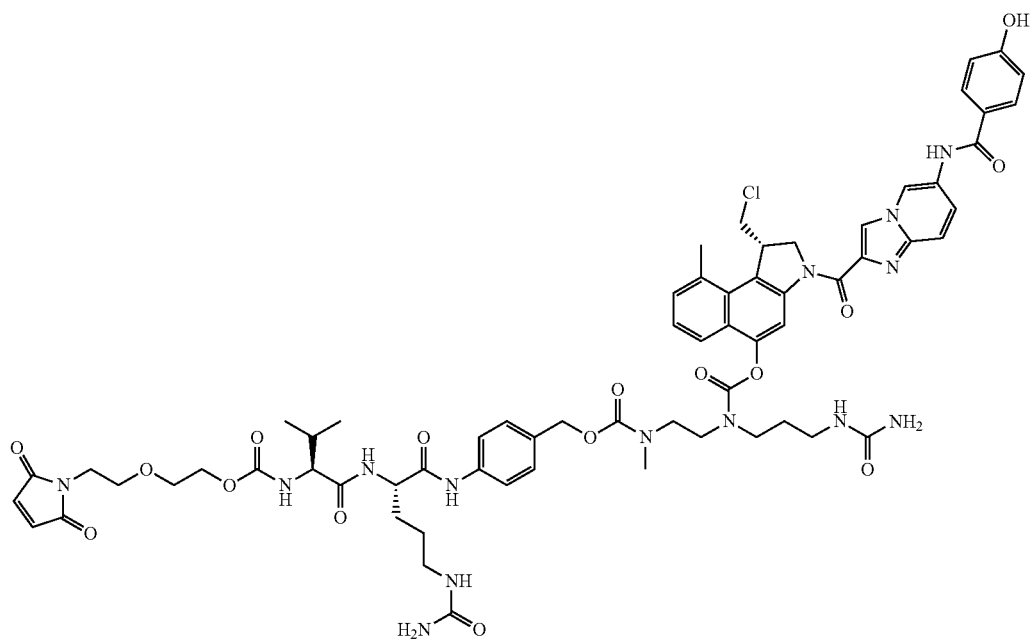

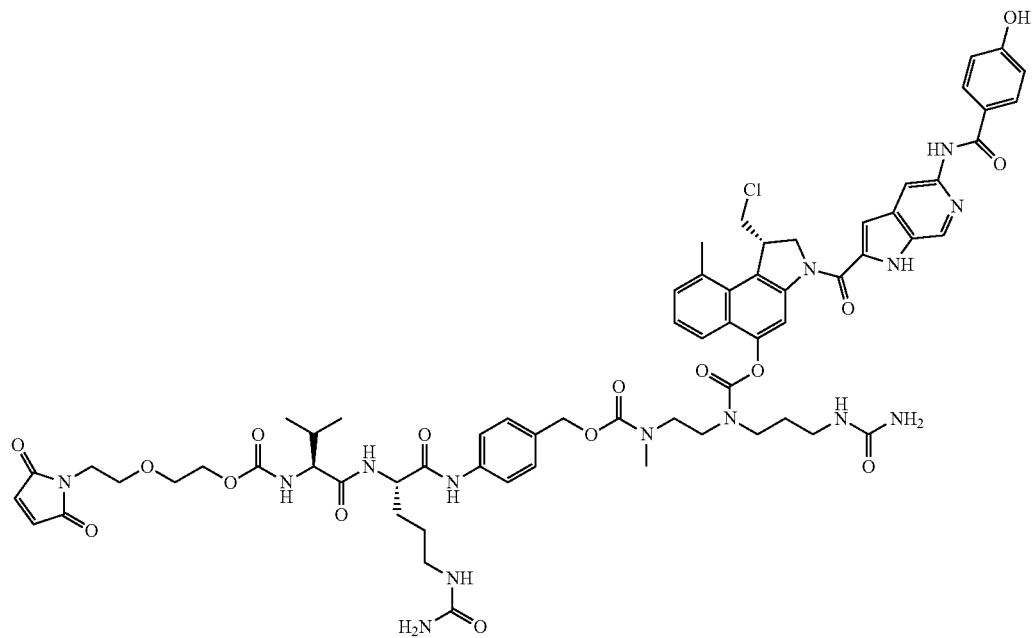
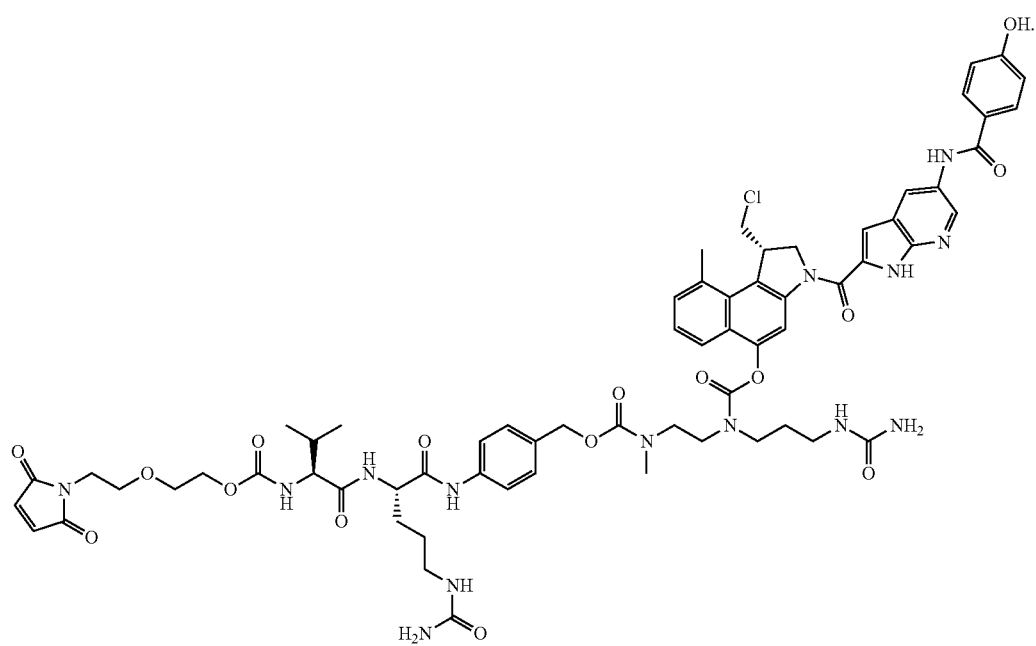 [SMILES: Cc1cccc2c(OC(=O)N(CCCNC(N)=O)CCN(C)C(=O)OCc3ccc(NC(=O)[C@H](CCCNC(N)=O)NC(=O)[C@@H](NC(=O)OCCOCCN4C(=O)C=CC4=O)C(C)C)cc3)cc3c(c12)[C@H](CCl)CN3C(=O)c1cc2cc(NC(=O)c3ccc(O)cc3)cnc2[nH]1]

In another embodiment, a compound of formula (IV) is selected from
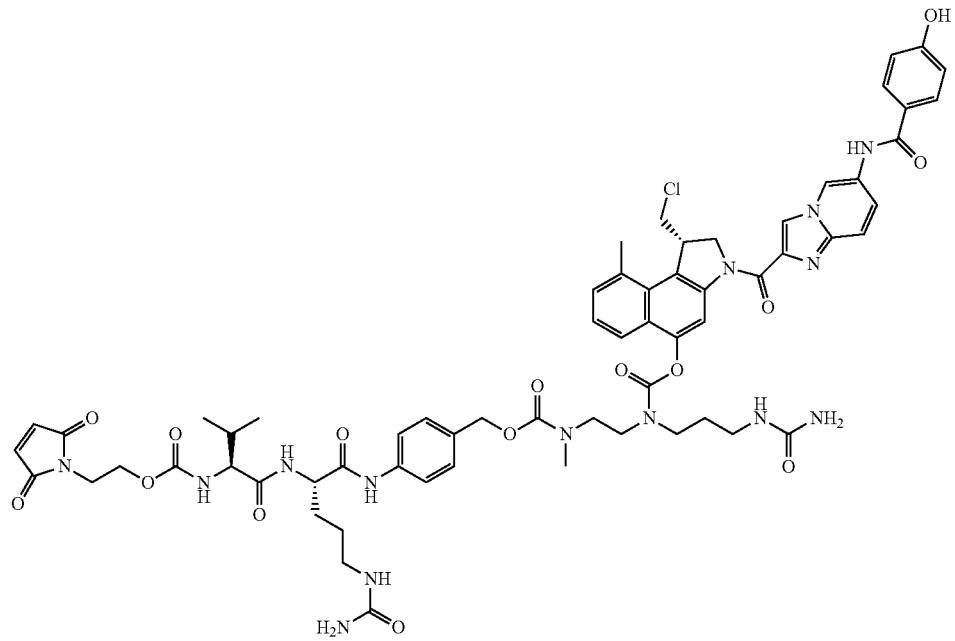
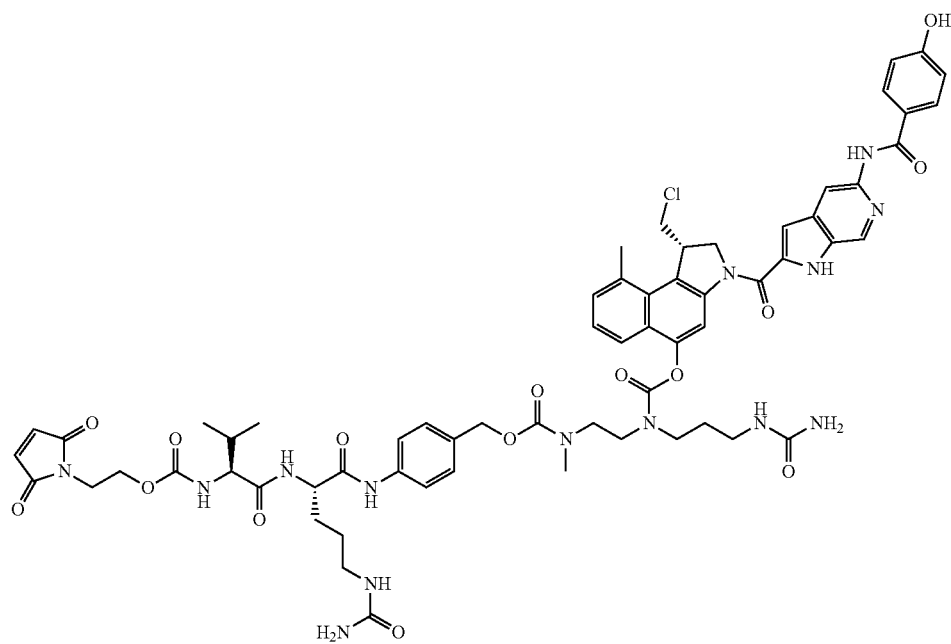 [SMILES: Cc1cccc2c(OC(=O)N(CCCNC(N)=O)CCN(C)C(=O)OCc3ccc(NC(=O)[C@H](CCCNC(N)=O)NC(=O)[C@@H](NC(=O)OCCN4C(=O)C=CC4=O)C(C)C)cc3)cc3c(c12)[C@H](CCl)CN3C(=O)c1cc2cc(NC(=O)c3ccc(O)cc3)cnc2[nH]1]

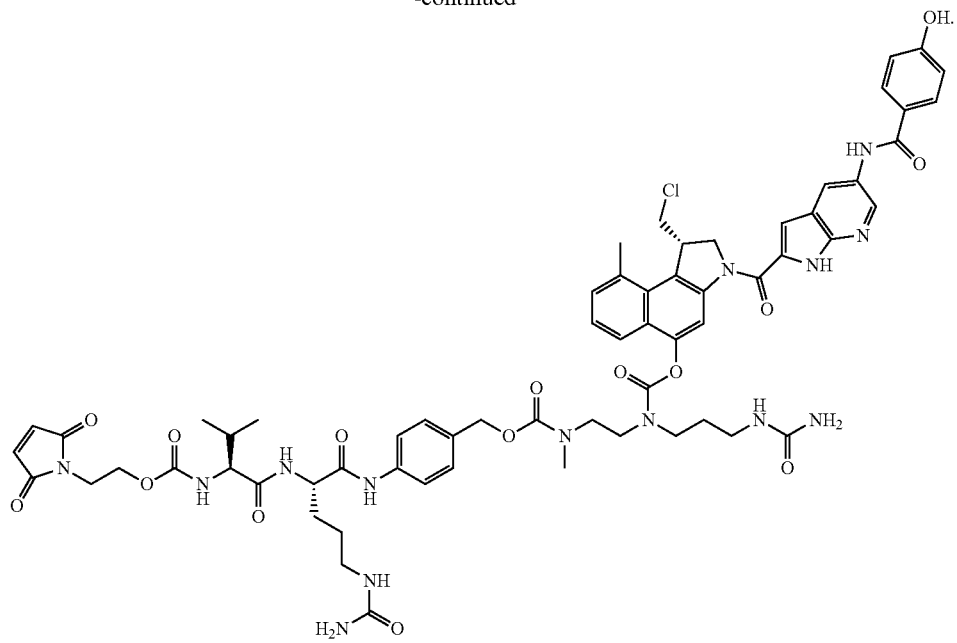
In another embodiment, a compound of formula (IV) is selected from
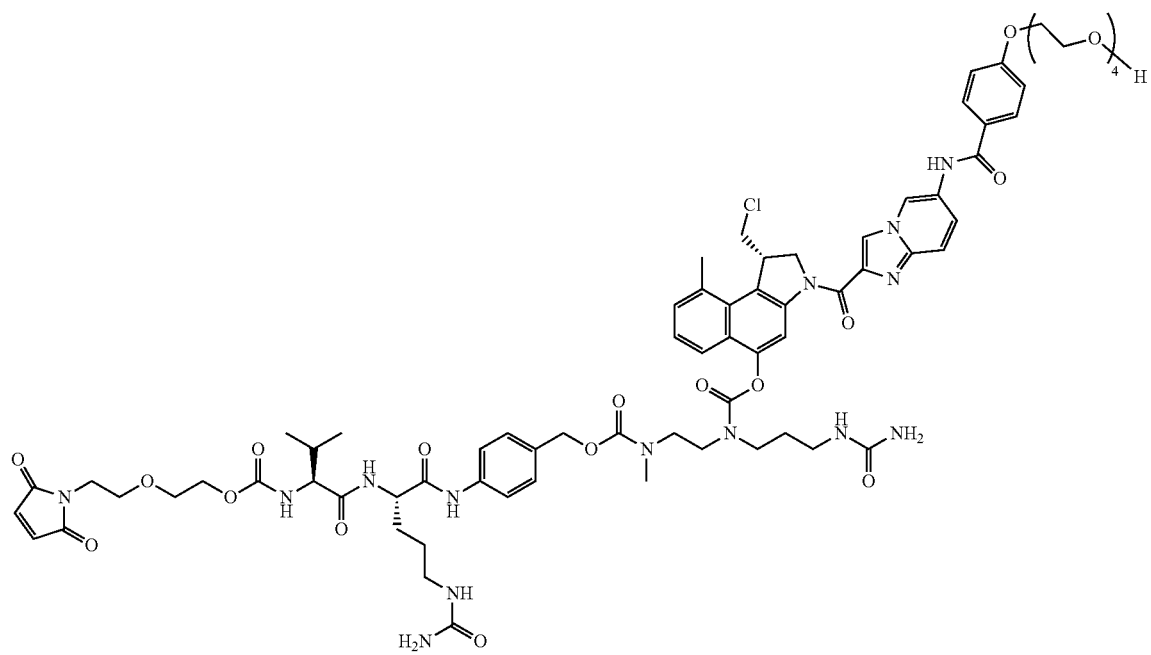

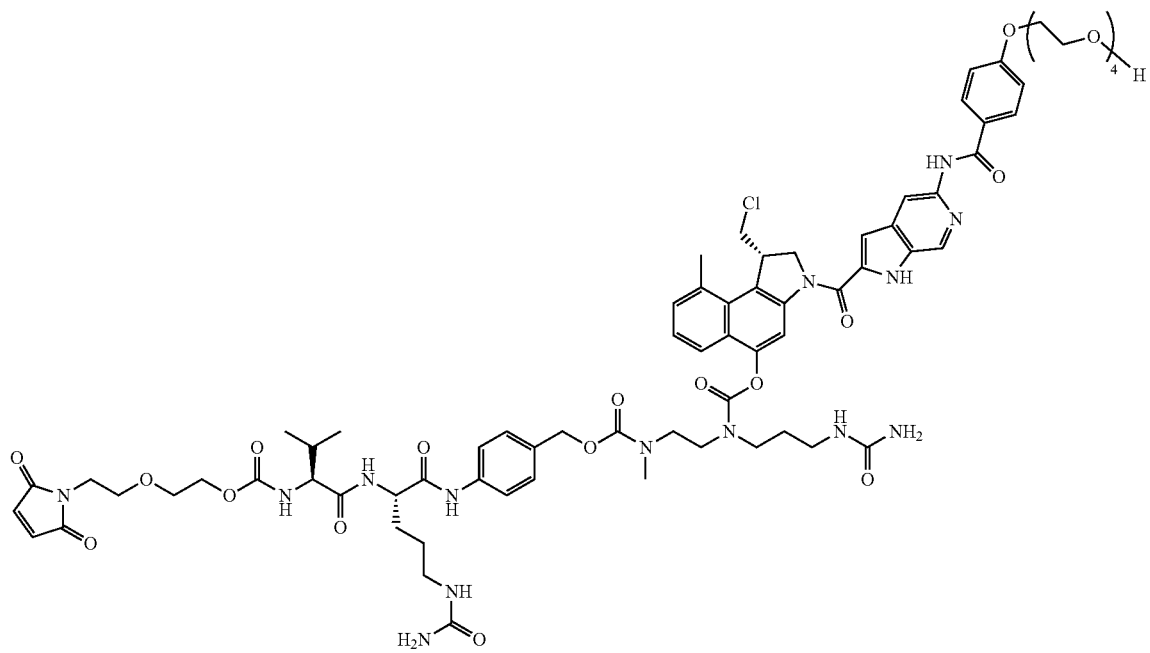
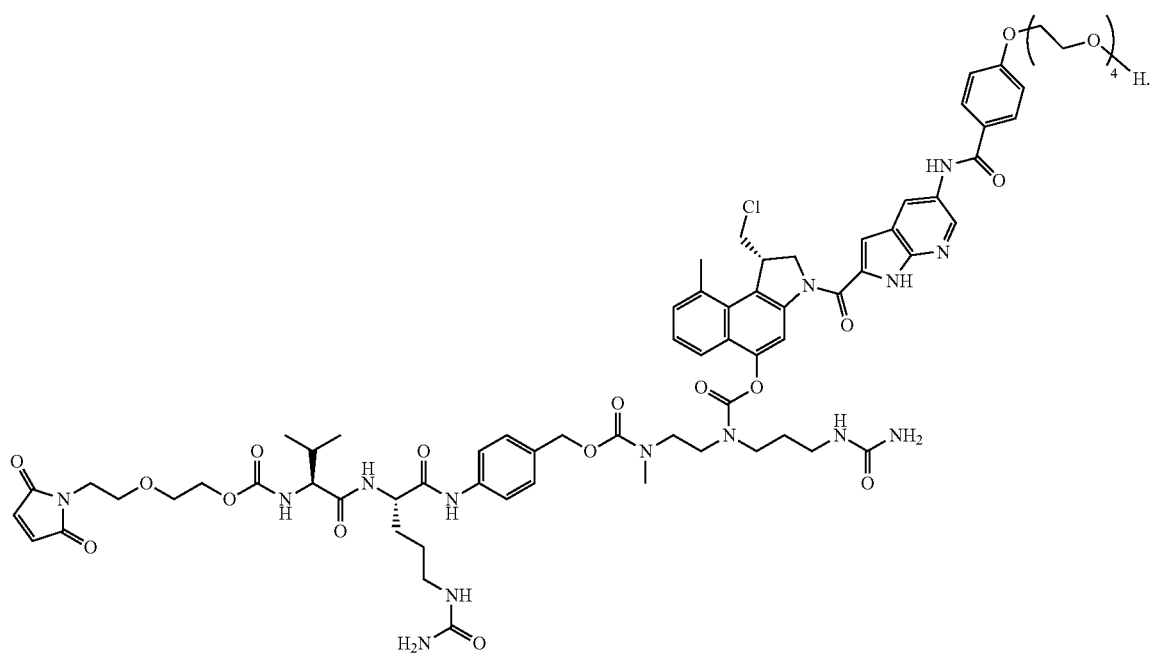

In another embodiment, a compound of formula (I) is selected from
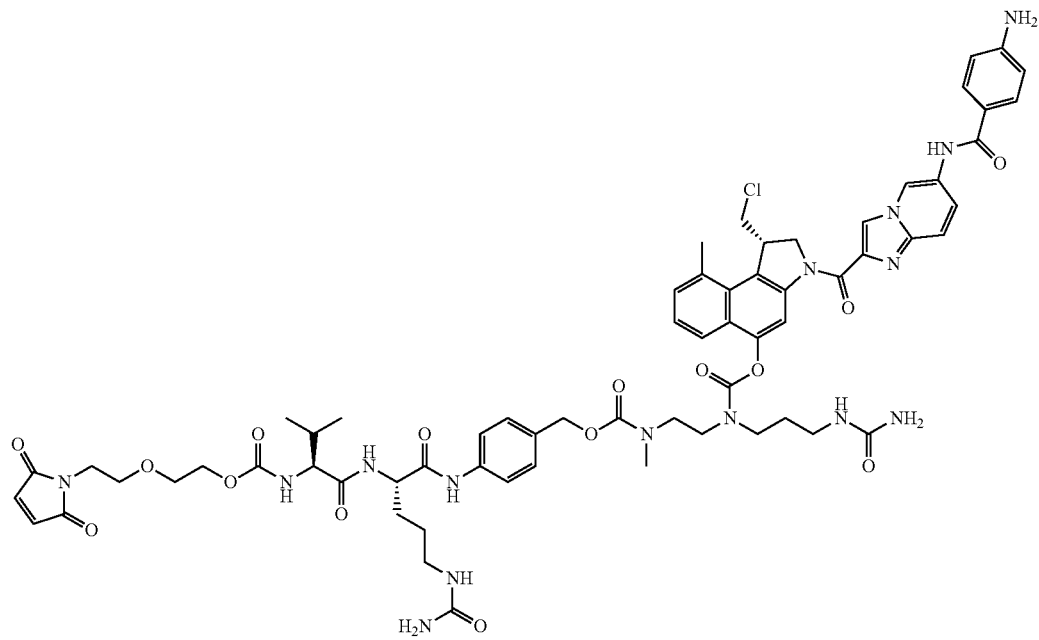 [SMILES: Cc1cccc2c(OC(=O)N(CCCNC(N)=O)CCN(C)C(=O)OCc3ccc(NC(=O)[C@H](CCCNC(N)=O)NC(=O)[C@@H](NC(=O)OCCOCCN4C(=O)C=CC4=O)C(C)C)cc3)cc3c(c12)[C@H](CCl)CN3C(=O)c1cc2cc(NC(=O)c3ccc(N)cc3)cnc2[nH]1]
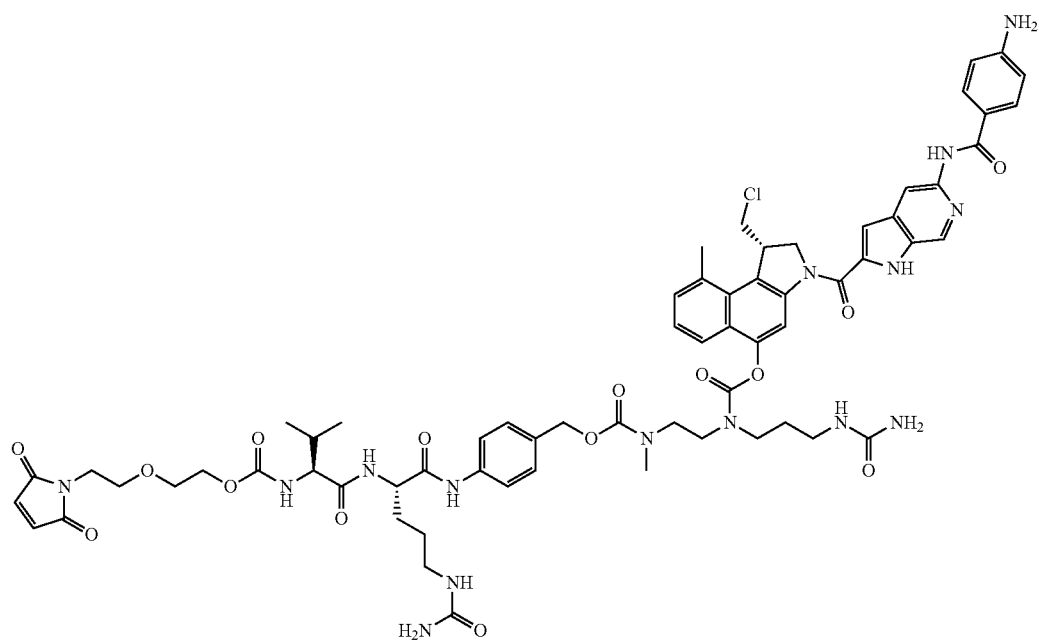

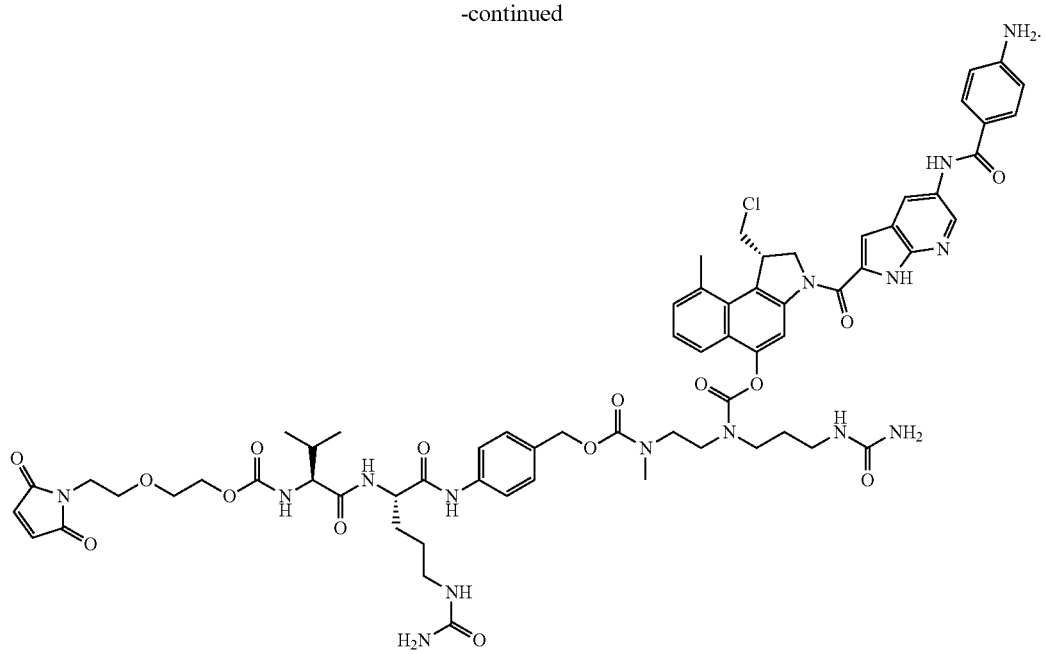
In another embodiment, a compound of formula (IV) is selected from
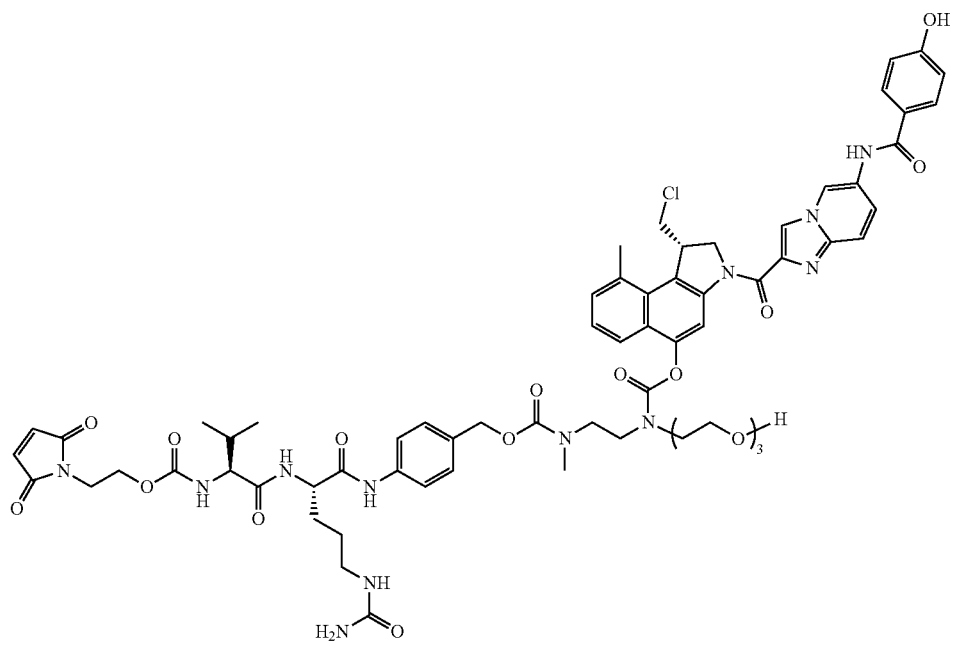

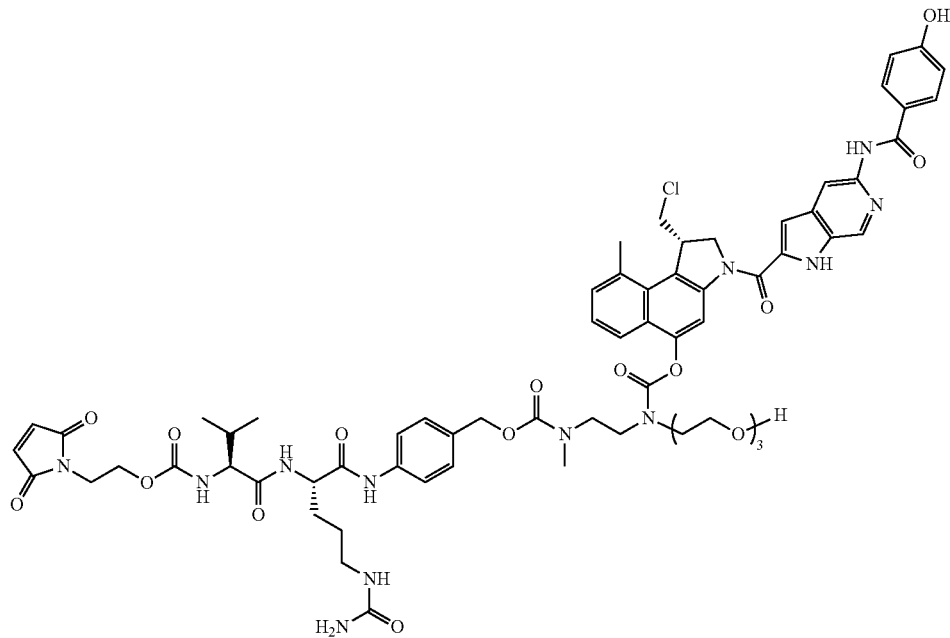
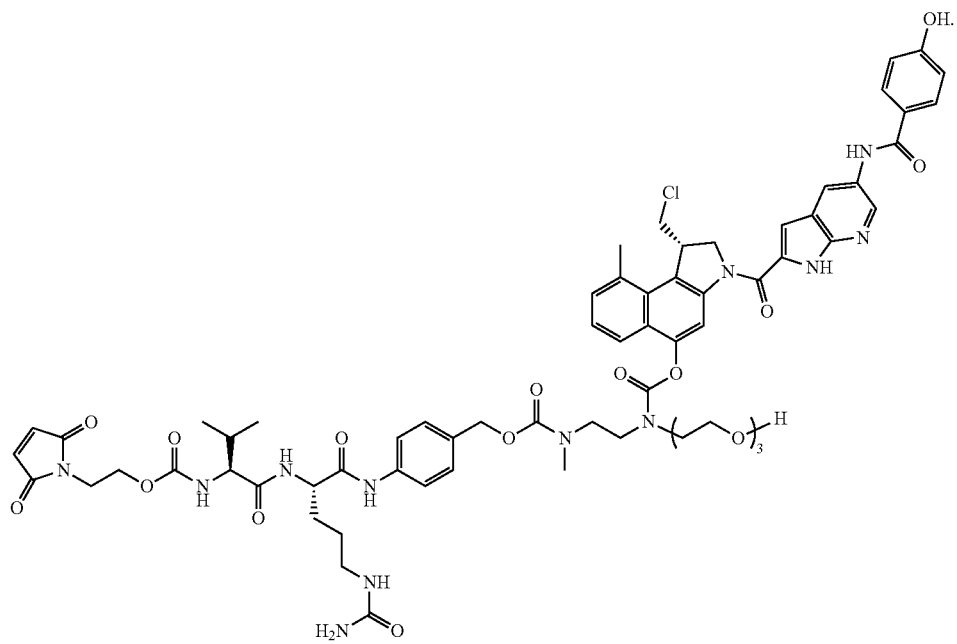

In another embodiment, a compound of formula (IV) is selected from
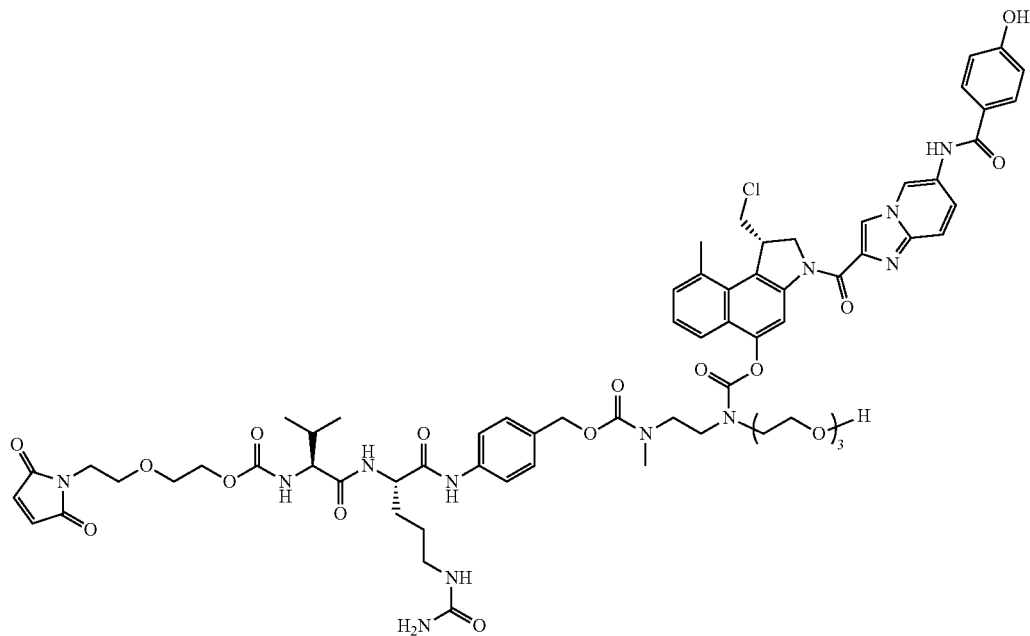
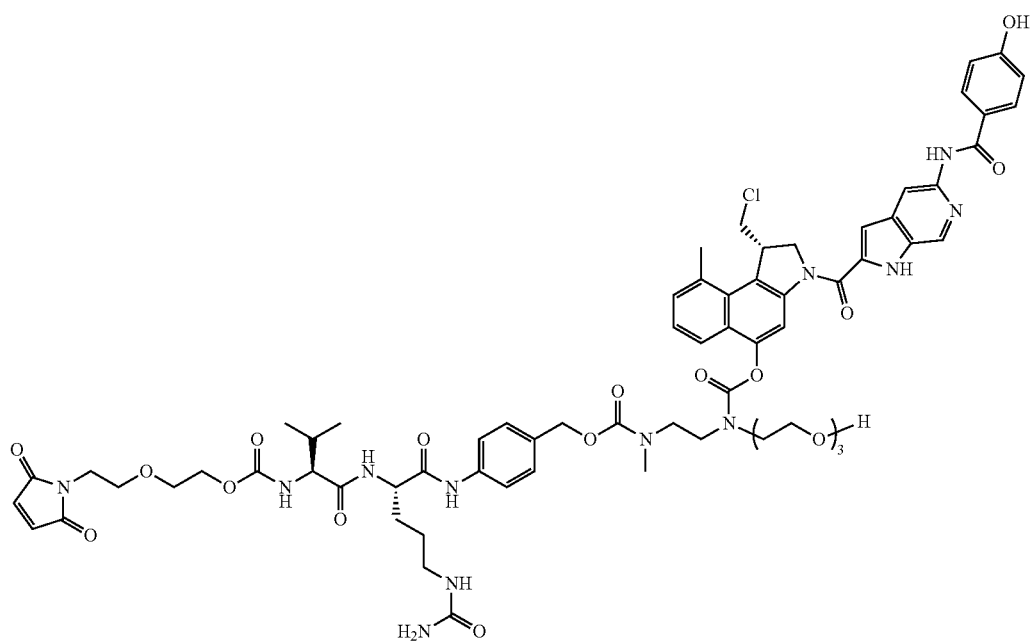

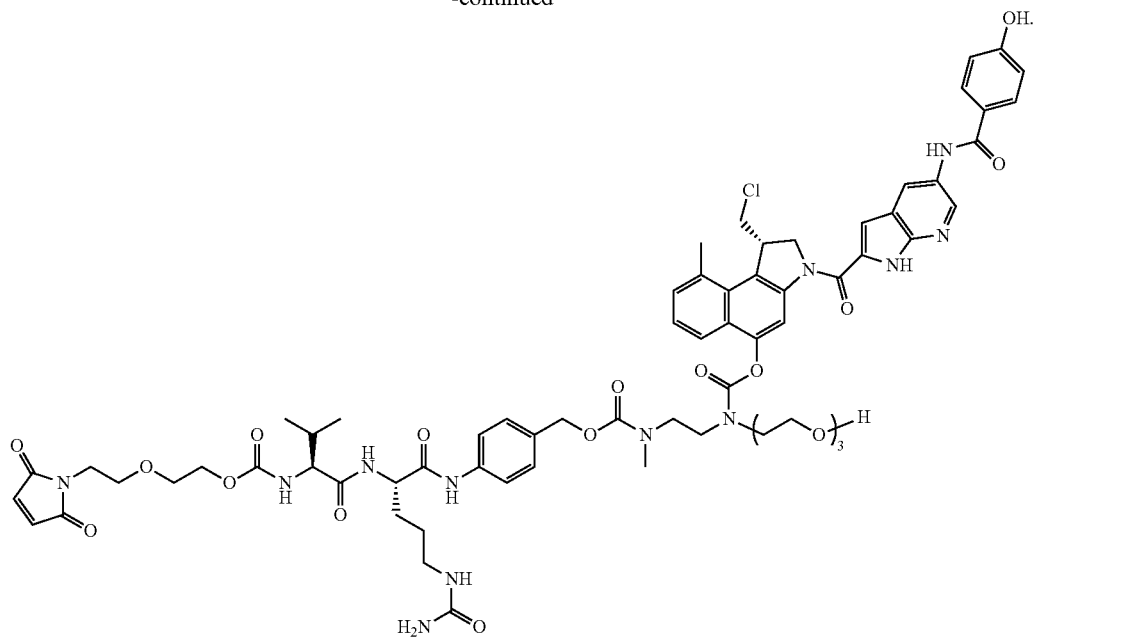
In another embodiment, a compound of formula (IV) is selected from
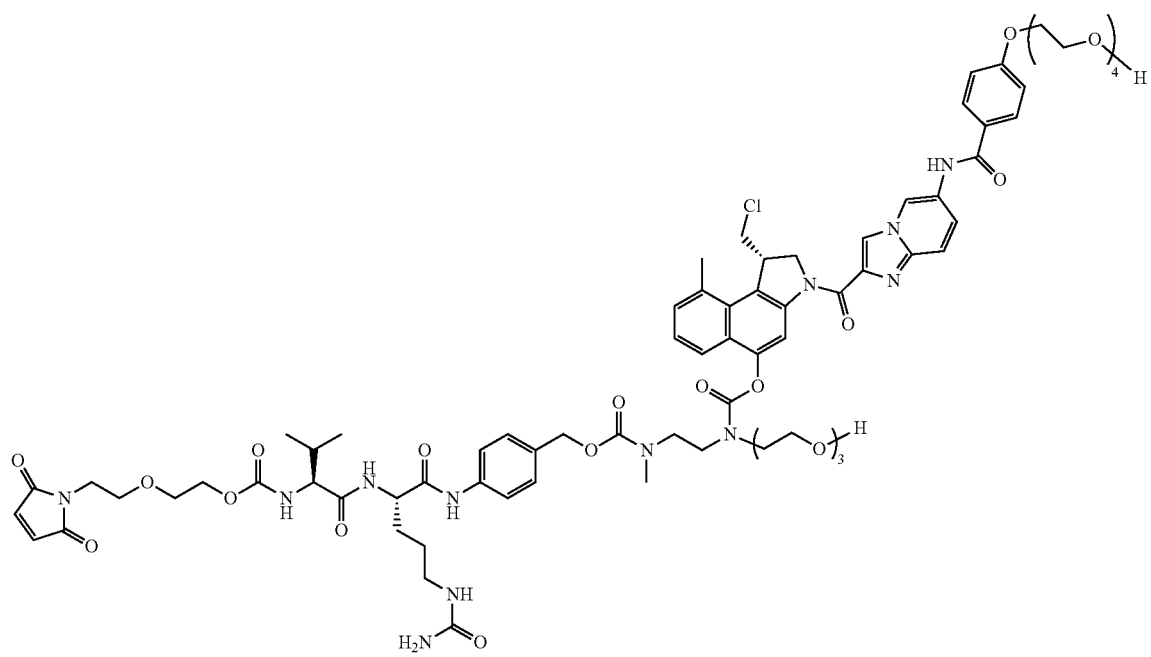

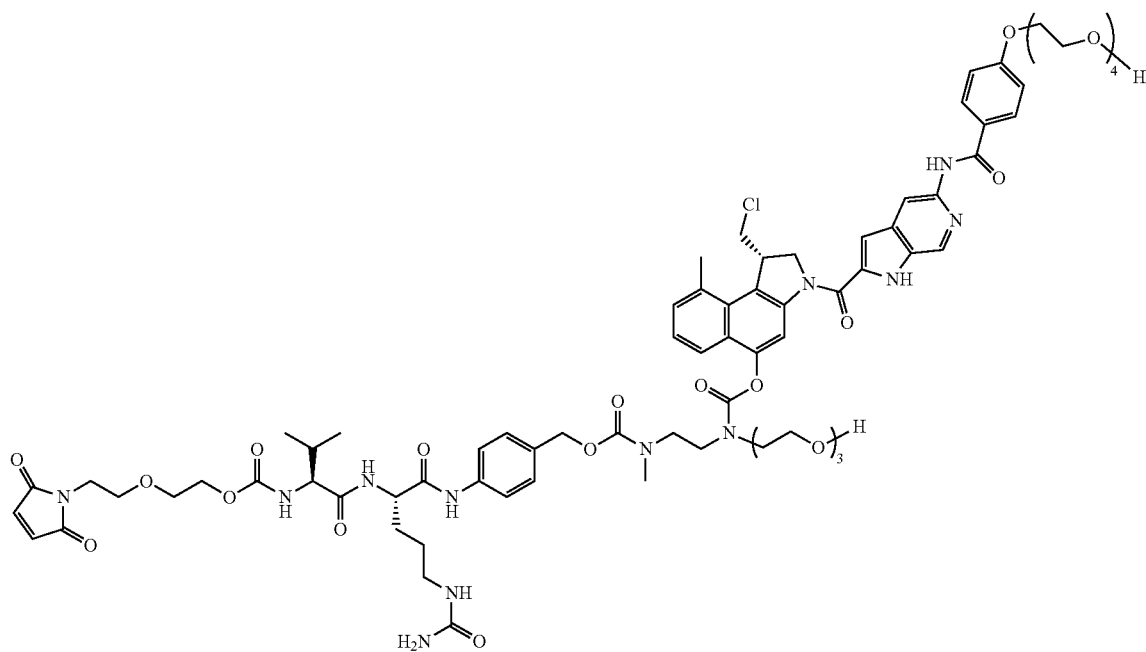
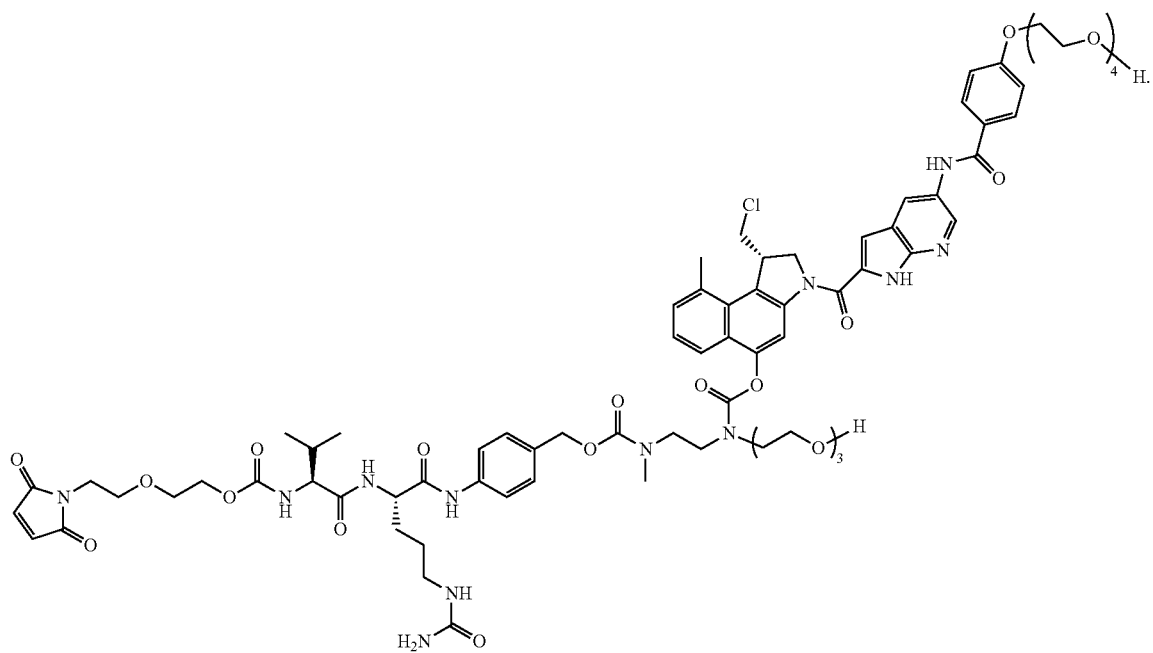

In another embodiment, a compound of formula (IV) is selected from
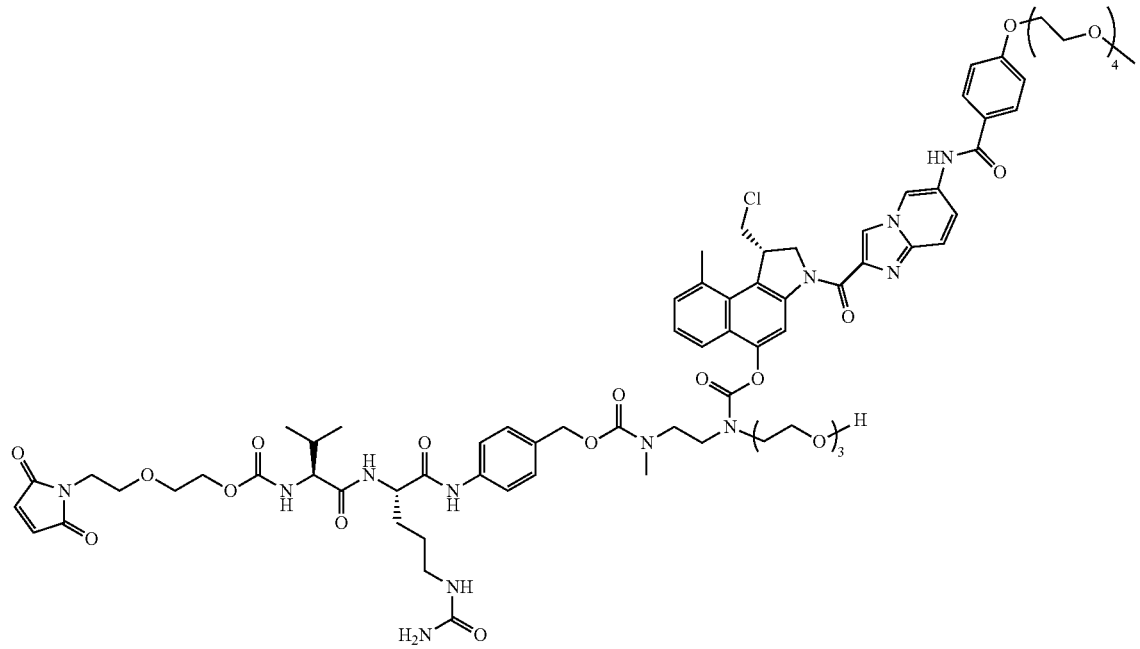
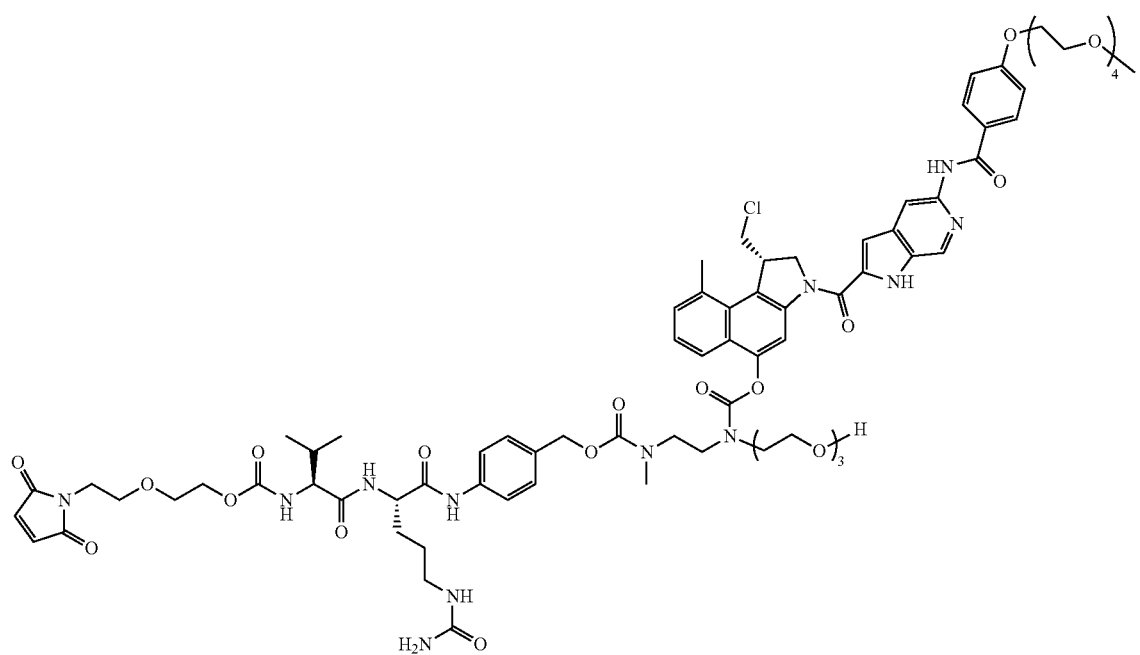

-continued

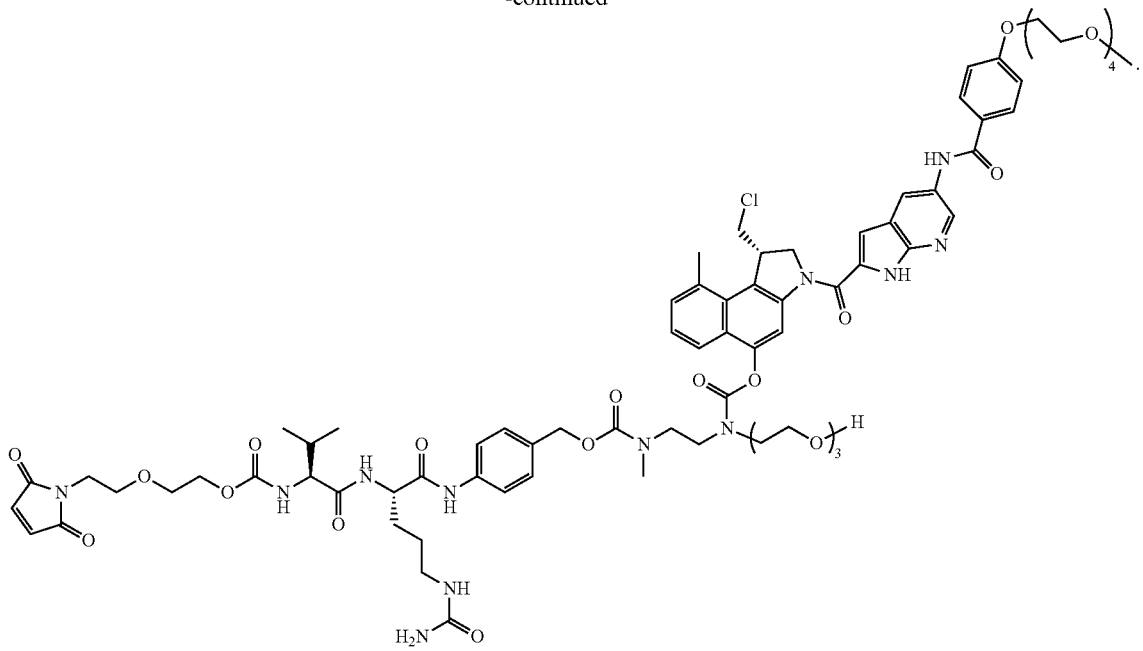

Synthesis of Compounds of the Invention

Compounds of formulae (I)-(IV) and (VIII) can be conveniently prepared in a way for some part analogous to compounds reported in WO 01/83448, WO 02/083180, WO 2004/043493, WO 2007/018431, WO 2007/089149, WO 2009/017394, and WO2010/062171. Further representative synthetic protocols can be found in the Examples.

In one embodiment, a compound of formula (I) or (II) is used to prepare a compound of formula (III). In another embodiment, a compound of formula (I) or (II) is used to prepare a compound of formula (IV). In another embodiment, a compound of formula (IV) is used to prepare a compound of formula (III). In another embodiment, a compound of formula (III) wherein $V^1$ is a protecting group is used to prepare another compound of formula (III) wherein $V^1$ is an in vivo cleavable/transformable moiety. In yet another embodiment, a compound of formula (VIII) is used to prepare a compound of formula (IV). In yet another embodiment, a compound of formula (VIII) is used to prepare a compound of formula (III), optionally via a compound of formula (IV).

Uses, Methods, and Compositions

In one aspect, this invention relates to use of a compound of formula (I) or (II) for the preparation of a compound of formula (III).

In another aspect, this invention relates to use of a compound of formula (IV) for the preparation of a compound of formula (III).

In yet another aspect, this invention relates to use of a compound of formula (I) or (II) for the preparation of a compound of formula (IV).

In yet another aspect, this invention relates to use of a compound of formula (VIII) for the preparation of a compound of formula (IV).

In yet another aspect, this invention relates to use of a compound of formula (VIII) for the preparation of a compound of formula (III), optionally via a compound of formula (III).

In yet another aspect, this invention relates to use of a compound of formula (VIII) for the preparation of conjugates and linker-agent conjugates similar to compounds of formulae (III) and (IV) in which the Z moiety is a therapeutic or diagnostic moiety different from a compound of formula (I), (II), (I'), or (II'), or a promoiety-containing derivative thereof.

In yet another aspect, this invention relates to use of a compound of formula (III) wherein $V^1$ is a protecting group for the preparation of another compound of formula (III) wherein $V^1$ is an in vivo cleavable/transformable moiety.

In yet another aspect, the invention relates to the use of any of the compounds defined hereinabove for the manufacture of a pharmaceutical composition for the treatment of a mammal being in need thereof. In one embodiment, the invention relates to the use of any of the compounds defined hereinabove for the manufacture of a pharmaceutical composition for the treatment of a tumor in a mammal. In another embodiment, the invention relates to the use of any of the compounds defined hereinabove for the manufacture of a pharmaceutical composition for the prevention of a tumor in a mammal. The invention can also be worded as any of the compounds defined hereinabove for use in the treatment of a mammal being in need thereof, or for use in the treatment of a tumor in a mammal or for use in the prevention of a tumor in a mammal.

The invention also relates to any of the compounds defined hereinabove as a medicament or an active component or active substance in a medicament.

In a further aspect, the invention relates to a process for preparing a pharmaceutical composition containing a compound as defined hereinabove, to provide a solid or a liquid formulation for administration orally, topically, or by injection. Such a method or process at least comprises the step of mixing the compound with a pharmaceutically acceptable carrier.

In one embodiment, a compound of the invention is used to treat or prevent an illness characterized by undesired proliferation. In another embodiment, a compound of the invention is used to treat or prevent an illness characterized by undesired cell proliferation. In another embodiment, a compound of the invention is used to treat a tumor. In another embodiment, a compound of the invention is used to prevent a tumor. In yet another embodiment, a compound of the invention is used to treat or prevent an inflammatory disease. In yet another embodiment, a compound of the invention is used to treat or prevent an autoimmune disease. In yet another embodiment, a compound of the invention is used to treat or prevent a bacterial, viral, or microbial infection.

In a further embodiment, this invention relates to a method of treating a mammal having an illness characterized by undesired (cell) proliferation with a compound of this invention. In another embodiment, this invention relates to a method of treating a mammal carrying a tumor with a compound of this invention. In yet another embodiment, this invention relates to a method of treating a mammal having an inflammatory disease with a compound of this invention. In yet another embodiment, this invention relates to a method of treating a mammal having an autoimmune disease with a compound of this invention. In yet another embodiment, this invention relates to a method of treating a mammal having a bacterial, viral, or microbial infection with a compound of this invention.

In a further embodiment, the invention relates to a method of treating a mammal being in need thereof, whereby the method comprises the administration of a pharmaceutical composition comprising a compound of this invention to the mammal in a therapeutically effective dose.

In one embodiment, the invention relates to a method of treating or preventing a tumor in a mammal, whereby the method comprises the administration of a pharmaceutical composition comprising a compound of this invention to the mammal in a therapeutically effective dose. In another embodiment, the invention relates to a method of treating a tumor in a mammal, whereby the method comprises the administration of a pharmaceutical composition comprising a compound of this invention to the mammal in a therapeutically effective dose. In yet another embodiment, the invention relates to a method of treating a tumor in a human, whereby the method comprises the administration of a pharmaceutical composition comprising a compound of this invention to the human in a therapeutically effective dose.

In another embodiment, the invention relates to a method of treating or preventing an inflammatory disease in a mammal, whereby the method comprises the administration of a pharmaceutical composition comprising a compound of this invention to the mammal in a therapeutically effective dose.

In another embodiment, the invention relates to a method of treating or preventing an autoimmune disease in a mammal, whereby the method comprises the administration of a pharmaceutical composition comprising a compound of this invention to the mammal in a therapeutically effective dose.

In another embodiment, the invention relates to a method of treating or preventing a bacterial, viral, or microbial infection in a mammal, whereby the method comprises the administration of a pharmaceutical composition comprising a compound of this invention to the mammal in a therapeutically effective dose.

The invention also relates to pharmaceutical compositions comprising the compounds of the invention as defined hereinabove. A compound of the invention may be administered in purified form together with a pharmaceutical carrier as a pharmaceutical composition. The preferred form depends on the intended mode of administration and therapeutic application. The pharmaceutical carrier can be any compatible, nontoxic substance suitable to deliver the compounds of the invention to the patient. Pharmaceutically acceptable carriers are well known in the art and include, for example, aqueous solutions such as (sterile) water or physiologically buffered saline or other solvents or vehicles such as glycols, glycerol, oils such as olive oil or injectable organic esters, alcohol, fats, waxes, and inert solids. A pharmaceutically acceptable carrier may further contain physiologically acceptable compounds that act for example to stabilize or to increase the absorption of the compounds of the invention. Such physiologically acceptable compounds include, for example, carbohydrates, such as glucose, sucrose, or dextrans, antioxidants, such as ascorbic acid or glutathione, chelating agents, low molecular weight proteins, or other stabilizers or excipients. One skilled in the art would know that the choice of a pharmaceutically acceptable carrier, including a physiologically acceptable compound, depends, for example, on the route of administration of the composition. Pharmaceutically acceptable adjuvants, buffering agents, dispersing agents, and the like, may also be incorporated into the pharmaceutical compositions.

For oral administration, the active ingredient can be administered in solid dosage forms, such as capsules, tablets, and powders, or in liquid dosage forms, such as elixirs, syrups, and suspensions. Active component(s) can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate, and the like. Examples of additional inactive ingredients that may be added to provide desirable color, taste, stability, buffering capacity, dispersion, or other known desirable features are red iron oxide, silica gel, sodium lauryl sulfate, titanium dioxide, edible white ink, and the like. Similar diluents can be used to make compressed tablets. Both tablets and capsules can be manufactured as sustained release products to provide for continuous release of medication over a period of hours. Compressed tablets can be sugar-coated or film-coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

The compounds of the invention are however preferably administered parenterally. Preparations of the compounds of the invention for parenteral administration must be sterile. Sterilization is readily accomplished by filtration through sterile filtration membranes, optionally prior to or following lyophilization and reconstitution. The parenteral route for administration of compounds of the invention is in accord with known methods, e.g. injection or infusion by intravenous, intraperitoneal, intramuscular, intraarterial, or intralesional routes. The compounds of the invention may be administered continuously by infusion or by bolus injection. A typical composition for intravenous infusion could be made up to contain 100 to 500 ml of sterile 0.9% NaCl or 5% glucose optionally supplemented with a 20% albumin solution and 1 mg to 10 g of the compound of the invention, depending on the particular type of compound of the invention and its required dosing regime. Methods for preparing parenterally administrable compositions are well known in the art and described in more detail in various sources, including, for example, Remington's Pharmaceutical Science[17].

A compound of the invention may also be used in combination therapy, in which a compound of this invention is used in combination with one or more other therapeutic agents. Combination of two or more therapeutics may favorably affect treatment outcome. The agents may be administered either sequentially or concomitantly. Therefore, in one embodiment this invention relates to use of a compound of this invention or a pharmaceutical composition comprising a compound of this invention in combination therapy.

The invention is further exemplified by the following examples. These examples are for illustrative purposes only and are not intended to limit the scope of the invention.

EXAMPLES

Example 1: Synthesis of Boc-Protected Cyclization Spacers

Route A: Reductive amination

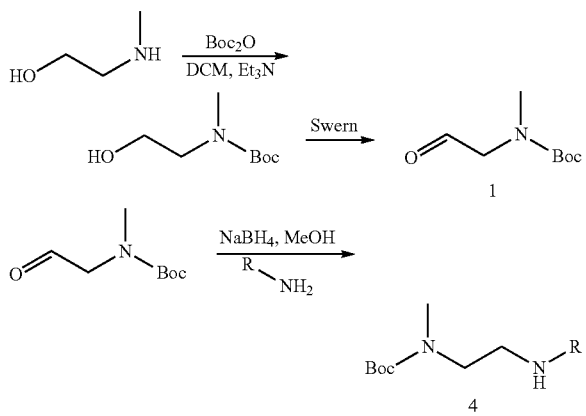

Route B: Alkylation

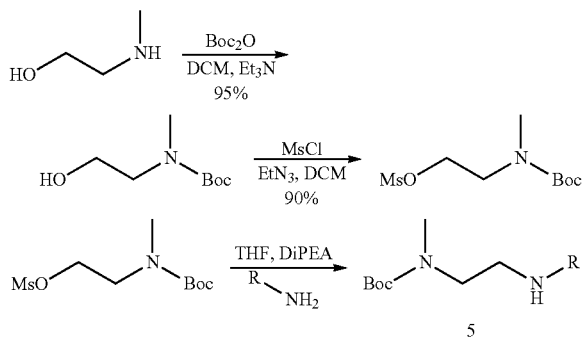

Route A

Synthesis of Compound 1:

7.5 ml (85 mmol) oxalyl chloride was dissolved in 200 ml DCM and cooled to T<−60° C. and 12.1 ml (171 mmol) DMSO in 10 ml DCM was added dropwise (T<−60° C.) and stirred an additional 10 min. 10.0 g (57 mmol) N-Boc-N-methylaminoethanol in 40 ml DCM were added dropwise (T<−60° C.) and stirred an additional 10 min. 40 ml (285 mmol) Et$_3$N was added dropwise followed by 50 ml DCM (T<−60° C.) and stirred for 30 min. The reaction mixture was warmed to 0° C. and washed with 3×100 ml water, 100 ml 0.5 M KHSO$_4$, 75 ml brine, dried with MgSO$_4$ and concentrated in vacuo. The product was purified by column chromatography (SiO$_2$, DCM/ethyl acetate, 1:0 to 9:1) to give 7.36 g (74%) of compound 1. $^1$H-NMR (300 MHz, CDCl$_3$): δ=1.42/1.46 (s, 9H, Boc), 2.93/2.96 (s, 3H, Me), 3.90/4.01 (s, 2H, CH$_2$), 9.60 (s, 1H, CHO). Z/E isomers.

General Procedure Reductive Amination:

1 mmol R-amine and 1 mmol compound 1 were stirred in 10 ml MeOH for 4 hrs. The reaction mixture was cooled in ice and 2 mmol sodium borohydride was added in portions and the mixture stirred at RT overnight. The mixture was concentrated and purified by column chromatography (SiO$_2$, DCM/MeOH, 1:0 to 1:1) to give N-Boc-N-Methyl-N′—R-diaminoethane.

Compound 4a, R═(CH$_2$CH$_2$O)$_2$H:

40% yield, $^1$H NMR (300 MHz, CDCl$_3$): δ=1.46 (9H, s, Boc), 2.75-2.87 (4H, m, 2×CH$_2$), 2.88 (3H, s, NMe), 3.35 (2H, t, J=6.6 Hz, CH$_2$), 3.56-3.63 (4H, m, 2×CH$_2$, CH), 3.70-3.75 (2H, m, CH$_2$, CH); MS (ESI) m/z=263.5 (M+H$^+$).

Compound 4b, R═(CH$_2$)$_3$COOMe:

61% yield, $^1$H NMR (300 MHz, CDCl$_3$): δ=1.46 (9H, s, Boc), 1.83 (2H, m, CH$_2$), 2.39 (2H, t, J=7.4 Hz, CH$_2$) 2.64-2.86 (3H, m, CH/CH$_2$), 2.88 (3H, s, NMe), 2.99 (1H, m, CH), 3.30-3.49 (2H, m, CH$_2$), 3.67 (3H, s, CH$_3$); MS (ESI) m/z=275.5 (M+H$^+$).

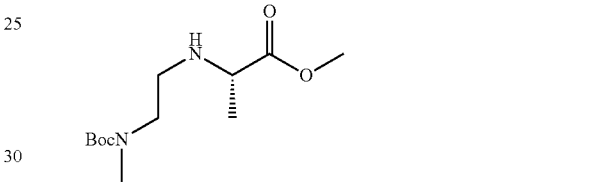

Compound 4c:

$^1$H-NMR (300 MHz, DMSO-d$_6$): δ=1.15 (3H, d, J=6.9 Hz, CH$_3$ Ala), 1.38 (9H, s, Boc), 2.57-2.67 (1H, m, (α-H), 2.76 (3H, s, NCH$_3$), 3.08-3.36 (4H, m, CH$_2$—CH$_2$), 3.63 (3H, s, OCH$_3$); MS (ESI): m/z=261.3 (M+H$^+$).

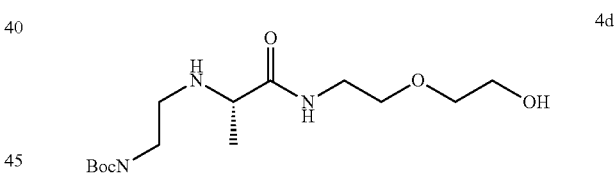

Compound 4d:

$^1$H-NMR (300 MHz, DMSO-d$_6$): δ=1.12 (3H, d, J=6.9 Hz, CH$_3$ Ala), 1.39 (9H, s, Boc), 2.54-2.61 (1H, m, (α-H), 2.77 (3H, s, NCH$_3$), 3.10-3.51 (13H, m, 6×CH$_2$+OH), 7.90 (1H, s, NH amide); MS (ESI): m/z=334.4 (M+H$^+$).

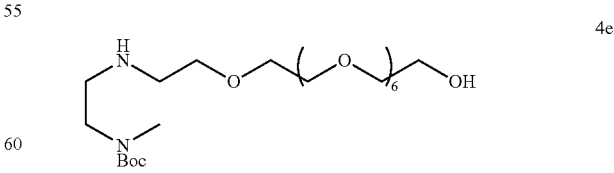

Compound 4e:

27% yield, $^1$H-NMR (300 MHz, CDCl$_3$): δ=1.44 (9H, s, Boc), 2.72-2.85 (4H, m, 2×CH$_2$), 2.81 (3H, s, MeN), 3.31 (2H, m, NCH$_2$), 3.5-3.7 (32H, m, 15×CH$_2$+OH+NH); MS (ESI): m/z=527.4 (M+H$^+$).

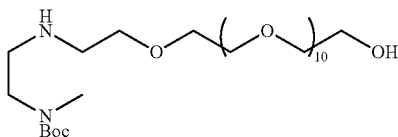

4f

Compound 4f:

30% yield, ¹H-NMR (300 MHz, CDCl₃): δ=1.44 (9H, s, Boc), 2.65-2.79 (4H, m, 2×CH₂), 2.80 (3H, s, MeN), 3.26 (2H, m, NCH₂), 3.5-3.7 (48H, m, 23×CH₂+OH+NH); MS (ESI): m/z 703.5 (M+H⁺).

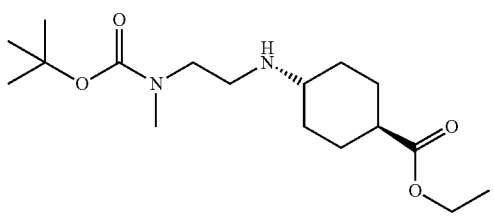

4g

Compound 4g:

¹H-NMR (300 MHz, DMSO-d₆): δ=1.14 (5H, m, 2 CH and CH₃), 1.35 (9H, s, Boc), 1.47 (4H, m, 4 CH), 1.74-2.38 (4H, m, 4 CH), 2.59 (2H, m, CH₂), 2.75 (3H, s, NCH₃), 3.16 (2H, m, CH₂), 3.99 (2H, m, CH₂); MS (ESI): m/z=329.4 (M+H⁺).

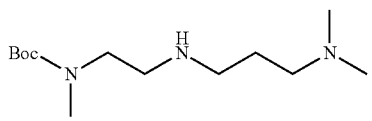

4h

Compound 4h:

63% yield, ¹H-NMR (300 MHz, CDCl₃): δ=1.46 (9H, s, Boc), 1.69 (2H, m, CH₂), 2.24 (6H, s, Me₂), 2.36 (2H, t, CH₂), 2.52 (1H, m, NH), 2.72 (2H, t, CH₂), 2.80 (2H, t, CH₂), 2.88 (3H, s, MeN), 3.37 (2H, m, CH₂); MS (ESI) m/z=260.2 (M+H⁺).

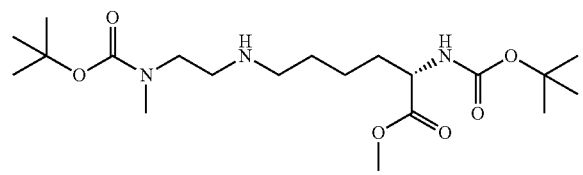

4i

Compound 4i:

¹H-NMR (300 MHz, DMSO-d₆): δ=1.30-1.36 (4H, m, 2 CH₂ Lys), 1.35 (18H, 2 s, 2 Boc), 1.53 (2H, m, CH₂ Lys), 2.46 (2H, m, CH₂ Lys), 2.56 (2H, m, CH₂), 2.75 (3H, s, NCH₃), 3.13 (3H, m, CH₂ and α-H Lys), 3.58 (3H, s, OCH₃); MS (ESI): m/z=481.4 (M+H⁺).

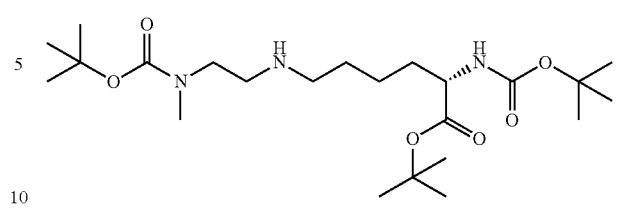

4j

Compound 4j:

¹H-NMR (300 MHz, DMSO-d₆): δ=1.36 (31H, m, 1 tBu, 2 Boc and 2 CH₂ Lys), 1.53 (2H, m, CH₂ Lys), 2.46 (2H, m, CH₂ Lys), 2.56 (2H, t, CH₂), 2.75 (3H, s, NCH₃), 3.14 (2H, t, CH₂) 3.64 (1H, m, α-H Lys), 7.01 (d, 1H, NH); MS (ESI): m/z=460.3 (M+H⁺).

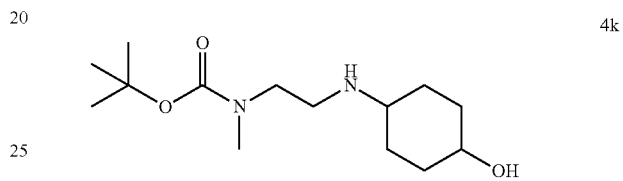

4k

Compound 4k:

¹H NMR (300 MHz, CDCl₃): δ=1.15 (2H, m), 1.30 (2H, m), 1.94 (4H, m), 2.46 (1H, m), 2.76 (2H, t, J=6.8 Hz), 2.87 (3H, s), 3.30 (2H, t, J=6.8 Hz), 3.60 (1H, m); MS (ESI): m/z=273.3 (M+H⁺).

Route B

General Procedure Alkylation Reaction:

To a solution of 1 mmol R-amine and 1 mmol mesylate in dry THF (1.5 mL) was added K₂CO₃ (1.5 mmol) and the mixture was stirred at 60° C. overnight. The mixture was cooled to RT, concentrated and purified by column chromatography (SiO₂, DCM/MeOH, 1:0 to 1:1) to give the N-Boc-N-Methyl-N'—R-diaminoethane.

Compound 5a, R=iso-propyl:

¹H NMR (300 MHz, CDCl₃), δ (ppm): 1.05 (6H, d, 2×CH₃), 1.46 (9H, s, Boc), 2.75 (2H, t, J=6.6 Hz, CH₂), 2.82 (1H, t, J=6.6 Hz, CH), 2.87 (3H, s, NMe), 3.31 (2H, t, J=6.6 Hz, CH₂); MS (ESI) m/z=217.2 (M+H⁺).

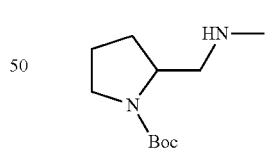

5b

Compound 5b:

Starting from N-Boc-prolinol[18] compound 5b was prepared according to route B. MS (ESI) m/z=215.2 (M+H⁺).

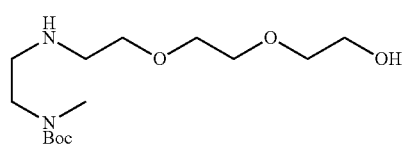

5c

Compound 5c:
$^1$H-NMR (300 MHz, DMSO-d$_6$): δ=1.39 (9H, s, Boc), 2.73-2.85 (7H, m, NCH$_3$+2×CH$_2$), 3.24-3.30 (2H, m, CH$_2$), 3.39-3.55 (11H, m, 5×CH$_2$+OH).

Example 2: Synthesis of Compound 2

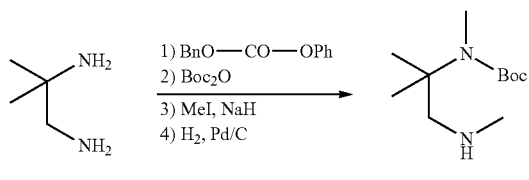

2.28 g (10 mmol) benzyl phenylcarbonate was dissolved in 20 ml ethanol and 1.03 ml (10 mmol) 1,2-diamino-1-methylpropane was added dropwise and stirred at RT overnight. The mixture was diluted with 25 ml water and acidified with 1M HCl until pH<3 and extracted with DCM. The aqueous phase was basified with 4M NaOH and extracted with DCM. The extract was dried with MgSO$_4$ and concentrated in vacuo. This gave 1.93 g (87%) monoprotected diamine. This material was dissolved in 25 ml dioxane, 2.028 g (10.5 mmol) Boc$_2$O and 0.12 g (1 mmol) DMAP were added and the reaction was stirred at RT overnight. The mixture was concentrated in vacuo and purified by column chromatography (SiO$_2$, ether/heptane, 1:0 to 7:3) to give 1.13 g (40%) of diprotected diamine. The diprotected diamine was dissolved in 10 ml dry DMF, 1.1 ml (17.5 mmol) iodomethane was added and the reaction mixture cooled in ice. 0.50 g (10.5 mmol) sodium hydride (60% in oil) was added in portions and stirred in ice for 2 hrs. The mixture was warmed to RT, quenched with 10 ml saturated NH$_4$Cl and 50 ml water, extracted with ethyl acetate, dried with MgSO$_4$ and concentrated in vacuo. The product was purified by column chromatography (SiO$_2$, DCM/ethyl acetate, 1:0 to 50:1) to give 0.358 g (29%) of Cbz-protected compound 2. $^1$H-NMR (300 MHz, CDCl$_3$): δ=1.29 (s, 3H, Me), 1.35 (s, 3H, Me), 1.46 (s, 9H, Boc), 2.82/2.86 (s, 3H, Me, Z/E), 2.93 (s, 3H, Me), 3.72 (s, 2H, CH$_2$N), 5.12 (s, 2H, benzyl), 7.35 (m, 5H, Phe). This material was dissolved in 20 ml methanol, 0.04 g Pd/C was added, the mixture was stirred under hydrogen for 3 hrs, filtered, and the filtrate concentrated. This gave 0.21 g (100%) of compound 2. MS (ESI): m/z=217.2 (M+H$^+$).

Example 3: Synthesis of Compound 3

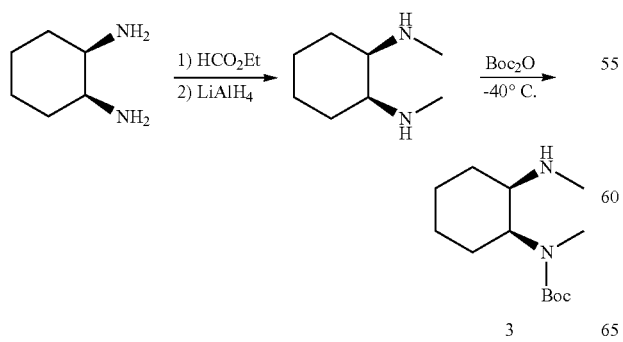

2.15 g (18.8 mmol) cis-1,2-diaminocyclohexane was dissolved in 20 ml ethyl formate and refluxed overnight. The suspension was cooled, filtered and dried under vacuum to give 2.59 g (80%) of product. The solid was added in portions to a cooled mixture of 2.1 g (53 mmol) lithium aluminumhydride in 50 ml THF and the mixture was stirred at RT for 1 hr and then refluxed overnight. The clear solution was cooled in ice and quenched by dropwise addition of 2.1 ml water followed by 15 ml 20% NaOH. The suspension was briefly heated until the salts were white. The mixture was cooled to RT and filtered. The residue was washed with 2 portions of 50 ml THF. The filtrate was concentrated and dissolved in 50 ml DCM and washed with 20 ml 4M NaOH. The aqueous phase was extracted with 25 ml DCM, dried with MgSO$_4$ and concentrated in vacuo to give 1.94 g (89%) of product. The crude product was dissolved in 50 ml DCM and the mixture cooled to −40° C. and 2.95 g (13.5 mmol) Boc$_2$O in 10 ml DCM was added dropwise. The mixture was slowly warmed to RT and washed with 20 ml 2M NaOH, dried with MgSO$_4$, concentrated in vacuo and the crude product purified by column chromatography (SiO$_2$, DCM/MeOH, 1:0 to 9:1) to give 2.09 g (63%) of compound 3. $^1$H-NMR (300 MHz, CDCl$_3$): δ=1.38 (m, 6H, cyclohex), 1.46 (s, 9H, Boc), 1.83 (m, 3H, cyclohex+NH), 2.35 (s, 3H, NMe), 2.89 (s, 3H, NMe), 2.95 (m, 1H, CHN), 3.86 (m, 1H, CHN); MS (ESI): m/z=243.2 (M+H$^+$).

Example 4: Synthesis of Compound 6

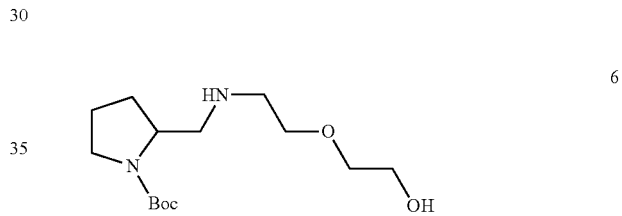

To a solution of 2.55 mmol N-Boc-prolinal in dry THF (5 mL) under an Argon atmosphere was added 0.7 mL glacial acetic acid and 272 mg 2-(2-aminoethoxy)ethanol (2.58 mmol). The mixture was stirred overnight at room temperature. 2.59 mmol sodium borohydride was added portion wise, and the mixture was stirred for another 4 hrs after which water was added. The mixture was washed with ethyl acetate, the aqueous layer basified up to pH 10 using Na$_2$CO$_3$ and extracted with ethyl acetate (9×). The combined organic layers were washed with brine, dried with MgSO$_4$, and concentrated in vacuo to give 335 mg (46%) crude 6, which was used without further purification. MS (ESI): m/z=289 (M+H$^+$).

Example 5: Synthesis of Compounds 7 and 8

0.17 g (1.5 mmol) N-methylpiperid-4-one and 0.178 g (1.0 mmol) N-Boc-N-methyl-1,2-diaminoethane were reacted with 0.42 g (2.0 mmol) sodium triacetoxyborohydride in 5 ml DCE at RT overnight. The reaction was quenched with MeOH and the mixture extracted with DCM and brine (basified to pH>12), dried with MgSO₄ and concentrated in vacuo to give 0.31 g (100%) of 7 as an oil. ¹H-NMR (300 MHz, CDCl₃): δ=¹H-NMR (300 MHz, CDCl₃): δ=1.38 (2, m, CH₂), 1.45 (9H, s, Boc), 1.76 (1H, br s, NH), 1.85 (2H, m, CH₂), 2.00 (2H, m, CH₂), 2.27 (3H, s, MeN), 2.46 (1H, m, CH), 2.76 (4H, m, 2×CH₂), 2.86 (3H, s, MeN), 3.30 (2H, t, CH₂); MS (ESI) m/z=272.2 (M+H⁺).

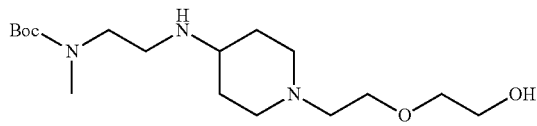

8

Compound 8 was prepared similarly to compound 7 using 0.75 g (4.0 mmol) N-hydroxyethoxyethyl-4-piperidine. The crude product was purified by column chromatography (SiO₂, DCM/MeOH, 1:0 to 95:5) to give 0.83 g (66%) of 8 as an oil. ¹H-NMR (300 MHz, CDCl₃): δ=1.46 (9H, s, Boc), 1.89 (2H, m, CH₂), 1.91 (2H, m, CH₂), 2.50 (3H, m, CH+OH+NH), 2.57 (2H, t, CH₂), 2.77 (2H, t, CH₂), 2.87 (3H, s, MeN), 2.94 (2H, m, CH₂), 3.30 (2H, t, CH₂), 3.64 (6H, m, 3×CH₂O); MS (ESI) m/z=346.3 (M+H⁺).

Example 6: Synthesis of Compound 9

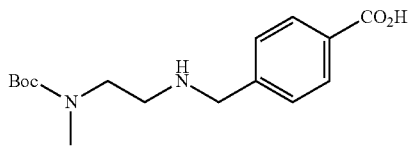

9

0.18 g (1.0 mmol) N-Boc-N-methyl-1,2-diaminoethane and 0.15 g (1.0 mmol) 4-formylbenzoic acid were reacted according to general procedure A of example 1 to give 0.34 g (90%) 9 (HCl salt). ¹H-NMR (300 MHz, DMSO-d₆): δ=2.89 (3H, s, MeN), 3.11 (2H, m, CH₂N), 3.57 (2H, t, CH₂N), 4.25 (2H, m, CH₂N), 7.33 (2H, d, ArH), 8.02 (2H, d, ArH), 9.03 (2H, br s, NH₂+), 13.03 (1H, s, CO₂H); MS (ESI) m/z=309.2 (M+H⁺).

Example 7: Synthesis of Compound 11

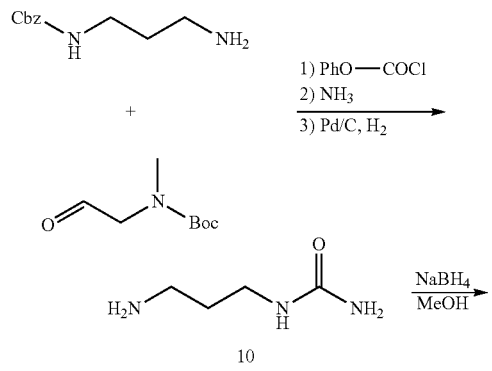

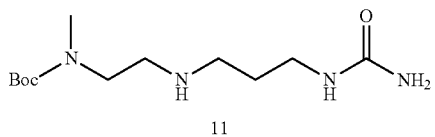

11

1.84 g (7.5 mmol) N-Cbz-1,3-diamine hydrochloride and 3 ml Et₃N were dissolved in 50 ml DCM, cooled in ice and 0.94 ml phenyl chloroformate dissolved in 5 ml DCM was added dropwise. The mixture was stirred at 0° C. for 2 hrs and concentrated in vacuo. The residue was dissolved in 50 ml DCM, washed with 25 ml 0.5 M KHSO₄, dried with MgSO₄ and concentrated in vacuo. The residue was dissolved in 25 ml EtOH, 4 ml concentrated ammonia was added and the mixture was stirred for 3 hrs. The mixture was concentrated in vacuo and the residue dissolved in 25 ml CHCl₃, washed with 10 ml 4 M NaOH and brine, dried with MgSO₄ and concentrated in vacuo to give 1.9 g of intermediate. This material was dissolved in 50 ml MeOH, 0.1 g Pd/C was added and the reaction mixture stirred under hydrogen for 5 hrs. The mixture was filtered and the filtrate concentrated in vacuo to give 0.87 g (95%) of compound 10. 0.26 g (1.7 mmol) of this amine was reacted according to general procedure A to give 0.17 g (36%) of 11 as an oil. ¹H-NMR (300 MHz, DMSO-d₆): δ=1.39 (9H, s, Boc), 1.45 (2H, m, CH₂), 2.48 (2H, t, CH₂), 2.58 (2H, t, CH₂), 2.78 (3H, s, MeN), 2.97 (2H, m, CH₂), 3.18 (2H, t, CH₂), 5.35 (2H, s, NH₂), 5.87 (1H, t, NH); MS (ESI) m/z=275.2 (M+H⁺).

Example 8: Synthesis of Compound 12

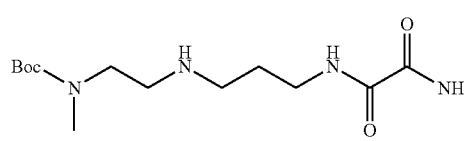

12

0.98 g (4.0 mmol) N-Cbz-1,3-diamine hydrochloride and 3 ml Et₃N were dissolved in 15 ml DCM and added dropwise to 1.65 ml (12 mmol) diethyl oxalate in 15 ml ethanol. The mixture was stirred at RT overnight, concentrated in vacuo and the residue purified by column chromatography (SiO₂, DCM/MeOH, 1:0 to 95:5) to give the mono-oxalamide. This material was dissolved in 15 ml ethanol and 5 ml concentrated ammonia was added and the mixture was stirred at RT overnight. The mixture was diluted with 50 ml MeOH and 100 mg Pd/C was added. The mixture was stirred under hydrogen atmosphere for 3 hrs. 10 ml water was added, the mixture was filtered over Celite and the filtrate concentrated in vacuo to give 0.57 g (94%) of white solid. This was reacted according to general procedure A of Example 1 to give 0.45 g (38%) of 12 as a white solid. ¹H-NMR (300 MHz, CDCl₃): δ=1.45 (9H, s, Boc), 1.80 (2H, m, CH₂), 2.80 (4H, m, 2×CH₂), 2.89 (3H, s, MeN), 3.39 (4H, m, 2×CH₂), 6.85 (1H, s, NH), 7.40 (1H, s, NH), 8.39 (1H, t, NH); MS (ESI) m/z=303.2 (M+H⁺).

Example 9: Synthesis of Compounds 14a-b and 15a-b

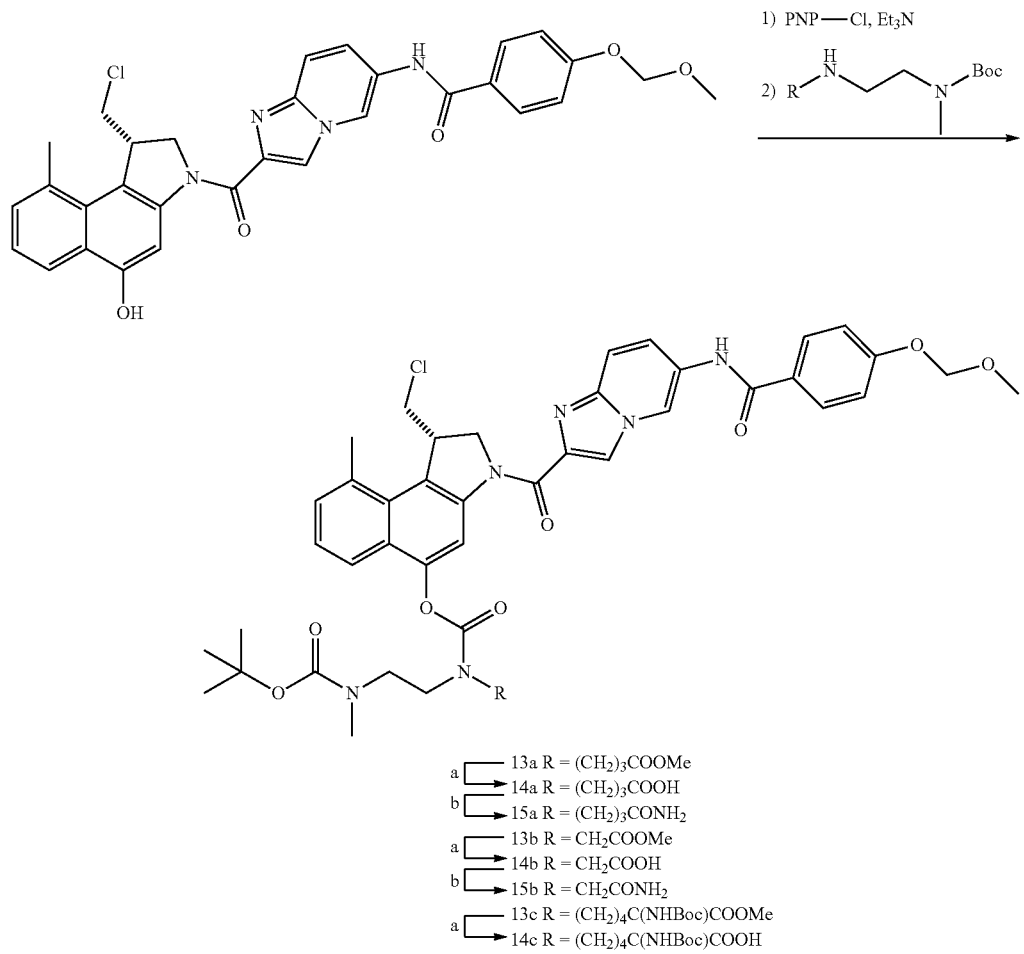

- a ⎡ 13a R = (CH$_2$)$_3$COOMe
- ⎣→ 14a R = (CH$_2$)$_3$COOH
- b ⎣→ 15a R = (CH$_2$)$_3$CONH$_2$
- a ⎡ 13b R = CH$_2$COOMe
- ⎣→ 14b R = CH$_2$COOH
- b ⎣→ 15b R = CH$_2$CONH$_2$
- a ⎡ 13c R = (CH$_2$)$_4$C(NHBoc)COOMe
- ⎣→ 14c R = (CH$_2$)$_4$C(NHBoc)COOH

Compound 14c:

Compound 13c (0.51 mmol) was dissolved in THF (12 ml); LiOH (1.02 mmol) and water (1 mL) were added and the reaction mixture was stirred for 4 h. Then, the mixture was acidified with aqueous HCl (1M, 1.5 ml), concentrated, concentrated and the residue purified by column chromatography (SiO$_2$, DCM/MeOH, 1:0 to 9:1) to yield compound 14c (0.41 mmol)

Compound 15a:

Compound 14a (0.11 mmol) was dissolved in dioxane (2 ml); pyridine (0.07 mmol) and Boc$_2$O (0.14 mmol) were added followed by NH$_4$HCO$_3$ (0.14 mmol). The resulting mixture was stirred for 8 hrs. Afterwards, the mixture was concentrated and purified by column chromatography (SiO$_2$, DCM/MeOH, 1:0 to 9:1) to yield compound 15a (0.06 mmol).

Example 10: Synthesis of Linker-Agent Conjugates

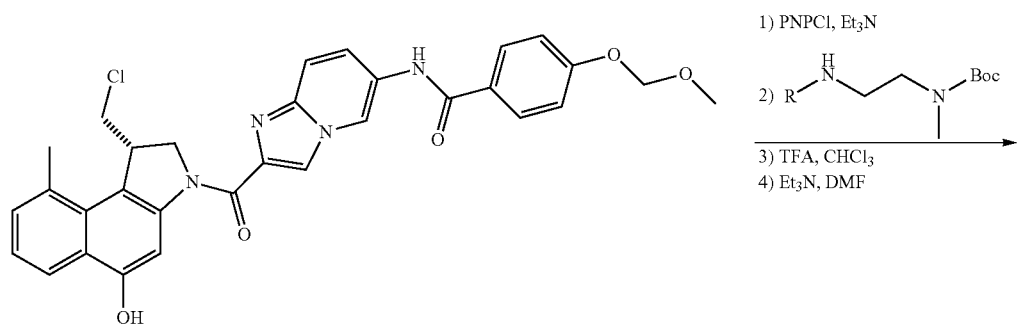

-continued
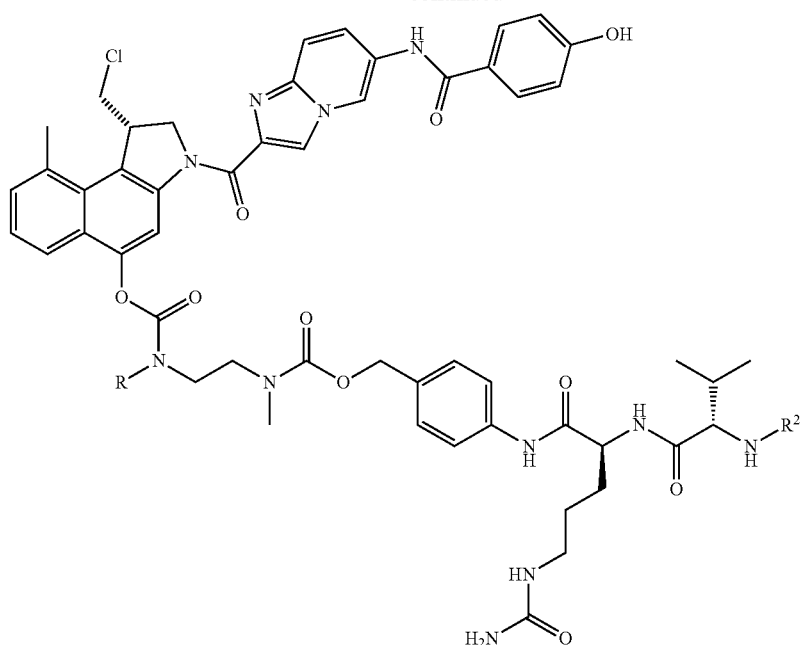
18a, b, c: R² =
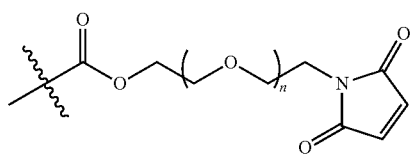
n = 0, 1, 3
18d: R² =
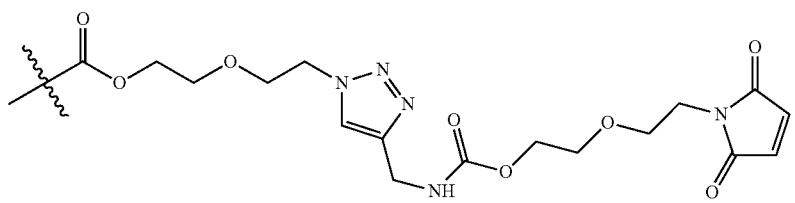
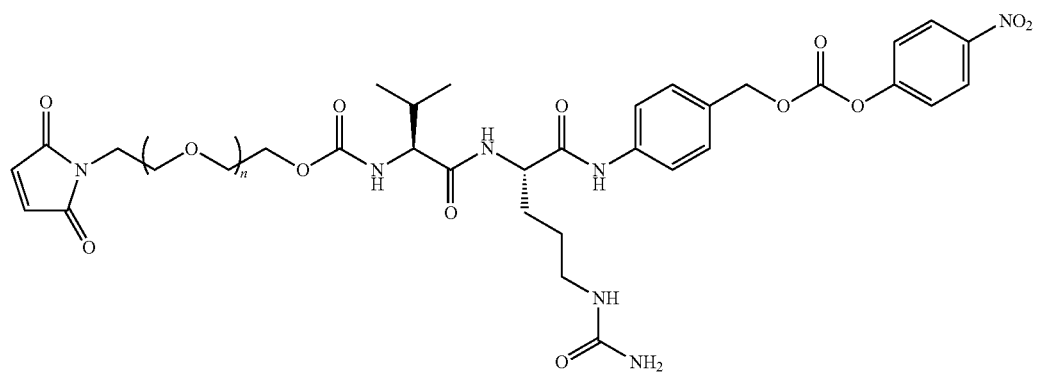
n = 0, 1, 3
16

-continued

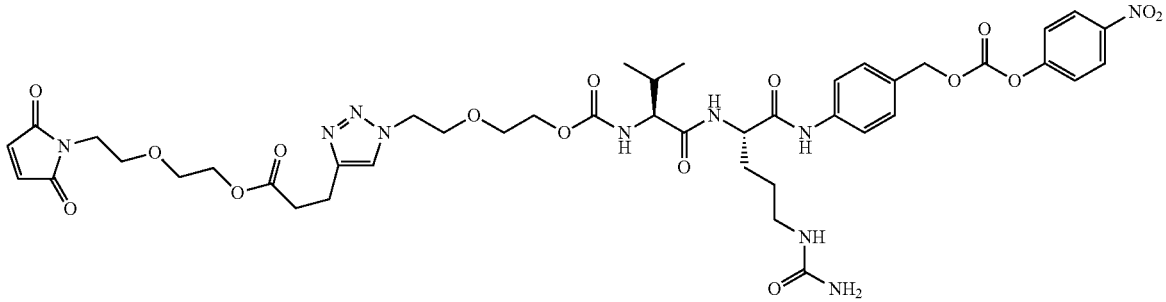

17

General Procedure for the Coupling of the Cyclization Spacer to the Activated Protected Drug (Step 2):

0.2 mmol activated protected drug, 0.6 mmol of mono-protected spacer, and 0.02 mmol HOBt were dissolved in 2 ml DMF, 1 mmol Et$_3$N was added and the mixture was heated at 50° C. for 2 hrs. The mixture was concentrated in vacuo and the crude product purified by column chromatography (SiO$_2$, DCM/MeOH) to give the cyclization spacer-drug.

General Procedure for Coupling of the Linker to the Cyclization Spacer-Drug Intermediate (Steps 3 and 4):

0.1 mmol cyclization spacer-drug was suspended in 6 ml CHCl$_3$, the reaction mixture was cooled in ice and 2 ml of TFA was added and the mixture stirred for 3 hrs. The mixture was then concentrated in vacuo. The residue was dissolved in 4 ml DMF, the solution cooled in ice and 0.13 mmol activated linker (16 or 17) and 1 mmol Et$_3$N were added. The mixture was stirred for 2 hrs, concentrated in vacuo and the residue purified by column chromatography (SiO$_2$, DCM/MeOH, 1:0 to 8:2) to an oil which was further purified by preparative reversed phase HPLC (acetonitrile/water+0.1% TFA) and freeze-dried to give construct 18 as a pale yellow solid.

Compound 18b, R=Me:
$^1$H-NMR (400 MHz, DMSO-d$_6$): δ=0.84 (6H, dd, J=6.4 Hz, 2×CH$_3$ Val), 1.32-1.47 (2H, m, CH$_2$ Cit), 1.52-1.71 (2H, m, CH$_2$ Cit), 1.91-1.99 (1H, m, β-H Val), 2.81-3.03 (11H, m, 3×CH$_3$+NCH$_2$), 4.36-4.43 (1H, m, H-2), 4.45-4.51 (1H, m, α-H), 4.63-4.41 (1H, m, H-2), 4.97-5.08 (3H, m, CH$_2$ PABA+H-1), 5.97 (1H, br s, NH), 6.90 (2H, d, J=8.8 Hz, H-3"), 7.01 (2H, s, CH=CH), 7.14-7.59 (7H, m, ArH+2×NH), 7.67-7.80 (3H, m, ArH), 7.91 (2H, d, J=8.8 Hz, H-2"), 8.06 (1H, br s, H-6), 8.33 (H, br s, H-4), 8.81 (1H, s, H-3'), 9.55 (1H, s, H-4'), 9.99 (1H, s, NH), 10.20 (1H, s, NH), 10.28 (1H, s, OH); MS (ESI): m/z=1257.3 (M+H$^+$).

Compound 18c, R=Me:
$^1$H NMR (400 MHz, DMSO-d$_6$), δ=0.84 (6H, dd, Val), 1.28-1.73 (4H, m, CH$_2$CH$_2$Cit), 1.95 (1H, m, βHVal), 2.85 (3H, s, MeAr), 2.94 (3H, s, MeN), 2.87-3.05 (4H, m, 2×CH$_2$NMe), 4.05 (2H, t, CH$_2$O), 4.40 (1H, m, H-1), 4.48 (1H, s, CH), 4.67 (1H, m, H-2), 5.05 (3H, m, CH$_2$O, H-2), 5.40 (2H, br s, NH$_2$), 5.96 (1H, br s, NH), 6.90 (2H, d, H-3"), 7.01 (2H, s, CH=CH), 7.2-7.7 (10H, m, ArH+NH), 7.91 (2H, d, H-2"), 8.05 (1H, s, H-6), 8.33 (1H, br s, H-4), 8.77 (1H, s, H-3'), 9.52 (1H, s, H-4'), 10.0 (1H, s, NH), 10.19 (1H, s, NH), 10.25 (1H, s, OH); MS (ESI): m/z=1345.7 (M+H$^+$).

Compound 18b, R=(CH$_2$CH$_2$O)$_2$H:
$^1$H NMR (400 MHz, DMSO-d$_6$), δ (ppm): δ=0.84 (6H, dd, Val), 1.28-1.73 (4H, m, CH$_2$CH$_2$Cit), 1.96 (1H, m, βHVal), 2.85 (3H, s, MeAr), 2.95 (3H, s, MeN), 2.87-3.05 (4H, m, 2×CH$_2$NMe), 4.00 (2H, t, CH$_2$O), 4.35 (1H, m, H-1), 4.48 (1H, m, CH), 4.67 (1H, m, H-2), 4.93-5.11 (4H, m, CH$_2$O, H-2, CH), 5.40 (2H, br s, NH$_2$), 5.97 (1H, br s, NH), 6.91 (2H, d, H-3"), 7.01 (2H, s, CH=CH), 7.2-7.7 (10H, m, ArH+NH), 7.91 (2H, d, H-2"), 8.06 (1H, d, H-6), 8.33 (1H, br s, H-4), 8.80 (1H, s, H-3'), 9.54 (1H, s, H-4'), 10.01 (1H, s, NH), 10.20 (1H, s, NH), 10.27 (1H, s, OH); MS (ESI): m/z=1331.7 (M+H$^+$).

Compound 18c, R=(CH$_2$)$_4$C(NH$_2$)COOH:
$^1$H-NMR (400 MHz, DMSO-d$_6$): δ=0.84 (6H, dd, J=6.4 Hz, 2×CH$_3$ Val), 1.29-1.98 (11H, m, 3×CH$_2$ Lys+2×CH$_2$ Cit+β-H Val), 2.82-3.04 (8H, m, 2×CH$_3$+NCH$_2$), 4.35-4.42 (1H, m, H-1), 4.45-4.51 (1H, m, α-H), 4.63-4.70 (1H, m, H-2), 4.95-5.07 (2H, m, CH$_2$ PABA), 5.09-5.16 (1H, m, H-2), 5.99 (1H, br s, NH), 6.90 (2H, d, J=8.4 Hz, H-3"), 7.01 (2H, s, CH=CH), 7.16-7.77 (11H, m, ArH+3×NH), 7.90 (2H, d, J=8.4 Hz, H-2"), 8.05-8.09 (1H, m, H-6), 8.19 (3H, br s, NH$_2$ Lys+OH), 8.31-8.37 (1H, m, H-4), 8.75 (1H, br s, H-3'), 9.53 (1H, br s, H-4'), 10.00 (1H, br s, NH), 10.16-10.26 (2H, m, NH+OH); MS (ESI): m/z=1460.7 (M+H$^+$).

Compound 18d, R=(CH$_2$CH$_2$O)$_2$H:
$^1$H NMR (400 MHz, DMSO-d$_6$), δ=0.84 (6H, dd, Val, J=6.8), 1.30-1.46 (2H, m, CH$_2$ Cit), 1.52-1.70 (2H, m, CH$_2$ Cit), 1.91-1.99 (1H, m, (β-H Val), 2.80-3.05 (10H, m, ArCH$_3$+NCH$_3$+2×NCH2), 3.97-4.06 (5H, m, 2×CH$_2$O+H-2), 4.20 (2H, d, J=5.6 Hz, NCH$_2$-triazole), 4.36-4.43 (1H, m, H-1), 4.44-4.52 (3H, m, CH$_2$-triazole+α-H), 4.63-4.71 (1H, m, H-2), 4.94-5.09 (3H, m, CH$_2$ PABA+H-2), 5.98 (1H, br s, NH), 6.90 (2H, d, J=8.8 Hz, H-3"), 6.99 (2H, s, CH=CH), 7.16-7.81 (11H, m, ArH+NH), 7.87 (1H, s, triazole-H), 7.91 (2H, d, J=8.8 Hz, H-2"), 8.05-8.09 (1H, m, H-6), 8.33 (H, m, H-4), 8.83 (1H, s, H-3'), 9.55 (1H, s, H-4'), 10-00 (1H, s, NH), 10.20 (1H, s, NH), 10.28 (1H, s, OH); MS (ESI): m/z=1543.7 (M+H$^+$).

Compound 18c, R=(CH$_2$CH$_2$O)$_2$H:
$^1$H NMR (400 MHz, DMSO-d$_6$), δ=0.84 (6H, dd, Val), 1.28-1.73 (4H, m, CH$_2$CH$_2$Cit), 1.96 (1H, m, βHVal), 2.85 (3H, s, MeAr), 2.94 (3H, s, MeN), 2.87-3.05 (4H, m, 2×CH$_2$NMe), 4.05 (2H, t, CH$_2$O), 4.40 (1H, m, H-1), 4.48 (1H, m, CH), 4.67 (1H, m, H-2), 4.93-5.16 (4H, m, CH$_2$O, CH, H-2), 5.40 (2H, br s, NH$_2$), 5.96 (1H, br s, NH), 6.90 (2H, d, H-3"), 7.01 (2H, s, CH=CH), 7.2-7.8 (11H, m, ArH+3×NH), 7.90 (2H, d, H-2"), 8.05 (1H, d, H-6), 8.32 (1H, br s, H-4), 8.76 (1H, s, H-3'), 9.51 (1H, s, H-4'), 10.01 (1H, s, NH), 10.19 (1H, s, NH), 10.24 (1H, s, OH); MS (ESI): m/z=1419.7 (M+H$^+$).

Compound 18a, R=(CH$_2$CH$_2$O)$_2$H:

$^1$H NMR (400 MHz, DMSO-d$_6$): δ=0.81 (6H, dd, J=6.4 Hz, 2×CH$_3$), 1.30-1.47 (2H, m, CH$_2$ Cit), 1.53-1.71 (2H, m, CH$_2$ Cit), 1.89-1.99 (1H, m, β-H Val), 2.82-3.05 (8H, m, 2×CH$_3$+NCH$_2$), 3.96-4.02 (1H, m), 4.15-4.23 (1H, m), 4.33-4.40 (1H, m, H-1), 4.44-4.52 (1H, m, α-H), 4.63-4.71 (1H, m, H-2), 4.94-5.12 (3H, m, CH$_2$+H-2), 5.96 (1H, br s, NH), 6.90 (2H, d, J=8.4 Hz, H-3"), 7.01 (2H, s, CH=CH), 7.10-7.54 (7H, m, 5 ArH+2×NH), 7.66-7.81 (3H, m, ArH), 7.91 (2H, d, J=8.8 Hz, H-2"), 8.00-8.05 (1H, m, H-6), 8.29-8.37 (1H, m, H-4), 8.79 (1H, br s, H-3'), 9.54 (1H, br s, H-4'), 9.91-10.00 (1H, m, NH), 10.20 (1H, br s, OH), 10.27 (1H, s, NH); MS (ESI): m/z=1287.7 (M+H$^+$).

Compound 18b, R=(CH$_2$)$_3$C(O)NH$_2$:

$^1$H-NMR (400 MHz, DMSO-d$_6$): δ=0.83 (6H, dd, J=6.4 Hz, 2×CH$_3$ Val), 1.25-2.15 (9H, m, 2×CH$_2$ butyramide+2× CH$_2$ Cit+β-H Val), 2.82-3.04 (8H, m, 2×CH$_3$+NCH$_2$), 3.18-3.98 (15H, m, 2×H-10+6×CH$_2$+α-H), 4.34-4.42 (1H, m, H-1), 4.46-4.54 (1H, m, α-H), 4.63-4.71 (1H, m, H-2), 4.93-5.07 (3H, m, CH$_2$ PABA+H-2), 5.98 (1H, br s, NH), 6.76 (1H, br s, NH), 6.91 (2H, d, J=8.8 Hz, H-3"), 7.00 (2H, s, CH=CH), 7.13-7.58 (8H, m, ArH+2×NH), 7.65-7.83 (3H, m, ArH), 7.91 (2H, d, J=8.4 Hz, H-2"), 8.04-8.09 (1H, m, H-6), 8.28-8.37 (1H, m, H-4), 8.89 (1H, br s, H-3'), 9.60 (1H, br s, H-4'), 9.93-10.02 (1H, m, NH), 10.34 (1H, br s, NH); MS (ESI): m/z=1328.3 (M+H$^+$).

Compound 18b, R=(CH$_2$)$_4$C(NH$_2$)COOH:

$^1$H-NMR (400 MHz, DMSO-d$_6$): δ=0.83 (6H, dd, J=6.4 Hz, 2×CH$_3$ Val), 1.30-1.98 (11H, m, 3×CH$_2$ Lys+2×CH$_2$ Cit+β-H Val), 2.82-3.04 (8H, m, 2×CH$_3$+NCH$_2$), 4.33-4.42 (1H, m, H-1), 4.45-4.51 (1H, m, α-H), 4.62-4.70 (1H, m, H-2), 4.95-5.07 (2H, m, CH$_2$ PABA), 5.10-5.16 (1H, m, H-2), 5.98 (1H, br s, NH), 6.90 (2H, d, J=8.8 Hz, H-3"), 7.01 (2H, s, CH=CH), 7.13-7.77 (11H, m, ArH+3×NH), 7.90 (2H, d, J=8.8 Hz, H-2"), 8.05-8.09 (1H, m, H-6), 8.19 (3H, br s, NH$_2$ Lys+OH), 8.31-8.37 (1H, m, H-4), 8.73 (1H, br s, H-3'), 9.51 (1H, br s, H-4'), 10.00 (1H, br s, NH), 10.17-10.25 (2H, m, NH+OH); MS (ESI): m/z=1372.6 (M+H$^+$).

Compound 18b, R=(CH$_2$)$_3$COOH:

$^1$H NMR (400 MHz, DMSO-d$_6$), δ=0.83 (6H, dd, Val), 1.28-1.73 (4H, m, CH$_2$CH$_2$Cit), 1.74-2.02 (2H, m, CH$_2$), 1.95 (1H, m, βHVal), 2.19-2.39 (2H, m, CH$_2$), 2.85 (3H, s, MeAr), 2.94 (3H, s, MeN), 2.87-3.05 (4H, m, 2×CH$_2$NMe), 4.00 (2H, m, CH$_2$O), 4.40 (1H, m, H-1), 4.48 (1H, m, CH), 4.67 (1H, m, H-2), 4.93-5.18 (4H, m, CH$_2$O, CH, H-2), 5.40 (2H, br s, NH$_2$), 5.96 (1H, br s, NH), 6.90 (2H, d, H-3"), 7.01 (2H, s, CH=CH), 7.2-7.8 (10H, m, ArH+NH), 7.91 (2H, d, H-2"), 8.06 (1H, d, H-6), 8.33 (1H, br s, H-4), 8.76 (1H, s, H-3'), 9.51 (1H, s, H-4'), 10.01 (1H, s, NH), 10.19 (1H, s, NH), 10.24 (1H, s, OH); MS (ESI): m/z=1329.8 (M+H$^+$).

Compound 18c, R=(CH$_2$)$_3$COOH:

$^1$H NMR (400 MHz, DMSO-d$_6$), δ=0.84 (6H, dd, Val), 1.30-1.73 (4H, m, CH$_2$CH$_2$Cit), 1.74-2.02 (2H, m, CH$_2$), 1.95 (1H, m, βHVal), 2.19-2.39 (2H, m, CH$_2$), 2.85 (3H, s, MeAr), 2.94 (3H, s, MeN), 2.87-3.05 (4H, m, 2×CH$_2$NMe), 4.05 (2H, m, CH$_2$O), 4.40 (1H, m, H-1), 4.48 (1H, m, CH), 4.67 (1H, m, H-2), 4.95-5.16 (4H, m, CH$_2$O, CH, H-2), 5.40 (2H, br s, NH$_2$), 5.96 (1H, br s, NH), 6.90 (2H, d, H-3"), 7.01 (2H, s, CH=CH), 7.2-7.8 (9H, m, ArH+NH), 7.91 (2H, d, H-2"), 8.05 (1H, d, H-6), 8.34 (1H, br s, H-4), 8.77 (1H, s, H-3'), 9.52 (1H, s, H-4'), 10.01 (1H, s, NH), 10.19 (1H, s, NH), 10.24 (1H, s, OH); MS (ESI): m/z=1417.9 (M+H$^+$).

Compound 18b, R=(CH$_2$)$_3$NHC(O)NH$_2$:

$^1$H-NMR (400 MHz, DMSO-d$_6$): δ=0.79 (6H, dd, Val), 1.25-1.8 (6H, m, 3×CH$_2$), 1.91 (1H, m, βHVal), 2.80 (3H, s, MeAr), 2.90 (3H, s, MeN), 2.95 (4H, m, 2×CH$_2$N), 4.34 (1H, m, H-1), 4.61 (1H, m, H-2), 4.94 (1H, m, H-2), 4.99 (2H, s, CH$_2$O), 5.32 (4H, br s, 2×NH$_2$), 5.91 (1H, br s, NH), 5.98 (1H, br s, NH), 6.86 (2H, d, H-3"), 6.95 (2H, s, CH=CH), 7.2-7.7 (10H, m, ArH+2×NH), 7.86 (2H, d, H-2"), 8.02 (1H, d, H-6), 8.28 (1H, br s, H-4), 8.82 (1H, s, H-3'), 9.54 (1H, s, H-4'), 9.95 (1H, s, NH), 10.15 (1H, s, NH), 10.27 (1H, s, OH); MS (ESI): m/z=1343.7 (M+H$^+$).

Compound 18c, R=(CH$_2$)$_3$NHC(O)NH$_2$:

$^1$H-NMR (400 MHz, DMSO-d$_6$): δ=0.79 (6H, dd, Val), 1.25-1.8 (6H, m, 3*CH$_2$), 1.91 (1H, m, 3HVal), 2.80 (3H, s, MeAr), 2.90 (3H, s, MeN), 2.95 (4H, m, 2×CH$_2$N), 4.34 (1H, m, CH), 4.45 (1H, m, CH), 4.61 (1H, m, H-2), 4.94 (1H, m, H-2), 4.99 (2H, s, CH$_2$O), 5.32 (4H, br s, 2×NH$_2$), 5.91 (1H, br s, NH), 5.98 (1H, br s, NH), 6.86 (2H, d, H-3"), 6.95 (2H, s, CH=CH), 7.2-7.7 (10H, m, ArH+2×NH), 7.86 (2H, d, H-2"), 8.02 (1H, d, H-6), 8.28 (H, br s, H-4), 8.82 (1H, s, H-3'), 9.54 (1H, s, H-4'), 9.95 (1H, s, NH), 10.15 (1H, s, NH), 10.27 (1H, s, OH); MS (ESI): m/z=1431.5 (M+H$^+$).

Compound 18d, R=(CH$_2$)$_3$NHC(O)NH$_2$:

$^1$H-NMR (400 MHz, DMSO-d$_6$): δ=0.83 (6H, dd, Val), 1.25-1.8 (6H, m, 3×CH$_2$), 1.95 (1H, m, βVal), 2.85 (3H, s, MeAr), 2.94 (3H, s, MeN), 2.95 (4H, m, 2×CH$_2$N), 4.20 (2H, d, NCH$_2$), 4.39 (1H, m, CH), 4.48 (3H, m, CH+CH$_2$), 4.67 (1H, m, H-2), 5.02 (3H, m, H-2, CH$_2$O), 5.41 (4H, br s, 2×NH$_2$), 5.97 (2H, br s, 2×NH), 6.91 (2H, d, H-3"), 6.99 (2H, s, CH=CH), 7.2-7.7 (11H, m, ArH+3×NH), 7.76 (1H, s, triazole-H), 7.88 (2H, d, H-2"), 8.08 (1H, d, H-6), 8.33 (H, br s, H-4), 8.84 (1H, s, H-3'), 9.57 (1H, s, H-4'), 10.00 (1H, s, NH), 10.20 (1H, s, NH), 10.30 (1H, s, OH); MS (ESI): m/z=1556.2 (M+H$^+$).

Compound 18b, R=(CH$_2$CH$_2$O)$_3$H:

$^1$H-NMR (400 MHz, DMSO): δ=0.83 (6H, dd, J=6.5 Hz, J=15.8 Hz, Val), 1.3-1.7 (4H, m), 1.96 (1H, m), 2.90 (8H, m), 3.00-4.00 (6H, m), 4.44 (2H, m), 4.67 (1H, m), 6.69 (1H, s), 5.04 (2H, d, J=9.8 Hz), 5.40 (1H, br s), 5.97 (1H, s, NH), 6.9 (2H, d, J=8.3 Hz), 7.00 (2H, s, CH=CH), 7.13-7.61 (7H, m), 7.75 (3H, m) 7.91 (2H, d, J=8.3 Hz), 8.06 (1H, m), 8.33 (1H, s), 8.83 (1H, s), 9.56 (1H, s), 9.97 (1H, s), 10.20 (1H, s), 10.30 (1H, s); MS (ESI): m/z=1376 (M+H$^+$).

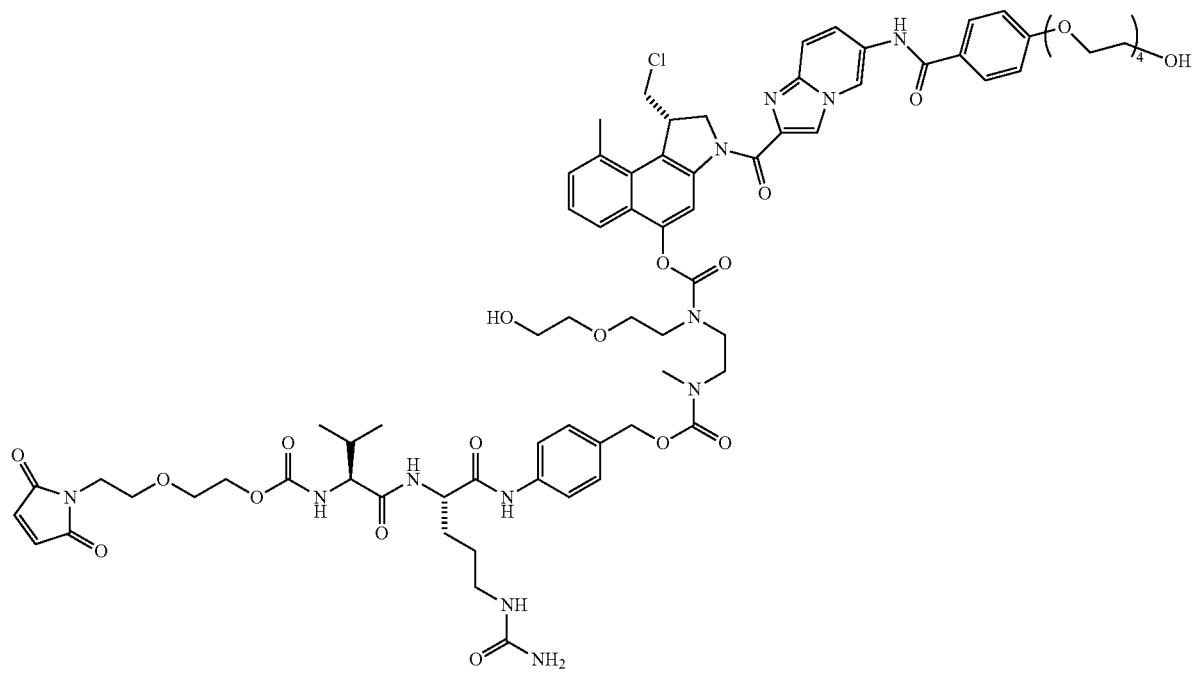
22
Compound 22:
Compound 22 was prepared analogously starting with the corresponding activated drug. $^1$H-NMR (400 MHz, DMSO-$d_6$): δ=0.84 (6H, dd, J=6.4 Hz, 2×CH$_3$ Val), 1.30-1.47 (2H, m, CH$_2$ Cit), 1.52-1.71 (2H, m, CH$_2$ Cit), 1.91-1.99 (1H, m, β-H Val), 2.82-3.03 (8H, m, 2×CH$_3$+NCH$_2$), 4.18-4.22 (2H, m, CH$_2$O), 4.35-4.43 (1H, m, H-1), 4.46-4.52 (1H, m, α-H), 4.63-4.71 (1H, m, H-2), 4.94-5.08 (3H, m, CH$_2$ PABA+H-2), 5.97 (1H, br s, NH), 7.01 (2H, s, CH=CH), 7.09-7.20 (4H, m, H-3"+2 ArH), 7.22-7.58 (5H, m, 3 ArH+2×NH), 7.69-7.82 (3H, m, ArH), 8.00 (2H, d, J=8.8 Hz, H-2"), 8.03-8.08 (1H, br s, H-6), 8.28-8.37 (1H, m, H-4), 8.83 (1H, br s, H-3'), 9.57 (1H, br s, H-4'), 9.93-10.02 (1H, m, NH), 10.39 (1H, s, NH); MS (ESI): m/z=1509.6 (M+H$^+$).
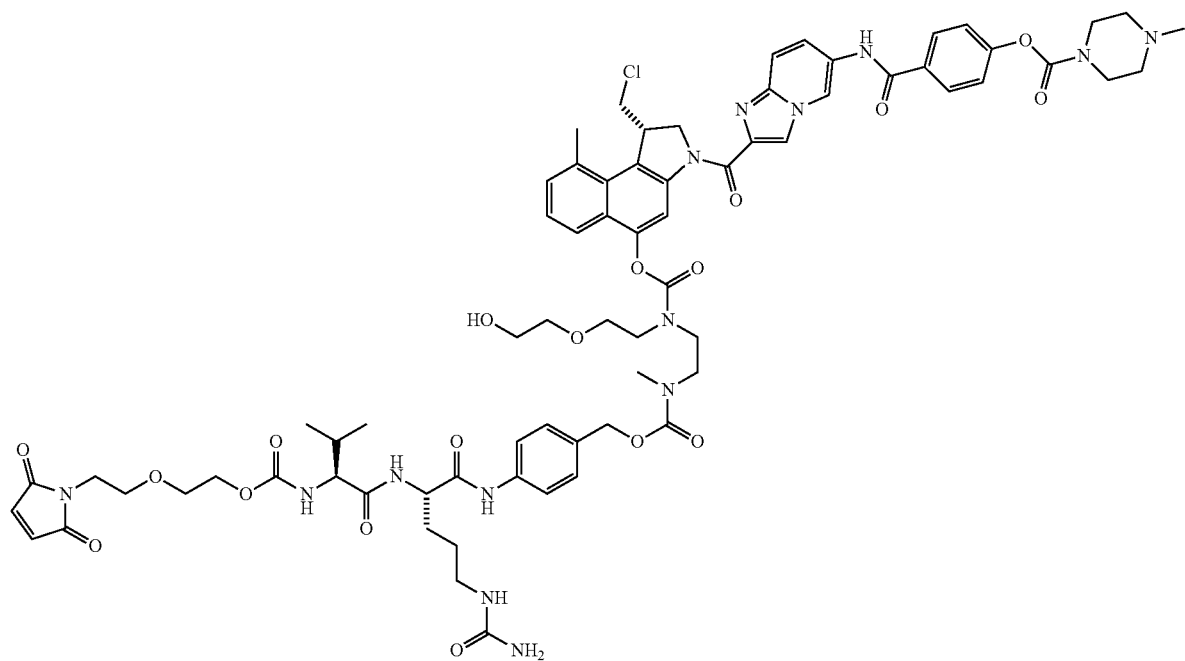
23

Compound 23:

Compound 23 was prepared analogously starting with the corresponding activated drug. ¹H-NMR (400 MHz, DMSO): δ=0.80 (6H, dd, J=6.5 Hz, J=15.9 Hz, 2×CH₃), 1.3-1.7 (4H, m), 1.93 (1H, m), 2.9 (11H, m), 3.00-4.50 (10H, m), 5.03 (3H, m), 5.40 (1H, br s), 5.94 (1H, s, NH), 6.98 (2H, s, CH=CH), 7.10-7.85 (11H, m), 8.03 (3H, m), 8.32 (1H, m) 8.76 (1H, s), 9.50 (1H, s), 9.78 (1H, s), 9.98 (1H, br s), 10.51 (1H, br s); MS (ESI): m/z=1457 (M+H⁺).

CH₂ Cit), 1.90-2.00 (1H, m, (β-H Val), 2.82-3.03 (10H, m, ArCH₃+NCH₃+2×NCH2), 3.19 (3H, s, OCH₃), 3.97-4.03 (2H, m, NCH₂-triazole), 4.37-4.52 (2H, m, H-1+α-H), 4.64-4.69 (3H, m, H-2+CH₂), 4.94-5.13 (3H, m, CH₂ PABA+H-2), 5.96 (1H, br s, NH), 7.01 (2H, s, CH=CH), 7.14-7.58 (7H, m, 5 ArH+3×NH), 7.72-7.84 (3H, m, ArH), 8.04-8.07 (1H, m, H-6), 8.29-8.38 (H, m, H-4), 8.74-8.80 (2H, s,

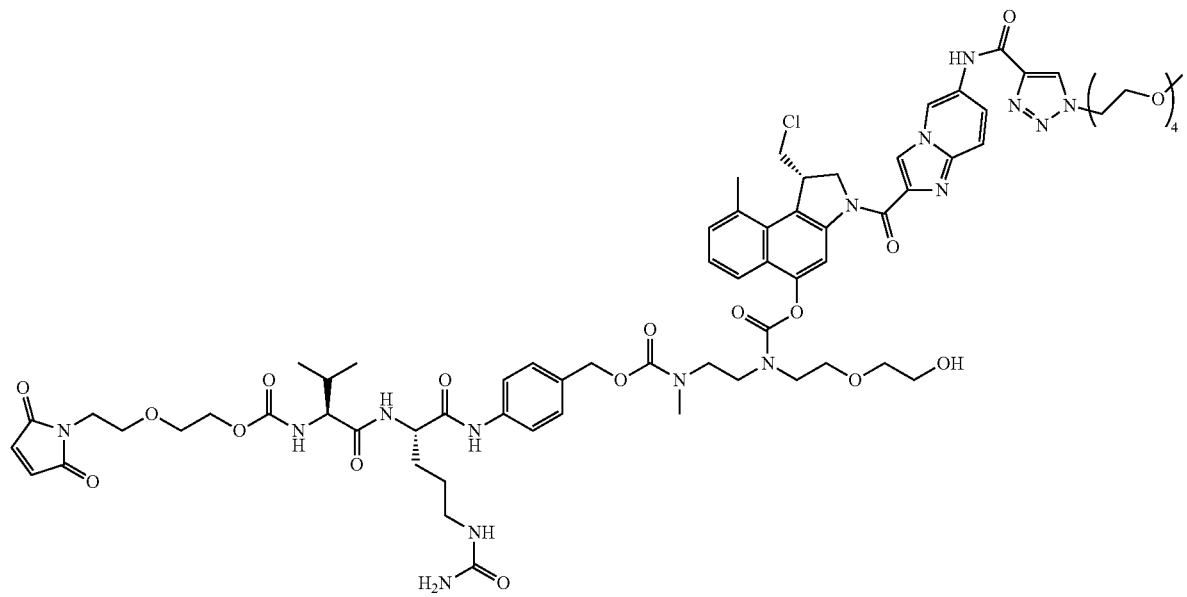

26

Compound 26:

¹H-NMR (400 MHz, DMSO-d₆): δ=0.83 (6H, dd, J=6.8 Hz, 2×CH₃), 1.30-1.47 (2H, m, CH₂ Cit), 1.54-1.71 (2H, m,

H-3'+triazole-H), 9.53 (1H, s, H-4'), 10-00 (1H, s, NH), 10.85 (1H, s, NH); MS (ESI): m/z=1496.9 (M+H⁺).

Example 11: Synthesis of Compound 19

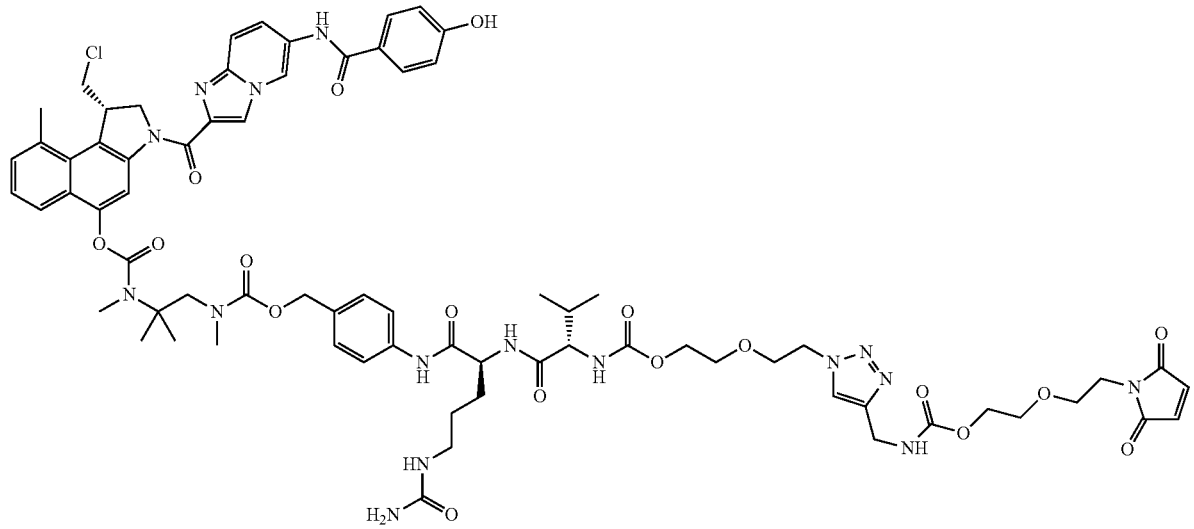

19

20

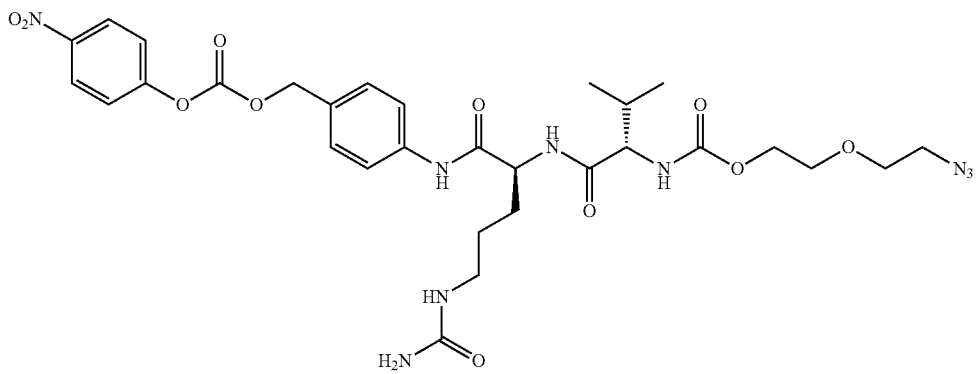

0.21 g (0.85 mmol) N-Boc-N-methyl-N'-1,2-diamino-1-methylpropane, 0.45 g (0.64 mmol) 20 and 8 mg HOBt were dissolved in 5 ml DMF. 0.75 ml DiPEA was added and the reaction mixture stirred at RT overnight. The mixture was concentrated in vacuo and purified by column chromatography (SiO$_2$, DCM/MeOH, 1:0 to 20:1) to give 0.50 g (100%) of intermediate. This material was suspended in 4 ml CHCl$_3$ and cooled in ice. 2 ml TFA was added and the reaction mixture was stirred for 2 hrs at 0° C. and then concentrated in vacuo. To this material in 6 ml DMF, 0.11 g (0.15 mmol) activated MOM-protected drug, 2 mg HOBt and 0.2 ml (1.2 mmol) Et$_3$N were added and the mixture was heated at 50° C. for 3 hrs. The mixture was concentrated in vacuo and purified by column chromatography (SiO$_2$, DCM/MeOH, 1:0 to 75:15) to give 0.14 g (72%) material. This was suspended in 6 ml CHCl$_3$ cooled in ice. 0.5 ml of TFA was added and the mixture was stirred for 2 hrs and then concentrated in vacuo. This material and 0.045 g (0.17 mmol) maleimide-alkyne linker were dissolved in 2 ml DMF. 0.6 mL of a solution of 0.025 g (0.1 mmol) CuSO$_4$, 0.022 g (0.11 mmol) 1,10-phenanthroline and 0.022 g (0.11 mmol) sodium ascorbate in 1 ml acetonitrile/water (1:2) was added to the reaction mixture and the mixture was stirred for 2.5 hrs. The mixture was acidified with acetic acid and concentrated in vacuo. The crude product was purified by column chromatography (SiO$_2$, DCM/MeOH, 1:0 to 8:2) to give 0.026 g (16%) material which was further purified by preparative reversed phase HPLC and freeze dried to give 0.015 g of 19. $^1$H-NMR (400 MHz, DMSO-d$_6$): δ=0.79 (6H, dd, Val), 1.34 (3H, br s, gem-Me$_2$), 1.38 (3H, br s, gem-Me$_2$), 1.3-1.7 (4H, m, CH$_2$CH$_2$Cit), 1.90 (1H, m, 3HVal), 2.80 (3H, s, MeAr), 2.91 (3H, s, MeN). 3.11 (3H, br s, MeN), 3.95 (2H, t, CH$_2$O), 3.98 (2H, t, CH$_2$O), 4.15 (2H, d, NCH$_2$-triazole), 4.30 (1H, m, H-1), 4.43 (2H, t, CH$_2$-triazole), 4.61 (1H, m, H-2), 5.00 (2H, s, CH$_2$O), 5.04 (1H, m, H-2), 5.37 (2H, br s, NH$_2$), 5.92 (1H, br s, NH), 6.85 (2H, d, H-3"), 6.94 (2H, s, CH=CH), 7.2-7.7 (11H, m, ArH+3× NH), 7.81 (1H, s, triazole-H), 7.84 (2H, d, H-2"), 8.03 (1H, d, H-6), 8.27 (H, br s, H-4), 8.73 (1H, s, H-3'), 9.48 (1H, s, H-4'), 9.98 (1H, s, NH), 10.15 (1H, s, NH), 10.21 (1H, s, OH); MS (ESI): m/z=1497.6 (M+H$^+$).

21

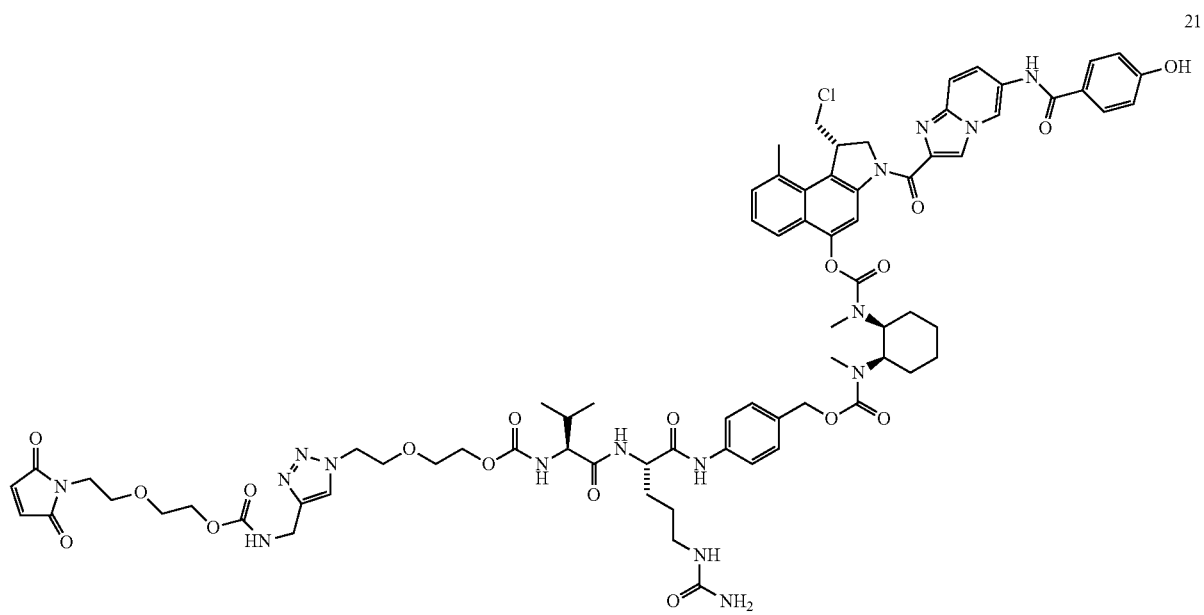 [SMILES: Cc1cccc2c(OC(=O)N(C)[C@H]3CCCC[C@H]3N(C)C(=O)OCc3ccc(NC(=O)[C@H](CCCNC(N)=O)NC(=O)[C@@H](NC(=O)OCCOCCn4cc(CNC(=O)OCCOCCN5C(=O)C=CC5=O)nn4)C(C)C)cc3)cc3c(c12)[C@H](CCl)CN3C(=O)c1cn2cc(NC(=O)c3ccc(O)cc3)ccc2n1]

Compound 21:

The same procedure was followed as for compound 19. $^1$H-NMR (400 MHz, DMSO-$d_6$): δ=0.83 (6H, dd, Val), 1.3-2.1 (3Hm, cyclohexyl+CH$_2$CH$_2$Cit+βHVal), 2.84 (3H, s, MeAr), 3.01 (8H, m, 2×MeNCH), 3.98 (4H, m, 2×CH$_2$O), 4.20 (2H, d, NCH$_2$-triazole), 4.36 (1H, m, H-1), 4.48 (2H, t, CH$_2$-triazole), 4.65 (1H, m, H-2), 5.04 (1H, m, H-2), 5.06 (2H, s, CH$_2$O), 5.39 (2H, br s, NH$_2$), 5.96 (1H, br s, NH), 6.90 (2H, d, H-3"), 6.99 (2H, s, CH=CH), 7.2-7.7 (11H, m, ArH+3×NH), 7.87 (1H, s, triazole-H), 7.91 (2H, d, H-2"), 8.06 (1H, d, H-6), 8.36 (H, br s, H-4), 8.80 (1H, s, H-3'), 9.55 (1H, s, H-4'), 9.97 (1H, s, NH), 10.20 (1H, s, NH), 10.27 (1H, s, OH); MS (ESI): m/z=1523.6 (M+H$^+$).

Example 12: Synthesis of Maleimide-Peptide Linkers

Compound 25b:

$^1$H-NMR (300 MHz, DMSO-$d_6$): δ=0.85 (6H, dd, J=6.9 Hz, 2×CH$_3$ Val), 1.32-1.50 (2H, m, CH$_2$ Cit), 1.54-1.76 (2H, m, CH$_2$ Cit), 1.91-2.02 (1H, m, β-H Val), 2.90-3.09 (2H, m, CH$_2$), 3.49-3.60 (6H, m, CH$_2$), 3.87-3.92 (1H, m, α-H), 3.97-4.06 (2H, m, CH$_2$), 4.37-4.46 (1H, m, α-H), 5.24 (2H, s, CH$_2$), 5.41 (2H, s, NH$_2$), 5.95-6.00 (1H, m, NH), 7.01 (2H, s, HC=CH), 7.15-7.18 (1H, m, NH), 7.41 (2H, d, J=8.7 Hz, Ar—H), 7.54-7.59 (2H, m, Ar—H), 7.64 (2H, d, J=8.4 Hz, Ar—H), 8.07-8.10 (1H, m, NH), 8.29-8.33 (2H, m, Ar—H), 10.11 (1H, s, NH); MS (ESI): m/z=756.5 (M+H$^+$).

Compound 25c:

$^1$H-NMR (300 MHz, CDCl$_3$/CD$_3$OD) δ=0.98 (6H, dd, J=6.9 Hz, J=14.4 Hz, CH$_3$), 1.59 (2H, m), 1.76 (1H, m), 1.94 (1H, m), 2.13 (1H, m), 3.08-3.28 (2H, m) 3.54-3.76 (10H, m, CH$_2$O), 4.00 (1H, d, J=6.3 Hz), 4.20 (2H, m), 4.57 (1H, m), 5.27 (2H, s, OCH$_2$Ar), 6.78 (2H, s, CH=CH), 7.42 (4H, m, ArH), 7.65 (2H, d, J=8.5 Hz), 8.30 (2H, d, J=9.2 Hz).

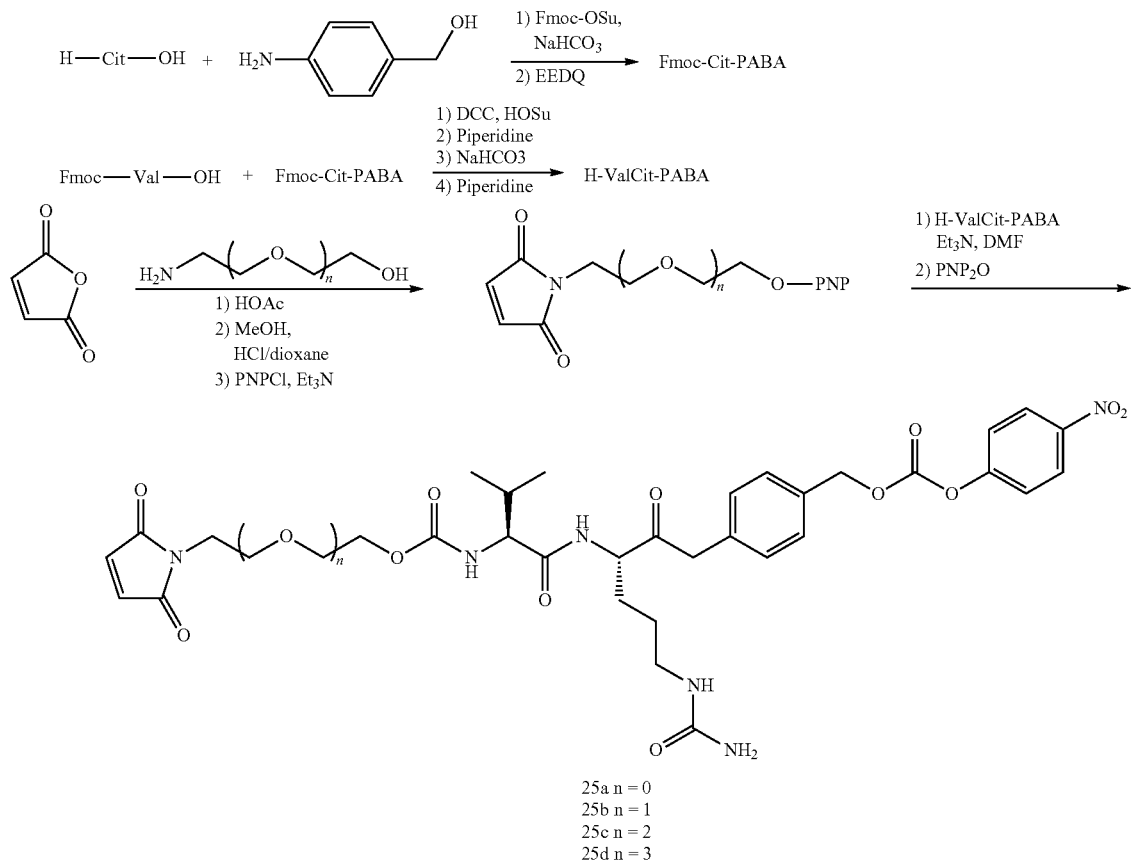

25a n = 0
25b n = 1
25c n = 2
25d n = 3

Compound 25a:

$^1$H-NMR (300 MHz, DMSO-$d_6$): δ=0.83 (6H, dd, J=6.9 Hz, 2×CH$_3$ Val), 1.30-1.51 (2H, m, CH$_2$ Cit), 1.53-1.76 (2H, m, CH$_2$ Cit), 1.90-2.01 (1H, m, β-H Val), 2.89-3.08 (2H, m, CH$_2$ Cit), 3.62 (2H, t, J=5.4 Hz, CH$_2$), 3.83-3.88 (1H, m, α-H), 3.97-4.05 (1H, m), 4.16-4.24 (1H, m), 4.35-4.43 (1H, m, α-H), 5.25 (2H, s, CH$_2$), 5.41 (2H, s, NH$_2$), 5.95-5.99 (1H, m, NH), 7.02 (2H, s, HC=CH), 7.11-7.14 (1H, m, NH), 7.40 (2H, d, J=8.7 Hz, Ar—H), 7.54-7.59 (2H, m, Ar—H), 7.64 (2H, d, J=8.4 Hz, Ar—H), 8.03-8.06 (1H, m, NH), 8.29-8.33 (2H, m, Ar—H), 10.08 (1H, s, NH); MS (ESI): m/z=712.5 (M+H$^+$).

Compound 25d:

$^1$H-NMR (400 MHz, CDCl$_3$/CD$_3$OD) δ=0.98 (6H, dd, J=6.9 Hz, J=14.4 Hz, CH$_3$), 1.59 (2H, m), 1.76 (1H, m), 1.94 (1H, m), 2.13 (1H, m), 3.08-3.28 (2H, m) 3.57-3.76 (14H, m, CH$_2$O), 4.00 (1H, m), 4.22 (2H, m), 4.57 (1H, m), 5.26 (2H, s, OCH$_2$Ar), 6.78 (2H, s, CH=CH), 7.42 (4H, m, ArH), 7.66 (2H, d, J=8.3 Hz), 8.29 (2H, d, J=9.3 Hz).

Figure 2:
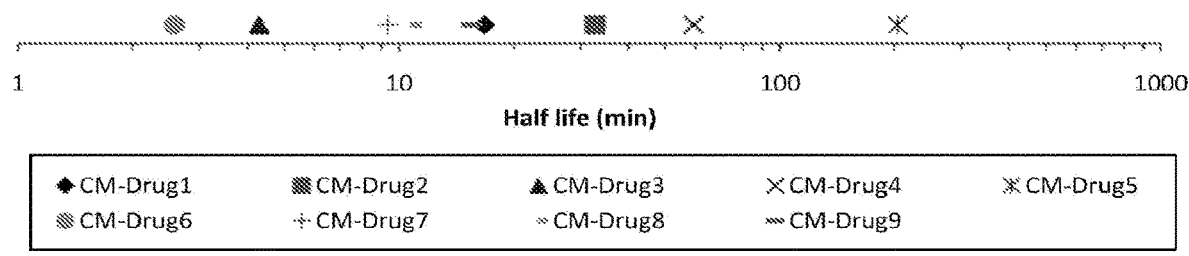
FIG. 2. Graphical illustration of cyclization rates for a series of cyclization spacer-duocarmycin compounds at 25° C. and pH 7.4 (upper line) and at 37° C. and pH 5 (lower line).
Figure 2:
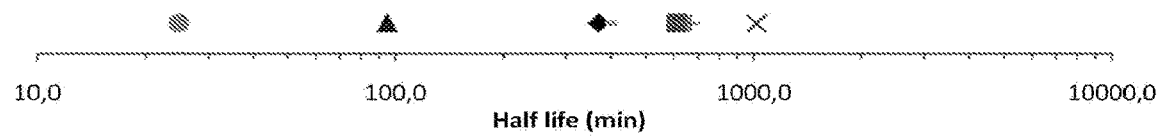

Example 13: Determination of the Cyclization Rate of Cyclization Spacer-Duocarmycin Compounds Cyclization spacer-duocarmycin compounds in which the cyclization spacer is coupled to the hydroxy group of the DNA-alkylator were prepared from the corresponding Boc-protected derivatives such as and similar to compound 14a by treatment with TFA in DCM for 10 minutes, followed by concentration. For measurement of the cyclization rate at pH 7.4, the cyclization spacer-duocarmycin compound was dissolved in a mixture of 100 mM phosphate buffer pH 7.4 and acetonitrile (60/40) at 25° C. and disappearance of starting material/appearance of free drug was followed over time by LC/MS (direct injection of reaction mixture). For measurement of the cyclization rate at pH 5, the cyclization spacer-duocarmycin compound was dissolved in a mixture of 100 mM sodium acetate buffer pH 5 and acetonitrile (60/40) at 37° C. and disappearance of starting material/appearance of free drug was followed over time by LC/MS (direct injection of reaction mixture). Cyclization rates were calculated from the LC/MS data. FIG. 2 shows some representative data. All cyclization spacer-duocarmycin compounds depicted in FIG. 2 contain the same duocarmycin compound. CM-Drug1 contains a cyclization spacer used in the prior art. All other cyclization spacer-duocarmycin compounds contain cyclization spacers selected from the ones described in Examples 1-9. The results presented in FIG. 2 indicate that the cyclization spacers of the present invention can be used to modulate the cyclization rate.

Example 14: Human Plasma Stability of HSA-Conjugated Linker-Agent Conjugates

Figure 3:
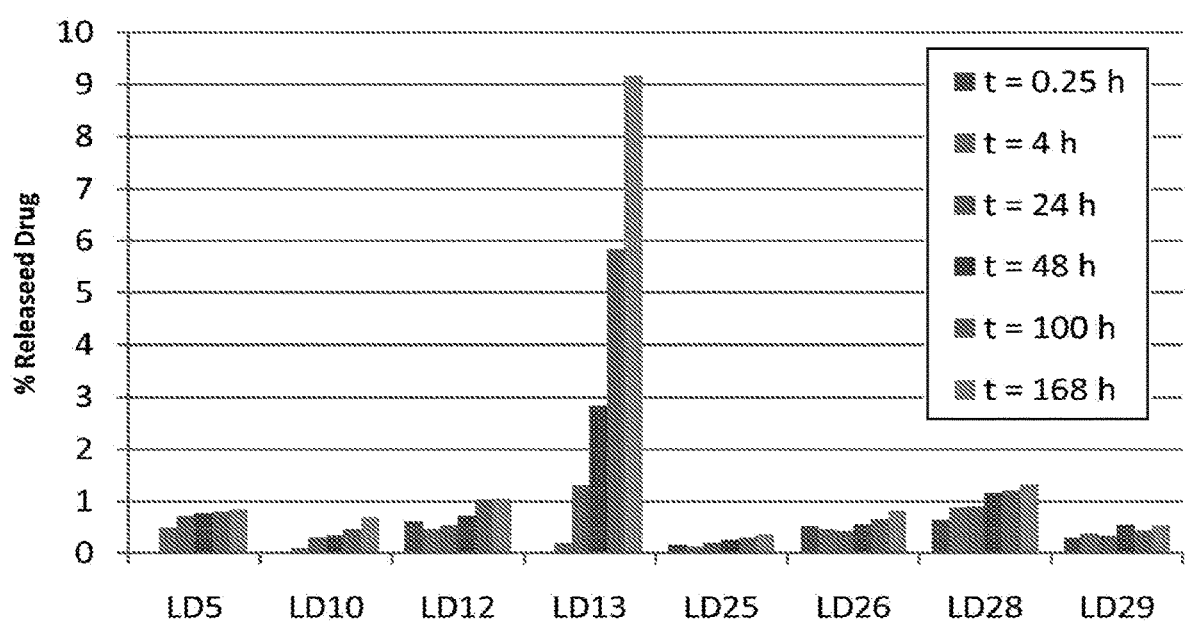
FIG. 3. Human plasma stability for a series of HSA-conjugated linker-agent conjugates.

Linker-agent conjugate containing a maleimide group was dissolved in DMSO and added to sodium heparine-stabilized human plasma at 37° C. such that the concentration of linker-agent conjugate was 7.5 µM and percentage DMSO was 2.5%. Linker-agent conjugate reacted in situ with human serum albumin within 5 minutes, as indicated by LC/MS. Formation of free drug was followed over time by LC/MS. Plasma samples were treated with acetonitrile and centrifuged before analysis. FIG. 3 presents the human plasma stability data for a representative selection of linker-agent conjugates of the present invention. All linker-agent conjugates contain the same duocarmycin analog and linkers are coupled to the DNA alkylator moiety, except for LD13, in which the linker is bound to the DNA binder moiety. LD5, LD12, and LD13 contain linkers that have been used in the prior art and that contain a relatively long linker as in compound 18d. LD10, LD25, LD26, LD28 and LD29 contain similar relatively short linkers as in compound 18b and have different cyclization spacers. LD10 and LD12 only differ in L moiety. The results in FIG. 3 demonstrate that conjugates with a relatively short linker have a high human plasma stability, which generally exceeds that of corresponding conjugates with a relatively long linker. Plasma stability is furthermore demonstrated to be affected by the cyclization spacer.

Example 15: Single Dose Efficacy Study in Female Nu/Nu Mice Bearing an N87 Xenograft Preparation of ADCs:
Trastuzumab (50 mg, 10 mg/mL) was reduced using 1.1 molar equivalents of TCEP by incubating at 20° C. for 90 minutes to generate 2 free thiols per mAb. The incorporation ratio was confirmed via the Ellman's assay. Linker-agent conjugate dissolved in DMSO was added to the reduced antibody solution dropwise at a ratio of 1.3 molar equivalents per free thiol such that the final concentration of DMSO was 10%. After mixing for a further 50 minutes at 20° C., the reaction was quenched by the addition of one molar equivalent of N-acetylcysteine per linker-agent conjugate. After quenching, the conjugate was desalted into PBS pH 7.4 buffer and then purified using a 5 ml r-Protein A column, with the product collected off this column being desalted into presentation buffer (same buffer as in commercially available Herceptin). The product was filtered to 0.2 m and characterized for aggregate (SEC), drug-to-antibody ratio (UV, 280 nm vs 335 nm), and free linker-agent conjugate (LC/MS). ADCs used in the efficacy study described below contain a representative selection of linker-agent conjugates of the present invention and have an average drug-to-antibody ratio of approximately 2.

Figure 4A:
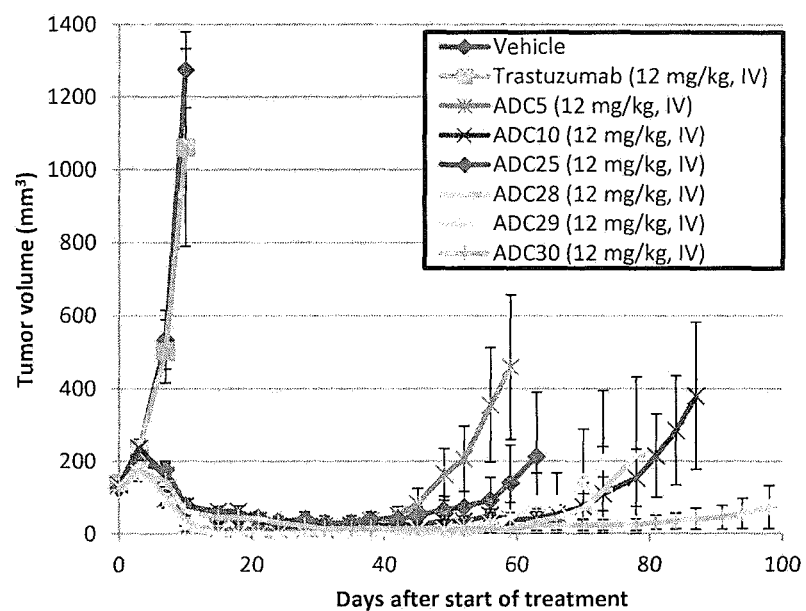
FIGS. 4A-4C. Single dose efficacy study with Trastuzumab-based antibody-drug conjugates (ADCs) in female nu/nu mice bearing an N87 xenograft described in Example 15.
Figure 4B:
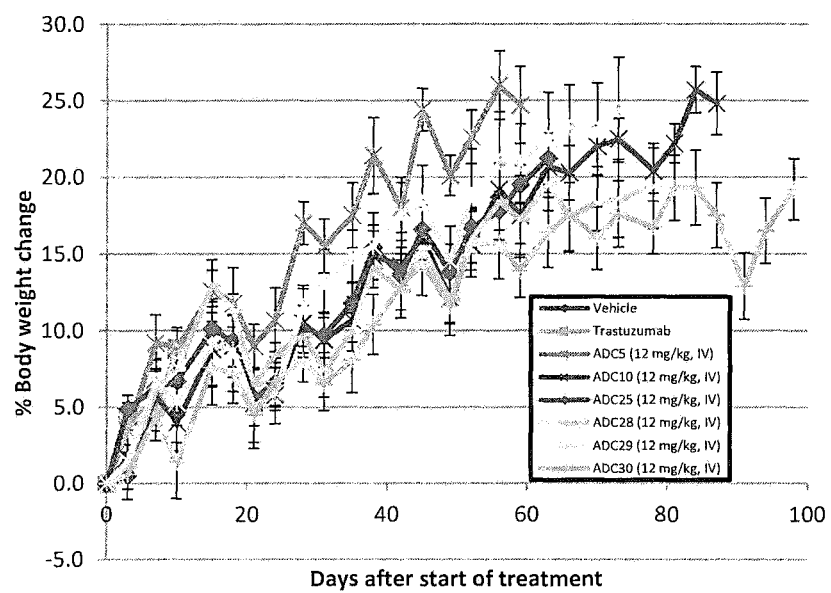
Figure 4C:
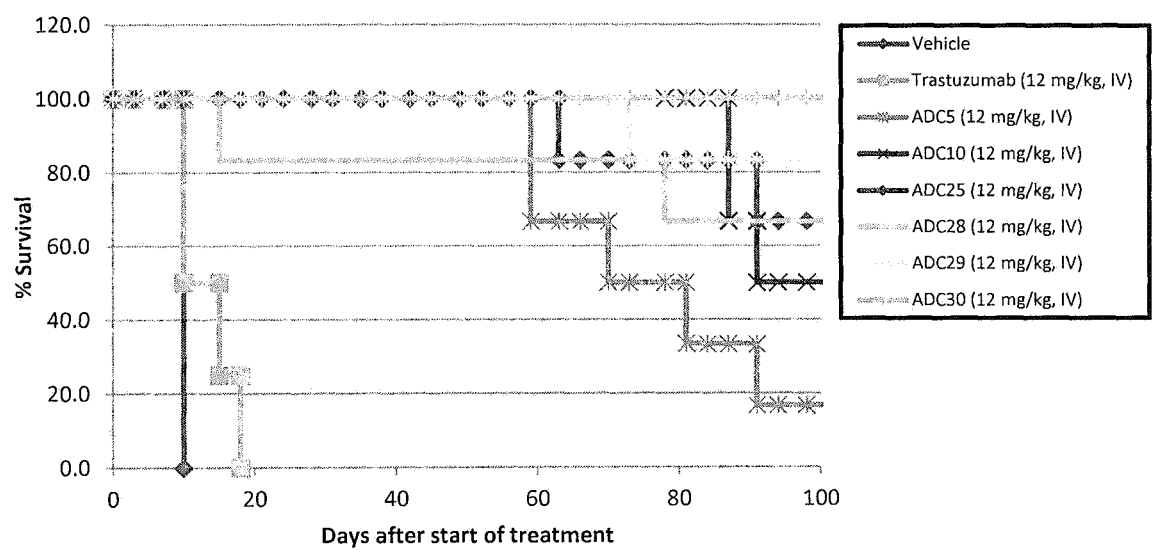

Efficacy Study:
7-8 week old female nu/nu mice were implanted with N87 tumor fragments subcutaneously. Treatment started 19 days after implant when the mean estimated tumor mass for all groups was 130 mg. ADC groups contained 6 animals per group; control groups contained 4 animals per group. Animals were treated with a single dose of 12 mg ADC/kg (0.2 mL/20 g for vehicle; 12 mg mAb/kg for trastuzumab) on day 0. Animals were euthanized when the tumor reached a mass of 1,000 mg. FIG. 4A shows the average tumor burden for each group. A line stops after a first animal in the corresponding group has been euthanized due to tumor burden. FIG. 4B shows the average body weight change for each group. FIG. 4C shows the survival percentage in each group. ADC5 is based on a linker-agent that contains a relatively long linker as in 18d, whereas the ADCs based on the other linker-agents contain a relatively short linker as in 18b. ADC30 contains a different drug than the other ADCs, but has the same linker as ADC28. ADC5 and ADC28 only differ in L moiety. The results in FIGS. 4A-4C demonstrate that conjugates that contain a relatively short linker have a better efficacy than the corresponding conjugate with a relatively long linker. Both the nature of the linker and the nature of the drug were demonstrated to have an effect on efficacy as well.

Example 16: Cleavage of Quenched Linker-Agent Conjugates by Cathepsin B

Figure 5:
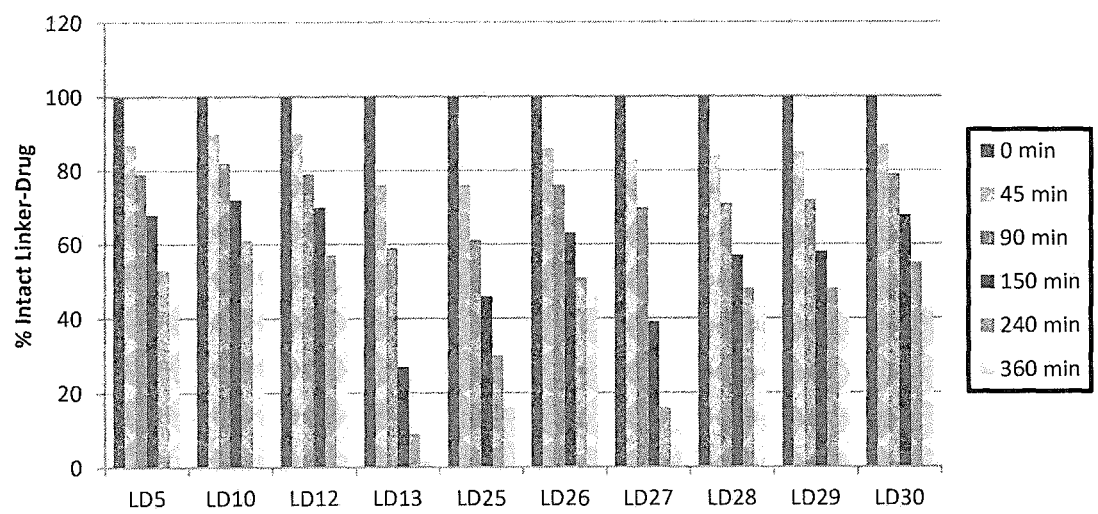
FIG. 5. Cleavage of N-acetylcysteine-quenched linker-agent conjugates by cathepsin B.

Linker-agent conjugate was dissolved in acetonitrile/water and 5 equivalents of N-acetylcysteine were added. The reaction mixture was incubated for 1 h at RT and subsequently freeze-dried to give the quenched linker-agent conjugate. Quenched linker-agent conjugate dissolved in DMSO was added to a 5 µg/mL solution of cathepsin B (>200 U/mg) in sodium acetate buffer pH 5 at 37° C. The final concentration of quenched linker-agent conjugate was 130 µM. Disappearance of starting material was monitored over time by LC/MS. FIG. 5 presents the cathepsin B cleavage data for a representative selection of quenched linker-agent conjugates of the present invention. LD5, LD12, and LD13 are based on linker-agents from the prior art and contain linkers that are relatively long as in 18d, whereas the linkers in the other quenched linker-agent conjugates are as in 18b. The said other quenched linker-agent conjugates primarily differ in cyclization spacer. The results from FIG. 5 demonstrate that all quenched linker-agent conjugates are cleaved efficiently by cathepsin B.

REFERENCES

[1] Boger, D. L.; Johnson, D. S.; Wrasidlo, W. *Bioorg. Med. Chem. Lett.* 1994, 4, 631-636.
[2] McGovren, J. P., Clarke, G. L., Pratt, E. A., DeKoning, T. F. *J. Antibiot.* 1984, 37, 63-70.

[3] Carter, P.; Smith, L.; Ryan, M. *Endocr.-Relat. Cancer* 2004, 11, 659-687.
[4] Bagshawe, K. D. *Drug Dev. Res.* 1995, 34, 220-230.
[5] Melton, R.; Connors, T.; Knox, R. J. *S.T.P. Pharma Sciences*, 1999, 13-33.
[6] Huber, B. E.; Richards, C. A.; Krenitsky, T. A. *Proc. Natl. Acad. Sci. USA*, 1991, 88, 8039-8043.
[7] Bagshawe, K. D.; Springer, C. J.; Searle, F.; Antoniw, P.; Sharma, S. K.; Melton, R. G.; Sherwood, R. F. *Br. J. Cancer*, 1988, 58, 700-703.
[8] Duncan, R. Nat. *Rev. Drug Discov.* 2003, 2, 347-360.
[9] Toki, B. E.; Cerveny, C. G.; Wahl, A. F.; Senter, P. D. *J. Org. Chem.*, 2002, 67, 1866-1872.
[10] See for some recently disclosed cyclization spacers for example WO 2005/079398, WO 2005/105154, and WO 2006/012527.
[11] Greenwald, R. B., Choe, Y. H., McGuire, J., Conover, C. D. *Adv. Drug Delivery Rev.* 2003, 55, 217-250.
[12] Kingsbury, W. D.; Boehm; J. C.; Mehta, R. J.; Grappel, S. F.; Gilvarg, C. *J. Med. Chem.* 1984, 27, 1447-1451.
[13] Greenwald, R. B.; Zhao, H.; Yang, K.; Reddy, P.; Martinez, A. *J. Med. Chem.* 2004, 47, 726-734.
[14] (a) Franke, A. E.; Sievers, E. L.; and Scheinberg, D. A. *Cancer Biother. Radiopharm.* 2000, 15, 459-476. (b) Murray, J. L. *Semin. Oncol.* 2000, 27, 2564-2570. (c) Breitling, F., and Dubel, S., Recombinant Antibodies, John Wiley and Sons, New York, 1998.
[15] Ringsdorf, H. *J. Polym. Sci., Polym. Symp.* 1975, 51, 135-153.
[16] Elvira, C.; Gallardo, A.; San Roman, J.; Cifuentes, A. *Molecules* 2005, 10, 114-125.
[17] Remington's Pharmaceutical Science (15th ed., Mack Publishing, Easton, Pa., 1980) (incorporated by reference in its entirety for all purposes)
[18] Pettit, G. R.; Burkett, D. D.; Barkóczy, J.; Breneman, G. L.; Pettit, W. E. *Synthesis* 1996, 719-725.

The invention claimed is:
1. A compound of formula (IV):

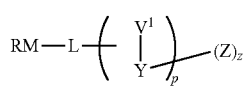

or a pharmaceutically acceptable salt thereof, wherein
RM is a reactive moiety,
L is independently absent or a linking group linking RM to one or more $V^1$ and/or Y;
each $V^1$ is independently absent or a conditionally-cleavable or conditionally-transformable moiety, which can be cleaved or transformed by a chemical, photochemical, physical, biological, or enzymatic process;
each Y is a self-eliminating spacer system which is comprised of 1 or more self-elimination ω-amino aminocarbonyl cyclization spacers selected from

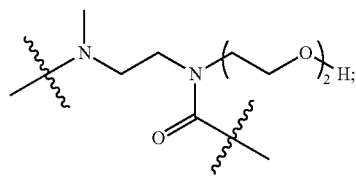

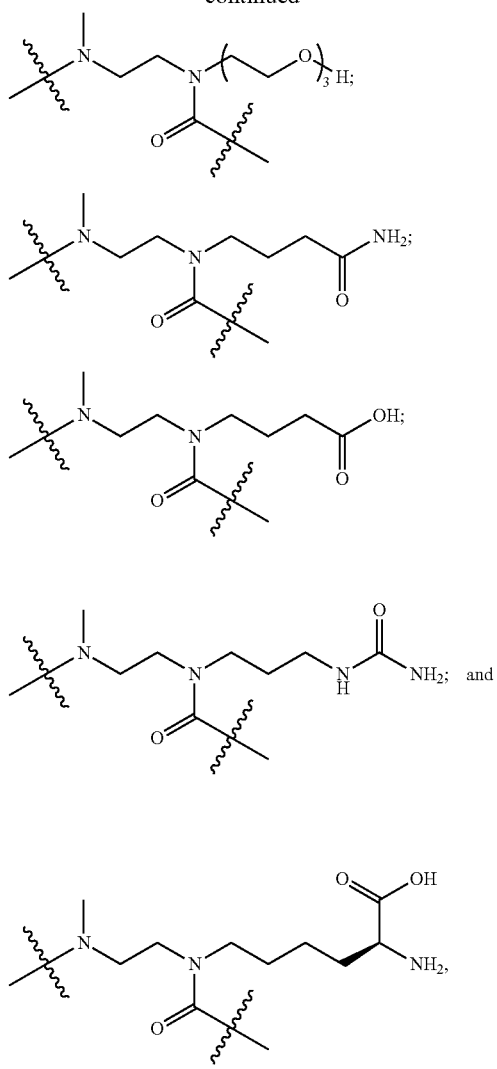

and each Y is linked to $V^1$, optionally L, and one or more Z;
p is a number representing a degree of branching and is a positive integer;
z is a positive integer equal to or smaller than the total number of attachment sites for Z;
each Z is independently a compound of formula (I), (II), (I'), or (II'):

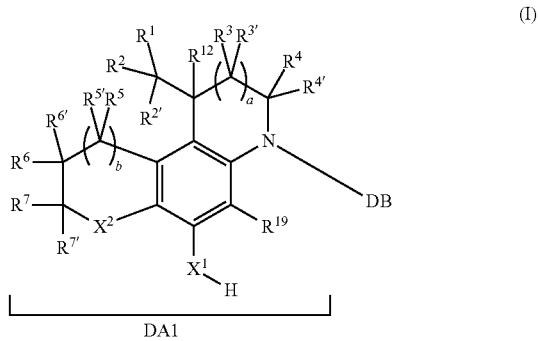

(II)
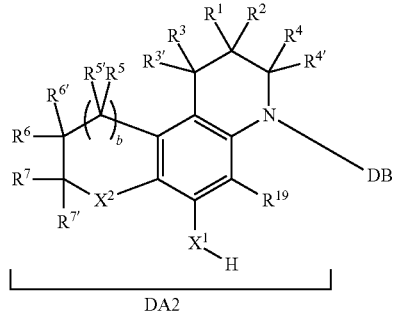
(I')
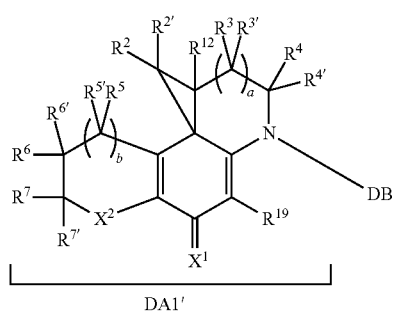
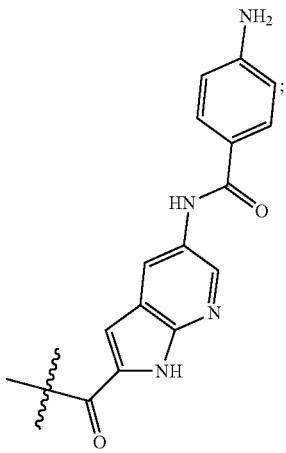
(II'')
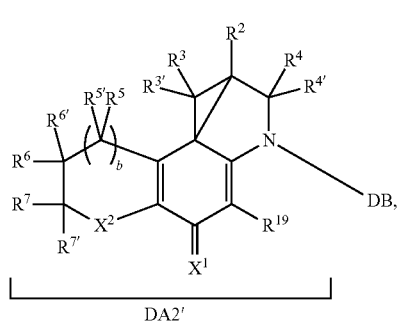
or a pharmaceutically acceptable salt thereof, wherein DB is a DNA-binding moiety which is selected from
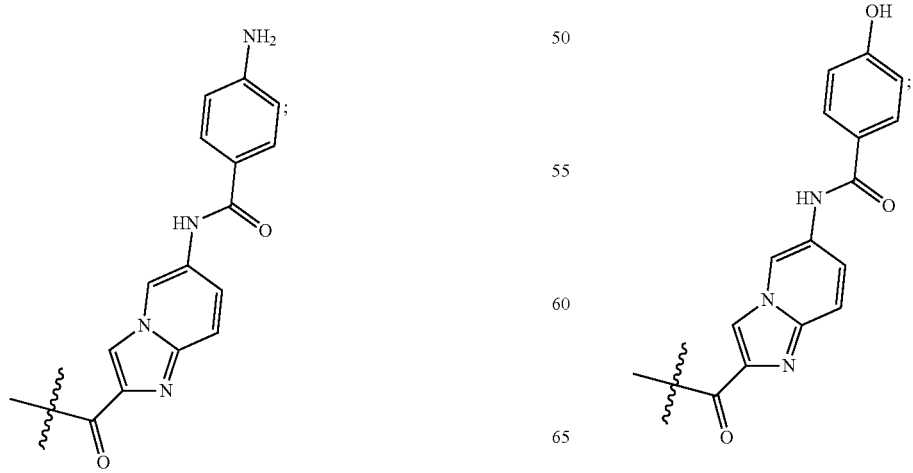

-continued
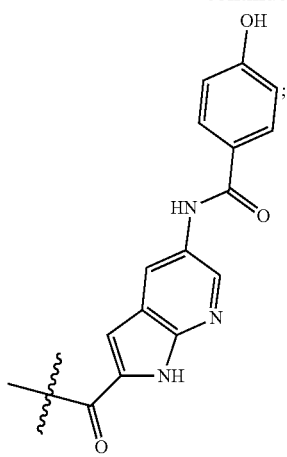
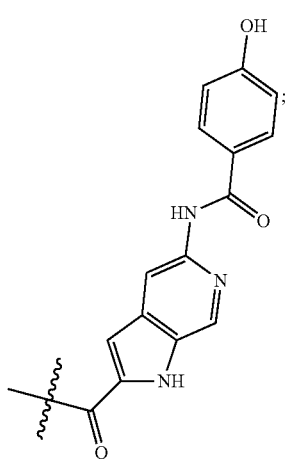
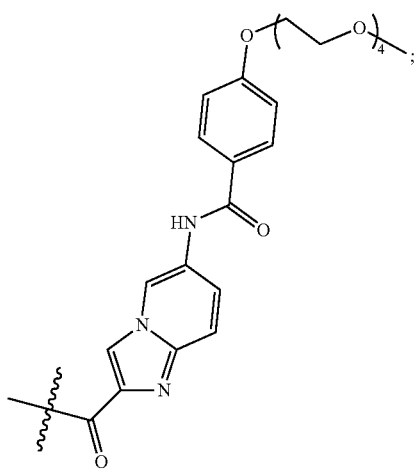
-continued
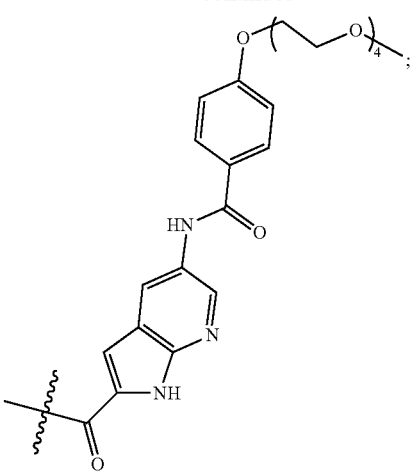
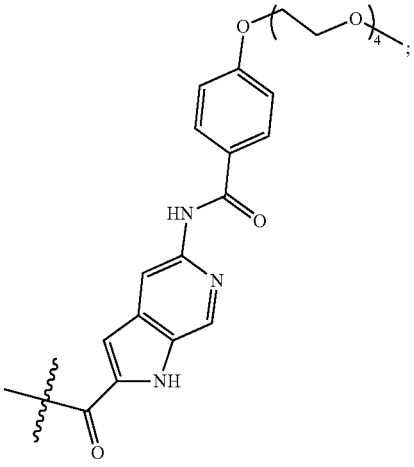
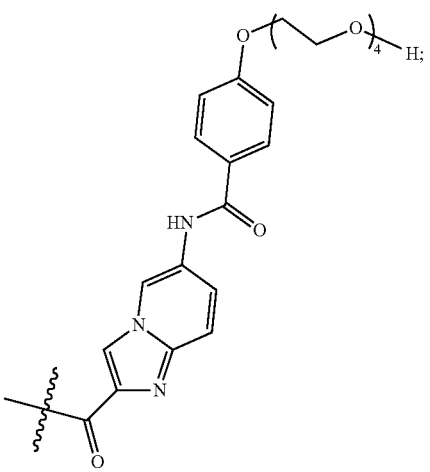

639
-continued
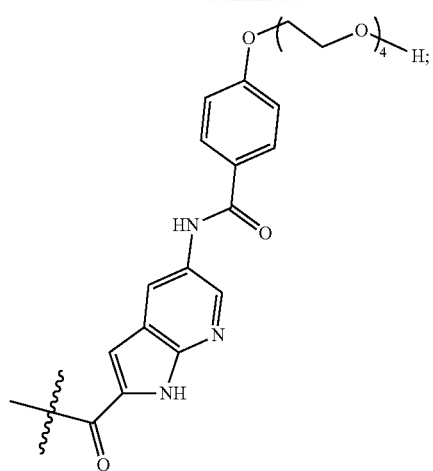
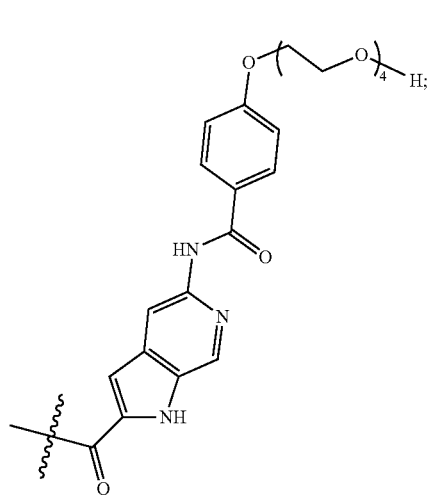
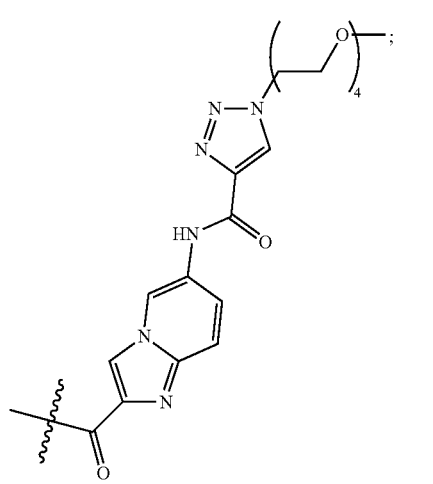
640
-continued
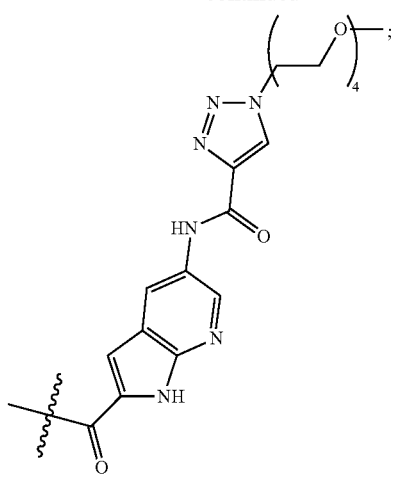
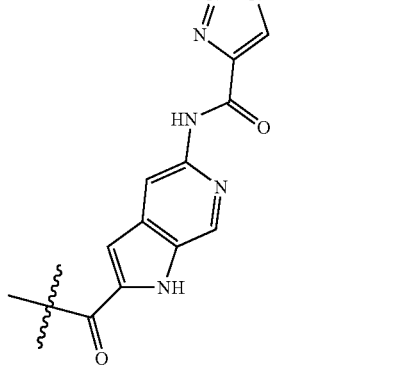
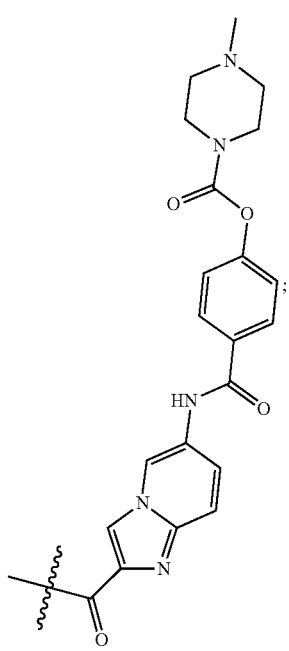 [SMILES: *C(=O)c1cc2cc(NC(=O)c3ccc(OC(=O)N4CCN(C)CC4)cc3)ncc2[nH]1]

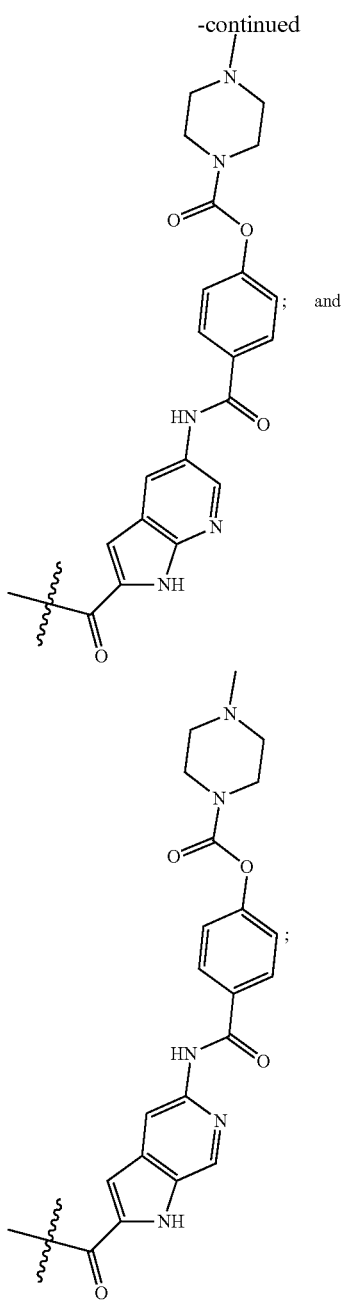

R¹ is a leaving group;

R², R²', R³, R³', R⁴, R⁴', R¹², and R¹⁹ are independently selected from the group consisting of H, OH, SH, NH₂, N₃, NO₂, NO, CF₃, CN, C(O)NH₂, C(O)H, C(O)OH, halogen, Rᵃ, SRᵃ, S(O)Rᵃ, S(O)₂Rᵃ, S(O)ORᵃ, S(O)₂ORᵃ, OS(O)Rᵃ, OS(O)₂Rᵃ, OS(O)ORᵃ, OS(O)₂ORᵃ, ORᵃ, NHRᵃ, N(Rᵃ)Rᵇ, ⁺N(Rᵃ)(Rᵇ)Rᶜ, P(O)(ORᵃ)(ORᵇ), OP(O)(ORᵃ)(ORᵇ), SiRᵃRᵇRᶜ, C(O)Rᵃ, C(O)ORᵃ, C(O)N(Rᵃ)Rᵇ, OC(O)Rᵃ, OC(O)ORᵃ, OC(O)N(Rᵃ)Rᵇ, N(Rᵃ)C(O)Rᵇ, N(Rᵃ)C(O)OR, and N(Rᵃ)C(O)N(Rᵇ)Rᶜ, wherein Rᵃ, Rᵇ, and Rᶜ are independently selected from H and optionally substituted C₁₋₃ alkyl or C₁₋₃ heteroalkyl, or R³+R³' and/or R⁴+R⁴' are independently selected from =O, =S, =NOR¹⁸, =C(R¹⁸)R¹⁸', and =NR¹⁸, R¹⁸ and R¹⁸' being independently selected from H and optionally substituted C₁₋₃ alkyl, two or more of R², R²', R³, R³', R⁴, R⁴', and R¹² optionally being joined by one or more bonds to form one or more optionally substituted carbocycles and/or heterocycles;

X² is selected from the group consisting of O, C(R¹⁴)(R¹⁴'), and NR¹⁴', wherein R¹⁴ and R¹⁴' have the same meaning as defined for R⁷ and are independently selected, or R¹⁴' and R⁷ are absent resulting in a double bond between the atoms designated to bear R⁷ and R¹⁴';

R⁵, R⁵', R⁶, R⁶', R⁷, and R⁷' are independently selected from the group consisting of H, OH, SH, NH₂, N₃, NO₂, NO, CF₃, CN, C(O)NH₂, C(O)H, C(O)OH, halogen, Rᵉ, SRᵉ, S(O)Rᵉ, S(O)₂Rᵉ, S(O)ORᵉ, S(O)₂ORᵉ, OS(O)Rᵉ, OS(O)₂Rᵉ, OS(O)ORᵉ, OS(O)₂ORᵉ, ORᵉ, NHRᵉ, N(Rᵉ)Rᶠ, ⁺N(Rᵉ)(Rᶠ)Rᵍ, P(O)(ORᵉ)(ORᶠ), OP(O)(ORᵉ)(ORᶠ), SiRᵉRᶠRᵍ, C(O)Rᵉ, C(O)ORᵉ, C(O)N(Rᵉ)Rᶠ, OC(O)Rᵉ, OC(O)ORᵉ, OC(O)N(Rᵉ)Rᶠ, N(Rᵉ)C(O)Rᶠ, N(Rᵉ)C(O)ORᶠ, N(Rᵉ)C(O)N(Rᶠ)Rᵍ, and a water-soluble group, wherein Rᵉ, Rᶠ, and Rᵍ are independently selected from H and optionally substituted (CH₂CH₂O)ₑₑCH₂CH₂X¹³Rᵉ¹, C₁₋₁₅ alkyl, C₁₋₁₅ heteroalkyl, C₃₋₁₅ cycloalkyl, C₁₋₁₅ heterocycloalkyl, C₅₋₁₅ aryl, or C₁₋₁₅ heteroaryl, wherein ee is selected from 1 to 1000, X¹³ is selected from O, S, and NRᶠ¹, and Rᶠ¹ and Rᵉ¹ are independently selected from H and C₁₋₃ alkyl, one or more of the optional substituents in Rᵉ, Rᶠ, and/or Rᵍ optionally being a water-soluble group, two or more of Rᵉ, Rᶠ, and Rᵍ optionally being joined by one or more bonds to form one or more optionally substituted carbocycles and/or heterocycles, or R⁵+R⁵' and/or R⁶+R⁶' and/or R⁷+R⁷' are independently selected from =O, =S, =NORᵉ³, =C(Rᵉ³)Rᵉ⁴, and =NRᵉ³, Rᵉ³ and Rᵉ⁴ being independently selected from H and optionally substituted C₁₋₃ alkyl, or R⁵'+R⁶' and/or R⁶'+R⁷' and/or R⁷'+R¹⁴' are absent, resulting in a double bond between the atoms designated to bear R⁵' and R⁶', and/or R⁶' and R⁷', and/or R⁷' and R¹⁴', respectively, two or more of R⁵, R⁵', R⁶, R⁶', R⁷, R⁷', R¹⁴, and R¹⁴' optionally being joined by one or more bonds to form one or more optionally substituted carbocycles and/or heterocycles;

X¹ is selected from the group consisting of O, S, and NR¹³, wherein R¹³ is selected from H and optionally substituted C₁₋₈ alkyl or C₁₋₈ heteroalkyl and not joined with any other substituent;

one of R⁴ and R⁴' may optionally be joined by one or more bonds to form one or more optionally substituted carbocycles and/or heterocycles;

one of R², R²', R³, and R³' and one of R⁵ and R⁵' may optionally be joined by one or more bonds to form one or more optionally substituted carbocycles and/or heterocycles;

a and b are independently selected from 0 and 1; and one or more of X¹, R⁵, R⁵', R⁶, R⁶', R⁷, R⁷', R¹⁴, and R¹⁴' may optionally in addition be substituted by or be a substituent of formula (V):

(V)

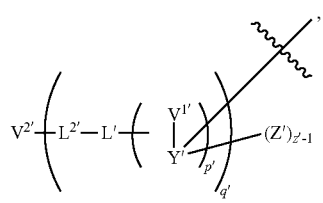

wherein each $V^{2'}$ is absent or a functional moiety,
each $L^{2'}$ is independently absent or a linking group linking $V^{2'}$ to $L'$,
q' is a number representing a degree of branching and is a positive integer,
$L'$, $V^{1'}$, $Y'$, $Z'$, p', and z' has the same meaning as defined for L, $V^1$, Y, Z, p, and z, respectively, and is independently selected, the one or more substituents of formula (V) being independently connected via $Y'$ to one or more of $X^1$, $R^5$, $R^{5'}$, $R^6$, $R^{6'}$, $R^7$, $R^{7'}$, $R^{14}$, $R^{14'}$, and/or to one or more atoms bearing these R substituents;
each Z is independently connected to Y through either Xi, an atom in $R^5$, $R^{5'}$, $R^6$, $R^{6'}$, $R^7$, $R^{7'}$, $R^{14}$, $R^{14'}$, or an atom bearing any of these R substituents,
$V^1$, Y, and Z may contain protecting groups, and the one or more $V^{2'}$-$L^{2'}$ moieties optionally present in Z as defined hereinabove may optionally and independently be RM' instead, which is a reactive moiety, and wherein, if there is more than 1 reactive moiety in (IV), some or all reactive moieties are the same or different.

2. The compound according to claim 1 wherein the reactive moiety RM is

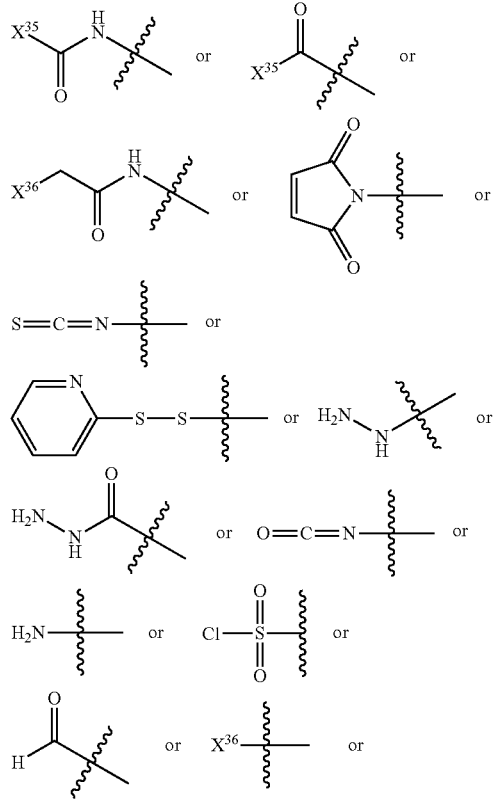

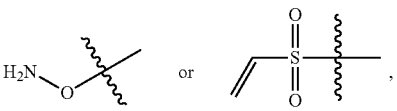

wherein $X^{35}$ is selected from the group consisting of halide, hydroxy, OC(O)$R^{dd}$, and OC(O)O$R^{dd}$, or C(O)—$X^{35}$ is an active ester, $X^{36}$ is selected from the group consisting of halide, mesyloxy, triflyloxy, and tosyloxy, and $R^{dd}$ is selected from the group consisting of optionally substituted $C_{1-10}$ alkyl, $C_{1-10}$ heteroalkyl, $C_{3-10}$ cycloalkyl, $C_{1-10}$ heterocycloalkyl, $C_{5-10}$ aryl, and $C_{1-10}$ heteroaryl.

3. The compound according to claim 1, which is

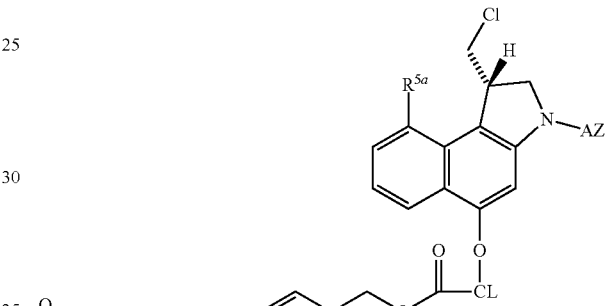

or an isomer, or a mixture of isomers, wherein $R^{5a}$ is selected from H, methyl and methoxy, AZ is

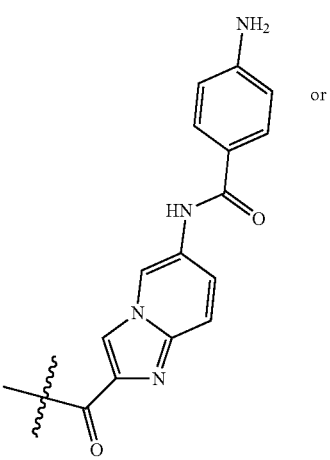

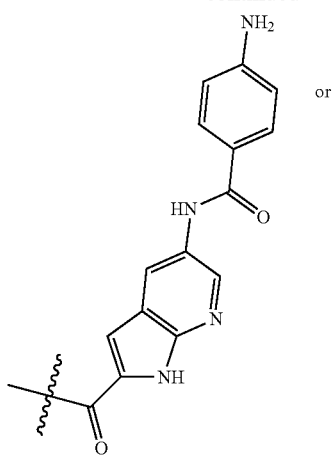 or
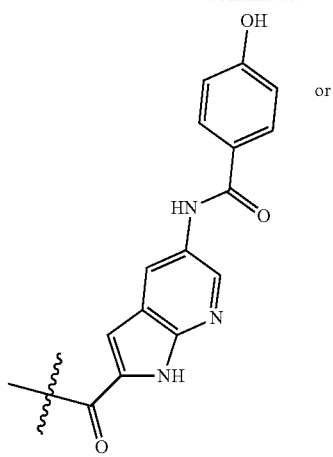 or
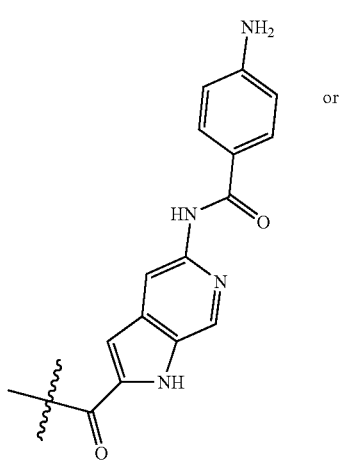 or
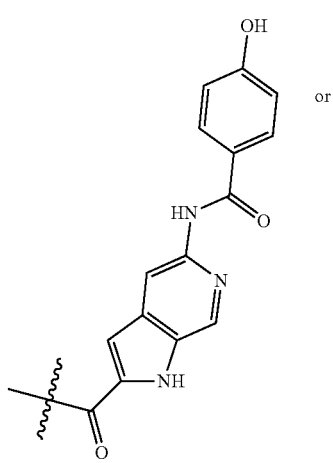 or
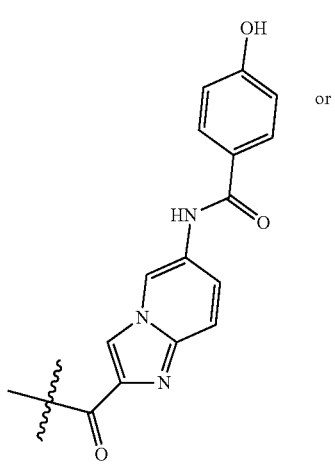 or
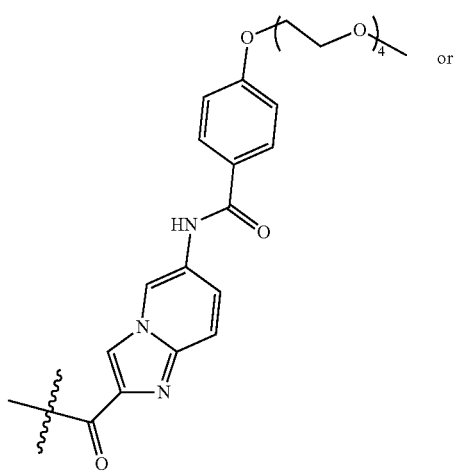 or 647
-continued
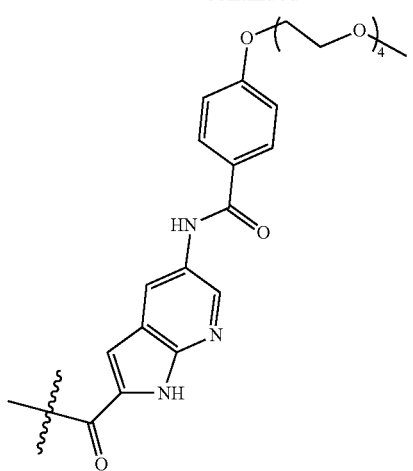
or
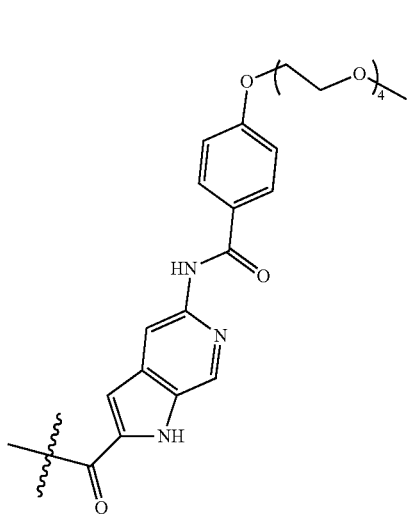
or
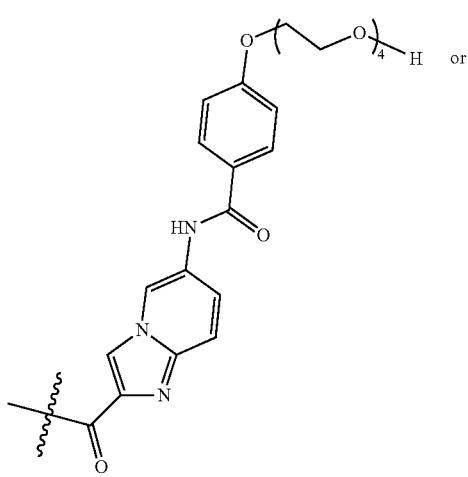
or
648
-continued
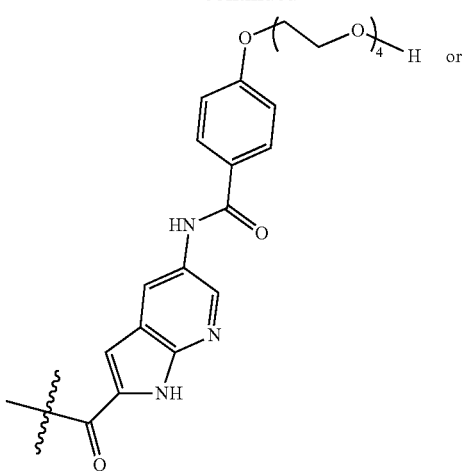
or
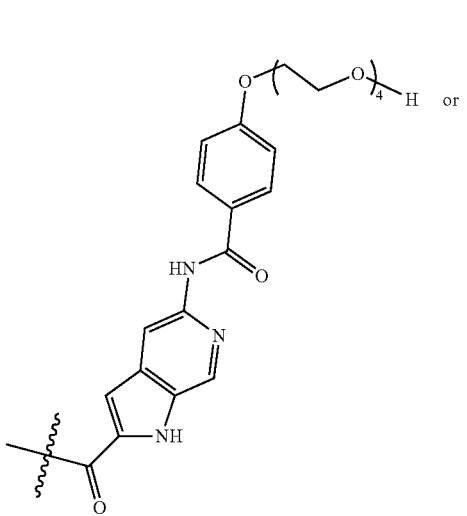
or
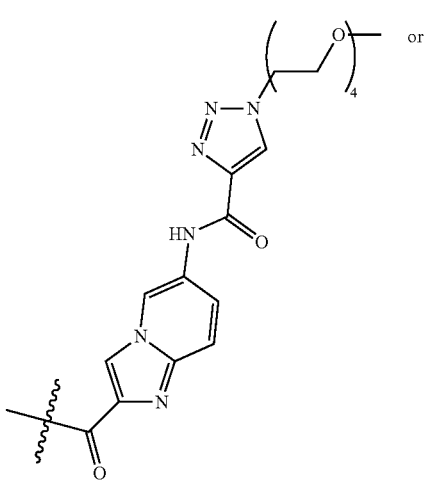
or 649
-continued
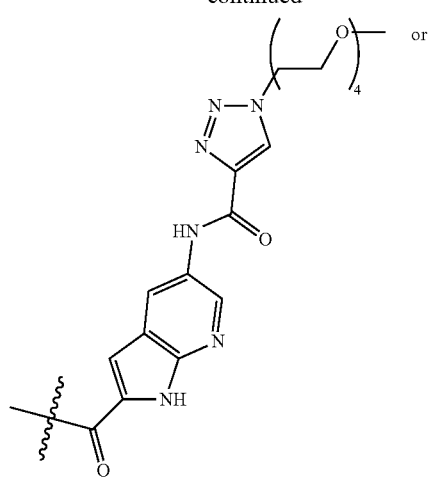
or
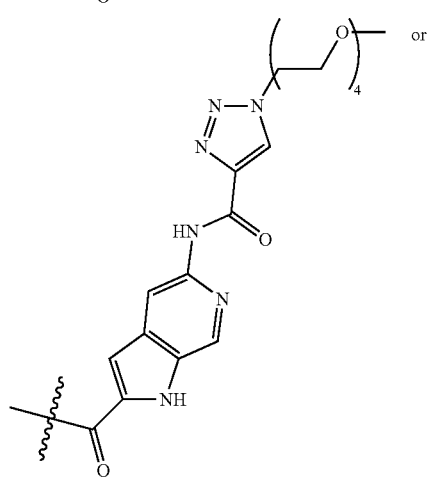
or
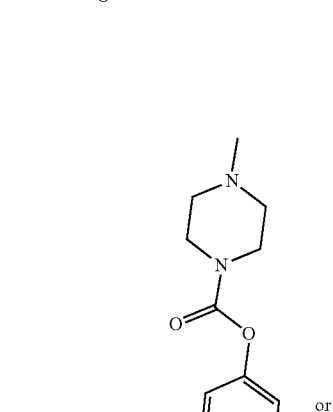
or
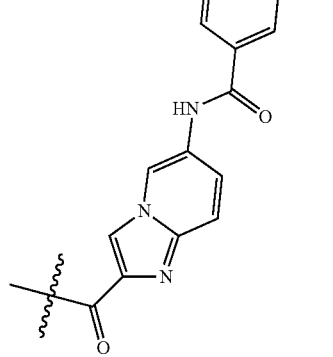
650
-continued
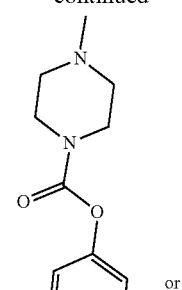
or
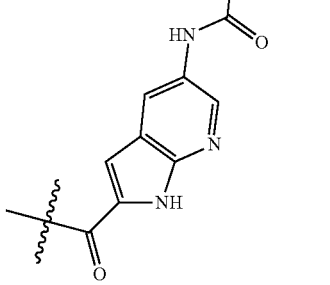
,
$V^1$ is selected from the group consisting of valylcitrulline, valyllysine, phenylalanyllysine, alanylphenylalanyllysine, and D-alanylphenylalanyllysine, CL is
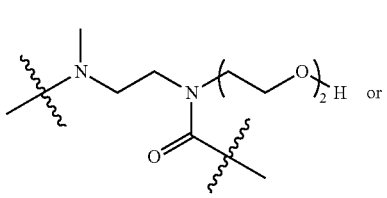
or 651
-continued
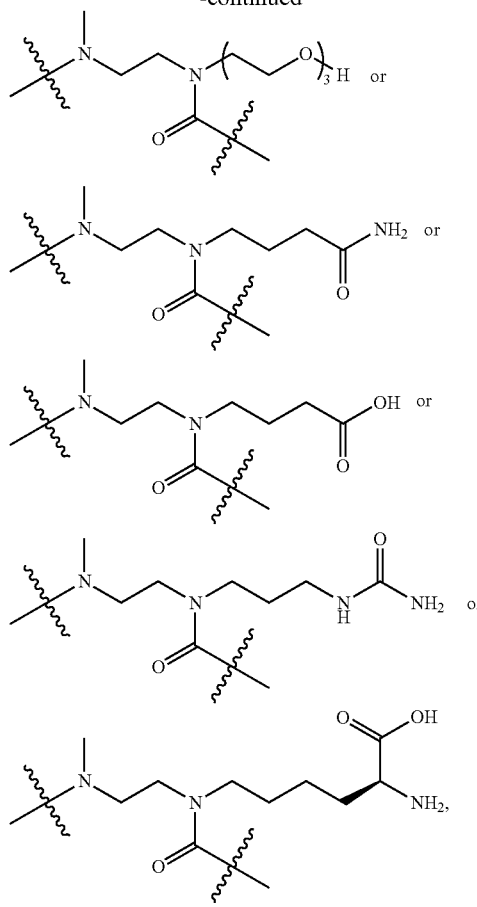
and L is selected from the group consisting of
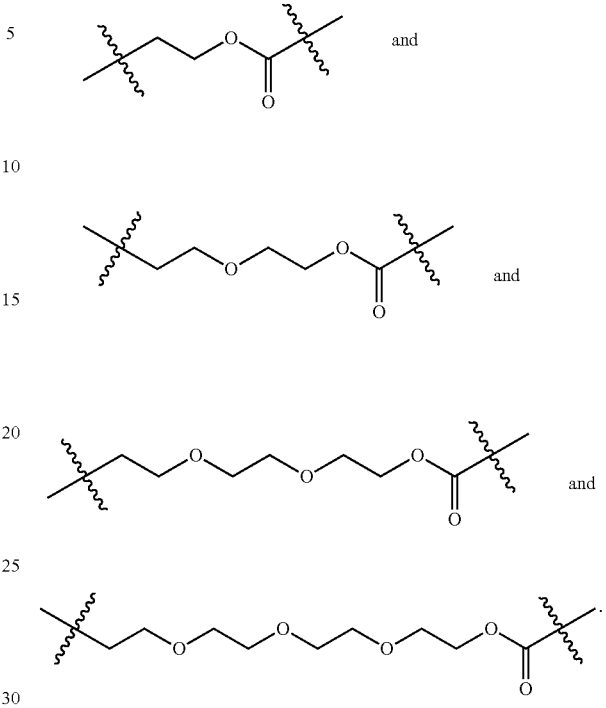
4. A pharmaceutical composition comprising a compound according to claim 1 and a pharmaceutically acceptable carrier.
5. The compound according to claim 1, wherein the compound has the formula
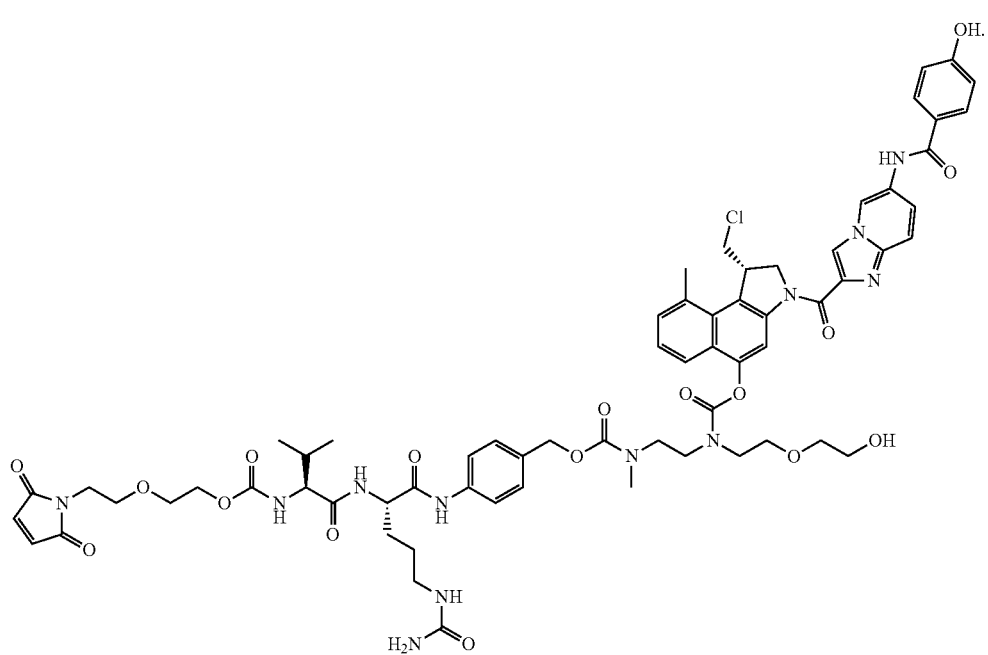 [SMILES: Cc1cccc2c(OC(=O)N(CCOCCO)CCN(C)C(=O)OCc3ccc(NC(=O)[C@H](CCCNC(N)=O)NC(=O)[C@@H](NC(=O)OCCOCCN4C(=O)C=CC4=O)C(C)C)cc3)cc3c(c12)[C@H](CCl)CN3C(=O)c1cn2cc(NC(=O)c3ccc(O)cc3)ccc2n1]

6. A pharmaceutical composition comprising a compound according to claim 2 and a pharmaceutically acceptable carrier.

7. A pharmaceutical composition comprising a compound according to claim 3 and a pharmaceutically acceptable carrier.

8. A pharmaceutical composition comprising a compound according to claim 5 and a pharmaceutically acceptable carrier.

\* \* \* \* \*

UNITED STATES PATENT AND TRADEMARK OFFICE
CERTIFICATE OF CORRECTION

Page 1 of 1

PATENT NO. : 11,052,155 B2
APPLICATION NO. : 15/461560
DATED : July 6, 2021
INVENTOR(S) : Beusker et al.

It is certified that error appears in the above-identified patent and that said Letters Patent is hereby corrected as shown below:

On the Title Page

Item (62), under "Related U.S. Application Data," delete "96,299,240" and insert -- 9,629,924 --, therefor.

In the Claims

In Column 642, Line 11, delete "$R^{14'}$ and $R^{7}$" and insert -- $R^{14'}$ and $R^{7'}$ --, therefor.

In Column 642, Line 13, delete "$R^{7}$ and $R^{14'}$" and insert -- $R^{7'}$ and $R^{14'}$ --, therefor.

In Column 642, Line 19, delete "$N(R^e)R^e$" and insert -- $N(R^e)R^f$ --, therefor.

In Column 643, Line 24, delete "Xi" and insert -- $X^1$ --, therefor.

Signed and Sealed this
Sixteenth Day of November, 2021

Drew Hirshfeld
*Performing the Functions and Duties of the
Under Secretary of Commerce for Intellectual Property and
Director of the United States Patent and Trademark Office*